US009133477B2

(12) United States Patent
Alphey

(10) Patent No.: US 9,133,477 B2
(45) **Date of Patent: *Sep. 15, 2015**

(54) EXPRESSION SYSTEMS

(75) Inventor: Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 1392 days.

This patent is subject to a terminal disclaimer.

(21) Appl. No.: 11/352,177

(22) Filed: Feb. 10, 2006

(65) Prior Publication Data

US 2006/0242717 A1 Oct. 26, 2006

Related U.S. Application Data

(63) Continuation-in-part of application No. 10/566,448, filed as application No. PCT/GB2004/003263 on Jul. 28, 2004.

(30) Foreign Application Priority Data

Jul. 28, 2003 (GB) .................................. 0317656.7

(51) Int. Cl.

| | |
|---|---|
| ***C12N 15/00*** | (2006.01) |
| ***A01K 67/00*** | (2006.01) |
| ***C12N 15/85*** | (2006.01) |
| ***A01K 67/033*** | (2006.01) |

(52) U.S. Cl.

CPC ........ *C12N 15/8509* (2013.01); *A01K 67/0333* (2013.01); *C12N 15/85* (2013.01); *A01K 2217/05* (2013.01); *A01K 2217/20* (2013.01); *A01K 2227/70* (2013.01); *A01K 2227/706* (2013.01); *A01K 2267/02* (2013.01); *C12N 2830/007* (2013.01); *C12N 2830/008* (2013.01)

(58) Field of Classification Search

CPC .................................................. C12N 15/8509
USPC ...................................................... 435/320.1
See application file for complete search history.

(56) References Cited

U.S. PATENT DOCUMENTS

| | | | |
|---|---|---|---|
| 5,254,801 | A | 10/1993 | Dotson et al. |
| 5,278,057 | A | 1/1994 | Jorgensen |
| 5,670,353 | A | 9/1997 | Ahlquist et al. |
| 5,674,747 | A | 10/1997 | Hammock et al. |
| 5,773,697 | A | 6/1998 | Tomes et al. |
| 5,851,796 | A | 12/1998 | Schatz |
| 5,977,441 | A | 11/1999 | Oliver et al. |
| 6,200,800 | B1 | 3/2001 | Choulika et al. |
| 6,338,040 | B1 | 1/2002 | Buman et al. |
| 6,962,810 | B2 | 11/2005 | Fraser et al. |
| 7,998,475 | B2 | 8/2011 | Alphey |
| 8,124,404 | B2 | 2/2012 | Alphey |
| 2003/0150007 | A1 | 8/2003 | Savakis et al. |
| 2003/0213005 | A1 | 11/2003 | Alphey et al. |
| 2004/0082032 | A1 | 4/2004 | Bovi et al. |
| 2005/0221430 | A1 | 10/2005 | Prentice |
| 2006/0212949 | A1 | 9/2006 | Alphey |
| 2006/0275276 | A1 | 12/2006 | Alphey |
| 2007/0056051 | A1 | 3/2007 | Alphey |
| 2008/0115233 | A1 | 5/2008 | Alphey et al. |
| 2009/0170793 | A1 | 7/2009 | Gaur |
| 2009/0183269 | A1 | 7/2009 | Alphey |

FOREIGN PATENT DOCUMENTS

| | | |
|---|---|---|
| EP | 0 636 310 | 2/1995 |
| EP | 0955364 | 11/1999 |
| GB | 2355459 | 4/2001 |
| WO | WO-90/08830 | 8/1990 |
| WO | WO-94/03619 | 2/1994 |
| WO | WO-96/04393 | 2/1996 |
| WO | WO-96/24605 | 8/1996 |
| WO | WO-97/30162 | 8/1997 |
| WO | 98/08960 | 3/1998 |
| WO | WO-99/10488 | 3/1999 |
| WO | 00/73510 | 12/2000 |
| WO | WO 01/39599 | 6/2001 |
| WO | 01/59088 | 8/2001 |
| WO | 01/91802 | 12/2001 |
| WO | 02/46444 | 6/2002 |
| WO | 02/101061 | 12/2002 |
| WO | 2004/044150 | 5/2004 |
| WO | 2004/098278 | 11/2004 |
| WO | 2004/108933 | 12/2004 |
| WO | 2005/003364 | 1/2005 |
| WO | WO 2005/012534 | 2/2005 |
| WO | 2007/091099 | 8/2007 |

OTHER PUBLICATIONS

Ernst et al, (Inaugural-Dissertation, Aus Frankfurt/Main, BRD, p. 1-55, 1991).*
Saccone et al, (Genetica, 116: 15-23, 2002).*
Blitvich et al, (Insect Molecular Biology, 11(5): 431-442, 2002).*
Arribas et al, [Biochim. Biophys. Acta, 868:119-127, 1986.*
Hondred et al (Plant Physiology, 119: 713-723, 1999).*
Guo et al. (1993, Mol. Cell. Biol., vol. 13(2), pp. 1104-1118).*
Alphey et al. (May 2002) "Dominant Lethality and Insect Population Control," *Mol. Biochem. Parasitol.* 121(2):173-178.
Bieschke et al. (Jun. 1998) "Doxycycline-Induced Transgene Expression During *Drosophila* Development and Aging," *Mol. Gen Genet.* 258(6):571-579.
Chen et al. (Oct. 2000) "The Use of Modified Tetracycline Regulatory Expression System with Reduced Basal Level to Develop and in Vivo Biopesticide Expression System," *Food Sci Agricult. Chem.* 2(4):220-225.

(Continued)

*Primary Examiner* — Anoop Singh
*Assistant Examiner* — David A Montanari
(74) *Attorney, Agent, or Firm* — Morrison & Foerster LLP

(57) ABSTRACT

A gene expression system is provided. The system comprises at least one coding sequence to be expressed in an organism, and at least one promoter operably linked thereto. It further comprises at least one splice control sequence which, in cooperation with a spliceosome, mediates alternative splicing of RNA transcripts of the coding sequence. The mediation of alternative splicing is in a sex-specific, stage-specific, germline-specific and tissue-specific manner.

12 Claims, 48 Drawing Sheets

(56) References Cited

OTHER PUBLICATIONS

Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD (Abstract Only).
Heinrich et al. (Jul. 18, 2000) "A Repressible Female-Specific Lethal Genetic System for Making Transgenic Insect Strains Suitable for a Sterile-Release Program," *Proc. Nat. Acad. Sci. USA* 97:8229-8232.
U.S. Appl. No. 10/566,448, filed Apr. 18, 2006, Alphey et al.
Hofmann et al.(1996) "Rapid Retroviral Delivery of Tetracycline-Inducible Genes in a Single Autoregulatory Cassette," *Proc. Nat. Acad. Sci. USA* 93:5185-5190.
Horn et al. (Jan. 2003) "A Transgene-Based Embryo-Specific Lethality System for Insect Pest Management," *Nat. Biotechnol.* 21(1):64-70.
Louis et al. (Nov. 2003) "A Theoretical Model for the Regulation of Sex-Lethal, a Gene That Controls Sex Determination and Dosage Compensation in *Drosophila melanogaster*," Genetics 165:1355-1384.
Saccone et al. (2000) "Sex Determination in Medfly: A Molecular Approach," In; *Area-Wide Control of Fruit Flies and Other Pest Insects*, Tan, K.H. ed., Penerbit USM, Penag, pp. 491-496.
Shockett et al. (Jul. 1995) "A Modified Tetracycline-Regulated System Provides Autoregulatory, Inducible Gene Expression in Cultured Cells and Transgenic Mice," *Proc. Nat. Acad. Sci. USA* 92:6522-6526.
Stebbins et al. (2001) "Tetracycline-Inducible Systems for *Drosophila," Proc. Nat. Acad. Sci. USA.* 98:10775-10780.
Stebbins et al. (2001) "Adaptable Doxycycline-Regulated Gene Expression Systems for *Drosophila," Gene* 270:103-111.
Thomas et al. (Mar. 2000) "Insect Population Control Using Dominant, Repressible, Lethal Genetic System," *Science* 287:2474-2476.
Wu et al. (Jun. 2000) "Expression of Highly Controllable Genes in Insect Cells Using a Modified Tetracycline-Regulated Gene Expression System," *J. Biotechnol.* 80(1):75-83.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report Corresponding to International Application No. PCT/GB2004/003263, Mailed May 11, 2004.
Prosecution history for related U.S. Appl. No. 10/562,843, 63 pp.
Prosecution history for related U.S. Appl. No. 10/556,804, 27 pp.
Prosecution history for related U.S. Appl. No. 10/566,448, 142 pp.
Prosecution history for related U.S. Appl. No. 12/278,849, 20 pp.
Examination Report for European patent application serial No. 04743590.4, dated Nov. 14, 2008, 4 pp.
Search Report corresponding to International Application No. PCT/GB2007/000488, parent of the present application.
Written Opinion corresponding to International Application No. PCT/GB2007/000488, parent of the present application.
International Preliminary Report on Patentability, corresponding to International Application No. PCT/GB2007/000488, parent of the present application.
Alphey et al. (2007) "Managing Insecticide Resistance by Mass Release of Engineered Insects" J. Econ. Entomol. 100(5):1642-1649.
Atkinson et al. (2000) "Hermes and Other hAT Elements as Gene Vectors in Insects," In; *Insect Transgenesis: Methods and Applications*, Hadler et al. eds., Boca Raton CRC Press, pp. 219-235.
Cabera et al. (2002) "Expression Pattern of Gal4 Enhancer Trap Insertions Into the bric à brac Locus Generated by P Element Replacement," Genesis 34:62-65.
Carriere and Tabashnik (2001) "Reversing Insect Adaptation to Transgenic Insecticidal Plants," Proc. R. Soc. Lond. B. 268:1475-1480.
Davis et al. (2001) "Engineered Underdominance Allows Efficient and Economical Introgression of Traits into Pest Populations," J. Theor. Biol. 212(1):83-98.
Elick et al. (1997) "Analysis of the Cis-Acting DNA Elements Required for piggyback Transposable Element Excision," Mol. Gen. Genet. 255:605-610.
Fu et al. (2007) "Female-specific insect lethality engineered using alternative splicing", Nature Biotechnology 25(3):353-357.
Funaguma et al. (2005) "The Bmdsx transgene including trimmed introns is sex-specifically spliced in tissues of the silkworm, *Bombyx mori*", Journal of Insect Science (online), 5(17):1-6.
Fussenegger et al. (1997) "Autoregulated Multicistronic Expression Vectors Provide One-Step Cloning of Regulated Product Gene Expression in Mammalian Cells" Biotechnol. Prog. 13:733-740.
Gloor et al. (1991) "Targeted Gene Replacement in *Drosophila* Via P Element-Induced Gap Repair," Science 253:1110-1117.
Gong et al. (2005) "A dominant lethal genetic system for autocidal control of the Mediterranean fruitfly", Nature Biotechnology 23(4):453-456.
Gonzy-Treboul et al. (1995) "Enhancer-Trap Targeting at the Broad-Complex Locus of *Drosophila melanogaster*," Genes Dev. 9:1137-1148.
Gossen and Bujard (2001) "Tetracyclines in the control of gene expression in eukaryotes" Tetracyclines in Biology, Chemistry and Medicine, pp. 139-157.
Handler et al. (2001) "A Current Prospective on Insect Gene Transformation," Insect Biochem. Mol. Biol. 31(2):111-128.
Handler, A. (2002) "Use of piggyback Transposon for Germ-Line Transformation of Insects," Insect Biochem. Mol. Biol. 32:1211-1220.
Heslip et al. (1994) "Targeted Transposition at the vestigial Locus of *Drosophila melanogaster*," Genetics 138:1127-1135.
Horn et al. (2000) "Highly sensitive, fluorescent transformation marker for *Drosophil49a* transgenesis" Dev Genes Evol 210:623-629.
Horn et al50. (2002) "Fluorescent Transformation Markers for Insect Transgenesis," Insect Biochem. Mol. Biol. 32:1221-1235.
Horn et al. (2003) "piggyBac -Based Insertional Metagenesis and Enhancer Detection as a Tool for Functional Insect Genomics," Genetics 163(2):647-661.
Imai, C. (1987) "Control of Insecticide Resistance in a Field Population of Houseflies, *Musca domestica*, by Releasing Susceptible Flies," Res. Popul. Ecol. 29:129-146.
Johnson-Schlitz et al. (1993) "P-Element-Induced Interallelic Gene Conversion of Insertions and Deletions in *Drosophila melanogaster*," Mol Cell Biol. 13:7006-7018.
Lankenau et al. (1996) "Comparison of Targeted-Gene Replacement Frequencies in *Drosophila melanogaster* at the Forked and White Loci," Mol. Cell Biol. 16:3535-3544.
Loukeris et al. (1995) "Introduction of the transposable element Minos into the germ line of *Drosophila melanogaster*" Proc. Natl. Acad. Sci. USA 92:9485-9489.
Munoz et al. (2004) "The AeAct-4 gene is expressed in the developing flight muscles of female *Aedes aegypti*", Insect Molecular Biology 13(5):563-568.
Pane et al. (2002) "The transformer gene in *Ceratitis capitata* provides a genetic basis for selecting and remembering the sexual fate" Development 129:3715-3725.
piggyBac website, http://piggybac.bio.nd.edu/, Mar. 21, 2006, 5 pp.
Robinson et al. (2002) "Mutations and Their Use in Insect Control," Mutation Research 511(2):113-132.
Rong et al. (2000) "Gene Targeting by Homologous Recombination in *Drosophila*," Science 288:2013-2018.
Rong et al. (2001) "A Targeted Gene Knockout in *Drosophila*," Genetics 157:1307-1312.
Russ et al. (1996) "Self-Deleting Retrovirus Vectors for Gene Therapy," J. Virol. 70:4927-4932.
Scali et al. (2005) "Identification of sex-specific transcripts of the *Anopheles gambiae* doublesex gene", Journal of Experimental Biology 208(19):3701-3709.
Sepp et al. (1999) "Conversion of lacZ Enhanced Trap Lines to GAL4 Lines Using Targeted Transposition in *Drosophila melanogaster*," Genetics 151:1093-1101.
Shelton et al. (2000) "Field Tests on Managing Resistance to Bt-Engineered Plants", Nature Biotechnology 18(3):339-342.

(56) References Cited

OTHER PUBLICATIONS

Steiner et al. (1995) "Homologous Recombination as the Main Mechanism for DNA Integration and Cause of Rearrangements in the Filamentous Ascomycete *Ashbya gossypii*," Genetics 140:973-987.
Wobus et al. (1990) "A New Transposable Element in *Chironomus thummi*," Mol. General Genet. 222:311-316.
Wool and Manheim (1980) "Genetically-Induced Susceptibility to Malathion in *Tribolium castaneum* Despite Selection for Resistance," Ent. Exp. & Appl. 28:183-190.
Prosecution history for related U.S. Appl. No. 10/148,041, 64 pp.
Prosecution history for related U.S. Appl. No. 11/733,737, 175 pp.
EP First Office Action, dated Feb. 16, 2012, in European Patent Application No. 04743590.4, a corresponding application, 8 pp.
Fussenegger et al. (1998) "Regulated Multicistronic Expression Technology for Mammalian Metabolic Engineering," Cytotechnology 28:111-125.
Fux et al. (2003) "Novel Macrolide-Adjustable Bidirectional Expression Modules for Coordinated Expression of Two Different Transgenes in Mice," J Gene Medicine 5:1067-1079.
Schwechheimer et al. (2000) "Transactivation of a Target Gene Through Feedforward Loop Activation in Plants," Funct Integr Genomics 1:35-43.
Adelman et al., "Formation and loss of large, unstable tandem arrays of the piggyBac transposable element in the yellow fever mosquito, Aedes aegypti," Transgenic Res (2004) 13(5):411-425.
Alphey et al., "Modeling resistance to genetic control of insects," Journal of Theoretical Biology (2011) 270:42-55.
Atkinson et al., "Genetic transformation systems in insects," Annu Rev Entomol (2001) 46:317-346.
Bello et al., "Spatial and temporal targeting of gene expression in Drosophila by means of a tetracycline-dependent transactivator system," Development (1998) 125(12):2193-2202.
Beullens et al., "The isolation of novel inhibitory polypeptides of protein phosphatase 1 from bovine thymus nuclei," J Biol Chem (1992) 267(23):16538-16544.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Boudrez et al., "Identification of MYPT1 and NIPP1 as subunits of protein phosphatase 1 in rat liver cytosol," FEBS Letters 455 (1999) 175-178.
Burcin et al., "A regulatory system for target gene expression," Frontiers in Biosc. (1998) 3:c1-7.
Communication pursuant to Article 96(2) EPC for EP 00979774.7, mailed Mar. 8, 2006, 4 pages.
Communication pursuant to Article 96(2) EPC for EP 00979774.7, mailed Aug. 2, 2005, 4 pages.
Communication pursuant to Article 96(2) EPC for EP 00979774.7, mailed Oct. 4, 2004, 4 pages.
Communication pursuant to Article 96(2) EPC for EP 00979774.7, mailed Nov. 28, 2003, 5 pages.
Communication under Rule 51(4) EPC, directed to EP 00979774.7, mailed May 9, 2007, 4 pages.
Decision on Further Processing for EP 00979774.7, mailed Jan. 29, 2007, 1 page.
Deng et al., "A targeted gene silencing technique shows that *Drosophila* myosin VI is required for egg chamber and imaginal disc morphogenesis," J Cell Science (1999) 112:3677-3690.
Devault et al., "Biotechnology and new integrated pest management approaches," Nature Biotechnology (1996) 14:46-49.
Egloff et al., "Structural basis for the recognition of regulatory subunits by the catalytic subunit of protein phosphatase 1," EMBO J (1997) 16(8):1876-1887.
Examination Report for NZ 519175, mailed Jul. 9, 2002, 2 pages.
Examination Report for NZ 519175, mailed Nov. 28, 2003, 1 page.
Fryxell et al., "Autocidal biological control: a general strategy for insect control based on genetic transformation with a highly conserved gene," J Econ Entomol (1995) 88(5):1221-1232.
Fu et al., "Female-specific flightless phenotype for mosquito control," PNAS (2010) 107(10):4550-4554.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Golovnin et al., "The su(Hw) insulator can disrupt enhancer-promoter interactions when located more than 20 kilobases away from the Drosophila achaete-scute complex," Mol Cell Biol (1999) 19(5):3443-3456.
Harris et al., "Field performance of engineered male mosquitoes," Nature Biotechnology (2011) 29(11):1034-1039.
Inoue et al., "Binding of the *Drosophila Sex-lethal* gene product to the alternative splice site of *transformer* primary transcript," Nature (1990) 344:461-463.
International Search Report for PCT/GB00/04541, mailed Dec. 5, 2001.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Krafsur, "Bionomics of the face fly, Musca autumnalis," Annu Rev Entomol (1997) 42:503-523 (Abstract).
Namciu et al., "Human matrix attachment regions insulate transgene expression from chromosomal position effects in Drosophila melanogaster," Mol Cell Biol (1998) 18(4):2382-2391.
Nitasaka et al., "Repressor of P elements in Drosophila melanogaster: Cytotype determination by a defective P element carrying only open reading frames 0 through 2," Proc Natl Acad Sci USA (1987) 84(21):7605-7608.
O'Brochta et al., "Gene vector and transposable element behavior in mosquitos," J Exp Biol (2003) 206(Pt 21):3823-3834.
Office Action in U.S. Appl. No. 10/556,804, mailed 12 May 2010, 8 pages.
Response to Office Action for U.S. Appl. No. 10/556,804, filed Nov. 12, 2010, 12 pages.
Office Action in U.S. Appl. No. 10/556,804, mailed Feb. 1, 2011, 4 pages.
Response to Office Action for U.S. Appl. No. 10/556,804, filed Mar. 25, 2011, 9 pages.
Office Action in U.S. Appl. No. 10/562,843, mailed Nov. 12, 2008, 6 pages.
Response for U.S. Appl. No. 10/562,843, filed Feb. 24, 2009, 13 pages.
Office Action in U.S. Appl. No. 10/562,843, mailed Jun. 9, 2009, 5 pages.
Response for U.S. Appl. No. 10/562,843, filed Oct. 5, 2009, 10 pages.
Final Office Action for U.S. Appl. No. 10/562,843, mailed Feb. 3, 2010, 5 pages.
Office Action in U.S. Appl. No. 10/562,843, mailed Jul. 30, 2010, 7 pages.
Response for U.S. Appl. No. 10/562,843, filed Nov. 30, 2010, 8 pages.
Office Action in U.S. Appl. No. 10/562,843, mailed Feb. 16, 2011, 4 pages.
Response to Office Action in U.S. Appl. No. 10/562,843, filed Jun. 16, 2011, 9 pages.
Final Office Action in U.S. Appl. No. 10/562,843, filed Aug. 25, 2011, 5 pages.
Response to Final Office Action in U.S. Appl. No. 10/562,843, filed Nov. 21, 2011, 6 pages.
Office Action in U.S. Appl. No. 12/278,849, dated Oct. 10, 2012, 12 pages.
Response to Office Action in U.S. Appl. No. 12/278,849, dated Apr. 10, 2013, 19 pages.
Final Office Action in U.S. Appl. No. 12/278,849, dated Jun. 6, 2013, 24 pages.
Office Action in U.S. Appl. No. 12/278,849, dated Aug. 9, 2013, 22 pages.

(56) References Cited

OTHER PUBLICATIONS

Response to Office Action in U.S. Appl. No. 12/278,849, dated Jan. 9, 2014, 21 pages.
Office Action in U.S. Appl. No. 12/278,849 dated Mar. 17, 2014, 24 pages.
Office Action for U.S. Appl. No. 13/942,601, mailed Nov. 4, 2013, 16 pages.
Response to Office Action for U.S. Appl. No. 13/942,601, dated Feb. 4, 2014, 45 pages.
Office Action for AU 17165/01, mailed Jul. 13, 2004, 3 pages.
Office Action for CN 00818682.0, fax dated Feb. 4, 2005, 7 pages.
Office Action for IL 149885, dated Apr. 26, 2007, 4 pages.
Oxitec Nov. 2011 Newsletter, http://www.oxitec.com/our-news/newsletters/november-2011-newsletter/, downloaded Dec. 13, 2011, 6 pages.
Parker et al., "Functional interaction between nuclear inhibitor of protein phosphatase type 1 (NIPP1) and protein phosphatase type 1 (PP1) in Drosophila: consequences of over-expression of NIPP1 in flies and suppression by co-expression of PP1," Biochem J (2002) 368:789-797.
Phuc et al., "Late-acting dominant lethal genetic systems and mosquito control," BMC Biology (2007) 5:11, 11 pages.
Rejection for CN 00818682.0, fax dated Jan. 26, 2006, 4 pages.
Request for Further Processing for EP 00979774.7, filed Jan. 4, 2007, 4 pages.
Response to Communication pursuant to Article 96(2) EPC for EP 00979774.7, filed Feb. 13, 2006, 8 pages.
Response to Communication for EP 00979774.7, filed Apr. 14, 2005, 7 pages.
Response to Communication for EP 00979774.7, filed Sep. 20, 2004, 8 pages.
Restriction Requirement for U.S. Appl. No. 10/556,804, mailed May 28, 2009, 5 pages.
Response to Restriction Requirement for U.S. Appl. No. 10/556,804, filed Jun. 29, 2009, 2 pages.
Restriction Requirement for U.S. Appl. No. 10/562,843, mailed Jun. 12, 2008, 6 pages.
Response to Restriction Requirement for U.S. Appl. No. 10/562,843, filed Jun. 27, 2008, 2 pages.
Restriction Requirement for U.S. Appl. No. 12/278,849, mailed May 28, 2010, 7 pages.
Response to Restriction Requirement for U.S. Appl. No. 12/278,849, filed Sep. 28, 2010, 13 pages.
Ronaldson et al., "Two independent cis-acting elements regulate the sex- and tissue-specific expression of yp3 in Drosophila melanogaster," Genet Res. (1995) 66(1):9-17.
Second Office Action for AU 17165/01, mailed Mar. 21, 2006, 2 pages.
Second Office Action for CN 00818682.0, dated Jul. 28, 2006, 4 pages.
Simmons et al., "Field Performance of a Genetically Engineered Strain of Pink Bollworm," PLoS ONE (2011) 6(9):1-11.
Sondergaard et al., "Nutritional response in a Drosophila yolk protein gene promoter," Mol Gen Genet (1995) 248(1):25-32.
Spradling et al., "Transposition of cloned P elements into Drosophila germ line chromosomes," Science (1982) 218(4570):341-347.
Stadtfeld et al., "Without a trace? PiggyBac-ing toward pluripotency," Nat Methods (2009) 6(5):329-330.
Summary of Office Action for MX PA/a/2002/005337, mailed Jan. 3, 2007, 2 pages.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the Drosophila slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Woltjen et al., "piggyBac transposition reprograms fibroblasts to induced pluripotent stem cells," Nature (2009) 458(7239):766-770.
Restriction Requirement for U.S. Appl. No. 10/566,448, mailed Jan. 9, 2008, 5 pages.
Response to Restriction Requirement for U.S. Appl. No. 10/566,448, filed Feb. 8, 2008, 9 pages.
Restriction Requirement for U.S. Appl. No. 10/566,448, mailed Aug. 29, 2008, 7 pages.
Response to Restriction Requirement for U.S. Appl. No. 10/566,448, filed Dec. 1, 2008, 9 pages.
Non-Final Office Action for U.S. Appl. No. 10/566,448, mailed Jan. 7, 2009, 14 pages.
Response to Non-Final Office Action for U.S. Appl. No. 10/566,448, filed Jul. 7, 2009, 15 pages.
Response to Non-Final Office Action for U.S. Appl. No. 10/566,448, filed Aug. 28, 2009, 15 pages.
Final Office Action for U.S. Appl. No. 10/566,448, mailed Nov. 10, 2009, 18 pages.
Request for Continued Examination for U.S. Appl. No. 10/566,448, filed Feb. 25, 2010, 21 pages.
Non-Final Office Action for U.S. Appl. No. 10/566,448, mailed Apr. 27, 2010, 12 pages.
Response to Non-Final Office Action for U.S. Appl. No. 10/566,448, filed Oct. 27, 2010, 20 pages.
Final Office Action for U.S. Appl. No. 10/566,448, mailed Feb. 2, 2011, 13 pages.
Request for Continued Examination for U.S. Appl. No. 10/566,448, filed Aug. 2, 2011, 23 pages.
Non-Final Office Action for U.S. Appl. No. 10/566,448, mailed Nov. 22, 2013, 24 pages.
Response to Non-Final Office Action for U.S. Appl. No. 10/566,448, filed Apr. 22, 2014, 17 pages.
Final Office Action for U.S. Appl. No. 10/566,448, mailedl Aug. 4, 2014, 24 pages.
Response to Final Office Action for U.S. Appl. No. 10/566,448, filed Dec. 15, 2014, 9 pages.
Notice of Appeal for U.S. Appl. No. 10/566,448, filed Feb. 18, 2015, 4 pages.
Notice of Allowance for U.S. Appl. No. 10/566,448, mailed Mar. 19, 2015, 10 pages.
Communication pursuant to Article 94(3) EPC for EP 07 712 717.3, mailed Jul. 11, 2014, 8 pages.
Alignment of SEQ ID No. 22 of D1 (WO 2005/012534) with tTAV, Jul. 4, 2014.
Restriction Requirement for U.S. Appl. No. 10/148,041, mailed Mar. 10, 2005, 5 pages.
Response to Restriction Requirement for U.S. Appl. No. 10/148,041, filed Apr. 13, 2005, 10 pages.
Office Action for U.S. Appl. No. 10/148,041, mailed Jul. 1, 2005, 14 pages.
Response to Office Action for U.S. Appl. No. 10/148,041, filed Dec. 5, 2005, 11 pages.
Final Office Action for U.S. Appl. No. 10/148,041, mailed Mar. 7, 2006, 9 pages.
Request for Continued Examination for U.S. Appl. No. 10/148,041, filed Sep. 11, 2006, 8 pages.
Office Action for U.S. Appl. No. 10/148,041, mailed Oct. 10, 2006, 8 pages.
Office Action for U.S. Appl. No. 11/733,737, mailed Apr. 10, 2008, 8 pages.

(56) References Cited

OTHER PUBLICATIONS

Response to Office Action for U.S. Appl. No. 11/733,737, filed Oct. 10, 2008, 8 pages.
Restriction Requirement for U.S. Appl. No. 11/733,737, mailed Dec. 31, 2008, 9 pages.
Response to Restriction Requirement for U.S. Appl. No. 11/733,737, filed Jan. 26, 2009, 8 pages.
Final Office Action for U.S. Appl. No. 11/733,737, mailed Apr. 17, 2009, 16 pages.
Response to Final Office Action for U.S. Appl. No. 11/733,737, filed Jul. 17, 2009, 26 pages.
Advisory Action for U.S. Appl. No. 11/733,737, mailed Aug. 5, 2009, 4 pages.
Request for Continued Examination for U.S. Appl. No. 11/733,737, filed Aug. 14, 2009, 1 page.
Office Action for U.S. Appl. No. 11/733,737, mailed Oct. 1, 2009, 21 pages.
Response to Office Action for U.S. Appl. No. 11/733,737, filed Jan. 29, 2010, 23 pages.
Final Office Action for U.S. Appl. No. 11/733,737, mailed Aug. 4, 2010, 18 pages.
Response to Final Office Action for U.S. Appl. No. 11/733,737, filed Dec. 6, 2010, 26 pages.
Office Action for U.S. Appl. No. 11/733,737, mailed Feb. 8, 2011, 6 pages.
Response to Office Action for U.S. Appl. No. 11/733,737, filed Feb. 18, 2011, 11 pages.
Office Action for U.S. Appl. No. 11/733,737, mailed Jun. 28, 2011, 14 pages.
Response to Office Action for U.S. Appl. No. 11/733,737, filed Oct. 28, 2011, 27 pages.
Office Action for U.S. Appl. No. 11/733,737, mailed Mar. 27, 2012, 17 pages.
Response to Office Action for U.S. Appl. No. 11/733,737, filed Aug. 9, 2012, 24 pages.
Final Office Action for U.S. Appl. No. 11/733,737, mailed Jan. 7, 2013, 26 pages.
Response to Final Office Action for U.S. Appl. No. 11/733,737, filed Apr. 8, 2013, 25 pages.
Advisory Action for U.S. Appl. No. 11/733,737, mailed Jun. 3, 2013, 7 pages.
Notice of Appeal for U.S. Appl. No. 11/733,737, filed Jul. 3, 2013, 1 page.
Appeal Brief for U.S. Appl. No. 11/733,737, filed Feb. 3, 2014, 40 pages.
Examiner's Answer to Appeal Brief for U.S. Appl. No. 11/733/737, mailed Jul. 18, 2014, 12 pages.
Reply Brief and Request for Oral Hearing for U.S. Appl. No. 11/733,737, filed Sep. 18, 2014, 16 pages.
Final Office Action for U.S. Appl. No. 13/942,601, mailed Jul. 31, 2014, 23 pages.
Notice of Appeal for U.S. Appl. No. 13/942,601, filed Feb. 2, 2015, 1 page.
Notice of Allowance for U.S. Appl. No. 13/942,601, mailed Apr. 10, 2015, 11 pages.
Notice of Appeal for U.S. Appl. No. 12/278,849, filed Jun. 17, 2014, 1 page.
Appeal Brief for U.S. Appl. No. 12/278,849, filed Oct. 16, 2014, 31 pages.
Office Action for U.S. Appl. No. 12/278,849, mailed Dec. 5, 2014, 15 pages.
Office Action for U.S. Appl. No. 12/278,849, mailed Mar. 10, 2015, 18 pages.
International Preliminary Examination Report for PCT/GB00/04541, mailed Apr. 4, 2002, 2 pages.
Written Opinion for PCT/GB2004/002021, received Oct. 4, 2004, 5 pages.
International Search Report for PCT/GB2004/002021, mailed Oct. 6, 2004, 3 pages.
International Preliminary Report on Patentability for PCT/GB2004/002021, issued Nov. 18, 2005, 6 pages.
International Search Report for PCT/GB2004/002869, mailed Jan. 11, 2005, 5 pages.
Written Opinion for PCT/GB2004/002869, received Jan. 12, 2005, 8 pages.
International Preliminary Report on Patentability for PCT/GB2004/002869, issued Jan. 3, 2006, 9 pages.
Written Opinion for PCT/GB2004/003263, received Nov. 5, 2004, 5 pages.
International Preliminary Report on Patentability for PCT/GB2004/003263, issued Jan. 30, 2006, 6 pages.
Further Search Report for GB 9928181.8, mailed Apr. 30, 2001.

* cited by examiner

Transactivator coding region:
A + C = transactivator
B = contains stop codon
or
A = DNA binding domain
B = Repression domain
C = Activation domain Diagram of tetO$_7$-tTA region of pJY2004

Schematic diagram of the LA513 transposon

Potential PCR products generated:

1. If intron is not excised → ~1550 bp
2. If intron is spliced in male form (M1 or M2)→ ~600 bp
3. If intron is spliced in female form → ~200 bp

```
Native: CGTAGATTTG¦GT...intron...AG¦GTGAAGGCTC
LA1188: CTACTG¦GCACGT...intron...AG¦GTGAAGAATA
LA3077: AACGAAGTTG¦GT...intron...AG¦GTATTGAGGG
LA3097: AGCCACCATG¦GT...intron...AG¦GTCAGCCGCC
```

Figure 33

| | NT Males | NT Females | TET Males | TET Females |
|---|---|---|---|---|
| 3077A | 111 | 32 | 73 | 44 |
| 3077B | 314 | 157 | 132 | 121 |
| 3077C | 161 | 116 | 60 | 84 |
| 3077D | 445 | 85 | 194 | 190 |
| | | | | |
| 3097A | 179 | 5 | 89 | 90 |
| 3097B | 440 | 0 | 59 | 27 |
| 3097C | 172 | 0 | 46 | 44 |
| | | | | |
| 3233A | 457 | 1 | 79 | 58 |
| 3233B | 171 | 0 | 14 | 13 |
| | | | | |
| 3014;1217 | 136 | 0 | 48 | 10 |
| 3166;1217 | 64 | 0 | 5 | 7 |

Figure 35

| | NT males | NTfemales | TET males | TET females |
|---|---|---|---|---|
| 3097A | 136 | 0 | 21 | 19 |
| 3097B | 295 | 11 | 14 | 11 |
| 3097C | 96 | 12 | 22 | 21 |
| 3097D | 103 | 15 | 82 | 67 |
| 3233A | 78 | 6 | 32 | 5 |

Figure 38

SEQUENCE LISTING

```
<160> NUMBER OF SEQ ID NOS: 106

<210> SEQ ID NO 1
<211> LENGTH: 44
<212> TYPE: DNA
<213> ORGANISM: Drosophila sp.

<400> SEQUENCE: 1

cacagcgcat gatgagcaca ttaacaaaat gtagtaaaat agga                       44


<210> SEQ ID NO 2
<211> LENGTH: 44
<212> TYPE: DNA
<213> ORGANISM: Drosophila sp.

<400> SEQUENCE: 2

gtttcgataa atattgctat ttaaaatgct tattttcaat gcta                       44


<210> SEQ ID NO 3
<211> LENGTH: 44
<212> TYPE: DNA
<213> ORGANISM: Drosophila sp.

<400> SEQUENCE: 3

tttgttttct aacgttaaag ttaaagagag tccagccaca tttt                       44


<210> SEQ ID NO 4
<211> LENGTH: 21
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 4

acgcgagagg tgaaattctt g                                                21


<210> SEQ ID NO 5
<211> LENGTH: 23
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 5

gaaaacatct ttggcaaatg ctt                                              23
```

<210> SEQ ID NO 6
<211> LENGTH: 16
<212> TYPE: DNA
<213> ORGANISM: Artificial Sequence
<220> FEATURE:
<223> OTHER INFORMATION: Synthetic construct, nucleotide portion of TaqMan MGB probe

<400> SEQUENCE: 6
ccgtcgtaag actaac 16

<210> SEQ ID NO 7
<211> LENGTH: 17
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 7
catgccgacg cgctaga 17

<210> SEQ ID NO 8
<211> LENGTH: 26
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 8
gtaaacatct gctcaaactc gaagtc 26

<210> SEQ ID NO 9
<211> LENGTH: 18
<212> TYPE: DNA
<213> ORGANISM: Artificial Sequence
<220> FEATURE:
<223> OTHER INFORMATION: Synthetic construct, nucleotide portion of TaqMan MGB probe

<400> SEQUENCE: 9
tcgatctgga catgttgg 18

<210> SEQ ID NO 10
<211> LENGTH: 25
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 10
gccctcgatg gtagacccgt aattg 25

<210> SEQ ID NO 11
<211> LENGTH: 27
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 11
gctaaacaat ctgcaggtac cctggcg 27

<210> SEQ ID NO 12
<211> LENGTH: 20
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 12
cctgccagga ctcgccttcc 20

<210> SEQ ID NO 13
<211> LENGTH: 22
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 13
gtcatcaact ccgcgttgga gc 22

<210> SEQ ID NO 14
<211> LENGTH: 2556
<212> TYPE: DNA
<213> ORGANISM: Artificial Sequence
<220> FEATURE:
<223> OTHER INFORMATION: Synthetic construct, Sequence of the tetO7-tTA region of JY2004-tTA

<400> SEQUENCE: 14
gcggccgcat agtcgacatt tcgagtttac cactccctat cagtgataga gaaaagtgaa 60
agtcgagttt accactccct atcagtgata gagaaaagtg aaagtcgagt ttaccactcc 120
ctatcagtga tagagaaaag tgaaagtcga gtttaccact ccctatcagt gatagagaaa 180
agtgaaagtc gagtttacca ctccctatca gtgatagaga aaagtgaaag tcgagtttac 240
cactccctat cagtgataga gaaaagtgaa agtcgagttt accactccct atcagtgata 300
gagaaaagtg aaagtcgagc tcggtacccg ggtcgaggta ggcgtgtacg gtgggaggcc 360
tatataagca gagctcgttt agtgaaccgt cagatcgcct ggagacgcca tccacgctgt 420
tttgacctcc atagaagaca ccgggaccga tccagcctcc gcggccccga attcgagctc 480
ggtacccggg gatccccgct cgagctgaat agggaattgg gaattggagc agaggtgggt 540
tcttcgcatt acactgttcg ccacaatctt gtttattcat tcgccttgca ggttgccacc 600
atggaattga gattagataa aagtaaagtg attaacagcg cattagagct gcttaatgag 660
gtcggaatcg aaggtttaac aacccgtaaa ctcgcccaga agctaggtgt agagcagcct 720
acattgtatt ggcatgtaaa aaataagcgg gctttgctcg acgccttagc cattgagatg 780
ttagataggc accatactca cttttgccct ttagaagggg aaagctggca agatttttta 840
cgtaataacg ctaaaagttt tagatgtgct ttactaagtc atcgcgatgg agcaaaagta 900
catttaggta cacggcctac agaaaaacag tatgaaactc tcgaaaatca attagccttt 960
ttatgccaac aaggtttttc actagagaat gcattatatg cactcagcgc tgtggggcat 1020
tttactttag gttgcgtatt ggaagatcaa gagcatcaag tcgctaaaga agaaagggaa 1080
acacctacta ctgatagtat gccgccatta ttacgacaag ctatcgaatt atttgatcac 1140
caaggtgcag agccagcctt cttattcggc cttgaattga tcatatgcgg attagaaaaa 1200
caacttaaat gtgaaagtgg gtccgcgtac agccgcgcgc gtacgaaaaa caattacggg 1260

```
tctaccatcg agggcctgct cgatctcccg gacgacgacg cccccgaaga ggcggggctg   1320
gcggctccgc gcctgtcctt tctccccgcg ggacacacgc gcagactgtc gacggccccc   1380
ccgaccgatg tcagcctggg ggacgagctc cacttagacg gcgaggacgt ggcgatggcg   1440
catgccgacg cgctagacga tttcgatctg gacatgttgg gggacgggga ttccccgggt   1500
ccgggattta ccccccacga ctccgccccc tacggcgctc tggatatggc cgacttcgag   1560
tttgagcaga tgtttaccga tgcccttgga attgacgagt acggtgggta gtgaaacgcg   1620
tctagagctg agaacttcag ggtgagtttg gggacccttg attgttcttt ctttttcgct   1680
attgtaaaat tcatgttata tggagggggc aaagttttca gggtgttgtt tagaatggga   1740
agatgtccct tgtatcacca tggaccctca tgataatttt gtttctttca ctttctactc   1800
tgttgacaac cattgtctcc tcttattttc ttttcatttt ctgtaacttt ttcgttaaac   1860
tttagcttgc atttgtaacg aatttttaaa ttcacttttg tttatttgtc agattgtaag   1920
tactttctct aatcactttt ttttcaaggc aatcagggta tattatattg tacttcagca   1980
cagttttaga gaacaattgt tataattaaa tgataaggta gaatatttct gcatataaat   2040
tctggctggc gtggaaatat tcttattggt agaaacaact acaccctggt catcatcctg   2100
cctttctctt tatggttaca atgatataca ctgtttgaga tgaggataaa atactctgag   2160
tccaaaccgg gcccctctgc taaccatgtt catgccttct tctctttcct acagctcctg   2220
ggcaacgtgc tggttgttgt gctgtctcat cattttggca aagaattcac tcctcaggtg   2280
caggctgcct atcagaaggt ggtggctggt gtggccaatg ccctggctca caaataccac   2340
tgagatcttt ttccctctgc caaaaattat ggggacatca tgaagcccct tgagcatctg   2400
acttctggct aataaaggaa atttattttc attgcaatag tgtgttggaa ttttttgtgt   2460
ctctcactcg gaaggacata tgggagggca aatcatttaa aacatcagaa tgagtatttg   2520
gtttagagtt tggcaacata tgcccatagc ggccgc                             2556
```

<210> SEQ ID NO 15
<211> LENGTH: 12087
<212> TYPE: DNA
<213> ORGANISM: Artificial Sequence
<220> FEATURE:
<223> OTHER INFORMATION: Synthetic construct, plasmid pP[Casper-Act5C-tTA]

<400> SEQUENCE: 15

```
gatccatgag caattagcat gaacgttctg aaaagcgcgt ttagctctcc actacttaca     60
catattctat gctgcaatat tgaaaatcta ataaacaaaa ctaatgtaca ttaattcttc    120
agttttgaat atccttctcc tgactttctt atttagaatt aatataatac tgcatacatt    180
aatactgtaa atatgataag tacctgcaaa acactgcagc tcaagtctta atgaggttct    240
gcgatagctt agcataatta gtaacttatc gcgcagaatt ccctaatgtt cccgacctac    300
atgtacttct gatagttgcc gaggtcaaat gttgttgtat ttgtattata cctcaatatt    360
ggtatattca atatctaata gtacccaatt caattgcaaa gatagtcatt aaaaaaacct    420
aaatcacttg caaattgact tttctgccgg aaaagcaacc ttgacacaca aagttaatta    480
gtttatctgg aagtcatgtg agaaatttgt aaataaaatt tttcgcagta atttaagtgg    540
gcctaatccc ttttaagcat cttggtttta cgatgacacc gcaataaggt acaactttat    600
attgtttttg caatcagctt gagtctttat taggcatcag tctttctctc taagtttctt    660
cgtgcaataa atgaggttcc aaactccgta gatttttcct tctttgttga atccagatcc    720
```

-continued

```
tgcaaagaaa aaagagcaaa cccctaggtc tgtccaggaa tgtattttcg tgtttgtcga    780
tcgaccatgg tctcgagagg ccttgcagcc aagctttgcg tactcgcaaa ttattaaaaa    840
taaaacttta aaaataattt cgtctaatta atattatgag ttaattcaaa ccccacggac    900
atgctaaggg ttaatcaaca atcatatcgc tgtctcactc agactcaata cgacactcag    960
aatactattc ctttcactcg cacttattgc aagcatacgt taagtggatg tctcttgccg   1020
acgggaccac cttatgttat ttcatcatgg tctggccatt ctcatcgtga gcttccgggt   1080
gctcgcatat ctggctctaa gacttcgggc ccgacgcaag gagtagccga catatatccg   1140
aaataactgc ttgttttttt ttttaccatt attaccatcg tgtttactgt ttattgcccc   1200
ctcaaaaagc taatgtaatt atatttgtgc caataaaaac aagatatgac ctatagaata   1260
caagtatttc cccttcgaac atccccacaa gtagactttg gatttgtctt ctaaccaaaa   1320
gacttacaca cctgcatacc ttacatcaaa aactcgttta tcgctacata aaacaccggg   1380
atatattttt tatatacata cttttcaaat cgcgcgccct cttcataatt cacctccacc   1440
acaccacgtt tcgtagttgc tctttcgctg tctcccaccc gctctccgca acacattcac   1500
cttttgttcg acgaccttgg agcgactgtc gttagttccg cgcgattcgg tgcggtattt   1560
cacaccgcat atggtgcact ctcagtacaa tctgctctga tgccgcatag ttaagccagc   1620
cccgacaccc gccaacaccc gctgacgcgc cctgacgggc ttgtctgctc ccggcatccg   1680
cttacagaca agctgtgacc gtctccggga gctgcatgtg tcagaggttt tcaccgtcat   1740
caccgaaacg cgcgagacga aagggcctcg tgatacgcct atttttatag gttaatgtca   1800
tgataataat ggtttcttag acgtcaggtg gcacttttcg gggaaatgtg cgcggaaccc   1860
ctatttgttt atttttctaa atacattcaa atatgtatcc gctcatgaga caataaccct   1920
gataaatgct tcaataatat tgaaaaagga agagtatgag tattcaacat ttccgtgtcg   1980
cccttattcc cttttttgcg gcattttgcc ttcctgtttt tgctcaccca gaaacgctgg   2040
tgaaagtaaa agatgctgaa gatcagttgg gtgcacgagt gggttacatc gaactggatc   2100
tcaacagcgg taagatcctt gagagttttc gccccgaaga acgttttcca atgatgagca   2160
cttttaaagt tctgctatgt ggcgcggtat tatcccgtat tgacgccggg caagagcaac   2220
tcggtcgccg catacactat tctcagaatg acttggttga gtactcacca gtcacagaaa   2280
agcatcttac ggatggcatg acagtaagag aattatgcag tgctgccata accatgagtg   2340
ataacactgc ggccaactta cttctgacaa cgatcggagg accgaaggag ctaaccgctt   2400
ttttgcacaa catgggggat catgtaactc gccttgatcg ttgggaaccg gagctgaatg   2460
aagccatacc aaacgacgag cgtgacacca cgatgcctgt agcaatggca acaacgttgc   2520
gcaaactatt aactggcgaa ctacttactc tagcttcccg gcaacaatta atagactgga   2580
tggaggcgga taaagttgca ggaccacttc tgcgctcggc ccttccggct ggctggttta   2640
ttgctgataa atctggagcc ggtgagcgtg ggtctcgcgg tatcattgca gcactggggc   2700
cagatggtaa gccctcccgt atcgtagtta tctacacgac ggggagtcag gcaactatgg   2760
atgaacgaaa tagacagatc gctgagatag gtgcctcact gattaagcat tggtaactgt   2820
cagaccaagt ttactcatat atactttaga ttgatttaaa acttcatttt taatttaaaa   2880
ggatctaggt gaagatcctt tttgataatc tcatgaccaa aatcccttaa cgtgagtttt   2940
cgttccactg agcgtcagac cccgtagaaa agatcaaagg atcttcttga gatccttttt   3000
ttctgcgcgt aatctgctgc ttgcaaacaa aaaaaccacc gctaccagcg gtggtttgtt   3060
tgccggatca agagctacca actctttttc cgaaggtaac tggcttcagc agagcgcaga   3120
```

```
taccaaatac tgtccttcta gtgtagccgt agttaggcca ccacttcaag aactctgtag   3180
caccgcctac atacctcgct ctgctaatcc tgttaccagt ggctgctgcc agtggcgata   3240
agtcgtgtct taccgggttg gactcaagac gatagttacc ggataaggcg cagcggtcgg   3300
gctgaacggg gggttcgtgc acacagccca gcttggagcg aacgacctac accgaactga   3360
gatacctaca gcgtgagcta tgagaaagcg ccacgcttcc cgaagggaga aaggcggaca   3420
ggtatccggt aagcggcagg gtcggaacag gagagcgcac gagggagctt ccagggggaa   3480
acgcctggta tctttatagt cctgtcgggt ttcgccacct ctgacttgag cgtcgatttt   3540
tgtgatgctc gtcagggggg cggagcctat ggaaaaacgc cttcttcttg aactcgggct   3600
cggtgccagt atacctcaaa tggttgtcgt acctctcatg gttccgttac gccaacgagg   3660
gtctgctgat taaccaatgg gcggacgtgg agccgggcga aattagctgc acatcgtcga   3720
acaccacgtg ccccagttcg ggcaaggtca tcctggagac gcttaacttc tccgccgccg   3780
atctgccgct ggactacgtg ggtctggccc atgatgaaat aacataaggt ggtcccgtcg   3840
aaagccgaag cttaccgaag tatacactta aattcagtgc acgtttgctt gttgagagga   3900
aaggttgtgt gcggacgaat ttttttttga aaacattaac ccttacgtgg aataaaaaaa   3960
aatgaaatat tgcaaatttt gctgcaaagc tgtgactgga gtaaaattaa ttcacgtgcc   4020
gaagtgtgct attaagagaa aattgtggga gcagagcctt gggtgcagcc ttggtgaaaa   4080
ctcccaaatt tgtgataccc actttaatga ttcgcagtgg aaggctgcac ctgcaaaagg   4140
tcagacattt aaaaggaggc gactcaacgc agatgccgta cctagtaaag tgatagagcc   4200
tgaaccagaa aagataaaag aaggctatac cagtgggagt acacaaacag agtaagtttg   4260
aatagtaaaa aaaatcattt atgtaaacaa taacgtgact gtgcgttagg tcctgttcat   4320
tgtttaatga aaataagagc ttgagggaaa aaattcgtac tttggagtac gaaatgcgtc   4380
gtttagagca gcagccgaat taattctagt tccagtgaaa tccaagcatt ttctaaatta   4440
aatgtattct tattattata gttgttattt ttgatatata taaacaacac tattatgccc   4500
accatttttt tgagatgcat ctacacaagg aacaaacact ggatgtcact ttcagttcaa   4560
attgtaacgc taatcactcc gaacaggtca caaaaaatta ccttaaaaag tcataatatt   4620
aaattagaat aaatatagct gtgagggaaa tatatacaaa tatattggag caaataaatt   4680
gtacatacaa atatttatta ctaatttcta ttgagacgaa atgaaccact cggaaccatt   4740
tgagcgaacc gaatcgcgcg gaactaacga cagtcgctcc aaggtcgtcg aacaaaaggt   4800
gaatgtgttg cggagagcgg gtgggagaca gcgaaagagc aactacgaaa cgtggtgtgg   4860
tggaggtgaa ttatgaagag ggcgcgcgat ttgaaaagta tgtatataaa aaatatatcc   4920
cggtgtttta tgtagcgata aacgagtttt tgatgtaagg tatgcaggtg tgtaagtctt   4980
ttggttagaa gacaaatcca aagtctactt gtggggatgt tcgaagggga aatacttgta   5040
ttctataggt catatcttgt ttttattggc acaaatataa ttacattagc tttttgaggg   5100
ggcaataaac agtaaacacg atggtaataa tggtaaaaaa aaaaaacaag cagttatttc   5160
ggatatatgt cggctactcc ttgcgtcggg cccgaagtct tagagccaga tatgcgagca   5220
cccggaagct cacgatgaga atggccagac ccacgtagtc cagcggcaga tcggcggcgg   5280
agaagttaag cgtctccagg atgaccttgc ccgaactggg gcacgtggtg ttcgacgatg   5340
tgcagctaat ttcgcccggc tccacgtccg cccattggtt aatcagcaga ccctcgttgg   5400
cgtaacggaa ccatgagagg tacgacaacc atttgaggta tactggcacc gagcccgagt   5460
```

-continued

```
tcaagaagaa gccgccaaag agcaggaatg gtatgataac cggcggaccc acagacagcg   5520
ccatcgaggt cgaggagctg gcgcaggata ttagatatcc gaaggacgtt gacacattgg   5580
ccaccagagt gaccagcgcc aggcagttga agaagtgcag cactccggcc cgcagtccga   5640
tcatcggata ggcaatcgcc gtgaagacca gtggcactgt gagaaaaagc ggcaattcgg   5700
caatcgtttt gcccagaaag tatgtgtcac agcgataaag tcgacttcgg gcctccctca   5760
taaaaactgg cagctctgag gtgaacacct aaatcgaatc gattcattag aaagttagta   5820
aattattgaa atgcaaatgt attctaaaca tgacttacat ttatcgtggc aaagacgttt   5880
tgaaaggtca tgttggtcag gaagaggaag atggctccgt tgatattcat cacacccact   5940
tgcgtgagtt gttggcccaa aaagatgagg ccaatcaaga tggcaaccat ctgcaaatta   6000
aaatgttact cgcatctcat taatattcgc gagttaaatg aaatttattt atcttctgca   6060
aaactataaa ctatacatct cattgaaaaa aactaagaag ggtgtggaat caggcaattc   6120
tatctaaaat ctagcgaatt tgtttccaag aattgtaagc gttatatcat ttgtttccac   6180
tggaaccact caccgttgtc tgaataagtc gcacttttac gaggagtggt tccttgagca   6240
ccgacagcca ggatcgccac aggaccgccc ggaactgcat gaaccaggtg gccttgtagg   6300
tgtacccatt ctccggctgc tccagtggct tctccagatt tttggtggcc aacaactgct   6360
ccatatcccg ggctactttg ctaatggcaa aattgtcgcc atatcttggc gatccgatca   6420
cgggactcga tctcccgtcc gggcacaacg gccaacacct gtacgtaaaa gtccgccgga   6480
ttgtagttgg taggacactg ggcacccacg ctggatagga gttgagatgt aatgtaatgc   6540
tagataccct taataaacac atcgaactca ctaggaaaag aagtcgacgg cttcgctggg   6600
agtgcccaag aaagctaccc tgccctcggc catcagaagg atcttgtcaa agagctcaaa   6660
cagctcggaa gacggctgat gaatggtcag gatgacggtc ttgcccttct gcgacagctt   6720
cttcagcacc tggacgacgc tgtgggcggt aaatgagtcc agtccggagg tgggctcatc   6780
gcagatcaga agcggcggat cggttagtgc ctcggaggcg aatgccagac gcttcctttc   6840
tccgccggac agacctttca ccctgccggg cacaccgatg atcgtgtgct gacatttgct   6900
gagcgaaagc tcctggatca cctgatccac gcgggccact cgctgccgat aggtcagatg   6960
tcgtggcatc cgcaccatgg cttggaaaat caggtgttcc ctggccgtta gggagccgat   7020
aaagaggtca tcctgctgga cataggcgca cctggcctgc atctccttgg cgtccacagg   7080
ttggccattg agcagtcgca tcccggatgg cgatacttgg atgccctgcg gcgatcgaaa   7140
ggcaagggca ttcagcaggg tcgtctttcc ggcaccggaa ctgcccatca cggccaaaag   7200
ttcgcccgga taggccacgc cgcaaactga gtttcaaatt ggtaattgga ccctttatta   7260
agatttcaca cagatcagcc gactgcgaat agaaactcac cgttcttgag caaatgtttc   7320
ctgggcgccg gtatgtgtcg ctcgttgcag aatagtccgc gtgtccggtt gaccagctgc   7380
cgccatccgg agcccggctg attgaccgcc ccaaagatgt ccatattgtg ccaggcatag   7440
gtgaggttct cggctagttg gccgctccct gaaccggagt cctccggcgg actgggtggc   7500
aggagcgtgc cgtagttttt ggcctgcccg aagccctggt taatgcagct ctgcgaagcg   7560
tccgctgtca ccctgcaatg ataggggatc tcaaatatca actacaagcg ttatgctcat   7620
ctaaccccga acaaaacgaa gtatcctacg aagtaggttt atacttttat ttattttttg   7680
tgcatagctt aaaatatctg gttgttatat tttttgtaaa aaagaatgta gtcgaaaatg   7740
aatgccttta gatgtcttga tcatgatatg atcttaaaaa ttgtcttata tagcgagcac   7800
agctaccaga ataatctgtt tcgtgtcact atttgtttgt gcgattgcgg tttgggattt   7860
```

ttgtgggtcg cagttctcac gccgcagaca atttgatgtt gcaatcgcag ttcctataga 7920
tcaagtgaac ttaagatgta tgcacatgta ctactcacat tgttcagatg ctcggcagat 7980
gggtgtttgc tgcctccgcg aattaatagc tcctgatcct cttggcccat tgccgggatt 8040
tttcacactt tcccctgctt acccacccaa aaccaatcac caccccaatc actcaaaaaa 8100
caaacaaaaa taagaagcga gaggagtttt ggcacagcac tttgtgttta attgatggcg 8160
taaaccgctt ggagcttcgt cacgaaaccg ctgacaaagt gcaactgaag gcggacattg 8220
acgctaggta acgctacaaa cggtggcgaa agagatagcg gacgcagcgg cgaaagagac 8280
ggcgatattt ctgtggacag agaaggaggc aaacagcgct gactttgagt ggaatgtcat 8340
tttgagtgag aggtaatcga aagaacctgg tacatcaaat acccttggat cgaagtaaat 8400
ttaaaactga tcagataagt tcaatgatat ccagtgcagt aaaaaaaaaa aatgtttttt 8460
ttatctactt tccgcaaaaa tgggttttat taacttacat acatactaga attctaaaaa 8520
aaatcatgaa tggcatcaac tctgaatcaa atctttgcag atgcacctac ttctcatttc 8580
cactgtcaca tcatttttcc agatctcgct gcctgttatg tggcccacaa accaagacac 8640
gttttatggc cattaaagct ggctgatcgt cgccaaacac caaatacata tcaatatgta 8700
cattcgagaa agaagcgatc aaagaagcgt cttcgggcga gtaggagaat gcggaggaga 8760
aggagaacga gctgatctag tatctctcca caatccaatg ccaactgacc aactggccat 8820
attcggagca atttgaagcc aatttccatc gcctggcgat cgctccattc ttggctatat 8880
gtttttcacc gttcccgggg ccattttcaa agactcgtcg gtaagataag attgtgtcac 8940
tcgctgtctc tcttcatttg tcgaagaatg ctgaggaatt tcgcgatgac gtcggcgagt 9000
attttgaaga atgagaataa tttgtattta tacgaaaatc agttagtgga attttctaca 9060
aaaacatgtt atctatagat aattttgttg caaaatatgt tgactatgac aaagattgta 9120
tgtatatacc tttaatgtat tctcattttc ttatgtattt ataatggcaa tgatgatact 9180
gatgatattt taagatgatg ccagaccaca ggctgatttc tgcgtctttt gccgaacgca 9240
gtgcatgtgc ggttgttgtt ttttggaata gtttcaattt tcggactgtc cgctttgatt 9300
tcagtttctt ggcttattca aaaagcaaag taaagccaaa aaagcgagat ggcaatacca 9360
aatgcggcaa aacggtagtg gaaggaaagg ggtgcggggc agcggaagga agggtggggc 9420
ggggcgtggc ggggtctgtg gctgggcgcg acgtcaccga cgttggagcc actcctttga 9480
ccatgtgtgc gtgtgtgtat tattcgtgtc tcgccactcg ccggttgttt ttttcttttt 9540
atctcgctct ctctagcgcc atctcgtacg catgctcaac gcaccgcatg ttgccgtgtc 9600
ctttatgcgt cattttggct cgaaataggc aattatttaa acaaagatta gtcaacgaaa 9660
acgctaaaat aaataagtct acaatatggt tacttattgc catgtgtgtg cagccaacga 9720
tagcaacaaa agcaacaaca cagtggcttt ccctctttca ctttttgttt gcaagcgcgt 9780
gcgagcaaga cggcacgacc ggcaaacgca attacgctga caaagagcag acgaagtttt 9840
ggccgaaaaa catcaaggcg cctgatacga atgcatttgc aataacaatt gcgatattta 9900
atattgttta tgaagctgtt tgacttcaaa acacacaaaa aaaaaaataa aacaaattat 9960
ttgaaagaga attaggaatc ggacagctta tcgttacggg ctaacagcac accgagacga 10020
aatagcttac ctgacgtcac agcctctgga agaactgccg ccaagcagac gatgcagagg 10080
acgacacata gagtagcgga gtaggccagc gtagtacgca tgtgcttgtg tgtgaggcgt 10140
ctctctcttc gtctcctgtt tgcgcaaacg catagactgc actgagaaaa tcgattacct 10200

-continued

```
atttttttatg aatgaatatt tgcactatta ctattcaaaa ctattaagat agcaatcaca  10260

ttcaatagcc aaatactata ccacctgagc gatgcaacga aatgatcaat ttgagcaaaa  10320

atgctgcata tttaggacgg catcattata gaaatgcttc ttgctgtgta cttttctctc  10380

gtctggcagc tgtttcgccg ttattgttaa aaccggctta agttaggtgt gttttctacg  10440

actagtgatg cccctactag aagatgtgtg ttgcacaaat gtccctgaat aaccaatttg  10500

aagtgcagat agcagtaaac gtaagctaat atgaatatta tttaactgta atgttttaat  10560

atcgctggac attactaata aacccactat aaacacatgt acatatgtat gttttggcat  10620

acaatgagta gttggggaaa aaatgtgtaa aagcaccgtg accatcacag cataaagata  10680

accagctgaa gtatcgaata tgagtaaccc ccaaattgaa tcacatgccg caactgatag  10740

gacccatgga agtacactct tcatggcgat atacaagaca cacacaagca cgaacaccca  10800

gttgcggagg aaattctccg taaatgaaaa cccaatcggc gaacaattca tacccatata  10860

tggtaaaagt tttgaacgcg acttgagagc ggagagcatt gcggctgata aggttttagc  10920

gctaagcggg ctttataaaa cggctgcgg gaccagtttt catatcacta ccgtttgagt  10980

tcttgtgctg tgtggatact cctcccgaca caaagccgct ccatcagcca gcagtcgtct  11040

aatccagaga ccccggatct agaaccaaaa tggctagatt agataaaagt aaagtgatta  11100

acagcgcatt agagctgctt aatgaggtcg gaatcgaagg tttaacaacc cgtaaactcg  11160

cccagaagct aggtgtagag cagcctacat tgtattggca tgtaaaaaat aagcgggctt  11220

tgctcgacgc cttagccatt gagatgttag ataggcacca tactcacttt tgccctttag  11280

aaggggaaag ctggcaagat tttttacgta ataacgctaa aagttttaga tgtgctttac  11340

taagtcatcg cgatggagca aaagtacatt taggtacacg gcctacagaa aaacagtatg  11400

aaactctcga aaatcaatta gcctttttat gccaacaagg tttttcacta gagaatgcat  11460

tatatgcact cagcgctgtg gggcatttta ctttaggttg cgtattggaa gatcaagagc  11520

atcaagtcgc taaagaagaa agggaaacac ctactactga tagtatgccg ccattattac  11580

gacaagctat cgaattattt gatcaccaag gtgcagagcc agccttctta ttcggccttg  11640

aattgatcat atgcggatta gaaaaacaac ttaaatgtga aagtgggtcc gcgtacagcc  11700

gcgcgcgtac gaaaaacaat tacgggtcta ccatcgaggg cctgctcgat ctcccggacg  11760

acgacgcccc cgaagaggcg gggctggcgg ctccgcgcct gtcctttctc cccgcgggac  11820

acacgcgcag actgtcgacg gccccccga ccgatgtcag cctgggggac gagctccact  11880

tagacggcga ggacgtggcg atggcgcatg ccgacgcgct agacgatttc gatctggaca  11940

tgttggggga cggggattcc ccgggtccgg gatttacccc ccacgactcc gccccctacg  12000

gcgctctgga tatggccgac ttcgagtttg agcagatgtt taccgatgcc cttggaattg  12060

acgagtacgg tgggtagggg gcgcgag                                        12087
```

<210> SEQ ID NO 16
<211> LENGTH: 11920
<212> TYPE: DNA
<213> ORGANISM: Artificial Sequence
<220> FEATURE:
<223> OTHER INFORMATION: Synthetic construct, plasmid pLA513

<400> SEQUENCE: 16

```
gggccgatct gacaatgttc agtgcagaga ctcggctacg cctcgtggac tttgaagttg     60

accaacaatg tttattctta cctctaatag tcctctgtgg caaggtcaag attctgttag    120

aagccaatga agaacctggt tgttcaataa cattttgttc gtctaatatt tcactaccgc    180
```

-continued

```
ttgacgttgg ctgcacttca tgtacctcat ctataaacgc ttcttctgta tcgctctgga    240
cgtcatcttc acttacgtga tctgatattt cactgtcaga atcctcacca acaagctcgt    300
catcgctttg cagaagagca gagaggatat gctcatcgtc taaagaacta cccattttat    360
tatatattag tcacgatatc tataacaaga aaatatatat ataataagtt atcacgtaag    420
tagaacatga aataacaata taattatcgt atgagttaaa tcttaaaagt cacgtaaaag    480
ataatcatgc gtcattttga ctcacgcggt cgttatagtt caaaatcagt gacacttacc    540
gcattgacaa gcacgcctca cgggagctcc aagcggcgac tgagatgtcc taaatgcaca    600
gcgacggatt cgcgctattt agaaagagag agcaatattt caagaatgca tgcgtcaatt    660
ttacgcagac tatctttcta gggttaaaaa agatttgcgc tttactcgac ctaaacttta    720
aacacgtcat agaatcttcg tttgacaaaa accacattgt ggccaagctg tgtgacgcga    780
cgcgcgctaa agaatggcaa accaagtcgc gcgagcgtcg acctgcaggc atgcaagctt    840
gcatgcctgc aggtcgaaat tcgtaatcat ggtcatagct gtttcctgtg tgaaattgtt    900
atccgctcac aattccacac aacatacgag ccggaagcat aaagtgtaaa gcctggggtg    960
cctaatgagt gagctaactc acattaattg cgttgcgctc actgcccgct ttccagtcgg   1020
gaaacctgtc gtgccagctg cattaatgaa tcggccaacg cgcggggaga ggcggtttgc   1080
gtattgggcg ctcttccgct tcctcgctca ctgactcgct gcgctcggtc gttcggctgc   1140
ggcgagcggt atcagctcac tcaaaggcgg taatacggtt atccacagaa tcaggggata   1200
acgcaggaaa gaacatgtga gcaaaaggcc agcaaaaggc caggaaccgt aaaaaggccg   1260
cgttgctggc gtttttccat aggctccgcc cccctgacga gcatcacaaa aatcgacgct   1320
caagtcagag gtggcgaaac ccgacaggac tataaagata ccaggcgttt ccccctggaa   1380
gctccctcgt gcgctctcct gttccgaccc tgccgcttac cggatacctg tccgcctttc   1440
tcccttcggg aagcgtggcg ctttctcaat gctcacgctg taggtatctc agttcggtgt   1500
aggtcgttcg ctccaagctg ggctgtgtgc acgaaccccc cgttcagccc gaccgctgcg   1560
ccttatccgg taactatcgt cttgagtcca acccggtaag acacgactta tcgccactgg   1620
cagcagccac tggtaacagg attagcagag cgaggtatgt aggcggtgct acagagttct   1680
tgaagtggtg gcctaactac ggctacacta gaaggacagt atttggtatc tgcgctctgc   1740
tgaagccagt taccttcgga aaaagagttg gtagctcttg atccggcaaa caaaccaccg   1800
ctggtagcgg tggttttttt gtttgcaagc agcagattac gcgcagaaaa aaaggatctc   1860
aagaagatcc tttgatcttt tctacggggt ctgacgctca gtggaacgaa aactcacgtt   1920
aagggatttt ggtcatgaga ttatcaaaaa ggatcttcac ctagatcctt ttaaattaaa   1980
aatgaagttt taaatcaatc taaagtatat atgagtaaac ttggtctgac agttaccaat   2040
gcttaatcag tgaggcacct atctcagcga tctgtctatt tcgttcatcc atagttgcct   2100
gactccccgt cgtgtagata actacgatac gggagggctt accatctggc cccagtgctg   2160
caatgatacc gcgagaccca cgctcaccgg ctccagattt atcagcaata aaccagccag   2220
ccggaagggc cgagcgcaga agtggtcctg caactttatc cgcctccatc cagtctatta   2280
attgttgccg ggaagctaga gtaagtagtt cgccagttaa tagtttgcgc aacgttgttg   2340
ccattgctac aggcatcgtg gtgtcacgct cgtcgtttgg tatggcttca ttcagctccg   2400
gttcccaacg atcaaggcga gttacatgat cccccatgtt gtgcaaaaaa gcggttagct   2460
ccttcggtcc tccgatcgtt gtcagaagta agttggccgc agtgttatca ctcatggtta   2520
```

```
tggcagcact gcataattct cttactgtca tgccatccgt aagatgcttt tctgtgactg   2580
gtgagtactc aaccaagtca ttctgagaat agtgtatgcg gcgaccgagt tgctcttgcc   2640
cggcgtcaat acgggataat accgcgccac atagcagaac tttaaaagtg ctcatcattg   2700
gaaaacgttc ttcggggcga aaactctcaa ggatcttacc gctgttgaga tccagttcga   2760
tgtaacccac tcgtgcaccc aactgatctt cagcatcttt tactttcacc agcgtttctg   2820
ggtgagcaaa aacaggaagg caaaatgccg caaaaaaggg aataagggcg acacggaaat   2880
gttgaatact catactcttc ctttttcaat attattgaag catttatcag ggttattgtc   2940
tcatgagcgg atacatattt gaatgtattt agaaaaataa acaaataggg gttccgcgca   3000
catttccccg aaaagtgcca cctgacgtct aagaaaccat tattatcatg acattaacct   3060
ataaaaatag gcgtatcacg aggccctttc gtctcgcgcg tttcggtgat gacggtgaaa   3120
acctctgaca catgcagctc ccggagacgg tcacagcttg tctgtaagcg gatgccggga   3180
gcagacaagc ccgtcagggc gcgtcagcgg gtgttggcgg gtgtcggggc tggcttaact   3240
atgcggcatc agagcagatt gtactgagag tgcaccatat gcggtgtgaa ataccgcaca   3300
gatgcgtaag gagaaaatac cgcatcaggc gccattcgcc attcaggctg cgcaactgtt   3360
gggaagggcg atcggtgcgg gcctcttcgc tattacgcca gctggcgaaa gggggatgtg   3420
ctgcaaggcg attaagttgg gtaacgccag ggttttccca gtcacgacgt tgtaaaacga   3480
cggccagtgc caagctttgt ttaaaatata acaaaattgt gatcccacaa aatgaagtgg   3540
ggcaaaatca aataattaat agtgtccgta aacttgttgg tcttcaactt tttgaggaac   3600
acgttggacg gcaaatccgt gactataaca caagttgatt taataatttt agccaacacg   3660
tcgggctgcg tgtttttgc cgacgcgtct gtgtacacgt tgattaactg gtcgattaaa   3720
ctgttgaaat aatttaattt ttggttcttc tttaaatctg tgatgaaatt ttttaaaata   3780
actttaaatt cttcattggt aaaaaatgcc acgttttgca acttgtgagg gtctaatatg   3840
aggtcaaact cagtaggagt tttatccaaa aaagaaaaca tgattacgtc tgtacacgaa   3900
cgcgtattaa cgcagagtgc aaagtataag agggttaaaa aatatatttt acgcaccata   3960
tacgcatcgg gttgatatcg ttaatatgga tcaatttgaa cagttgatta acgtgtctct   4020
gctcaagtct ttgatcaaaa cgcaaatcga cgaaaatgtg tcggacaata tcaagtcgat   4080
gagcgaaaaa ctaaaaaggc tagaatacga caatctcaca gacagcgttg agatatacgg   4140
tattcacgac agcaggctga ataataaaaa aattagaaac tattatttaa ccctagaaag   4200
ataatcatat tgtgacgtac gttaaagata atcatgcgta aaattgacgc atgtgtttta   4260
tcggtctgta tatcgaggtt tatttattaa tttgaataga tattaagttt tattatattt   4320
acacttacat actaataata aattcaacaa acaatttatt tatgtttatt tatttattaa   4380
aaaaaaacaa aaactcaaaa tttcttctat aaagtaacaa aacttttaaa cattctctct   4440
tttacaaaaa taaacttatt ttgtacttta aaaacagtca tgttgtatta taaaataagt   4500
aattagctta acttatacat aatagaaaca aattatactt attagtcagt cagaaacaac   4560
tttggcacat atcaatatta tgctctcgac aaataacttt tttgcatttt ttgcacgatg   4620
catttgcctt tcgccttatt ttagaggggc agtaagtaca gtaagtacgt tttttcatta   4680
ctggctcttc agtactgtca tctgatgtac caggcacttc atttggcaaa atattagaga   4740
tattatcgcg caaatatctc ttcaaagtag gagcttctaa acgcttacgc ataaacgatg   4800
acgtcaggct catgtaaagg tttctcataa attttttgcg actttggacc ttttctccct   4860
tgctactgac attatggctg tatataataa aagaatttat gcaggcaatg tttatcattc   4920
```

```
cgtacaataa tgccataggc cacctattcg tcttcctact gcaggtcatc acagaacaca   4980
tttggtctag cgtgtccact ccgcctttag tttgattata atacataacc atttgcggtt   5040
taccggtact ttcgttgata gaagcatcct catcacaaga tgataataag tataccatct   5100
tagctggctt cggtttatat gagacgagag taaggggtcc gtcaaaacaa aacatcgatg   5160
ttcccactgg cctggagcga ctgtttttca gtacttccgg tatctcgcgt ttgtttgatc   5220
gcacggttcc cacaatggtt gcggccggcc agatttaaat gagcggccgc agatatccag   5280
tgcagtaaaa aaaaaaaatg tttttttat ctactttccg caaaaatggg ttttattaac    5340
ttacatacat actagaattc tatattctaa aaacacaaat gatacttcta aaaaaaatca   5400
tgaatggcat caactctgaa tcaaatcttt gcagatgcac ctacttctca tttccactgt   5460
cacatcattt ttccagatct cgctgcctgt tatgtggccc acaaaccaag acacgtttta   5520
tggccattaa agctggctga tcgtcgccaa acaccaaata catatcaata tgtacattcg   5580
agaaagaagc gatcaaagaa gcgtcttcgg gcgagtagga gaatgcggag gagaaggaga   5640
acgagctgat ctagtatctc tccacaatcc aatgccaact gaccaactgg ccatattcgg   5700
agcaatttga agccaatttc catcgcctgg cgatcgctcc attcttggct atatgttttt   5760
caccgttccc ggggccattt tcaaagactc gtcggtaaga taagattgtg tcactcgctg   5820
tctctcttca tttgtcgaag aatgctgagg aatttcgcga tgacgtcggc gagtattttg   5880
aagaatgaga ataatttgta tttatacgaa aatcagttag tggaatttc tacaaaaaca    5940
tgttatctat agataatttt gttgcaaaat atgttgacta tgacaaagat tgtatgtata   6000
tacctttaat gtattctcat tttcttatgt atttataatg gcaatgatga tactgatgat   6060
attttaagat gatgccagac cacaggctga tttctgcgtc ttttgccgaa cgcagtgcat   6120
gtgcggttgt tgttttttgg aatagtttca attttcggac tgtccgcttt gatttcagtt   6180
tcttggctta ttcaaaaagc aaagtaaagc caaaaaagcg agatggcaat accaaatgcg   6240
gcaaaacggt agtggaagga aaggggtgcg gggcagcgga aggaagggtg gggcggggcg   6300
tggcggggtc tgtggctggg cgcgacgtca ccgacgttgg agccactcct ttgaccatgt   6360
gtgcgtgtgt gtattattcg tgtctcgcca ctcgccggtt gttttttct ttttatctcg    6420
ctctctctag cgccatctcg tacgcatgct caacgcaccg catgttgccg tgtcctttat   6480
gcgtcatttt ggctcgaaat aggcaattat ttaaacaaag attagtcaac gaaaacgcta   6540
aaataaataa gtctacaata tggttactta ttgccatgtg tgtgcagcca acgatagcaa   6600
caaaagcaac aacacagtgg ctttccctct ttcacttttt gtttgcaagc gcgtgcgagc   6660
aagacggcac gaccggcaaa cgcaattacg ctgacaaaga gcagacgaag ttttggccga   6720
aaaacatcaa ggcgcctgat acgaatgcat ttgcaataac aattgcgata tttaatattg   6780
tttatgaagc tgtttgactt caaaacacac aaaaaaaaaa ataaaacaaa ttatttgaaa   6840
gagaattagg aatcggacag cttatcgtta cgggctaaca gcacaccgag acgaaatagc   6900
ttacctgacg tcacagcctc tggaagaact gccgccaagc agacgatgca gaggacgaca   6960
catagagtag cggagtaggc cagcgtagta cgcatgtgct tgtgtgtgag gcgtctctct   7020
cttcgtctcc tgtttgcgca aacgcataga ctgcactgag aaaatcgatt acctattttt   7080
tatgaatgaa tatttgcact attactattc aaaactatta agatagcaat cacattcaat   7140
agccaaatac tataccacct gagcgatgca acgaaatgat caatttgagc aaaaatgctg   7200
catatttagg acggcatcat tatagaaatg cttcttgctg tgtacttttc tctcgtctgg   7260
```

cagctgtttc gccgttattg ttaaaaccgg cttaagttag gtgtgttttc tacgactagt 7320
gatgccccta ctagaagatg tgtgttgcac aaatgtccct gaataaccaa tttgaagtgc 7380
agatagcagt aaacgtaagc taatatgaat attatttaac tgtaatgttt taatatcgct 7440
ggacattact aataaaccca ctataaacac atgtacatat gtatgttttg gcatacaatg 7500
agtagttggg gaaaaaatgt gtaaaagcac cgtgaccatc acagcataaa gataaccagc 7560
tgaagtatcg aatatgagta acccccaaat tgaatcacat gccgcaactg ataggaccca 7620
tggaagtaca ctcttcatgg cgatatacaa gacacacaca agcacgaaca cccagttgcg 7680
gaggaaattc tccgtaaatg aaaacccaat cggcgaacaa ttcataccca tatatggtaa 7740
aagttttgaa cgcgacttga gagcggagag cattgcggct gataaggttt tagcgctaag 7800
cgggctttat aaaacgggct gcgggaccag ttttcatatc actaccgttt gagttcttgt 7860
gctgtgtgga tactcctccc gacacaaagc cgctccatca gccagcagtc gtctaatcca 7920
gagaccccgg atctagaacc aaaatggcta gaatggcctc ctccgagaac gtcatcaccg 7980
agttcatgcg cttcaaggtg cgcatggagg gcaccgtgaa cggccacgag ttcgagatcg 8040
agggcgaggg cgagggccgc ccctacgagg gccacaacac cgtgaagctg aaggtgacca 8100
agggcggccc cctgcccttc gcctgggaca tcctgtcccc ccagttccag tacggctcca 8160
aggtgtacgt gaagcacccc gccgacatcc ccgactacaa gaagctgtcc ttccccgagg 8220
gcttcaagtg ggagcgcgtg atgaacttcg aggacggcgg cgtggcgacc gtgacccagg 8280
actcctccct gcaggacggc tgcttcatct acaaggtgaa gttcatcggc gtgaacttcc 8340
cctccgacgg ccccgtgatg cagaagaaga ccatgggctg ggaggcctcc accgagcgcc 8400
tgtacccccg cgacggcgtg ctgaagggcg agacccacaa ggccctgaag ctgaaggacg 8460
gcggccacta cctggtggag ttcaagtcca tctacatggc caagaagccc gtgcagctgc 8520
ccggctacta ctacgtggac gccaagctgg acatcacctc ccacaacgag gactacacca 8580
tcgtggagca gtacgagcgc accgagggcc gccaccacct gttcctgtga gatccatgag 8640
caattagcat gaacgttctg aaaagcgcgt ttagctctcc actacttaca catattctat 8700
gctgcaatat tgaaaatcta ataaacaaaa ctaatgtaca ttaattcttc agttttgaat 8760
atccttctcc tgactttctt atttagaatt aatataatac tgcatacatt aatactgtaa 8820
atatgataag tacctgcaaa acactgcagc tcaagtctta atgaggttct gcgatagctt 8880
agcataatta gtaacttatc gcgcagaatt ccctaatgtt cccgacctac atgtacttct 8940
gatagttgcc gaggtcaaat gttgttgtat ttgtattata cctcaatatt ggtatattca 9000
atatctaata gtacccaatt caattgcaaa gatagtcatt aaaaaaacct aaatcacttg 9060
caaattgact tttctgccgg aaaagcaacc ttgacacaca aagttaatta gtttatctgg 9120
aagtcatgtg agaaatttgt aaataaaatt tttcgcagta atttaagtgg gcctaatccc 9180
ttttaagcat cttggtttta cgatgacacc gcaataaggt acaactttat attgtttttg 9240
caatcagctt gagtctttat taggcatcag tctttctctc taagtttctt cgtgcaataa 9300
atgaggttcc aaactccgta gatttttcct tctttgttga atccagatcc tgcaaagaaa 9360
aaagagcaaa cccctaggtc tgtccaggaa tgtattttcg tgtttgtcga tcgaccatgg 9420
tctcgagggg gggccttaat taagaggcgc gccaggtttc gactttcact tttctctatc 9480
actgataggg agtggtaaac tcgactttca cttttctcta tcactgatag ggagtggtaa 9540
actcgacttt cacttttctc tatcactgat agggagtggt aaactcgact ttcacttttc 9600
tctatcactg atagggagtg gtaaactcga ctttcacttt tctctatcac tgatagggag 9660
tggtaaactc gactttcact tttctctatc actgataggg agtggtaaac tcgactttca 9720
cttttctcta tcactgatag ggagtggtaa actcgaaaac gagcgccgga gtataaatag 9780
aggcgcttcg tctacggagc gacaattcaa ttcaaacaag caaagtgaac acgtcgctaa 9840
gcgaaagcta agcaaataaa caagcgcagc tgaacaagct aaacaatctg cggtaccctg 9900
gcggtaagtt gatcaaagga aacgcaaagt tttcaagaaa aaacaaaact aatttgattt 9960
ataacacctt tagaaaccac catgggcagc cgcctggata agtccaaagt catcaactcc 10020
gcgttggagc tgttgaacga agttggcatt gagggactga cgacccgcaa gttggcgcag 10080
aagctgggcg tggagcagcc caccctctac tggcacgtga agaataagcg ggcgctgctg 10140
gatgccctgg ccatcgagat gctcgaccgc caccacacgc atttttgccc gttggaaggc 10200
gagtcctggc aggacttcct ccgcaataac gccaagtcgt tccgctgcgc tctgctgtcc 10260
caccgagacg gtgccaaagt ccatctcggc acgcgcccga ccgaaaagca atacgagaca 10320
ctggagaacc agctcgcgtt cctgtgccag caaggcttca gcctggaaaa tgctctctac 10380
gctctgagcg ccgtcggtca ctttaccctg ggctgcgtgc tggaggacca agagcatcaa 10440
gtcgcaaaag aggagcgcga gaccccaaca accgattcga tgcccccact gctgcgtcag 10500
gcaatcgagc tgttcgatca tcaaggagcc gagccggcat tcctgttcgg cttggagctg 10560
attatctgcg gattggaaaa gcaactgaaa tgcgagtcgg gctcgggccc cgcgtacagc 10620
cgcgcgcgta cgaaaaacaa ttacgggtct accatcgagg gcctgctcga tctcccggac 10680
gacgacgccc ccgaagaggc ggggctggcg gctccgcgcc tgtcctttct ccccgcggga 10740
cacacgcgca gactgtcgac ggcccccccg accgatgtca gcctggggga cgagctccac 10800
ttagacggcg aggacgtggc gatggcgcat gccgacgcgc tagacgattt cgatctggac 10860
atgttggggg acggggattc cccgggtccg ggatttaccc cccacgactc cgccccctac 10920
ggcgctctgg atatggccga cttcgagttt gagcagatgt ttaccgatgc ccttggaatt 10980
gacgagtacg gtgggtagtt ctagagtcga cctcgaacgt taacgttaac gtaacgttaa 11040
ctcgaggagc ttgataacat tatacctaaa cccatggtca agagtaaaca tttctgcctt 11100
tgaagttgag aacacaatta agcatcccct ggttaaacct gacattcata cttgttaata 11160
gcgccataaa catagcacca atttcgaaga aatcagttaa aagcaattag caattagcaa 11220
ttagcaataa ctctgctgac ttcaaaacga gaagagttgc aagtatttgt aaggcacagt 11280
ttatagacca ccgacggctc attagggctc gtcatgtaac taagcgcggt gaaacccaat 11340
tgaacatata gtggaattat tattatcaat ggggaagatt taaccctcag gtagcaaagt 11400
aatttaattg caaatagaga gtcctaagac taaataatat atttaaaaat ctggcccttt 11460
gaccttgctt gtcaggtgca tttgggttca atcgtaagtt gcttctatat aaacactttc 11520
cccatccccg caataatgaa gaataccgca gaataaagag agatttgcaa caaaaaataa 11580
aggcattgcg aaaacttttt atgggggatc attacactcg ggcctacggt tacaattccc 11640
agccacttaa gcgacaagtt tggccaacaa tccatctaat agctaatagc gcaatcactg 11700
gtaatcgcaa gagtatatag gcaatagaac ccatggattt gaccaaaggt aaccgagaca 11760
atggagaagc aagaggattt caaactgaac acccacagta ctgtgtacta ccactggcgc 11820
gtttgggagc tccaagcggc gactgagatg tcctaaatgc acagcgacgg attcgcgcta 11880
tttagaaaga gagagcaata tttcaagaaa aacggcgccc 11920

<210> SEQ ID NO 17

<211> LENGTH: 11570
<212> TYPE: DNA
<213> ORGANISM: Artificial Sequence
<220> FEATURE:
<223> OTHER INFORMATION: Synthetic construct, plasmid pLA517

<400> SEQUENCE: 17
ggccgctcat ttaaatctgg ccggccgcaa ccattgtggg aaccgtgcga tcaaacaaac 60
gcgagatacc ggaagtactg aaaaacagtc gctccaggcc agtgggaaca tcgatgtttt 120
gttttgacgg accccttact ctcgtctcat ataaaccgaa gccagctaag atggtatact 180
tattatcatc ttgtgatgag gatgcttcta tcaacgaaag taccggtaaa ccgcaaatgg 240
ttatgtatta taatcaaact aaaggcggag tggacacgct agaccaaatg tgttctgtga 300
tgacctgcag taggaagacg aataggtggc ctatggcatt attgtacgga atgataaaca 360
ttgcctgcat aaattctttt attatataca gccataatgt cagtagcaag ggagaaaagg 420
tccaaagtcg caaaaaattt atgagaaacc tttacatgag cctgacgtca tcgtttatgc 480
gtaagcgttt agaagctcct actttgaaga gatatttgcg cgataaatatc tctaatattt 540 tgccaaatga agtgcctggt acatcagatg acagtactga agagccagta atgaaaaaac 600
gtacttactg tacttactgc ccctctaaaa taaggcgaaa ggcaaatgca tcgtgcaaaa 660
aatgcaaaaa agttatttgt cgagagcata atattgatat gtgccaaagt tgtttctgac 720
tgactaataa gtataatttg tttctattat gtataagtta agctaattac ttattttata 780
atacaacatg actgttttta aagtacaaaa taagtttatt tttgtaaaag agagaatgtt 840
taaaagtttt gttactttat agaagaaatt ttgagttttt gttttttttt aataaataaa 900
taaacataaa taaattgttt gttgaattta ttattagtat gtaagtgtaa atataataaa 960
acttaatatc tattcaaatt aataaataaa cctcgatata cagaccgata aaacacatgc 1020
gtcaatttta cgcatgatta tctttaacgt acgtcacaat atgattatct ttctagggtt 1080
aaataatagt ttctaatttt tttattattc agcctgctgt cgtgaatacc gtatatctca 1140
acgctgtctg tgagattgtc gtattctagc ctttttagtt tttcgctcat cgacttgata 1200
ttgtccgaca cattttcgtc gatttgcgtt ttgatcaaag acttgagcag agacacgtta 1260
atcaactgtt caaattgatc catattaacg atatcaaccc gatgcgtata tggtgcgtaa 1320
aatatatttt ttaaccctct tatactttgc actctgcgtt aatacgcgtt cgtgtacaga 1380
cgtaatcatg ttttcttttt tggataaaac tcctactgag tttgacctca tattagaccc 1440
tcacaagttg caaaacgtgg catttttttac caatgaagaa tttaaagtta ttttaaaaaa 1500
tttcatcaca gatttaaaga agaaccaaaa attaaattat ttcaacagtt taatcgacca 1560
gttaatcaac gtgtacacag acgcgtcggc aaaaaacacg cagcccgacg tgttggctaa 1620
aattattaaa tcaacttgtg ttatagtcac ggatttgccg tccaacgtgt tcctcaaaaa 1680
gttgaagacc aacaagttta cggacactat taattatttg attttgcccc acttcatttt 1740
gtgggatcac aattttgtta tattttaaac aaagcttggc actggccgtc gttttacaac 1800
gtcgtgactg ggaaaaccct ggcgttaccc aacttaatcg ccttgcagca catccccctt 1860
tcgccagctg gcgtaatagc gaagaggccc gcaccgatcg cccttcccaa cagttgcgca 1920
gcctgaatgg cgaatggcgc ctgatgcggt attttctcct tacgcatctg tgcggtattt 1980
cacaccgcat atggtgcact ctcagtacaa tctgctctga tgccgcatag ttaagccagc 2040
cccgacaccc gccaacaccc gctgacgcgc cctgacgggc ttgtctgctc ccggcatccg 2100
cttacagaca agctgtgacc gtctccggga gctgcatgtg tcagaggttt tcaccgtcat 2160

-continued

```
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
ctgcaggtcg acgctcgcgc gacttggttt gccattcttt agcgcgcgtc gcgtcacaca   4500
```

-continued gcttggccac aatgtggttt ttgtcaaacg aagattctat gacgtgttta aagtttaggt 4560
cgagtaaagc gcaaatcttt tttaacccta gaaagatagt ctgcgtaaaa ttgacgcatg 4620
cattcttgaa atattgctct ctctttctaa atagcgcgaa tccgtcgctg tgcatttagg 4680
acatctcagt cgccgcttgg agctcccgtg aggcgtgctt gtcaatgcgg taagtgtcac 4740
tgattttgaa ctataacgac cgcgtgagtc aaaatgacgc atgattatct tttacgtgac 4800
ttttaagatt taactcatac gataattata ttgttatttc atgttctact tacgtgataa 4860
cttattatat atatattttc ttgttataga tatcgtgact aatatataat aaaatgggta 4920
gttctttaga cgatgagcat atcctctctg ctcttctgca aagcgatgac gagcttgttg 4980
gtgaggattc tgacagtgaa atatcagatc acgtaagtga agatgacgtc cagagcgata 5040
cagaagaagc gtttatagat gaggtacatg aagtgcagcc aacgtcaagc ggtagtgaaa 5100
tattagacga acaaaatgtt attgaacaac caggttcttc attggcttct aacagaatct 5160
tgaccttgcc acagaggact attagaggta agaataaaca ttgttggtca acttcaaagt 5220
ccacgaggcg tagccgagtc tctgcactga acattgtcag atcggcccgg gcgccgtttc 5280
ccaaacgcgc cagtggtagt acacagtact gtgggtgttc agtttgaaat cctcttgctt 5340
ctccattgtc tcggttacct ttggtcaaat ccatgggttc tattgcctat atactcttgc 5400
gattaccagt gattgcgcta ttagctatta gatggattgt tggccaaact tgtcgcttaa 5460
gtggctggga attgtaaccg taggcccgag tgtaatgatc ccccataaaa agttttcgca 5520
atgcctttat tttttgttgc aaatctctct ttattctgcg gtattcttca ttattgcggg 5580
gatggggaaa gtgtttatat agaagcaact tacgattgaa cccaaatgca cctgacaagc 5640
aaggtcaaag ggccagattt ttaaatatat tatttagtct taggactctc tatttgcaat 5700
taaattactt tgctacctga gggttaaatc ttccccattg ataataataa ttccactata 5760
tgttcaattg ggtttcaccg cgcttagtta catgacgagc cctaatgagc cgtcggtggt 5820
ctataaactg tgccttacaa atacttgcaa ctcttctcgt tttgaagtca gcagagttat 5880
tgctaattgc taattgctaa ttgcttttaa ctgatttctt cgaaattggt gctatgttta 5940
tggcgctatt aacaagtatg aatgtcaggt ttaaccaggg gatgcttaat tgtgttctca 6000
acttcaaagg cagaaatgtt tactcttgac catgggttta ggtataatgt tatcaagctc 6060
ctcgagttaa cgttacgtta acgttaacgt tcgaggtcga ctctagatta ttacagcatg 6120
tcgagatcaa agtcgtccaa agcatcagcg ggcaacatat ccaagtcaaa atcatcgaga 6180
gcgtccgccg gcagcatatc caggtcgaag tcatccaggg catcggcggg gcccgagccc 6240
gactcgcatt tcagttgctt ttccaatccg cagataatca gctccaagcc gaacaggaat 6300
gccggctcgg ctccttgatg atcgaacagc tcgattgcct gacgcagcag tgggggcatc 6360
gaatcggttg ttggggtctc gcgctcctct tttgcgactt gatgctcttg gtcctccagc 6420
acgcagccca gggtaaagtg accgacggcg ctcagagcgt agagagcatt ttccaggctg 6480
aagccttgct ggcacaggaa cgcgagctgg ttctccagtg tctcgtattg cttttcggtc 6540
gggcgcgtgc cgagatggac tttggcaccg tctcggtggg acagcagagc gcagcggaac 6600
gacttggcgt tattgcggag gaagtcctgc caggactcgc cttccaacgg gcaaaaatgc 6660
gtgtggtggc ggtcgagcat ctcgatggcc agggcatcca gcagcgcccg cttattcttc 6720
acgtgccagt agagggtggg ctgctccacg cccagcttct gcgccaactt gcgggtcgtc 6780
agtccctcaa tgccaacttc gttcaacagc tccaacgcgg agttgatgac tttggactta 6840
tccaggcggc tgcccatggt ggtttctaaa ggtgttataa atcaaattag ttttgttttt 6900

-continued

```
tcttgaaaac tttgcgtttc ctttgatcaa cttaccgcca gggtaccgca gattgtttag   6960
cttgttcagc tgcgcttgtt tatttgctta gctttcgctt agcgacgtgt tcactttgct   7020
tgtttgaatt gaattgtcgc tccgtagacg aagcgcctct atttatactc cggcgctcgt   7080
tttcgagttt accactccct atcagtgata gagaaaagtg aaagtcgagt ttaccactcc   7140
ctatcagtga tagagaaaag tgaaagtcga gtttaccact ccctatcagt gatagagaaa   7200
agtgaaagtc gagtttacca ctccctatca gtgatagaga aaagtgaaag tcgagtttac   7260
cactccctat cagtgataga gaaaagtgaa agtcgagttt accactccct atcagtgata   7320
gagaaaagtg aaagtcgagt ttaccactcc ctatcagtga tagagaaaag tgaaagtcga   7380
aacctggcgc gcctcttaat taaggccccc cctcgagacc atggtcgatc gacaaacacg   7440
aaaatacatt cctggacaga cctaggggtt tgctcttttt tctttgcagg atctggattc   7500
aacaaagaag gaaaaatcta cggagtttgg aacctcattt attgcacgaa gaaacttaga   7560
gagaaagact gatgcctaat aaagactcaa gctgattgca aaaacaatat aaagttgtac   7620
cttattgcgg tgtcatcgta aaaccaagat gcttaaaagg gattaggccc acttaaatta   7680
ctgcgaaaaa ttttatttac aaatttctca catgacttcc agataaacta attaactttg   7740
tgtgtcaagg ttgcttttcc ggcagaaaag tcaatttgca agtgatttag gtttttttaa   7800
tgactatctt tgcaattgaa ttgggtacta ttagatattg aatataccaa tattgaggta   7860
taatacaaat acaacaacat ttgacctcgg caactatcag aagtacatgt aggtcgggaa   7920
cattagggaa ttctgcgcga taagttacta attatgctaa gctatcgcag aacctcatta   7980
agacttgagc tgcagtgttt tgcaggtact tatcatattt acagtattaa tgtatgcagt   8040
attatattaa ttctaaataa gaaagtcagg agaaggatat tcaaaactga agaattaatg   8100
tacattagtt ttgtttatta gattttcaat attgcagcat agaatatgtg taagtagtgg   8160
agagctaaac gcgcttttca gaacgttcat gctaattgct catggatctc acaggaacag   8220
gtggtggcgg ccctcggtgc gctcgtactg ctccacgatg gtgtagtcct cgttgtggga   8280
ggtgatgtcc agcttggcgt ccacgtagta gtagccgggc agctgcacgg gcttcttggc   8340
catgtagatg gacttgaact ccaccaggta gtggccgccg tccttcagct tcagggcctt   8400
gtgggtctcg cccttcagca cgccgtcgcg ggggtacagg cgctcggtgg aggcctccca   8460
gcccatggtc ttcttctgca tcacggggcc gtcggagggg aagttcacgc cgatgaactt   8520
caccttgtag atgaagcagc cgtcctgcag ggaggagtcc tgggtcacgg tcgccacgcc   8580
gccgtcctcg aagttcatca cgcgctccca cttgaagccc tcggggaagg acagcttctt   8640
gtagtcgggg atgtcggcgg ggtgcttcac gtacaccttg gagccgtact ggaactgggg   8700
ggacaggatg tcccaggcga agggcagggg gccgcccttg gtcaccttca gcttcacggt   8760
gttgtggccc tcgtaggggc ggccctcgcc ctcgccctcg atctcgaact cgtggccgtt   8820
cacggtgccc tccatgcgca ccttgaagcg catgaactcg gtgatgacgt tctcggagga   8880
ggccattcta gccattttgg ttctagatcc ggggtctctg gattagacga ctgctggctg   8940
atggagcggc tttgtgtcgg gaggagtatc cacacagcac aagaactcaa acggtagtga   9000
tatgaaaact ggtcccgcag cccgttttat aaagcccgct tagcgctaaa accttatcag   9060
ccgcaatgct ctccgctctc aagtcgcgtt caaaactttt accatatatg ggtatgaatt   9120
gttcgccgat tgggttttca tttacggaga atttcctccg caactgggtg ttcgtgcttg   9180
tgtgtgtctt gtatatcgcc atgaagagtg tacttccatg ggtcctatca gttgcggcat   9240
```

-continued

```
gtgattcaat ttgggggtta ctcatattcg atacttcagc tggttatctt tatgctgtga   9300
tggtcacggt gcttttacac atttttttccc caactactca ttgtatgcca aaacatacat   9360
atgtacatgt gtttatagtg ggtttattag taatgtccag cgatattaaa acattacagt   9420
taaataatat tcatattagc ttacgtttac tgctatctgc acttcaaatt ggttattcag   9480
ggacatttgt gcaacacaca tcttctagta ggggcatcac tagtcgtaga aaacacacct   9540
aacttaagcc ggttttaaca ataacggcga aacagctgcc agacgagaga aaagtacaca   9600
gcaagaagca tttctataat gatgccgtcc taaatatgca gcatttttgc tcaaattgat   9660
catttcgttg catcgctcag gtggtatagt atttggctat tgaatgtgat tgctatctta   9720
atagttttga atagtaatag tgcaaatatt cattcataaa aaataggtaa tcgattttct   9780
cagtgcagtc tatgcgtttg cgcaaacagg agacgaagag agagacgcct cacacacaag   9840
cacatgcgta ctacgctggc ctactccgct actctatgtg tcgtcctctg catcgtctgc   9900
ttggcggcag ttcttccaga ggctgtgacg tcaggtaagc tatttcgtct cggtgtgctg   9960
ttagcccgta acgataagct gtccgattcc taattctctt tcaaataatt tgttttattt  10020
tttttttgt gtgttttgaa gtcaaacagc ttcataaaca atattaaata tcgcaattgt  10080
tattgcaaat gcattcgtat caggcgcctt gatgtttttc ggccaaaact tcgtctgctc  10140
tttgtcagcg taattgcgtt tgccggtcgt gccgtcttgc tcgcacgcgc ttgcaaacaa  10200
aaagtgaaag agggaaagcc actgtgttgt tgcttttgtt gctatcgttg gctgcacaca  10260
catggcaata agtaaccata ttgtagactt atttatttta gcgttttcgt tgactaatct  10320
ttgtttaaat aattgcctat ttcgagccaa aatgacgcat aaaggacacg gcaacatgcg  10380
gtgcgttgag catgcgtacg agatggcgct agagagagcg agataaaaag aaaaaaacaa  10440
ccggcgagtg gcgagacacg aataatacac acacgcacac atggtcaaag gagtggctcc  10500
aacgtcggtg acgtcgcgcc cagccacaga ccccgccacg ccccgcccca cccttccttc  10560
cgctgccccg cacccctttc cttccactac cgttttgccg catttggtat tgccatctcg  10620
ctttttggc tttactttgc tttttgaata agccaagaaa ctgaaatcaa agcggacagt  10680
ccgaaaattg aaactattcc aaaaaacaac aaccgcacat gcactgcgtt cggcaaaaga  10740
cgcagaaatc agcctgtggt ctggcatcat cttaaaatat catcagtatc atcattgcca  10800
ttataaatac ataagaaaat gagaatacat taaaggtata tacatacaat ctttgtcata  10860
gtcaacatat tttgcaacaa aattatctat agataacatg tttttgtaga aaattccact  10920
aactgatttt cgtataaata caaattattc tcattcttca aaatactcgc cgacgtcatc  10980
gcgaaattcc tcagcattct tcgacaaatg aagagagaca gcgagtgaca caatcttatc  11040
ttaccgacga gtctttgaaa atggccccgg gaacggtgaa aaacatatag ccaagaatgg  11100
agcgatcgcc aggcgatgga aattggcttc aaattgctcc gaatatggcc agttggtcag  11160
ttggcattgg attgtggaga gatactagat cagctcgttc tccttctcct ccgcattctc  11220
ctactcgccc gaagacgctt ctttgatcgc ttctttctcg aatgtacata ttgatatgta  11280
tttggtgttt ggcgacgatc agccagcttt aatggccata aaacgtgtct tggtttgtgg  11340
gccacataac aggcagcgag atctggaaaa atgatgtgac agtggaaatg agaagtaggt  11400
gcatctgcaa agatttgatt cagagttgat gccattcatg atttttttta gaagtatcat  11460
ttgtgttttt agaatataga attctagtat gtatgtaagt taataaaacc catttttgcg  11520
gaaagtagat aaaaaaaaca ttttttttt ttactgcact ggatatctgc              11570
```

<210> SEQ ID NO 18
<211> LENGTH: 11251
<212> TYPE: DNA
<213> ORGANISM: Artificial Sequence
<220> FEATURE:
<223> OTHER INFORMATION: Synthetic construct, plasmid pLA656

<400> SEQUENCE: 18
cgccaggcga tggaaattgg cttcaaattg ctccgaatat ggccagttgg tcagttggca 60
ttggattgtg gagagatact agatcagctc gttctccttc tcctccgcat tctcctactc 120
gcccgaagac gcttctttga tcgcttcttt ctcgaatgta catattgata tgtatttggt 180
gtttggcgac gatcagccag ctttaatggc cataaaacgt gtcttggttt gtgggccaca 240
taacaggcag cgagatctgg aaaaatgatg tgacagtgga aatgagaagt aggtgcatct 300
gcaaagattt gattcagagt tgatgccatt catgattttt tttagaagta tcatttgtgt 360
ttttagaata tagaattcta gtatgtatgt aagttaataa aacccatttt tgcggaaagt 420
agataaaaaa aacatttttt ttttttactg cactggatat ctgcggccgc tcatttaaat 480
ctggccggcc gcaaccattg tgggaaccgt gcgatcaaac aaacgcgaga taccggaagt 540
actgaaaaac agtcgctcca ggccagtggg aacatcgatg ttttgttttg acggacccct 600
tactctcgtc tcatataaac cgaagccagc taagatggta tacttattat catcttgtga 660
tgaggatgct tctatcaacg aaagtaccgg taaaccgcaa atggttatgt attataatca 720
aactaaaggc ggagtggaca cgctagacca aatgtgttct gtgatgacct gcagtaggaa 780
gacgaatagg tggcctatgg cattattgta cggaatgata aacattgcct gcataaattc 840
ttttattata tacagccata atgtcagtag caagggagaa aaggtccaaa gtcgcaaaaa 900
atttatgaga aacctttaca tgagcctgac gtcatcgttt atgcgtaagc gtttagaagc 960
tcctactttg aagagatatt tgcgcgataa tatctctaat attttgccaa atgaagtgcc 1020
tggtacatca gatgacagta ctgaagagcc agtaatgaaa aaacgtactt actgtactta 1080
ctgcccctct aaaataaggc gaaaggcaaa tgcatcgtgc aaaaaatgca aaaaagttat 1140
ttgtcgagag cataatattg atatgtgcca aagttgtttc tgactgacta ataagtataa 1200
tttgtttcta ttatgtataa gttaagctaa ttacttattt tataatacaa catgactgtt 1260
tttaaagtac aaaataagtt tatttttgta aaagagagaa tgtttaaaag ttttgttact 1320
ttatagaaga aattttgagt ttttgttttt ttttaataaa taaataaaca taaataaatt 1380
gtttgttgaa tttattatta gtatgtaagt gtaaatataa taaaacttaa tatctattca 1440
aattaataaa taaacctcga tatacagacc gataaaacac atgcgtcaat tttacgcatg 1500
attatcttta acgtacgtca caatatgatt atctttctag ggttaaataa tagtttctaa 1560
tttttttatt attcagcctg ctgtcgtgaa taccgtatat ctcaacgctg tctgtgagat 1620
tgtcgtattc tagccttttt agtttttcgc tcatcgactt gatattgtcc gacacatttt 1680
cgtcgatttg cgttttgatc aaagacttga gcagagacac gttaatcaac tgttcaaatt 1740
gatccatatt aacgatatca acccgatgcg tatatggtgc gtaaaatata ttttttaacc 1800
ctcttatact ttgcactctg cgttaatacg cgttcgtgta cagacgtaat catgttttct 1860
tttttggata aaactcctac tgagtttgac ctcatattag accctcacaa gttgcaaaac 1920
gtggcatttt ttaccaatga agaatttaaa gttattttaa aaaatttcat cacagattta 1980
aagaagaacc aaaaattaaa ttatttcaac agtttaatcg accagttaat caacgtgtac 2040
acagacgcgt cggcaaaaaa cacgcagccc gacgtgttgg ctaaaattat taaatcaact 2100

```
tgtgttatag tcacggattt gccgtccaac gtgttcctca aaaagttgaa gaccaacaag   2160
tttacggaca ctattaatta tttgattttg ccccacttca ttttgtggga tcacaatttt   2220
gttatatttt aaacaaagct tggcactggc cgtcgtttta caacgtcgtg actgggaaaa   2280
ccctggcgtt acccaactta atcgccttgc agcacatccc cctttcgcca gctggcgtaa   2340
tagcgaagag gcccgcaccg atcgcccttc ccaacagttg cgcagcctga atggcgaatg   2400
gcgcctgatg cggtattttc tccttacgca tctgtgcggt atttcacacc gcatatggtg   2460
cactctcagt acaatctgct ctgatgccgc atagttaagc cagccccgac acccgccaac   2520
acccgctgac gcgccctgac gggcttgtct gctcccggca tccgcttaca gacaagctgt   2580
gaccgtctcc gggagctgca tgtgtcagag gttttcaccg tcatcaccga aacgcgcgag   2640
acgaaagggc ctcgtgatac gcctattttt ataggttaat gtcatgataa taatggtttc   2700
ttagacgtca ggtggcactt ttcggggaaa tgtgcgcgga acccctattt gtttattttt   2760
ctaaatacat tcaaatatgt atccgctcat gagacaataa ccctgataaa tgcttcaata   2820
atattgaaaa aggaagagta tgagtattca acatttccgt gtcgccctta ttcccttttt   2880
tgcggcattt tgccttcctg tttttgctca cccagaaacg ctggtgaaag taaaagatgc   2940
tgaagatcag ttgggtgcac gagtgggtta catcgaactg gatctcaaca gcggtaagat   3000
ccttgagagt tttcgccccg aagaacgttt tccaatgatg agcactttta aagttctgct   3060
atgtggcgcg gtattatccc gtattgacgc cgggcaagag caactcggtc gccgcataca   3120
ctattctcag aatgacttgg ttgagtactc accagtcaca gaaaagcatc ttacggatgg   3180
catgacagta agagaattat gcagtgctgc cataaccatg agtgataaca ctgcggccaa   3240
cttacttctg acaacgatcg gaggaccgaa ggagctaacc gcttttttgc acaacatggg   3300
ggatcatgta actcgccttg atcgttggga accggagctg aatgaagcca taccaaacga   3360
cgagcgtgac accacgatgc ctgtagcaat ggcaacaacg ttgcgcaaac tattaactgg   3420
cgaactactt actctagctt cccggcaaca attaatagac tggatggagg cggataaagt   3480
tgcaggacca cttctgcgct cggcccttcc ggctggctgg tttattgctg ataaatctgg   3540
agccggtgag cgtgggtctc gcggtatcat tgcagcactg gggccagatg gtaagccctc   3600
ccgtatcgta gttatctaca cgacggggag tcaggcaact atggatgaac gaaatagaca   3660
gatcgctgag ataggtgcct cactgattaa gcattggtaa ctgtcagacc aagtttactc   3720
atatatactt tagattgatt taaaacttca tttttaattt aaaaggatct aggtgaagat   3780
cctttttgat aatctcatga ccaaaatccc ttaacgtgag ttttcgttcc actgagcgtc   3840
agaccccgta gaaaagatca aaggatcttc ttgagatcct ttttttctgc gcgtaatctg   3900
ctgcttgcaa acaaaaaaac caccgctacc agcggtggtt tgtttgccgg atcaagagct   3960
accaactctt tttccgaagg taactggctt cagcagagcg cagataccaa atactgtcct   4020
tctagtgtag ccgtagttag gccaccactt caagaactct gtagcaccgc ctacatacct   4080
cgctctgcta atcctgttac cagtggctgc tgccagtggc gataagtcgt gtcttaccgg   4140
gttggactca agacgatagt taccggataa ggcgcagcgg tcgggctgaa cggggggttc   4200
gtgcacacag cccagcttgg agcgaacgac ctacaccgaa ctgagatacc tacagcgtga   4260
gcattgagaa agcgccacgc ttcccgaagg gagaaaggcg gacaggtatc cggtaagcgg   4320
cagggtcgga acaggagagc gcacgaggga gcttccaggg ggaaacgcct ggtatcttta   4380
tagtcctgtc gggtttcgcc acctctgact tgagcgtcga tttttgtgat gctcgtcagg   4440
gggggcggagc ctatggaaaa acgccagcaa cgcggccttt ttacggttcc tggccttttg   4500
```

-continued

```
ctggcctttt gctcacatgt tctttcctgc gttatcccct gattctgtgg ataaccgtat   4560
taccgccttt gagtgagctg ataccgctcg ccgcagccga acgaccgagc gcagcgagtc   4620
agtgagcgag gaagcggaag agcgcccaat acgcaaaccg cctctccccg cgcgttggcc   4680
gattcattaa tgcagctggc acgacaggtt tcccgactgg aaagcgggca gtgagcgcaa   4740
cgcaattaat gtgagttagc tcactcatta ggcaccccag gctttacact ttatgcttcc   4800
ggctcgtatg ttgtgtggaa ttgtgagcgg ataacaattt cacacaggaa acagctatga   4860
ccatgattac gaatttcgac ctgcaggcat gcaagcttgc atgcctgcag gtcgacgctc   4920
gcgcgacttg gtttgccatt ctttagcgcg cgtcgcgtca cacagcttgg ccacaatgtg   4980
gtttttgtca aacgaagatt ctatgacgtg tttaaagttt aggtcgagta aagcgcaaat   5040
ctttttaac cctagaaaga tagtctgcgt aaaattgacg catgcattct tgaaatattg   5100
ctctctcttt ctaaatagcg cgaatccgtc gctgtgcatt taggacatct cagtcgccgc   5160
ttggagctcc cgtgaggcgt gcttgtcaat gcggtaagtg tcactgattt tgaactataa   5220
cgaccgcgtg agtcaaaatg acgcatgatt atcttttacg tgacttttaa gatttaactc   5280
atacgataat tatattgtta tttcatgttc tacttacgtg ataacttatt atatatatat   5340
tttcttgtta tagatatcgt gactaatata taataaaatg ggtagttctt tagacgatga   5400
gcatatcctc tctgctcttc tgcaaagcga tgacgagctt gttggtgagg attctgacag   5460
tgaaatatca gatcacgtaa gtgaagatga cgtccagagc gatacagaag aagcgtttat   5520
agatgaggta catgaagtgc agccaacgtc aagcggtagt gaaatattag acgaacaaaa   5580
tgttattgaa caaccaggtt cttcattggc ttctaacaga atcttgacct tgccacagag   5640
gactattaga ggtaagaata aacattgttg gtcaacttca aagtccacga ggcgtagccg   5700
agtctctgca ctgaacattg tcagatcggc ccgggcgccg tttttcttga aatattgctc   5760
tctctttcta aatagcgcga atccgtcgct gtgcatttag gacatctcag tcgccgcttg   5820
gagctcccaa acgcgccagt ggtagtacac agtactgtgg gtgttcagtt tgaaatcctc   5880
ttgcttctcc attgtctcgg ttacctttgg tcaaatccat gggttctatt gcctatatac   5940
tcttgcgatt accagtgatt gcgctattag ctattagatg gattgttggc caaacttgtc   6000
gcttaagtgg ctgggaattg taaccgtagg cccgagtgta atgatccccc ataaaaagtt   6060
ttcgcaatgc ctttattttt tgttgcaaat ctctctttat tctgcggtat tcttcattat   6120
tgcggggatg gggaaagtgt ttatatagaa gcaacttacg attgaaccca aatgcacctg   6180
acaagcaagg tcaaagggcc agatttttaa atatattatt tagtcttagg actctctatt   6240
tgcaattaaa ttactttgct acctgagggt taaatcttcc ccattgataa taataattcc   6300
actatatgtt caattgggtt tcaccgcgct tagttacatg acgagcccta atgagccgtc   6360
ggtggtctat aaactgtgcc ttacaaatac ttgcaactct tctcgttttg aagtcagcag   6420
agttattgct aattgctaat tgctaattgc ttttaactga tttcttcgaa attggtgcta   6480
tgtttatggc gctattaaca agtatgaatg tcaggtttaa ccaggggatg cttaattgtg   6540
ttctcaactt caaaggcaga aatgtttact cttgaccatg ggtttaggta taatgttatc   6600
aagctcctcg agttaacgtt acgttaacgt taacgttcga ggtcgactct agaactaccc   6660
accgtactcg tcaattccaa gggcatcggt aaacatctgc tcaaactcga agtcggccat   6720
atccagagcg ccgtaggggg cggagtcgtg gggggtaaat cccggacccg gggaatcccc   6780
gtcccccaac atgtccagat cgaaatcgtc tagcgcgtcg gcatgcgcca tcgccacgtc   6840
```

```
ctcgccgtct aagtggagct cgtcccccag gctgacatcg gtcggggggg ccgtcgacag   6900
tctgcgcgtg tgtcccgcgg ggagaaagga caggcgcgga gccgccagcc ccgcctcttc   6960
gggggcgtcg tcgtccggga gatcgagcag gccctcgatg gtagacccgt aattgttttt   7020
cgtacgcgcg cggctgtacg cggggcccga gcccgactcg catttcagtt gcttttccaa   7080
tccgcagata atcagctcca agccgaacag gaatgccggc tcggctcctt gatgatcgaa   7140
cagctcgatt gcctgacgca gcagtggggg catcgaatcg gttgttgggg tctcgcgctc   7200
ctcttttgcg acttgatgct cttggtcctc cagcacgcag cccagggtaa agtgaccgac   7260
ggcgctcaga gcgtagagag cattttccag gctgaagcct tgctggcaca ggaacgcgag   7320
ctggttctcc agtgtctcgt attgcttttc ggtcgggcgc gtgccgagat ggactttggc   7380
accgtctcgg tgggacagca gagcgcagcg gaacgacttg gcgttattgc ggaggaagtc   7440
ctgccaggac tcgccttcca acgggcaaaa atgcgtgtgg tggcggtcga gcatctcgat   7500
ggccagggca tccagcagcg cccgcttatt cttcacgtgc cagtagaggg tgggctgctc   7560
cacgcccagc ttctgcgcca acttgcgggt cgtcagtccc tcaatgccaa cttcgttcaa   7620
cagctccaac gcggagttga tgactttgga cttatccagg cggctgccca tggtggtttc   7680
taaaggtgtt ataaatcaaa ttagttttgt tttttcttga aaactttgcg tttcctttga   7740
tcaacttacc gccagggtac cgcagattgt ttagcttgtt cagctgcgct tgtttatttg   7800
cttagctttc gcttagcgac gtgttcactt tgcttgtttg aattgaattg tcgctccgta   7860
gacgaagcgc ctctatttat actccggcgc tcgttttcga gtttaccact ccctatcagt   7920
gatagagaaa agtgaaagtc gagtttacca ctccctatca gtgatagaga aaagtgaaag   7980
tcgagtttac cactccctat cagtgataga gaaaagtgaa agtcgagttt accactccct   8040
atcagtgata gagaaaagtg aaagtcgagt ttaccactcc ctatcagtga tagagaaaag   8100
tgaaagtcga gtttaccact ccctatcagt gatagagaaa agtgaaagtc gagtttacca   8160
ctccctatca gtgatagaga aaagtgaaag tcgaaacctg gcgcgcctct taattaactc   8220
gcgttaagat acattgatga gtttggacaa accacaacta gaatgcagtg aaaaaaatgc   8280
tttatttgtg aaatttgtga tgctattgct ttatttgtaa ccattataag ctgcaataaa   8340
caagttaaca acaacaattg cattcatttt atgtttcagg ttcaggggga ggtgtgggag   8400
gtttttttaaa gcaagtaaaa cctctacaaa tgtggtatgg ctgattatga tcagttatct   8460
agatccggtg gatcttacgg gtcctccacc ttccgctttt tcttgggtcg agatctcagg   8520
aacaggtggt ggcggccctc ggtgcgctcg tactgctcca cgatggtgta gtcctcgttg   8580
tgggaggtga tgtccagctt ggcgtccacg tagtagtagc cgggcagctg cacgggcttc   8640
ttggccatgt agatggactt gaactccacc aggtagtggc cgccgtcctt cagcttcagg   8700
gccttgtggg tctcgccctt cagcacgccg tcgcgggggt acaggcgctc ggtggaggcc   8760
tcccagccca tggtcttctt ctgcatcacg gggccgtcgg aggggaagtt cacgccgatg   8820
aacttcacct tgtagatgaa gcagccgtcc tgcagggagg agtcctgggt cacggtcgcc   8880
acgccgccgt cctcgaagtt catcacgcgc tcccacttga agccctcggg gaaggacagc   8940
ttcttgtagt cggggatgtc ggcggggtgc ttcacgtaca ccttggagcc gtactggaac   9000
tggggggaca ggatgtccca ggcgaagggc agggggccgc ccttggtcac cttcagcttc   9060
acggtgttgt ggccctcgta ggggcggccc tcgccctcgc cctcgatctc gaactcgtgg   9120
ccgttcacgg tgccctccat gcgcaccttg aagcgcatga actcggtgat gacgttctcg   9180
gaggaggcca tggtggcgac cggtttgcgc ttcttcttgg gtggggtggg atccccgatc   9240
```

```
tgcattttgg attattctgc gggtcaaaat agagatgtgg aaaattagta cgaaatcaaa   9300
tgagtttcgt tgaaattaca aaactattga aactaacttc ctggctgggg aataaaaatg   9360
ggaaacttat ttatcgacgc caactttgtt gagaaacccc tattaaccct ctacgaatat   9420
tggaacaaag gaaagcgaag aaacaggaac aaaggtagtt gagaaacctg ttccgttgct   9480
cgtcatcgtt ttcataatgc gagtgtgtgc atgtatatat acacagctga aacgcatgca   9540
tacacattat tttgtgtgta tatggtgacg tcacaactac taagcaataa gaaattttcc   9600
agacgtggct ttcgtttcaa gcaacctact ctatttcagc taaaaataag tggatttcgt   9660
tggtaaaata cttcaattaa gcaaagaact aactaactaa taacatgcac acaaatgctc   9720
gagtgcgttc gtgatttctc gaattttcaa atgcgtcact gcgaatttca caatttgcca   9780
ataaatcttg gcgaaaatca acacgcaagt tttatttata gatttgtttg cgttttgatg   9840
ccaattgatt gggaaaacaa gatgcgtggc tgccaatttc ttattttgta attacgtaga   9900
gcgttgaata aaaaaaaaat ggccgaacaa agaccttgaa atgcagtttt tcttgaaatt   9960
actcaacgtc ttgttgctct tattactaat tggtaacagc gagttaaaaa cttacgtttc  10020
ttgtgacttt cgagaatgtt cttttaattg tactttaatc accaacaatt aagtataaat  10080
ttttcgctga ttgcgcttta ctttctgctt gtacttgctg ctgcaaatgt caattggttt  10140
tgaaggcgac cgttcgcgaa cgctgtttat ataccttcgg tgtccgttga aaatcactaa  10200
aaaataccgt agtgttcgta acactttagt acagagaaaa aaaattgtgc cgaaatgttt  10260
ttgatacgta cgaatacctt gtattaaaat tttttatgat ttctgtgtat cacttttttt  10320
ttgtgttttt cgtttaaact caccacagta caaaacaata aaatattttt aagacaattt  10380
caaattgaga cctttctcgt actgacttga ccggctgaat gaggatttct acctagacga  10440
cctacttctt accatgacat tgaatgcaat gccacctttg atctaaactt acaaaagtcc  10500
aaggcttgtt aggattggtg tttatttagt ttgcttttga aatagcactg tcttctctac  10560
cggctataat tttgaaactc gcagcttgac tggaaattta aaaagtaatt ctgtgtaggt  10620
aaagggtgtt ttaaaagtgt gatgtgttga gcgttgcggc aacgactgct atttatgtat  10680
atattttcaa aacttattgt ttttgaagtg ttttaaatgg agctatctgg caacgctgcg  10740
cataatctta cacaagcttt tcttaatcca tttttaagtg aaatttgttt ttactctttc  10800
ggcaaataat tgttaaatcg ctttaagtgg gcttacatct ggataagtaa tgaaaacctg  10860
catattataa tattaaaaca tataatccac tgtgctttcc ccgtgtgtgg ccatatacct  10920
aaaaaagttt attttcgcag agccccgcac ggtcacacta cggttcggcg attttcgatt  10980
ttggacagta ctgattgcaa gcgcaccgaa agcaaaatgg agctggagat tttgaacgcg  11040
aagaacagca agccgtacgg caaggtgaag gtgccctccg gcgccacgcc catcggcgat  11100
ctgcgcgccc taattcacaa gaccctgaag cagaccccac acgcgaatcg ccagtcgctt  11160
cgtctggaac tgaagggcaa aagcctgaaa gatacggaca cattggaatc tctgtcgctg  11220
cgttccggcg acaagatcgg ggtaccgcga t                                 11251
```

<210> SEQ ID NO 19
<211> LENGTH: 9468
<212> TYPE: DNA
<213> ORGANISM: Artificial Sequence
<220> FEATURE:
<223> OTHER INFORMATION: Synthetic construct, plasmid pLA710

<400> SEQUENCE: 19

-continued

```
ggccgctcat ttaaatctgg ccggccgcaa ccattgtggg aaccgtgcga tcaaacaaac      60
gcgagatacc ggaagtactg aaaaacagtc gctccaggcc agtgggaaca tcgatgtttt     120
gttttgacgg acccccttact ctcgtctcat ataaaccgaa gccagctaag atggtatact     180
tattatcatc ttgtgatgag gatgcttcta tcaacgaaag taccggtaaa ccgcaaatgg     240
ttatgtatta taatcaaact aaaggcggag tggacacgct agaccaaatg tgttctgtga     300
tgacctgcag taggaagacg aataggtggc ctatggcatt attgtacgga atgataaaca     360
ttgcctgcat aaattctttt attatataca gccataatgt cagtagcaag ggagaaaagg     420
tccaaagtcg caaaaaattt atgagaaacc tttacatgag cctgacgtca tcgtttatgc     480
gtaagcgttt agaagctcct actttgaaga gatatttgcg cgataatatc tctaatattt     540
tgccaaatga agtgcctggt acatcagatg acagtactga agagccagta atgaaaaaac     600
gtacttactg tacttactgc ccctctaaaa taaggcgaaa ggcaaatgca tcgtgcaaaa     660
aatgcaaaaa agttatttgt cgagagcata atattgatat gtgccaaagt tgtttctgac     720
tgactaataa gtataatttg tttctattat gtataagtta agctaattac ttattttata     780
atacaacatg actgttttta aagtacaaaa taagtttatt tttgtaaaag agagaatgtt     840
taaaagtttt gttactttat agaagaaatt ttgagttttt gttttttttt aataaataaa     900
taaacataaa taaattgttt gttgaattta ttattagtat gtaagtgtaa atataataaa     960
acttaatatc tattcaaatt aataaataaa cctcgatata cagaccgata aaacacatgc    1020
gtcaatttta cgcatgatta tctttaacgt acgtcacaat atgattatct ttctagggtt    1080
aaataatagt ttctaatttt tttattattc agcctgctgt cgtgaatacc gtatatctca    1140
acgctgtctg tgagattgtc gtattctagc ctttttagtt tttcgctcat cgacttgata    1200
ttgtccgaca cattttcgtc gatttgcgtt ttgatcaaag acttgagcag agacacgtta    1260
atcaactgtt caaattgatc catattaacg atatcaaccc gatgcgtata tggtgcgtaa    1320
aatatatttt ttaaccctct tatactttgc actctgcgtt aatacgcgtt cgtgtacaga    1380
cgtaatcatg ttttcttttt tggataaaac tcctactgag tttgacctca tattagaccc    1440
tcacaagttg caaaacgtgg catttttttac caatgaagaa tttaaagtta ttttaaaaaa    1500
tttcatcaca gatttaaaga agaaccaaaa attaaattat ttcaacagtt taatcgacca    1560
gttaatcaac gtgtacacag acgcgtcggc aaaaaaacacg cagcccgacg tgttggctaa    1620
aattattaaa tcaacttgtg ttatagtcac ggatttgccg tccaacgtgt tcctcaaaaa    1680
gttgaagacc aacaagttta cggacactat taattatttg attttgcccc acttcatttt    1740
gtgggatcac aattttgtta tattttaaac aaagcttggc actggccgtc gttttacaac    1800
gtcgtgactg ggaaaaccct ggcgttaccc aacttaatcg ccttgcagca catccccctt    1860
tcgccagctg gcgtaatagc gaagaggccc gcaccgatcg cccttcccaa cagttgcgca    1920
gcctgaatgg cgaatggcgc ctgatgcggt attttctcct tacgcatctg tgcggtattt    1980
cacaccgcat atggtgcact ctcagtacaa tctgctctga tgccgcatag ttaagccagc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgagacga aagggcctcg tgatacgcct atttttatag gttaatgtca    2220
tgataataat ggtttcttag acgtcaggtg gcacttttcg gggaaatgtg cgcggaaccc    2280
ctatttgttt atttttctaa atacattcaa atatgtatcc gctcatgaga caataaccct    2340
gataaatgct tcaataatat tgaaaaagga agagtatgag tattcaacat ttccgtgtcg    2400
```

```
cccttattcc ctttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
ctgcaggtcg acgctcgcgc gacttggttt gccattcttt agcgcgcgtc gcgtcacaca   4500
gcttggccac aatgtggttt ttgtcaaacg aagattctat gacgtgttta aagtttaggt   4560
cgagtaaagc gcaaatcttt tttaacccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
```

-continued

```
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatattttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagacga acaaaatgtt attgaacaac caggttcttc attggcttct aacagaatct   5160
tgaccttgcc acagaggact attagaggta agaataaaca ttgttggtca acttcaaagt   5220
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tcccccataa aaagttttcg caatgccttt attttttgtt gcaaatctct ctttattctg   5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
ggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
acccgtaatt gtttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
```

-continued

```
tgccaacttc gttcaacagc tccaacgcgg agttgatgac tttggactta tccaggcggc   7200
tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
gggggaggtg tgggaggttt tttaaagcaa gtaaaacctc tacaaatgtg gtatggctga   7980
ttatgatcag ttatctagat ccggtggatc ttacgggtcc tccaccttcc gctttttctt   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatcc tcgtcgcaca tcttgaatta gtctgcaaga aaagaaaaaa aacaattcaa   8820
actacattct cattccatac attatactaa gtaaacgaca aatttatttg cgtccatcta   8880
tttagtgacg ttaaagaaaa ctgtataaga ttcataattc actgttccca atttctgttt   8940
ccgaattgat cgatgcgagt ggacactttg aaatgtgcgt ccaataaact tatttcttat   9000
ttagtagtgt ttattaacat ctgcagtaca ctaaattccg aaaaatgttt tttttttataa   9060
aaaatttcac ttcactagtt atgcaacaat tatgtaacgt aacacgttat cattagcgta   9120
ttattaaaaa aaaaaaacac tcaaacatat gtaatactta aaggtaaagg gacggagaac   9180
cttcgaaatt caaattttac aaataaataa atatgttttt ttttctttcg caattttaaa   9240
attaaaactt acatagtatt attaaataag tgacaagtac gtagatgcga atgcgcactg   9300
ttcgagcaca ccttagtaaa tgagaaccga ctcgtgagga taaactatat aaaagagccg   9360
ttatcacaat ttacacagta tcggctccag tttgtttttc caccaatcgc gggctgactc   9420
agtttttgtc accatatatg gtaacgcgca cgctatcagg taccatgc                9468
```

<210> SEQ ID NO 20
<211> LENGTH: 10140
<212> TYPE: DNA
<213> ORGANISM: Artificial Sequence
<220> FEATURE:
<223> OTHER INFORMATION: Synthetic construct, plasmid pLA928

<400> SEQUENCE: 20
ggccgctcat ttaaatctgg ccggccgcaa ccattgtggg aaccgtgcga tcaaacaaac 60
gcgagatacc ggaagtactg aaaaacagtc gctccaggcc agtgggaaca tcgatgtttt 120
gttttgacgg accccttact ctcgtctcat ataaaccgaa gccagctaag atggtatact 180
tattatcatc ttgtgatgag gatgcttcta tcaacgaaag taccggtaaa ccgcaaatgg 240
ttatgtatta taatcaaact aaaggcggag tggacacgct agaccaaatg tgttctgtga 300
tgacctgcag taggaagacg aataggtggc ctatggcatt attgtacgga atgataaaca 360
ttgcctgcat aaattctttt attatataca gccataatgt cagtagcaag ggagaaaagg 420
tccaaagtcg caaaaaattt atgagaaacc tttacatgag cctgacgtca tcgtttatgc 480
gtaagcgttt agaagctcct actttgaaga gatatttgcg cgataatatc tctaatattt 540
tgccaaatga agtgcctggt acatcagatg acagtactga agagccagta atgaaaaaac 600
gtacttactg tacttactgc ccctctaaaa taaggcgaaa ggcaaatgca tcgtgcaaaa 660
aatgcaaaaa agttatttgt cgagagcata atattgatat gtgccaaagt tgtttctgac 720
tgactaataa gtataatttg tttctattat gtataagtta agctaattac ttattttata 780
atacaacatg actgttttta aagtacaaaa taagtttatt tttgtaaaag agagaatgtt 840
taaaagtttt gttactttat agaagaaatt ttgagttttt gttttttttt aataaataaa 900
taaacataaa taaattgttt gttgaattta ttattagtat gtaagtgtaa atataataaa 960
acttaatatc tattcaaatt aataaataaa cctcgatata cagaccgata aaacacatgc 1020
gtcaatttta cgcatgatta tctttaacgt acgtcacaat atgattatct ttctagggtt 1080
aaataatagt ttctaatttt tttattattc agcctgctgt cgtgaatacc gtatatctca 1140
acgctgtctg tgagattgtc gtattctagc ctttttagtt tttcgctcat cgacttgata 1200
ttgtccgaca cattttcgtc gatttgcgtt ttgatcaaag acttgagcag agacacgtta 1260
atcaactgtt caaattgatc catattaacg atatcaaccc gatgcgtata tggtgcgtaa 1320
aatatatttt ttaaccctct tatactttgc actctgcgtt aatacgcgtt cgtgtacaga 1380
cgtaatcatg ttttcttttt tggataaaac tcctactgag tttgacctca tattagaccc 1440
tcacaagttg caaaacgtgg catttttttac caatgaagaa tttaaagtta ttttaaaaaa 1500
tttcatcaca gatttaaaga agaaccaaaa attaaattat ttcaacagtt taatcgacca 1560
gttaatcaac gtgtacacag acgcgtcggc aaaaaaacacg cagcccgacg tgttggctaa 1620
aattattaaa tcaacttgtg ttatagtcac ggatttgccg tccaacgtgt tcctcaaaaa 1680
gttgaagacc aacaagttta cggacactat taattatttg attttgcccc acttcatttt 1740
gtgggatcac aattttgtta tattttaaac aaagcttggc actggccgtc gttttacaac 1800
gtcgtgactg ggaaaaccct ggcgttaccc aacttaatcg ccttgcagca catccccctt 1860
tcgccagctg gcgtaatagc gaagaggccc gcaccgatcg cccttcccaa cagttgcgca 1920
gcctgaatgg cgaatggcgc ctgatgcggt attttctcct tacgcatctg tgcggtattt 1980
cacaccgcat atggtgcact ctcagtacaa tctgctctga tgccgcatag ttaagccagc 2040
cccgacaccc gccaacaccc gctgacgcgc cctgacgggc ttgtctgctc ccggcatccg 2100

-continued

```
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
```

-continued

```
ctgcaggtcg acgctcgcgc gacttggttt gccattcttt agcgcgcgtc gcgtcacaca   4500
gcttggccac aatgtggttt ttgtcaaacg aagattctat gacgtgttta aagtttaggt   4560
cgagtaaagc gcaaatcttt tttaacccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatatttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagacga acaaaatgtt attgaacaac caggttcttc attggcttct aacagaatct   5160
tgaccttgcc acagaggact attagaggta agaataaaca ttgttggtca acttcaaagt   5220
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tcccccataa aaagttttcg caatgccttt attttttgtt gcaaatctct ctttattctg   5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
ggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
acccgtaatt gtttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
```

```
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
tgccaacttc gttcaacagc tccaacgcgg agttgatgac tttggactta tccaggcggc   7200
tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
gggggaggtg tgggaggttt tttaaagcaa gtaaaacctc tacaaatgtg gtatggctga   7980
ttatgatcag ttatctagat ccggtggatc ttacgggtcc tccaccttcc gctttttctt   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatct cccatggtgg cctgaatctc aacttgcacc tgaaggtagt gcagcaagga   8820
tgagcaaaag ggaagaaccc agaaaagaac gggaaaactt accccaatta gaattgcttg   8880
tcgccgccag tgtcaacttg caactgaaac aatatccaac atgaacgtca atttatactg   8940
ccctaatggc gaacacgata acaatatttc ttttattatg ccctctaaaa ccaacgcggt   9000
tatcgtttat ttattcaaat tagatataga acatccgccg acatacaatg ttaatgcaaa   9060
aacgcgtttg gtgagcggat acgaaaacag tcggccgata aacattaatc tgaggtcgat   9120
aacaccgtcc ttgaacggaa cacgaggagc gtacgtgatc agctgcattc gcgcgccgcg   9180
```

cctttatcga gatttatttg catacaacaa gtacactgcg ccgttgggat ttgtggtaac 9240
gcgcacacat gcagagctgc aagtgtggca cattttgtct gtgcgcaaaa cctttgaagc 9300
caaaagtacg aggtccgtta cgggcatgct agcgcacacg gacaatggac ccgacaaatt 9360
ctacgccaag gatttaatga taatgtcggg caacgtatcc gttcatttta tcaataacct 9420
acaaaaatgt cgcgcgcatc acaaagacat cgatatattt aaacatttat gtcccgaact 9480
gcaaatcgat aatagtgttg tgcaacctcg agcgtccgtt tgatttaacg tatagcttgc 9540
aaatgaatta tttaattatc aatcatgttt tacgcgtaga attctacccg taaagcgagt 9600
ttagttatga gccatgtgca aaacatgaca tcagctttta tttttataac aaatgacatc 9660
atttcttgat tgtgttttac acgtagaatt ctactcgtaa agcgagttca gttttgaaaa 9720
acaaatgaca tcatcttttt gattgtgctt tacaagtaga attctacccg taaatcaagt 9780
tcggttttga aaaacaaatg agtcatattg tatgatatca tattgcaaaa caaatgactc 9840
atcaatcgat cgtgcgttac acgtagaatt ctactcgtaa agcgagttta tgagccgtgt 9900
gcaaaacatg acatcatctc gatttgaaaa acaaatgaca tcatccactg atcgtgcatt 9960
acaagtagaa ttctactcgt aaagccagtt cggttatgag ccgtgtacaa aacatgacat 10020
cagattatga ctcatacttg attgtgtttt acgcgtagaa ttctactcgt aaagccagtt 10080
caattttaaa aacaaatgac atcatccaaa ttaataaatg acaagcaatg ggtaccatgc 10140

<210> SEQ ID NO 21
<211> LENGTH: 10522
<212> TYPE: DNA
<213> ORGANISM: Artificial Sequence
<220> FEATURE:
<223> OTHER INFORMATION: Synthetic construct, plasmid pLA1124

<400> SEQUENCE: 21
gtggtttttg tcaaacgaag attctatgac gtgtttaaag tttaggtcga gtaaagcgca 60
aatctttttt aaccctagaa agatagtctg cgtaaaattg acgcatgcat tcttgaaata 120
ttgctctctc tttctaaata gcgcgaatcc gtcgctgtgc atttaggaca tctcagtcgc 180
cgcttggagc tcccgtgagg cgtgcttgtc aatgcggtaa gtgtcactga ttttgaacta 240
taacgaccgc gtgagtcaaa atgacgcatg attatctttt acgtgacttt taagatttaa 300
ctcatacgat aattatattg ttatttcatg ttctacttac gtgataactt attatatata 360
tattttcttg ttatagatat cgtgactaat atataataaa atgggtagtt ctttagacga 420
tgagcatatc ctctctgctc ttctgcaaag cgatgacgag cttgttggtg aggattctga 480
cagtgaaata tcagatcacg taagtgaaga tgacgtccag agcgatacag aagaagcgtt 540
tatagatgag gtacatgaag tgcagccaac gtcaagcggt agtgaaatat tagacgaaca 600
aaatgttatt gaacaaccag gttcttcatt ggcttctaac agaatcttga ccttgccaca 660
gaggactatt agaggtaaga ataaacattg ttggtcaact tcaaagtcca cgaggcgtag 720
ccgagtctct gcactgaaca ttgtcagatc ggcccgggcg ccgtttttct tgaaatattg 780
ctctctcttt ctaaatagcg cgaatccgtc gctgtgcatt taggacatct cagtcgccgc 840
ttggagctcc caaacgcgcc agtggtagta cacagtactg tgggtgttca gtttgaaatc 900
ctcttgcttc tccattgtct cggttacctt tggtcaaatc catgggttct attgcctata 960
tactcttgcg attaccagtg attgcgctat tagctattag atggattgtt ggccaaactt 1020
gtcgcttaag tggctgggaa ttgtaaccgt aggcccgagt gtaatgatcc cccataaaaa 1080
gttttcgcaa tgcctttatt ttttgttgca aatctctctt tattctgcgg tattcttcat 1140

```
tattgcgggg atggggaaag tgtttatata gaagcaactt acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
gtcggtggtc tataaactgt gccttacaaa tacttgcaac tcttctcgtt ttgaagtcag   1440
cagagttatt gctaattgct aattgctaat tgcttttaac tgatttcttc gaaattggtg   1500
ctatgtttat ggcgctatta acaagtatga atgtcaggtt taaccagggg atgcttaatt   1560
gtgttctcaa cttcaaaggc agaaatgttt actcttgacc atgggtttag gtataatgtt   1620
atcaagctcc tcgagttaac gttacgttaa cgttaacgtt cgaggtcgac tctagaacta   1680
cccaccgtac tcgtcaattc caagggcatc ggtaaacatc tgctcaaact cgaagtcggc   1740
catatccaga gcgccgtagg gggcggagtc gtggggggta aatcccggac ccggggaatc   1800
cccgtccccc aacatgtcca gatcgaaatc gtctagcgcg tcggcatgcg ccatcgccac   1860
gtcctcgccg tctaagtgga gctcgtcccc caggctgaca tcggtcgggg gggccgtcga   1920
cagtctgcgc gtgtgtcccg cggggagaaa ggacaggcgc ggagccgcca gccccgcctc   1980
ttcgggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacg tgccagtaga gggtgggctg   2580
ctccacgccc agcttctgcg ccaacttgcg ggtcgtcagt ccctcaatgc caacttcgtt   2640
caacagctcc aacgcggagt tgatgacttt ggacttatcc aggcggctgc ccatggtggt   2700
ttctaaaggt gttataaatc aaattagttt tgtttttttct tgaaaacttt gcgtttcctt   2760
tgatcaactt accgccaggg taccgcagat tgtttagctt gttcagctgc gcttgtttat   2820
ttgcttagct ttcgcttagc gacgtgttca ctttgcttgt ttgaattgaa ttgtcgctcc   2880
gtagacgaag cgcctctatt tatactccgg cgctcgtttt cgagtttacc actccctatc   2940
agtgatagag aaaagtgaaa gtcgagttta ccactcccta tcagtgatag agaaaagtga   3000
aagtcgagtt taccactccc tatcagtgat agagaaaagt gaaagtcgag tttaccactc   3060
cctatcagtg atagagaaaa gtgaaagtcg agtttaccac tccctatcag tgatagagaa   3120
aagtgaaagt cgagtttacc actccctatc agtgatagag aaaagtgaaa gtcgagttta   3180
ccactcccta tcagtgatag agaaaagtga aagtcgaaac ctggcgcgcc ccggccatcg   3240
agaaagagag agagaagaga agagagagaa cattcgagaa agagagagag aagagaagag   3300
agagaacata ctccctatca gtgatagaga agtccctatc agtgatagag atgtccctat   3360
cagtgataga gagttcccta tcagtgatag agacgtccct atcagtgata gagaagtccc   3420
tatcagtgat agagagatcc ctatcagtga tagagatttc cctatcagtg atagagaggt   3480
```

```
ccctatcagt gatagagact tccctatcag tgatagagaa atccctatca gtgatagaga   3540
catccctatc agtgatagag aactccctat cagtgataga gacctcccta tcagtgatag   3600
agatcgatgc ggccgcatgg tacccattgc ttgtcattta ttaatttgga tgatgtcatt   3660
tgtttttaaa attgaactgg ctttacgagt agaattctac gcgtaaaaca caatcaagta   3720
tgagtcataa tctgatgtca tgttttgtac acggctcata accgaactgg ctttacgagt   3780
agaattctac ttgtaatgca cgatcagtgg atgatgtcat ttgtttttca aatcgagatg   3840
atgtcatgtt ttgcacacgg ctcataaact cgctttacga gtagaattct acgtgtaacg   3900
cacgatcgat tgatgagtca tttgttttgc aatatgatat catacaatat gactcatttg   3960
tttttcaaaa ccgaacttga tttacgggta gaattctact tgtaaagcac aatcaaaaag   4020
atgatgtcat ttgtttttca aaactgaact cgctttacga gtagaattct acgtgtaaaa   4080
cacaatcaag aaatgatgtc atttgttata aaaataaaag ctgatgtcat gttttgcaca   4140
tggctcataa ctaaactcgc tttacgggta gaattctacg cgtaaaacat gattgataat   4200
taaataattc atttgcaagc tatacgttaa atcaaacgga cgctcgaggt tgcacaacac   4260
tattatcgat ttgcagttcg ggacataaat gtttaaatat atcgatgtct ttgtgatgcg   4320
cgcgacattt ttgtaggtta ttgataaaat gaacggatac gttgcccgac attatcatta   4380
aatccttggc gtagaatttg tcgggtccat tgtccgtgtg cgctagcatg cccgtaacgg   4440
acctcgtact tttggcttca aaggttttgc gcacagacaa aatgtgccac acttgcagct   4500
ctgcatgtgt gcgcgttacc acaaatccca acggcgcagt gtacttgttg tatgcaaata   4560
aatctcgata aaggcgcggc gcgcgaatgc agctgatcac gtacgctcct cgtgttccgt   4620
tcaaggacgg tgttatcgac ctcagattaa tgtttatcgg ccgactgttt tcgtatccgc   4680
tcaccaaacg cgtttttgca ttaacattgt atgtcggcgg atgttctata tctaatttga   4740
ataaataaac gataaccgcg ttggttttag agggcataat aaaagaaata ttgttatcgt   4800
gttcgccatt agggcagtat aaattgacgt tcatgttgga tattgtttca gttgcaagtt   4860
gacactggcg gcgacaagca attctaattg gggtaagttt tcccgttctt ttctgggttc   4920
ttccctttgg ctcatccttg ctgcactacc ttcaggtgca agttgagatt caggccacca   4980
tgggagatcc caccccaccc aagaagaagc gcaaaccggt cgccaccatg gcctcctccg   5040
agaacgtcat caccgagttc atgcgcttca aggtgcgcat ggagggcacc gtgaacggcc   5100
acgagttcga gatcgagggc gagggcgagg gccgccccta cgagggccac aacaccgtga   5160
agctgaaggt gaccaagggc ggcccctgc ccttcgcctg ggacatcctg tccccccagt   5220
tccagtacgg ctccaaggtg tacgtgaagc accccgccga catccccgac tacaagaagc   5280
tgtccttccc cgagggcttc aagtgggagc gcgtgatgaa cttcgaggac ggcggcgtgg   5340
cgaccgtgac ccaggactcc tccctgcagg acggctgctt catctacaag gtgaagttca   5400
tcggcgtgaa cttcccctcc gacggccccg tgatgcagaa gaagaccatg ggctgggagg   5460
cctccaccga gcgcctgtac ccccgcgacg gcgtgctgaa gggcgagacc cacaaggccc   5520
tgaagctgaa ggacggcggc cactacctgg tggagttcaa gtccatctac atggccaaga   5580
agcccgtgca gctgcccggc tactactacg tggacgccaa gctggacatc acctcccaca   5640
acgaggacta caccatcgtg gagcagtacg agcgcaccga gggccgccac cacctgttcc   5700
tgagatctcg acccaagaaa aagcggaagg tggaggaccc gtaagatcca ccggatctag   5760
ataactgatc ataatcagcc ataccacatt tgtagaggtt ttacttgctt taaaaaacct   5820
cccacacctc cccctgaacc tgaaacataa aatgaatgca attgttgttg ttaacttgtt   5880
```

-continued

```
tattgcagct tataatggtt acaaataaag caatagcatc acaaatttca caaataaagc   5940
atttttttca ctgcattcta gttgtggttt gtccaaactc atcaatgtat cttaacgcga   6000
gttaattaag gccgctcatt taaatctggc cggccgcaac cattgtggga accgtgcgat   6060
caaacaaacg cgagataccg gaagtactga aaaacagtcg ctccaggcca gtgggaacat   6120
cgatgttttg ttttgacgga ccccttactc tcgtctcata taaaccgaag ccagctaaga   6180
tggtatactt attatcatct tgtgatgagg atgcttctat caacgaaagt accggtaaac   6240
cgcaaatggt tatgtattat aatcaaacta aaggcggagt ggacacgcta gaccaaatgt   6300
gttctgtgat gacctgcagt aggaagacga ataggtggcc tatggcatta ttgtacggaa   6360
tgataaacat tgcctgcata aattctttta ttatatacag ccataatgtc agtagcaagg   6420
gagaaaaggt ccaaagtcgc aaaaaattta tgagaaacct ttacatgagc ctgacgtcat   6480
cgtttatgcg taagcgttta gaagctccta ctttgaagag atatttgcgc gataatatct   6540
ctaatatttt gccaaatgaa gtgcctggta catcagatga cagtactgaa gagccagtaa   6600
tgaaaaaacg tacttactgt acttactgcc cctctaaaat aaggcgaaag gcaaatgcat   6660
cgtgcaaaaa atgcaaaaaa gttatttgtc gagagcataa tattgatatg tgccaaagtt   6720
gtttctgact gactaataag tataatttgt ttctattatg tataagttaa gctaattact   6780
tattttataa tacaacatga ctgtttttaa agtacaaaat aagtttattt ttgtaaaaga   6840
gagaatgttt aaaagttttg ttactttata gaagaaattt tgagtttttg ttttttttta   6900
ataaataaat aaacataaat aaattgtttg ttgaatttat tattagtatg taagtgtaaa   6960
tataataaaa cttaatatct attcaaatta ataaataaac ctcgatatac agaccgataa   7020
aacacatgcg tcaattttac gcatgattat ctttaacgta cgtcacaata tgattatctt   7080
tctagggtta aataatagtt tctaattttt ttattattca gcctgctgtc gtgaataccg   7140
tatatctcaa cgctgtctgt gagattgtcg tattctagcc tttttagttt ttcgctcatc   7200
gacttgatat tgtccgacac attttcgtcg atttgcgttt tgatcaaaga cttgagcaga   7260
gacacgttaa tcaactgttc aaattgatcc atattaacga tatcaacccg atgcgtatat   7320
ggtgcgtaaa atatattttt taaccctctt atactttgca ctctgcgtta atacgcgttc   7380
gtgtacagac gtaatcatgt tttctttttt ggataaaact cctactgagt ttgacctcat   7440
attagaccct cacaagttgc aaaacgtggc attttttacc aatgaagaat ttaaagttat   7500
tttaaaaaat ttcatcacag atttaaagaa gaaccaaaaa ttaaattatt tcaacagttt   7560
aatcgaccag ttaatcaacg tgtacacaga cgcgtcggca aaaaacacgc agcccgacgt   7620
gttggctaaa attattaaat caacttgtgt tatagtcacg gatttgccgt ccaacgtgtt   7680
cctcaaaaag ttgaagacca acaagtttac ggacactatt aattatttga ttttgcccca   7740
cttcattttg tgggatcaca attttgttat attttaaaca aagcttggca ctggccgtcg   7800
ttttacaacg tcgtgactgg gaaaaccctg gcgttaccca acttaatcgc cttgcagcac   7860
atcccccttt cgccagctgg cgtaatagcg aagaggcccg caccgatcgc ccttcccaac   7920
agttgcgcag cctgaatggc gaatggcgcc tgatgcggta ttttctcctt acgcatctgt   7980
gcggtatttc acaccgcata tggtgcactc tcagtacaat ctgctctgat gccgcatagt   8040
taagccagcc ccgacacccg ccaacacccg ctgacgcgcc ctgacgggct tgtctgctcc   8100
cggcatccgc ttacagacaa gctgtgaccg tctccgggag ctgcatgtgt cagaggtttt   8160
caccgtcatc accgaaacgc gcgagacgaa agggcctcgt gatacgccta tttttatagg   8220
```

-continued

```
ttaatgtcat gataataatg gtttcttaga cgtcaggtgg cacttttcgg ggaaatgtgc   8280
gcggaacccc tatttgttta tttttctaaa tacattcaaa tatgtatccg ctcatgagac   8340
aataaccctg ataaatgctt caataatatt gaaaaaggaa gagtatgagt attcaacatt   8400
tccgtgtcgc ccttattccc ttttttgcgg cattttgcct tcctgttttt gctcacccag   8460
aaacgctggt gaaagtaaaa gatgctgaag atcagttggg tgcacgagtg ggttacatcg   8520
aactggatct caacagcggt aagatccttg agagttttcg ccccgaagaa cgttttccaa   8580
tgatgagcac ttttaaagtt ctgctatgtg gcgcggtatt atcccgtatt gacgccgggc   8640
aagagcaact cggtcgccgc atacactatt ctcagaatga cttggttgag tactcaccag   8700
tcacagaaaa gcatcttacg gatggcatga cagtaagaga attatgcagt gctgccataa   8760
ccatgagtga taacactgcg gccaacttac ttctgacaac gatcggagga ccgaaggagc   8820
taaccgcttt tttgcacaac atgggggatc atgtaactcg ccttgatcgt tgggaaccgg   8880
agctgaatga agccatacca aacgacgagc gtgacaccac gatgcctgta gcaatggcaa   8940
caacgttgcg caaactatta actggcgaac tacttactct agcttcccgg caacaattaa   9000
tagactggat ggaggcggat aaagttgcag gaccacttct gcgctcggcc cttccggctg   9060
gctggtttat tgctgataaa tctggagccg gtgagcgtgg gtctcgcggt atcattgcag   9120
cactggggcc agatggtaag ccctcccgta tcgtagttat ctacacgacg gggagtcagg   9180
caactatgga tgaacgaaat agacagatcg ctgagatagg tgcctcactg attaagcatt   9240
ggtaactgtc agaccaagtt tactcatata tactttagat tgatttaaaa cttcattttt   9300
aatttaaaag gatctaggtg aagatccttt ttgataatct catgaccaaa atcccttaac   9360
gtgagttttc gttccactga gcgtcagacc ccgtagaaaa gatcaaagga tcttcttgag   9420
atcctttttt tctgcgcgta atctgctgct tgcaaacaaa aaaaccaccg ctaccagcgg   9480
tggtttgttt gccggatcaa gagctaccaa ctctttttcc gaaggtaact ggcttcagca   9540
gagcgcagat accaaatact gtccttctag tgtagccgta gttaggccac cacttcaaga   9600
actctgtagc accgcctaca tacctcgctc tgctaatcct gttaccagtg gctgctgcca   9660
gtggcgataa gtcgtgtctt accgggttgg actcaagacg atagttaccg gataaggcgc   9720
agcggtcggg ctgaacgggg ggttcgtgca cacagcccag cttggagcga acgacctaca   9780
ccgaactgag atacctacag cgtgagcatt gagaaagcgc cacgcttccc gaagggagaa   9840
aggcggacag gtatccggta agcggcaggg tcggaacagg agagcgcacg agggagcttc   9900
caggggggaaa cgcctggtat ctttatagtc ctgtcgggtt tcgccacctc tgacttgagc   9960
gtcgattttt gtgatgctcg tcaggggggc ggagcctatg gaaaaacgcc agcaacgcgg  10020
cctttttacg gttcctggcc ttttgctggc cttttgctca catgttcttt cctgcgttat  10080
cccctgattc tgtggataac cgtattaccg cctttgagtg agctgatacc gctcgccgca  10140
gccgaacgac cgagcgcagc gagtcagtga gcgaggaagc ggaagagcgc ccaatacgca  10200
aaccgcctct ccccgcgcgt tggccgattc attaatgcag ctggcacgac aggtttcccg  10260
actggaaagc gggcagtgag cgcaacgcaa ttaatgtgag ttagctcact cattaggcac  10320
cccaggcttt acactttatg cttccggctc gtatgttgtg tggaattgtg agcggataac  10380
aatttcacac aggaaacagc tatgaccatg attacgaatt tcgacctgca ggcatgcaag  10440
cttgcatgcc tgcaggtcga cgctcgcgcg acttggtttg ccattcttta gcgcgcgtcg  10500
cgtcacacag cttggccaca at                                           10522
```

<210> SEQ ID NO 22
<211> LENGTH: 11867
<212> TYPE: DNA
<213> ORGANISM: Artificial Sequence
<220> FEATURE:
<223> OTHER INFORMATION: Synthetic construct, plasmid pLA1188

<400> SEQUENCE: 22 gtggttttg tcaaacgaag attctatgac gtgtttaaag tttaggtcga gtaaagcgca 60 aatcttttt aaccctagaa agatagtctg cgtaaaattg acgcatgcat tcttgaaata 120
ttgctctctc tttctaaata gcgcgaatcc gtcgctgtgc atttaggaca tctcagtcgc 180
cgcttggagc tcccgtgagg cgtgcttgtc aatgcggtaa gtgtcactga ttttgaacta 240
taacgaccgc gtgagtcaaa atgacgcatg attatctttt acgtgacttt taagatttaa 300
ctcatacgat aattatattg ttatttcatg ttctacttac gtgataactt attatatata 360
tattttcttg ttatagatat cgtgactaat atataataaa atgggtagtt ctttagacga 420
tgagcatatc ctctctgctc ttctgcaaag cgatgacgag cttgttggtg aggattctga 480
cagtgaaata tcagatcacg taagtgaaga tgacgtccag agcgatacag aagaagcgtt 540
tatagatgag gtacatgaag tgcagccaac gtcaagcggt agtgaaatat tagacgaaca 600
aaatgttatt gaacaaccag gttcttcatt ggcttctaac agaatcttga ccttgccaca 660
gaggactatt agaggtaaga ataaacattg ttggtcaact tcaaagtcca cgaggcgtag 720
ccgagtctct gcactgaaca ttgtcagatc ggcccgggcg ccgtttttct tgaaatattg 780
ctctctcttt ctaaatagcg cgaatccgtc gctgtgcatt taggacatct cagtcgccgc 840
ttggagctcc caaacgcgcc agtggtagta cacagtactg tgggtgttca gtttgaaatc 900
ctcttgcttc tccattgtct cggttacctt tggtcaaatc catgggttct attgcctata 960
tactcttgcg attaccagtg attgcgctat tagctattag atggattgtt ggccaaactt 1020
gtcgcttaag tggctgggaa ttgtaaccgt aggcccgagt gtaatgatcc cccataaaaa 1080
gttttcgcaa tgcctttatt ttttgttgca aatctctctt tattctgcgg tattcttcat 1140
tattgcgggg atggggaaag tgtttatata gaagcaactt acgattgaac ccaaatgcac 1200
ctgacaagca aggtcaaagg gccagatttt taaatatatt atttagtctt aggactctct 1260
atttgcaatt aaattacttt gctacctgag ggttaaatct tccccattga taataataat 1320
tccactatat gttcaattgg gtttcaccgc gcttagttac atgacgagcc ctaatgagcc 1380
gtcggtggtc tataaactgt gccttacaaa tacttgcaac tcttctcgtt ttgaagtcag 1440
cagagttatt gctaattgct aattgctaat tgcttttaac tgatttcttc gaaattggtg 1500
ctatgtttat ggcgctatta acaagtatga atgtcaggtt taaccagggg atgcttaatt 1560
gtgttctcaa cttcaaaggc agaaatgttt actcttgacc atgggtttag gtataatgtt 1620
atcaagctcc tcgagttaac gttacgttaa cgttaacgtt cgaggtcgac tctagaacta 1680
cccaccgtac tcgtcaattc caagggcatc ggtaaacatc tgctcaaact cgaagtcggc 1740
catatccaga gcgccgtagg gggcggagtc gtggggggta aatcccggac ccggggaatc 1800
cccgtccccc aacatgtcca gatcgaaatc gtctagcgcg tcggcatgcg ccatcgccac 1860
gtcctcgccg tctaagtgga gctcgtcccc caggctgaca tcggtcgggg gggccgtcga 1920
cagtctgcgc gtgtgtcccg cggggagaaa ggacaggcgc ggagccgcca gccccgcctc 1980
ttcgggggcg tcgtcgtccg ggagatcgag caggccctcg atggtagacc cgtaattgtt 2040
tttcgtacgc gcgcggctgt acgcggggcc cgagcccgac tcgcatttca gttgcttttc 2100

-continued

```
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacc tatagatacc atagatgtat   2580
ggattagtat catatacata caaaggctat ttttgggaca tattaatatt aacaatttcc   2640
gtgatagttt tcaccatttt tgttgaatgt tacgttgaaa atttaaattt gttttaaatt   2700
aattttacca gtcatgtgtt cttaaaagtt tttatgattg aaacggcata aagtggttca   2760
aaaatttatc aagaaaggct ttcctttttt aaatcttatc tttttctctt aaaaatcact   2820
agtcaattca ttattaattt gttaacttga atttggaatg tctatttact ttcagataaa   2880
ttaaagcaag aaacttaata ttcgaaaaaa attgattcta aatggaattt cacttgatct   2940
tcatgtatgc atatcaattt ttatttacat tgtataataa gtttcgagtt gattgttgta   3000
atccacaggt gtcccagaga attaaattcc aaattaccca agtttattga atgttgattg   3060
tagtttcagt tgctttgttg ctgcaacaat ggcttgttga ttgtagatat tttccctttc   3120
cttggtttac ttattacata gactgaaaaa gaggtttact tttttgatac ttatgaaaaa   3180
tttctattag tgattactaa ccaatcgcta tatgtttact agaaaacaaa taaactcttt   3240
acattaacat tcaataatgt ttgctctgta accgacaatt gaaggcgtta cagcaacagt   3300
aatataacta gcttcttaac cctcatctat taaccccatc gtttaaaaca ctatgttaaa   3360
tggtctaaca aatctagata ctaatagatg tcttattact tagcagccac agctgcaaca   3420
tccaagacaa tttttgaaac ttcttattga gctcttggca gcagaaatgt tggtattttt   3480
cacagctttc tgaaagaccg gcaccttcct ccggttcccg tttctgaatt caagaggatt   3540
tccgaccccc aattaatccc gaaacaaata aggtatattc aaaatgatgg aaaagtcatg   3600
gctgctgacc ttatttttat tcctattgat agaatattat tcccctttta aatacactgt   3660
actaagaggt ccggctataa ttttactcac ttgtcgatta tcccatagaa tgttgattgt   3720
agttggttgc ttttccaggt gagagttgat caagtcacaa aagttagcgt gtgttgattg   3780
tagatttgaa ggtaaaataa tttttgcacc cattcatcgg gtaaaacgtt ctccatagaa   3840
tacatttcca tcgataattg ataacttatg aatttcaaag aaaaaaatat gcttttaaaa   3900
ttacgtgcca gtagagggtg ggctgctcca cgcccagctt ctgcgccaac ttgcgggtcg   3960
tcagtccctc aatgccaact tcgttcaaca gctccaacgc ggagttgatg actttggact   4020
tatccaggcg gctgcccatg gtggtttcta aaggtgttat aaatcaaatt agttttgttt   4080
tttcttgaaa actttgcgtt tcctttgatc aacttaccgc cagggtaccg cagattgttt   4140
agcttgttca gctgcgcttg tttatttgct tagctttcgc ttagcgacgt gttcactttg   4200
cttgtttgaa ttgaattgtc gctccgtaga cgaagcgcct ctatttatac tccggcgctc   4260
gttttcgagt ttaccactcc ctatcagtga tagagaaaag tgaaagtcga gtttaccact   4320
ccctatcagt gatagagaaa agtgaaagtc gagtttacca ctccctatca gtgatagaga   4380
aaagtgaaag tcgagtttac cactccctat cagtgataga gaaaagtgaa agtcgagttt   4440
accactccct atcagtgata gagaaaagtg aaagtcgagt ttaccactcc ctatcagtga   4500
```

```
tagagaaaag tgaaagtcga gtttaccact ccctatcagt gatagagaaa agtgaaagtc   4560
gaaacctggc gcgccccggc catcgagaaa gagagagaga agagaagaga gagaacattc   4620
gagaaagaga gagagaagag aagagagaga acatactccc tatcagtgat agagaagtcc   4680
ctatcagtga tagagatgtc cctatcagtg atagagagtt ccctatcagt gatagagacg   4740
tccctatcag tgatagagaa gtccctatca gtgatagaga gatccctatc agtgatagag   4800
atttccctat cagtgataga gaggtcccta tcagtgatag agacttccct atcagtgata   4860
gagaaatccc tatcagtgat agagacatcc ctatcagtga tagagaactc cctatcagtg   4920
atagagacct ccctatcagt gatagagatc gatgcggccg catggtaccc attgcttgtc   4980
atttattaat ttggatgatg tcatttgttt ttaaaattga actggcttta cgagtagaat   5040
tctacgcgta aaacacaatc aagtatgagt cataatctga tgtcatgttt tgtacacggc   5100
tcataaccga actggcttta cgagtagaat tctacttgta atgcacgatc agtggatgat   5160
gtcatttgtt tttcaaatcg agatgatgtc atgttttgca cacggctcat aaactcgctt   5220
tacgagtaga attctacgtg taacgcacga tcgattgatg agtcatttgt tttgcaatat   5280
gatatcatac aatatgactc atttgttttt caaaaccgaa cttgatttac gggtagaatt   5340
ctacttgtaa agcacaatca aaaagatgat gtcatttgtt tttcaaaact gaactcgctt   5400
tacgagtaga attctacgtg taaaacacaa tcaagaaatg atgtcatttg ttataaaaat   5460
aaaagctgat gtcatgtttt gcacatggct cataactaaa ctcgctttac gggtagaatt   5520
ctacgcgtaa aacatgattg ataattaaat aattcatttg caagctatac gttaaatcaa   5580
acggacgctc gaggttgcac aacactatta tcgatttgca gttcgggaca taaatgttta   5640
aatatatcga tgtctttgtg atgcgcgcga catttttgta ggttattgat aaaatgaacg   5700
gatacgttgc ccgacattat cattaaatcc ttggcgtaga atttgtcggg tccattgtcc   5760
gtgtgcgcta gcatgcccgt aacggacctc gtacttttgg cttcaaaggt tttgcgcaca   5820
gacaaaatgt gccacacttg cagctctgca tgtgtgcgcg ttaccacaaa tcccaacggc   5880
gcagtgtact tgttgtatgc aaataaatct cgataaaggc gcggcgcgcg aatgcagctg   5940
atcacgtacg ctcctcgtgt tccgttcaag gacggtgtta tcgacctcag attaatgttt   6000
atcggccgac tgttttcgta tccgctcacc aaacgcgttt ttgcattaac attgtatgtc   6060
ggcggatgtt ctatatctaa tttgaataaa taaacgataa ccgcgttggt tttagagggc   6120
ataataaaag aaatattgtt atcgtgttcg ccattagggc agtataaatt gacgttcatg   6180
ttggatattg tttcagttgc aagttgacac tggcggcgac aagcaattct aattggggta   6240
agttttcccg ttcttttctg ggttcttccc ttttgctcat ccttgctgca ctaccttcag   6300
gtgcaagttg agattcaggc caccatggga gatcccaccc cacccaagaa gaagcgcaaa   6360
ccggtcgcca ccatggcctc ctccgagaac gtcatcaccg agttcatgcg cttcaaggtg   6420
cgcatggagg gcaccgtgaa cggccacgag ttcgagatcg agggcgaggg cgagggccgc   6480
ccctacgagg gccacaacac cgtgaagctg aaggtgacca agggcggccc cctgcccttc   6540
gcctgggaca tcctgtcccc ccagttccag tacggctcca aggtgtacgt gaagcacccc   6600
gccgacatcc ccgactacaa gaagctgtcc ttccccgagg gcttcaagtg ggagcgcgtg   6660
atgaacttcg aggacggcgg cgtggcgacc gtgacccagg actcctccct gcaggacggc   6720
tgcttcatct acaaggtgaa gttcatcggc gtgaacttcc cctccgacgg ccccgtgatg   6780
cagaagaaga ccatgggctg ggaggcctcc accgagcgcc tgtacccccg cgacggcgtg   6840
```

-continued

```
ctgaagggcg agacccacaa ggccctgaag ctgaaggacg gcggccacta cctggtggag   6900
ttcaagtcca tctacatggc caagaagccc gtgcagctgc ccggctacta ctacgtggac   6960
gccaagctgg acatcacctc ccacaacgag gactacacca tcgtggagca gtacgagcgc   7020
accgagggcc gccaccacct gttcctgaga tctcgaccca agaaaaagcg gaaggtggag   7080
gacccgtaag atccaccgga tctagataac tgatcataat cagccatacc acatttgtag   7140
aggttttact tgctttaaaa aacctcccac acctcccccct gaacctgaaa cataaaatga   7200
atgcaattgt tgttgttaac ttgtttattg cagcttataa tggttacaaa taaagcaata   7260
gcatcacaaa tttcacaaat aaagcatttt tttcactgca ttctagttgt ggtttgtcca   7320
aactcatcaa tgtatcttaa cgcgagttaa ttaaggccgc tcatttaaat ctggccggcc   7380
gcaaccattg tgggaaccgt gcgatcaaac aaacgcgaga taccggaagt actgaaaaac   7440
agtcgctcca ggccagtggg aacatcgatg ttttgttttg acggacccct tactctcgtc   7500
tcatataaac cgaagccagc taagatggta tacttattat catcttgtga tgaggatgct   7560
tctatcaacg aaagtaccgg taaaccgcaa atggttatgt attataatca aactaaaggc   7620
ggagtggaca cgctagacca aatgtgttct gtgatgacct gcagtaggaa gacgaatagg   7680
tggcctatgg cattattgta cggaatgata aacattgcct gcataaattc ttttattata   7740
tacagccata atgtcagtag caagggagaa aaggtccaaa gtcgcaaaaa atttatgaga   7800
aacctttaca tgagcctgac gtcatcgttt atgcgtaagc gtttagaagc tcctactttg   7860
aagagatatt tgcgcgataa tatctctaat attttgccaa atgaagtgcc tggtacatca   7920
gatgacagta ctgaagagcc agtaatgaaa aaacgtactt actgtactta ctgcccctct   7980
aaaataaggc gaaaggcaaa tgcatcgtgc aaaaaatgca aaaaagttat ttgtcgagag   8040
cataatattg atatgtgcca aagttgtttc tgactgacta ataagtataa tttgtttcta   8100
ttatgtataa gttaagctaa ttacttattt tataatacaa catgactgtt tttaaagtac   8160
aaaataagtt tatttttgta aaagagagaa tgtttaaaag ttttgttact ttatagaaga   8220
aattttgagt ttttgttttt ttttaataaa taaataaaca taaataaatt gtttgttgaa   8280
tttattatta gtatgtaagt gtaaatataa taaaacttaa tatctattca aattaataaa   8340
taaacctcga tatacagacc gataaaacac atgcgtcaat tttacgcatg attatcttta   8400
acgtacgtca caatatgatt atctttctag ggttaaataa tagtttctaa ttttttttatt   8460
attcagcctg ctgtcgtgaa taccgtatat ctcaacgctg tctgtgagat tgtcgtattc   8520
tagccttttt agtttttcgc tcatcgactt gatattgtcc gacacatttt cgtcgatttg   8580
cgttttgatc aaagacttga gcagagacac gttaatcaac tgttcaaatt gatccatatt   8640
aacgatatca acccgatgcg tatatggtgc gtaaaatata ttttttaacc ctcttatact   8700
ttgcactctg cgttaatacg cgttcgtgta cagacgtaat catgttttct tttttggata   8760
aaactcctac tgagtttgac ctcatattag accctcacaa gttgcaaaac gtggcatttt   8820
ttaccaatga agaatttaaa gttattttaa aaaatttcat cacagattta aagaagaacc   8880
aaaaattaaa ttatttcaac agtttaatcg accagttaat caacgtgtac acagacgcgt   8940
cggcaaaaaa cacgcagccc gacgtgttgg ctaaaattat taaatcaact tgtgttatag   9000
tcacggattt gccgtccaac gtgttcctca aaaagttgaa gaccaacaag tttacggaca   9060
ctattaatta tttgattttg ccccacttca ttttgtggga tcacaatttt gttatatttt   9120
aaacaaagct tggcactggc cgtcgtttta caacgtcgtg actgggaaaa ccctggcgtt   9180
acccaactta atcgccttgc agcacatccc cctttcgcca gctggcgtaa tagcgaagag   9240
```

gcccgcaccg atcgcccttc ccaacagttg cgcagcctga atggcgaatg gcgcctgatg 9300
cggtattttc tccttacgca tctgtgcggt atttcacacc gcatatggtg cactctcagt 9360
acaatctgct ctgatgccgc atagttaagc cagccccgac acccgccaac acccgctgac 9420
gcgccctgac gggcttgtct gctcccggca tccgcttaca gacaagctgt gaccgtctcc 9480
gggagctgca tgtgtcagag gttttcaccg tcatcaccga aacgcgcgag acgaaagggc 9540
ctcgtgatac gcctattttt ataggttaat gtcatgataa taatggtttc ttagacgtca 9600
ggtggcactt ttcggggaaa tgtgcgcgga acccctattt gtttattttt ctaaatacat 9660
tcaaatatgt atccgctcat gagacaataa ccctgataaa tgcttcaata atattgaaaa 9720
aggaagagta tgagtattca acatttccgt gtcgccctta ttcccttttt tgcggcattt 9780
tgccttcctg tttttgctca cccagaaacg ctggtgaaag taaaagatgc tgaagatcag 9840
ttgggtgcac gagtgggtta catcgaactg gatctcaaca gcggtaagat ccttgagagt 9900
tttcgccccg aagaacgttt tccaatgatg agcactttta aagttctgct atgtggcgcg 9960
gtattatccc gtattgacgc cgggcaagag caactcggtc gccgcataca ctattctcag 10020
aatgacttgg ttgagtactc accagtcaca gaaaagcatc ttacggatgg catgacagta 10080
agagaattat gcagtgctgc cataaccatg agtgataaca ctgcggccaa cttacttctg 10140
acaacgatcg gaggaccgaa ggagctaacc gcttttttgc acaacatggg ggatcatgta 10200
actcgccttg atcgttggga accggagctg aatgaagcca taccaaacga cgagcgtgac 10260
accacgatgc ctgtagcaat ggcaacaacg ttgcgcaaac tattaactgg cgaactactt 10320
actctagctt cccggcaaca attaatagac tggatggagg cggataaagt tgcaggacca 10380
cttctgcgct cggcccttcc ggctggctgg tttattgctg ataaatctgg agccggtgag 10440
cgtgggtctc gcggtatcat tgcagcactg gggccagatg gtaagccctc ccgtatcgta 10500
gttatctaca cgacggggag tcaggcaact atggatgaac gaaatagaca gatcgctgag 10560
ataggtgcct cactgattaa gcattggtaa ctgtcagacc aagtttactc atatatactt 10620
tagattgatt taaaacttca tttttaattt aaaaggatct aggtgaagat cctttttgat 10680
aatctcatga ccaaaatccc ttaacgtgag ttttcgttcc actgagcgtc agaccccgta 10740
gaaaagatca aaggatcttc ttgagatcct ttttttctgc gcgtaatctg ctgcttgcaa 10800
acaaaaaaac caccgctacc agcggtggtt tgtttgccgg atcaagagct accaactctt 10860
tttccgaagg taactggctt cagcagagcg cagataccaa atactgtcct tctagtgtag 10920
ccgtagttag gccaccactt caagaactct gtagcaccgc ctacatacct cgctctgcta 10980
atcctgttac cagtggctgc tgccagtggc gataagtcgt gtcttaccgg gttggactca 11040
agacgatagt taccggataa ggcgcagcgg tcgggctgaa cggggggttc gtgcacacag 11100
cccagcttgg agcgaacgac ctacaccgaa ctgagatacc tacagcgtga gcattgagaa 11160
agcgccacgc ttcccgaagg gagaaaggcg gacaggtatc cggtaagcgg cagggtcgga 11220
acaggagagc gcacgaggga gcttccaggg ggaaacgcct ggtatcttta tagtcctgtc 11280
gggtttcgcc acctctgact tgagcgtcga tttttgtgat gctcgtcagg ggggcggagc 11340
ctatggaaaa acgccagcaa cgcggccttt ttacggttcc tggccttttg ctggcctttt 11400
gctcacatgt tctttcctgc gttatcccct gattctgtgg ataaccgtat taccgccttt 11460
gagtgagctg ataccgctcg ccgcagccga acgaccgagc gcagcgagtc agtgagcgag 11520
gaagcggaag agcgcccaat acgcaaaccg cctctccccg cgcgttggcc gattcattaa 11580

-continued

```
tgcagctggc acgacaggtt tcccgactgg aaagcgggca gtgagcgcaa cgcaattaat  11640

gtgagttagc tcactcatta ggcaccccag gctttacact ttatgcttcc ggctcgtatg  11700

ttgtgtggaa ttgtgagcgg ataacaattt cacacaggaa acagctatga ccatgattac  11760

gaatttcgac ctgcaggcat gcaagcttgc atgcctgcag gtcgacgctc gcgcgacttg  11820

gtttgccatt ctttagcgcg cgtcgcgtca cacagcttgg ccacaat                11867
```

<210> SEQ ID NO 23
<211> LENGTH: 10786
<212> TYPE: DNA
<213> ORGANISM: Artificial Sequence
<220> FEATURE:
<223> OTHER INFORMATION: Synthetic construct, plasmid pLA670

<400> SEQUENCE: 23

```
ggccgctcat ttaaatctgg ccggccgcaa ccattgtggg aaccgtgcga tcaaacaaac     60

gcgagatacc ggaagtactg aaaaacagtc gctccaggcc agtgggaaca tcgatgtttt    120

gttttgacgg accccttact ctcgtctcat ataaaccgaa gccagctaag atggtatact    180

tattatcatc ttgtgatgag gatgcttcta tcaacgaaag taccggtaaa ccgcaaatgg    240

ttatgtatta taatcaaact aaaggcggag tggacacgct agaccaaatg tgttctgtga    300

tgacctgcag taggaagacg aataggtggc ctatggcatt attgtacgga atgataaaca    360

ttgcctgcat aaattctttt attatataca gccataatgt cagtagcaag ggagaaaagg    420

tccaaagtcg caaaaaattt atgagaaacc tttacatgag cctgacgtca tcgtttatgc    480

gtaagcgttt agaagctcct actttgaaga gatatttgcg cgataatatc tctaatattt    540

tgccaaatga agtgcctggt acatcagatg acagtactga agagccagta atgaaaaaac    600

gtacttactg tacttactgc ccctctaaaa taaggcgaaa ggcaaatgca tcgtgcaaaa    660

aatgcaaaaa agttatttgt cgagagcata atattgatat gtgccaaagt tgtttctgac    720

tgactaataa gtataatttg tttctattat gtataagtta agctaattac ttattttata    780

atacaacatg actgttttta aagtacaaaa taagtttatt tttgtaaaag agagaatgtt    840

taaaagtttt gttactttat agaagaaatt ttgagttttt gttttttttt aataaataaa    900

taaacataaa taaattgttt gttgaattta ttattagtat gtaagtgtaa atataataaa    960

acttaatatc tattcaaatt aataaataaa cctcgatata cagaccgata aaacacatgc   1020

gtcaatttta cgcatgatta tctttaacgt acgtcacaat atgattatct ttctagggtt   1080

aaataatagt ttctaatttt tttattattc agcctgctgt cgtgaatacc gtatatctca   1140

acgctgtctg tgagattgtc gtattctagc ctttttagtt tttcgctcat cgacttgata   1200

ttgtccgaca cattttcgtc gatttgcgtt ttgatcaaag acttgagcag agacacgtta   1260

atcaactgtt caaattgatc catattaacg atatcaaccc gatgcgtata tggtgcgtaa   1320

aatatatttt ttaaccctct tatactttgc actctgcgtt aatacgcgtt cgtgtacaga   1380

cgtaatcatg ttttcttttt tggataaaac tcctactgag tttgacctca tattagaccc   1440

tcacaagttg caaaacgtgg catttttttac caatgaagaa tttaaagtta ttttaaaaaa   1500

tttcatcaca gatttaaaga agaaccaaaa attaaattat ttcaacagtt taatcgacca   1560

gttaatcaac gtgtacacag acgcgtcggc aaaaaacacg cagcccgacg tgttggctaa   1620

aattattaaa tcaacttgtg ttatagtcac ggatttgccg tccaacgtgt tcctcaaaaa   1680

gttgaagacc aacaagttta cggacactat taattatttg attttgcccc acttcatttt   1740

gtgggatcac aattttgtta tattttaaac aaagcttggc actggccgtc gttttacaac   1800
```

-continued

```
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
```

-continued

```
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
ctgcaggtcg acgctcgcgc gacttggttt gccattcttt agcgcgcgtc gcgtcacaca   4500
gcttggccac aatgtggttt ttgtcaaacg aagattctat gacgtgttta aagtttaggt   4560
cgagtaaagc gcaaatcttt tttaacccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatattttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagacga acaaaatgtt attgaacaac caggttcttc attggcttct aacagaatct   5160
tgaccttgcc acagaggact attagaggta agaataaaca ttgttggtca acttcaaagt   5220
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tccccccataa aaagttttcg caatgccttt attttttgtt gcaaatctct ctttattctg   5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
ggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
```

-continued

```
acccgtaatt gtttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
tgccaacttc gttcaacagc tccaacgcgg agttgatgac tttggactta tccaggcggc   7200
tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
gggggaggtg tgggaggttt tttaaagcaa gtaaaacctc tacaaatgtg gtatggctga   7980
ttatgatcag ttatctagat ccggtggatc ttacgggtcc tccaccttcc gctttttctt   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatcc ccgatctgca ttttggatta ttctgcgggt caaaatagag atgtggaaaa   8820
ttagtacgaa atcaaatgag tttcgttgaa attacaaaac tattgaaact aacttcctgg   8880
```

-continued

```
ctggggaata aaaatgggaa acttatttat cgacgccaac tttgttgaga aacccctatt   8940
aaccctctac gaatattgga acaaaggaaa gcgaagaaac aggaacaaag gtagttgaga   9000
aacctgttcc gttgctcgtc atcgttttca taatgcgagt gtgtgcatgt atatatacac   9060
agctgaaacg catgcataca cattattttg tgtgtatatg gtgacgtcac aactactaag   9120
caataagaaa ttttccagac gtggctttcg tttcaagcaa cctactctat ttcagctaaa   9180
aataagtgga tttcgttggt aaaatacttc aattaagcaa agaactaact aactaataac   9240
atgcacacaa atgctcgagt gcgttcgtga tttctcgaat tttcaaatgc gtcactgcga   9300
atttcacaat ttgccaataa atcttggcga aaatcaacac gcaagtttta tttatagatt   9360
tgtttgcgtt ttgatgccaa ttgattggga aaacaagatg cgtggctgcc aatttcttat   9420
tttgtaatta cgtagagcgt tgaataaaaa aaaaatggcc gaacaaagac cttgaaatgc   9480
agtttttctt gaaattactc aacgtcttgt tgctcttatt actaattggt aacagcgagt   9540
taaaaactta cgtttcttgt gactttcgag aatgttcttt taattgtact ttaatcacca   9600
acaattaagt ataaattttt cgctgattgc gctttacttt ctgcttgtac ttgctgctgc   9660
aaatgtcaat tggttttgaa ggcgaccgtt cgcgaacgct gtttatatac cttcggtgtc   9720
cgttgaaaat cactaaaaaa taccgtagtg ttcgtaacac tttagtacag agaaaaaaaa   9780
ttgtgccgaa atgtttttga tacgtacgaa taccttgtat taaaattttt tatgatttct   9840
gtgtatcact tttttttgt gtttttcgtt taaactcacc acagtacaaa acaataaaat   9900
atttttaaga caatttcaaa ttgagacctt tctcgtactg acttgaccgg ctgaatgagg   9960
atttctacct agacgaccta cttcttacca tgacattgaa tgcaatgcca cctttgatct  10020
aaacttacaa aagtccaagg cttgttagga ttggtgttta tttagtttgc ttttgaaata  10080
gcactgtctt ctctaccggc tataattttg aaactcgcag cttgactgga aatttaaaaa  10140
gtaattctgt gtaggtaaag ggtgttttaa aagtgtgatg tgttgagcgt tgcggcaacg  10200
actgctattt atgtatatat tttcaaaact tattgttttt gaagtgtttt aaatggagct  10260
atctggcaac gctgcgcata atcttacaca agcttttctt aatccatttt taagtgaaat  10320
ttgtttttac tctttcggca aataattgtt aaatcgcttt aagtgggctt acatctggat  10380
aagtaatgaa aacctgcata ttataatatt aaaacatata atccactgtg ctttccccgt  10440
gtgtggccat atacctaaaa aagtttattt tcgcagagcc ccgcacggtc acactacggt  10500
tcggcgattt tcgattttgg acagtactga ttgcaagcgc accgaaagca aaatggagct  10560
ggagattttg aacgcgaaga acagcaagcc gtacggcaag gtgaaggtgc cctccggcgc  10620
cacgcccatc ggcgatctgc gcgccctaat tcacaagacc ctgaagcaga ccccacacgc  10680
gaatcgccag tcgcttcgtc tggaactgaa gggcaaaagc ctgaaagata cggacacatt  10740
ggaatctctg tcgctgcgtt ccggcgacaa gatcggggta ccatgc                 10786
```

<210> SEQ ID NO 24
<211> LENGTH: 14720
<212> TYPE: DNA
<213> ORGANISM: Artificial Sequence
<220> FEATURE:
<223> OTHER INFORMATION: Synthetic construct, plasmid pLA1038

<400> SEQUENCE: 24

```
gggctatggc gcgccggacg cggcaagtct gcgagcttat atttacgtgg atctccggtg     60
tgtccatgat tcggcatcat atcataaacg acgaattcca ataaaaactt tgcttgttga    120
taacacctga tgttcagaga tgcccgataa aatcacagct gttctggttc acagtcacca    180
```

-continued

```
gaaataaaaa atattggaat tgagatgtac acaattaacg atatttataa atatcttccg    240
atagtctatc gtccggttaa tcaaaataaa gtgcgacgaa ttaacatatt ttcaaaatta    300
agacgctttg atagatgtat ttgtatagag atagaaatta aggttaaaat aacataaatg    360
ccaaagttta gagcactatt caataattct cttgatttca aattgaaata atacacaata    420
taacattttc taacactaca aagtcacgat attcttccac caaccgatag tatcgcacac    480
ttgccattcg cctcatcacg cacacgcccg cttcacaatt caaacgaacg gcattttatt    540
ttcacaggat cccgggagtc gtgaatgttt tacccaatat cgactttcat tgttaactga    600
ccaaaattgt aatctgttct gttagttgtc gagtgcctgt gccgcgatcg ctatgggcat    660
atgttgccaa actctaaacc aaatactcat tctgatgttt taaatgattt gccctcccat    720
atgtccttcc gagtgagaga cacaaaaaat tccaacacac tattgcaatg aaaataaatt    780
tcctttatta gccagaagtc agatgctcaa ggggcttcat gatgtcccca taatttttgg    840
cagagggaaa aagatctcag tggtatttgt gagccagggc attggccaca ccagccacca    900
ccttctgata ggcagcctgc acctgaggag tgaattcttt gccaaaatga tgagacagca    960
caacaaccag cacgttgccc aggagctgta ggaaagagaa gaaggcatga acatggttag   1020
cagaggggcc cggtttggac tcagagtatt ttatcctcat ctcaaacagt gtatatcatt   1080
gtaaccataa agagaaaggc aggatgatga ccagggtgta gttgtttcta ccaataagaa   1140
tatttccacg ccagccagaa tttatatgca gaaatattct accttatcat ttaattataa   1200
caattgttct ctaaaactgt gctgaagtac aatataatat accctgattg ccttgaaaaa   1260
aaagtgatta gagaaagtac ttacaatctg acaaataaac aaaagtgaat ttaaaaattc   1320
gttacaaatg caagctaaag tttaacgaaa aagttacaga aaatgaaaag aaaataagag   1380
gagacaatgg ttgtcaacag agtagaaagt gaaagaaaca aaattatcat gagggtccat   1440
ggtgatacaa gggacatctt cccattctaa acaacaccct gaaaactttg ccccctccat   1500
ataacatgaa ttttacaata gcgaaaaaga aagaacaatc aagggtcccc aaactcaccc   1560
tgaagttctc agctctagac gcgtttcact acccaccgta ctcgtcaatt ccaagggcat   1620
cggtaaacat ctgctcaaac tcgaagtcgg ccatatccag agcgccgtag gggcggagt    1680
cgtgggggt aaatcccgga cccggggaat ccccgtcccc caacatgtcc agatcgaaat    1740
cgtctagcgc gtcggcatgc gccatcgcca cgtcctcgcc gtctaagtgg agctcgtccc   1800
ccaggctgac atcggtcggg ggggccgtcg acagtctgcg cgtgtgtccc gcggggagaa   1860
aggacaggcg cggagccgcc agccccgcct cttcgggggc gtcgtcgtcc gggagatcga   1920
gcaggccctc gatggtagac ccgtaattgt ttttcgtacg cgcgcggctg tacgcggacc   1980
cactttcaca tttaagttgt ttttctaatc cgcatatgat caattcaagg ccgaataaga   2040
aggctggctc tgcaccttgg tgatcaaata attcgatagc ttgtcgtaat aatggcggca   2100
tactatcagt agtaggtgtt tccctttctt ctttagcgac ttgatgctct tgatcttcca   2160
atacgcaacc taaagtaaaa tgccccacag cgctgagtgc atataatgca ttctctagtg   2220
aaaaaccttg ttggcataaa aaggctaatt gattttcgag agtttcatac tgtttttctg   2280
taggccgtgt acctaaatgt acttttgctc catcgcgatg acttagtaaa gcacatctaa   2340
aacttttagc gttattacgt aaaaaatctt gccagctttc cccttctaaa gggcaaaagt   2400
gagtatggtg cctatctaac atctcaatgg ctaaggcgtc gagcaaagcc cgcttatttt   2460
ttacatgcca atacaatgta ggctgctcta cacctagctt ctgggcgagt ttacgggttg   2520
```

-continued ttaaaccttc gattccgacc tcattaagca gctctaatgc gctgttaatc actttacttt 2580
tatctaatct caattccatg gtggcaacct gcaaggcgaa tgaataaaca agattgtggc 2640
gaacagtgta atgcgaagaa cccacctctg ctccaattcc caattcccta ttcagctcga 2700
gcggggatcc ccgggtaccg agctcgaatt cggggccgcg gaggctggat cggtcccggt 2760
gtcttctatg gaggtcaaaa cagcgtggat ggcgtctcca ggcgatctga cggttcacta 2820
aacgagctct gcttatatag gcctcccacc gtacacgcct acctcgaccc gggtaccgag 2880
ctcgactttc acttttctct atcactgata gggagtggta aactcgactt tcacttttct 2940
ctatcactga tagggagtgg taaactcgac tttcactttt ctctatcact gatagggagt 3000
ggtaaactcg actttcactt ttctctatca ctgataggga gtggtaaact cgactttcac 3060
ttttctctat cactgatagg gagtggtaaa ctcgactttc acttttctct atcactgata 3120
gggagtggta aactcgactt tcacttttct ctatcactga tagggagtgg taaactcgaa 3180
atgtcgacta tgcggaccga gcgccggagt ataaatagag gcgcttcgtc tacggagcga 3240
caattcaatt caaacaagca aagtgaacac gtcgctaagc gaaagctaag caaataaaca 3300
agcgcagctg aacaagctaa acaatctgcg ctagccacca tggttgttat taaacgtaga 3360
tttggtaatt ttaaaagcat attttttcct ttgaaattca taagttatca attatcgatg 3420
gaaatgtatt ctatggagaa cgttttaccc gatgaatggg tgcaaaaatt attttacctt 3480
caaatctaca atcaacacac gctaactttt gtgacttgat caactctcac ctggaaaagc 3540
aaccaactac aatcaacatt ctatgggata atcgacaagt gagtaaaatt atagccggac 3600
ctcttagtac agtgtattta aaaggggaat aatattctat caataggaat aaaaataagg 3660
tcagcagcca tgacttttcc atcattttga atataccita tttgtttcgg gattaattgg 3720
gggtcggaaa tcctcttgaa ttcagaaacg ggaaccggag gaaggtgccg gtctttcaga 3780
aagctgtgaa aaataccaac atttctgctg ccaagagctc aataagaagt ttcaaaaatt 3840
gtcttggatg ttgcagctgt ggctgctaag taataagaca tctattagta tctagatttg 3900
ttagaccatt taacatagtg ttttaaacga tggggttaat agatgagggt taagaagcta 3960
gttatattac tgttgctgta acgccttcaa ttgtcggtta cagagcaaac attattgaat 4020
gttaatgtaa agagtttatt tgttttctag taaacatata gcgattggtt agtaatcact 4080
aatagaaatt tttcataagt atcaaaaaag taaacctctt tttcagtcta tgtaataagt 4140
aaaccaagga aagggaaaat atctacaatc aacaagccat tgttgcagca acaaagcaac 4200
tgaaactaca atcaacattc aataaacttg ggtaatttgg aatttaattc tctgggacac 4260
ctgtggatta caacaatcaa ctcgaaactt attatacaat gtaaataaaa attgatatgc 4320
atacatgaag atcaagtgaa attccattta gaatcaattt ttttcgaata ttaagtttct 4380
tgctttaatt tatctgaaag taaatagaca ttccaaattc aagttaacaa attaataatg 4440
aattgactag tgatttttaa gagaaaaaga taagatttaa aaaaggaaag cctttcttga 4500
taaatttttg aaccacttta tgccgtttca atcataaaaa cttttaagaa cacatgactg 4560
gtaaaattaa tttaaaacaa atttaaattt tcaacgtaac attcaacaaa aatggtgaaa 4620
actatcacgg aaattgttaa tattaatatg tcccaaaaat agcctttgta tgtatatgat 4680
actaatccat acatctatgg tatctatagg tgaaggctca aagcctctgg gcgctctcct 4740
gggcctgccc gaaagccaaa cggagcttga taatcttaca gaatacaaca cggcccacaa 4800
tcggcgcatc tcaatgctgg gcatcgatga tgataccaat atgcgaaagc aaaacgcctt 4860
gaaacaggga cggcgcactc gaaatgtcac atttaacgat gaggagattg tcatcaatcc 4920

```
tgaggatgtg gatcctaatg tgggacgctt caggaacttg gtacaaacca ctgtggtgcc   4980
cgccaagagg gctcgctgcg acgtcaacca ttagtgataa cgcgtctaga gctgagaact   5040
tcagggtgag tttggggacc cttgattgtt ctttcttttt cgctattgta aaattcatgt   5100
tatatggagg gggcaaagtt ttcagggtgt tgtttagaat gggaagatgt cccttgtatc   5160
accggtgatc ataatcagcc ataccacatt tgtagaggtt ttacttgctt taaaaaacct   5220
cccacacctc cccctgaacc tgaaacataa aatgaatgca attgttgttg ttaacttgtt   5280
tattgcagct tataatggtt acaaataaag caatagcatc acaaatttca caaataaagc   5340
atttttttca ctgcattcta gttgtggttt gtccaaactc atcaatgtat cttaacgcga   5400
gtttaaacgc gtccgcatac gtccgctcac gttaagttcc gcagagagaa gttgttgaaa   5460
acataaacag aatcacttgt tgcactcttt gagaaaactg ggctattgc ggaaaaaacc   5520
aactaaaaat attgcaggtt aggggtacta cgctcgattg gcgtacggcc accacttttg   5580
cgacttcact gttaaccgct accttcatag agacttttac ccgataaatg ttatgtagtt   5640
tgactttctc tgttaatcac aagaaaaaat attgtggaaa ttaaaattat ctcaaactca   5700
ataaggaaat aataatatat acacctatgt tttatagaag tcaacagtaa ataagttatt   5760
tggaaaacca ttgtagccgt ttaaataaat ctccttgagt gtgttttaaa taacggtcat   5820
taagtatatt acttggccct ctgaatttct tgaattacac catttttttga aataaatcaa   5880
tccaaaagac tactttttgg tggcaaatga actgcataaa aagtaacaaa agaaatatgt   5940
ttttgaaata acagtatagc tgaagtgtat taaaaaatac cgtcatatga gcgacccgct   6000
gttaccgctt cgctgcgaat gacaaaacgg gctgagcaag aaaatggcgt agaaggcgac   6060
gaaaattcgt ttcactcgtg aagaaaacct cgataactga ggaatacagc tgggatttaa   6120
agagcatatt cgaactacaa gcagagatgt ttcctggtgg aaacggaaac gccgatttgg   6180
gctacaacaa gcatgcccac gtccatggac ttggacaaca tggccatggg cacaaccata   6240
atcacaatca gttcctgcgc agcccccacc accccccaca catttttcac tgccctccgg   6300
gggcggtcag ggcatggtga cgcccatggt agccgccggc ctgccgctcg ccatgcaggg   6360
tggcgttggc atcgattggc gcagctcgcc cagcaatgga ttaattaact cgcgttaaga   6420
tacattgatg agtttggaca aaccacaact agaatgcagt gaaaaaaatg ctttatttgt   6480
gaaatttgtg atgctattgc tttatttgta accattataa gctgcaataa acaagttaac   6540
aacaacaatt gcattcattt tatgtttcag gttcaggggg aggtgtggga ggttttttaa   6600
agcaagtaaa acctctacaa atgtggtatg gctgattatg atcagttatc tagatccggt   6660
ggatcttacg ggtcctccac cttccgcttt ttcttgggtc gagatctcag gaacaggtgg   6720
tggcggccct cggtgcgctc gtactgctcc acgatggtgt agtcctcgtt gtgggaggtg   6780
atgtccagct tggcgtccac gtagtagtag ccgggcagct gcacgggctt cttggccatg   6840
tagatggact tgaactccac caggtagtgg ccgccgtcct tcagcttcag ggccttgtgg   6900
gtctcgccct tcagcacgcc gtcgcggggg tacaggcgct cggtggaggc ctcccagccc   6960
atggtcttct tctgcatcac ggggccgtcg gaggggaagt tcacgccgat gaacttcacc   7020
ttgtagatga agcagccgtc ctgcagggag gagtcctggg tcacggtcgc cacgccgccg   7080
tcctcgaagt tcatcacgcg ctcccacttg aagccctcgg ggaaggacag cttcttgtag   7140
tcggggatgt cggcggggtg cttcacgtac accttggagc cgtactggaa ctggggggac   7200
aggatgtccc aggcgaaggg caggggggccg cccttggtca ccttcagctt cacggtgttg   7260
```

```
tggccctcgt aggggcggcc ctcgccctcg ccctcgatct cgaactcgtg gccgttcacg   7320
gtgccctcca tgcgcacctt gaagcgcatg aactcggtga tgacgttctc ggaggaggcc   7380
atggtggcga ccggtttgcg cttcttcttg ggtggggtgg gatccccgat ctgcattttg   7440
gattattctg cgggtcaaaa tagagatgtg gaaaattagt acgaaatcaa atgagtttcg   7500
ttgaaattac aaaactattg aaactaactt cctggctggg gaataaaaat gggaaactta   7560
tttatcgacg ccaactttgt tgagaaaccc ctattaaccc tctacgaata ttggaacaaa   7620
ggaaagcgaa gaaacaggaa caaaggtagt tgagaaacct gttccgttgc tcgtcatcgt   7680
tttcataatg cgagtgtgtg catgtatata tacacagctg aaacgcatgc atacacatta   7740
ttttgtgtgt atatggtgac gtcacaacta ctaagcaata agaaattttc cagacgtggc   7800
tttcgtttca agcaacctac tctatttcag ctaaaaataa gtggatttcg ttggtaaaat   7860
acttcaatta agcaaagaac taactaacta ataacatgca cacaaatgct cgagtgcgtt   7920
cgtgatttct cgaattttca aatgcgtcac tgcgaatttc acaatttgcc aataaatctt   7980
ggcgaaaatc aacacgcaag ttttatttat agatttgttt gcgttttgat gccaattgat   8040
tgggaaaaca agatgcgtgg ctgccaattt cttattttgt aattacgtag agcgttgaat   8100
aaaaaaaaaa tggccgaaca aagaccttga aatgcagttt ttcttgaaat tactcaacgt   8160
cttgttgctc ttattactaa ttggtaacag cgagttaaaa acttacgttt cttgtgactt   8220
tcgagaatgt tcttttaatt gtactttaat caccaacaat taagtataaa tttttcgctg   8280
attgcgcttt actttctgct tgtacttgct gctgcaaatg tcaattggtt ttgaaggcga   8340
ccgttcgcga acgctgttta tataccttcg gtgtccgttg aaaatcacta aaaaataccg   8400
tagtgttcgt aacactttag tacagagaaa aaaaattgtg ccgaaatgtt tttgatacgt   8460
acgaatacct tgtattaaaa ttttttatga tttctgtgta tcactttttt tttgtgtttt   8520
tcgtttaaac tcaccacagt acaaaacaat aaaatatttt taagacaatt tcaaattgag   8580
acctttctcg tactgacttg accggctgaa tgaggatttc tacctagacg acctacttct   8640
taccatgaca ttgaatgcaa tgccaccttt gatctaaact tacaaaagtc caaggcttgt   8700
taggattggt gtttatttag tttgcttttg aaatagcact gtcttctcta ccggctataa   8760
ttttgaaact cgcagcttga ctggaaattt aaaaagtaat tctgtgtagg taaagggtgt   8820
tttaaaagtg tgatgtgttg agcgttgcgg caacgactgc tatttatgta tatattttca   8880
aaacttattg tttttgaagt gttttaaatg gagctatctg gcaacgctgc gcataatctt   8940
acacaagctt ttcttaatcc atttttaagt gaaatttgtt tttactcttt cggcaaataa   9000
ttgttaaatc gctttaagtg ggcttacatc tggataagta atgaaaacct gcatattata   9060
atattaaaac atataatcca ctgtgctttc cccgtgtgtg gccatatacc taaaaaagtt   9120
tattttcgca gagccccgca cggtcacact acggttcggc gattttcgat tttggacagt   9180
actgattgca agcgcaccga aagcaaaatg gagctggaga ttttgaacgc gaagaacagc   9240
aagccgtacg gcaaggtgaa ggtgccctcc ggcgccacgc ccatcggcga tctgcgcgcc   9300
ctaattcaca agaccctgaa gcagacccca cacgcgaatc gccagtcgct tcgtctggaa   9360
ctgaagggca aaagcctgaa agatacggac acattggaat ctctgtcgct gcgttccggc   9420
gacaagatcg gggtaccatg cggccgctca tttaaatctg gccggcctgg ccgatctgac   9480
aatgttcagt gcagagactc ggctacgcct cgtggacttt gaagttgacc aacaatgttt   9540
attcttacct ctaatagtcc tctgtggcaa ggtcaagatt ctgttagaag ccaatgaaga   9600
acctggttgt tcaataacat tttgttcgtc taatatttca ctaccgcttg acgttggctg   9660
```

```
cacttcatgt acctcatcta taaacgcttc ttctgtatcg ctctggacgt catcttcact   9720
tacgtgatct gatatttcac tgtcagaatc ctcaccaaca agctcgtcat cgctttgcag   9780
aagagcagag aggatatgct catcgtctaa agaactaccc attttattat atattagtca   9840
cgatatctat aacaagaaaa tatatatata ataagttatc acgtaagtag aacatgaaat   9900
aacaatataa ttatcgtatg agttaaatct taaaagtcac gtaaaagata atcatgcgtc   9960
attttgactc acgcggtcgt tatagttcaa aatcagtgac acttaccgca ttgacaagca  10020
cgcctcacgg gagctccaag cggcgactga gatgtcctaa atgcacagcg acggattcgc  10080
gctatttaga aagagagagc aatatttcaa gaatgcatgc gtcaatttta cgcagactat  10140
ctttctaggg ttaaaaaaga tttgcgcttt actcgaccta aactttaaac acgtcataga  10200
atcttcgttt gacaaaaacc acattgtggc caagctgtgt gacgcgacgc gcgctaaaga  10260
atggcaaacc aagtcgcgcg agcgtcgacc tgcaggcatg caagcttgca tgcctgcagg  10320
tcgaaattcg taatcatggt catagctgtt tcctgtgtga aattgttatc cgctcacaat  10380
tccacacaac atacgagccg gaagcataaa gtgtaaagcc tggggtgcct aatgagtgag  10440
ctaactcaca ttaattgcgt tgcgctcact gcccgctttc cagtcgggaa acctgtcgtg  10500
ccagctgcat taatgaatcg gccaacgcgc ggggagaggc ggtttgcgta ttgggcgctc  10560
ttccgcttcc tcgctcactg actcgctgcg ctcggtcgtt cggctgcggc gagcggtatc  10620
agctcactca aaggcggtaa tacggttatc cacagaatca ggggataacg caggaaagaa  10680
catgtgagca aaaggccagc aaaaggccag gaaccgtaaa aaggccgcgt tgctggcgtt  10740
tttccatagg ctccgccccc ctgacgagca tcacaaaaat cgacgctcaa gtcagaggtg  10800
gcgaaacccg acaggactat aaagatacca ggcgtttccc cctggaagct ccctcgtgcg  10860
ctctcctgtt ccgaccctgc cgcttaccgg atacctgtcc gcctttctcc cttcgggaag  10920
cgtggcgctt tctcaatgct cacgctgtag gtatctcagt tcggtgtagg tcgttcgctc  10980
caagctgggc tgtgtgcacg aaccccccgt tcagcccgac cgctgcgcct tatccggtaa  11040
ctatcgtctt gagtccaacc cggtaagaca cgacttatcg ccactggcag cagccactgg  11100
taacaggatt agcagagcga ggtatgtagg cggtgctaca gagttcttga agtggtggcc  11160
taactacggc tacactagaa ggacagtatt tggtatctgc gctctgctga agccagttac  11220
cttcggaaaa agagttggta gctcttgatc cggcaaacaa accaccgctg gtagcggtgg  11280
tttttttgtt tgcaagcagc agattacgcg cagaaaaaaa ggatctcaag aagatccttt  11340
gatcttttct acggggtctg acgctcagtg gaacgaaaac tcacgttaag ggattttggt  11400
catgagatta tcaaaaagga tcttcaccta gatcctttta aattaaaaat gaagttttaa  11460
atcaatctaa agtatatatg agtaaacttg gtctgacagt taccaatgct taatcagtga  11520
ggcacctatc tcagcgatct gtctatttcg ttcatccata gttgcctgac tccccgtcgt  11580
gtagataact acgatacggg agggcttacc atctggcccc agtgctgcaa tgataccgcg  11640
agacccacgc tcaccggctc cagatttatc agcaataaac cagccagccg gaagggccga  11700
gcgcagaagt ggtcctgcaa ctttatccgc ctccatccag tctattaatt gttgccggga  11760
agctagagta agtagttcgc cagttaatag tttgcgcaac gttgttgcca ttgctacagg  11820
catcgtggtg tcacgctcgt cgtttggtat ggcttcattc agctccggtt cccaacgatc  11880
aaggcgagtt acatgatccc ccatgttgtg caaaaaagcg gttagctcct tcggtcctcc  11940
gatcgttgtc agaagtaagt tggccgcagt gttatcactc atggttatgg cagcactgca  12000
```

```
taattctctt actgtcatgc catccgtaag atgcttttct gtgactggtg agtactcaac  12060
caagtcattc tgagaatagt gtatgcggcg accgagttgc tcttgcccgg cgtcaatacg  12120
ggataatacc gcgccacata gcagaacttt aaaagtgctc atcattggaa aacgttcttc  12180
ggggcgaaaa ctctcaagga tcttaccgct gttgagatcc agttcgatgt aacccactcg  12240
tgcacccaac tgatcttcag catcttttac tttcaccagc gtttctgggt gagcaaaaac  12300
aggaaggcaa aatgccgcaa aaaagggaat aagggcgaca cggaaatgtt gaatactcat  12360
actcttcctt tttcaatatt attgaagcat ttatcagggt tattgtctca tgagcggata  12420
catatttgaa tgtatttaga aaaataaaca aataggggtt ccgcgcacat ttccccgaaa  12480
agtgccacct gacgtctaag aaaccattat tatcatgaca ttaacctata aaaataggcg  12540
tatcacgagg ccctttcgtc tcgcgcgttt cggtgatgac ggtgaaaacc tctgacacat  12600
gcagctcccg gagacggtca cagcttgtct gtaagcggat gccgggagca gacaagcccg  12660
tcagggcgcg tcagcgggtg ttggcgggtg tcggggctgg cttaactatg cggcatcaga  12720
gcagattgta ctgagagtgc accatatatg cggtgtgaaa taccgcacag atgcgtaagg  12780
agaaaatacc gcatcaggcg ccattcgcca ttcaggctgc gcaactgttg ggaagggcga  12840
tcggtgcggg cctcttcgct attacgccag ctggcgaaag ggggatgtgc tgcaaggcga  12900
ttaagttggg taacgccagg gttttcccag tcacgacgtt gtaaaacgac ggccagtgcc  12960
aagctttgtt taaaatataa caaaattgtg atcccacaaa atgaagtggg gcaaaatcaa  13020
ataattaata gtgtccgtaa acttgttggt cttcaacttt ttgaggaaca cgttggacgg  13080
caaatccgtg actataacac aagttgattt aataatttta gccaacacgt cgggctgcgt  13140
gtttttgcc gacgcgtctg tgtacacgtt gattaactgg tcgattaaac tgttgaaata  13200
atttaatttt tggttcttct ttaaatctgt gatgaaattt tttaaaataa ctttaaattc  13260
ttcattggta aaaaatgcca cgttttgcaa cttgtgaggg tctaatatga ggtcaaactc  13320
agtaggagtt ttatccaaaa aagaaaacat gattacgtct gtacacgaac gcgtattaac  13380
gcagagtgca aagtataaga gggttaaaaa atatatttta cgcaccatat acgcatcggg  13440
ttgatatcgt taatatggat caatttgaac agttgattaa cgtgtctctg ctcaagtctt  13500
tgatcaaaac gcaaatcgac gaaaatgtgt cggacaatat caagtcgatg agcgaaaaac  13560
taaaaaggct agaatacgac aatctcacag acagcgttga gatatacggt attcacgaca  13620
gcaggctgaa taataaaaaa attagaaact attatttaac cctagaaaga taatcatatt  13680
gtgacgtacg ttaaagataa tcatgcgtaa aattgacgca tgtgttttat cggtctgtat  13740
atcgaggttt atttattaat ttgaatagat attaagtttt attatattta cacttacata  13800
ctaataataa attcaacaaa caatttattt atgtttattt atttattaaa aaaaaacaaa  13860
aactcaaaat ttcttctata aagtaacaaa acttttaaac attctctctt ttacaaaaat  13920
aaacttattt tgtactttaa aaacagtcat gttgtattat aaaataagta attagcttaa  13980
cttatacata atagaaacaa attatactta ttagtcagtc agaaacaact ttggcacata  14040
tcaatattat gctctcgaca aataactttt ttgcattttt tgcacgatgc atttgccttt  14100
cgccttattt tagaggggca gtaagtacag taagtacgtt ttttcattac tggctcttca  14160
gtactgtcat ctgatgtacc aggcacttca tttggcaaaa tattagagat attatcgcgc  14220
aaatatctct tcaaagtagg agcttctaaa cgcttacgca taaacgatga cgtcaggctc  14280
atgtaaaggt ttctcataaa ttttttgcga ctttggacct tttctccctt gctactgaca  14340
ttatggctgt atataataaa agaatttatg caggcaatgt ttatcattcc gtacaataat  14400
```

gccataggcc acctattcgt cttcctactg caggtcatca cagaacacat ttggtctagc 14460
gtgtccactc cgcctttagt ttgattataa tacataacca tttgcggttt accggtactt 14520
tcgttgatag aagcatcctc atcacaagat gataataagt ataccatctt agctggcttc 14580
ggtttatatg agacgagagt aaggggtccg tcaaaacaaa acatcgatgt tcccactggc 14640
ctggagcgac tgtttttcag tacttccggt atctcgcgtt tgtttgatcg cacggttccc 14700
acaatggttg cggccagccc 14720

<210> SEQ ID NO 25
<211> LENGTH: 23
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 25
catcgatgcc cagcattgag atg 23

<210> SEQ ID NO 26
<211> LENGTH: 34
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 26
caagcaaagt gaacacgtcg ctaagcgaaa gcta 34

<210> SEQ ID NO 27
<211> LENGTH: 28
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 27
gccatccacg ctgttttgac ctccatag 28

<210> SEQ ID NO 28
<211> LENGTH: 27
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 28
gccaatacaa tgtaggctgc tctacac 27

<210> SEQ ID NO 29
<211> LENGTH: 1005
<212> TYPE: DNA
<213> ORGANISM: Artificial Sequence
<220> FEATURE:
<223> OTHER INFORMATION: Synthetic construct, coding region of tTA from pUHD15-1

<400> SEQUENCE: 29
atgtctagat tagataaaag taaagtgatt aacagcgcat tagagctgct taatgaggtc 60
ggaatcgaag gtttaacaac ccgtaaactc gcccagaagc taggtgtaga gcagcctaca 120
ttgtattggc atgtaaaaaa taagcgggct ttgctcgacg ccttagccat tgagatgtta 180
gataggcacc atactcactt ttgcccttta gaaggggaaa gctggcaaga tttttacgt 240 aataacgcta aaagttttag atgtgcttta ctaagtcatc gcgatggagc aaaagtacat 300
ttaggtacac ggcctacaga aaaacagtat gaaactctcg aaaatcaatt agcctttta 360 tgccaacaag gtttttcact agagaatgca ttatatgcac tcagcgctgt ggggcatttt 420
actttaggtt gcgtattgga agatcaagag catcaagtcg ctaaagaaga aagggaaaca 480
cctactactg atagtatgcc gccattatta cgacaagcta tcgaattatt tgatcaccaa 540
ggtgcagagc cagccttctt attcggcctt gaattgatca tatgcggatt agaaaaacaa 600
cttaaatgtg aaagtgggtc cgcgtacagc cgcgcgcgta cgaaaaacaa ttacgggtct 660
accatcgagg gcctgctcga tctcccggac gacgacgccc ccgaagaggc ggggctggcg 720
gctccgcgcc tgtcctttct ccccgcggga cacacgcgca gactgtcgac ggcccccccg 780
accgatgtca gcctgggga cgagctccac ttagacggcg aggacgtggc gatggcgcat 840
gccgacgcgc tagacgattt cgatctggac atgttgggg acggggattc cccgggtccg 900
ggatttaccc cccacgactc cgccccctac ggcgctctgg atatggccga cttcgagttt 960
gagcagatgt ttaccgatgc ccttggaatt gacgagtacg gtggg 1005

<210> SEQ ID NO 30
<211> LENGTH: 336
<212> TYPE: PRT
<213> ORGANISM: Artificial Sequence
<220> FEATURE:
<223> OTHER INFORMATION: Synthetic construct, tTA

<400> SEQUENCE: 30

Met Gly Ser Arg Leu Asp Lys Ser Lys Val Ile Asn Ser Ala Leu Glu
1 5 10 15

Leu Leu Asn Glu Val Gly Ile Glu Gly Leu Thr Thr Arg Lys Leu Ala
20 25 30

Gln Lys Leu Gly Val Glu Gln Pro Thr Leu Tyr Trp His Val Lys Asn
35 40 45

Lys Arg Ala Leu Leu Asp Ala Leu Ala Ile Glu Met Leu Asp Arg His
50 55 60

His Thr His Phe Cys Pro Leu Glu Gly Glu Ser Trp Gln Asp Phe Leu
65 70 75 80

Arg Asn Asn Ala Lys Ser Phe Arg Cys Ala Leu Leu Ser His Arg Asp
85 90 95

Gly Ala Lys Val His Leu Gly Thr Arg Pro Thr Glu Lys Gln Tyr Glu
100 105 110

Thr Leu Glu Asn Gln Leu Ala Phe Leu Cys Gln Gln Gly Phe Ser Leu
115 120 125

Glu Asn Ala Leu Tyr Ala Leu Ser Ala Val Gly His Phe Thr Leu Gly
130 135 140

Cys Val Leu Glu Asp Gln Glu His Gln Val Ala Lys Glu Glu Arg Glu
145 150 155 160

Thr Pro Thr Thr Asp Ser Met Pro Pro Leu Leu Arg Gln Ala Ile Glu
165 170 175

Leu Phe Asp His Gln Gly Ala Glu Pro Ala Phe Leu Phe Gly Leu Glu
180 185 190

Leu Ile Ile Cys Gly Leu Glu Lys Gln Leu Lys Cys Glu Ser Gly Ser
195 200 205

```
Ala Tyr Ser Arg Ala Arg Thr Lys Asn Asn Tyr Gly Ser Thr Ile Glu
    210                 215                 220

Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335
```

<210> SEQ ID NO 31
<211> LENGTH: 1017
<212> TYPE: DNA
<213> ORGANISM: Artificial Sequence
<220> FEATURE:
<223> OTHER INFORMATION: Synthetic construct, DNA sequence of tTAV

<400> SEQUENCE: 31

```
atgggcagcc gcctggataa gtccaaagtc atcaactccg cgttggagct gttgaacgaa     60

gttggcattg agggactgac gacccgcaag ttggcgcaga agctgggcgt ggagcagccc    120

accctctact ggcacgtgaa gaataagcgg gcgctgctgg atgccctggc catcgagatg    180

ctcgaccgcc accacacgca tttttgcccg ttggaaggcg agtcctggca ggacttcctc    240

cgcaataacg ccaagtcgtt ccgctgcgct ctgctgtccc accgagacgg tgccaaagtc    300

catctcggca cgcgcccgac cgaaaagcaa tacgagacac tggagaacca gctcgcgttc    360

ctgtgccagc aaggcttcag cctggaaaat gctctctacg ctctgagcgc cgtcggtcac    420

tttaccctgg gctgcgtgct ggaggaccaa gagcatcaag tcgcaaaaga ggagcgcgag    480

accccaacaa ccgattcgat gcccccactg ctgcgtcagg caatcgagct gttcgatcat    540

caaggagccg agccggcatt cctgttcggc ttggagctga ttatctgcgg attggaaaag    600

caactgaaat gcgagtcggg ctcgggcccc gcgtacagcc gcgcgcgtac gaaaaacaat    660

tacgggtcta ccatcgaggg cctgctcgat ctcccggacg acgacgcccc cgaagaggcg    720

gggctggcgg ctccgcgcct gtcctttctc cccgcgggac acacgcgcag actgtcgacg    780

gcccccccga ccgatgtcag cctgggggac gagctccact tagacggcga ggacgtggcg    840

atggcgcatg ccgacgcgct agacgatttc gatctggaca tgttgggggga cggggattcc    900

ccgggtccgg gatttacccc ccacgactcc gccccctacg gcgctctgga tatggccgac    960

ttcgagtttg agcagatgtt taccgatgcc cttggaattg acgagtacgg tgggtag      1017
```

<210> SEQ ID NO 32
<211> LENGTH: 338
<212> TYPE: PRT
<213> ORGANISM: Artificial Sequence
<220> FEATURE:
<223> OTHER INFORMATION: Synthetic construct, amino acid sequence of
      tTAV protein

<400> SEQUENCE: 32

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly


<210> SEQ ID NO 33
<211> LENGTH: 4455
<212> TYPE: DNA
<213> ORGANISM: Artificial Sequence
<220> FEATURE:
<223> OTHER INFORMATION: Synthetic construct, plasmid pUHD15-1

<400> SEQUENCE: 33

ctcgaggagc ttggcccatt gcatacgttg tatccatatc ataatatgta catttatatt      60

ggctcatgtc caacattacc gccatgttga cattgattat tgactagtta ttaatagtaa     120
```

-continued

```
tcaattacgg ggtcattagt tcatagccca tatatggagt tccgcgttac ataacttacg    180
gtaaatggcc cgcctggctg accgcccaac gacccccgcc cattgacgtc aataatgacg    240
tatgttccca tagtaacgcc aatagggact ttccattgac gtcaatgggt ggagtattta    300
cgctaaactg cccacttggc agtacatcaa gtgtatcata tgccaagtac gccccctatt    360
gacgtcaatg acggtaaatg gcccgcctgg cattatgccc agtacatgac cttatgggac    420
tttcctactt ggcagtacat ctacgtatta gtcatcgcta ttaccatggt gatgcggttt    480
tggcagtaca tcaatgggcg tggatagcgg tttgactcac ggggatttcc aagtctccac    540
cccattgacg tcaatgggag tttgttttgg caccaaaatc aacgggactt tccaaaatgt    600
cgtaacaact ccgccccatt gacgcaaatg ggcggtaggc gtgtacggtg ggaggtctat    660
ataagcagag ctcgtttagt gaaccgtcag atcgcctgga gacgccatcc acgctgtttt    720
gacctccata gaagacaccg ggaccgatcc agcctccgcg gccccgaatt catatgtcta    780
gattagataa aagtaaagtg attaacagcg cattagagct gcttaatgag gtcggaatcg    840
aaggtttaac aacccgtaaa ctcgcccaga agctaggtgt agagcagcct acattgtatt    900
ggcatgtaaa aaataagcgg gctttgctcg acgccttagc cattgagatg ttagataggc    960
accatactca cttttgccct ttagaagggg aaagctggca agatttttta cgtaataacg   1020
ctaaaagttt tagatgtgct ttactaagtc atcgcgatgg agcaaaagta catttaggta   1080
cacggcctac agaaaaacag tatgaaactc tcgaaaatca attagccttt ttatgccaac   1140
aaggtttttc actagagaat gcattatatg cactcagcgc tgtggggcat tttactttag   1200
gttgcgtatt ggaagatcaa gagcatcaag tcgctaaaga agaaagggaa acacctacta   1260
ctgatagtat gccgccatta ttacgacaag ctatcgaatt atttgatcac caaggtgcag   1320
agccagcctt cttattcggc cttgaattga tcatatgcgg attagaaaaa caacttaaat   1380
gtgaaagtgg gtccgcgtac agccgcgcgc gtacgaaaaa caattacggg tctaccatcg   1440
agggcctgct cgatctcccg gacgacgacg cccccgaaga ggcggggctg gcggctccgc   1500
gcctgtcctt tctccccgcg ggacacacgc gcagactgtc gacggccccc ccgaccgatg   1560
tcagcctggg ggacgagctc cacttagacg gcgaggacgt ggcgatggcg catgccgacg   1620
cgctagacga tttcgatctg gacatgttgg gggacgggga ttccccgggt ccgggattta   1680
ccccccacga ctccgccccc tacggcgctc tggatatggc cgacttcgag tttgagcaga   1740
tgtttaccga tgcccttgga attgacgagt acggtgggta gggggcgcga ggatccagac   1800
atgataagat acattgatga gtttggacaa accacaacta gaatgcagtg aaaaaaatgc   1860
tttatttgtg aaatttgtga tgctattgct ttatttgtaa ccattataag ctgcaataaa   1920
caagttaaca acaacaattg cattcatttt atgtttcagg ttcaggggga ggtgtgggag   1980
gttttttaaa gcaagtaaaa cctctacaaa tgtggtatgg ctgattatga tcctgcaagc   2040
ctcgtcgtct ggccggacca cgctatctgt gcaaggtccc cggacgcgcg ctccatgagc   2100
agagcgcccg ccgccgaggc aagactcggg cggcgccctg cccgtcccac caggtcaaca   2160
ggcggtaacc ggcctcttca tcgggaatgc gcgcgacctt cagcatcgcc ggcatgtccc   2220
ctggcggacg ggaagtatca gctcgaccaa gcttggcgag attttcagga gctaaggaag   2280
ctaaaatgga gaaaaaaatc actggatata ccaccgttga tatatcccaa tggcatcgta   2340
aagaacattt tgaggcattt cagtcagttg ctcaatgtac ctataaccag accgttcagc   2400
tgcattaatg aatcggccaa cgcgcgggga gaggcggttt gcgtattggg cgctcttccg   2460
```

-continued

```
cttcctcgct cactgactcg ctgcgctcgg tcgttcggct gcggcgagcg gtatcagctc   2520

actcaaaggc ggtaatacgg ttatccacag aatcagggga taacgcagga aagaacatgt   2580

gagcaaaagg ccagcaaaag gccaggaacc gtaaaaaggc cgcgttgctg gcgtttttcc   2640

ataggctccg cccccctgac gagcatcaca aaaatcgacg ctcaagtcag aggtggcgaa   2700

acccgacagg actataaaga taccaggcgt ttccccctgg aagctccctc gtgcgctctc   2760

ctgttccgac cctgccgctt accggatacc tgtccgcctt tctcccttcg ggaagcgtgg   2820

cgctttctca atgctcacgc tgtaggtatc tcagttcggt gtaggtcgtt cgctccaagc   2880

tgggctgtgt gcacgaaccc cccgttcagc ccgaccgctg cgccttatcc ggtaactatc   2940

gtcttgagtc caacccggta agacacgact tatcgccact ggcagcagcc actggtaaca   3000

ggattagcag agcgaggtat gtaggcggtg ctacagagtt cttgaagtgg tggcctaact   3060

acggctacac tagaaggaca gtatttggta tctgcgctct gctgaagcca gttaccttcg   3120

gaaaaagagt tggtagctct tgatccggca aacaaaccac cgctggtagc ggtggttttt   3180

ttgtttgcaa gcagcagatt acgcgcagaa aaaaaggatc tcaagaagat cctttgatct   3240

tttctacggg gtctgacgct cagtggaacg aaaactcacg ttaagggatt ttggtcatga   3300

gattatcaaa aaggatcttc acctagatcc ttttaaatta aaaatgaagt tttaaatcaa   3360

tctaaagtat atatgagtaa acttggtctg acagttacca atgcttaatc agtgaggcac   3420

ctatctcagc gatctgtcta tttcgttcat ccatagttgc ctgactcccc gtcgtgtaga   3480

taactacgat acgggagggc ttaccatctg gccccagtgc tgcaatgata ccgcgagacc   3540

cacgctcacc ggctccagat ttatcagcaa taaaccagcc agccggaagg gccgagcgca   3600

gaagtggtcc tgcaacttta tccgcctcca tccagtctat taattgttgc cgggaagcta   3660

gagtaagtag ttcgccagtt aatagtttgc gcaacgttgt tgccattgct acaggcatcg   3720

tggtgtcacg ctcgtcgttt ggtatggctt cattcagctc cggttcccaa cgatcaaggc   3780

gagttacatg atcccccatg ttgtgcaaaa aagcggttag ctccttcggt cctccgatcg   3840

ttgtcagaag taagttggcc gcagtgttat cactcatggt tatggcagca ctgcataatt   3900

ctcttactgt catgccatcc gtaagatgct tttctgtgac tggtgagtac tcaaccaagt   3960

cattctgaga atagtgtatg cggcgaccga gttgctcttg cccggcgtca atacgggata   4020

ataccgcgcc acatagcaga actttaaaag tgctcatcat tggaaaacgt tcttcggggc   4080

gaaaactctc aaggatctta ccgctgttga gatccagttc gatgtaaccc actcgtgcac   4140

ccaactgatc ttcagcatct tttactttca ccagcgtttc tgggtgagca aaaacaggaa   4200

ggcaaaatgc cgcaaaaaag ggaataaggg cgacacggaa atgttgaata ctcatactct   4260

tcctttttca atattattga agcatttatc agggttattg tctcatgagc ggatacatat   4320

ttgaatgtat ttagaaaaat aaacaaatag gggttccgcg cacatttccc cgaaaagtgc   4380

cacctgacgt ctaagaaacc attattatca tgacattaac ctataaaaat aggcgtatca   4440

cgaggccctt tcgtc                                                    4455
```

```
<210> SEQ ID NO 34
<211> LENGTH: 1014
<212> TYPE: DNA
<213> ORGANISM: Artificial Sequence
<220> FEATURE:
<223> OTHER INFORMATION: Synthetic construct, open reading frame of tTAV
      construct

<400> SEQUENCE: 34
```

-continued

```
atgggcagcc gcctggataa gtccaaagtc atcaactccg cgttggagct gttgaacgaa      60

gttggcattg agggactgac gacccgcaag ttggcgcaga agctgggcgt ggagcagccc     120

accctctact ggcacgtgaa gaataagcgg gcgctgctgg atgccctggc catcgagatg     180

ctcgaccgcc accacacgca tttttgcccg ttggaaggcg agtcctggca ggacttcctc     240

cgcaataacg ccaagtcgtt ccgctgcgct ctgctgtccc accgagacgg tgccaaagtc     300

catctcggca cgcgcccgac cgaaaagcaa tacgagacac tggagaacca gctcgcgttc     360

ctgtgccagc aaggcttcag cctggaaaat gctctctacg ctctgagcgc cgtcggtcac     420

tttaccctgg gctgcgtgct ggaggaccaa gagcatcaag tcgcaaaaga ggagcgcgag     480

accccaacaa ccgattcgat gcccccactg ctgcgtcagg caatcgagct gttcgatcat     540

caaggagccg agccggcatt cctgttcggc ttggagctga ttatctgcgg attggaaaag     600

caactgaaat gcgagtcggg ctcgggcccc gcgtacagcc gcgcgcgtac gaaaaacaat     660

tacgggtcta ccatcgaggg cctgctcgat ctcccggacg acgacgcccc cgaagaggcg     720

gggctggcgg ctccgcgcct gtcctttctc cccgcgggac acacgcgcag actgtcgacg     780

gcccccccga ccgatgtcag cctgggggac gagctccact tagacggcga ggacgtggcg     840

atggcgcatg ccgacgcgct agacgatttc gatctggaca tgttggggga cggggattcc     900

ccgggtccgg gatttacccc ccacgactcc gccccctacg gcgctctgga tatggccgac     960

ttcgagtttg agcagatgtt taccgatgcc cttggaattg acgagtacgg tggg          1014
```

```
<210> SEQ ID NO 35
<211> LENGTH: 338
<212> TYPE: PRT
<213> ORGANISM: Artificial Sequence
<220> FEATURE:
<223> OTHER INFORMATION: Synthetic construct, Protein sequence of tTAV

<400> SEQUENCE: 35

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190
```

```
Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly
```

<210> SEQ ID NO 36
<211> LENGTH: 1014
<212> TYPE: DNA
<213> ORGANISM: Sequence
<220> FEATURE:
<223> OTHER INFORMATION: Open reading frame of tTAV2

<400> SEQUENCE: 36

```
atgagccgcc tggataagtc caaagtcatc aactccgcgt tggagctgtt gaacgaagtt      60

ggcattgagg gactgacgac ccgcaagttg gcgcagaagc tgggcgtgga gcagcccacc     120

ctctactggc acgtgaagaa taagcgggcg ctgctggatg ccctggccat cgagatgctc     180

gaccgccacc acacgcattt ttgcccgttg gaaggcgagt cctggcagga cttcctccgc     240

aataacgcca agtcgttccg ctgcgctctg ctgtcccacc gagacggtgc caaagtccat     300

ctcggcacgc gcccgaccga aaagcaatac gagacactgg agaaccagct cgcgttcctg     360

tgccagcaag gcttcagcct ggaaaatgct ctctacgctc tgagcgccgt cggtcacttt     420

accctgggct gcgtgctgga ggaccaagag catcaagtcg caaaagagga gcgcgagacc     480

ccaacaaccg attcgatgcc cccactgctg cgtcaggcaa tcgagctgtt cgatcatcaa     540

ggagccgagc cggcattcct gttcggcttg gagctgatta tctgcggatt ggaaaagcaa     600

ctgaaatgcg agtcgggctc gggcccgcc tacagccgcg cccgcaccaa gaacaactac     660

ggcagcacca tcgagggcct gctggatctg ccggatgatg atgccccgga ggaggcgggc     720

ctggccgccc cgcgcctgag cttcctgccg gccggacaca cccgccgcct gtcgaccgcc     780

ccgccgaccg acgtgagcct gggcgatgag ctgcacctgg atggcgagga tgtggcgatg     840

gcccacgccg atgccctgga cgacttcgac ctggacatgc tgggcgatgg cgatagcccg     900

ggaccgggat tcaccccgca cgatagcgcc ccctacggcg ccctggatat ggccgatttc     960

gagttcgagc agatgttcac cgacgccctg ggcatcgatg agtacggcgg ctaa          1014
```

<210> SEQ ID NO 37
<211> LENGTH: 337
<212> TYPE: PRT
<213> ORGANISM: Artificial Sequence
<220> FEATURE:
<223> OTHER INFORMATION: Synthetic construct, Protein sequence of tTAV2

<400> SEQUENCE: 37

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly
```

<210> SEQ ID NO 38
<211> LENGTH: 1011
<212> TYPE: DNA
<213> ORGANISM: Artificial sequence
<220> FEATURE:
<223> OTHER INFORMATION: Synthetic construct, open reading frame of tTAV3

<400> SEQUENCE: 38

```
atgggcagcc gcctggacaa gagcaaggtg atcaacagcg ccctggagct gctgaacgaa      60
gttggtatcg agggcctgac cacccgcaag ctggcccaga agctgggcgt ggaacagccg     120
accctgtact ggcacgtgaa gaacaagcgc gccctgctgg acgccctggc catcgaaatg     180
ctggatcgcc accacaccca cttctgcccg ctggagggcg agagctggca ggatttcctg     240
cgcaacaacg ccaagagctt ccgctgcgcc ctgctgtcgc accgcgatgg cgccaaggtg     300
cacctgggca cccgcccgac cgagaagcag tacgagaccc tggagaacca gctggccttc     360
ctgtgccagc agggcttcag cctggagaac gccctgtacg ccctgagcgc cgtgggccac     420
ttcaccctgg gctgtgtgct ggaggatcag gagcaccagg tggccaagga ggagcgcgag     480
accccgacca ccgatagcat gccgccgctg ctgcgccagg ccatcgagct gttcgatcac     540
cagggcgccg agccggcctt cctgttcggc ctggagctga tcatctgcgg cctggaaaag     600
cagctgaagt gcgagagcgg cagcgcctac agccgcgccc gtaccaagaa caactatggc     660
agcaccatcg agggactgct ggacctgccg gatgacgatg ccccggagga agccggcctg     720
gccgcccccc gcctgagctt cctgcccgcc ggacacacgc gccgcctgag caccgccccg     780
ccgaccgatg tgagcctggg cgacgagctg cacctggatg gagaggatgt ggcaatggcc     840
cacgccgacg ccctggacga tttcgacctg gatatgctgg gcgatggaga tagcccggga     900
ccgggcttca cgccccacga tagcgccccg tacggcgccc tggacatggc cgacttcgag     960
ttcgagcaaa tgttcaccga cgcgctgggc atcgatgagt atggcgggta g             1011
```

<210> SEQ ID NO 39
<211> LENGTH: 336
<212> TYPE: PRT
<213> ORGANISM: Artificial Sequence
<220> FEATURE:
<223> OTHER INFORMATION: Synthetic construct, Protein sequence of tTAV3

<400> SEQUENCE: 39

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175
```

-continued

```
Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335


<210> SEQ ID NO 40
<211> LENGTH: 568
<212> TYPE: DNA
<213> ORGANISM: Pectinophora gossypiella

<400> SEQUENCE: 40

gctagtggag aactgccaca aactgctgga aaagttccac tactcctggg aaatgatgcc     60

cctggtgctg gtcattctaa actacgccgg ctccgacctc gacgaggctt ctagaaaaat    120

tgatgaaggg aagatgatca tcaacgagta cgcgaggaag cacaatctga acatcttcga    180

tggccacgag ctaaggaact cgactcgcca gtacggactt taatacagta atattagttt    240

tctccaacaa cactaaacac gacataacac gctacacgca aaaaatacac gagtctttaa    300

tgttttacac gctcagtaaa ttattcactt acacgcttaa ctaaaatttt acacaatcgg    360

taaaaaaata caacaattta ttatcgtaaa aattacacaa aataaatgag atttaaatgt    420

cgtttaataa aataaaataa aaatagcatc gggaatatct tttcacctat tgccggagaa    480

cagtttaaat ggatactctc atttgaatca ttttaattgt agtagcattt tattttatta    540

ttaatagcaa taagtacaca aacataaa                                       568


<210> SEQ ID NO 41
<211> LENGTH: 610
<212> TYPE: DNA
<213> ORGANISM: Pectinophora gossypiella

<400> SEQUENCE: 41

gtagtggaga actgccacaa actgctggaa aagttccact actcctggga aatgatgccc     60

ctggtgctgg tcattctaaa ctacgccggc tccgacctcg acgaggcttc tagaaaaatt    120

gatgaaggga agatgatcat caacgagtac gcgaggaagc acaatctgaa catcttcgat    180

ggccacgagc tgaggaactc gactcgccag tacggacttt aatacagaaa atgctgagcg    240

aaattaataa tataagtggt gtactatcgt cgtccatgaa gttattttgc gaatgatact    300

ttgttttgta tgtgctgtgt gttgtgtgga cttttgctgt gcgttgctgt ttgcgatgga    360

aggactattg tgtcgtcgcc acgctggact attcgcacat tgggtggtcc accagtggcg    420
```

gatgtacgag cggtcgctgt gctcgctcct ggagctgcaa gcgcgcaaag ggacgtactc 480
ggtgtgctgc tcaccccgct acgtcatcgc gcccgagtac gcgtcacacc tgttgcctct 540
gccgcttacc acgcagagat catccccgcc gcccgcgcac ttgtagcgat gcgaacctgc 600
gccgcgggaa 610

<210> SEQ ID NO 42
<211> LENGTH: 449
<212> TYPE: DNA
<213> ORGANISM: Pectinophora gossypiella
<220> FEATURE:
<221> NAME/KEY: misc_feature
<222> LOCATION: (26)..(26)
<223> OTHER INFORMATION: At position 26, n is a, c, g, or t

<400> SEQUENCE: 42
gctagtggag aactgccaca aactgntgga aaagttccac tactcctggg aaatgatgcc 60
cctggtgctg gtcattctaa actacgccgg ctccgacctc gacgaggctt ctagaaaaat 120
tgatgaagca cattgggtgg tccaccagtg gcggatgtac gagcggtcgc tgtgctcgct 180
cctggagctg caagcgcgca aagggacgta ctcggtgtgc tgctcacccc gctacgtcat 240
cgcgcccgag tgcgcgtcac acctgttgcc tctgccgctt accacgcaga gatcatcccc 300
gccgcccgcg cacttgtagc gatgcgaacc tgcgccgcgg gaagtaagta ctatttcatt 360
tattattctt tttatttttg gttttaaggt gctgacagac ttgaatttca agcaaatagt 420
gtctgacaaa gagctcaaaa tagacatgt 449

<210> SEQ ID NO 43
<211> LENGTH: 28774
<212> TYPE: DNA
<213> ORGANISM: Aedes aegypti

<400> SEQUENCE: 43
acagtgaaat ttgatcgatc actcatcgaa acgagatcac tttcgattga tcgtgacaat 60
tttttagaat ccatttcaca gtcgttggga ctgttgaccc tgtcacttta aactagctag 120
tgagtagctt tgctctagtg aaagctaact agcactgtta aaaaatctta ggtaaagtgt 180
cagcaaccct gacaactggg ccacctcttg ccgaccataa gcaaatgaaa tcaaatggtt 240
cgctacgaag gttaattggg tttcgatcta cttcgtccta agcgctattt ttcgtcatac 300
ggtggagaac ggctggtatt cgtttacttt agtttaccaa gcgatgcttc caattaaccc 360
aaagctagat gaagcaggat tcgcgataaa aagcagtatg cgaacttaaa atgttctact 420
acattacggc gggtattcaa atttacctgc cacataaatt tattttccaa gtataatttg 480
cgaaagctgc aatggttcat gcttgaattt tacaagatga tgtaatgccg cccataagtt 540
taaatggacg gtgtatttaa ataaaaggtt catattaaac gctttcgacg ttaccaagta 600
ccatttgtac acaaacatgt aataaaacta ttgtatttct ataaataact tcagttcaat 660
catccacttt gcacattttc accgaaatcg catggacgaa ggtaaacatg tgtttgtaca 720
ttattttgat aacataaaga tatttattga agtcaagtta gtaggtgaaa cgtgtaaaag 780
tggctttagc gtacctgctt gacgtaccga gcgaaatctg attagcggtc gactaagcca 840
taaaacttct acaattcaca aaattttgaa aaattccctc gctgccacga tactaatgca 900
ctgcatggct cgctttagac taatcgccag ctgattcggt attttgaaga tgttaagtgt 960
tttaaaactt tttaagggag cgacggtgct atgattacgt aatcaaatgt tctttctttt 1020
actttcagac caattgcaga acaagcttta tcctaatcca tctcattttg ggaacagcac 1080
tagccgcgac cattagccgt ttagtttaca agaaagaaaa tgaaagtctg gttaacgtct 1140
tgttcgaaat aggattaggt agagtaaaac ccttgtcgtg atcggcgctg gtaatcggca 1200
tctgcgtaga gaacatgttg tacttcctcg aggacgattg ctcgcgctcg cacggttctt 1260
attgctacca tggtgaaacc actagcgccg aggaagtgct agacgcatct cttgtacaac 1320
atgaaggagc tcctgctaac gagcgcgagc gtgccaagaa taacgatggt accactttgg 1380
tgatcgcggc tccttcacga taccgttgtg aaggttttct gaattgcgca tcgtctccga 1440
agggtgtgtc caggtgcatt gtctcccaac tgacctgttc ccgacaatat cgagcactaa 1500
atggcaacac ttccaaaaga cttaacgcgt agcagaggct tcccacacag gtccacgtaa 1560
cagagggttg actggacaag ggctgttata gctcgtgatt ggtttccatt agagagcagt 1620
atctcgtagt agcgtaggag agtccattag agtgcgatat tccgtgagtt tgtgtgaccg 1680
gcgatagaga agccctgacg ccaaaggtaa tctctcgtca tagagcatca tcgcatcctc 1740
tcaggtaatc tcacgctata aggcactcaa acacactggc cgctatctct tcgggactgc 1800
cgcgcttcaa gacgattgta actcggaaac tgacctgatt agtacataaa aagagaccta 1860
ttgcgtaagc ttataagaaa cgagtttgtc cacacggttg gcgcgaagtt ctgctaacat 1920
tgagcctttg actggactaa tcatgtattt ttctctggat aacgcattcg aatattcttt 1980
gctcaaacag gtgtgccaac atggtttcgc aagatcgctg gatggtaaag atgtccgagg 2040
cagggtacga taaccgggcg gatggcagtg gagcttccag cagcagcctg aacccgcgaa 2100
taccaaagcg ttctagcgac ctaccatttc tacaggctcc gtcccatgct attggcccgc 2160
ctaccgtcac ctcgaaggtc gtcgtcggac ttgggcgctt cgccgccgaa ctgtgcccgc 2220
tgccggaacc acggtcacaa gatcggcctg aagggacaca agcgctattg taagtatcgc 2280
aattgtacct gcgaaaagtg gcggcggctt gacacgggcg acggccttgg tgccagtgtt 2340
ctagccggac ttccctgtgt tcgcgataac attcatagcg ttaacatgga cgcttttcac 2400
ctgcctgacg gccgaacggc agcgggtcat ggccctgcag acggctctcc gaagggcgca 2460
aacccaggac gaacagcggt tgctggtaga cggagaggtg gacggactgc cggcttgccg 2520
tcgcccagta ccgggacgtc tgccgagagg cttcccgcgt ttgggtcctg cttgtcgcca 2580
acgaccatct gcctctccac cccgccgaac cggtacatag ccttcaaata ccaaaattgt 2640
ctgacctaaa agagatgatc cataattctc agcagaggtc gttgatcgac tgcgactcgt 2700
gggcggcttg gccatgtatc ggaagtttat ggttttaaca gactggattt tctctactag 2760
gtattaagag tcgtctccag caactagctg acgctgagca ccaccggctc gatgaactcc 2820
accccgggca gctcgttggt aacgctgtcc cagcaccgaa gatcaccctg ctccgccgcg 2880
tcggtccacc ccagcgaggc ggtggccgag ctacttgagg tggggcccgt cgagcaacca 2940
ttgcgacagg gtcgtggctt ctagtgggac gaggcggcgc agccaggtgg ggtcgctccg 3000
tcagcaaaac gttgcaggta ggtgtgaggc atatctattt cgttattctc tcaatgtttg 3060
tggagaaccg gccggaattc aacatcgaag tcggtttctg agtcgttttg caacgtccat 3120
ccacactccg tatagataaa gcaataagag agttacaaac acctcttggc cggccttaag 3180
ttgtagcttc agccaaagac ttctattgat ttatgataaa tttctctcaa atgtttgcgc 3240
ggagggtgga tttttgagag ctgagtggtg tagaaacgaa atgggcatca aacgttatgc 3300
aagataacta aatactattt aaagagagtt tacaaacgcg cctcccacct aaaaactctc 3360
gactcaccac atctttgctt tacccgtagt ttgcaatacg ggcgctgctt gaaacaggtt 3420

-continued

```
tatgttaggg gtttcctgtg tttcatacag tcaccccatt gttatgtata gcacacagat   3480
atggataaaa gttggattaa ccgcgacgaa ctttgtccaa atacaatccc caaaggacac   3540
aaagtatgtc agtggggtaa caatacatat cgtgtgtcta tacctatttt caacctaatt   3600
gcagtgaata tcccatcaaa tagagttgca attgagtaga acacatttta ccaacgtata   3660
aagcatcgta atcaattata atatacttaa gcaaaataca cgtcacttat agggtagttt   3720
atctcaacgt taactcatct tgtgtaaaat ggttgcatat ttcgtagcat tagttaatat   3780
tatatgaatt cgttttatgt atggggaaat aatttgtcaa ccacatttct agaaaagttg   3840
attcatacat gtgtgctttt gaaagccata taccacatta tgtttgattc atatctctta   3900
taccccttta ttaaacagtt ggtgtaaaga tcttttcaac taagtatgta cacacgaaaa   3960
ctttcggtat atggtgtaat acaaactaag tatagagaat taatatgagt cgatttatcg   4020
cgaaattttt caaaatgtcc tatgtaccaa tgaaagatac tctcttatct cgctctgttt   4080
tgaacataac aactgaaact attatactca gctaaatagc gctttaaaaa gttttacagg   4140
atacatggtt actttctatg agagaataga gcgagacaaa acttgtattg ttgactttga   4200
tttgggaagt ttttcactat agataaaaaa atgtccttga ctagcgtttc atacaaaaaa   4260
aaaaaaaaac gcaaccaaaa atgttaatgt ggttcagtga aaacccttca aaaagtgata   4320
tctatttttt tacaggaact gatcgcaaag tatgtttttt tttttttttg cgttggtttt   4380
tacaattaca ccaagtcact ttgattaaag aggaagtaaa ctaagatagt gtctcaatgt   4440
tggataggtc atttagaaaa ggtccgcgag attggatcca taataatgat tctcctctct   4500
aactaatttc tccttcattt gattctatca cagagttaca acctatccag taaatctttt   4560
ccaggcgctc taacctaggt attattacta agaggagaga cactgatccg catctgtggg   4620
atggacaacg tttgtaattt ctatcggtat cgaaaataat cgcgcatttt cgggcgtatt   4680
ccagaaaaca acaatgaaat gtgactaggc gtagacaccc tacctgttgc aaacattaaa   4740
gatagccata gcttttatta gcgcgtaaaa gcccgcataa ggtcttttgt tgttacttta   4800
atactgaagc aaatgtgcac aattttcatt acatgatatt attcaatggg gtaggtgggc   4860
gacaaaatag attcattaat gttggataat aggggcgttt tatgacttcg tttacacgtg   4920
ttaaaagtaa tgtactataa taagttaccc catccacccg ctgttttatc taagtaatta   4980
caacctatta tccccgcaaa gtcattatcc ctaaatgctc cacctcagct ggtggccccg   5040
tcagtcagtt gatcgggaaa gcagcaatca atccggagac aggtcgacct ccatcgaaca   5100
cagtaatagg gatttacgag gtggagtcga ccaccggggc agtcagtcaa ctagcccttt   5160
cgtcgttagt taggcctctg tccagctgga ggtagcttgt ggaaccgaac aacactagat   5220
gttcgatttc taacgaccga ctaagaacat cgtcggaagc gtctggttca ttcgacgagc   5280
cggaaggggt tcatctttcg ccttggcttg ttgtgatcta caagctaaag attgctggct   5340
gattcttgta gcagccttcg cagaccaagt aagctgctcg gccttcccca agtagaaagc   5400
ctcgtcgtcg aacgaatagc tgctgctaca cttcgcgtcg ttatcgtcgt cgggggattg   5460
gtgtttgtaa ctgcgcactc gtttatacat tgttgtttgc gagcagcagc ttgcttatcg   5520
acgacgatgt gaagcgcagc aatagcagca gccccctaac cacaaacatt gacgcgtgag   5580
caaatatgta acaacaaacg cgatcggcgg gcgctgtaac tgcctgcagt cacgcgttca   5640
ttcgcagtcg ttgtcgtagt catacacacg ccgtcgttcc tttgtatcag ctgtgtagca   5700
gctagccgcc cgcgacattg acggacgtca gtgcgcaagt aagcgtcagc aacagcatca   5760
```

```
gtatgtgtgc ggcagcaagg aaacatagtc gacacatcgt tttagtggtg ttacaacatt   5820
gagctacttt ttgcgtttcg ctttcgtgct gcggcggcgg cggcgggact tcgctgcact   5880
gataggaacg gaatgcatgc aaatcaccac aatgttgtaa ctcgatgaaa aacgcaaagc   5940
gaaagcacga cgccgccgcc gccgccctga agcgacgtga ctatccttgc cttacgtacg   6000
tgctccggtt gaagagagct ctgcgccact tgtggcgggt ttcactcaaa aggcatcgtc   6060
gcgtcgcaac aaagtgcgca cattcgacgc gtaactgtaa acgaggccaa cttctctcga   6120
gacgcggtga acaccgccca aagtgagttt tccgtagcag cgcagcgttg tttcacgcgt   6180
gtaagctgcg cattgacatt gtaaatagaa agactttggt gcgtttagaa aaagggtcac   6240
aaagggtggc aagtgagtat gtatgtgagc tcatttcatt ctcgatggca ttgagacgta   6300
catttatctt tctgaaacca cgcaaatctt tttcccagtg tttcccaccg ttcactcata   6360
catacactcg agtaaagtaa gagctaccgt aactctgcat atctattctg agaacgaaag   6420
ttcaatggat gcattttatg caatgccacc ggaattttcc tatgaactgc tttcacactt   6480
cttttaagaa aattttgcag tagataagac tcttgctttc aagttaccta cgtaaaatac   6540
gttacggtgg ccttaaaagg atacttgacg aaagtgtgaa gaaaattctt ttaaaacgtc   6600
atttaattta ttcactccat ttagttctga cgtaacattc cagataacac acttcaaagt   6660
catggtcagt tcatgttgaa cgaatgtgca ccgcgatcca taaattaaat aagtgaggta   6720
aatcaagact gcattgtaag gtctattgtg tgaagtttca gtaccagtca agtacaactt   6780
gcttacacgt ggcgctaggt cgcagaacga ttccatgtct taatgtcgtc acttatcata   6840
taatcaccca gtttttgccc cacttaaaaa aacgatgtcc actttttatc tgagtttctt   6900
gcgtcttgct aaggtacaga attacagcag tgaatagtat attagtgggt caaaaacggg   6960
gtgaattttt ttgctacagg tgaaaaatag actcaaagaa tctcctctct tttcagccaa   7020
ccactccagc ggaacccctg aacccggaaa catggtacca ggtgagttcg ctgttgaaat   7080
actaatttgc agaaaacata agaggagaga aaagtcggtt ggtgaggtcg ccttggggac   7140
ttgggccttt gtaccatggt ccactcaagc gacaacttta tgattaaacg tcttttgtat   7200
agaaattttg ctaccgattt accataactg gaatcgaaga caatatgact tcatcacacc   7260
agcagtaaac acggcgtaaa aatgattcat caggacccgc tctttaaaac gatggctaaa   7320
tggtattgac cttagcttct gttatactga agtagtgtgg tcgtcatttg tgccgcattt   7380
ttactaagta gtcctgggcg tcaatagccc tgtttttcca cgctcatctt gggtttcaca   7440
tcggtgaaca ccacttggag acgttttcac acaatgttca tgttcttctt tgagtaaatg   7500
agttatcggg acaaaaaggt gcgagtagaa cccaaagtgt agccacttgt ggtgaacctc   7560
tgcaaaagtg tgttacaagt acaagaagaa actcatttac aagttatgcg tggtcccgtg   7620
ctcatcaaga tagtgtgcca cacataagaa ttatcttaat tgaggccttc tgcgggccgt   7680
gagcttgttt gctacgccct ttcaatacgc accagggcac gagtagttct atcacacggt   7740
gtgtattctt aatagaatta actccggaag acgcccggca ctcgaacaaa cgatgcggga   7800
tccttggcgt tgagttttag tttctttgac agagaaagac ttttgataat ctactttctg   7860
cagctacgac ctttctctga actatttgga aaattataac aggaaccgca actcaaaatc   7920
aaagaaactg tctctttctg aaaactatta gatgaaagac gtcgatgctg gaaagagact   7980
tgataaacct tttaatattg ttatgttgac aatatttatc ccttcgatta acaaaaaact   8040
tcaagccagg gaaacatcca gtgtgaaaac actaagcggc gcactttggt tcatttcatt   8100
aatacaactg ttataaatag ggaagctaat tgttttttga agttcggtcc ctttgtaggt   8160
```

```
cacacttttg tgattcgccg cgtgaaacca agtaaagtaa cgtatcgatc actcttaatt   8220
caagatgaca aagtggttga gtagtagagt acgtggctca caatcggaag gttcttggct   8280
cgaatctcaa tgtatgctat gcatagctag tgagaattaa gttctactgt ttcaccaact   8340
catcatctca tgcaccgagt gttagccttc caagaaccga gcttagagtt acatacgata   8400
ttttaacttt ttttttattt tgtcgatcat aaacggatgc gcgactcagc atttttggca   8460
tttgaatcat gattccgagt aatcagctac aaaaacctaa aaaattgaaa aaaaaataaa   8520
acagctagta tttgcctacg cgctgagtcg taaaaaccgt aaacttagta ctaaggctca   8580
ttagtcgatg tttttggatt cgcgtgtgtt gcgttacggc aatctgactc atgatatcat   8640
gagtccaaat catggtgtat tttcataaga cgaaaacacg ctggaatcat gatatcatga   8700
gcgcacacaa cgcaatgccg ttagactgag tactatagta ctcaggttta gtaccacata   8760
aaagtattct gcttttgtgc gaccttagta ctatagtact gtaataatct tgtttttgga   8820
ttctgatttc tacccgtgca tttctaaagt ttgcaaagaa ggaagcttca aaaaacttcc   8880
aaaagcttat gttacagaag cattattaga acaaaaacct aagactaaag atgggcacgt   8940
aaagatttca aacgtttctt ccttcgaagt tttttgaagg ttttcgaata caatgtcttc   9000
cttggaaagc ttaagttaca gcagtttccg taccagaacg ttggaaagct tatattacga   9060
aacagtaata gggtttctat gcggtggaag tgctgttata gaacctttcg aattcaatgt   9120
cgtcaaaggc atggtcttgc aacctttcga atataatgct ttgtcattat cccaaagata   9180
cgccaccttc acgacaatat tggcgtgtaa gcatttataa tacatctggg tatcatcgaa   9240
atcattagaa aaaatgcggt ataagtttca cttgaattca gatcagtgat cgattgttac   9300
accgcacatt cgtaaatatt atgtagaccc atagtagctt tagtaatctt ttttacgcca   9360
tattcaaagt gaacttaagt ctagtcacta gctaacaatg agttcaaata gatccaaata   9420
tatgagggtg aaacgtcatt gcgatccact gtgaactgca gttgattggc cgcaatttca   9480
aaatatgtac acccgagtga tcaagtttat ctaggtttat atactcccac tttgcagtaa   9540
cgctaggtga cacttgacgt caactaaccg gcgttaaagt tttatacatg tgggctcact   9600
tctgcacggc tgttcagctg acatccttca ttgtcccagt cgttcataca aacttgcccg   9660
tcaagatcaa ggaagttggc gcttgatcaa tgttctgttt agacgtgccg acaagtcgac   9720
tgtaggaagt aacagggtca gcaagtatgt ttgaacgggc agttctagtt ccttcaaccg   9780
cgaactagtt acaagacaaa catttctttt ttcttaagta gtattgggcg ctgcggtcac   9840
ctcatttatc tttttgaaat tgtttcggaa ataatgcacg agatgcaata acggttcttg   9900
gtaaagaaaa aagaattcat cataacccgc gacgccagtg gagtaaatag aaaaacttta   9960
acaaagcctt tattacgtgc tctacgttat tgccaagaac aacatagtca tgtagaacct  10020
tacaaatgat cagaattgat ttgatcaatt catttccagc tttcaaactg acgatcgccc  10080
aatgctaccg tccatcacga ttgtatcagt acatcttgga atgtttacta gtcttaacta  10140
aactagttaa gtaaaggtcg aaagtttgac tgctagcggg ttacgatggc aggtagtgct  10200
tattccacgc actggctgtc atgttccctg ccagatttac gtagtgttct tttgtaaagg  10260
caacactgct gcactgctcc aagtcactcc aagcttcatc ataaggtgcg tgaccgacag  10320
tacaagggac ggtctaaatg catcacaaga aaacatttcc gttgtgacga cgtgacgagg  10380
ttcagtgagg ttcgaagtag tgcgagttga agcaaactgt gaaggattga tattttgaat  10440
taaatcaagc tctcgcgttg caggcagctg taacttgcca ccaagtatga tcggtcttcc  10500
```

acgctcaact tcgtttgaca cttcctaact ataaaactta atttagttcg agagcgcaac 10560
gtccgtcgac attgaacggt ggttcatact agccagaagg gacttcgttc cataaaaagt 10620
ggaatgctcc tcgtccgatt tccagaaaca gtcggttatg caataaaaca ggatcaggtt 10680
cgatgactct tggcgatatc ctgaagcaag gtatttttca ccttacgagg agcaggctaa 10740
aggtctttgt cagccaatac gttattttgt cctagtccaa gctactgaga accgctatag 10800
tgaattggag tcgttaccta tcccccgata aagatatcct ctcgcaattc gagggggatt 10860
aggattagaa accgtttgct gatatttgcg agatataaaa acttaacctc agcaatggat 10920
agggggctat ttctatagga gagcgttaag ctccccctaa tcctaatctt tggcaaacga 10980
ctataaacgc tctatatttt actaataaaa tcttcaattc gctaaaagca cttcaattct 11040
tgttttctct tctggtttca gttgaccccc atatgcgagt gcagcatcac ggaccggact 11100
tgattatttt agaagttaag cgattttcgt gaagttaaga acaaaagaga agaccaaagt 11160
caactggggg tatacgctca cgtcgtagtg cctggcctga caggaacagg tgcgtacttc 11220
cttaacttca ctatcaataa aaccgtacct cctccagtcc atcgaaacaa caataaaata 11280
ctgcaccgat cagctggaat gtccttgtcc acgcatgaag gaattgaagt gatagttatt 11340
ttggcatgga ggaggtcagg tagctttgtt gttattttat gacgtggcta gtcgacctta 11400
ttctatcccg ggaggtccaa tcgctacaat ttatgcacat ttaattccac tggagccatg 11460
tgcgttcggg catcttatca ggcgttcggg aattgaaact aagatagggc cctccaggtt 11520
agcgatgtta aatacgtgta aattaaggtg acctcggtac acgcaagccc gtagaatagt 11580
ccgcaagccc ttaactttga ttacgacctc atttgtcatt aacgggatgc attcgtacgc 11640
agtcagcgtc ttatcggcat atatgcggta gccccccgag tgacaattaa accatggagc 11700
aatgctggag taaacagtaa ttgccctacg taagcatgcg tcagtcgcag aatagccgta 11760
tatacgccat cggggggctc actgttaatt tggtacctcg cgaaaccaat ttcacagcgg 11820
tccaccaact accgaatgcg atgcattttt atacgacagt ggcgttacta ggtgcttaac 11880
atatcaaaac ttggaagctt gctttggtta aagtgtcgcc aggtggttga tggcttacgc 11940
tacgtaaaaa tatgctgtca ccgcaatgat ccacgaattg tatagttttg aaccttcgaa 12000
cctttcaaaa gcttgcaaag cttccttcca ggagcttgga aagcttcctt ccaggagctt 12060
ggaaagcttc cttccaggag cttggaaagc ttccttccag ggaaagtttt cgaacgtttc 12120
gaaggaaggt cctcgaacct ttcgaaggaa ggtcctcgaa cctttcgaag gaaggtcctc 12180
gaacctttcg aaggaaggtc gagcttggaa agcttccttc caggagcttg gaaagcttcc 12240
ttccagtagc ttggaaagct tccttccagg agcttggaaa gcttccttcc aggagcttgg 12300
ctcgaacctt tcgaaggaag gtcctcgaac ctttcgaagg aaggtcatcg aacctttcga 12360
aggaaggtcc tcgaaccttt cgaaggaagg tcctcgaacc aaagcttcct tccaggagct 12420
tggaaagctt ccttccagga gcttggaaag cttccttcca ggagcttgga aagcttcctt 12480
ccaggagctt ggaaagcttc tttcgaagga aggtcctcga acctttcgaa ggaaggtcct 12540
cgaacctttc gaaggaaggt cctcgaacct ttcgaaggaa ggtcctcgaa cctttcgaag 12600
cttccaggag cttggaaagc ttccttccag gagcttggaa agcttccttc caggagcttg 12660
gaaagcttcc ttccaggagc ttggaaagct tccttccagg gaaggtcctc gaacctttcg 12720
aaggaaggtc ctcgaacctt tcgaaggaag gtcctcgaac ctttcgaagg aaggtcctcg 12780
aacctttcga aggaaggtcc agcttggaaa gcttccttcc aggagcttgg aaagcttcct 12840
tccaggagct tggaaagctt ccttccagga gcttggaaag cttccttcca ggagcttgga 12900
tcgaaccttt cgaaggaagg tcctcgaacc tttcgaagga aggtcctcga acctttcgaa 12960
ggaaggtcct cgaacctttc gaaggaaggt cctcgaacct aagcttcctt ccaggagctt 13020
ggaaagcttc cttccaggag cttggaaagc ttccttccag gagcttggaa agcttccttc 13080
caggagcttg gaaagcttcc ttcgaaggaa ggtcctcgaa cctttcgaag gaaggtcctc 13140
gaacctttcg aaggaaggtc ctcgaacctt tcgaaggaag gtcctcgaac ctttcgaagg 13200
ttccaggagt ggaaaagatt cctgaaaagt acttggagaa attcctcgag ttatttcagt 13260
aaagattata ctggaggaac caatggtgga atcacttgag aaggtcctca ccttttctaa 13320
ggacttttca tgaacctctt taaggagctc aataaagtca tttctaatat gacctccttg 13380
gttaccacct tagtgaactc gcatttcggc agaaatccct ggcaaaatcg ctatggaaaa 13440
atccctgcaa aaaatcctgg aataatcctt gccggaatct catgaggaac tcctggtaaa 13500
cgtaaagccg tctttaggga ccgttttagc gataccttttt tagggacgtt ttttaggacc 13560
ttattaggaa cggccttaga gtactccttg aggaccattt attctttaac aaatttctgt 13620
ttattttctc tacaaagtta cagctccttt accgtgccga ttggccagaa atgaccccaa 13680
agactcatgg ggtacgatct taagaaattg tttaaagaca aataaaagag atgtttcaat 13740
gtcgaggaaa tggcacggct aaccggtctt tactggggtt tctgagtacc ccatgctaga 13800
tatttctgcc aaatatactg tatgtttgtt tctttctgat atgcttttaa gctcaatttt 13860
ctttggaatg gtggagattt gttttggcct ccaatatact ataaagacgg tttatatgac 13920
atacaaacaa agaaagacta tacgaaaatt cgagttaaaa gaaaccttac cacctctaaa 13980
caaaaccgga ggttatatga tgctagctcg tagttcgtac ctgaagtcaa ctcctcaatt 14040
cctaaatgct acaataatat ataaaatttt aggaaataac tgcaaaatat tctgaaggcc 14100
acgatcgagc atcaagcatg gacttcagtt gaggagttaa ggatttacga tgttattata 14160
tattttaaaa tcctttattg acgttttata agacttccgg atgtcttgat ctatcttgat 14220
gtatctaata tgtaatccca gaagcattct agttttttct gataatctgt gaaataagtt 14280
gtttttacga actttgactt tacagaacta gatagaacta catagattat acattagggt 14340
cttcgtaaga tcaaaaaaga ctattagaca ctttattcaa caaaaatgct tgaaactgaa 14400
ttcgggattt gaggtacaag ctttcaaata tattggaggt tctgcgatat taacttcaat 14460
gaattattgg aaattagaaa tcgtcttgtg catacgggtt aagccctaaa ctccatgttc 14520
gaaagtttat ataacctcca agacgctata attgaagtta cttaataacc tttaatcttt 14580
agcagaacac gtatgcccaa aatcgatttt agtctctggt agatttcgag agggaatgtc 14640
tgaagaaatt ttctgaccta catgtgaagt attgtctgtc aaattcaaaa tattttctgt 14700
ttagctaaaa tcagagacca tctaaagctc tcccttacag acttctttaa aagactggat 14760
gtacacttca taacagacag tttaagtttt ataaaagaca aggaaattaa aattttttgg 14820
ggaaaactcg aaactccttg gatatccaag gaaacaaaaa aaaaagaaat atctgaagaa 14880
gtgcatcgtc ctttttcctt tcctttaatt ttaaaaaacc ccttttgagc tttgaggaac 14940
ctataggttc ctttgttttt tttttcttta tagacttctt cacgtagcag gaaaaaggaa 15000
aattattgtt ttaattaact aatagttctg ctagaaaggt ttttggcaga accccaaaat 15060
gatattcaaa gcaactaaca gctcgatttc ccctcgtttc ttaataacaa aattaattga 15120
ttatcaagac gatctttcca aaaaccgtct tggggtttta ctataagttt cgttgattgt 15180
cgagctaaag gggagcaaag caatttcaga cgacgaactt gtcaaacgat ctcaatggct 15240

-continued

```
cctggagaag ctgcgatacc cctgggagat gatgcccctg atgtacgtga tactgaaagg  15300
gttaaagtct gctgcttgaa cagtttgcta gagttaccga ggacctcttc gacgctatgg  15360
ggaccctcta ctacggggac tacatgcact atgactttcc cgccgacgga gacgtcaata  15420
aagcgcgcca acggattgac gaaggtatgg gggttcttac cggttgggac tgtttccgag  15480
gtatcgatcg ggtgtcactc gcggctgcct ctgcagttat ttcgcgcggt tgcctaactg  15540
cttccatacc cccaagaatg gccaaccctg acaaaggctc catagctagc ccacagtgag  15600
acttcctggg tgctcccatt ttgtaactgc taacgcttat tattgagttt caggacatct  15660
gggatcttcg gtcgacggag tctattccca acagtgccct tgaaggaccc acgagggtaa  15720
aacattgacg attgcgaata ataactcaaa gtcctgtaga ccctagaagc cagctgcctc  15780
agataagggt tgtcacggga ggatcaaaca ctgccatcat gcagtttccg tagcctgttg  15840
ggctacgctc cccgacttga catcccccat tcttatcaaa caacaactca aggcctgaga  15900
cctagtttgt gacggtagta cgtcaaaggc atcggacaac ccgatgcgag gggctgaact  15960
gtagggggta agaatagttt gttgttgagt tccggactct caacgagtgg tggaatttgc  16020
gcacgaagtc attggtttgt cctggtaaaa gttaaaaggg ttaactggag ggttaattga  16080
cacggtttca actgatggcc gttgctcacc accttaaacg cgtgcttcag taaccaaaca  16140
ggaccatttt caattttccc aattgacctc ccaattaact gtgccaaagt tgactaccgg  16200
ttattgacac acggatgaaa gacttgcacg cttgaccttc tgtctgtact aataaaagtt  16260
acgttggctg ggttttgggg tcataatggc cccaaaatcg aataactgtg tgcctacttt  16320
ctgaacgtgc gaactggaag acagacatga ttattttcaa tgcaaccgac ccaaaacccc  16380
agtattaccg gggttttagc aatcgtcata acttcttgaa atacaactca cgtttaagac  16440
cattcaagag tattagatca tcgtctataa tagcagattt gaaatttact tcacatttcg  16500
ttagcagtat tgaagaactt tatgttgagt gcaaattctg gtaagttctc ataatctagt  16560
agcagatatt atcgtctaaa ctttaaatga agtgtaaagc gtattgcagt gccccttgct  16620
tccacaatgg aattagttaa agtttcgaga gcattgtcaa tatcaagtgt tgttagcaaa  16680
caaatgctaa catcaagatt cataacgtca cggggaacga aggtgttacc ttaatcaatt  16740
tcaaagctct cgtaacagtt atagttcaca acaatcgttt gtttacgatt gtagttctaa  16800
actatcgatg tttgattcac atgtattcca atcagctcgt aaaaaatgga aagtggagct  16860
gatagggttg agaatcgctt catgggataa ttggaaacag tgatagctac aaactaagtg  16920
tacataaggt tagtcgagca ttttttacct ttcacctcga ctatcccaac tcttagcgaa  16980
gtaccctatt aacctttgtc ggacatgatc agaatgaaaa tcagcgtgag taaccagttg  17040
actacaaaga tgactagagt cggttaagaa aaattcaagt agggctatca ggttattgaa  17100
cctgtactag tcttactttt agtcgcactc attggtcaac tgatgtttct actgatctca  17160
gccaattctt tttaagttca tcccgatagt ccaataactt ttgaaaaata tcccgaaggg  17220
ccctcatcaa ttaaaatttt gcctttggaa atgtttggca ttcaagtagc aaattttaac  17280
atactgcgat tcgatttccg aactttttat agggcttccc gggagtagtt aattttaaaa  17340
cggaaacctt tacaaaccgt aagttcatcg tttaaaattg tatgacgcta agctaaaggc  17400
caagttagtt tgaaacaaat taacttgcta cccagtgcat taaaaaggca agtaggcagc  17460
tttggaagta taaacttagc tgtgttttaa cagaagcact gttcaatcaa actttgttta  17520
attgaacgat gggtcacgta atttttccgt tcatccgtcg aaaccttcat atttgaatcg  17580
acacaaaatt gtcttcgtga cgcaagtttc aaaaattttg gtttcgaatg acaaaaaaag  17640
```

```
ttgatgttat atacgcctat tgaatgatga ttccagttga tcatttcgac aaacaaaaaa  17700
gcgttcaaag tttttaaaac caaagcttac tgtttttttc aactacaata tatgcggata  17760
acttactact aaggtcaact agtaaagctg tttgtttttt gaatctcttt tgatttcaga  17820
tccaggattc aaataacatt ccgttatcag ataaagggtt aatgccacaa tcgtgtggtc  17880
cattatcccc ggaaacttca cttagagaaa actaaagtct aggtcctaag tttattgtaa  17940
ggcaatagtc tatttcccaa ttacggtgtt agcacaccag gtaatagggg cctttgaagt  18000
caccgtcaca ctcgatccag atctgatgtg atctctgccg tcgggcgcct cagaagcgaa  18060
aaccacattc gcccgcgctc tccggaatta tgtcgtaaaa gtggcagtgt gagctaggtc  18120
tagactacac tagagacggc agcccgcgga gtcttcgctt ttggtgtaag cgggcgcgag  18180
aggccttaat acagcatttt taaaacttta caaccataat tattcagaac ttcgacgact  18240
gcgcgatgac ttggccgcgg tgtgcctgct tgggatggac ctccgagcac tgaaagcagt  18300
attttgaaat gttggtatta ataagtcttg aagctgctga cgcgctactg aaccggcgcc  18360
acacggacga accctacctg gaggctcgtg actttcgtca ggtttgtaca aattgaatgg  18420
gctatttgaa attaattggg ctgcgataac ttcaaagtgt gacatcaaaa tggtgtgagt  18480
tttttactgc acaaattcca ccaaacatgt ttaacttacc cgataaactt taattaaccc  18540
gacgctattg aagtttcaca ctgtagtttt accacactca aaaaatgacg tgtttaaggt  18600
agttatttcc tacttcatat caatcggagc tccaggagtg aagatccaaa ttaccaagct  18660
tggccatttc gtatgaaaaa cggcaaaatg atcttttttt tcaataaagg atgaagtata  18720
gttagcctcg aggtcctcac ttctaggttt aatggttcga accggtaaag catacttttt  18780
gccgttttac tagaaaaaaa cgccagtcac tgtatctcat gatccagatg agataaaaaa  18840
gttcgagtct tcgacaaagt tgttttggaa gtcatggaca ttcttaagca aacaacttag  18900
gcggtcagtg acatagagta ctaggtctac tctatttttt caagctcaga agctgtttca  18960
acaaaacctt cagtacctgt aagaattcgt ttgttgaatc ttttgccact aggtggcgcc  19020
agtaagcata ttcgtcatca aacgtcaaca tcccaccgca aaatcgctag tgtttggagg  19080
ggattttaac ctccaaattg aaaacggtga tccaccgcgg tcattcgtat aagcagtagt  19140
ttgcagttgt agggtggcgt tttagcgatc acaaacctcc cctaaaattg gaggtttaac  19200
ccaaataacc tccaaatcat cacctccaag ttagttctaa tacactccgt tatatgaaat  19260
atggtggtgc gtcgatcgtc gcaagtttat cgttaaacag ggtttattgg aggtttagta  19320
gtggaggttc aatcaagatt atgtgaggca atatacttta taccaccacg cagctagcag  19380
cgttcaaata gcaatttgtc tcaataaaat gagcatttta tatcgtgata catatgagaa  19440
gatagaggtt tcaattaaaa caaatccaca tggtgtcgct aataaaattg tgcattttaa  19500
agttatttta ctcgtaaaat atagcactat gtatactctt ctatctccaa agttaatttt  19560
gtttaggtgt accacagcga ttattttaac acgtaaaatt gcgagttata tcctctgatc  19620
aagataaaat agaaaattcg atttttgaat attcaattat aagagcctga ataactacaa  19680
catgtagtga atcgaaactg cgctcaatat aggagactag ttctatttta tcttttaagc  19740
taaaaactta taagttaata ttctcggact tattgatgtt gtacatcact tagctttgac  19800
atttatgacg gtttgtgaag gttacacgtc ctaagcattt ggattcaaga aaagcaagag  19860
atatgacgaa tgtaaacttt atcgtatcaa tgaagtaact taaatactgc caaacacttc  19920
caatgtgcag gattcgtaaa cctaagttct tttcgttctc tatactgctt acatttgaaa  19980
```

-continued

```
tagcatagtt acttcattga agcgtccaga acagtacaaa ccaacatcgt accgtcgtat  20040
tccactccgg tcgttgcaat atctctaggt ccaccgaaaa acactcatga ccaagatcgt  20100
tcgcaggtct tgtcatgttt ggttgtagca tggcagcata aggtgaggcc agcaacgtta  20160
tagagatcca ggtggctttt tgtgagtact ggttctagca gtcgtcgatc ttggtccacc  20220
gaaacaccga tgtccatatc gtttcgtcga acttggacca acgattcatg caactgatga  20280
caacgcggcc cccgggtcgt cagcagctag aaccaggtgg ctttgtggct acaggtatag  20340
caaagcagct tgaacctggt tgctaagtac gttgactact gttgcgccgg gggcccagca  20400
accaatatcc gaaaaatcca actgttcttc tctgcctcgc aggtcaagcc gtggtcaatg  20460
aatactcacg attgcacaat ctgaacatgt tcgacggtgt tggttatagg ctttttaggt  20520
tgacaagaag agacggagcg tccagttcgg caccagttac ttatgagtgc taacgtgtta  20580
gacttgtaca agctgccaca agagttgcgc agtacgacgc gccagtccgg atgatagact  20640
ttttacacga tcagcacgac ccactgcgct gcggcaaagg tcgaaccgaa acaagaataa  20700
tctcaacgcg tcatgctgcg cggtcaggcc tactatctga aaaatgtgct agtcgtgctg  20760
ggtgacgcga cgccgtttcc agcttggctt tgttcttatt accacgaaga tcagatcgat  20820
tcgacggaag aagcaatcga atgcaaagaa gaatcggaac gaagaaaact ctaaagcatc  20880
gcatatttac aaagcataac tggtgcttct agtctagcta agctgccttc ttcgttagct  20940
tacgtttctt cttagccttg cttcttttga gatttcgtag cgtataaatg tttcgtattg  21000
ggaaaacccg caagttcaaa ctagtgatta gtgtaagatg aagcaaagca gaaatgtagt  21060
atctagattt ttcgacgtta gtttacaaag ataaaaaatg ccttttgggc gttcaagttt  21120
gatcactaat cacattctac ttcgtttcgt ctttacatca tagatctaaa aagctgcaat  21180
caaatgtttc tattttttac aggttggaca tacaatcgtg ggtattcgtc tgagttcgtc  21240
acaactgcac cggaaactgt gaaacagaat agagccaacc tgtgcgcgga gaatgttgag  21300
tccaacctgt atgttagcac ccataagcag actcaagcag tgttgacgtg gcctttgaca  21360
ctttgtctta tctcggttgg acacgcgcct cttacaactc gtcattataa gcttccttag  21420
catccacggg tgaaagtcga tcgacggaag cctgcaagac tctgtcgatg ggctttcgtc  21480
ctagaagaat aagattaaac cagtaatatt cgaaggaatc gtaggtgccc actttcagct  21540
agctgccttc ggacgttctg agacagctac ccgaaagcag gatcttctta ttctaatttg  21600
ctgaaatgta ttctcccgtg gaatggtttc atttgagtaa ttctgtatct tctccttccc  21660
aattccacga acgcgacgaa ctctaataca aacaacataa gactttacat aagagggcac  21720
cttaccaaag taaactcatt aagacataga agaggaaggg ttaaggtgct tgcgctgctt  21780
gagattatgt ttgttgtatt tgaccacagt gcaaatgctg tttaacgata atagcgacat  21840
gcagccattc tggggctacc acgtgtagct ctacttgtga gacagcgttc ctaaagagtg  21900
actggtgtca cgtttacgac aaattgctat tatcgctgta cgtcggtaag accccgatgg  21960
tgcacatcga gatgaacact ctgtcgcaag gatttctcac tgaaagtgca aacaagtgat  22020
gaaaccaata gtgcaaagca agtttagagg gaaaatttaa aaaatgcaaa acagcagtag  22080
tacttaactt ttaagattgt actttcacgt ttgttcacta ctttggttat cacgtttcgt  22140
tcaaatctcc cttttaaatt ttttacgttt tgtcgtcatc atgaattgaa aattctaaca  22200
gtttcgaaag ccgaagtgtg ttccatctgc caccggaaaa aaacgacgac agcagaatca  22260
tcaacaagca acatccatcc gaaaaaatcc gggaaaccgg caaagctttc ggcttcacac  22320
aaggtagacg gtggcctttt tttgctgctg tcgtcttagt agttgttcgt tgtaggtagg  22380
```

-continued

```
cttttttagg ccctttggcc atcttcaacc aaccatccta caatctacaa accagagatt  22440
atatctcttc aatcgtttcc gacatcggtc ggtttcggtg cccaaaatga tctgataaac  22500
tagaagttgg ttggtaggat gttagatgtt tggtctctaa tatagagaag ttagcaaagg  22560
ctgtagccag ccaaagccac gggttttact agactatttg acttatctct ctgtagcttg  22620
catgccattg cgagcgtatt ttggtagctg gccgttgcca aacggctccg acaggtactg  22680
ctattggagg ttgtgcacga tgaatagaga gacatcgaac gtacggtaac gctcgcataa  22740
aaccatcgac cggcaacggt ttgccgaggc tgtccatgac gataacctcc aacacgtgct  22800
ccacgttgag tttgcctttt gagttggaga gtgtgtcttt tcgtcatata tttggccttt  22860
tcaagggtga ttttcaggct gcgtaaagat tgtatagttt ggtgcaactc aaacggaaaa  22920
ctcaacctct cacacagaaa agcagtatat aaaccggaaa agttcccact aaaagtccga  22980
cgcatttcta acatatcaaa aaccagctaa aacatattga tgacaagttc tatttcagca  23040
ccacaaacaa gcctgttaat gtctctcacc gcaaccattg ttctgcgcgc gttataatca  23100
ttggtcgatt ttgtataact actgttcaag ataaagtcgt ggtgtttgtt cggacaatta  23160
cagagagtgg cgttggtaac aagacgcgcg caatattagt gcatagaagt ttattttctt  23220
tgggatgatt caaatattac gtgacgcaaa gtttgccaat tttagaaccc ctccctcctc  23280
cacgtaacgg cttttgtgtg cgtatcttca aataaaagaa accctactaa gtttataatg  23340
cactgcgttt caaacggtta aaatcttggg gagggaggag gtgcattgcc gaaaacacac  23400
aaaaatttaa attttgtgta tagaccgtag catttcggaa gaccccctcc cttactctgt  23460
tgagttacgt aaaatttcaa cgatcctttt gtagttctga tttttaaatt taaaacacat  23520
atctggcatc gtaaagcctt ctgggggagg gaatgagaca actcaatgca ttttaaagtt  23580
gctaggaaaa catcaagact attttatatc agcgtgcagt gttatgaaga tatccacagt  23640
ataaaatatt attttatttt aaattctatg ctgattatca atgtgttact agtggctttt  23700
taaaatatag tcgcacgtca caatacttct ataggtgtca tattttataa taaaataaaa  23760
tttaagatac gactaatagt tacacaatga tcaccgaaaa catactcatg ttgcgagctc  23820
gatttggcgc acggggtcat ctacacctga tacctttagg gtcgttgggg gaccacttag  23880
cgtgcacgta cggacattca gtatgagtac aacgctcgag ctaaaccgcg tgccccagta  23940
gatgtggact atggaaatcc cagcaacccc ctggtgaatc gcacgtgcat gcctgtaagt  24000
aaatgttgtt caaatttttt tcttaccaag acgagcactt tacaatgaca aactctggct  24060
ctgctctggc tctgctctgg ctctgctctg gctctgctct tttacaacaa gtttaaaaaa  24120
agaatggttc tgctcgtgaa atgttactgt ttgagaccga gacgagaccg agacgagacc  24180
gagacgagac cgagacgaga ggctctgctc tggctctgct ctggctctgc tctggctctg  24240
ctctggctct gctctggctc tgctctggct ctgctctggc tctgctctgg ctctgctctg  24300
ccgagacgag accgagacga gaccgagacg agaccgagac gagaccgaga cgagaccgag  24360
acgagaccga gacgagaccg agacgagacc gagacgagac gctctgctct ggctctgctc  24420
tggctctgct ctggctctgc tctggctctg ctctggctct gctctggctc tgctctggct  24480
ctgctctggc tctgctctgg cgagacgaga ccgagacgag accgagacga gaccgagacg  24540
agaccgagac gagaccgaga cgagaccgag acgagaccga gacgagaccg agacgagacc  24600
ctctgctctg caaaatgctc tggattaatt tattgctcac actcttttgc tgttggacca  24660
ctattcattt caaatcttca atatgttcct attacccccca gagacgagac gttttacgag  24720
```

-continued

```
acctaattaa ataacgagtg tgagaaaacg acaacctggt gataagtaaa gtttagaagt  24780
tatacaagga taatgggggt aacacggtcc acacggatcg atttcaacta actccactct  24840
cgtatgcata ttttgtgtat aaattttgaa taatcgaaaa gggttgctgc aaatgttaat  24900
ttgtgccagg tgtgcctagc taaagttgat tgaggtgaga gcatacgtat aaaacacata  24960
tttaaaactt attagctttt cccaacgacg tttacaatta attttttccc tctacccccct  25020
cactctgtcg ttggcgttgg aaaaaaatca ccactgcata caaaacactc attggttggg  25080
tggaaggacg gtttagcaga taaaaaaggg agatgggga gtgagacagc aaccgcaacc  25140
ttttttagt ggtgacgtat gttttgtgag taaccaaccc accttcctgc caaatcgtct  25200
gttgctaaat tttccatatc acgctgattg atttgtgatt aaaaataaat ataaatagaa  25260
aatgaataat tcccacatgt gtttcggtat taggcaccgg caacgattta aaaggtatag  25320
tgcgactaac taaacactaa tttttattta tatttatctt ttacttatta agggtgtaca  25380
caaagccata atccgtggcc catggggcgg cgaagtgcag acggttctag ttctcattat  25440
ttggcatcga ttggcggtca aactacaacc tccatggaga aacaggcccc atccgtactt  25500
gtaccccgcc gcttcacgtc tgccaagatc aagagtaata aaccgtagct aaccgccagt  25560
ttgatgttgg aggtacctct ttgtccgggg taggcatgaa agttattaat aaataacaat  25620
gatttgaatt tgaatcattc atgctgcggc gtggctgatt tcggtgaatt gttgttctct  25680
tagagaaaga gggggatttg tcaataatta tttattgtta ctaaacttaa acttagtaag  25740
tacgacgccg caccgactaa agccacttaa caacaagaga atctctttct ccccctaaac  25800
aatttggacg agtaaataac attgaatatt acactttatg actaatcacc agtaatgaaa  25860
caacacgggt gatgatttca aaagcttcat tctaaatgca ttaaacctgc tcatttattg  25920
taacttataa tgtgaaatac tgattagtgg tcattacttt gttgtgccca ctactaaagt  25980
tttcgaagta agatttacgt tggttcactt ttggtggcag atttaaaact cttatcttcc  26040
tcttttcttc aacaggtttc acgccatcaa agacgcttgg cagccgcttc catttgcgta  26100
accaagtgaa aaccaccgtc taaattttga gaatagaagg agaaaagaag ttgtccaaag  26160
tgcggtagtt tctgcgaacc gtcggcgaag gtaaacgcat gcaaacgtat gttaacctta  26220
ggttttaatg ttaaaagtat caccaaaaat caagtcccaa gacttctgca agaatggttt  26280
atgctgaatt tattcgaaat cgtttgcata caattggaat ccaaaattac aattttcata  26340
gtggttttta gttcagggtt ctgaagacgt tcttaccaaa tacgacttaa ataagcttta  26400
ggttttattt tcatcgaaac atgtgtgatg taggctacta ttttggtaaa accgttggca  26460
acgactgtat ttaaactcac aaaatttgaa ccaaacttat ccaaaataaa agtagctttg  26520
tacacactac atccgatgat aaaaccattt tggcaaccgt tgctgacata aatttgagtg  26580
ttttaaactt ggtttgaata aattgtaact tttaattgag taaacatagg cgaaagagag  26640
tgattcaaat gggattcgga atcgaacggt tcttctaagt aagacaaacg aaaaaaacaa  26700
ttaacattga aaattaactc atttgtatcc gctttctctc actaagttta ccctaagcct  26760
tagcttgcca agaagattca ttctgtttgc tttttttgtt ccaaacgagt caaagctgca  26820
aaaacttcaa gtttgaactg tgatatcaat gaaattaaat acgaactatg tatcaagatt  26880
acagtaaaat ttaaagaaga ggtttgctca gtttcgacgt ttttgaagtt caaacttgac  26940
actatagtta ctttaattta tgcttgatac atagttctaa tgtcatttta aatttcttct  27000
ctttcaacgc atgaaacagg agggtggcaa ccgaaaagtg actgaatcaa ttgcgggtta  27060
tcattcgaga tatccagggg ttgaattgtg agaaaacttc gaaagttgcg tactttgtcc  27120
```

tcccaccgtt ggcttttcac tgacttagtt aacgcccaat agtaagctct ataggtcccc 27180
aacttaacac tcttttgaag ttcttcttct tattcttggc aatacgtcct cactgggata 27240
gagtctgctt cctaacttca tgttcaatga ccacttccac agttattaac tgagagcttt 27300
aagaagaaga ataagaaccg ttatgcagga gtgaccctat ctcagacgaa ggattgaagt 27360
acaagttact ggtgaaggtg tcaataattg actctcgaaa ctttgccaaa gttgccattt 27420
tcgcattcgt atatcgtgtg gcagcagtgt tgtgaaaaac tcaatttctc ataactaacg 27480
cttgagattt ttcatgcgtg gaaacggttt caacggtaaa agcgtaagca tatagcacac 27540
cgtcgtcaca acacttttg agttaaagag tattgattgc gaactctaaa aagtacgcac 27600
agttgtcaat cacgcaactc agcagtcaaa attttccaca gtatacttac acacggcaat 27660
aatttcttgc tagtctggta aaattatagt aatcttttct tcaacagtta gtgcgttgag 27720
tcgtcagttt taaaaggtgt catatgaatg tgtgccgtta ttaaagaacg atcagaccat 27780
tttaatatca ttagaaaaga aacgtaaaca acaaaattcg ggtttcaaga gtttttgacg 27840
ggagcaagca aaataggatt tagaattttg catgagacga agtttgaaaa ttttattgtc 27900
ttgcatttgt tgttttaagc ccaaagttct caaaaactgc cctcgttcgt tttatcctaa 27960
atcttaaaac gtactctgct tcaaactttt aaaataacag aaatttagta tcggttcaat 28020
cgaattttcg aacacaattg taggctctat ataaactaca tttattccct tattttgcca 28080
gatacaatac tcgcataact tttaaatcat agccaagtta gcttaaaagc ttgtgttaac 28140
atccgagata tatttgatgt aaataaggga ataaaacggt ctatgttatg agcgtattga 28200
tgagatctcg cctaaaaagc cattggtaac cgagtgtgta gctctttgtt tctaagccaa 28260
ttaatggacc tggatgaaaa ctatcatcac tgggaaatag actctagagc ggatttttcg 28320
gtaaccattg gctcacacat cgagaaacaa agattcggtt aattacctgg acctactttt 28380
gatagtagtg accctttatc aggaggaact tgtctttatc gtagcattgt taaataacgt 28440
gtaaacccat ttgtttcctc ggtagctgca agctacacac tcgattacca atggctttta 28500
tcctccttga acagaaatag catcgtaaca atttattgca catttgggta aacaaaggag 28560
ccatcgacgt tcgatgtgtg agctaatggt taccgaaaat gggcgagatc acaagttatg 28620
cgagaatact tcccgaaatc accacctttt acccttttaa ataacgaaat tactacaaac 28680
ttcgttaccc gctctagtgt tcaatacgct cttatgaagg gctttagtgg tggaaaatgg 28740
gaaaatttat tgctttaatg atgtttgaag caat 28774

<210> SEQ ID NO 44
<211> LENGTH: 3399
<212> TYPE: DNA
<213> ORGANISM: Cydia pomonella
<220> FEATURE:
<221> NAME/KEY: misc_feature
<222> LOCATION: (1179)..(1184)
<223> OTHER INFORMATION: At positions 1179-1184, n, at each occurrence, is a or c or g or t

<400> SEQUENCE: 44
catcagacgg gcccaggctc aggatgaagc tagagcgcgg gcggcggacg cagggctcca 60
ccctcccggg atcgagctag atcggcctga gccgccagtg gtgaaagcgc cgaggagtcc 120
cgtgatcccg ccgccgccgc cgcgctccat gggatcggcg agctgcgact ccgttccggg 180
atcgcccggg gtatcgccgt atgcgccgaa cccgccgtcc gctccgcctc cgccgatgcc 240
gccgctcccg cctccgcaac cagtggccct ggactccctg gtagaaaact gccacaagct 300

-continued

```
gctggaaaaa ttccactaca gttgggagat gatgccgctc gtgctggtca tcctcaacta    360
cgccggctcc gacctggagg aggcctcgcg gaagattgac gaaggtaagt ttaaatttaa    420
gtacataaca atgcttacag acgaattgaa agggaatgtg actcggctaa tccaccagga    480
tataattttg tagagtgcgc taaagaattc tagcaacgga cgctgttatt ctgccaccgc    540
cgttgatgcc gccgtcttct gatagtgata ctttaagatc cgtatactac gctcacttcc    600
attcacttat gtcgtacgga gtattaatat gggtaaactc gcggacacga aacgattacg    660
aaaacgcaga gtacttagat tggagcaaag cccagggatt cgccgagact tttttgttac    720
ggaagattga tgaaggtaag caagttggga ctgtggcgag ttgacacatg aaacaagtca    780
aggtcacagc tggagttcca ttaaagctgg atgctaccgc tagtcatcct gaggccggct    840
ccgacttcgt gcaatgaggt attaagctgc tggaattgaa tggaatatag tggtgaaaca    900
ctactactag gtttaagcgt ttagttatat ggttgttttc ttatttttaa tttttaaatg    960
ctctgctaag ctaaaacggc waatgtctat ttttgattat aaagacttat ataaaacaac   1020
ttgtttagct tctttkacgt ctttttgtta agctgtgccc tggttttaaa wkgggcgaac   1080
acytcacgaa taagacgtaa ttttaaaaag aaaatagata tcggccctct tggttcgcat   1140
ttatacatat gtattgctgc ccgtgcgaat gttggggann nnnnaaacag taccccctagt   1200
gtaartaaat tcgatttcga aacgtgacgt acgcgtttgc gtttagtctc mwtttgtatt   1260
ggatttagaa agagcgcgcc aagcgggacg ttttggaaac tcaaaatcct atacaaaatg   1320
agacttaacg caaasgcgtt tcgtcacgtt atgatgtcga tcaaatttac actaggggta   1380
cagaggtatt gcagtaactg tacaaatact aaactaaatt aataaattag ctaaatctaa   1440
aatataccct tcaggcattg tactaaggat gctggcggaa ttacttgtgc gaggaagccg   1500
ccagcttttc ggtcaccatt tacgagtacg tataccaaac gcttcgttgc tgcaaaaaag   1560
tttcaacgcc aaatggtaca aaatgcttta tattgttctc tatatattat attaacacat   1620
cgttatttta acctaggtct tagttatgta caaggttaca taaaatagat gttcctagtc   1680
cattcctccg tgtatgttgt gtctattata aagcaaggct gcattttgta atcagtcaat   1740
ttcaatataa aaaagttgca tcgttttttt ttactkttcg acaattaaat tcaagtagca   1800
aaaaataacc caccttaatt tgtcatggtc ataatgaaac aatgacaarg ttttttttat   1860
cgcccgatac atgtacgtgt tctccaaaat gcagtctccg cgccgccaag cgaacgttca   1920
aactgtgcga tttccgttgt ccccaggcaa aatgatcatc aacgattacg ccaggaagca   1980
taatctgaac atcttcgacg ggctcgagct gaggaactcg acacgccact ccatttcgga   2040
tggcgatgaa aaacgcccac cgcaacctaa gcaagtctca aagtaaggtt ccatttaaat   2100
catctcaaaa ccgttagaaa cactcaaaaa gaaaccaaaa ttctgttcgg aaaccgacct   2160
ttgtttttta cacacactta gaccgaattt gcaaatttta acccccttatt cctaaaacta   2220
gcaatggtaa gctcggctga atttcacata caaacggagt ttcgttctca ttataaaact   2280
gcgtgttgga ttgtaatgga actttgcaca tacaatgaca tgaggtatgt ctagggctga   2340
aattagttta tacttggtat ctgaggctac ataaactaat tacagcctta gacttggagg   2400
atttaacaac tggaaacacc ttgtctgtaa ttctctgtac aacgatttta cgggggagga   2460
gcaaatatgt cagttaaacg tcagtccaaa caatacatat gactattggc cgtggtattt   2520
cgacggaggg gtaataagct cttaaaggcg actccgatat gcctaatcct attgttagta   2580
caaagtttca gagcaattta gctagtcgtt ttaaaatgag agcgtaacta cgttagcttg   2640
```

-continued

```
ctcttcttcc tcctgctctt atcccacgtt atgtggggtc ggcacaacat gttcctctct   2700

tctcactcct ttctttctca tatcctcttt cacacaatcc atccatcgtt tacttacaac   2760

cgagcttgct ggggaccgtt aaggcgccgc gagttcaggt tcttctctca ctctcactct   2820

cactggtgtg agcggagcga gacagcgttt tattttcgcc ttatcgaggt tccactgtat   2880

tataaataac ttacatttat aaagacgctg taatcgataa gaagttgagt cacgcttacg   2940

tcgcttacgt actacgtata gtaacgtagc ctgccgttta caaacaatgt acggagctac   3000

aacgttgcaa gttcggtccc cacacaacac aatgtgtcat aacacattaa caacattgtt   3060

acacacccac acatacaaat ttgctaagtt gataaaagag tggtgtgtcc gacgaatcag   3120

aacatcacta acccagtcgt gatttcattt ccacagtgac cggacgaagg tggagaagtt   3180

cgaaatttaa aaaaagtgac cacattttat ttaatagtga tgtgcaagtg atactatttt   3240

tattttgttt ttcttttgta ggaaaatgct gagcgaaata aataatttta gtggtgtgct   3300

atcgtcatcg atgaagttgt tttgcgaatg atactatgtt cttcaagtgc tgtgttttgt   3360

ggactgtggg gtgactgttc ctgtaaataa gcttcgttg                          3399
```

<210> SEQ ID NO 45
<211> LENGTH: 996
<212> TYPE: DNA
<213> ORGANISM: Cydia pomonella

<400> SEQUENCE: 45

```
catcagacgg gcccaggctc aggatgaagc tagagcgcgg gcggcggacg cagggctcca     60

ccctcccggg atcgagctag atcggcctga gccgccagtg gtgaaagcgc cgaggagtcc    120

cgtgatcccg ccgccgccgc cgcgctccat gggatcggcg agctgcgact ccgttccggg    180

atcgcccggg gtatcgccgt atgcgccgca cccgccgtcc gctccgcctc cgccgatgcc    240

gccgctcccg cctccgcaac cagtggcctt ggactccctg gtagaaaact gccacaagct    300

gctggaaaaa ttccactaca gttgggagat gatgccgctc gtgctggtca tcctcaacta    360

cgccggctcc gacctggagg aggcctcgcg gaagattgac gaagcctcct gggtggtgca    420

ccagtggcgg ctgtacgagc gctcactgtg ctcgctgctg gagctgcaag cgcgcaaaga    480

gtcgttttgc tgctcgccgc gctatgtgct gtcgcgcgag tacgcgccgc acctgcccgt    540

gccgctcatg cgctcgccgc cgccagcgca cttgtagccc cacaccgcgc cgcgacagac    600

ggcgcacgag cccactgagc catctacttc ggccaaaccc gagtaggccc gaggccgacc    660

cgagcccgac ccgagaggac ccgagtgggc tattccggac tttacctagt tttatatgtg    720

ctatacgtgt tacaacacgc atatttgtat attatcacgg acattaagtt ggagagcggt    780

taccttatct tgttaacccg gtccttgaag taattattcc cagatatatt aagaaaacca    840

gtgaatactt tgcctgatgt ataattaaca gttgttaagc aaccatgaga attatggtat    900

ttcttgtgga catgttgcag ctagaaattt catatcatcg gtgataaaat ttaaccacac    960

tgtggttggc ggaaaaccac attgtttgta atattg                              996
```

<210> SEQ ID NO 46
<211> LENGTH: 6751
<212> TYPE: DNA
<213> ORGANISM: Artificial Sequence
<220> FEATURE:
<223> OTHER INFORMATION: Synthetic construct, pLA3435-Bombyx mori-dsx
construct/plasmid.
<220> FEATURE:
<221> NAME/KEY: misc_feature
<222> LOCATION: (1617)..(1622)

<223> OTHER INFORMATION: At positions 1617-1622, n, at each occurrence,
is a, c, g, or t

<400> SEQUENCE: 46

```
ggccgcatgg tacccattgc ttgtcattta ttaatttgga tgatgtcatt tgtttttaaa     60
attgaactgg ctttacgagt agaattctac gcgtaaaaca caatcaagta tgagtcataa    120
tctgatgtca tgttttgtac acggctcata accgaactgg ctttacgagt agaattctac    180
ttgtaatgca cgatcagtgg atgatgtcat ttgtttttca aatcgagatg atgtcatgtt    240
ttgcacacgg ctcataaact cgctttacga gtagaattct acgtgtaacg cacgatcgat    300
tgatgagtca tttgttttgc aatatgatat catacaatat gactcatttg tttttcaaaa    360
ccgaacttga tttacgggta gaattctact tgtaaagcac aatcaaaaag atgatgtcat    420
ttgtttttca aaactgaact cgctttacga gtagaattct acgtgtaaaa cacaatcaag    480
aaatgatgtc atttgttata aaaataaaag ctgatgtcat gttttgcaca tggctcataa    540
ctaaactcgc tttacgggta gaattctacg cgtaaaacat gattgataat taaataattc    600
atttgcaagc tatacgttaa atcaaacgga cgctcgaggt tgcacaacac tattatcgat    660
ttgcagttcg ggacataaat gtttaaatat atcgatgtct ttgtgatgcg cgcgacattt    720
ttgtaggtta ttgataaaat gaacggatac gttgcccgac attatcatta aatccttggc    780
gtagaatttg tcgggtccat tgtccgtgtg cgctagcatg cccgtaacgg acctcgtact    840
tttggcttca aaggttttgc gcacagacaa aatgtgccac acttgcagct ctgcatgtgt    900
gcgcgttacc acaaatccca acggcgcagt gtacttgttg tatgcaaata aatctcgata    960
aaggcgcggc gcgcgaatgc agctgatcac gtacgctcct cgtgttccgt tcaaggacgg   1020
tgttatcgac ctcagattaa tgtttatcgg ccgactgttt tcgtatccgc tcaccaaacg   1080
cgtttttgca ttaacattgt atgtcggcgg atgttctata tctaatttga ataaataaac   1140
gataaccgcg ttggttttag agggcataat aaaagaaata ttgttatcgt gttcgccatt   1200
agggcagtat aaattgacgt tcatgttgga tattgtttca gttgcaagtt gacactggcg   1260
gcgacaagca attctaattg gggtaagttt tcccgttctt ttctgggttc ttccctttg    1320
ctcatccttg ctgcactacc ttcaggtgca agttgagatt caggccacca tgggagatcc   1380
caccccaccc aagaagaagc gcaaaccggt ccgtcccctc ggagacgctt gtggagaact   1440
gtcacagact cctcgagaag ttccattact cgtgggagat gatgccgctt gtgctcgtca   1500
tcatgaacta cgcccgcagc gacttggatg aggcttcaag gaaaatctac gaaggtaccg   1560
aatgtgtaaa tacgagtgta gcgttgatta gaaaacggac attgttcgtg agtttannnn   1620
nnggtctctc tggccagcaa gacatttgaa acactgtaaa aaaattcatt gaaaaaaaag   1680
aacactgtaa tgaaaatatt ctgaatgctt aatctggtat ttcagggatt aaactgattg   1740
tgatgaaaag tgattaaact attttcttta agtaccaaat taaccgaaca ggtttgggtc   1800
tttcctttca gtaacaaaca aaatctatcg aaggtaagaa ataaacaaca ggatattttc   1860
ttttactaaa aatcaataag gagactgcac tatttcaatg ttcaacttcc tttatcgaat   1920
gcatgaaaaa tttaattgtc taaaaatcta aattactaat taacgcaaag gaacctttgc   1980
ctaaaaaaaa aaataagcta ttaaacgaat gcctaaaata cgtaacagtg ttgccagttg   2040
taaaaattgc gaatccgaga agtgcagttt cctgaaatgc ccagcgatac gaatttccta   2100
tgttagagtc ttgtccgcag ggaagatgat cgtcgacgag tacgcgagga agcacaactt   2160
gaacgtgttc gacggactag aactaaggaa ctcgacacgc caggcgcgcc ggatccggcc   2220
```

-continued

```
ggccgaaaat gctggaaatt aataatataa gtggtgtact gtcttcgtca atgaagttat   2280
tttgcgaatg atacttagtt ttacaagtgc cgtggtgtgt gttgacactt gctgtgcgat   2340
gctgtgcgaa tttcaacgga aatatttgtt gtcgtaacat tggatctatg ggtaagttta   2400
gtataataac tttactctgt tcacattagt gaaacataca tttgtaaaat ttgtgtttta   2460
ctaatgtgaa atttattttt ggaaattcac gttaacacta ttgaataaaa aaaaatcgat   2520
aatgtaattt aaaaaaaata caaaaatata gttttcgctt attgttagaa agaaaatttt   2580
acatacgcca ttttgaataa ttccttccgg gtacattggg ccctaaacca gcgatcgggg   2640
aactttttta attattaccc taaaatattt ttatgtaagt tgatattacc gatggcgaag   2700
aacaacaaaa aaaaaaacga aatcgcttct ttttagcatc tttcatatta tagaccccac   2760
gataatttta aatcacaacg attataaaga agtttcactt caatatatac tttttactca   2820
caaaagtttc atttttaccc catttgggat aatttagccc ggttccccc ccgaccgctg   2880
gcctaaacgt atcaccgaca atagctaaaa taacaaggta cgttcgattt gccgagctga   2940
actaacatta cacagctttg cattattcat atgtacattg cgactgaaac gtccggaccg   3000
ttacaggtta ttggatgatg catcaatggc gattgcagca gtattcgttg tgctacggag   3060
cgctggagtt gtcggcgcgc aaggatgtgg ccgcgctatg ttgcctccga gatacgtgct   3120
ggcgcccgag gtcccgccgc gtctggtgcc cctccagctg atctagataa ctgatcataa   3180
tcagccatac cacatttgta gaggttttac ttgctttaaa aaacctccca cacctccccc   3240
tgaacctgaa acataaaatg aatgcaattg ttgttgttaa cttgtttatt gcagcttata   3300
atggttacaa ataaagcaat agcatcacaa atttcacaaa taaagcattt ttttcactgc   3360
attctagttg tggtttgtcc aaactcatca atgtatctta acgcgagtta attaagtgcg   3420
cgtaaattgt aagcgttaat attttgttaa aattcgcgtt aaatttttgt taaatcagct   3480
cattttttaa ccaataggcc gaaatcggca aaatccctta taaatcaaaa gaatagaccg   3540
agatagggtt gagtgttgtt ccagtttgga acaagagtcc actattaaag aacgtggact   3600
ccaacgtcaa agggcgaaaa accgtctatc agggcgatgg cccactacgt gaaccatcac   3660
cctaatcaag ttttttgggg tcgaggtgcc gtaaagcact aaatcggaac cctaaaggga   3720
gcccccgatt tagagcttga cggggaaagc cggcgaacgt ggcgagaaag gaagggaaga   3780
aagcgaaagg agcgggcgct agggcgctgg caagtgtagc ggtcacgctg cgcgtaacca   3840
ccacacccgc cgcgcttaat gcgccgctac agggcgcgtc aggtggcact tttcggggaa   3900
atgtgcgcgg aacccctatt tgtttatttt tctaaataca ttcaaatatg tatccgctca   3960
tgagacaata accctgataa atgcttcaat aatattgaaa aaggaagagt cctgaggcgg   4020
aaagaaccag ctgtggaatg tgtgtcagtt agggtgtgga aagtccccag gctccccagc   4080
aggcagaagt atgcaaagca tgcatctcaa ttagtcagca accaggtgtg gaaagtcccc   4140
aggctcccca gcaggcagaa gtatgcaaag catgcatctc aattagtcag caaccatagt   4200
cccgccccta actccgccca tcccgcccct aactccgccc agttccgccc attctccgcc   4260
ccatggctga ctaatttttt ttatttatgc agaggccgag gccgcctcgg cctctgagct   4320
attccagaag tagtgaggag gcttttttgg aggcctaggc ttttgcaaag atcgatcaag   4380
agacaggatg aggatcgttt cgcatgattg aacaagatgg attgcacgca ggttctccgg   4440
ccgcttgggt ggagaggcta ttcggctatg actgggcaca acagacaatc ggctgctctg   4500
atgccgccgt gttccggctg tcagcgcagg ggcgcccggt tctttttgtc aagaccgacc   4560
tgtccggtgc cctgaatgaa ctgcaagacg aggcagcgcg gctatcgtgg ctggccacga   4620
```

-continued cgggcgttcc ttgcgcagct gtgctcgacg ttgtcactga agcgggaagg gactggctgc 4680
tattgggcga agtgccgggg caggatctcc tgtcatctca ccttgctcct gccgagaaag 4740
tatccatcat ggctgatgca atgcggcggc tgcatacgct tgatccggct acctgcccat 4800
tcgaccacca agcgaaacat cgcatcgagc gagcacgtac tcggatggaa gccggtcttg 4860
tcgatcagga tgatctggac gaagagcatc aggggctcgc gccagccgaa ctgttcgcca 4920
ggctcaaggc gagcatgccc gacggcgagg atctcgtcgt gacccatggc gatgcctgct 4980
tgccgaatat catggtggaa aatggccgct tttctggatt catcgactgt ggccggctgg 5040
gtgtggcgga ccgctatcag gacatagcgt tggctacccg tgatattgct gaagagcttg 5100
gcggcgaatg ggctgaccgc ttcctcgtgc tttacggtat cgccgctccc gattcgcagc 5160
gcatcgcctt ctatcgcctt cttgacgagt tcttctgagc gggactctgg ggttcgaaat 5220
gaccgaccaa gcgacgccca acctgccatc acgagatttc gattccaccg ccgccttcta 5280
tgaaaggttg ggcttcggaa tcgttttccg ggacgccggc tggatgatcc tccagcgcgg 5340
ggatctcatg ctggagttct tcgcccaccc tagggggagg ctaactgaaa cacggaagga 5400
gacaataccg gaaggaaccc gcgctatgac ggcaataaaa agacagaata aaacgcacgg 5460
tgttgggtcg tttgttcata aacgcggggt tcggtcccag ggctggcact ctgtcgatac 5520
cccaccgaga ccccattggg gccaatacgc ccgcgtttct tccttttccc caccccaccc 5580
cccaagttcg ggtgaaggcc cagggctcgc agccaacgtc ggggcggcag gccctgccat 5640
agcctcaggt tactcatata tactttagat tgatttaaaa cttcattttt aatttaaaag 5700
gatctaggtg aagatccttt ttgataatct catgaccaaa atcccttaac gtgagttttc 5760
gttccactga gcgtcagacc ccgtagaaaa gatcaaagga tcttcttgag atcctttttt 5820
tctgcgcgta atctgctgct tgcaaacaaa aaaaccaccg ctaccagcgg tggtttgttt 5880
gccggatcaa gagctaccaa ctctttttcc gaaggtaact ggcttcagca gagcgcagat 5940
accaaatact gtccttctag tgtagccgta gttaggccac cacttcaaga actctgtagc 6000
accgcctaca tacctcgctc tgctaatcct gttaccagtg gctgctgcca gtggcgataa 6060
gtcgtgtctt accgggttgg actcaagacg atagttaccg gataaggcgc agcggtcggg 6120
ctgaacgggg ggttcgtgca cacagcccag cttggagcga acgacctaca ccgaactgag 6180
atacctacag cgtgagctat gagaaagcgc cacgcttccc gaagggagaa aggcggacag 6240
gtatccggta agcggcaggg tcggaacagg agagcgcacg agggagcttc caggggggaaa 6300 cgcctggtat ctttatagtc ctgtcgggtt tcgccacctc tgacttgagc gtcgattttt 6360
gtgatgctcg tcaggggggc ggagcctatg gaaaaacgcc agcaacgcgg cctttttacg 6420
gttcctggcc ttttgctggc cttttgctca catgttcttt cctgcgttat cccctgattc 6480
tgtggataac cgtattaccg ccatgcatta gttattaata gtaatcaatt acggggtcat 6540
tagttcatag cccatatatg gagttccgcg ttacataact tacggtaaat ggcccgcctg 6600
gctgaccgcc caacgacccc cgcccattga cgtcaataat gacgtatgtt cccatagtaa 6660
cgccaatagg gactttccat tgacgtcaat gggtggagta tttacggtaa actgcccact 6720
tggcagtaca tcaagtgtat catagcgatg c 6751

<210> SEQ ID NO 47
<211> LENGTH: 8183
<212> TYPE: DNA
<213> ORGANISM: Artificial Sequence
<220> FEATURE:

<223> OTHER INFORMATION: Synthetic construct, pLA3359-Anopheles gambiae dsx construct

<400> SEQUENCE: 47
ccggtgctgc tgttgctgat gctacgatcc tcgacagtga ttggaaacgc ctggagatgg 60
tgggaaaaaa tcaaacacaa aaacggtcct aatgaacatc gtgtgttctc attcgctgcc 120
acgattgaca ccttcgataa gacgcacata atgagctaaa ggagagggga cagggtcttg 180
tctttgccac gagcgataag attgcaatca ctcgtgagcg tgtgctgctg ggctgaagaa 240
gaaacacttt ccacagcagt aggtgggaag tgggattgtg gaacgtggca ttgaaaagaa 300
cctattttct aaagcccgag agcccgttct cgaactggaa aacgagatgc agaagttttt 360
tattgtcccc cgccaggaaa acaaatgtat ttaatgcttt ctctgccttt tccgccccgt 420
ttcagacgac gagctagtga agcgagccca atggctgttg gagaaactcg gctacccgtg 480
ggagatgatg cccctgatgt acgtcatact gaagagcgcc gatggcgatg tacaaaaagc 540
acaccagcgg atcgacgaag gtaagctggc gatgatggtg tcgttcgaca tcactttcat 600
caccgtgtca gacatctact gtgcctagca ccggtccagt ggtcacaggg tgtagcaaaa 660
acgtgttctt ttttgcgaga gactctacct catgatgcag ctgttaagga aaggtttcag 720
atgaagacaa tttttcctag gataatatga tcttaagtta cctgcgtatg agtgtttaac 780
attgtcgtct caactccaag gaatgtttta accgtctagg gctagtttat ttatactgtt 840
ctcattgaaa tgtcgttaaa tccaacatgt taagttagct agctcagaca cgagaagtta 900
ggagtatctg catcttgaag gtagcggcat atggtgttat gccacgttca ctgacttcaa 960
aattcgatac aaaaaaaaac aaaatcaaaa acaaaattgt gaattccgtc agccagcagc 1020
agtgaccttc aaagccttac ctttccattc atttatgttt aacacaggtc aagcggtggt 1080
caacgaatac tcacgattgc ataatctgaa catgtttgat ggcgtggagt tgcgcaatac 1140
cacccgtcag agtggatgat aaactttccg caccactgta actgtccgta tctttgtatg 1200
tgggtgtgtg tatgtgtgtt tggtgaaacg aattcaattg ttctgtgcta ttttaaatca 1260
agccgcgtgc gcaactgatg ccgataagtt caaactagtg tttaaggagt ggagagagag 1320
agccgcacca cggtacagaa gggcagcaga atgggtcggc agcctagctg cactggtgcg 1380
gtgcgtccgg cgtctcgggg ggagggcggg gaaattctag tgttaaatcg gagcagcaaa 1440
aacaaaacag tggtcgtccc gttcaagaaa cggcctgtac acacacagaa aacactgcag 1500
catgtttgta catagtagat cctagagcag gtggtcgttg ctcctcgaac gctctggacg 1560
cacggcttcg cgcgtacttg cgtagcgttc caccgatcgt gggtattcgt actgccacaa 1620
gcccgctttc tcccatgcaa tctctgcaac caaaccaaca aacaacaaca aaataccaat 1680
cgacacaatg aatcacaccc cttttgtatc atctgtatat tcttgttctt tgcgttcttt 1740
tccatgtggc ccacgccccg gcgggtacgt aattgcgtcg aaaaccccga aaaccccggc 1800
acatacagtg tacatacggt ttgaggacaa ctttgacctg cagcccttct ggggctgcca 1860
cgtgtagcta tacttgtgag atcgggcgcc gacggtgtaa agcgcgaatg gccgccacac 1920
agtgtgtcca ctccaacact acccctctgg aactaccccg tccagggatg caccggctcg 1980
gctcatgccc ctgcaaaaca gtccgggctc cactgtagta gctccggcgt tgctctgaga 2040
gaaggatgcc cttcgaagtg tcgaaagcgt gcattgggcg ttcaagtgtg tgtctgtgtt 2100
aggtttagcg agaaacagca gcagttgcgt gtgctgaaaa gcgaaggagt aatagagtgc 2160
ataatgaaaa tgaaaatgaa aatgaagcaa aagtagaagg cggaggagag caacctgtgt 2220

```
tccactagta gcgaatagtt tagtctagtt tcgtcaccaa tcaaccttcc aaccatcgtt   2280
caaccaatac ctgagtcaac atcgtcatcg ttatcgtgcc acaactttat taaaaatgaa   2340
ccttgtccgc gccaccgtag ggtgatctga ggcgaccttt cttacgggcg cgactcacat   2400
gccatcgtca ccttctccaa tcaaaaccaa cagcctgtac cgatggtgtg caattgtgcg   2460
tgcgtgtgtg ttattagcaa aaaaagagaa agagacggcg agagagagat agatcgagat   2520
cgagagtaca aaagagcagt agaaatgttc gttgtttgtt ttccgtaaca cagttgttta   2580
gccaaaatgg gaatttccaa taatcccggg ggcggggaaa tgcgggaata ctgcgtacac   2640
acatacatca atcaaaaaga aaaatccttg cgctacatca ctaccgtttg cgcggtgctg   2700
atctagagca gaccactttc cacgccattc tacaatcaat caatctgtgc agaaggtatg   2760
gtaagacggc ctttgagcga gtcacggtcg ccaccataac gccgtccgac gagggctgaa   2820
tgcgaacttt gctaatcgat ttccgcttt cttttatcc caccccctt tctctctctc   2880
tcttttgcac cgccccttgt aacccccaaa aaggtaaacg acacattaag acctacgaag   2940
cgctggtgaa gtcatcgctc gatccgaaca gcgaccggct gacggaagac gacgacgagg   3000
acgagaacat ctcggtgacc cgcaccaact ccaccattcg gtcgaggtcc agctcgctgt   3060
cgcggtcccg gtcctgctcg cgccaggccg aaactccccg ggccgacgat cgggccctga   3120
accttgacac caaatagatc tcgacccaag aaaaagcgga aggtggagga cccgtaagat   3180
ccaccggatc tagataactg atcataatca gccataccac atttgtagag gttttacttg   3240
ctttaaaaaa cctcccacac ctccccctga acctgaaaca taaaatgaat gcaattgttg   3300
ttgttaactt gtttattgca gcttataatg gttacaaata aagcaatagc atcacaaatt   3360
tcacaaataa agcatttttt tcactgcatt ctagttgtgg tttgtccaaa ctcatcaatg   3420
tatcttaacg cgagttaatt aagtgcgcgt aaattgtaag cgttaatatt ttgttaaaat   3480
tcgcgttaaa tttttgttaa atcagctcat tttttaacca ataggccgaa atcggcaaaa   3540
tcccttataa atcaaaagaa tagaccgaga tagggttgag tgttgttcca gtttggaaca   3600
agagtccact attaaagaac gtggactcca acgtcaaagg gcgaaaaacc gtctatcagg   3660
gcgatggccc actacgtgaa ccatcaccct aatcaagttt tttggggtcg aggtgccgta   3720
aagcactaaa tcggaaccct aaagggagcc cccgatttag agcttgacgg ggaaagccgg   3780
cgaacgtggc gagaaaggaa gggaagaaag cgaaaggagc gggcgctagg gcgctggcaa   3840
gtgtagcggt cacgctgcgc gtaaccacca cacccgccgc gcttaatgcg ccgctacagg   3900
gcgcgtcagg tggcactttt cggggaaatg tgcgcggaac ccctatttgt ttattttct   3960
aaatacattc aaatatgtat ccgctcatga gacaataacc ctgataaatg cttcaataat   4020
attgaaaaag gaagagtcct gaggcggaaa gaaccagctg tggaatgtgt gtcagttagg   4080
gtgtggaaag tccccaggct ccccagcagg cagaagtatg caaagcatgc atctcaatta   4140
gtcagcaacc aggtgtggaa agtccccagg ctccccagca ggcagaagta tgcaaagcat   4200
gcatctcaat tagtcagcaa ccatagtccc gcccctaact ccgcccatcc cgcccctaac   4260
tccgcccagt tccgcccatt ctccgcccca tggctgacta atttttttta tttatgcaga   4320
ggccgaggcc gcctcggcct ctgagctatt ccagaagtag tgaggaggct tttttggagg   4380
cctaggcttt tgcaaagatc gatcaagaga caggatgagg atcgtttcgc atgattgaac   4440
aagatggatt gcacgcaggt tctccggccg cttgggtgga gaggctattc ggctatgact   4500
gggcacaaca gacaatcggc tgctctgatg ccgccgtgtt ccggctgtca gcgcaggggc   4560
gcccggttct ttttgtcaag accgacctgt ccggtgccct gaatgaactg caagacgagg   4620
```

```
cagcgcggct atcgtggctg gccacgacgg gcgttccttg cgcagctgtg ctcgacgttg   4680
tcactgaagc gggaagggac tggctgctat tgggcgaagt gccggggcag gatctcctgt   4740
catctcacct tgctcctgcc gagaaagtat ccatcatggc tgatgcaatg cggcggctgc   4800
atacgcttga tccggctacc tgcccattcg accaccaagc gaaacatcgc atcgagcgag   4860
cacgtactcg gatggaagcc ggtcttgtcg atcaggatga tctggacgaa gagcatcagg   4920
ggctcgcgcc agccgaactg ttcgccaggc tcaaggcgag catgcccgac ggcgaggatc   4980
tcgtcgtgac ccatggcgat gcctgcttgc cgaatatcat ggtggaaaat ggccgctttt   5040
ctggattcat cgactgtggc cggctgggtg tggcggaccg ctatcaggac atagcgttgg   5100
ctacccgtga tattgctgaa gagcttggcg gcgaatgggc tgaccgcttc ctcgtgcttt   5160
acggtatcgc cgctcccgat tcgcagcgca tcgccttcta tcgccttctt gacgagttct   5220
tctgagcggg actctggggt tcgaaatgac cgaccaagcg acgcccaacc tgccatcacg   5280
agatttcgat tccaccgccg ccttctatga aaggttgggc ttcggaatcg ttttccggga   5340
cgccggctgg atgatcctcc agcgcgggga tctcatgctg gagttcttcg cccaccctag   5400
ggggaggcta actgaaacac ggaaggagac aataccggaa ggaacccgcg ctatgacggc   5460
aataaaaaga cagaataaaa cgcacggtgt tgggtcgttt gttcataaac gcggggttcg   5520
gtcccagggc tggcactctg tcgatacccc accgagaccc cattggggcc aatacgcccg   5580
cgtttcttcc ttttccccac cccacccccc aagttcgggt gaaggcccag ggctcgcagc   5640
caacgtcggg gcggcaggcc ctgccatagc ctcaggttac tcatatatac tttagattga   5700
tttaaaactt catttttaat ttaaaaggat ctaggtgaag atcctttttg ataatctcat   5760
gaccaaaatc ccttaacgtg agttttcgtt ccactgagcg tcagaccccg tagaaaagat   5820
caaaggatct tcttgagatc ctttttttct gcgcgtaatc tgctgcttgc aaacaaaaaa   5880
accaccgcta ccagcggtgg tttgtttgcc ggatcaagag ctaccaactc tttttccgaa   5940
ggtaactggc ttcagcagag cgcagatacc aaatactgtc cttctagtgt agccgtagtt   6000
aggccaccac ttcaagaact ctgtagcacc gcctacatac ctcgctctgc taatcctgtt   6060
accagtggct gctgccagtg gcgataagtc gtgtcttacc gggttggact caagacgata   6120
gttaccggat aaggcgcagc ggtcgggctg aacggggggt tcgtgcacac agcccagctt   6180
ggagcgaacg acctacaccg aactgagata cctacagcgt gagctatgag aaagcgccac   6240
gcttcccgaa gggagaaagg cggacaggta tccggtaagc ggcagggtcg gaacaggaga   6300
gcgcacgagg gagcttccag ggggaaacgc ctggtatctt tatagtcctg tcgggtttcg   6360
ccacctctga cttgagcgtc gatttttgtg atgctcgtca ggggggcgga gcctatggaa   6420
aaacgccagc aacgcggcct ttttacggtt cctggccttt tgctggcctt ttgctcacat   6480
gttctttcct gcgttatccc ctgattctgt ggataaccgt attaccgcca tgcattagtt   6540
attaatagta atcaattacg gggtcattag ttcatagccc atatatggag ttccgcgtta   6600
cataacttac ggtaaatggc ccgcctggct gaccgcccaa cgacccccgc ccattgacgt   6660
caataatgac gtatgttccc atagtaacgc caatagggac tttccattga cgtcaatggg   6720
tggagtattt acggtaaact gcccacttgg cagtacatca agtgtatcat agcgatgcgg   6780
ccgcatggta cccattgctt gtcatttatt aatttggatg atgtcatttg tttttaaaat   6840
tgaactggct ttacgagtag aattctacgc gtaaaacaca atcaagtatg agtcataatc   6900
tgatgtcatg ttttgtacac ggctcataac cgaactggct ttacgagtag aattctactt   6960
```

gtaatgcacg atcagtggat gatgtcattt gtttttcaaa tcgagatgat gtcatgtttt 7020
gcacacggct cataaactcg ctttacgagt agaattctac gtgtaacgca cgatcgattg 7080
atgagtcatt tgttttgcaa tatgatatca tacaatatga ctcatttgtt tttcaaaacc 7140
gaacttgatt tacgggtaga attctacttg taaagcacaa tcaaaaagat gatgtcattt 7200
gtttttcaaa actgaactcg ctttacgagt agaattctac gtgtaaaaca caatcaagaa 7260
atgatgtcat ttgttataaa aataaaagct gatgtcatgt tttgcacatg gctcataact 7320
aaactcgctt tacgggtaga attctacgcg taaaacatga ttgataatta aataattcat 7380
ttgcaagcta tacgttaaat caaacggacg ctcgaggttg cacaacacta ttatcgattt 7440
gcagttcggg acataaatgt ttaaatatat cgatgtcttt gtgatgcgcg cgacattttt 7500
gtaggttatt gataaaatga acggatacgt tgcccgacat tatcattaaa tccttggcgt 7560
agaatttgtc gggtccattg tccgtgtgcg ctagcatgcc cgtaacggac ctcgtacttt 7620
tggcttcaaa ggttttgcgc acagacaaaa tgtgccacac ttgcagctct gcatgtgtgc 7680
gcgttaccac aaatcccaac ggcgcagtgt acttgttgta tgcaaataaa tctcgataaa 7740
ggcgcggcgc gcgaatgcag ctgatcacgt acgctcctcg tgttccgttc aaggacggtg 7800
ttatcgacct cagattaatg tttatcggcc gactgttttc gtatccgctc accaaacgcg 7860
tttttgcatt aacattgtat gtcggcggat gttctatatc taatttgaat aaataaacga 7920
taaccgcgtt ggttttagag ggcataataa aagaaatatt gttatcgtgt tcgccattag 7980
ggcagtataa attgacgttc atgttggata ttgtttcagt tgcaagttga cactggcggc 8040
gacaagcaat tctaattggg gtaagttttc ccgttctttt ctgggttctt cccttttgct 8100
catccttgct gcactacctt caggtgcaag ttgagattca ggccaccatg ggagatccca 8160
ccccacccaa gaagaagcgc aaa 8183

<210> SEQ ID NO 48
<211> LENGTH: 7342
<212> TYPE: DNA
<213> ORGANISM: Artificial Sequence
<220> FEATURE:
<223> OTHER INFORMATION: Synthetic construct, pLA3433-Agdsx (Anopheles gambiae) construct with exon 2 included

<400> SEQUENCE: 48
ctagtgtcga cgatgtaggt cacggtctcg aagccgcggt gcgggtgcca gggcgtgccc 60
ttgggctccc cgggcgcgta ctccacctca cccatctggt ccatcatgat gaacgggtcg 120
aggtggcggt agttgatccc ggcgaacgcg cggcgcaccg ggaagccctc gccctcgaaa 180
ccgctgggcg cggtggtcac ggtgagcacg ggacgtgcga cggcgtcggc gggtgcggat 240
acgcggggca gcgtcagcgg gttctcgacg gtcacggcgg gcatgtcgac cgccggcgcc 300
ttaattaact cgcgttaaga tacattgatg agtttggaca aaccacaact agaatgcagt 360
gaaaaaaatg ctttatttgt gaaatttgtg atgctattgc tttatttgta accattataa 420
gctgcaataa acaagttaac aacaacaatt gcattcattt tatgtttcag gttcaggggg 480
aggtgtggga ggttttttaa agcaagtaaa acctctacaa atgtggtatg gctgattatg 540
atcagttatc tagatccggt ggatcttacg ggtcctccac cttccgcttt ttcttgggtc 600
gagatctgag tccggaatcc tcgtcgctac cgatggcgct ggtgatgcgg ggcacgctgt 660
gggcgtaggt cacctcgcgc tggcacacgt ggtcgcgctt gtcgctggtg tccctcatct 720
gcttggtgat gatggtcacg aagtgggggc cggggatctt gatggcgcgg ctgccgttga 780

-continued

```
aggtcatctt gctgtcgaag tggcccatca tcaggccgcc gtcggcggtg gtgaagccga    840
tgaaggccag ctggcgcacg gcgttggggc cgtgggggaa catgtgggtc tcgttgggca    900
ggatgtccac cagctggtcg cgcatgatgg ggccgtcggg ctggaagccg tcgcagttca    960
cggtgatgcg gctgaccacg caggtgccgt ccagctcgta ggtgtggtgg ctggtcatgg   1020
tgccgtcgtt ctcgaagcgc acggtgcggt cgatgctcag gccctcgggg aagcactcct   1080
gggcgaagtg gctgatgccg ttggggtagc gggcgaagaa gggctcgccg tactggatca   1140
ggtggcagat gggcttccag ctcatgggca gcttgccggt ctcgcacacg gcgtgcacgt   1200
tgaagtcgcc gtgggggaac ttgctgctgc cgtcggccac gatggtgaac ttctggccgt   1260
tcacctcgcc gtcgatgaag attttgaagg tcatgtcgct ctggaacagg gcggggccgc   1320
cctctgaacc atcctcgtcc atggtggcga ccggtttgcg cttcttcttg ggtggggtgg   1380
gatccaccag agacaggttg cggcggcggt tggatggcgt gggcgcgttg gcgttgttgg   1440
accggctcat gttgtgtcgc tgtaacagat gctgttcaac tgtgtttacc agatcgttgc   1500
gggctgtatt tataggcgcg ataagcggga cgggcgcctc gtgtccggtc acgcgcatga   1560
gataacgcgc ggctgatatg gaggcgcgtc ctgttccgat aaggagttgc gtccggctgc   1620
ggttagcaac acaggaagct ggcgtcctgt cacgataaga caacactcgt ccggtccgat   1680
aatgtgattc gtacgtgaca ggacgcgacc cgataaggcc ggcctacgtg actgccgaca   1740
cgtacttttt tgcactgcaa aaaggttcaa tgtgtggtag tgtatttgga gcgtatacaa   1800
cggtgtagac tatttatgta aaatagtcta cgaaacgtag agtttgtact atgtatgggc   1860
ccgcgtgcaa aagcgtgttt ttttgcagtg caaaaaagtt ggtggtgggg aggccaccga   1920
gtatggtacc atgcggccgc gtacgcgccc ggggagccca agggcacgcc ctggcacccg   1980
tccggtgctt atctagagcg cgcttggcgt aatcatggtc atagctgttt cctgtgtgaa   2040
attgttatcc gctcacaatt ccacacaaca tacgagccgg aagcataaag tgtaaagcct   2100
ggggtgccta atgagtgagc taactcacat taattgcgtt gcgctcactg cccgctttcc   2160
agtcgggaaa cctgtcgtgc cagctgcatt aatgaatcgg ccaacgcgcg gggagaggcg   2220
gtttgcgtat tgggcgctct tccgcttcct cgctcactga ctcgctgcgc tcggtcgttc   2280
ggctgcggcg agcggtatca gctcactcaa aggcggtaat acggttatcc acagaatcag   2340
gggataacgc aggaaagaac atgtgagcaa aaggccagca aaaggccagg aaccgtaaaa   2400
aggccgcgtt gctggcgttt ttccataggc tccgcccccc tgacgagcat cacaaaaatc   2460
gacgctcaag tcagaggtgg cgaaacccga caggactata aagataccag gcgtttcccc   2520
ctggaagctc cctcgtgcgc tctcctgttc cgaccctgcc gcttaccgga tacctgtccg   2580
cctttctccc ttcgggaagc gtggcgcttt ctcatagctc acgctgtagg tatctcagtt   2640
cggtgtaggt cgttcgctcc aagctgggct gtgtgcacga accccccgtt cagcccgacc   2700
gctgcgcctt atccggtaac tatcgtcttg agtccaaccc ggtaagacac gacttatcgc   2760
cactggcagc agccactggt aacaggatta gcagagcgag gtatgtaggc ggtgctacag   2820
agttcttgaa gtggtggcct aactacggct acactagaag gacagtattt ggtatctgcg   2880
ctctgctgaa gccagttacc ttcggaaaaa gagttggtag ctcttgatcc ggcaaacaaa   2940
ccaccgctgg tagcggtggt ttttttgttt gcaagcagca gattacgcgc agaaaaaaag   3000
gatctcaaga agatcctttg atcttttcta cggggtctga cgctcagtgg aacgaaaact   3060
cacgttaagg gattttggtc atgagattat caaaaaggat cttcacctag atccttttaa   3120
attaaaaatg aagttttaaa tcaatctaaa gtatatatga gtaaacttgg tctgacagtt   3180
```

-continued

```
accaatgctt aatcagtgag gcacctatct cagcgatctg tctatttcgt tcatccatag   3240
ttgcctgact ccccgtcgtg tagataacta cgatacggga gggcttacca tctggcccca   3300
gtgctgcaat gataccgcga gacccacgct caccggctcc agatttatca gcaataaacc   3360
agccagccgg aagggccgag cgcagaagtg gtcctgcaac tttatccgcc tccatccagt   3420
ctattaattg ttgccgggaa gctagagtaa gtagttcgcc agttaatagt ttgcgcaacg   3480
ttgttgccat tgctacaggc atcgtggtgt cacgctcgtc gtttggtatg gcttcattca   3540
gctccggttc ccaacgatca aggcgagtta catgatcccc catgttgtgc aaaaaagcgg   3600
ttagctcctt cggtcctccg atcgttgtca gaagtaagtt ggccgcagtg ttatcactca   3660
tggttatggc agcactgcat aattctctta ctgtcatgcc atccgtaaga tgcttttctg   3720
tgactggtga gtactcaacc aagtcattct gagaatagtg tatgcggcga ccgagttgct   3780
cttgcccggc gtcaatacgg gataataccg cgccacatag cagaacttta aaagtgctca   3840
tcattggaaa acgttcttcg gggcgaaaac tctcaaggat cttaccgctg ttgagatcca   3900
gttcgatgta acccactcgt gcacccaact gatcttcagc atcttttact ttcaccagcg   3960
tttctgggtg agcaaaaaca ggaaggcaaa atgccgcaaa aaagggaata agggcgacac   4020
ggaaatgttg aatactcata ctcttccttt ttcaatatta ttgaagcatt tatcagggtt   4080
attgtctcat gagcggatac atatttgaat gtatttagaa aaataaacaa ataggggttc   4140
cgcgcacatt tccccgaaaa gtgccaccta aattgtaagc gttaatattt tgttaaaatt   4200
cgcgttaaat ttttgttaaa tcagctcatt ttttaaccaa taggccgaaa tcggcaaaat   4260
cccttataaa tcaaaagaat agaccgagat agggttgagt gttgttccag tttggaacaa   4320
gagtccacta ttaaagaacg tggactccaa cgtcaaaggg cgaaaaaccg tctatcaggg   4380
cgatggccca ctacgtgaac catcacccta atcaagtttt ttggggtcga ggtgccgtaa   4440
agcactaaat cggaacccta aagggagccc ccgatttaga gcttgacggg gaaagccggc   4500
gaacgtggcg agaaaggaag ggaagaaagc gaaaggagcg ggcgctaggg cgctggcaag   4560
tgtagcggtc acgctgcgcg taaccaccac acccgccgcg cttaatgcgc cgctacaggg   4620
cgcgtcccat tcgccattca ggctgcgcaa ctgttgggaa gggcgatcgg tgcgggcctc   4680
ttcgctatta cgccagctgg cgaaaggggg atgtgctgca aggcgattaa gttgggtaac   4740
gccagggttt tcccagtcac gacgttgtaa aacgacggcc agtgagcgcg ctagcgttta   4800
aacgagctct aagatacatt gatgagtttg gacaaaccac aactagaatg cagtgaaaaa   4860
aatgctttat ttgtgaaatt tgtgatgcta ttgctttatt tgtaaccatt ataagctgca   4920
ataaacaagt taacaacaac aattgcattc attttatgtt tcaggttcag ggggaggtgt   4980
gggaggtttt ttaaagcaag taaaacctct acaaatgtgg tatggctgat tatgatcctg   5040
cagctacgcc gctacgtctt ccgtgccgtc ctgggcgtcg tcttcgtcgt cgtcggtcgg   5100
cggcttcgcc cacgtgatcg aagcgcgctt ctcgatgggc gttccctgcc ccctgcccgt   5160
agtcgacttc gtgacaacga tcttgtctac gaagagcccg acgaacacgc gcttgtcgtc   5220
tactgacgcg cgcccccacc acgacttagg gccggtcggg tcagcgtcgg cgtcttcggg   5280
gaaccattgg tcaaggggaa gcttcggggc ttcggcggct tcaagttcgg caagccgctc   5340
ttccgcccct tgctgccgga gcgtcagcgc tgcctgttgc ttccggaagt gcttcctgcc   5400
aacgggtccg tcgtacgcgc ctgccgcgcg gtcttcgtac agctcttcaa gggcgttcag   5460
ggcgtcggcg cgctccgcaa caaggttcgc ccgttcgccg ctcttctcag gcgcctcagt   5520
```

```
gagcttgccg aagcgtcggg cggcttccca cagaagcgcc aacgtctctt cgtcgccttc   5580
ggcgtgcctg atcttgttga agatgcgttc cgcaacgaac ttgtcgagtg ccgccatgct   5640
gacgttgcac gtgccttcgt gctgcccagg tgcggacggg tcgaccacct tccggcgacg   5700
gcagcggtaa gagtccttga tcgattcttc cccgcgcttc gaagtcatga cggcgccaca   5760
ctcgcagtac agcttgtcca tggcggacag aatggcttgc ccccgggaaa gccccttgcc   5820
gcgccccctg ccgtccaacc acgcctgaag ctcataccac tcagcgggct cgatgatcgg   5880
tccgcaatca agctcgaccg gccggagcgt gatcgggtcg cgctgaatgc ggtaaccctc   5940
aatcttcgtg gtcggcgtgc cgtccggctt cttcttgtag atcacctcag cggcgaagcc   6000
cgcaatacgc gggtcccgaa ggattcgcat aacggttgcc gggtcccagg cgcttgaagc   6060
ggtcttcttc ccaatcgtct cgccccgggt cggcacggcg tcagcgtcca tgcgcttaca   6120
aagccccgtg atgctgcccg ggtgaatggc ggcttgactg cccggcttga agggaaggtg   6180
tttgtgcgtc ttgatctcac gccaccacca ccggattacg tcgggctcga actcgaaggg   6240
tccggtaagg ggagtggtcg agtgcgcaag cttgttgatg acgacattga ccattcggcc   6300
gttgcgcgtg atctccttcg tctccgaaac aagctcgaag ccgtaaggcg ccttcccgcc   6360
gacgtacccg cccaattcgc gctgaaggtt cttcgtgtcg agaatcttcg ccgacttcag   6420
cgaagattct ttgtgcgacg cgtcgagccg cataatcagg tgaatcaggt ccatgacgtt   6480
tccctgccgg aagacgcctt cctgagtgga aacaatcgtc acgcccaggg cgagcaattc   6540
cgagacaatc ggaatcgcgt ccatgacctt caggcgcgag aagcgcgaca cgtcatagac   6600
aatgatcatg ttgagccgcc cggcgcggca ttcgttcagg atgcgttcga actccgggcg   6660
ctccgccgtc ccgaacgccg acgtgcccgg cgcttcgctg aaatgcccga cgaacctgaa   6720
ccggcccccg tcgcgctcga cttcgcgctg aaggtcggcc gccttgtctt cgttggcgct   6780
acgctgtgtc gctgggcttg ctgcgctcga attctcgcgc tcgcgcgact gacggtcgta   6840
agcacccgcg tacgtgtcca tggcggatcc gtgtcgctgt aacagatgct gttcaactgt   6900
gtttaccaga tcgttgcggg ctgtatttat aggcgcgata agcgggacgg gcgcctcgtg   6960
tccggtcacg cgcatgagat aacgcgcggc tgatatggag gcgcgtcctg ttccgataag   7020
gagttgcgtc cggctgcggt tagcaacaca ggaagctggc gtcctgtcac gataagacaa   7080
cactcgtccg gtccgataat gtgattcgta cgtgacagga cgcgacccga taaggccggc   7140
ctacgtgact gccgacacgt actttttgc actgcaaaaa ggttcaatgt gtggtagtgt   7200
atttggagcg tatacaacgg tgtagactat ttatgtaaaa tagtctacga aacgtagagt   7260
ttgtactatg tatgggcccg cgtgcaaaag cgtgtttttt tgcagtgcaa aaaagttggt   7320
ggtggggagg ccaccgagta ta                                              7342
```

```
<210> SEQ ID NO 49
<211> LENGTH: 11868
<212> TYPE: DNA
<213> ORGANISM: Artificial Sequence
<220> FEATURE:
<223> OTHER INFORMATION: Synthetic construct, pLA1188-cctra intron
      construct

<400> SEQUENCE: 49
```

```
gtggtttttg tcaaacgaag attctatgac gtgtttaaag tttaggtcga gtaaagcgca     60
aatctttttt aaccctagaa agatagtctg cgtaaaattg acgcatgcat tcttgaaata    120
ttgctctctc tttctaaata gcgcgaatcc gtcgctgtgc atttaggaca tctcagtcgc    180
```

```
cgcttggagc tcccgtgagg cgtgcttgtc aatgcggtaa gtgtcactga ttttgaacta    240
taacgaccgc gtgagtcaaa atgacgcatg attatctttt acgtgacttt taagatttaa    300
ctcatacgat aattatattg ttatttcatg ttctacttac gtgataactt attatatata    360
tattttcttg ttatagatat cgtgactaat atataataaa atgggtagtt ctttagacga    420
tgagcatatc ctctctgctc ttctgcaaag cgatgacgag cttgttggtg aggattctga    480
cagtgaaata tcagatcacg taagtgaaga tgacgtccag agcgatacag aagaagcgtt    540
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg gccgtttttc ttgaaatatt    780
gctctctctt tctaaatagc gcgaatccgt cgctgtgcat ttaggacatc tcagtcgccg    840
cttggagctc ccaaacgcgc cagtggtagt acacagtact gtgggtgttc agtttgaaat    900
cctcttgctt ctccattgtc tcggttacct ttggtcaaat ccatgggttc tattgcctat    960
atactcttgc gattaccagt gattgcgcta ttagctatta gatggattgt tggccaaact   1020
tgtcgcttaa gtggctggga attgtaaccg taggcccgag tgtaatgatc ccccataaaa   1080
agttttcgca atgcctttat tttttgttgc aaatctctct ttattctgcg gtattcttca   1140
ttattgcggg gatggggaaa gtgtttatat agaagcaact tacgattgaa cccaaatgca   1200
cctgacaagc aaggtcaaag ggccagattt ttaaatatat tatttagtct taggactctc   1260
tatttgcaat taaattactt tgctacctga gggttaaatc ttccccattg ataataataa   1320
ttccactata tgttcaattg ggtttcaccg cgcttagtta catgacgagc cctaatgagc   1380
cgtcggtggt ctataaactg tgccttacaa atacttgcaa ctcttctcgt tttgaagtca   1440
gcagagttat tgctaattgc taattgctaa ttgcttttaa ctgatttctt cgaaattggt   1500
gctatgttta tggcgctatt aacaagtatg aatgtcaggt ttaaccaggg gatgcttaat   1560
tgtgttctca acttcaaagg cagaaatgtt tactcttgac catgggttta ggtataatgt   1620
tatcaagctc ctcgagttaa cgttacgtta acgttaacgt tcgaggtcga ctctagaact   1680
acccaccgta ctcgtcaatt ccaagggcat cggtaaacat ctgctcaaac tcgaagtcgg   1740
ccatatccag agcgccgtag gggcggagt cgtgggggt aaatcccgga cccggggaat      1800
ccccgtcccc caacatgtcc agatcgaaat cgtctagcgc gtcggcatgc gccatcgcca   1860
cgtcctcgcc gtctaagtgg agctcgtccc ccaggctgac atcggtcggg ggggccgtcg   1920
acagtctgcg cgtgtgtccc gcggggagaa aggacaggcg cggagccgcc agccccgcct   1980
cttcgggggc gtcgtcgtcc gggagatcga gcaggccctc gatggtagac ccgtaattgt   2040
ttttcgtacg cgcgcggctg tacgcggggc ccgagcccga ctcgcatttc agttgctttt   2100
ccaatccgca gataatcagc tccaagccga acaggaatgc cggctcggct ccttgatgat   2160
cgaacagctc gattgcctga cgcagcagtg gggcatcga atcggttgtt ggggtctcgc    2220
gctcctcttt tgcgacttga tgctcttggt cctccagcac gcagcccagg gtaaagtgac   2280
cgacggcgct cagagcgtag agagcatttt ccaggctgaa gccttgctgg cacaggaacg   2340
cgagctggtt ctccagtgtc tcgtattgct tttcggtcgg gcgcgtgccg agatggactt   2400
tggcaccgtc tcggtgggac agcagagcgc agcggaacga cttggcgtta ttgcggagga   2460
agtcctgcca ggactcgcct tccaacgggc aaaaatgcgt gtggtggcgg tcgagcatct   2520
cgatggccag ggcatccagc agcgcccgct tattcttcac ctatagatac catagatgta   2580
```

-continued

```
tggattagta tcatatacat acaaaggcta tttttgggac atattaatat taacaatttc   2640
cgtgatagtt ttcaccattt ttgttgaatg ttacgttgaa aatttaaatt tgttttaaat   2700
taattttacc agtcatgtgt tcttaaaagt ttttatgatt gaaacggcat aaagtggttc   2760
aaaaatttat caagaaaggc tttccttttt taaatcttat ctttttctct taaaaatcac   2820
tagtcaattc attattaatt tgttaacttg aatttggaat gtctatttac tttcagataa   2880
attaaagcaa gaaacttaat attcgaaaaa aattgattct aaatggaatt tcacttgatc   2940
ttcatgtatg catatcaatt tttatttaca ttgtataata agtttcgagt tgattgttgt   3000
aatccacagg tgtcccagag aattaaattc caaattaccc aagtttattg aatgttgatt   3060
gtagtttcag ttgctttgtt gctgcaacaa tggcttgttg attgtagata ttttcccttt   3120
ccttggttta cttattacat agactgaaaa agaggtttac tttttgata cttatgaaaa   3180
atttctatta gtgattacta accaatcgct atatgtttac tagaaaacaa ataaactctt   3240
tacattaaca ttcaataatg tttgctctgt aaccgacaat tgaaggcgtt acagcaacag   3300
taatataact agcttcttaa ccctcatcta ttaaccccat cgtttaaaac actatgttaa   3360
atggtctaac aaatctagat actaatagat gtcttattac ttagcagcca cagctgcaac   3420
atccaagaca atttttgaaa cttcttattg agctcttggc agcagaaatg ttggtatttt   3480
tcacagcttt ctgaaagacc ggcaccttcc tccggttccc gtttctgaat tcaagaggat   3540
ttccgacccc caattaatcc cgaaacaaat aaggtatatt caaaatgatg gaaaagtcat   3600
ggctgctgac cttattttta ttcctattga tagaatatta ttcccctttt aaatacactg   3660
tactaagagg tccggctata attttactca cttgtcgatt atcccataga atgttgattg   3720
tagttggttg cttttccagg tgagagttga tcaagtcaca aaagttagcg tgtgttgatt   3780
gtagatttga aggtaaaata atttttgcac ccattcatcg ggtaaaacgt tctccataga   3840
atacatttcc atcgataatt gataacttat gaatttcaaa gaaaaaaata tgcttttaaa   3900
attacgtgcc agtagagggt gggctgctcc acgcccagct tctgcgccaa cttgcgggtc   3960
gtcagtccct caatgccaac ttcgttcaac agctccaacg cggagttgat gactttggac   4020
ttatccaggc ggctgcccat ggtggtttct aaaggtgtta taaatcaaat tagttttgtt   4080
ttttcttgaa aactttgcgt ttcctttgat caacttaccg ccagggtacc gcagattgtt   4140
tagcttgttc agctgcgctt gtttatttgc ttagctttcg cttagcgacg tgttcacttt   4200
gcttgtttga attgaattgt cgctccgtag acgaagcgcc tctatttata ctccggcgct   4260
cgttttcgag tttaccactc cctatcagtg atagagaaaa gtgaaagtcg agtttaccac   4320
tccctatcag tgatagagaa aagtgaaagt cgagtttacc actccctatc agtgatagag   4380
aaaagtgaaa gtcgagttta ccactcccta tcagtgatag agaaaagtga aagtcgagtt   4440
taccactccc tatcagtgat agagaaaagt gaaagtcgag tttaccactc cctatcagtg   4500
atagagaaaa gtgaaagtcg agtttaccac tccctatcag tgatagagaa aagtgaaagt   4560
cgaaacctgg cgcgccccgg ccatcgagaa agagagagag aagagaagag agagaacatt   4620
cgagaaagag agagagaaga gaagagagag aacatactcc ctatcagtga tagagaagtc   4680
cctatcagtg atagagatgt ccctatcagt gatagagagt tccctatcag tgatagagac   4740
gtccctatca gtgatagaga agtccctatc agtgatagag agatccctat cagtgataga   4800
gatttcccta tcagtgatag agaggtccct atcagtgata gagacttccc tatcagtgat   4860
agagaaatcc ctatcagtga tagagacatc cctatcagtg atagagaact ccctatcagt   4920
```

-continued gatagagacc tccctatcag tgatagagat cgatgcggcc gcatggtacc cattgcttgt 4980
catttattaa tttggatgat gtcatttgtt tttaaaattg aactggcttt acgagtagaa 5040
ttctacgcgt aaaacacaat caagtatgag tcataatctg atgtcatgtt ttgtacacgg 5100
ctcataaccg aactggcttt acgagtagaa ttctacttgt aatgcacgat cagtggatga 5160
tgtcatttgt ttttcaaatc gagatgatgt catgttttgc acacggctca taaactcgct 5220
ttacgagtag aattctacgt gtaacgcacg atcgattgat gagtcatttg ttttgcaata 5280
tgatatcata caatatgact catttgtttt tcaaaaccga acttgattta cgggtagaat 5340
tctacttgta aagcacaatc aaaaagatga tgtcatttgt ttttcaaaac tgaactcgct 5400
ttacgagtag aattctacgt gtaaaacaca atcaagaaat gatgtcattt gttataaaaa 5460
taaaagctga tgtcatgttt tgcacatggc tcataactaa actcgcttta cgggtagaat 5520
tctacgcgta aaacatgatt gataattaaa taattcattt gcaagctata cgttaaatca 5580
aacggacgct cgaggttgca caacactatt atcgatttgc agttcgggac ataaatgttt 5640
aaatatatcg atgtctttgt gatgcgcgcg acatttttgt aggttattga taaaatgaac 5700
ggatacgttg cccgacatta tcattaaatc cttggcgtag aatttgtcgg gtccattgtc 5760
cgtgtgcgct agcatgcccg taacggacct cgtacttttg gcttcaaagg ttttgcgcac 5820
agacaaaatg tgccacactt gcagctctgc atgtgtgcgc gttaccacaa atcccaacgg 5880
cgcagtgtac ttgttgtatg caaataaatc tcgataaagg cgcggcgcgc gaatgcagct 5940
gatcacgtac gctcctcgtg ttccgttcaa ggacggtgtt atcgacctca gattaatgtt 6000
tatcggccga ctgttttcgt atccgctcac caaacgcgtt tttgcattaa cattgtatgt 6060
cggcggatgt tctatatcta atttgaataa ataaacgata accgcgttgg ttttagaggg 6120
cataataaaa gaaatattgt tatcgtgttc gccattaggg cagtataaat tgacgttcat 6180
gttggatatt gtttcagttg caagttgaca ctggcggcga caagcaattc taattggggt 6240
aagttttccc gttcttttct gggttcttcc cttttgctca tccttgctgc actaccttca 6300
ggtgcaagtt gagattcagg ccaccatggg agatcccacc ccacccaaga agaagcgcaa 6360
accggtcgcc accatggcct cctccgagaa cgtcatcacc gagttcatgc gcttcaaggt 6420
gcgcatggag ggcaccgtga acggccacga gttcgagatc gagggcgagg gcgagggccg 6480
cccctacgag ggccacaaca ccgtgaagct gaaggtgacc aagggcggcc ccctgccctt 6540
cgcctgggac atcctgtccc cccagttcca gtacggctcc aaggtgtacg tgaagcaccc 6600
cgccgacatc cccgactaca agaagctgtc cttccccgag ggcttcaagt gggagcgcgt 6660
gatgaacttc gaggacggcg gcgtggcgac cgtgacccag gactcctccc tgcaggacgg 6720
ctgcttcatc tacaaggtga agttcatcgg cgtgaacttc ccctccgacg gccccgtgat 6780
gcagaagaag accatgggct gggaggcctc caccgagcgc ctgtaccccc gcgacggcgt 6840
gctgaagggc gagacccaca aggccctgaa gctgaaggac ggcggccact acctggtgga 6900
gttcaagtcc atctacatgg ccaagaagcc cgtgcagctg cccggctact actacgtgga 6960
cgccaagctg gacatcacct cccacaacga ggactacacc atcgtggagc agtacgagcg 7020
caccgagggc cgccaccacc tgttcctgag atctcgaccc aagaaaaagc ggaaggtgga 7080
ggacccgtaa gatccaccgg atctagataa ctgatcataa tcagccatac cacatttgta 7140
gaggttttac ttgctttaaa aaacctccca cacctccccc tgaacctgaa acataaaatg 7200
aatgcaattg ttgttgttaa cttgtttatt gcagcttata atggttacaa ataaagcaat 7260
agcatcacaa atttcacaaa taaagcattt ttttcactgc attctagttg tggtttgtcc 7320

```
aaactcatca atgtatctta acgcgagtta attaaggccg ctcatttaaa tctggccggc   7380
cgcaaccatt gtgggaaccg tgcgatcaaa caaacgcgag ataccggaag tactgaaaaa   7440
cagtcgctcc aggccagtgg gaacatcgat gttttgtttt gacggacccc ttactctcgt   7500
ctcatataaa ccgaagccag ctaagatggt atacttatta tcatcttgtg atgaggatgc   7560
ttctatcaac gaaagtaccg gtaaaccgca aatggttatg tattataatc aaactaaagg   7620
cggagtggac acgctagacc aaatgtgttc tgtgatgacc tgcagtagga agacgaatag   7680
gtggcctatg gcattattgt acggaatgat aaacattgcc tgcataaatt cttttattat   7740
atacagccat aatgtcagta gcaagggaga aaaggtccaa agtcgcaaaa aatttatgag   7800
aaacctttac atgagcctga cgtcatcgtt tatgcgtaag cgtttagaag ctcctacttt   7860
gaagagatat ttgcgcgata atatctctaa tattttgcca aatgaagtgc ctggtacatc   7920
agatgacagt actgaagagc cagtaatgaa aaaacgtact tactgtactt actgcccctc   7980
taaaataagg cgaaaggcaa atgcatcgtg caaaaaatgc aaaaaagtta tttgtcgaga   8040
gcataatatt gatatgtgcc aaagttgttt ctgactgact aataagtata atttgtttct   8100
attatgtata agttaagcta attacttatt ttataataca acatgactgt ttttaaagta   8160
caaaataagt ttatttttgt aaaagagaga atgtttaaaa gttttgttac tttatagaag   8220
aaattttgag tttttgtttt tttttaataa ataaataaac ataaataaat tgtttgttga   8280
atttattatt agtatgtaag tgtaaatata ataaaactta atatctattc aaattaataa   8340
ataaacctcg atatacagac cgataaaaca catgcgtcaa ttttacgcat gattatcttt   8400
aacgtacgtc acaatatgat tatctttcta gggttaaata atagtttcta atttttttat   8460
tattcagcct gctgtcgtga ataccgtata tctcaacgct gtctgtgaga ttgtcgtatt   8520
ctagcctttt tagtttttcg ctcatcgact tgatattgtc cgacacattt tcgtcgattt   8580
gcgttttgat caaagacttg agcagagaca cgttaatcaa ctgttcaaat tgatccatat   8640
taacgatatc aacccgatgc gtatatggtg cgtaaaatat attttttaac cctcttatac   8700
tttgcactct gcgttaatac gcgttcgtgt acagacgtaa tcatgttttc tttttggat   8760
aaaactccta ctgagtttga cctcatatta gaccctcaca agttgcaaaa cgtggcattt   8820
tttaccaatg aagaatttaa agttatttta aaaaatttca tcacagattt aaagaagaac   8880
caaaaattaa attatttcaa cagtttaatc gaccagttaa tcaacgtgta cacagacgcg   8940
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc ccctttcgcc agctggcgta atagcgaaga   9240
ggcccgcacc gatcgccctt cccaacagtt gcgcagcctg aatggcgaat ggcgcctgat   9300
gcggtatttt ctccttacgc atctgtgcgg tatttcacac cgcatatggt gcactctcag   9360
tacaatctgc tctgatgccg catagttaag ccagccccga cacccgccaa cacccgctga   9420
cgcgccctga cgggcttgtc tgctcccggc atccgcttac agacaagctg tgaccgtctc   9480
cgggagctgc atgtgtcaga ggttttcacc gtcatcaccg aaacgcgcga gacgaaaggg   9540
cctcgtgata cgcctatttt tataggttaa tgtcatgata ataatggttt cttagacgtc   9600
aggtggcact tttcggggaa atgtgcgcgg aacccctatt tgtttatttt tctaaataca   9660
```

-continued

```
ttcaaatatg tatccgctca tgagacaata accctgataa atgcttcaat aatattgaaa    9720
aaggaagagt atgagtattc aacatttccg tgtcgccctt attccctttt ttgcggcatt    9780
ttgccttcct gtttttgctc acccagaaac gctggtgaaa gtaaaagatg ctgaagatca    9840
gttgggtgca cgagtgggtt acatcgaact ggatctcaac agcggtaaga tccttgagag    9900
ttttcgcccc gaagaacgtt ttccaatgat gagcactttt aaagttctgc tatgtggcgc    9960
ggtattatcc cgtattgacg ccgggcaaga gcaactcggt cgccgcatac actattctca   10020
gaatgacttg gttgagtact caccagtcac agaaaagcat cttacggatg gcatgacagt   10080
aagagaatta tgcagtgctg ccataaccat gagtgataac actgcggcca acttacttct   10140
gacaacgatc ggaggaccga aggagctaac cgcttttttg cacaacatgg gggatcatgt   10200
aactcgcctt gatcgttggg aaccggagct gaatgaagcc ataccaaacg acgagcgtga   10260
caccacgatg cctgtagcaa tggcaacaac gttgcgcaaa ctattaactg gcgaactact   10320
tactctagct tcccggcaac aattaataga ctggatggag gcggataaag ttgcaggacc   10380
acttctgcgc tcggcccttc cggctggctg gtttattgct gataaatctg gagccggtga   10440
gcgtgggtct cgcggtatca ttgcagcact ggggccagat ggtaagccct cccgtatcgt   10500
agttatctac acgacgggga gtcaggcaac tatggatgaa cgaaatagac agatcgctga   10560
gataggtgcc tcactgatta agcattggta actgtcagac caagtttact catatatact   10620
ttagattgat ttaaaacttc atttttaatt taaaaggatc taggtgaaga tcctttttga   10680
taatctcatg accaaaatcc cttaacgtga gttttcgttc cactgagcgt cagaccccgt   10740
agaaaagatc aaaggatctt cttgagatcc tttttttctg cgcgtaatct gctgcttgca   10800
aacaaaaaaa ccaccgctac cagcggtggt ttgtttgccg gatcaagagc taccaactct   10860
ttttccgaag gtaactggct tcagcagagc gcagatacca aatactgtcc ttctagtgta   10920
gccgtagtta ggccaccact tcaagaactc tgtagcaccg cctacatacc tcgctctgct   10980
aatcctgtta ccagtggctg ctgccagtgg cgataagtcg tgtcttaccg ggttggactc   11040
aagacgatag ttaccggata aggcgcagcg gtcgggctga acggggggtt cgtgcacaca   11100
gcccagcttg gagcgaacga cctacaccga actgagatac ctacagcgtg agcattgaga   11160
aagcgccacg cttcccgaag ggagaaaggc ggacaggtat ccggtaagcg gcagggtcgg   11220
aacaggagag cgcacgaggg agcttccagg gggaaacgcc tggtatcttt atagtcctgt   11280
cgggtttcgc cacctctgac ttgagcgtcg atttttgtga tgctcgtcag gggggcggag   11340
cctatggaaa aacgccagca acgcggcctt tttacggttc ctggcctttt gctggccttt   11400
tgctcacatg ttctttcctg cgttatcccc tgattctgtg gataaccgta ttaccgcctt   11460
tgagtgagct gataccgctc gccgcagccg aacgaccgag cgcagcgagt cagtgagcga   11520
ggaagcggaa gagcgcccaa tacgcaaacc gcctctcccc gcgcgttggc cgattcatta   11580
atgcagctgg cacgacaggt ttcccgactg gaaagcgggc agtgagcgca acgcaattaa   11640
tgtgagttag ctcactcatt aggcacccca ggctttacac tttatgcttc cggctcgtat   11700
gttgtgtgga attgtgagcg gataacaatt tcacacagga aacagctatg accatgatta   11760
cgaatttcga cctgcaggca tgcaagcttg catgcctgca ggtcgacgct cgcgcgactt   11820
ggtttgccat tctttagcgc gcgtcgcgtc acacagcttg gccacaat                11868
```

<210> SEQ ID NO 50
<211> LENGTH: 11868
<212> TYPE: DNA
<213> ORGANISM: Artificial Sequence
<220> FEATURE:
<223> OTHER INFORMATION: Synthetic construct, pLA3077-a Cctra intron-
tTAV construct.

<400> SEQUENCE: 50

```
gtggtttttg tcaaacgaag attctatgac gtgtttaaag tttaggtcga gtaaagcgca     60
aatctttttt aaccctagaa agatagtctg cgtaaaattg acgcatgcat tcttgaaata    120
ttgctctctc tttctaaata gcgcgaatcc gtcgctgtgc atttaggaca tctcagtcgc    180
cgcttggagc tcccgtgagg cgtgcttgtc aatgcggtaa gtgtcactga ttttgaacta    240
taacgaccgc gtgagtcaaa atgacgcatg attatctttt acgtgacttt taagatttaa    300
ctcatacgat aattatattg ttatttcatg ttctacttac gtgataactt attatatata    360
tattttcttg ttatagatat cgtgactaat atataataaa atgggtagtt ctttagacga    420
tgagcatatc ctctctgctc ttctgcaaag cgatgacgag cttgttggtg aggattctga    480
cagtgaaata tcagatcacg taagtgaaga tgacgtccag agcgatacag aagaagcgtt    540
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg ccgtttttct tgaaatattg    780
ctctctcttt ctaaatagcg cgaatccgtc gctgtgcatt taggacatct cagtcgccgc    840
ttggagctcc caaacgcgcc agtggtagta cacagtactg tgggtgttca gtttgaaatc    900
ctcttgcttc tccattgtct cggttacctt tggtcaaatc catgggttct attgcctata    960
tactcttgcg attaccagtg attgcgctat tagctattag atggattgtt ggccaaactt   1020
gtcgcttaag tggctgggaa ttgtaaccgt aggcccgagt gtaatgatcc cccataaaaa   1080
gttttcgcaa tgcctttatt ttttgttgca aatctctctt tattctgcgg tattcttcat   1140
tattgcgggg atggggaaag tgtttatata gaagcaactt acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
gtcggtggtc tataaactgt gccttacaaa tacttgcaac tcttctcgtt ttgaagtcag   1440
cagagttatt gctaattgct aattgctaat tgcttttaac tgatttcttc gaaattggtg   1500
ctatgtttat ggcgctatta acaagtatga atgtcaggtt taaccagggg atgcttaatt   1560
gtgttctcaa cttcaaaggc agaaatgttt actcttgacc atgggtttag gtataatgtt   1620
atcaagctcc tcgagttaac gttacgttaa cgttaacgtt cgaggtcgac tctagaacta   1680
cccaccgtac tcgtcaattc caagggcatc ggtaaacatc tgctcaaact cgaagtcggc   1740
catatccaga gcgccgtagg gggcggagtc gtgggggta aatcccggac ccggggaatc    1800
cccgtccccc aacatgtcca gatcgaaatc gtctagcgcg tcggcatgcg ccatcgccac   1860
gtcctcgccg tctaagtgga gctcgtcccc caggctgaca tcggtcgggg gggccgtcga   1920
cagtctgcgc gtgtgtcccg cggggagaaa ggacaggcgc ggagccgcca gccccgcctc   1980
ttcgggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg ggtctcgcg    2220
```

```
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacg tgccagtaga gggtgggctg   2580
ctccacgccc agcttctgcg ccaacttgcg ggtcgtcagt ccctcaatac ctatagatac   2640
catagatgta tggattagta tcatatacat acaaaggcta tttttgggac atattaatat   2700
taacaatttc cgtgatagtt ttcaccattt ttgttgaatg ttacgttgaa aatttaaatt   2760
tgttttaaat taattttacc agtcatgtgt tcttaaaagt ttttatgatt gaaacggcat   2820
aaagtggttc aaaaatttat caagaaaggc tttccttttt taaatcttat ctttttctct   2880
taaaaatcac tagtcaattc attattaatt tgttaacttg aatttggaat gtctatttac   2940
tttcagataa attaaagcaa gaaacttaat attcgaaaaa aattgattct aaatggaatt   3000
tcacttgatc ttcatgtatg catatcaatt tttatttaca ttgtataata agtttcgagt   3060
tgattgttgt aatccacagg tgtcccagag aattaaattc caaattaccc aagtttattg   3120
aatgttgatt gtagtttcag ttgctttgtt gctgcaacaa tggcttgttg attgtagata   3180
ttttcccttt ccttggttta cttattacat agactgaaaa agaggtttac tttttttgata   3240
cttatgaaaa atttctatta gtgattacta accaatcgct atatgtttac tagaaaacaa   3300
ataaactctt tacattaaca ttcaataatg tttgctctgt aaccgacaat tgaaggcgtt   3360
acagcaacag taatataact agcttcttaa ccctcatcta ttaaccccat cgtttaaaac   3420
actatgttaa atggtctaac aaatctagat actaatagat gtcttattac ttagcagcca   3480
cagctgcaac atccaagaca atttttgaaa cttcttattg agctcttggc agcagaaatg   3540
ttggtatttt tcacagcttt ctgaaagacc ggcaccttcc tccggttccc gtttctgaat   3600
tcaagaggat ttccgacccc caattaatcc cgaaacaaat aaggtatatt caaaatgatg   3660
gaaaagtcat ggctgctgac cttattttta ttcctattga tagaatatta ttcccctttt   3720
aaatacactg tactaagagg tccggctata attttactca cttgtcgatt atcccataga   3780
atgttgattg tagttggttg cttttccagg tgagagttga tcaagtcaca aaagttagcg   3840
tgtgttgatt gtagatttga aggtaaaata atttttgcac ccattcatcg ggtaaaacgt   3900
tctccataga atacatttcc atcgataatt gataacttat gaatttcaaa gaaaaaaata   3960
tgcttttaaa attaccaact tcgttcaaca gctccaacgc ggagttgatg actttggact   4020
tatccaggcg gctgcccatg gtggtttcta aaggtgttat aaatcaaatt agttttgttt   4080
tttcttgaaa actttgcgtt tcctttgatc aacttaccgc cagggtacct gcagattgtt   4140
tagcttgttc agctgcgctt gtttatttgc ttagctttcg cttagcgacg tgttcacttt   4200
gcttgtttga attgaattgt cgctccgtag acgaagcgcc tctatttata ctccggcgct   4260
cgttttcgag tttaccactc cctatcagtg atagagaaaa gtgaaagtcg agtttaccac   4320
tccctatcag tgatagagaa aagtgaaagt cgagtttacc actccctatc agtgatagag   4380
aaaagtgaaa gtcgagttta ccactcccta tcagtgatag agaaaagtga aagtcgagtt   4440
taccactccc tatcagtgat agagaaaagt gaaagtcgag tttaccactc cctatcagtg   4500
atagagaaaa gtgaaagtcg agtttaccac tccctatcag tgatagagaa aagtgaaagt   4560
```

-continued

```
cgaaacctgg cgcgccccgg ccatcgagaa agagagagag aagagaagag agagaacatt   4620
cgagaaagag agagagaaga gaagagagag aacatactcc ctatcagtga tagagaagtc   4680
cctatcagtg atagagatgt ccctatcagt gatagagagt tccctatcag tgatagagac   4740
gtccctatca gtgatagaga agtccctatc agtgatagag agatccctat cagtgataga   4800
gatttcccta tcagtgatag agaggtccct atcagtgata gagacttccc tatcagtgat   4860
agagaaatcc ctatcagtga tagagacatc cctatcagtg atagagaact ccctatcagt   4920
gatagagacc tccctatcag tgatagagat cgatgcggcc gcatggtacc cattgcttgt   4980
catttattaa tttggatgat gtcatttgtt tttaaaattg aactggcttt acgagtagaa   5040
ttctacgcgt aaaacacaat caagtatgag tcataatctg atgtcatgtt ttgtacacgg   5100
ctcataaccg aactggcttt acgagtagaa ttctacttgt aatgcacgat cagtggatga   5160
tgtcatttgt ttttcaaatc gagatgatgt catgttttgc acacggctca taaactcgct   5220
ttacgagtag aattctacgt gtaacgcacg atcgattgat gagtcatttg ttttgcaata   5280
tgatatcata caatatgact catttgtttt tcaaaaccga acttgattta cgggtagaat   5340
tctacttgta aagcacaatc aaaaagatga tgtcatttgt ttttcaaaac tgaactcgct   5400
ttacgagtag aattctacgt gtaaaacaca atcaagaaat gatgtcattt gttataaaaa   5460
taaaagctga tgtcatgttt tgcacatggc tcataactaa actcgcttta cgggtagaat   5520
tctacgcgta aaacatgatt gataattaaa taattcattt gcaagctata cgttaaatca   5580
aacggacgct cgaggttgca caacactatt atcgatttgc agttcgggac ataaatgttt   5640
aaatatatcg atgtctttgt gatgcgcgcg acatttttgt aggttattga taaaatgaac   5700
ggatacgttg cccgacatta tcattaaatc cttggcgtag aatttgtcgg gtccattgtc   5760
cgtgtgcgct agcatgcccg taacggacct cgtacttttg gcttcaaagg ttttgcgcac   5820
agacaaaatg tgccacactt gcagctctgc atgtgtgcgc gttaccacaa atcccaacgg   5880
cgcagtgtac ttgttgtatg caaataaatc tcgataaagg cgcggcgcgc gaatgcagct   5940
gatcacgtac gctcctcgtg ttccgttcaa ggacggtgtt atcgacctca gattaatgtt   6000
tatcggccga ctgttttcgt atccgctcac caaacgcgtt tttgcattaa cattgtatgt   6060
cggcggatgt tctatatcta atttgaataa ataaacgata accgcgttgg ttttagaggg   6120
cataataaaa gaaatattgt tatcgtgttc gccattaggg cagtataaat tgacgttcat   6180
gttggatatt gtttcagttg caagttgaca ctggcggcga caagcaattc taattggggt   6240
aagttttccc gttcttttct gggttcttcc cttttgctca tccttgctgc actaccttca   6300
ggtgcaagtt gagattcagg ccaccatggg agatcccacc ccacccaaga agaagcgcaa   6360
accggtcgcc accatggcct cctccgagaa cgtcatcacc gagttcatgc gcttcaaggt   6420
gcgcatggag ggcaccgtga acggccacga gttcgagatc gagggcgagg gcgagggccg   6480
cccctacgag ggccacaaca ccgtgaagct gaaggtgacc aagggcggcc ccctgccctt   6540
cgcctgggac atcctgtccc cccagttcca gtacggctcc aaggtgtacg tgaagcaccc   6600
cgccgacatc cccgactaca agaagctgtc cttccccgag ggcttcaagt gggagcgcgt   6660
gatgaacttc gaggacggcg gcgtggcgac cgtgacccag gactcctccc tgcaggacgg   6720
ctgcttcatc tacaaggtga agttcatcgg cgtgaacttc ccctccgacg gccccgtgat   6780
gcagaagaag accatgggct gggaggcctc caccgagcgc ctgtaccccc gcgacggcgt   6840
gctgaagggc gagacccaca aggccctgaa gctgaaggac ggcggccact acctggtgga   6900
gttcaagtcc atctacatgg ccaagaagcc cgtgcagctg cccggctact actacgtgga   6960
```

```
cgccaagctg gacatcacct cccacaacga ggactacacc atcgtggagc agtacgagcg   7020
caccgagggc cgccaccacc tgttcctgag atctcgaccc aagaaaaagc ggaaggtgga   7080
ggacccgtaa gatccaccgg atctagataa ctgatcataa tcagccatac cacatttgta   7140
gaggttttac ttgctttaaa aaacctccca cacctccccc tgaacctgaa acataaaatg   7200
aatgcaattg ttgttgttaa cttgtttatt gcagcttata atggttacaa ataaagcaat   7260
agcatcacaa atttcacaaa taaagcattt ttttcactgc attctagttg tggtttgtcc   7320
aaactcatca atgtatctta acgcgagtta attaaggccg ctcatttaaa tctggccggc   7380
cgcaaccatt gtgggaaccg tgcgatcaaa caaacgcgag ataccggaag tactgaaaaa   7440
cagtcgctcc aggccagtgg gaacatcgat gttttgtttt gacggacccc ttactctcgt   7500
ctcatataaa ccgaagccag ctaagatggt atacttatta tcatcttgtg atgaggatgc   7560
ttctatcaac gaaagtaccg gtaaaccgca aatggttatg tattataatc aaactaaagg   7620
cggagtggac acgctagacc aaatgtgttc tgtgatgacc tgcagtagga agacgaatag   7680
gtggcctatg gcattattgt acggaatgat aaacattgcc tgcataaatt cttttattat   7740
atacagccat aatgtcagta gcaagggaga aaaggtccaa agtcgcaaaa aatttatgag   7800
aaacctttac atgagcctga cgtcatcgtt tatgcgtaag cgtttagaag ctcctacttt   7860
gaagagatat ttgcgcgata atatctctaa tattttgcca aatgaagtgc ctggtacatc   7920
agatgacagt actgaagagc cagtaatgaa aaaacgtact tactgtactt actgcccctc   7980
taaaataagg cgaaaggcaa atgcatcgtg caaaaaatgc aaaaaagtta tttgtcgaga   8040
gcataatatt gatatgtgcc aaagttgttt ctgactgact aataagtata atttgtttct   8100
attatgtata agttaagcta attacttatt ttataataca acatgactgt ttttaaagta   8160
caaaataagt ttatttttgt aaaagagaga atgtttaaaa gttttgttac tttatagaag   8220
aaattttgag tttttgtttt tttttaataa ataaataaac ataaataaat tgtttgttga   8280
atttattatt agtatgtaag tgtaaatata ataaaactta atatctattc aaattaataa   8340
ataaacctcg atatacagac cgataaaaca catgcgtcaa ttttacgcat gattatcttt   8400
aacgtacgtc acaatatgat tatctttcta gggttaaata atagtttcta atttttttat   8460
tattcagcct gctgtcgtga ataccgtata tctcaacgct gtctgtgaga ttgtcgtatt   8520
ctagcctttt tagtttttcg ctcatcgact tgatattgtc cgacacattt tcgtcgattt   8580
gcgttttgat caaagacttg agcagagaca cgttaatcaa ctgttcaaat tgatccatat   8640
taacgatatc aacccgatgc gtatatggtg cgtaaaatat attttttaac cctcttatac   8700
tttgcactct gcgttaatac gcgttcgtgt acagacgtaa tcatgttttc tttttggat    8760
aaaactccta ctgagtttga cctcatatta gaccctcaca agttgcaaaa cgtggcattt   8820
tttaccaatg aagaatttaa agttatttta aaaaatttca tcacagattt aaagaagaac   8880
caaaaattaa attatttcaa cagtttaatc gaccagttaa tcaacgtgta cacagacgcg   8940
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc ccctttcgcc agctggcgta atagcgaaga   9240
ggcccgcacc gatcgccctt cccaacagtt gcgcagcctg aatggcgaat ggcgcctgat   9300
```

gcggtatttt ctccttacgc atctgtgcgg tatttcacac cgcatatggt gcactctcag 9360
tacaatctgc tctgatgccg catagttaag ccagccccga cacccgccaa cacccgctga 9420
cgcgccctga cgggcttgtc tgctcccggc atccgcttac agacaagctg tgaccgtctc 9480
cgggagctgc atgtgtcaga ggttttcacc gtcatcaccg aaacgcgcga gacgaaaggg 9540
cctcgtgata cgcctatttt tataggttaa tgtcatgata ataatggttt cttagacgtc 9600
aggtggcact tttcggggaa atgtgcgcgg aacccctatt tgtttatttt tctaaataca 9660
ttcaaatatg tatccgctca tgagacaata accctgataa atgcttcaat aatattgaaa 9720
aaggaagagt atgagtattc aacatttccg tgtcgccctt attccctttt ttgcggcatt 9780
ttgccttcct gtttttgctc acccagaaac gctggtgaaa gtaaaagatg ctgaagatca 9840
gttgggtgca cgagtgggtt acatcgaact ggatctcaac agcggtaaga tccttgagag 9900
ttttcgcccc gaagaacgtt ttccaatgat gagcactttt aaagttctgc tatgtggcgc 9960
ggtattatcc cgtattgacg ccgggcaaga gcaactcggt cgccgcatac actattctca 10020
gaatgacttg gttgagtact caccagtcac agaaaagcat cttacggatg gcatgacagt 10080
aagagaatta tgcagtgctg ccataaccat gagtgataac actgcggcca acttacttct 10140
gacaacgatc ggaggaccga aggagctaac cgcttttttg cacaacatgg gggatcatgt 10200
aactcgcctt gatcgttggg aaccggagct gaatgaagcc ataccaaacg acgagcgtga 10260
caccacgatg cctgtagcaa tggcaacaac gttgcgcaaa ctattaactg gcgaactact 10320
tactctagct tcccggcaac aattaataga ctggatggag gcggataaag ttgcaggacc 10380
acttctgcgc tcggcccttc cggctggctg gtttattgct gataaatctg gagccggtga 10440
gcgtgggtct cgcggtatca ttgcagcact ggggccagat ggtaagccct cccgtatcgt 10500
agttatctac acgacgggga gtcaggcaac tatggatgaa cgaaatagac agatcgctga 10560
gataggtgcc tcactgatta agcattggta actgtcagac caagtttact catatatact 10620
ttagattgat ttaaaacttc atttttaatt taaaaggatc taggtgaaga tcctttttga 10680
taatctcatg accaaaatcc cttaacgtga gttttcgttc cactgagcgt cagaccccgt 10740
agaaaagatc aaaggatctt cttgagatcc tttttttctg cgcgtaatct gctgcttgca 10800
aacaaaaaaa ccaccgctac cagcggtggt ttgtttgccg gatcaagagc taccaactct 10860
ttttccgaag gtaactggct tcagcagagc gcagatacca aatactgtcc ttctagtgta 10920
gccgtagtta ggccaccact tcaagaactc tgtagcaccg cctacatacc tcgctctgct 10980
aatcctgtta ccagtggctg ctgccagtgg cgataagtcg tgtcttaccg ggttggactc 11040
aagacgatag ttaccggata aggcgcagcg gtcgggctga acggggggtt cgtgcacaca 11100
gcccagcttg gagcgaacga cctacaccga actgagatac ctacagcgtg agcattgaga 11160
aagcgccacg cttcccgaag ggagaaaggc ggacaggtat ccggtaagcg gcagggtcgg 11220
aacaggagag cgcacgaggg agcttccagg gggaaacgcc tggtatcttt atagtcctgt 11280
cgggtttcgc cacctctgac ttgagcgtcg atttttgtga tgctcgtcag gggggcggag 11340
cctatggaaa aacgccagca acgcggcctt tttacggttc ctggcctttt gctggccttt 11400
tgctcacatg ttctttcctg cgttatcccc tgattctgtg gataaccgta ttaccgcctt 11460
tgagtgagct gataccgctc gccgcagccg aacgaccgag cgcagcgagt cagtgagcga 11520
ggaagcggaa gagcgcccaa tacgcaaacc gcctctcccc gcgcgttggc cgattcatta 11580
atgcagctgg cacgacaggt ttcccgactg gaaagcgggc agtgagcgca acgcaattaa 11640
tgtgagttag ctcactcatt aggcacccca ggctttacac tttatgcttc cggctcgtat 11700
gttgtgtgga attgtgagcg gataacaatt tcacacagga aacagctatg accatgatta 11760
cgaatttcga cctgcaggca tgcaagcttg catgcctgca ggtcgacgct cgcgcgactt 11820
ggtttgccat tctttagcgc gcgtcgcgtc acacagcttg gccacaat 11868

<210> SEQ ID NO 51
<211> LENGTH: 11788
<212> TYPE: DNA
<213> ORGANISM: Artificial Sequence
<220> FEATURE:
<223> OTHER INFORMATION: Synthetic construct, pLA3097-a Cctra intron-tTAV construct.

<400> SEQUENCE: 51
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gaactaccca ccgtactcgt caattccaag ggcatcggta 960
aacatctgct caaactcgaa gtcggccata tccagagcgc cgtagggggc ggagtcgtgg 1020
ggggtaaatc ccggacccgg ggaatccccg tcccccaaca tgtccagatc gaaatcgtct 1080
agcgcgtcgg catgcgccat cgccacgtcc tcgccgtcta agtggagctc gtcccccagg 1140
ctgacatcgg tcgggggggc cgtcgacagt ctgcgcgtgt gtcccgcggg gagaaaggac 1200
aggcgcggag ccgccagccc cgcctcttcg ggggcgtcgt cgtccgggag atcgagcagg 1260
ccctcgatgg tagacccgta attgtttttc gtacgcgcgc ggctgtacgc ggggcccgag 1320
cccgactcgc atttcagttg cttttccaat ccgcagataa tcagctccaa gccgaacagg 1380
aatgccggct cggctccttg atgatcgaac agctcgattg cctgacgcag cagtgggggc 1440
atcgaatcgg ttgttggggt ctcgcgctcc tcttttgcga cttgatgctc ttggtcctcc 1500
agcacgcagc ccagggtaaa gtgaccgacg gcgctcagag cgtagagagc attttccagg 1560
ctgaagcctt gctggcacag gaacgcgagc tggttctcca gtgtctcgta ttgcttttcg 1620
gtcgggcgcg tgccgagatg gactttggca ccgtctcggt gggacagcag agcgcagcgg 1680
aacgacttgg cgttattgcg gaggaagtcc tgccaggact cgccttccaa cgggcaaaaa 1740
tgcgtgtggt ggcggtcgag catctcgatg gccagggcat ccagcagcgc ccgcttattc 1800
ttcacgtgcc agtagagggt gggctgctcc acgcccagct tctgcgccaa cttgcgggtc 1860
gtcagtccct caatgccaac ttcgttcaac agctccaacg cggagttgat gactttggac 1920
ttatccaggc ggctgaccta tagataccat agatgtatgg attagtatca tatacataca 1980
aaggctattt ttgggacata ttaatattaa caatttccgt gatagttttc accatttttg 2040
ttgaatgtta cgttgaaaat ttaaatttgt tttaaattaa ttttaccagt catgtgttct 2100
taaaagtttt tatgattgaa acggcataaa gtggttcaaa aatttatcaa gaaaggcttt 2160 cctttttaa atcttatctt tttctcttaa aaatcactag tcaattcatt attaatttgt 2220
taacttgaat ttggaatgtc tatttacttt cagataaatt aaagcaagaa acttaatatt 2280
cgaaaaaaat tgattctaaa tggaatttca cttgatcttc atgtatgcat atcaattttt 2340
atttacattg tataataagt ttcgagttga ttgttgtaat ccacaggtgt cccagagaat 2400
taaattccaa attacccaag tttattgaat gttgattgta gtttcagttg ctttgttgct 2460
gcaacaatgg cttgttgatt gtagatattt tccctttcct tggtttactt attacataga 2520
ctgaaaaaga ggtttacttt tttgatactt atgaaaaatt tctattagtg attactaacc 2580
aatcgctata tgtttactag aaaacaaata aactctttac attaacattc aataatgttt 2640
gctctgtaac cgacaattga aggcgttaca gcaacagtaa tataactagc ttcttaaccc 2700
tcatctatta accccatcgt ttaaaacact atgttaaatg gtctaacaaa tctagatact 2760
aatagatgtc ttattactta gcagccacag ctgcaacatc caagacaatt tttgaaactt 2820
cttattgagc tcttggcagc agaaatgttg gtatttttca cagctttctg aaagaccggc 2880
accttcctcc ggttcccgtt tctgaattca agaggatttc cgacccccaa ttaatcccga 2940
aacaaataag gtatattcaa aatgatggaa aagtcatggc tgctgacctt atttttattc 3000
ctattgatag aatattattc cccttttaaa tacactgtac taagaggtcc ggctataatt 3060
ttactcactt gtcgattatc ccatagaatg ttgattgtag ttggttgctt ttccaggtga 3120
gagttgatca agtcacaaaa gttagcgtgt gttgattgta gatttgaagg taaaataatt 3180
tttgcaccca ttcatcgggt aaaacgttct ccatagaata catttccatc gataattgat 3240
aacttatgaa tttcaaagaa aaaaatatgc ttttaaaatt accatggtgg ctagcgcaga 3300
ttgtttagct tgttcagctg cgcttgttta tttgcttagc tttcgcttag cgacgtgttc 3360
actttgcttg tttgaattga attgtcgctc cgtagacgaa gcgcctctat ttatactccg 3420
gcgctcgttt tcgagtttac cactccctat cagtgataga gaaaagtgaa agtcgagttt 3480
accactccct atcagtgata gagaaaagtg aaagtcgagt ttaccactcc ctatcagtga 3540
tagagaaaag tgaaagtcga gtttaccact ccctatcagt gatagagaaa agtgaaagtc 3600
gagtttacca ctccctatca gtgatagaga aaagtgaaag tcgagtttac cactccctat 3660
cagtgataga gaaaagtgaa agtcgagttt accactccct atcagtgata gagaaaagtg 3720
aaagtcgaaa cctggcgcgc cccggccatc gagaaagaga gagagaagag aagagagaga 3780
acattcgaga aagagagaga gaagagaaga gagagaacat actccctatc agtgatagag 3840
aagtccctat cagtgataga gatgtcccta tcagtgatag agagttccct atcagtgata 3900
gagacgtccc tatcagtgat agagaagtcc ctatcagtga tagagagatc cctatcagtg 3960
atagagattt ccctatcagt gatagagagg tccctatcag tgatagagac ttccctatca 4020
gtgatagaga aatccctatc agtgatagag acatccctat cagtgataga gaactcccta 4080
tcagtgatag agacctccct atcagtgata gagatcgatg cggccgcatg gtacccattg 4140
cttgtcattt attaatttgg atgatgtcat ttgtttttaa aattgaactg gctttacgag 4200

```
tagaattcta cgcgtaaaac acaatcaagt atgagtcata atctgatgtc atgttttgta   4260
cacggctcat aaccgaactg gctttacgag tagaattcta cttgtaatgc acgatcagtg   4320
gatgatgtca tttgtttttc aaatcgagat gatgtcatgt tttgcacacg gctcataaac   4380
tcgctttacg agtagaattc tacgtgtaac gcacgatcga ttgatgagtc atttgttttg   4440
caatatgata tcatacaata tgactcattt gtttttcaaa accgaacttg atttacgggt   4500
agaattctac ttgtaaagca caatcaaaaa gatgatgtca tttgtttttc aaaactgaac   4560
tcgctttacg agtagaattc tacgtgtaaa acacaatcaa gaaatgatgt catttgttat   4620
aaaaataaaa gctgatgtca tgttttgcac atggctcata actaaactcg ctttacgggt   4680
agaattctac gcgtaaaaca tgattgataa ttaaataatt catttgcaag ctatacgtta   4740
aatcaaacgg acgctcgagg ttgcacaaca ctattatcga tttgcagttc gggacataaa   4800
tgtttaaata tatcgatgtc tttgtgatgc gcgcgacatt tttgtaggtt attgataaaa   4860
tgaacggata cgttgcccga cattatcatt aaatccttgg cgtagaattt gtcgggtcca   4920
ttgtccgtgt gcgctagcat gcccgtaacg gacctcgtac ttttggcttc aaaggttttg   4980
cgcacagaca aaatgtgcca cacttgcagc tctgcatgtg tgcgcgttac cacaaatccc   5040
aacggcgcag tgtacttgtt gtatgcaaat aaatctcgat aaaggcgcgg cgcgcgaatg   5100
cagctgatca cgtacgctcc tcgtgttccg ttcaaggacg gtgttatcga cctcagatta   5160
atgtttatcg gccgactgtt ttcgtatccg ctcaccaaac gcgtttttgc attaacattg   5220
tatgtcggcg gatgttctat atctaatttg aataaataaa cgataaccgc gttggtttta   5280
gagggcataa taaaagaaat attgttatcg tgttcgccat tagggcagta taaattgacg   5340
ttcatgttgg atattgtttc agttgcaagt tgacactggc ggcgacaagc aattctaatt   5400
ggggtaagtt ttcccgttct tttctgggtt cttccctttt gctcatcctt gctgcactac   5460
cttcaggtgc aagttgagat tcaggccacc atgggagatc ccaccccacc caagaagaag   5520
cgcaaaccgg tcgccaccat ggcctcctcc gagaacgtca tcaccgagtt catgcgcttc   5580
aaggtgcgca tggagggcac cgtgaacggc cacgagttcg agatcgaggg cgagggcgag   5640
ggccgcccct acgagggcca caacaccgtg aagctgaagg tgaccaaggg cggccccctg   5700
cccttcgcct gggacatcct gtcccccag ttccagtacg gctccaaggt gtacgtgaag   5760
caccccgccg acatccccga ctacaagaag ctgtccttcc ccgagggctt caagtgggag   5820
cgcgtgatga acttcgagga cggcggcgtg gcgaccgtga cccaggactc ctccctgcag   5880
gacggctgct tcatctacaa ggtgaagttc atcggcgtga acttcccctc cgacggcccc   5940
gtgatgcaga agaagaccat gggctgggag gcctccaccg agcgcctgta cccccgcgac   6000
ggcgtgctga agggcgagac ccacaaggcc ctgaagctga aggacggcgg ccactacctg   6060
gtggagttca agtccatcta catggccaag aagcccgtgc agctgcccgg ctactactac   6120
gtggacgcca agctggacat cacctcccac aacgaggact acaccatcgt ggagcagtac   6180
gagcgcaccg agggccgcca ccacctgttc ctgagatctc gacccaagaa aaagcggaag   6240
gtggaggacc cgtaagatcc accggatcta gataactgat cataatcagc cataccacat   6300
ttgtagaggt tttacttgct ttaaaaaacc tcccacacct ccccctgaac ctgaaacata   6360
aaatgaatgc aattgttgtt gttaacttgt ttattgcagc ttataatggt tacaaataaa   6420
gcaatagcat cacaaatttc acaaataaag catttttttc actgcattct agttgtggtt   6480
tgtccaaact catcaatgta tcttaacgcg agttaattaa ggccgctcat ttaaatctgg   6540
ccggccgcaa ccattgtggg aaccgtgcga tcaaacaaac gcgagatacc ggaagtactg   6600
```

-continued

```
aaaaacagtc gctccaggcc agtgggaaca tcgatgtttt gttttgacgg acccccttact   6660
ctcgtctcat ataaaccgaa gccagctaag atggtatact tattatcatc ttgtgatgag   6720
gatgcttcta tcaacgaaag taccggtaaa ccgcaaatgg ttatgtatta taatcaaact   6780
aaaggcggag tggacacgct agaccaaatg tgttctgtga tgacctgcag taggaagacg   6840
aataggtggc ctatggcatt attgtacgga atgataaaca ttgcctgcat aaattctttt   6900
attatataca gccataatgt cagtagcaag ggagaaaagg tccaaagtcg caaaaaattt   6960
atgagaaacc tttacatgag cctgacgtca tcgtttatgc gtaagcgttt agaagctcct   7020
actttgaaga gatatttgcg cgataaatatc tctaatattt tgccaaatga agtgcctggt   7080
acatcagatg acagtactga agagccagta atgaaaaaac gtacttactg tacttactgc   7140
ccctctaaaa taaggcgaaa ggcaaatgca tcgtgcaaaa aatgcaaaaa agttatttgt   7200
cgagagcata atattgatat gtgccaaagt tgtttctgac tgactaataa gtataatttg   7260
tttctattat gtataagtta agctaattac ttattttata atacaacatg actgtttttta   7320
aagtacaaaa taagtttatt tttgtaaaag agagaatgtt taaaagtttt gttactttat   7380
agaagaaatt ttgagttttt gtttttttt aataaataaa taaacataaa taaattgttt   7440
gttgaattta ttattagtat gtaagtgtaa atataataaa acttaatatc tattcaaatt   7500
aataaataaa cctcgatata cagaccgata aaacacatgc gtcaatttta cgcatgatta   7560
tctttaacgt acgtcacaat atgattatct ttctagggtt aaataatagt ttctaatttt   7620
tttattattc agcctgctgt cgtgaatacc gtatatctca acgctgtctg tgagattgtc   7680
gtattctagc ctttttagtt tttcgctcat cgacttgata ttgtccgaca cattttcgtc   7740
gatttgcgtt ttgatcaaag acttgagcag agacacgtta atcaactgtt caaattgatc   7800
catattaacg atatcaaccc gatgcgtata tggtgcgtaa aatatatttt ttaaccctct   7860
tatactttgc actctgcgtt aatacgcgtt cgtgtacaga cgtaatcatg ttttcttttt   7920
tggataaaac tcctactgag tttgacctca tattagaccc tcacaagttg caaaacgtgg   7980
catttttttac caatgaagaa tttaaagtta ttttaaaaaa tttcatcaca gatttaaaga   8040
agaaccaaaa attaaattat ttcaacagtt taatcgacca gttaatcaac gtgtacacag   8100
acgcgtcggc aaaaaacacg cagcccgacg tgttggctaa aattattaaa tcaacttgtg   8160
ttatagtcac ggatttgccg tccaacgtgt tcctcaaaaa gttgaagacc aacaagttta   8220
cggacactat taattatttg attttgcccc acttcatttt gtgggatcac aattttgtta   8280
tattttaaac aaagcttggc actggccgtc gttttacaac gtcgtgactg ggaaaaccct   8340
ggcgttaccc aacttaatcg ccttgcagca catccccctt tcgccagctg gcgtaatagc   8400
gaagaggccc gcaccgatcg cccttcccaa cagttgcgca gcctgaatgg cgaatggcgc   8460
ctgatgcggt attttctcct tacgcatctg tgcggtattt cacaccgcat atggtgcact   8520
ctcagtacaa tctgctctga tgccgcatag ttaagccagc cccgacaccc gccaacaccc   8580
gctgacgcgc cctgacgggc ttgtctgctc ccggcatccg cttacagaca agctgtgacc   8640
gtctccggga gctgcatgtg tcagaggttt tcaccgtcat caccgaaacg cgcgagacga   8700
aagggcctcg tgatacgcct atttttatag gttaatgtca tgataataat ggtttcttag   8760
acgtcaggtg gcacttttcg gggaaatgtg cgcggaaccc ctatttgttt atttttctaa   8820
atacattcaa atatgtatcc gctcatgaga caataaccct gataaatgct tcaataatat   8880
tgaaaaagga agagtatgag tattcaacat ttccgtgtcg cccttattcc cttttttgcg   8940
```

-continued

```
gcattttgcc ttcctgtttt tgctcaccca gaaacgctgg tgaaagtaaa agatgctgaa   9000
gatcagttgg gtgcacgagt gggttacatc gaactggatc tcaacagcgg taagatcctt   9060
gagagttttc gccccgaaga acgttttcca atgatgagca cttttaaagt tctgctatgt   9120
ggcgcggtat tatcccgtat tgacgccggg caagagcaac tcggtcgccg catacactat   9180
tctcagaatg acttggttga gtactcacca gtcacagaaa agcatcttac ggatggcatg   9240
acagtaagag aattatgcag tgctgccata accatgagtg ataacactgc ggccaactta   9300
cttctgacaa cgatcggagg accgaaggag ctaaccgctt ttttgcacaa catgggggat   9360
catgtaactc gccttgatcg ttgggaaccg gagctgaatg aagccatacc aaacgacgag   9420
cgtgacacca cgatgcctgt agcaatggca acaacgttgc gcaaactatt aactggcgaa   9480
ctacttactc tagcttcccg gcaacaatta atagactgga tggaggcgga taaagttgca   9540
ggaccacttc tgcgctcggc ccttccggct ggctggttta ttgctgataa atctggagcc   9600
ggtgagcgtg ggtctcgcgg tatcattgca gcactggggc cagatggtaa gccctcccgt   9660
atcgtagtta tctacacgac ggggagtcag gcaactatgg atgaacgaaa tagacagatc   9720
gctgagatag gtgcctcact gattaagcat tggtaactgt cagaccaagt ttactcatat   9780
atactttaga ttgatttaaa acttcatttt taatttaaaa ggatctaggt gaagatcctt   9840
tttgataatc tcatgaccaa aatcccttaa cgtgagtttt cgttccactg agcgtcagac   9900
cccgtagaaa agatcaaagg atcttcttga gatccttttt ttctgcgcgt aatctgctgc   9960
ttgcaaacaa aaaaaccacc gctaccagcg gtggtttgtt tgccggatca agagctacca  10020
actctttttc cgaaggtaac tggcttcagc agagcgcaga taccaaatac tgtccttcta  10080
gtgtagccgt agttaggcca ccacttcaag aactctgtag caccgcctac atacctcgct  10140
ctgctaatcc tgttaccagt ggctgctgcc agtggcgata agtcgtgtct taccgggttg  10200
gactcaagac gatagttacc ggataaggcg cagcggtcgg gctgaacggg gggttcgtgc  10260
acacagccca gcttggagcg aacgacctac accgaactga gatacctaca gcgtgagcat  10320
tgagaaagcg ccacgcttcc cgaagggaga aaggcggaca ggtatccggt aagcggcagg  10380
gtcggaacag gagagcgcac gagggagctt ccagggggaa acgcctggta tctttatagt  10440
cctgtcgggt ttcgccacct ctgacttgag cgtcgatttt tgtgatgctc gtcagggggg  10500
cggagcctat ggaaaaacgc cagcaacgcg gcctttttac ggttcctggc cttttgctgg  10560
ccttttgctc acatgttctt tcctgcgtta tcccctgatt ctgtggataa ccgtattacc  10620
gcctttgagt gagctgatac cgctcgccgc agccgaacga ccgagcgcag cgagtcagtg  10680
agcgaggaag cggaagagcg cccaatacgc aaaccgcctc tccccgcgcg ttggccgatt  10740
cattaatgca gctggcacga caggtttccc gactggaaag cgggcagtga gcgcaacgca  10800
attaatgtga gttagctcac tcattaggca ccccaggctt tacactttat gcttccggct  10860
cgtatgttgt gtggaattgt gagcggataa caatttcaca caggaaacag ctatgaccat  10920
gattacgaat ttcgacctgc aggcatgcaa gcttgcatgc ctgcaggtcg acgctcgcgc  10980
gacttggttt gccattcttt agcgcgcgtc gcgtcacaca gcttggccac aatgtggttt  11040
ttgtcaaacg aagattctat gacgtgttta aagtttaggt cgagtaaagc gcaaatcttt  11100
tttaacccta gaaagatagt ctgcgtaaaa ttgacgcatg cattcttgaa atattgctct  11160
ctctttctaa atagcgcgaa tccgtcgctg tgcatttagg acatctcagt cgccgcttgg  11220
agctcccgtg aggcgtgctt gtcaatgcgg taagtgtcac tgattttgaa ctataacgac  11280
cgcgtgagtc aaaatgacgc atgattatct tttacgtgac ttttaagatt taactcatac  11340
```

```
gataattata ttgttatttc atgttctact tacgtgataa cttattatat atatattttc  11400

ttgttataga tatcgtgact aatatataat aaaatgggta gttctttaga cgatgagcat  11460

atcctctctg ctcttctgca aagcgatgac gagcttgttg gtgaggattc tgacagtgaa  11520

atatcagatc acgtaagtga agatgacgtc cagagcgata cagaagaagc gtttatagat  11580

gaggtacatg aagtgcagcc aacgtcaagc ggtagtgaaa tattagacga acaaaatgtt  11640

attgaacaac caggttcttc attggcttct aacagaatct tgaccttgcc acagaggact  11700

attagaggta agaataaaca ttgttggtca acttcaaagt ccacgaggcg tagccgagtc  11760

tctgcactga acattgtcag atcggccc                                     11788
```

```
<210> SEQ ID NO 52
<211> LENGTH: 13292
<212> TYPE: DNA
<213> ORGANISM: Artificial Sequence
<220> FEATURE:
<223> OTHER INFORMATION: Synthetic construct, pLA3233-Cctra-intron-tTAV2
      construct.

<400> SEQUENCE: 52

gggcggccgt ttttcttgaa atattgctct ctctttctaa atagcgcgaa tccgtcgctg     60

tgcatttagg acatctcagt cgccgcttgg agctcccaaa cgcgccagtg gtagtacaca    120

gtactgtggg tgttcagttt gaaatcctct tgcttctcca ttgtctcggt tacctttggt    180

caaatccatg ggttctattg cctatatact cttgcgatta ccagtgattg cgctattagc    240

tattagatgg attgttggcc aaacttgtcg cttaagtggc tgggaattgt aaccgtaggc    300

ccgagtgtaa tgatccccca taaaaagttt tcgcaatgcc tttatttttt gttgcaaatc    360

tctctttatt ctgcggtatt cttcattatt gcggggatgg ggaaagtgtt tatatagaag    420

caacttacga ttgaacccaa atgcacctga caagcaaggt caaagggcca gatttttaaa    480

tatattattt agtcttagga ctctctattt gcaattaaat tactttgcta cctgagggtt    540

aaatcttccc cattgataat aataattcca ctatatgttc aattgggttt caccgcgctt    600

agttacatga cgagccctaa tgagccgtcg gtggtctata aactgtgcct tacaaatact    660

tgcaactctt ctcgttttga agtcagcaga gttattgcta attgctaatt gctaattgct    720

tttaactgat ttcttcgaaa ttggtgctat gtttatggcg ctattaacaa gtatgaatgt    780

caggtttaac caggggatgc ttaattgtgt tctcaacttc aaaggcagaa atgtttactc    840

ttgaccatgg gtttaggtat aatgttatca agctcctcga gttaacgtta cgttaacgtt    900

aacgttcgag gtcgactcta gacaccggtg ttagccgccg tactcatcga tgcccagggc    960

gtcggtgaac atctgctcga actcgaaatc ggccatatcc agggcgccgt agggggcgct   1020

atcgtgcggg gtgaatcccg gtcccgggct atcgccatcg cccagcatgt ccaggtcgaa   1080

gtcgtccagg gcatcggcgt gggccatcgc cacatcctcg ccatccaggt gcagctcatc   1140

gcccaggctc acgtcggtcg gcggggcggt cgacaggcgg cgggtgtgtc cggccggcag   1200

gaagctcagg cgcggggcgg ccaggcccgc ctcctccggg gcatcatcat ccggcagatc   1260

cagcaggccc tcgatggtgc tgccgtagtt gttcttggtg cgggcgcggc tgtaggcggg   1320

gcccgagccc gactcgcatt tcagttgctt ttccaatccg cagataatca gctccaagcc   1380

gaacaggaat gccggctcgg ctccttgatg atcgaacagc tcgattgcct gacgcagcag   1440

tgggggcatc gaatcggttg ttggggtctc gcgctcctct tttgcgactt gatgctcttg   1500

gtcctccagc acgcagccca gggtaaagtg accgacggcg ctcagagcgt agagagcatt   1560
```

ttccaggctg aagccttgct ggcacaggaa cgcgagctgg ttctccagtg tctcgtattg 1620
cttttcggtc gggcgcgtgc cgagatggac tttggcaccg tctcggtggg acagcagagc 1680
gcagcggaac gacttggcgt tattgcggag gaagtcctgc caggactcgc cttccaacgg 1740
gcaaaaatgc gtgtggtggc ggtcgagcat ctcgatggcc agggcatcca gcagcgcccg 1800
cttattcttc acgtgccagt agagggtggg ctgctccacg cccagcttct gcgccaactt 1860
gcgggtcgtc agtccctcaa tgccaacttc gttcaacagc tccaacgcgg agttgatgac 1920
tttggactta tccaggcggc tgacctatag ataccataga tgtatggatt agtatcatat 1980
acatacaaag gctatttttg ggacatatta atattaacaa tttccgtgat agttttcacc 2040
atttttgttg aatgttacgt tgaaaattta aatttgtttt aaattaattt taccagtcat 2100
gtgttcttaa aagtttttat gattgaaacg gcataaagtg gttcaaaaat ttatcaagaa 2160
aggctttcct tttttaaatc ttatcttttt ctcttaaaaa tcactagtca attcattatt 2220
aatttgttaa cttgaatttg gaatgtctat ttactttcag ataaattaaa gcaagaaact 2280
taatattcga aaaaaattga ttctaaatgg aatttcactt gatcttcatg tatgcatatc 2340
aatttttatt tacattgtat aataagtttc gagttgattg ttgtaatcca caggtgtccc 2400
agagaattaa attccaaatt acccaagttt attgaatgtt gattgtagtt tcagttgctt 2460
tgttgctgca acaatggctt gttgattgta gatattttcc ctttccttgg tttacttatt 2520
acatagactg aaaaagaggt ttactttttt gatacttatg aaaaatttct attagtgatt 2580
actaaccaat cgctatatgt ttactagaaa acaaataaac tctttacatt aacattcaat 2640
aatgtttgct ctgtaaccga caattgaagg cgttacagca acagtaatat aactagcttc 2700
ttaaccctca tctattaacc ccatcgttta aaacactatg ttaaatggtc taacaaatct 2760
agatactaat agatgtctta ttacttagca gccacagctg caacatccaa gacaattttt 2820
gaaacttctt attgagctct tggcagcaga aatgttggta tttttcacag ctttctgaaa 2880
gaccggcacc ttcctccggt tcccgtttct gaattcaaga ggatttccga cccccaatta 2940
atcccgaaac aaataaggta tattcaaaat gatggaaaag tcatggctgc tgaccttatt 3000
tttattccta ttgatagaat attattcccc ttttaaatac actgtactaa gaggtccggc 3060
tataatttta ctcacttgtc gattatccca tagaatgttg attgtagttg gttgcttttc 3120
caggtgagag ttgatcaagt cacaaaagtt agcgtgtgtt gattgtagat ttgaaggtaa 3180
aataattttt gcacccattc atcgggtaaa acgttctcca tagaatacat ttccatcgat 3240
aattgataac ttatgaattt caaagaaaaa aatatgcttt taaaattacc atggtggcta 3300
gcgcagattg tttagcttgt tcagctgcgc ttgtttattt gcttagcttt cgcttagcga 3360
cgtgttcact ttgcttgttt gaattgaatt gtcgctccgt agacgaagcg cctctattta 3420
tactccggcg ctcgttttcg agtttaccac tccctatcag tgatagagaa aagtgaaagt 3480
cgagtttacc actccctatc agtgatagag aaaagtgaaa gtcgagttta ccactcccta 3540
tcagtgatag agaaaagtga aagtcgagtt taccactccc tatcagtgat agagaaaagt 3600
gaaagtcgag tttaccactc cctatcagtg atagagaaaa gtgaaagtcg agtttaccac 3660
tccctatcag tgatagagaa aagtgaaagt cgagtttacc actccctatc agtgatagag 3720
aaaagtgaaa gtcgaaacct ggcgcgcccc ggccatcgag aaagagagag agaagagaag 3780
agagagaaca ttcgagaaag agagagagaa gagaagagag agaacatact ccctatcagt 3840
gatagagaag tccctatcag tgatagagat gtccctatca gtgatagaga gttccctatc 3900

-continued

```
agtgatagag acgtccctat cagtgataga gaagtcccta tcagtgatag agagatccct   3960
atcagtgata gagatttccc tatcagtgat agagaggtcc ctatcagtga tagagacttc   4020
cctatcagtg atagagaaat ccctatcagt gatagagaca tccctatcag tgatagagaa   4080
ctccctatca gtgatagaga cctccctatc agtgatagag atcgatgcgg ccgcatggta   4140
cccattgctt gtcatttatt aatttggatg atgtcatttg tttttaaaat tgaactggct   4200
ttacgagtag aattctacgc gtaaaacaca atcaagtatg agtcataatc tgatgtcatg   4260
ttttgtacac ggctcataac cgaactggct ttacgagtag aattctactt gtaatgcacg   4320
atcagtggat gatgtcattt gtttttcaaa tcgagatgat gtcatgtttt gcacacggct   4380
cataaactcg ctttacgagt agaattctac gtgtaacgca cgatcgattg atgagtcatt   4440
tgttttgcaa tatgatatca tacaatatga ctcatttgtt tttcaaaacc gaacttgatt   4500
tacgggtaga attctacttg taaagcacaa tcaaaaagat gatgtcattt gtttttcaaa   4560
actgaactcg ctttacgagt agaattctac gtgtaaaaca caatcaagaa atgatgtcat   4620
ttgttataaa aataaaagct gatgtcatgt tttgcacatg gctcataact aaactcgctt   4680
tacgggtaga attctacgcg taaaacatga ttgataatta aataattcat ttgcaagcta   4740
tacgttaaat caaacggacg ctcgaggttg cacaacacta ttatcgattt gcagttcggg   4800
acataaatgt ttaaatatat cgatgtcttt gtgatgcgcg cgacattttt gtaggttatt   4860
gataaaatga acggatacgt tgcccgacat tatcattaaa tccttggcgt agaatttgtc   4920
gggtccattg tccgtgtgcg ctagcatgcc cgtaacggac ctcgtacttt tggcttcaaa   4980
ggttttgcgc acagacaaaa tgtgccacac ttgcagctct gcatgtgtgc gcgttaccac   5040
aaatcccaac ggcgcagtgt acttgttgta tgcaaataaa tctcgataaa ggcgcggcgc   5100
gcgaatgcag ctgatcacgt acgctcctcg tgttccgttc aaggacggtg ttatcgacct   5160
cagattaatg tttatcggcc gactgttttc gtatccgctc accaaacgcg tttttgcatt   5220
aacattgtat gtcggcggat gttctatatc taatttgaat aaataaacga taaccgcgtt   5280
ggttttagag ggcataataa aagaaatatt gttatcgtgt tcgccattag ggcagtataa   5340
attgacgttc atgttggata ttgtttcagt tgcaagttga cactggcggc gacaagcaat   5400
tctaattggg gtaagttttc ccgttctttt ctgggttctt ccctttttgct catccttgct   5460
gcactacctt caggtgcaag ttgagattca ggccaccatg ggagatccca ccccacccaa   5520
gaagaagcgc aaaccggtcg ccaccatgga cgaggatggt tcagagggcg gccccgccct   5580
gttccagagc gacatgacct tcaaaatctt catcgacggc gaggtgaacg gccagaagtt   5640
caccatcgtg gccgacggca gcagcaagtt cccccacggc gacttcaacg tgcacgccgt   5700
gtgcgagacc ggcaagctgc ccatgagctg gaagcccatc tgccacctga tccagtacgg   5760
cgagcccttc ttcgcccgct accccaacgg catcagccac ttcgcccagg agtgcttccc   5820
cgagggcctg agcatcgacc gcaccgtgcg cttcgagaac gacggcacca tgaccagcca   5880
ccacacctac gagctggacg gcacctgcgt ggtcagccgc atcaccgtga actgcgacgg   5940
cttccagccc gacggcccca tcatgcgcga ccagctggtg gacatcctgc ccaacgagac   6000
ccacatgttc ccccacggcc ccaacgccgt gcgccagctg gccttcatcg gcttcaccac   6060
cgccgacggc ggcctgatga tgggccactt cgacagcaag atgaccttca acggcagccg   6120
cgccatcaag atccccggcc cccacttcgt gaccatcatc accaagcaga tgagggacac   6180
cagcgacaag cgcgaccacg tgtgccagcg cgaggtgacc tacgcccaca gcgtgccccg   6240
catcaccagc gccatcggta gcgacgagga ttccggactc agatctcgac ccaagaaaaa   6300
```

```
gcggaaggtg gaggacccgt aagatccacc ggatctagat aactgatcat aatcagccat   6360
accacatttg tagaggtttt acttgcttta aaaaacctcc cacacctccc cctgaacctg   6420
aaacataaaa tgaatgcaat tgttgttgtt aacttgttta ttgcagctta taatggttac   6480
aaataaagca atagcatcac aaatttcaca aataaagcat ttttttcact gcattctagt   6540
tgtggtttgt ccaaactcat caatgtatct taacgcgagt taattaacac cgaaatcgta   6600
attcacggca tcattacaaa atattttgac gttttggacc tcgtccctaa tgacaccata   6660
acggtggcct tgaagtatat ttaaccctag aaagatagtc tgcgtaaaat tgacgcatgc   6720
attcttgaaa tattgctctc tctttctaaa tagcgcgaat ccgtcgctgt gcatttagga   6780
catctcagtc gccgcttgga gctcccgtga ggcgtgcttg tcaatgcggt aagtgtcact   6840
gattttgaac tataacgacc gcgtgagtca aaatgacgca tgattatctt ttacgtgact   6900
tttaagattt aactcatacg ataattatat tgttatttca tgttctactt acgtgataac   6960
ttattatata tatattttct tgttatagat atcgtgacta atatataata aaatgggtag   7020
ttctttagac gatgagcata tcctctctgc tcttctgcaa agcgatgacg agcttgttgg   7080
tgaggattct gacagtgaaa tatcagatca cgtaagtgaa gatgacgtcc aggaaatctg   7140
gccggccgca accattgtgg gaaccgtgcg atcaaacaaa cgcgagatac cggaagtact   7200
gaaaaacagt cgctccaggc cagtgggaac atcgatgttt tgttttgacg gaccccttac   7260
tctcgtctca tataaaccga agccagctaa gatggtatac ttattatcat cttgtgatga   7320
ggatgcttct atcaacgaaa gtaccggtaa accgcaaatg gttatgtatt ataatcaaac   7380
taaaggcgga gtggacacgc tagaccaaat gtgttctgtg atgacctgca gtaggaagac   7440
gaataggtgg cctatggcat tattgtacgg aatgataaac attgcctgca taaattcttt   7500
tattatatac agccataatg tcagtagcaa gggagaaaag gtccaaagtc gcaaaaaatt   7560
tatgagaaac ctttacatga gcctgacgtc atcgtttatg cgtaagcgtt tagaagctcc   7620
tactttgaag agatatttgc gcgataatat ctctaatatt ttgccaaatg aagtgcctgg   7680
tacatcagat gacagtactg aagagccagt aatgaaaaaa cgtacttact gtacttactg   7740
cccctctaaa ataaggcgaa aggcaaatgc atcgtgcaaa aaatgcaaaa aagttatttg   7800
tcgagagcat aatattgata tgtgccaaag ttgtttctga ctgactaata agtataattt   7860
gtttctatta tgtataagtt aagctaatta cttattttat aatacaacat gactgttttt   7920
aaagtacaaa ataagtttat ttttgtaaaa gagagaatgt ttaaaagttt tgttacttta   7980
tagaagaaat tttgagtttt tgttttttttt taataaataa ataaacataa ataaattgtt   8040
tgttgaattt attattagta tgtaagtgta aatataataa aacttaatat ctattcaaat   8100
taataaataa acctcgatat acagaccgat aaaacacatg cgtcaatttt acgcatgatt   8160
atctttaacg tacgtcacaa tatgattatc tttctagggt taaataatag tttctaattt   8220
ttttattatt cagcctgctg tcgtgaatac cgtatatctc aacgctgtct gtgagattgt   8280
cgtattctag cctttttagt ttttcgctca tcgacttgat attgtccgac acattttcgt   8340
cgatttgcgt tttgatcaaa gacttgagca gagacacgtt aatcaactgt tcaaattgat   8400
ccatattaac gatatcaacc cgatgcgtat atggtgcgta aaatatattt tttaaccctc   8460
ttatactttg cactctgcgt taatacgcgt tcgtgtacag acgtaatcat gttttctttt   8520
ttggataaaa ctcctactga gtttgacctc atattagacc ctcacaagtt gcaaaacgtg   8580
gcattttttta ccaatgaaga atttaaagtt attttaaaaa atttcatcac agatttaaag   8640
```

-continued

```
aagaaccaaa aattaaatta tttcaacagt ttaatcgacc agttaatcaa cgtgtacaca   8700
gacgcgtcgg caaaaaacac gcagcccgac gtgttggcta aaattattaa atcaacttgt   8760
gttatagtca cggatttgcc gtccaacgtg ttcctcaaaa agttgaagac caacaagttt   8820
acggacacta ttaattattt gattttgccc cacttcattt tgtgggatca caattttgtt   8880
atattttaaa caaagcttgg cactggccgt cgttttacaa cgtcgtgact gggaaaaccc   8940
tggcgttacc caacttaatc gccttgcagc acatccccct ttcgccagct ggcgtaatag   9000
cgaagaggcc cgcaccgatc gcccttccca acagttgcgc agcctgaatg gcgaatggcg   9060
cctgatgcgg tattttctcc ttacgcatct gtgcggtatt tcacaccgca tatggtgcac   9120
tctcagtaca atctgctctg atgccgcata gttaagccag ccccgacacc cgccaacacc   9180
cgctgacgcg ccctgacggg cttgtctgct cccggcatcc gcttacagac aagctgtgac   9240
cgtctccggg agctgcatgt gtcagaggtt ttcaccgtca tcaccgaaac gcgcgagacg   9300
aaagggcctc gtgatacgcc tatttttata ggttaatgtc atgataataa tggtttctta   9360
gacgtcaggt ggcacttttc ggggaaatgt gcgcggaacc cctatttgtt tatttttcta   9420
aatacattca aatatgtatc cgctcatgag acaataaccc tgataaatgc ttcaataata   9480
ttgaaaaagg aagagtatga gtattcaaca tttccgtgtc gcccttattc ccttttttgc   9540
ggcattttgc cttcctgttt ttgctcaccc agaaacgctg gtgaaagtaa aagatgctga   9600
agatcagttg ggtgcacgag tgggttacat cgaactggat ctcaacagcg gtaagatcct   9660
tgagagtttt cgccccgaag aacgttttcc aatgatgagc acttttaaag ttctgctatg   9720
tggcgcggta ttatcccgta ttgacgccgg gcaagagcaa ctcggtcgcc gcatacacta   9780
ttctcagaat gacttggttg agtactcacc agtcacagaa aagcatctta cggatggcat   9840
gacagtaaga gaattatgca gtgctgccat aaccatgagt gataacactg cggccaactt   9900
acttctgaca acgatcggag gaccgaagga gctaaccgct tttttgcaca acatgggga    9960
tcatgtaact cgccttgatc gttgggaacc ggagctgaat gaagccatac caaacgacga  10020
gcgtgacacc acgatgcctg tagcaatggc aacaacgttg cgcaaactat taactggcga  10080
actacttact ctagcttccc ggcaacaatt aatagactgg atggaggcgg ataaagttgc  10140
aggaccactt ctgcgctcgg cccttccggc tggctggttt attgctgata aatctggagc  10200
cggtgagcgt gggtctcgcg gtatcattgc agcactgggg ccagatggta agccctcccg  10260
tatcgtagtt atctacacga cggggagtca ggcaactatg gatgaacgaa atagacagat  10320
cgctgagata ggtgcctcac tgattaagca ttggtaactg tcagaccaag tttactcata  10380
tatactttag attgatttaa aacttcattt ttaatttaaa aggatctagg tgaagatcct  10440
ttttgataat ctcatgacca aaatccctta acgtgagttt tcgttccact gagcgtcaga  10500
ccccgtagaa aagatcaaag gatcttcttg agatcctttt tttctgcgcg taatctgctg  10560
cttgcaaaca aaaaaaccac cgctaccagc ggtggtttgt ttgccggatc aagagctacc  10620
aactcttttt ccgaaggtaa ctggcttcag cagagcgcag ataccaaata ctgtccttct  10680
agtgtagccg tagttaggcc accacttcaa gaactctgta gcaccgccta catacctcgc  10740
tctgctaatc ctgttaccag tggctgctgc cagtggcgat aagtcgtgtc ttaccgggtt  10800
ggactcaaga cgatagttac cggataaggc gcagcggtcg ggctgaacgg ggggttcgtg  10860
cacacagccc agcttggagc gaacgaccta caccgaactg agatacctac agcgtgagca  10920
ttgagaaagc gccacgcttc ccgaagggag aaaggcggac aggtatccgg taagcggcag  10980
ggtcggaaca ggagagcgca cgagggagct tccaggggga aacgcctggt atctttatag  11040
```

```
tcctgtcggg tttcgccacc tctgacttga gcgtcgattt ttgtgatgct cgtcaggggg  11100
gcggagccta tggaaaaacg ccagcaacgc ggccttttta cggttcctgg ccttttgctg  11160
gccttttgct cacatgttct ttcctgcgtt atcccctgat tctgtggata accgtattac  11220
cgcctttgag tgagctgata ccgctcgccg cagccgaacg accgagcgca gcgagtcagt  11280
gagcgaggaa gcggaagagc gcccaatacg caaaccgcct ctccccgcgc gttggccgat  11340
tcattaatgc agctggcacg acaggtttcc cgactggaaa gcgggcagtg agcgcaacgc  11400
aattaatgtg agttagctca ctcattaggc accccaggct ttacacttta tgcttccggc  11460
tcgtatgttg tgtggaattg tgagcggata acaatttcac acaggaaaca gctatgacca  11520
tgattacgaa tttcgacctg caggcatgca agcttgcatg cctgcaggtc gacgctcgcg  11580
cgacttggtt tgccattctt tagcgcgcgt cgcgtcacac agcttggcca caatgtggtt  11640
tttgtcaaac gaagattcta tgacgtgttt aaagtttagg tcgagtaaag cgcaaatctt  11700
ttttaaccct agaaagatag tctgcgtaaa attgacgcat gcattcttga aatattgctc  11760
tctctttcta aatagcgcga atccgtcgct gtgcatttag gacatctcag tcgccgcttg  11820
gagctcccgt gaggcgtgct tgtcaatgcg gtaagtgtca ctgattttga actataacga  11880
ccgcgtgagt caaaatgacg catgattatc ttttacgtga cttttaagat ttaactcata  11940
cgataattat attgttattt catgttctac ttacgtgata acttattata tatatatttt  12000
cttgttatag atatcgtgac taatatataa taaaatgggt agttctttag acgatgagca  12060
tatcctctct gctcttctgc aaagcgatga cgagcttgtt ggtgaggatt ctgacagtga  12120
aatatcagat cacgtaagtg aagatgacgt ccagagcgat acagaagaag cgtttataga  12180
tgaggtacat gaagtgcagc caacgtcaag cggtagtgaa atattagacg aacaaaatgt  12240
tattgaacaa ccaggttctt cattggcttc taacagaatc ttgaccttgc cacagaggac  12300
tattagaggt aagaataaac attgttggtc aacttcaaag tccacgaggc gtagccgagt  12360
ctctgcactg aacattgtca gatcggcccg gcggagtgga cacgctagac caaatgtgtt  12420
ctgtgatgac ctgcagtagg aagacgaata ggtggcctat ggcattattg tacggaatga  12480
taaacattgc ctgcataaat tcttttatta tatacagcca taatgtcagt agcaagggag  12540
aaaaggtcca aagtcgcaaa aaatttatga gaaacccttta catgagcctg acgtcatcgt  12600
ttatgcgtaa gcgtttagaa gctcctactt tgaagagata tttgcgcgat aatatctcta  12660
atattttgcc aaatgaagtg cctggtacat cagatgacag tactgaagag ccagtaatga  12720
aaaaacgtac ttactgtact tactgcccct ctaaaataag gcgaaaggca aatgcatcgt  12780
gcaaaaaatg caaaaaagtt atttgtcgag agcataatat tgatatgtgc caaagttgtt  12840
tctgactgac taataagtat aatttgtttc tattatgtat aagttaagct aattacttat  12900
tttataatac aacatgactg tttttaaagt acaaaataag tttatttttg taaaagagag  12960
aatgtttaaa agttttgtta ctttatagaa gaaattttga gtttttgttt tttttaata  13020
aataaataaa cataaataaa ttgtttgttg aatttattat tagtatgtaa gtgtaaatat  13080
aataaaactt aatatctatt caaattaata aataaacctc gatatacaga ccgataaaac  13140
acatgcgtca attttacgca tgattatctt taacgtacgt cacaatatga ttatctttct  13200
agggttaaaa tgaatgtaag cactttatta acgaaatctt tgggaatatt tcgctcatca  13260
gcattttatt tgagcaggag tccgagatgc cc                                13292
```

<210> SEQ ID NO 53

<211> LENGTH: 14713
<212> TYPE: DNA
<213> ORGANISM: Artificial Sequence
<220> FEATURE:
<223> OTHER INFORMATION: Synthetic construct, pLA3014-Cctra-intron-Ubiquitin-reaperKR construct.

<400> SEQUENCE: 53
cgcgccggac gcggcaagtc tgcgagctta tatttacgtg gatctccggt gtgtccatga 60
ttcggcatca tatcataaac gacgaattcc aataaaaact ttgcttgttg ataacacctg 120
atgttcagag atgcccgata aaatcacagc tgttctggtt cacagtcacc agaaataaaa 180
aatattggaa ttgagatgta cacaattaac gatatttata aatatcttcc gatagtctat 240
cgtccggtta atcaaaataa agtgcgacga attaacatat tttcaaaatt aagacgcttt 300
gatagatgta tttgtataga gatagaaatt aaggttaaaa taacataaat gccaaagttt 360
agagcactat tcaataattc tcttgatttc aaattgaaat aatacacaat ataacatttt 420
ctaacactac aaagtcacga tattcttcca ccaaccgata gtatcgcaca cttgccattc 480
gcctcatcac gcacacgccc gcttcacaat tcaaacgaac ggcattttat tttcacagga 540
tcccgggagt cgtgaatgtt ttacccaata tcgactttca ttgttaactg accaaaattg 600
taatctgttc tgttagttgt cgagtgcctg tgccgcgatc gctatgggca tatgttgcca 660
aactctaaac caaatactca ttctgatgtt ttaaatgatt tgccctccca tatgtccttc 720
cgagtgagag acacaaaaaa ttccaacaca ctattgcaat gaaaataaat ttcctttatt 780
agccagaagt cagatgctca aggggcttca tgatgtcccc ataatttttg gcagagggaa 840
aaagatctca gtggtatttg tgagccaggg cattggccac accagccacc accttctgat 900
aggcagcctg cacctgagga gtgaattctt tgccaaaatg atgagacagc acaacaacca 960
gcacgttgcc caggagctgt aggaaagaga agaaggcatg aacatggtta gcagaggggc 1020
ccggtttgga ctcagagtat tttatcctca tctcaaacag tgtatatcat tgtaaccata 1080
aagagaaagg caggatgatg accagggtgt agttgtttct accaataaga atatttccac 1140
gccagccaga atttatatgc agaaatattc taccttatca tttaattata acaattgttc 1200
tctaaaactg tgctgaagta caatataata taccctgatt gccttgaaaa aaaagtgatt 1260
agagaaagta cttacaatct gacaaataaa caaaagtgaa tttaaaaatt cgttacaaat 1320
gcaagctaaa gtttaacgaa aaagttacag aaaatgaaaa gaaaataaga ggagacaatg 1380
gttgtcaaca gagtagaaag tgaaagaaac aaaattatca tgagggtcca tggtgataca 1440
agggacatct tcccattcta aacaacaccc tgaaaacttt gccccctcca tataacatga 1500
attttacaat agcgaaaaag aaagaacaat caagggtccc caaactcacc ctgaagttct 1560
cagctctaga cgcgtttcac tacccaccgt actcgtcaat tccaagggca tcggtaaaca 1620
tctgctcaaa ctcgaagtcg gccatatcca gagcgccgta gggggcggag tcgtgggggg 1680
taaatcccgg acccggggaa tccccgtccc ccaacatgtc cagatcgaaa tcgtctagcg 1740
cgtcggcatg cgccatcgcc acgtcctcgc cgtctaagtg gagctcgtcc cccaggctga 1800
catcggtcgg gggggccgtc gacagtctgc gcgtgtgtcc cgcggggaga aaggacaggc 1860
gcggagccgc cagccccgcc tcttcggggg cgtcgtcgtc cgggagatcg agcaggccct 1920
cgatggtaga cccgtaattg tttttcgtac gcgcgcggct gtacgcggac ccactttcac 1980
atttaagttg tttttctaat ccgcatatga tcaattcaag gccgaataag aaggctggct 2040
ctgcaccttg gtgatcaaat aattcgatag cttgtcgtaa taatggcggc atactatcag 2100

-continued tagtaggtgt ttccctttct tctttagcga cttgatgctc ttgatcttcc aatacgcaac 2160
ctaaagtaaa atgccccaca gcgctgagtg catataatgc attctctagt gaaaaacctt 2220
gttggcataa aaaggctaat tgattttcga gagtttcata ctgtttttct gtaggccgtg 2280
tacctaaatg tacttttgct ccatcgcgat gacttagtaa agcacatcta aaacttttag 2340
cgttattacg taaaaaatct tgccagcttt ccccttctaa agggcaaaag tgagtatggt 2400
gcctatctaa catctcaatg gctaaggcgt cgagcaaagc ccgcttattt tttacatgcc 2460
aatacaatgt aggctgctct acacctagct tctgggcgag tttacgggtt gttaaacctt 2520
cgattccgac ctcattaagc agctctaatg cgctgttaat cactttactt ttatctaatc 2580
tcaattccat ggtggcaacc tgcaaggcga atgaataaac aagattgtgg cgaacagtgt 2640
aatgcgaaga acccacctct gctccaattc ccaattccct attcagctcg agcggggatc 2700
cccgggtacc gagctcgaat tcggggccgc ggaggctgga tcggtcccgg tgtcttctat 2760
ggaggtcaaa acagcgtgga tggcgtctcc aggcgatctg acggttcact aaacgagctc 2820
tgcttatata ggcctcccac cgtacacgcc tacctcgacc cgggtaccga gctcgacttt 2880
cacttttctc tatcactgat agggagtggt aaactcgact ttcacttttc tctatcactg 2940
atagggagtg gtaaactcga ctttcacttt tctctatcac tgatagggag tggtaaactc 3000
gactttcact tttctctatc actgataggg agtggtaaac tcgactttca cttttctcta 3060
tcactgatag ggagtggtaa actcgacttt cacttttctc tatcactgat agggagtggt 3120
aaactcgact ttcacttttc tctatcactg atagggagtg gtaaactcga aatgtcgact 3180
atgcggaccg agcgccggag tataaataga ggcgcttcgt ctacggagcg acaattcaat 3240
tcaaacaagc aaagtgaaca cgtcgctaag cgaaagctaa gcaaataaac aagcgcagct 3300
gaacaagcta aacaatctgc gctagccacc atggttgtta ttaaacgtag atttggtaat 3360
tttaaaagca tatttttttc tttgaaattc ataagttatc aattatcgat ggaaatgtat 3420
tctatggaga acgttttacc cgatgaatgg gtgcaaaaat tattttacct tcaaatctac 3480
aatcaacaca cgctaacttt tgtgacttga tcaactctca cctggaaaag caaccaacta 3540
caatcaacat tctatgggat aatcgacaag tgagtaaaat tatagccgga cctcttagta 3600
cagtgtattt aaaaggggaa taatattcta tcaataggaa taaaaataag gtcagcagcc 3660
atgacttttc catcattttg aatatacctt atttgtttcg ggattaattg ggggtcggaa 3720
atcctcttga attcagaaac gggaaccgga ggaaggtgcc ggtctttcag aaagctgtga 3780
aaaataccaa catttctgct gccaagagct caataagaag tttcaaaaat tgtcttggat 3840
gttgcagctg tggctgctaa gtaataagac atctattagt atctagattt gttagaccat 3900
ttaacatagt gttttaaacg atggggttaa tagatgaggg ttaagaagct agttatatta 3960
ctgttgctgt aacgccttca attgtcggtt acagagcaaa cattattgaa tgttaatgta 4020
aagagtttat ttgttttcta gtaaacatat agcgattggt tagtaatcac taatagaaat 4080
ttttcataag tatcaaaaaa gtaaacctct ttttcagtct atgtaataag taaaccaagg 4140
aaagggaaaa tatctacaat caacaagcca ttgttgcagc aacaaagcaa ctgaaactac 4200
aatcaacatt caataaactt gggtaatttg gaatttaatt ctctgggaca cctgtggatt 4260
acaacaatca actcgaaact tattatacaa tgtaaataaa aattgatatg catacatgaa 4320
gatcaagtga aattccattt agaatcaatt tttttcgaat attaagtttc ttgctttaat 4380
ttatctgaaa gtaaatagac attccaaatt caagttaaca aattaataat gaattgacta 4440
gtgattttta agagaaaaag ataagattta aaaaaggaaa gcctttcttg ataaattttt 4500

-continued gaaccacttt atgccgtttc aatcataaaa acttttaaga acacatgact ggtaaaatta 4560
atttaaaaca aatttaaatt ttcaacgtaa cattcaacaa aaatggtgaa aactatcacg 4620
gaaattgtta atattaatat gtcccaaaaa tagcctttgt atgtatatga tactaatcca 4680
tacatctatg gtatctatag gtgaaggctc aaagcctctg atgcagatct ttgtgaagac 4740
tttgaccgga aagaccatca ccctcgaggt agagccatcg gacaccattg agaatgtaaa 4800
ggccaagatt caggataagg agggaatccc cccagatcag cagcgtctga tcttcgctgg 4860
caagcaactg gaagacggac gcaccctgtc cgattacaac atccagaagg agtccaccct 4920
tcacttggtc cttcgtctcc gtggtggcgc cgtggccttc tacatcccgg atcaggccac 4980
cctgctgcgc gaggccgagc agcgcgagca gcagatcctg cgcctgcgcg agagccagtg 5040
gcgcttcctg gccaccgtgg tgctggagac cctgcgccag tacaccagct gccacccgcg 5100
caccggccgc cgcagcggcc gttaccgccg tccgagccag taacaccggt gatcataatc 5160
agccatacca catttgtaga ggttttactt gctttaaaaa acctcccaca cctccccctg 5220
aacctgaaac ataaaatgaa tgcaattgtt gttgttaact tgtttattgc agcttataat 5280
ggttacaaat aaagcaatag catcacaaat ttcacaaata aagcattttt ttcactgcat 5340
tctagttgtg gtttgtccaa actcatcaat gtatcttaac gcgagtttaa acgcgtccgc 5400
atacgtccgc tcacgttaag ttccgcagag agaagttgtt gaaaacataa acagaatcac 5460
ttgttgcact ctttgagaaa actggggcta ttgcggaaaa aaccaactaa aaatattgca 5520
ggttaggggt actacgctcg attggcgtac ggccaccact tttgcgactt cactgttaac 5580
cgctaccttc atagagactt ttacccgata aatgttatgt agtttgactt tctctgttaa 5640
tcacaagaaa aaatattgtg gaaattaaaa ttatctcaaa ctcaataagg aaataataat 5700
atatacacct atgttttata gaagtcaaca gtaaataagt tatttggaaa accattgtag 5760
ccgtttaaat aaatctcctt gagtgtgttt taaataacgg tcattaagta tattacttgg 5820
ccctctgaat ttcttgaatt acaccatttt ttgaaataaa tcaatccaaa agactacttt 5880
ttggtggcaa atgaactgca taaaaagtaa caaaagaaat atgtttttga aataacagta 5940
tagctgaagt gtattaaaaa ataccgtcat atgagcgacc cgctgttacc gcttcgctgc 6000
gaatgacaaa acgggctgag caagaaaatg gcgtagaagg cgacgaaaat tcgtttcact 6060
cgtgaagaaa acctcgataa ctgaggaata cagctgggat ttaaagagca tattcgaact 6120
acaagcagag atgtttcctg gtggaaacgg aaacgccgat ttgggctaca acaagcatgc 6180
ccacgtccat ggacttggac aacatggcca tgggcacaac cataatcaca atcagttcct 6240
gcgcagcccc caccaccccc cacacatttt tcactgccct ccgggggcgg tcagggcatg 6300
gtgacgccca tggtagccgc cggcctgccg ctcgccatgc agggtggcgt tggcatcgat 6360
tggcgcagct cgcccagcaa tggattaatt aactcgcgtt aagatacatt gatgagtttg 6420
gacaaaccac aactagaatg cagtgaaaaa aatgctttat ttgtgaaatt tgtgatgcta 6480
ttgctttatt tgtaaccatt ataagctgca ataaacaagt taacaacaac aattgcattc 6540
attttatgtt tcaggttcag ggggaggtgt gggaggtttt ttaaagcaag taaaacctct 6600
acaaatgtgg tatggctgat tatgatcagt tatctagatc cggtggatct tacgggtcct 6660
ccaccttccg ctttttcttg ggtcgagatc tcaggaacag gtggtggcgg ccctcggtgc 6720
gctcgtactg ctccacgatg gtgtagtcct cgttgtggga ggtgatgtcc agcttggcgt 6780
ccacgtagta gtagccgggc agctgcacgg gcttcttggc catgtagatg gacttgaact 6840

```
ccaccaggta gtggccgccg tccttcagct tcagggcctt gtgggtctcg cccttcagca   6900
cgccgtcgcg gggtacaggg cgctcggtgg aggcctccca gcccatggtc ttcttctgca   6960
tcacggggcc gtcggagggg aagttcacgc cgatgaactt caccttgtag atgaagcagc   7020
cgtcctgcag ggaggagtcc tgggtcacgg tcgccacgcc gccgtcctcg aagttcatca   7080
cgcgctccca cttgaagccc tcggggaagg acagcttctt gtagtcgggg atgtcggcgg   7140
ggtgcttcac gtacaccttg gagccgtact ggaactgggg ggacaggatg tcccaggcga   7200
agggcagggg gccgcccttg gtcaccttca gcttcacggt gttgtggccc tcgtaggggc   7260
ggccctcgcc ctcgccctcg atctcgaact cgtggccgtt cacggtgccc tccatgcgca   7320
ccttgaagcg catgaactcg gtgatgacgt tctcggagga ggccatggtg gcgaccggtt   7380
tgcgcttctt cttgggtggg gtgggatccc cgatctgcat tttggattat tctgcgggtc   7440
aaaatagaga tgtggaaaat tagtacgaaa tcaaatgagt ttcgttgaaa ttacaaaact   7500
attgaaacta acttcctggc tggggaataa aaatgggaaa cttatttatc gacgccaact   7560
ttgttgagaa accctatta accctctacg aatattggaa caaaggaaag cgaagaaaca   7620
ggaacaaagg tagttgagaa acctgttccg ttgctcgtca tcgttttcat aatgcgagtg   7680
tgtgcatgta tatatacaca gctgaaacgc atgcatacac attattttgt gtgtatatgg   7740
tgacgtcaca actactaagc aataagaaat tttccagacg tggctttcgt ttcaagcaac   7800
ctactctatt tcagctaaaa ataagtggat ttcgttggta aaatacttca attaagcaaa   7860
gaactaacta actaataaca tgcacacaaa tgctcgagtg cgttcgtgat ttctcgaatt   7920
ttcaaatgcg tcactgcgaa tttcacaatt tgccaataaa tcttggcgaa aatcaacacg   7980
caagttttat ttatagattt gtttgcgttt tgatgccaat tgattgggaa aacaagatgc   8040
gtggctgcca atttcttatt ttgtaattac gtagagcgtt gaataaaaaa aaaatggccg   8100
aacaaagacc ttgaaatgca gtttttcttg aaattactca acgtcttgtt gctcttatta   8160
ctaattggta acagcgagtt aaaaacttac gtttcttgtg actttcgaga atgttctttt   8220
aattgtactt taatcaccaa caattaagta taaatttttc gctgattgcg ctttactttc   8280
tgcttgtact tgctgctgca aatgtcaatt ggttttgaag gcgaccgttc gcgaacgctg   8340
tttatatacc ttcggtgtcc gttgaaaatc actaaaaaat accgtagtgt tcgtaacact   8400
ttagtacaga gaaaaaaaat tgtgccgaaa tgtttttgat acgtacgaat accttgtatt   8460
aaaatttttt atgatttctg tgtatcactt ttttttgtg tttttcgttt aaactcacca   8520
cagtacaaaa caataaaata tttttaagac aatttcaaat tgagaccttt ctcgtactga   8580
cttgaccggc tgaatgagga tttctaccta gacgacctac ttcttaccat gacattgaat   8640
gcaatgccac ctttgatcta aacttacaaa agtccaaggc ttgttaggat tggtgtttat   8700
ttagtttgct tttgaaatag cactgtcttc tctaccggct ataattttga aactcgcagc   8760
ttgactggaa atttaaaaag taattctgtg taggtaaagg gtgttttaaa agtgtgatgt   8820
gttgagcgtt gcggcaacga ctgctattta tgtatatatt ttcaaaactt attgtttttg   8880
aagtgtttta aatggagcta tctggcaacg ctgcgcataa tcttacacaa gcttttctta   8940
atccattttt aagtgaaatt tgtttttact ctttcggcaa ataattgtta aatcgcttta   9000
agtgggctta catctggata agtaatgaaa acctgcatat tataatatta aaacatataa   9060
tccactgtgc tttccccgtg tgtggccata tacctaaaaa agtttatttt cgcagagccc   9120
cgcacggtca cactacggtt cggcgatttt cgattttgga cagtactgat tgcaagcgca   9180
ccgaaagcaa aatggagctg gagattttga acgcgaagaa cagcaagccg tacggcaagg   9240
```

```
tgaaggtgcc ctccggcgcc acgcccatcg gcgatctgcg cgccctaatt cacaagaccc   9300
tgaagcagac cccacacgcg aatcgccagt cgcttcgtct ggaactgaag ggcaaaagcc   9360
tgaaagatac ggacacattg gaatctctgt cgctgcgttc cggcgacaag atcggggtac   9420
catgcggccg ctcatttaaa tctggccggc ctggccgatc tgacaatgtt cagtgcagag   9480
actcggctac gcctcgtgga ctttgaagtt gaccaacaat gtttattctt acctctaata   9540
gtcctctgtg gcaaggtcaa gattctgtta gaagccaatg aagaacctgg ttgttcaata   9600
acattttgtt cgtctaatat ttcactaccg cttgacgttg gctgcacttc atgtacctca   9660
tctataaacg cttcttctgt atcgctctgg acgtcatctt cacttacgtg atctgatatt   9720
tcactgtcag aatcctcacc aacaagctcg tcatcgcttt gcagaagagc agagaggata   9780
tgctcatcgt ctaaagaact acccatttta ttatatatta gtcacgatat ctataacaag   9840
aaaatatata tataataagt tatcacgtaa gtagaacatg aaataacaat ataattatcg   9900
tatgagttaa atcttaaaag tcacgtaaaa gataatcatg cgtcattttg actcacgcgg   9960
tcgttatagt tcaaaatcag tgacacttac cgcattgaca agcacgcctc acgggagctc  10020
caagcggcga ctgagatgtc ctaaatgcac agcgacggat tcgcgctatt tagaaagaga  10080
gagcaatatt tcaagaatgc atgcgtcaat tttacgcaga ctatctttct agggttaaaa  10140
aagatttgcg ctttactcga cctaaacttt aaacacgtca tagaatcttc gtttgacaaa  10200
aaccacattg tggccaagct gtgtgacgcg acgcgcgcta aagaatggca aaccaagtcg  10260
cgcgagcgtc gacctgcagg catgcaagct tgcatgcctg caggtcgaaa ttcgtaatca  10320
tggtcatagc tgtttcctgt gtgaaattgt tatccgctca caattccaca caacatacga  10380
gccggaagca taaagtgtaa agcctggggt gcctaatgag tgagctaact cacattaatt  10440
gcgttgcgct cactgcccgc tttccagtcg ggaaacctgt cgtgccagct gcattaatga  10500
atcggccaac gcgcggggag aggcggtttg cgtattgggc gctcttccgc ttcctcgctc  10560
actgactcgc tgcgctcggt cgttcggctg cggcgagcgg tatcagctca ctcaaaggcg  10620
gtaatacggt tatccacaga atcaggggat aacgcaggaa agaacatgtg agcaaaaggc  10680
cagcaaaagg ccaggaaccg taaaaaggcc gcgttgctgg cgtttttcca taggctccgc  10740
ccccctgacg agcatcacaa aaatcgacgc tcaagtcaga ggtggcgaaa cccgacagga  10800
ctataaagat accaggcgtt tccccctgga agctccctcg tgcgctctcc tgttccgacc  10860
ctgccgctta ccggatacct gtccgccttt ctcccttcgg gaagcgtggc gctttctcaa  10920
tgctcacgct gtaggtatct cagttcggtg taggtcgttc gctccaagct gggctgtgtg  10980
cacgaacccc ccgttcagcc cgaccgctgc gccttatccg gtaactatcg tcttgagtcc  11040
aacccggtaa gacacgactt atcgccactg gcagcagcca ctggtaacag gattagcaga  11100
gcgaggtatg taggcggtgc tacagagttc ttgaagtggt ggcctaacta cggctacact  11160
agaaggacag tatttggtat ctgcgctctg ctgaagccag ttaccttcgg aaaaagagtt  11220
ggtagctctt gatccggcaa acaaaccacc gctggtagcg gtggtttttt tgtttgcaag  11280
cagcagatta cgcgcagaaa aaaaggatct caagaagatc ctttgatctt ttctacgggg  11340
tctgacgctc agtggaacga aaactcacgt taagggattt tggtcatgag attatcaaaa  11400
aggatcttca cctagatcct tttaaattaa aaatgaagtt ttaaatcaat ctaaagtata  11460
tatgagtaaa cttggtctga cagttaccaa tgcttaatca gtgaggcacc tatctcagcg  11520
atctgtctat ttcgttcatc catagttgcc tgactccccg tcgtgtagat aactacgata  11580
```

cgggagggct taccatctgg ccccagtgct gcaatgatac cgcgagaccc acgctcaccg 11640
gctccagatt tatcagcaat aaaccagcca gccggaaggg ccgagcgcag aagtggtcct 11700
gcaactttat ccgcctccat ccagtctatt aattgttgcc gggaagctag agtaagtagt 11760
tcgccagtta atagtttgcg caacgttgtt gccattgcta caggcatcgt ggtgtcacgc 11820
tcgtcgtttg gtatggcttc attcagctcc ggttcccaac gatcaaggcg agttacatga 11880
tcccccatgt tgtgcaaaaa agcggttagc tccttcggtc ctccgatcgt tgtcagaagt 11940
aagttggccg cagtgttatc actcatggtt atggcagcac tgcataattc tcttactgtc 12000
atgccatccg taagatgctt ttctgtgact ggtgagtact caaccaagtc attctgagaa 12060
tagtgtatgc ggcgaccgag ttgctcttgc ccggcgtcaa tacgggataa taccgcgcca 12120
catagcagaa ctttaaaagt gctcatcatt ggaaaacgtt cttcggggcg aaaactctca 12180
aggatcttac cgctgttgag atccagttcg atgtaaccca ctcgtgcacc caactgatct 12240
tcagcatctt ttactttcac cagcgtttct gggtgagcaa aaacaggaag gcaaaatgcc 12300
gcaaaaaagg gaataagggc gacacggaaa tgttgaatac tcatactctt cctttttcaa 12360
tattattgaa gcatttatca gggttattgt ctcatgagcg gatacatatt tgaatgtatt 12420
tagaaaaata aacaaatagg ggttccgcgc acatttcccc gaaaagtgcc acctgacgtc 12480
taagaaacca ttattatcat gacattaacc tataaaaata ggcgtatcac gaggcccttt 12540
cgtctcgcgc gtttcggtga tgacggtgaa aacctctgac acatgcagct cccggagacg 12600
gtcacagctt gtctgtaagc ggatgccggg agcagacaag cccgtcaggg cgcgtcagcg 12660
ggtgttggcg ggtgtcgggg ctggcttaac tatgcggcat cagagcagat tgtactgaga 12720
gtgcaccata tatgcggtgt gaaataccgc acagatgcgt aaggagaaaa taccgcatca 12780
ggcgccattc gccattcagg ctgcgcaact gttgggaagg gcgatcggtg cgggcctctt 12840
cgctattacg ccagctggcg aaagggggat gtgctgcaag gcgattaagt tgggtaacgc 12900
cagggttttc ccagtcacga cgttgtaaaa cgacggccag tgccaagctt tgtttaaaat 12960
ataacaaaat tgtgatccca caaaatgaag tggggcaaaa tcaaataatt aatagtgtcc 13020
gtaaacttgt tggtcttcaa ctttttgagg aacacgttgg acggcaaatc cgtgactata 13080
acacaagttg atttaataat tttagccaac acgtcgggct gcgtgttttt tgccgacgcg 13140
tctgtgtaca cgttgattaa ctggtcgatt aaactgttga aataatttaa tttttggttc 13200
ttctttaaat ctgtgatgaa attttttaaa ataactttaa attcttcatt ggtaaaaaat 13260
gccacgtttt gcaacttgtg agggtctaat atgaggtcaa actcagtagg agttttatcc 13320
aaaaaagaaa acatgattac gtctgtacac gaacgcgtat taacgcagag tgcaaagtat 13380
aagagggtta aaaaatatat tttacgcacc atatacgcat cgggttgata tcgttaatat 13440
ggatcaattt gaacagttga ttaacgtgtc tctgctcaag tctttgatca aaacgcaaat 13500
cgacgaaaat gtgtcggaca atatcaagtc gatgagcgaa aaactaaaaa ggctagaata 13560
cgacaatctc acagacagcg ttgagatata cggtattcac gacagcaggc tgaataataa 13620
aaaaattaga aactattatt taaccctaga aagataatca tattgtgacg tacgttaaag 13680
ataatcatgc gtaaaattga cgcatgtgtt ttatcggtct gtatatcgag gtttatttat 13740
taatttgaat agatattaag ttttattata tttacactta catactaata ataaattcaa 13800
caaacaattt atttatgttt atttatttat taaaaaaaaa caaaaactca aaatttcttc 13860
tataaagtaa caaaactttt aaacattctc tcttttacaa aaataaactt attttgtact 13920
ttaaaaacag tcatgttgta ttataaaata agtaattagc ttaacttata cataatagaa 13980
acaaattata cttattagtc agtcagaaac aactttggca catatcaata ttatgctctc 14040
gacaaataac ttttttgcat tttttgcacg atgcatttgc ctttcgcctt attttagagg 14100
ggcagtaagt acagtaagta cgttttttca ttactggctc ttcagtactg tcatctgatg 14160
taccaggcac ttcatttggc aaaatattag agatattatc gcgcaaatat ctcttcaaag 14220
taggagcttc taaacgctta cgcataaacg atgacgtcag gctcatgtaa aggtttctca 14280
taaatttttt gcgactttgg accttttctc ccttgctact gacattatgg ctgtatataa 14340
taaaagaatt tatgcaggca atgtttatca ttccgtacaa taatgccata ggccacctat 14400
tcgtcttcct actgcaggtc atcacagaac acatttggtc tagcgtgtcc actccgcctt 14460
tagtttgatt ataatacata accatttgcg gtttaccggt actttcgttg atagaagcat 14520
cctcatcaca agatgataat aagtatacca tcttagctgg cttcggttta tatgagacga 14580
gagtaagggg tccgtcaaaa caaaacatcg atgttcccac tggcctggag cgactgtttt 14640
tcagtacttc cggtatctcg cgtttgtttg atcgcacggt tcccacaatg gttgcggcca 14700
gcccgggcta tgg 14713

<210> SEQ ID NO 54
<211> LENGTH: 15848
<212> TYPE: DNA
<213> ORGANISM: Artificial Sequence
<220> FEATURE:
<223> OTHER INFORMATION: Synthetic construct, pLA3166-Cctra intron-
Ubiquitin-reaperKR construct.

<400> SEQUENCE: 54
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gaactaccca ccgtactcgt caattccaag ggcatcggta 960
aacatctgct caaactcgaa gtcggccata tccagagcgc cgtagggggc ggagtcgtgg 1020
ggggtaaatc ccggacccgg ggaatccccg tcccccaaca tgtccagatc gaaatcgtct 1080
agcgcgtcgg catgcgccat cgccacgtcc tcgccgtcta agtggagctc gtcccccagg 1140
ctgacatcgg tcgggggggc cgtcgacagt ctgcgcgtgt gtcccgcggg gagaaaggac 1200
aggcgcggag ccgccagccc cgcctcttcg gggcgtcgt cgtccgggag atcgagcagg 1260

```
ccctcgatgg tagacccgta attgttttc gtacgcgcgc ggctgtacgc ggggcccgag   1320
cccgactcgc atttcagttg cttttccaat ccgcagataa tcagctccaa gccgaacagg   1380
aatgccggct cggctccttg atgatcgaac agctcgattg cctgacgcag cagtgggggc   1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgcttttcg   1620
gtcgggcgcg tgccgagatg gactttggca ccgtctcggt gggacagcag agcgcagcgg   1680
aacgacttgg cgttattgcg gaggaagtcc tggaaatggg atagatattg gtgttattgt   1740
tcatgtggca tataaaggac aagcaacaaa aaacgaacat aacatgagag atggttctga   1800
atcagaactt ctgaatatta tcctcccaaa agggttaaag tttttattaa gcatattacg   1860
ttttatacca cttccttatg taaaattttc ttcgtagttt aatatcatgt gaaatcatat   1920
ataatttcta tcgaacgttt gttcaaattg aatgatgtca ttttttgaat aattggttat   1980
aattttataa catctcccga cttcgacatg tggttggtac taatgattgc gaaatcgccc   2040
tccgagaatg agaacaaccg aggtccaccg tctggtcgag attaaaacac ttgaggagtg   2100
ctttggtgac tcgatcaata ggtacagggc tcgttgccaa caatctggcc agctggacat   2160
ccgggacctc gttccccccct ggggtatcaa aatttttgta gtgtaaatag tagtacactc   2220
ttaaaaataa tgaaaattac tgcggacgta attcacatta tgattgaatg acactatcat   2280
tgacatttcc cgaatcagac accatcgtat ttaaaatgtg acacaaattc acctcatttg   2340
gctcgcttct tttatgtgca tccaaaagac gtaaaatcgc atgatttttt cggagtgtgt   2400
agtaagattg tcaaatttta attttaaata accagagccc ataaagcaaa gcaacactag   2460
gaaaaaaccc acaaactcaa cctgtccaaa aaaaaatata acaatcaaag ttgagggaat   2520
cggggtcaaa cgtcatgtaa aaatattttt tgtaaaaacc aaaccaggaa taaatatgaa   2580
tttaatcgga aaaaattgca aaatcgcata atttaatcct ccaactgtac tttatccagc   2640
ctgttgcaga aatgatgttt aaaggttcta atctgtaatt gttattagcc ttcaatactg   2700
atgtagtatt tatttcttat tgaaacattg agagctttat tttccaaagt tgtcattttc   2760
tcattcgtat atcgtaatat gtatattcgt aaatggcaag cacaatgata cttagggtag   2820
tcaaggatat ttcaattacg aaaagatcct gaaacgaccg ggaatcgaac ccttcagcat   2880
ggttttgctt tgtagctgct gaatctaacc actaggctga tgaagatccc attttagggt   2940
tgcaagttct caaagagcaa gaatgccaaa atagtgtcaa aagaagccct atttgacgat   3000
atacctttta gtctctacgt taatttgcta tgataattta tcatcaatta attggcaaag   3060
cctgatgcac gaaaagatct tcttctaaaa tttcagttgt tcttttcaac acattatgta   3120
atcataaaat ttaattaata aaccttttt ttttgtaact atccacagtt gatcaggcat   3180
aattttcttg gaaagtaaag tccatattta ggttgatgtt gaataaaaaa actttcaatt   3240
cactcttctg tttcacttca gaacttacgt aatacgacat tatgcatggt gcacacggaa   3300
caggataaga cgttcacaag ggatcaacat cacatcggat cgtaatcact ggatctggaa   3360
cacatatgac gccacaagac agcacatttt acacgatcac cagacgtgaa caaggaactg   3420
gatccacaag acgtcacagg aagacggcac atttccaacg gcttcgatgg aacttttctc   3480
gagtcttttt ccaccaatca taaacaccga cctgccagga ctcgccttcc aacgggcaaa   3540
aatgcgtgtg gtggcggtcg agcatctcga tggccagggc atccagcagc gcccgcttat   3600
```

```
tcttcacgtg ccagtagagg gtgggctgct ccacgcccag cttctgcgcc aacttgcggg   3660

tcgtcagtcc ctcaatgcca acttcgttca acagctccaa cgcggagttg atgactttgg   3720

acttatccag gcggctgccc atggtggttt ctaaaggtgt tataaatcaa attagttttg   3780

tttttcttg aaaactttgc gtttcctttg atcaacttac cgccagggta ccgcagattg   3840

tttagcttgt tcagctgcgc ttgtttattt gcttagcttt cgcttagcga cgtgttcact   3900

ttgcttgttt gaattgaatt gtcgctccgt agacgaagcg cctctattta tactccggcg   3960

ctcgttttcg agtttaccac tccctatcag tgatagagaa aagtgaaagt cgagtttacc   4020

actccctatc agtgatagag aaaagtgaaa gtcgagttta ccactcccta tcagtgatag   4080

agaaaagtga aagtcgagtt taccactccc tatcagtgat agagaaaagt gaaagtcgag   4140

tttaccactc cctatcagtg atagagaaaa gtgaaagtcg agtttaccac tccctatcag   4200

tgatagagaa aagtgaaagt cgagtttacc actccctatc agtgatagag aaaagtgaaa   4260

gtcgaaacct ggcgcgcccc ggccatcgag aaagagagag agaagagaag agagagaaca   4320

ttcgagaaag agagagagaa gagaagagag agaacatact ccctatcagt gatagagaag   4380

tccctatcag tgatagagat gtccctatca gtgatagaga gttccctatc agtgatagag   4440

acgtccctat cagtgataga gaagtcccta tcagtgatag agagatccct atcagtgata   4500

gagatttccc tatcagtgat agagaggtcc ctatcagtga tagagacttc cctatcagtg   4560

atagagaaat ccctatcagt gatagagaca tccctatcag tgatagagaa ctccctatca   4620

gtgatagaga cctccctatc agtgatagag atcgatgcgg ccgcatggta cccattgctt   4680

gtcatttatt aatttggatg atgtcatttg tttttaaaat tgaactggct ttacgagtag   4740

aattctacgc gtaaaacaca atcaagtatg agtcataatc tgatgtcatg ttttgtacac   4800

ggctcataac cgaactggct ttacgagtag aattctactt gtaatgcacg atcagtggat   4860

gatgtcattt gtttttcaaa tcgagatgat gtcatgtttt gcacacggct cataaactcg   4920

ctttacgagt agaattctac gtgtaacgca cgatcgattg atgagtcatt tgttttgcaa   4980

tatgatatca tacaatatga ctcatttgtt tttcaaaacc gaacttgatt tacgggtaga   5040

attctacttg taaagcacaa tcaaaaagat gatgtcattt gtttttcaaa actgaactcg   5100

ctttacgagt agaattctac gtgtaaaaca caatcaagaa atgatgtcat ttgttataaa   5160

aataaaagct gatgtcatgt tttgcacatg gctcataact aaactcgctt tacgggtaga   5220

attctacgcg taaaacatga ttgataatta aataattcat ttgcaagcta tacgttaaat   5280

caaacggacg ctcgaggttg cacaacacta ttatcgattt gcagttcggg acataaatgt   5340

ttaaatatat cgatgtcttt gtgatgcgcg cgacattttt gtaggttatt gataaaatga   5400

acggatacgt tgcccgacat tatcattaaa tccttggcgt agaatttgtc gggtccattg   5460

tccgtgtgcg ctagcatgcc cgtaacggac ctcgtacttt tggcttcaaa ggttttgcgc   5520

acagacaaaa tgtgccacac ttgcagctct gcatgtgtgc gcgttaccac aaatcccaac   5580

ggcgcagtgt acttgttgta tgcaaataaa tctcgataaa ggcgcggcgc gcgaatgcag   5640

ctgatcacgt acgctcctcg tgttccgttc aaggacggtg ttatcgacct cagattaatg   5700

tttatcggcc gactgttttc gtatccgctc accaaacgcg tttttgcatt aacattgtat   5760

gtcggcggat gttctatatc taatttgaat aaataaacga taaccgcgtt ggttttagag   5820

ggcataataa aagaaatatt gttatcgtgt tcgccattag ggcagtataa attgacgttc   5880

atgttggata ttgtttcagt tgcaagttga cactggcggc gacaagcaat tctaattggg   5940

gtaagtttc ccgttctttt ctgggttctt cccttttgct catccttgct gcactacctt   6000
```

```
caggtgcaag ttgagattca ggccaccatg ggagatccca ccccacccaa gaagaagcgc   6060
aaaccggtcg ccaccatgga cgaggatggt tcagagggcg gccccgccct gttccagagc   6120
gacatgacct tcaaaatctt catcgacggc gaggtgaacg gccagaagtt caccatcgtg   6180
gccgacggca gcagcaagtt cccccacggc gacttcaacg tgcacgccgt gtgcgagacc   6240
ggcaagctgc ccatgagctg gaagcccatc tgccacctga tccagtacgg cgagcccttc   6300
ttcgcccgct accccaacgg catcagccac ttcgcccagg agtgcttccc cgagggcctg   6360
agcatcgacc gcaccgtgcg cttcgagaac gacggcacca tgaccagcca ccacacctac   6420
gagctggacg gcacctgcgt ggtcagccgc atcaccgtga actgcgacgg cttccagccc   6480
gacggcccca tcatgcgcga ccagctggtg gacatcctgc ccaacgagac ccacatgttc   6540
ccccacggcc ccaacgccgt gcgccagctg gccttcatcg gcttcaccac cgccgacggc   6600
ggcctgatga tgggccactt cgacagcaag atgaccttca acggcagccg cgccatcaag   6660
atccccggcc cccacttcgt gaccatcatc accaagcaga tgagggacac cagcgacaag   6720
cgcgaccacg tgtgccagcg cgaggtgacc tacgcccaca gcgtgccccg catcaccagc   6780
gccatcggta gcgacgagga ttccggactc agatctcgac ccaagaaaaa gcggaaggtg   6840
gaggacccgt aagatccacc ggatctagat aactgatcat aatcagccat accacatttg   6900
tagaggtttt acttgcttta aaaaacctcc cacacctccc cctgaacctg aaacataaaa   6960
tgaatgcaat tgttgttgtt aacttgttta ttgcagctta taatggttac aaataaagca   7020
atagcatcac aaatttcaca aataaagcat ttttttcact gcattctagt tgtggtttgt   7080
ccaaactcat caatgtatct taacgcgagt taattaatcc attgctgggc gagctgcgcc   7140
aatcgatgcc aacgccaccc tgcatggcga gcggcaggcc ggcggctacc atgggcgtca   7200
ccatgccctg accgcccccg gagggcagtg aaaaatgtgt ggggggtggt gggggctgcg   7260
caggaactga ttgtgattat ggttgtgccc atggccatgt tgtccaagtc catggacgtg   7320
ggcatgcttg ttgtagccca aatcggcgtt tccgtttcca ccaggaaaca tctctgcttg   7380
tagttcgaat atgctcttta aatcccagct gtattcctca gttatcgagg ttttcttcac   7440
gagtgaaacg aattttcgtc gccttctacg ccattttctt gctcagcccg ttttgtcatt   7500
cgcagcgaag cggtaacagc gggtcgctca tatgacggta ttttttaata cacttcagct   7560
atactgttat ttcaaaaaca tatttctttt gttacttttt atgcagttca tttgccacca   7620
aaaagtagtc ttttggattg atttatttca aaaaatggtg taattcaaga aattcagagg   7680
gccaagtaat atacttaatg accgttattt aaaacacact caaggagatt tatttaaacg   7740
gctacaatgg ttttccaaat aacttattta ctgttgactt ctataaaaca taggtgtata   7800
tattattatt tccttattga gtttgagata attttaattt ccacaatatt ttttcttgtg   7860
attaacagag aaagtcaaac tacataacat ttatcgggta aaagtctcta tgaaggtagc   7920
ggttaacagt gaagtcgcaa aagtggtggc cgtacgccaa tcgagcgtag taccccctaac   7980
ctgcaatatt tttagttggt tttttccgca atagccccag ttttctcaaa gagtgcaaca   8040
agtgattctg tttatgtttt caacaacttc tctctgcgga acttaacgtg agcggacgta   8100
tgcggacgcg tttaaactcg cgttaagata cattgatgag tttggacaaa ccacaactag   8160
aatgcagtga aaaaaatgct ttatttgtga aatttgtgat gctattgctt tatttgtaac   8220
cattataagc tgcaataaac aagttaacaa caacaattgc attcatttta tgtttcaggt   8280
tcagggggag gtgtgggagg ttttttaaag caagtaaaac ctctacaaat gtggtatggc   8340
```

tgattatgat caccggtgtt actggctcgg acggcggtaa cggccgctgc ggcggccggt 8400
gcgcgggtgg cagctggtgt actggcgcag ggtctccagc accacggtgg ccaggaagcg 8460
ccactggctc tcgcgcaggc gcaggatctg ctgctcgcgc tgctcggcct cgcgcagcag 8520
ggtggcctga tccgggatgt agaaggccac ggcgccacca cggagacgaa ggaccaagtg 8580
aagggtggac tccttctgga tgttgtaatc ggacagggtg cgtccgtctt ccagttgctt 8640
acctatagat accatagatg tatggattag tatcatatac atacaaaggc tatttttggg 8700
acatattaat attaacaatt tccgtgatag ttttcaccat ttttgttgaa tgttacgttg 8760
aaaatttaaa tttgttttaa attaatttta ccagtcatgt gttcttaaaa gtttttatga 8820
ttgaaacggc ataaagtggt tcaaaaattt atcaagaaag gctttccttt tttaaatctt 8880
atctttttct cttaaaaatc actagtcaat tcattattaa tttgttaact tgaatttgga 8940
atgtctattt actttcagat aaattaaagc aagaaactta atattcgaaa aaaattgatt 9000
ctaaatggaa tttcacttga tcttcatgta tgcatatcaa tttttattta cattgtataa 9060
taagtttcga gttgattgtt gtaatccaca ggtgtcccag agaattaaat tccaaattac 9120
ccaagtttat tgaatgttga ttgtagtttc agttgctttg ttgctgcaac aatggcttgt 9180
tgattgtaga tattttccct ttccttggtt tacttattac atagactgaa aaagaggttt 9240
actttttga tacttatgaa aaatttctat tagtgattac taaccaatcg ctatatgttt 9300
actagaaaac aaataaactc tttacattaa cattcaataa tgtttgctct gtaaccgaca 9360
attgaaggcg ttacagcaac agtaatataa ctagcttctt aaccctcatc tattaacccc 9420
atcgtttaaa acactatgtt aaatggtcta acaaatctag atactaatag atgtcttatt 9480
acttagcagc cacagctgca acatccaaga caatttttga aacttcttat tgagctcttg 9540
gcagcagaaa tgttggtatt tttcacagct ttctgaaaga ccggcacctt cctccggttc 9600
ccgtttctga attcaagagg atttccgacc cccaattaat cccgaaacaa ataaggtata 9660
ttcaaaatga tggaaaagtc atggctgctg accttatttt tattcctatt gatagaatat 9720
tattcccctt ttaaatacac tgtactaaga ggtccggcta taattttact cacttgtcga 9780
ttatcccata gaatgttgat tgtagttggt tgcttttcca ggtgagagtt gatcaagtca 9840
caaaagttag cgtgtgttga ttgtagattt gaaggtaaaa taatttttgc acccattcat 9900
cgggtaaaac gttctccata gaatacattt ccatcgataa ttgataactt atgaatttca 9960
aagaaaaaaa tatgctttta aaattaccag cgaagatcag acgctgctga tctgggggga 10020
ttccctcctt atcctgaatc ttggccttta cattctcaat ggtgtccgat ggctctacct 10080
cgagggtgat ggtctttccg gtcaaagtct tcacaaagat ctgcattttg gattgctagc 10140
gcagattgtt tagcttgttc agctgcgctt gtttatttgc ttagctttcg cttagcgacg 10200
tgttcacttt gcttgtttga attgaattgt cgctccgtag acgaagcgcc tctatttata 10260
ctccggcgct cggtccgcat agtcgacatt tcgagtttac cactccctat cagtgataga 10320
gaaaagtgaa agtcgagttt accactccct atcagtgata gagaaaagtg aaagtcgagt 10380
ttaccactcc ctatcagtga tagagaaaag tgaaagtcga gtttaccact ccctatcagt 10440
gatagagaaa agtgaaagtc gagtttacca ctccctatca gtgatagaga aaagtgaaag 10500
tcgagtttac cactccctat cagtgataga gaaaagtgaa agtcgagttt accactccct 10560
atcagtgata gagaaaagtg aaagtcgagc tcggtacccg ggtcgaggta ggcgtgtacg 10620
gtgggaggaa atctggccgg ccgcaaccat tgtgggaacc gtgcgatcaa acaaacgcga 10680
gataccggaa gtactgaaaa acagtcgctc caggccagtg ggaacatcga tgttttgttt 10740
tgacggaccc cttactctcg tctcatataa accgaagcca gctaagatgg tatacttatt 10800
atcatcttgt gatgaggatg cttctatcaa cgaaagtacc ggtaaaccgc aaatggttat 10860
gtattataat caaactaaag gcggagtgga cacgctagac caaatgtgtt ctgtgatgac 10920
ctgcagtagg aagacgaata ggtggcctat ggcattattg tacggaatga taaacattgc 10980
ctgcataaat tcttttatta tatacagcca taatgtcagt agcaagggag aaaaggtcca 11040
aagtcgcaaa aaatttatga gaaaccttta catgagcctg acgtcatcgt ttatgcgtaa 11100
gcgtttagaa gctcctactt tgaagagata tttgcgcgat aatatctcta atattttgcc 11160
aaatgaagtg cctggtacat cagatgacag tactgaagag ccagtaatga aaaaacgtac 11220
ttactgtact tactgcccct ctaaaataag gcgaaaggca aatgcatcgt gcaaaaaatg 11280
caaaaaagtt atttgtcgag agcataatat tgatatgtgc caaagttgtt tctgactgac 11340
taataagtat aatttgtttc tattatgtat aagttaagct aattacttat tttataatac 11400
aacatgactg tttttaaagt acaaaataag tttatttttg taaaagagag aatgtttaaa 11460
agttttgtta ctttatagaa gaaattttga gtttttgttt ttttttaata aataaataaa 11520
cataaataaa ttgtttgttg aatttattat tagtatgtaa gtgtaaatat aataaaactt 11580
aatatctatt caaattaata aataaacctc gatatacaga ccgataaaac acatgcgtca 11640
attttacgca tgattatctt taacgtacgt cacaatatga ttatctttct agggttaaat 11700
aatagtttct aatttttta ttattcagcc tgctgtcgtg aataccgtat atctcaacgc 11760
tgtctgtgag attgtcgtat tctagccttt ttagtttttc gctcatcgac ttgatattgt 11820
ccgacacatt ttcgtcgatt tgcgttttga tcaaagactt gagcagagac acgttaatca 11880
actgttcaaa ttgatccata ttaacgatat caacccgatg cgtatatggt gcgtaaaata 11940
tatttttaa ccctcttata ctttgcactc tgcgttaata cgcgttcgtg tacagacgta 12000
atcatgtttt ctttttgga taaaactcct actgagtttg acctcatatt agaccctcac 12060
aagttgcaaa acgtggcatt ttttaccaat gaagaattta aagttatttt aaaaaatttc 12120
atcacagatt taaagaagaa ccaaaaatta aattatttca acagtttaat cgaccagtta 12180
atcaacgtgt acacagacgc gtcggcaaaa aacacgcagc ccgacgtgtt ggctaaaatt 12240
attaaatcaa cttgtgttat agtcacggat ttgccgtcca acgtgttcct caaaaagttg 12300
aagaccaaca agtttacgga cactattaat tatttgattt tgccccactt cattttgtgg 12360
gatcacaatt ttgttatatt ttaaacaaag cttggcactg gccgtcgttt tacaacgtcg 12420
tgactgggaa aaccctggcg ttacccaact taatcgcctt gcagcacatc ccccttcgc 12480
cagctggcgt aatagcgaag aggcccgcac cgatcgccct tcccaacagt tgcgcagcct 12540
gaatggcgaa tggcgcctga tgcggtattt tctccttacg catctgtgcg gtatttcaca 12600
ccgcatatgg tgcactctca gtacaatctg ctctgatgcc gcatagttaa gccagccccg 12660
acacccgcca acacccgctg acgcgccctg acgggcttgt ctgctcccgg catccgctta 12720
cagacaagct gtgaccgtct ccgggagctg catgtgtcag aggttttcac cgtcatcacc 12780
gaaacgcgcg agacgaaagg gcctcgtgat acgcctattt ttataggtta atgtcatgat 12840
aataatggtt tcttagacgt caggtggcac ttttcgggga aatgtgcgcg gaacccctat 12900
ttgtttattt ttctaaatac attcaaatat gtatccgctc atgagacaat aaccctgata 12960
aatgcttcaa taatattgaa aaaggaagag tatgagtatt caacatttcc gtgtcgccct 13020
tattcccttt tttgcggcat tttgccttcc tgtttttgct cacccagaaa cgctggtgaa 13080

```
agtaaaagat gctgaagatc agttgggtgc acgagtgggt tacatcgaac tggatctcaa  13140
cagcggtaag atccttgaga gttttcgccc cgaagaacgt tttccaatga tgagcacttt  13200
taaagttctg ctatgtggcg cggtattatc ccgtattgac gccgggcaag agcaactcgg  13260
tcgccgcata cactattctc agaatgactt ggttgagtac tcaccagtca cagaaaagca  13320
tcttacggat ggcatgacag taagagaatt atgcagtgct gccataacca tgagtgataa  13380
cactgcggcc aacttacttc tgacaacgat cggaggaccg aaggagctaa ccgctttttt  13440
gcacaacatg ggggatcatg taactcgcct tgatcgttgg gaaccggagc tgaatgaagc  13500
cataccaaac gacgagcgtg acaccacgat gcctgtagca atggcaacaa cgttgcgcaa  13560
actattaact ggcgaactac ttactctagc ttcccggcaa caattaatag actggatgga  13620
ggcggataaa gttgcaggac cacttctgcg ctcggccctt ccggctggct ggtttattgc  13680
tgataaatct ggagccggtg agcgtgggtc tcgcggtatc attgcagcac tggggccaga  13740
tggtaagccc tcccgtatcg tagttatcta cacgacgggg agtcaggcaa ctatggatga  13800
acgaaataga cagatcgctg agataggtgc ctcactgatt aagcattggt aactgtcaga  13860
ccaagtttac tcatatatac tttagattga tttaaaactt catttttaat ttaaaaggat  13920
ctaggtgaag atcctttttg ataatctcat gaccaaaatc ccttaacgtg agttttcgtt  13980
ccactgagcg tcagaccccg tagaaaagat caaaggatct tcttgagatc cttttttct  14040
gcgcgtaatc tgctgcttgc aaacaaaaaa accaccgcta ccagcggtgg tttgtttgcc  14100
ggatcaagag ctaccaactc tttttccgaa ggtaactggc ttcagcagag cgcagatacc  14160
aaatactgtc cttctagtgt agccgtagtt aggccaccac ttcaagaact ctgtagcacc  14220
gcctacatac ctcgctctgc taatcctgtt accagtggct gctgccagtg gcgataagtc  14280
gtgtcttacc gggttggact caagacgata gttaccggat aaggcgcagc ggtcgggctg  14340
aacggggggt tcgtgcacac agcccagctt ggagcgaacg acctacaccg aactgagata  14400
cctacagcgt gagcattgag aaagcgccac gcttcccgaa gggagaaagg cggacaggta  14460
tccggtaagc ggcagggtcg gaacaggaga gcgcacgagg gagcttccag ggggaaacgc  14520
ctggtatctt tatagtcctg tcgggtttcg ccacctctga cttgagcgtc gatttttgtg  14580
atgctcgtca ggggggcgga gcctatggaa aaacgccagc aacgcggcct ttttacggtt  14640
cctggccttt tgctggcctt ttgctcacat gttctttcct gcgttatccc ctgattctgt  14700
ggataaccgt attaccgcct ttgagtgagc tgataccgct cgccgcagcc gaacgaccga  14760
gcgcagcgag tcagtgagcg aggaagcgga agagcgccca atacgcaaac cgcctctccc  14820
cgcgcgttgg ccgattcatt aatgcagctg gcacgacagg tttcccgact ggaaagcggg  14880
cagtgagcgc aacgcaatta atgtgagtta gctcactcat taggcacccc aggctttaca  14940
ctttatgctt ccggctcgta tgttgtgtgg aattgtgagc ggataacaat ttcacacagg  15000
aaacagctat gaccatgatt acgaatttcg acgctcgcgc gacttggttt gccattcttt  15060
agcgcgcgtc gcgtcacaca gcttggccac aatgtggttt ttgtcaaacg aagattctat  15120
gacgtgttta aagtttaggt cgagtaaagc gcaaatcttt tttaacccta gaaagatagt  15180
ctgcgtaaaa ttgacgcatg cattcttgaa atattgctct ctctttctaa atagcgcgaa  15240
tccgtcgctg tgcatttagg acatctcagt cgccgcttgg agctcccgtg aggcgtgctt  15300
gtcaatgcgg taagtgtcac tgattttgaa ctataacgac cgcgtgagtc aaaatgacgc  15360
atgattatct tttacgtgac ttttaagatt taactcatac gataattata ttgttatttc  15420
atgttctact tacgtgataa cttattatat atatattttc ttgttataga tatcgtgact  15480
```

aatatataat aaaatgggta gttctttaga cgatgagcat atcctctctg ctcttctgca 15540
aagcgatgac gagcttgttg gtgaggattc tgacagtgaa atatcagatc acgtaagtga 15600
agatgacgtc cagagcgata cagaagaagc gtttatagat gaggtacatg aagtgcagcc 15660
aacgtcaagc ggtagtgaaa tattagacga acaaaatgtt attgaacaac caggttcttc 15720
attggcttct aacagaatct tgaccttgcc acagaggact attagaggta agaataaaca 15780
ttgttggtca acttcaaagt ccacgaggcg tagccgagtc tctgcactga acattgtcag 15840
atcggccc 15848

<210> SEQ ID NO 55
<211> LENGTH: 17802
<212> TYPE: DNA
<213> ORGANISM: Artificial Sequence
<220> FEATURE:
<223> OTHER INFORMATION: Synthetic construct, pLA3376-Bztra intron-reaperKR and Bztra-intron-tTAV3.

<400> SEQUENCE: 55
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gacaccggtg ttagccgccg tactcatcga tgcccagggc 960
gtcggtgaac atctgctcga actcgaaatc ggccatatcc agggcgccgt agggggcgct 1020
atcgtgcggg gtgaatcccg gtcccgggct atcgccatcg cccagcatgt ccaggtcgaa 1080
gtcgtccagg gcatcggcgt gggccatcgc cacatcctcg ccatccaggt gcagctcatc 1140
gcccaggctc acgtcggtcg gcggggcggt cgacaggcgg cgggtgtgtc cggccggcag 1200
gaagctcagg cgcggggcgg ccaggcccgc ctcctccggg gcatcatcat ccggcagatc 1260
cagcaggccc tcgatggtgc tgccgtagtt gttcttggtg cgggcgcggc tgtaggcggg 1320
gcccgagccc gactcgcatt tcagttgctt ttccaatccg cagataatca gctccaagcc 1380
gaacaggaat gccggctcgg ctccttgatg atcgaacagc tcgattgcct gacgcagcag 1440
tgggggcatc gaatcggttg ttggggtctc gcgctcctct tttgcgactt gatgctcttg 1500
gtcctccagc acgcagccca gggtaaagtg accgacggcg ctcagagcgt agagagcatt 1560
ttccaggctg aagccttgct ggcacaggaa cgcgagctgg ttctccagtg tctcgtattg 1620

```
cttttcggtc gggcgcgtgc cgagatggac tttggcaccg tctcggtggg acagcagagc   1680
gcagcggaac gacttggcgt tattgcggag gaagtcctgc caggactcgc cttccaacgg   1740
gcaaaaatgc gtgtggtggc ggtcgagcat ctcgatggcc agggcatcca gcagcgcccg   1800
cttattcttc acgtgccagt agagggtggg ctgctccacg cccagcttct gcgccaactt   1860
gcgggtcgtc agtccctcaa tgccaacttc gttcaacagc tccaacgcgg agttgatgac   1920
tttggactta tccaggcggc tgacctatag ataccataga tgtatggatt agtatcatat   1980
acatacaaag gctatttttg ggacatatta atattaacaa tttccgtgat agttttcacc   2040
atttttgttg aatgttacgt tgaaaattta aatttgtttt aaattaattt taccagtcat   2100
gtgttcttaa aagtttttat gattgaaacg gcataaagtg gttcaaaaat ttatcaagaa   2160
aggctttcct tttttaaatc ttatcttttt ctcttaaaaa tcactagtca attcattatt   2220
aatttgttaa cttgaatttg gaatgtctat ttactttcag ataaattaaa gcaagaaact   2280
taatattcga aaaaaattga ttctaaatgg aatttcactt gatcttcatg tatgcatatc   2340
aatttttatt tacattgtat aataagtttc gagttgattg ttgtaatcca caggtgtccc   2400
agagaattaa attccaaatt acccaagttt attgaatgtt gattgtagtt tcagttgctt   2460
tgttgctgca acaatggctt gttgattgta gatattttcc ctttccttgg tttacttatt   2520
acatagactg aaaaagaggt ttactttttt gatacttatg aaaaatttct attagtgatt   2580
actaaccaat cgctatatgt ttactagaaa acaaataaac tctttacatt aacattcaat   2640
aatgtttgct ctgtaaccga caattgaagg cgttacagca acagtaatat aactagcttc   2700
ttaaccctca tctattaacc ccatcgttta aaacactatg ttaaatggtc taacaaatct   2760
agatactaat agatgtctta ttacttagca gccacagctg caacatccaa gacaattttt   2820
gaaacttctt attgagctct tggcagcaga aatgttggta tttttcacag ctttctgaaa   2880
gaccggcacc ttcctccggt tcccgtttct gaattcaaga ggatttccga cccccaatta   2940
atcccgaaac aaataaggta tattcaaaat gatggaaaag tcatggctgc tgaccttatt   3000
tttattccta ttgatagaat attattcccc ttttaaatac actgtactaa gaggtccggc   3060
tataatttta ctcacttgtc gattatccca tagaatgttg attgtagttg gttgcttttc   3120
caggtgagag ttgatcaagt cacaaaagtt agcgtgtgtt gattgtagat ttgaaggtaa   3180
aataattttt gcacccattc atcgggtaaa acgttctcca tagaatacat ttccatcgat   3240
aattgataac ttatgaattt caaagaaaaa aatatgcttt taaaattacc atggtggcta   3300
gcgcagattg tttagcttgt tcagctgcgc ttgtttattt gcttagcttt cgcttagcga   3360
cgtgttcact ttgcttgttt gaattgaatt gtcgctccgt agacgaagcg cctctattta   3420
tactccggcg ctcgttttcg agtttaccac tccctatcag tgatagagaa aagtgaaagt   3480
cgagtttacc actccctatc agtgatagag aaaagtgaaa gtcgagttta ccactcccta   3540
tcagtgatag agaaaagtga aagtcgagtt taccactccc tatcagtgat agagaaaagt   3600
gaaagtcgag tttaccactc cctatcagtg atagagaaaa gtgaaagtcg agtttaccac   3660
tccctatcag tgatagagaa aagtgaaagt cgagtttacc actccctatc agtgatagag   3720
aaaagtgaaa gtcgaaacct gcgcgccgtt taaactcgcg ttaagataca ttgatgagtt   3780
tggacaaacc acaactagaa tgcagtgaaa aaaatgcttt atttgtgaaa tttgtgatgc   3840
tattgcttta tttgtaacca ttataagctg caataaacaa gttaacaaca acaattgcat   3900
tcattttatg tttcaggttc agggggaggt gtgggaggtt ttttaaagca agtaaaacct   3960
```

```
ctacaaatgt ggtatggctg attatgatcg ctctagacac cggtgctacc cgccatactc   4020
atcgatgccc agcgcgtcgg tgaacatttg ctcgaactcg aagtcggcca tgtccagggc   4080
gccgtacggg gcgctatcgt ggggcgtgaa gcccggtccc gggctatctc catcgcccag   4140
catatccagg tcgaaatcgt ccagggcgtc ggcgtgggcc attgccacat cctctccatc   4200
caggtgcagc tcgtcgccca ggctcacatc ggtcggcggg gcggtgctca ggcggcgcgt   4260
gtgtccggcg ggcaggaagc tcaggcgggg ggcggccagg ccggcttcct ccggggcatc   4320
gtcatccggc aggtccagca gtccctcgat ggtgctgcca tagttgttct tggtacgggc   4380
gcggctgtag gcgctgccgc tctcgcactt cagctgcttt tccaggccgc agatgatcag   4440
ctccaggccg aacaggaagg ccggctcggc gccctggtga tcgaacagct cgatggcctg   4500
gcgcagcagc ggcggcatgc tatcggtggt cggggtctcg cgctcctcct tggccacctg   4560
gtgctcctga tcctccagca cacagcccag ggtgaagtgg cccacggcgc tcagggcgta   4620
cagggcgttc tccaggctga agccctgctg gcacaggaag gccagctggt tctccagggt   4680
ctcgtactgc ttctcggtcg ggcgggtgcc caggtgcacc ttggcgccat cgcggtgcga   4740
cagcagggcg cagcggaagc tcttggcgtt gttgcgcagg aaatcctgcc agctctcgcc   4800
ctccagcggg cagaagtggg tgtggtggcg atccagcatt tcgatggcca gggcgtccag   4860
cagggcgcgc ttgttcttca cgtgccagta cagggtcggc tgttccacgc ccagcttctg   4920
ggccagcttg cgggtggtca ggccctcgat accaacttcg ttcagcagct ccagggcgct   4980
gttgatcacc ttgctcttgt ccaggcggct gacctgtgaa tacggttaat gtcactatta   5040
gtgatttata aaaataaatt tgatttatat atcaacaatt tttcatcgca gccttcagct   5100
ttttgttgaa taattataat gatatttttt acgattcaaa tcatttaatt gttactcaac   5160
gaaataagtt taattcaaat tttaaaacaa gattatatat taagattaga ataagaaaga   5220
actttgttag attatttaat taaaaagatt aaaatttaag tctccagtca ctatttaaag   5280
atcatctttc aaacgttaaa gtgaattcaa acgagacgtt caaatttcga ttaaacagta   5340
attaactcta aatttctatc acgaattaag ttattgaata tgaaggttta tatttattta   5400
catcatctaa taggtttgag ttgattgttg taatccgcat gtgccagaag atatcaattt   5460
ccaaattgtc cgagttcatg gaatgttgat tgttgtttgt gttgctttgt aattgttgca   5520
gggagtattt atggtttgtt gattgtagta taaggctgtt tctaaaggct agaaaataat   5580
tttatttatt tgaaaataag taaatataca taatattact aacaataggt cgtcctattt   5640
tttgatattc tgcacaaatt tttaaaacac aaagattgca atacttttag acactaatac   5700
tgcacactct gaaaaattat taaattattt ttaaaaactt accttaatac tttagagaaa   5760
aatattatac cgcacctttc tactttatac tcactttatt ataccagttg catgttgatt   5820
gtagttcttt gacaagaaaa tattccatat tgctccaaat tatcttggta agttgattgg   5880
tgcgtcattt gagcaagcta acaccttgtc tcatttaagt tcgcctcaag atctcatagc   5940
atttttaaat atcactatat ttagtaagta attagaatta ccatggtggt ttgctagccg   6000
ttctatcaga tgtgctccgg gaaacagaaa tgttcaacta agttctggcg gacgacgcaa   6060
cacctttata tactttgcca agcgcacagg tagaaaggac ctattttggg gattaaaaaa   6120
catctgcctg ttttattgcc atacccgcga aaattcgcga aatccgctac tttacctact   6180
ggggttcctg gaaaatgggc gaagaacggc aaagaactgg tactttccgt caataattgt   6240
ttagaagaga gagaacatac tccctatcag tgatagagaa gtccctatca gtgatagaga   6300
tgtccctatc agtgatagag agttccctat cagtgataga gacgtcccta tcagtgatag   6360
```

agaagtccct atcagtgata gagagatccc tatcagtgat agagatttcc ctatcagtga 6420
tagagaggtc cctatcagtg atagagactt ccctatcagt gatagagaaa tccctatcag 6480
tgatagagac atccctatca gtgatagaga actccctatc agtgatagag acctccctat 6540
cagtgataga gatcgatgcg gccgcatggt acccattgct tgtcatttat taatttggat 6600
gatgtcattt gtttttaaaa ttgaactggc tttacgagta gaattctacg cgtaaaacac 6660
aatcaagtat gagtcataat ctgatgtcat gttttgtaca cggctcataa ccgaactggc 6720
tttacgagta gaattctact tgtaatgcac gatcagtgga tgatgtcatt tgtttttcaa 6780
atcgagatga tgtcatgttt tgcacacggc tcataaactc gctttacgag tagaattcta 6840
cgtgtaacgc acgatcgatt gatgagtcat ttgttttgca atatgatatc atacaatatg 6900
actcatttgt ttttcaaaac cgaacttgat ttacgggtag aattctactt gtaaagcaca 6960
atcaaaaaga tgatgtcatt tgtttttcaa aactgaactc gctttacgag tagaattcta 7020
cgtgtaaaac acaatcaaga aatgatgtca tttgttataa aaataaaagc tgatgtcatg 7080
ttttgcacat ggctcataac taaactcgct ttacgggtag aattctacgc gtaaaacatg 7140
attgataatt aaataattca tttgcaagct atacgttaaa tcaaacggac gctcgaggtt 7200
gcacaacact attatcgatt tgcagttcgg gacataaatg tttaaatata tcgatgtctt 7260
tgtgatgcgc gcgacatttt tgtaggttat tgataaaatg aacggatacg ttgcccgaca 7320
ttatcattaa atccttggcg tagaatttgt cgggtccatt gtccgtgtgc gctagcatgc 7380
ccgtaacgga cctcgtactt ttggcttcaa aggttttgcg cacagacaaa atgtgccaca 7440
cttgcagctc tgcatgtgtg cgcgttacca caaatcccaa cggcgcagtg tacttgttgt 7500
atgcaaataa atctcgataa aggcgcggcg cgcgaatgca gctgatcacg tacgctcctc 7560
gtgttccgtt caaggacggt gttatcgacc tcagattaat gtttatcggc cgactgtttt 7620
cgtatccgct caccaaacgc gtttttgcat taacattgta tgtcggcgga tgttctatat 7680
ctaatttgaa taaataaacg ataaccgcgt tggttttaga gggcataata aaagaaatat 7740
tgttatcgtg ttcgccatta gggcagtata aattgacgtt catgttggat attgtttcag 7800
ttgcaagttg acactggcgg cgacaagcaa ttctaattgg ggtaagtttt cccgttcttt 7860
tctgggttct tccctttttgc tcatccttgc tgcactacct tcaggtgcaa gttgagattc 7920
aggccaccat gggagatccc accccaccca agaagaagcg caaaccggtc gccaccatgg 7980
agagcgacga gagcggcctg cccgccatgg agatcgagtg ccgcatcacc ggcaccctga 8040
acggcgtgga gttcgagctg gtgggcggcg gagagggcac ccccgagcag ggccgcatga 8100
ccaacaagat gaagagcacc aaaggcgccc tgaccttcag cccctacctg ctgagccacg 8160
tgatgggcta cggcttctac cacttcggca cctaccccag cggctacgag aaccccttcc 8220
tgcacgccat caacaacggc ggctacacca acacccgcat cgagaagtac gaggacggcg 8280
gcgtgctgca cgtgagcttc agctaccgct acgaggccgg ccgcgtgatc ggcgacttca 8340
aggtgatggg caccggcttc cccgaggaca gcgtgatctt caccgacaag atcatccgca 8400
gcaacgccac cgtggagcac ctgcacccca tgggcgataa cgatctggat ggcagcttca 8460
cccgcacctt cagcctgcgc gacggcggct actacagctc cgtggtggac agccacatgc 8520
acttcaagag cgccatccac cccagcatcc tgcagaacgg gggccccatg ttcgccttcc 8580
gccgcgtgga ggaggatcac agcaacaccg agctgggcat cgtggagtac cagcacgcct 8640
tcaagacccc ggatgcagat gccggtgaag aaagatctcg acccaagaaa aagcggaagg 8700

-continued

```
tggaggaccc gtaagatcca ccggatctag ataactgatc ataatcagcc ataccacatt   8760
tgtagaggtt ttacttgctt taaaaaacct cccacacctc cccctgaacc tgaaacataa   8820
aatgaatgca attgttgttg ttaacttgtt tattgcagct tataatggtt acaaataaag   8880
caatagcatc acaaatttca caaataaagc atttttttca ctgcattcta gttgtggttt   8940
gtccaaactc atcaatgtat cttaacgcga gttatcgcgc tcgcgcgact gacggtcgta   9000
agcacccgcg tacgtgtcca ccccggtcac aaccccttgt gtcatgtcgg cgaccctacg   9060
cccccaactg agagaactca aaggttaccc cagttggggc actactcccg aaaaccgctt   9120
ctgacctggg aaaacgtgaa gccccggggc atccgctgag ggttgccgcc ggggcttcgg   9180
tgtgtccgtc agtacttaat taacaccgaa atcgtaattc acggcatcat tacaaaatat   9240
tttgacgttt tggacctcgt ccctaatgac accataacgg tggccttgaa gtatatttaa   9300
ccctagaaag atagtctgcg taaaattgac gcatgcattc ttgaaatatt gctctctctt   9360
tctaaatagc gcgaatccgt cgctgtgcat ttaggacatc tcagtcgccg cttggagctc   9420
ccgtgaggcg tgcttgtcaa tgcggtaagt gtcactgatt ttgaactata acgaccgcgt   9480
gagtcaaaat gacgcatgat tatcttttac gtgactttta agatttaact catacgataa   9540
ttatattgtt atttcatgtt ctacttacgt gataacttat tatatatata ttttcttgtt   9600
atagatatcg tgactaatat ataataaaat gggtagttct ttagacgatg agcatatcct   9660
ctctgctctt ctgcaaagcg atgacgagct tgttggtgag gattctgaca gtgaaatatc   9720
agatcacgta agtgaagatg acgtccagga aatctggccg gccgcaacca ttgtgggaac   9780
cgtgcgatca aacaaacgcg agataccgga agtactgaaa aacagtcgct ccaggccagt   9840
gggaacatcg atgttttgtt ttgacggacc ccttactctc gtctcatata aaccgaagcc   9900
agctaagatg gtatacttat tatcatcttg tgatgaggat gcttctatca acgaaagtac   9960
cggtaaaccg caaatggtta tgtattataa tcaaactaaa ggcggagtgg acacgctaga  10020
ccaaatgtgt tctgtgatga cctgcagtag gaagacgaat aggtggccta tggcattatt  10080
gtacggaatg ataaacattg cctgcataaa ttcttttatt atatacagcc ataatgtcag  10140
tagcaaggga gaaaaggtcc aaagtcgcaa aaaatttatg agaaaccttt acatgagcct  10200
gacgtcatcg tttatgcgta agcgtttaga agctcctact ttgaagagat atttgcgcga  10260
taatatctct aatattttgc caaatgaagt gcctggtaca tcagatgaca gtactgaaga  10320
gccagtaatg aaaaaacgta cttactgtac ttactgcccc tctaaaataa ggcgaaaggc  10380
aaatgcatcg tgcaaaaaat gcaaaaaagt tatttgtcga gagcataata ttgatatgtg  10440
ccaaagttgt ttctgactga ctaataagta taatttgttt ctattatgta taagttaagc  10500
taattactta ttttataata caacatgact gtttttaaag tacaaaataa gtttattttt  10560
gtaaaagaga gaatgtttaa aagttttgtt actttataga agaaattttg agtttttgtt  10620
ttttttaat aaataaataa acataaataa attgtttgtt gaatttatta ttagtatgta  10680
agtgtaaata taataaaact taatatctat tcaaattaat aaataaacct cgatatacag  10740
accgataaaa cacatgcgtc aattttacgc atgattatct ttaacgtacg tcacaatatg  10800
attatctttc tagggttaaa taatagtttc taattttttt attattcagc ctgctgtcgt  10860
gaataccgta tatctcaacg ctgtctgtga gattgtcgta ttctagcctt tttagttttt  10920
cgctcatcga cttgatattg tccgacacat tttcgtcgat ttgcgttttg atcaaagact  10980
tgagcagaga cacgttaatc aactgttcaa attgatccat attaacgata tcaacccgat  11040
gcgtatatgg tgcgtaaaat atattttta accctcttat actttgcact ctgcgttaat  11100
```

acgcgttcgt gtacagacgt aatcatgttt tctttttttgg ataaaactcc tactgagttt 11160
gacctcatat tagaccctca caagttgcaa aacgtggcat tttttaccaa tgaagaattt 11220
aaagttattt taaaaaattt catcacagat ttaaagaaga accaaaaatt aaattatttc 11280
aacagtttaa tcgaccagtt aatcaacgtg tacacagacg cgtcggcaaa aaacacgcag 11340
cccgacgtgt tggctaaaat tattaaatca acttgtgtta tagtcacgga tttgccgtcc 11400
aacgtgttcc tcaaaaagtt gaagaccaac aagtttacgg acactattaa ttatttgatt 11460
ttgccccact tcattttgtg ggatcacaat tttgttatat tttaaacaaa gcttggcact 11520
ggccgtcgtt ttacaacgtc gtgactggga aaaccctggc gttacccaac ttaatcgcct 11580
tgcagcacat ccccctttcg ccagctggcg taatagcgaa gaggcccgca ccgatcgccc 11640
ttcccaacag ttgcgcagcc tgaatggcga atggcgcctg atgcggtatt ttctccttac 11700
gcatctgtgc ggtatttcac accgcatatg gtgcactctc agtacaatct gctctgatgc 11760
cgcatagtta agccagcccc gacacccgcc aacacccgct gacgcgccct gacgggcttg 11820
tctgctcccg gcatccgctt acagacaagc tgtgaccgtc tccgggagct gcatgtgtca 11880
gaggttttca ccgtcatcac cgaaacgcgc gagacgaaag ggcctcgtga tacgcctatt 11940
tttataggtt aatgtcatga taataatggt ttcttagacg tcaggtggca cttttcgggg 12000
aaatgtgcgc ggaaccccta tttgtttatt tttctaaata cattcaaata tgtatccgct 12060
catgagacaa taaccctgat aaatgcttca ataatattga aaaaggaaga gtatgagtat 12120
tcaacatttc cgtgtcgccc ttattccctt ttttgcggca ttttgccttc ctgtttttgc 12180
tcacccagaa acgctggtga aagtaaaaga tgctgaagat cagttgggtg cacgagtggg 12240
ttacatcgaa ctggatctca acagcggtaa gatccttgag agttttcgcc ccgaagaacg 12300
ttttccaatg atgagcactt ttaaagttct gctatgtggc gcggtattat cccgtattga 12360
cgccgggcaa gagcaactcg gtcgccgcat acactattct cagaatgact tggttgagta 12420
ctcaccagtc acagaaaagc atcttacgga tggcatgaca gtaagagaat tatgcagtgc 12480
tgccataacc atgagtgata acactgcggc caacttactt ctgacaacga tcggaggacc 12540
gaaggagcta accgcttttt tgcacaacat gggggatcat gtaactcgcc ttgatcgttg 12600
ggaaccggag ctgaatgaag ccataccaaa cgacgagcgt gacaccacga tgcctgtagc 12660
aatggcaaca acgttgcgca aactattaac tggcgaacta cttactctag cttcccggca 12720
acaattaata gactggatgg aggcggataa agttgcagga ccacttctgc gctcggccct 12780
tccggctggc tggtttattg ctgataaatc tggagccggt gagcgtgggt ctcgcggtat 12840
cattgcagca ctggggccag atggtaagcc ctcccgtatc gtagttatct acacgacggg 12900
gagtcaggca actatggatg aacgaaatag acagatcgct gagataggtg cctcactgat 12960
taagcattgg taactgtcag accaagttta ctcatatata ctttagattg atttaaaact 13020
tcatttttaa tttaaaagga tctaggtgaa gatccttttt gataatctca tgaccaaaat 13080
cccttaacgt gagttttcgt tccactgagc gtcagacccc gtagaaaaga tcaaaggatc 13140
ttcttgagat cctttttttc tgcgcgtaat ctgctgcttg caaacaaaaa aaccaccgct 13200
accagcggtg gtttgtttgc cggatcaaga gctaccaact ctttttccga aggtaactgg 13260
cttcagcaga gcgcagatac caaatactgt ccttctagtg tagccgtagt taggccacca 13320
cttcaagaac tctgtagcac cgcctacata cctcgctctg ctaatcctgt taccagtggc 13380
tgctgccagt ggcgataagt cgtgtcttac cgggttggac tcaagacgat agttaccgga 13440

```
taaggcgcag cggtcgggct gaacgggggg ttcgtgcaca cagcccagct tggagcgaac  13500
gacctacacc gaactgagat acctacagcg tgagcattga gaaagcgcca cgcttcccga  13560
agggagaaag gcggacaggt atccggtaag cggcagggtc ggaacaggag agcgcacgag  13620
ggagcttcca gggggaaacg cctggtatct ttatagtcct gtcgggtttc gccacctctg  13680
acttgagcgt cgatttttgt gatgctcgtc aggggggcgg agcctatgga aaaacgccag  13740
caacgcggcc tttttacggt tcctggcctt ttgctggcct tttgctcaca tgttctttcc  13800
tgcgttatcc cctgattctg tggataaccg tattaccgcc tttgagtgag ctgataccgc  13860
tcgccgcagc cgaacgaccg agcgcagcga gtcagtgagc gaggaagcgg aagagcgccc  13920
aatacgcaaa ccgcctctcc ccgcgcgttg gccgattcat taatgcagct ggcacgacag  13980
gtttcccgac tggaaagcgg gcagtgagcg caacgcaatt aatgtgagtt agctcactca  14040
ttaggcaccc caggctttac actttatgct tccggctcgt atgttgtgtg gaattgtgag  14100
cggataacaa tttcacacag gaaacagcta tgaccatgat tacgaatttc gacctgcagg  14160
catgcaagct tgcatgcctg caggtcgacg ctcgcgcgac ttggtttgcc attctttagc  14220
gcgcgtcgcg tcacacagct tggccacaat gtggtttttg tcaaacgaag attctatgac  14280
gtgtttaaag tttaggtcga gtaaagcgca aatctttttt aaccctagaa agatagtctg  14340
cgtaaaattg acgcatgcat tcttgaaata ttgctctctc tttctaaata gcgcgaatcc  14400
gtcgctgtgc atttaggaca tctcagtcgc cgcttggagc tcccgtgagg cgtgcttgtc  14460
aatgcggtaa gtgtcactga ttttgaacta taacgaccgc gtgagtcaaa atgacgcatg  14520
attatctttt acgtgacttt taagatttaa ctcatacgat aattatattg ttatttcatg  14580
ttctacttac gtgataactt attatatata tattttcttg ttatagatat cgtgactaat  14640
atataataaa atgggtagtt ctttagacga tgagcatatc ctctctgctc ttctgcaaag  14700
cgatgacgag cttgttggtg aggattctga cagtgaaata tcagatcacg taagtgaaga  14760
tgacgtccag agcgatacag aagaagcgtt tatagatgag gtacatgaag tgcagccaac  14820
gtcaagcggt agtgaaatat tagacgaaca aaatgttatt gaacaaccag gttcttcatt  14880
ggcttctaac agaatcttga ccttgccaca gaggactatt agaggtaaga ataaacattg  14940
ttggtcaact tcaaagtcca cgaggcgtag ccgagtctct gcactgaaca ttgtcagatc  15000
ggcccggcgg agtggacacg ctagaccaaa tgtgttctgt gatgacctgc agtaggaaga  15060
cgaataggtg gcctatggca ttattgtacg gaatgataaa cattgcctgc ataaattctt  15120
ttattatata cagccataat gtcagtagca agggagaaaa ggtccaaagt cgcaaaaaat  15180
ttatgagaaa cctttacatg agcctgacgt catcgtttat gcgtaagcgt ttagaagctc  15240
ctactttgaa gagatatttg cgcgataata tctctaatat tttgccaaat gaagtgcctg  15300
gtacatcaga tgacagtact gaagagccag taatgaaaaa acgtacttac tgtacttact  15360
gcccctctaa aataaggcga aaggcaaatg catcgtgcaa aaaatgcaaa aaagttattt  15420
gtcgagagca taatattgat atgtgccaaa gttgtttctg actgactaat aagtataatt  15480
tgtttctatt atgtataagt taagctaatt acttatttta taatacaaca tgactgtttt  15540
taaagtacaa aataagttta tttttgtaaa agagagaatg tttaaaagtt ttgttacttt  15600
atagaagaaa ttttgagttt ttgttttttt ttaataaata aataaacata aataaattgt  15660
ttgttgaatt tattattagt atgtaagtgt aaatataata aaacttaata tctattcaaa  15720
ttaataaata aacctcgata tacagaccga taaaacacat gcgtcaattt tacgcatgat  15780
tatctttaac gtacgtcaca atatgattat ctttctaggg ttaaaatgaa tgtaagcact  15840
```

ttattaacga aatctttggg aatatttcgc tcatcagcat tttatttgag caggagtccg 15900
agatgcccgg ccgcgccggc catcgagaaa gagagagaga agagaagaga gagaacattc 15960
gagaaagaga gagagaagag aagagagaga acatactccc tatcagtgat agagaagtcc 16020
ctatcagtga tagagatgtc cctatcagtg atagagagtt ccctatcagt gatagagacg 16080
tccctatcag tgatagagaa gtccctatca gtgatagaga gatccctatc agtgatagag 16140
atttccctat cagtgataga gaggtcccta tcagtgatag agacttccct atcagtgata 16200
gagaaatccc tatcagtgat agagacatcc ctatcagtga tagagaactc cctatcagtg 16260
atagagacct ccctatcagt gatagagatc gatccgtcta cctgagcgat atataaacta 16320
atgcctgttg caattgttca gtcagtcacg agtttgttac cactgcgaca agctagcaac 16380
caccatggcg gtaattctaa ttacttacta aatatagtga tatttaaaaa tgctatgaga 16440
tcttgaggcg aacttaaatg agacaaggtg ttagcttgct caaatgacgc accaatcaac 16500
ttaccaagat aatttggagc aatatggaat attttcttgt caaagaacta caatcaacat 16560
gcaactggta taataaagtg agtataaagt agaaaggtgc ggtataatat ttttctctaa 16620
agtattaagg taagttttta aaaataattt aataattttt cagagtgtgc agtattagtg 16680
tctaaaagta ttgcaatctt tgtgttttaa aaatttgtgc agaatatcaa aaaataggac 16740
gacctattgt tagtaatatt atgtatattt acttattttc aaataaataa aattattttc 16800
tagcctttag aaacagcctt atactacaat caacaaacca taaatactcc ctgcaacaat 16860
tacaaagcaa cacaaacaac aatcaacatt ccatgaactc ggacaatttg gaaattgata 16920
tcttctggca catgcggatt acaacaatca actcaaacct attagatgat gtaaataaat 16980
ataaaccttc atattcaata acttaattcg tgatagaaat ttagagttaa ttactgttta 17040
atcgaaattt gaacgtctcg tttgaattca ctttaacgtt tgaaagatga tctttaaata 17100
gtgactggag acttaaattt taatcttttt aattaaataa tctaacaaag ttctttctta 17160
ttctaatctt aatatataat cttgttttaa aatttgaatt aaacttattt cgttgagtaa 17220
caattaaatg atttgaatcg taaaaaatat cattataatt attcaacaaa aagctgaagg 17280
ctgcgatgaa aaattgttga tatataaatc aaatttattt ttataaatca ctaatagtga 17340
cattaaccgt attcacaggt ggccttctac atcccggatc aggccaccct gctgcgcgag 17400
gccgagcagc gcgagcagca gatcctgcgc ctgcgcgaga gccagtggcg cttcctggcc 17460
accgtggtgc tggagaccct gcgccagtac accagctgcc acccgcgcac cggccgccgc 17520
agcggccgtt accgccgtcc gagccagtaa caccggtgat cataatcagc cataccacat 17580
ttgtagaggt tttacttgct ttaaaaaacc tcccacacct ccccctgaac ctgaaacata 17640
aaatgaatgc aattgttgtt gttaacttgt ttattgcagc ttataatggt tacaaataaa 17700
gcaatagcat cacaaatttc acaaataaag catttttttc actgcattct agttgtggtt 17760
tgtccaaact catcaatgta tcttaacgcg agtttaggcg cg 17802

<210> SEQ ID NO 56
<211> LENGTH: 15134
<212> TYPE: DNA
<213> ORGANISM: Artificial Sequence
<220> FEATURE:
<223> OTHER INFORMATION: Synthetic construct, pLA3242-Crtra intron-
reaperKR construct.

<400> SEQUENCE: 56
gggcggccgt ttttcttgaa atattgctct ctctttctaa atagcgcgaa tccgtcgctg 60

```
tgcatttagg acatctcagt cgccgcttgg agctcccaaa cgcgccagtg gtagtacaca    120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaaagttt tcgcaatgcc tttatttttt gttgcaaatc    360
tctctttatt ctgcggtatt cttcattatt gcggggatgg ggaaagtgtt tatatagaag    420
caacttacga ttgaacccaa atgcacctga caagcaaggt caaagggcca gatttttaaa    480
tatattattt agtcttagga ctctctattt gcaattaaat tactttgcta cctgagggtt    540
aaatcttccc cattgataat aataattcca ctatatgttc aattgggttt caccgcgctt    600
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
caggtttaac caggggatgc ttaattgtgt tctcaacttc aaaggcagaa atgtttactc    840
ttgaccatgg gtttaggtat aatgttatca agctcctcga gttaacgtta cgttaacgtt    900
aacgttcgag gtcgactcta gaactaccca ccgtactcgt caattccaag ggcatcggta    960
aacatctgct caaactcgaa gtcggccata tccagagcgc cgtagggggc ggagtcgtgg   1020
ggggtaaatc ccggacccgg ggaatccccg tcccccaaca tgtccagatc gaaatcgtct   1080
agcgcgtcgg catgcgccat cgccacgtcc tcgccgtcta agtggagctc gtcccccagg   1140
ctgacatcgg tcgggggggc cgtcgacagt ctgcgcgtgt gtcccgcggg gagaaaggac   1200
aggcgcggag ccgccagccc cgcctcttcg ggggcgtcgt cgtccgggag atcgagcagg   1260
ccctcgatgg tagacccgta attgtttttc gtacgcgcgc ggctgtacgc ggggcccgag   1320
cccgactcgc atttcagttg cttttccaat ccgcagataa tcagctccaa gccgaacagg   1380
aatgccggct cggctccttg atgatcgaac agctcgattg cctgacgcag cagtgggggc   1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgcttttcg   1620
gtcgggcgcg tgccgagatg gactttggca ccgtctcggt gggacagcag agcgcagcgg   1680
aacgacttgg cgttattgcg gaggaagtcc tgccaggact cgccttccaa cgggcaaaaa   1740
tgcgtgtggt ggcggtcgag catctcgatg gccagggcat ccagcagcgc ccgcttattc   1800
ttcacgtgcc agtagagggt gggctgctcc acgcccagct tctgcgccaa cttgcgggtc   1860
gtcagtccct caatgccaac ttcgttcaac agctccaacg cggagttgat gactttggac   1920
ttatccaggc ggctgaccta tagataccat agatgtatgg attagtatca tatacataca   1980
aaggctattt ttgggacata ttaatattaa caatttccgt gatagttttc accatttttg   2040
ttgaatgtta cgttgaaaat ttaaatttgt tttaaattaa ttttaccagt catgtgttct   2100
taaaagtttt tatgattgaa acggcataaa gtggttcaaa aatttatcaa gaaaggcttt   2160
ccttttttaa atcttatctt tttctcttaa aaatcactag tcaattcatt attaatttgt   2220
taacttgaat ttggaatgtc tatttacttt cagataaatt aaagcaagaa acttaatatt   2280
cgaaaaaaat tgattctaaa tggaatttca cttgatcttc atgtatgcat atcaattttt   2340
atttacattg tataataagt ttcgagttga ttgttgtaat ccacaggtgt cccagagaat   2400
```

-continued

```
taaattccaa attacccaag tttattgaat gttgattgta gtttcagttg ctttgttgct   2460
gcaacaatgg cttgttgatt gtagatattt tccctttcct tggtttactt attacataga   2520
ctgaaaaaga ggtttacttt tttgatactt atgaaaaatt tctattagtg attactaacc   2580
aatcgctata tgtttactag aaaacaaata aactctttac attaacattc aataatgttt   2640
gctctgtaac cgacaattga aggcgttaca gcaacagtaa tataactagc ttcttaaccc   2700
tcatctatta accccatcgt ttaaaacact atgttaaatg gtctaacaaa tctagatact   2760
aatagatgtc ttattactta gcagccacag ctgcaacatc caagacaatt tttgaaactt   2820
cttattgagc tcttggcagc agaaatgttg gtatttttca cagctttctg aaagaccggc   2880
accttcctcc ggttcccgtt tctgaattca agaggatttc cgacccccaa ttaatcccga   2940
aacaaataag gtatattcaa aatgatggaa aagtcatggc tgctgacctt atttttattc   3000
ctattgatag aatattattc cccttttaaa tacactgtac taagaggtcc ggctataatt   3060
ttactcactt gtcgattatc ccatagaatg ttgattgtag ttggttgctt ttccaggtga   3120
gagttgatca agtcacaaaa gttagcgtgt gttgattgta gatttgaagg taaaataatt   3180
tttgcaccca ttcatcgggt aaaacgttct ccatagaata catttccatc gataattgat   3240
aacttatgaa tttcaaagaa aaaaatatgc ttttaaaatt accatggtgg ctagcgcaga   3300
ttgtttagct tgttcagctg cgcttgttta tttgcttagc tttcgcttag cgacgtgttc   3360
actttgcttg tttgaattga attgtcgctc cgtagacgaa gcgcctctat ttatactccg   3420
gcgctcgttt tcgagtttac cactccctat cagtgataga gaaaagtgaa agtcgagttt   3480
accactccct atcagtgata gagaaaagtg aaagtcgagt ttaccactcc ctatcagtga   3540
tagagaaaag tgaaagtcga gtttaccact ccctatcagt gatagagaaa agtgaaagtc   3600
gagtttacca ctccctatca gtgatagaga aaagtgaaag tcgagtttac cactccctat   3660
cagtgataga gaaaagtgaa agtcgagttt accactccct atcagtgata gagaaaagtg   3720
aaagtcgaaa cctggcgcgc ctaaactcgc gttaagatac attgatgagt ttggacaaac   3780
cacaactaga atgcagtgaa aaaaatgctt tatttgtgaa atttgtgatg ctattgcttt   3840
atttgtaacc attataagct gcaataaaca agttaacaac aacaattgca ttcattttat   3900
gtttcaggtt cagggggagg tgtgggaggt tttttaaagc aagtaaaacc tctacaaatg   3960
tggtatggct gattatgatc accggtgtta ctggctcgga cggcggtaac ggccgctgcg   4020
gcggccggtg cgcgggtggc agctggtgta ctggcgcagg gtctccagca ccacggtggc   4080
caggaagcgc cactggctct cgcgcaggcg caggatctgc tgctcgcgct gctcggcctc   4140
gcgcagcagg gtggcctgat ccgggatgta gaaggccacc taaagatacc atggatgtat   4200
gaattagtat catatacata taaatgcttt ttttttggc atattaatgt taaaaatatc   4260
aacaatttcc gtgatagttt ttaccatttt tgttgaatgt ttactttgaa aacttaaata   4320
tttttaact aattttacca gtcatgtgtt attaaaagta tttatgaata aaactgcaag   4380
taaagcgttt caaaaattta tcaagtaaaa ctttactttt tttaaatctt aactgtcaat   4440
tcattattaa tttattaatt taaatttgca atgtctattt actttaagac aaattaaagc   4500
aagaaactaa atattcgaat caattctttt ttaaatgaaa ttttacttca tcatcatgta   4560
tgtgtgtatc aatttttatt tacattgtat aataagtttc gagttgattg ttgtaatccg   4620
caggtgtccc gaagtattaa attccgaatt cccaagttta ttgaatgttg attgtagttt   4680
cagttgtttt gttattgcaa caatggcttg ttgattggag atattttcct tttccttggt   4740
ttacttacta catagactga aaaagatgtt tgactttttt gatactattg taaaatttct   4800
```

```
attagtgatt actaaccaat cgctataagt ttaatagaaa acaaataaac tctttgcatc   4860
cagatatacc tagcttctta acccttatct attaactcca ttgcttgtaa caaatctaga   4920
tattaataga tgtctaatta cttagcaaaa cttctttttg attaagcagc cacagctgtc   4980
gattttggtc atatttaaag gaaataaatg cgtttaaaat aataattaat ataagttttg   5040
aaacttttta ctaacacttg gcagcaggaa gtaggtgttt ttcacagctt tctgaaccac   5100
cggcaccttc cccggtctcc gttgtcggag ttcagcagga tttccggccc ccaattaacc   5160
ccgaaacaaa acatgtctta ttaataaggt gtattcaaaa tagtgggaat gtcatgactg   5220
ctgaccttat ttttattcct attgtaagtg ttccggctat aattttactc acttgtccat   5280
tatcccatag aatgttatgt tgattgtagt tgtttgcttt tccaggtgag agttgatcaa   5340
gtcgcaaaag ttagcgtgtg ttgattgtag atttgaaggt aaaataattt tgtacacatt   5400
catcaggcaa aacgttctcc atcgaataaa cttccatcga taattgatag cttatgaatt   5460
tcaaaaaaaa atatgctttt aaaattaccg ccatggtggt tgctagcttg tcgcagtggt   5520
aacaaactcg tgactgactg aacaattgca acaggcatta gtttatatat cgctcaggta   5580
gacggatcga tctctatcac tgatagggag gtctctatca ctgataggga gttctctatc   5640
actgataggg atgtctctat cactgatagg gatttctcta tcactgatag ggaagtctct   5700
atcactgata gggacctctc tatcactgat agggaaatct ctatcactga tagggatctc   5760
tctatcactg atagggactt ctctatcact gatagggacg tctctatcac tgatagggaa   5820
ctctctatca ctgataggga catctctatc actgataggg acttctctat cactgatagg   5880
gagtatgttc tctctcttct cttctctctc tctttctcga atgttctctc tcttctcttc   5940
tctctctctt tctcgatggc cggcctggct taattaactc gcgttaagat acattgatga   6000
gtttggacaa accacaacta gaatgcagtg aaaaaaatgc tttatttgtg aaatttgtga   6060
tgctattgct ttatttgtaa ccattataag ctgcaataaa caagttaaca acaacaattg   6120
cattcatttt atgtttcagg ttcaggggga ggtgtgggag gttttttaaa gcaagtaaaa   6180
cctctacaaa tgtggtatgg ctgattatga tcagttatct agatccggtg gatcttacgg   6240
gtcctccacc ttccgctttt tcttgggtcg agatctgagt ccggaatcct cgtcgctacc   6300
gatggcgctg gtgatgcggg gcacgctgtg ggcgtaggtc acctcgcgct ggcacacgtg   6360
gtcgcgcttg tcgctggtgt ccctcatctg cttggtgatg atggtcacga agtgggggcc   6420
ggggatcttg atggcgcggc tgccgttgaa ggtcatcttg ctgtcgaagt ggcccatcat   6480
caggccgccg tcggcggtgg tgaagccgat gaaggccagc tggcgcacgg cgttggggcc   6540
gtgggggaac atgtgggtct cgttgggcag gatgtccacc agctggtcgc gcatgatggg   6600
gccgtcgggc tggaagccgt cgcagttcac ggtgatgcgg ctgaccacgc aggtgccgtc   6660
cagctcgtag gtgtggtggc tggtcatggt gccgtcgttc tcgaagcgca cggtgcggtc   6720
gatgctcagg ccctcgggga agcactcctg ggcgaagtgg ctgatgccgt tggggtagcg   6780
ggcgaagaag ggctcgccgt actggatcag gtggcagatg ggcttccagc tcatgggcag   6840
cttgccggtc tcgcacacgg cgtgcacgtt gaagtcgccg tgggggaact tgctgctgcc   6900
gtcggccacg atggtgaact tctggccgtt cacctcgccg tcgatgaaga ttttgaaggt   6960
catgtcgctc tggaacaggg cggggccgcc ctctgaacca tcctcgtcca tggtggcgac   7020
cggtttgcgc ttcttcttgg gtggggtggg atctcccatg gtggcctgaa tctcaacttg   7080
cacctgaagg tagtgcagca aggatgagca aaagggaaga acccagaaaa gaacgggaaa   7140
```

-continued

```
acttacccca attagaattg cttgtcgccg ccagtgtcaa cttgcaactg aaacaatatc   7200
caacatgaac gtcaatttat actgccctaa tggcgaacac gataacaata tttcttttat   7260
tatgccctct aaaaccaacg cggttatcgt ttatttattc aaattagata tagaacatcc   7320
gccgacatac aatgttaatg caaaaacgcg tttggtgagc ggatacgaaa acagtcggcc   7380
gataaacatt aatctgaggt cgataacacc gtccttgaac ggaacacgag gagcgtacgt   7440
gatcagctgc attcgcgcgc cgcgccttta tcgagattta tttgcataca acaagtacac   7500
tgcgccgttg ggatttgtgg taacgcgcac acatgcagag ctgcaagtgt ggcacatttt   7560
gtctgtgcgc aaaacctttg aagccaaaag tacgaggtcc gttacgggca tgctagcgca   7620
cacggacaat ggacccgaca aattctacgc caaggattta atgataatgt cgggcaacgt   7680
atccgttcat tttatcaata acctacaaaa atgtcgcgcg catcacaaag acatcgatat   7740
atttaaacat ttatgtcccg aactgcaaat cgataatagt gttgtgcaac ctcgagcgtc   7800
cgtttgattt aacgtatagc ttgcaaatga attatttaat tatcaatcat gttttacgcg   7860
tagaattcta cccgtaaagc gagtttagtt atgagccatg tgcaaaacat gacatcagct   7920
tttattttta taacaaatga catcatttct tgattgtgtt ttacacgtag aattctactc   7980
gtaaagcgag ttcagttttg aaaaacaaat gacatcatct tttgattgt gctttacaag   8040
tagaattcta cccgtaaatc aagttcggtt ttgaaaaaca aatgagtcat attgtatgat   8100
atcatattgc aaaacaaatg actcatcaat cgatcgtgcg ttacacgtag aattctactc   8160
gtaaagcgag tttatgagcc gtgtgcaaaa catgacatca tctcgatttg aaaaacaaat   8220
gacatcatcc actgatcgtg cattacaagt agaattctac tcgtaaagcc agttcggtta   8280
tgagccgtgt acaaaacatg acatcagatt atgactcata cttgattgtg ttttacgcgt   8340
agaattctac tcgtaaagcc agttcaattt taaaaacaaa tgacatcatc caaattaata   8400
aatgacaagc aatgggtacc atgcggccgc accgaaatcg taattcacgg catcattaca   8460
aaatattttg acgttttgga cctcgtccct aatgacacca taacggtggc cttgaagtat   8520
atttaaccct agaaagatag tctgcgtaaa attgacgcat gcattcttga aatattgctc   8580
tctctttcta aatagcgcga atccgtcgct gtgcatttag gacatctcag tcgccgcttg   8640
gagctcccgt gaggcgtgct tgtcaatgcg gtaagtgtca ctgattttga actataacga   8700
ccgcgtgagt caaaatgacg catgattatc ttttacgtga cttttaagat ttaactcata   8760
cgataattat attgttattt catgttctac ttacgtgata acttattata tatatatttt   8820
cttgttatag atatcgtgac taatatataa taaaatgggt agttctttag acgatgagca   8880
tatcctctct gctcttctgc aaagcgatga cgagcttgtt ggtgaggatt ctgacagtga   8940
aatatcagat cacgtaagtg aagatgacgt ccaggaaatc tggccggccg caaccattgt   9000
gggaaccgtg cgatcaaaca aacgcgagat accggaagta ctgaaaaaca gtcgctccag   9060
gccagtggga acatcgatgt tttgttttga cggacccctt actctcgtct catataaacc   9120
gaagccagct aagatggtat acttattatc atcttgtgat gaggatgctt ctatcaacga   9180
aagtaccggt aaaccgcaaa tggttatgta ttataatcaa actaaaggcg gagtggacac   9240
gctagaccaa atgtgttctg tgatgacctg cagtaggaag acgaataggt ggcctatggc   9300
attattgtac ggaatgataa acattgcctg cataaattct tttattatat acagccataa   9360
tgtcagtagc aagggagaaa aggtccaaag tcgcaaaaaa tttatgagaa acctttacat   9420
gagcctgacg tcatcgttta tgcgtaagcg tttagaagct cctactttga agagatattt   9480
gcgcgataat atctctaata ttttgccaaa tgaagtgcct ggtacatcag atgacagtac   9540
```

```
tgaagagcca gtaatgaaaa aacgtactta ctgtacttac tgcccctcta aaataaggcg   9600
aaaggcaaat gcatcgtgca aaaaatgcaa aaaagttatt tgtcgagagc ataatattga   9660
tatgtgccaa agttgtttct gactgactaa taagtataat ttgtttctat tatgtataag   9720
ttaagctaat tacttatttt ataatacaac atgactgttt ttaaagtaca aaataagttt   9780
atttttgtaa aagagagaat gtttaaaagt tttgttactt tatagaagaa attttgagtt   9840
tttgtttttt tttaataaat aaataaacat aaataaattg tttgttgaat ttattattag   9900
tatgtaagtg taaatataat aaaacttaat atctattcaa attaataaat aaacctcgat   9960
atacagaccg ataaaacaca tgcgtcaatt ttacgcatga ttatctttaa cgtacgtcac  10020
aatatgatta tctttctagg gttaaataat agtttctaat ttttttatta ttcagcctgc  10080
tgtcgtgaat accgtatatc tcaacgctgt ctgtgagatt gtcgtattct agccttttta  10140
gtttttcgct catcgacttg atattgtccg acacattttc gtcgatttgc gttttgatca  10200
aagacttgag cagagacacg ttaatcaact gttcaaattg atccatatta acgatatcaa  10260
cccgatgcgt atatggtgcg taaaatatat tttttaaccc tcttatactt tgcactctgc  10320
gttaatacgc gttcgtgtac agacgtaatc atgttttctt ttttggataa aactcctact  10380
gagtttgacc tcatattaga ccctcacaag ttgcaaaacg tggcattttt taccaatgaa  10440
gaatttaaag ttattttaaa aaatttcatc acagatttaa agaagaacca aaaattaaat  10500
tatttcaaca gtttaatcga ccagttaatc aacgtgtaca cagacgcgtc ggcaaaaaac  10560
acgcagcccg acgtgttggc taaaattatt aaatcaactt gtgttatagt cacggatttg  10620
ccgtccaacg tgttcctcaa aaagttgaag accaacaagt ttacggacac tattaattat  10680
ttgattttgc cccacttcat tttgtgggat cacaattttg ttatatttta aacaaagctt  10740
ggcactggcc gtcgttttac aacgtcgtga ctgggaaaac cctggcgtta cccaacttaa  10800
tcgccttgca gcacatcccc ctttcgccag ctggcgtaat agcgaagagg cccgcaccga  10860
tcgcccttcc caacagttgc gcagcctgaa tggcgaatgg cgcctgatgc ggtattttct  10920
ccttacgcat ctgtgcggta tttcacaccg catatggtgc actctcagta caatctgctc  10980
tgatgccgca tagttaagcc agccccgaca cccgccaaca cccgctgacg cgccctgacg  11040
ggcttgtctg ctcccggcat ccgcttacag acaagctgtg accgtctccg ggagctgcat  11100
gtgtcagagg ttttcaccgt catcaccgaa acgcgcgaga cgaaagggcc tcgtgatacg  11160
cctattttta taggttaatg tcatgataat aatggtttct tagacgtcag gtggcacttt  11220
tcggggaaat gtgcgcggaa cccctatttg tttatttttc taaatacatt caaatatgta  11280
tccgctcatg agacaataac cctgataaat gcttcaataa tattgaaaaa ggaagagtat  11340
gagtattcaa catttccgtg tcgcccttat tccctttttt gcggcatttt gccttcctgt  11400
ttttgctcac ccagaaacgc tggtgaaagt aaaagatgct gaagatcagt tgggtgcacg  11460
agtgggttac atcgaactgg atctcaacag cggtaagatc cttgagagtt ttcgccccga  11520
agaacgtttt ccaatgatga gcacttttaa agttctgcta tgtggcgcgg tattatcccg  11580
tattgacgcc gggcaagagc aactcggtcg ccgcatacac tattctcaga atgacttggt  11640
tgagtactca ccagtcacag aaaagcatct tacggatggc atgacagtaa gagaattatg  11700
cagtgctgcc ataaccatga gtgataacac tgcggccaac ttacttctga caacgatcgg  11760
aggaccgaag gagctaaccg cttttttgca caacatgggg gatcatgtaa ctcgccttga  11820
tcgttgggaa ccggagctga atgaagccat accaaacgac gagcgtgaca ccacgatgcc  11880
```

tgtagcaatg gcaacaacgt tgcgcaaact attaactggc gaactactta ctctagcttc 11940
ccggcaacaa ttaatagact ggatggaggc ggataaagtt gcaggaccac ttctgcgctc 12000
ggcccttccg gctggctggt ttattgctga taaatctgga gccggtgagc gtgggtctcg 12060
cggtatcatt gcagcactgg ggccagatgg taagccctcc cgtatcgtag ttatctacac 12120
gacggggagt caggcaacta tggatgaacg aaatagacag atcgctgaga taggtgcctc 12180
actgattaag cattggtaac tgtcagacca agtttactca tatatacttt agattgattt 12240
aaaacttcat ttttaattta aaaggatcta ggtgaagatc ctttttgata atctcatgac 12300
caaaatccct taacgtgagt tttcgttcca ctgagcgtca gaccccgtag aaaagatcaa 12360
aggatcttct tgagatcctt tttttctgcg cgtaatctgc tgcttgcaaa caaaaaaacc 12420
accgctacca gcggtggttt gtttgccgga tcaagagcta ccaactcttt ttccgaaggt 12480
aactggcttc agcagagcgc agataccaaa tactgtcctt ctagtgtagc cgtagttagg 12540
ccaccacttc aagaactctg tagcaccgcc tacatacctc gctctgctaa tcctgttacc 12600
agtggctgct gccagtggcg ataagtcgtg tcttaccggg ttggactcaa gacgatagtt 12660
accggataag gcgcagcggt cgggctgaac ggggggttcg tgcacacagc ccagcttgga 12720
gcgaacgacc tacaccgaac tgagatacct acagcgtgag cattgagaaa gcgccacgct 12780
tcccgaaggg agaaaggcgg acaggtatcc ggtaagcggc agggtcggaa caggagagcg 12840
cacgagggag cttccagggg gaaacgcctg gtatctttat agtcctgtcg ggtttcgcca 12900
cctctgactt gagcgtcgat ttttgtgatg ctcgtcaggg gggcggagcc tatggaaaaa 12960
cgccagcaac gcggcctttt tacggttcct ggccttttgc tggccttttg ctcacatgtt 13020
ctttcctgcg ttatcccctg attctgtgga taaccgtatt accgcctttg agtgagctga 13080
taccgctcgc cgcagccgaa cgaccgagcg cagcgagtca gtgagcgagg aagcggaaga 13140
gcgcccaata cgcaaaccgc ctctccccgc gcgttggccg attcattaat gcagctggca 13200
cgacaggttt cccgactgga aagcgggcag tgagcgcaac gcaattaatg tgagttagct 13260
cactcattag gcaccccagg ctttacactt tatgcttccg gctcgtatgt tgtgtggaat 13320
tgtgagcgga taacaatttc acacaggaaa cagctatgac catgattacg aatttcgacc 13380
tgcaggcatg caagcttgca tgcctgcagg tcgacgctcg cgcgacttgg tttgccattc 13440
tttagcgcgc gtcgcgtcac acagcttggc cacaatgtgg tttttgtcaa acgaagattc 13500
tatgacgtgt ttaaagttta ggtcgagtaa agcgcaaatc tttttaacc ctagaaagat 13560
agtctgcgta aaattgacgc atgcattctt gaaatattgc tctctctttc taaatagcgc 13620
gaatccgtcg ctgtgcattt aggacatctc agtcgccgct tggagctccc gtgaggcgtg 13680
cttgtcaatg cggtaagtgt cactgatttt gaactataac gaccgcgtga gtcaaaatga 13740
cgcatgatta tcttttacgt gacttttaag atttaactca tacgataatt atattgttat 13800
ttcatgttct acttacgtga taacttatta tatatatatt ttcttgttat agatatcgtg 13860
actaatatat aataaaatgg gtagttcttt agacgatgag catatcctct ctgctcttct 13920
gcaaagcgat gacgagcttg ttggtgagga ttctgacagt gaaatatcag atcacgtaag 13980
tgaagatgac gtccagagcg atacagaaga agcgtttata gatgaggtac atgaagtgca 14040
gccaacgtca agcggtagtg aaatattaga cgaacaaaat gttattgaac aaccaggttc 14100
ttcattggct tctaacagaa tcttgacctt gccacagagg actattagag gtaagaataa 14160
acattgttgg tcaacttcaa agtccacgag gcgtagccga gtctctgcac tgaacattgt 14220
cagatcggcc cggcggagtg gacacgctag accaaatgtg ttctgtgatg acctgcagta 14280

```
ggaagacgaa taggtggcct atggcattat tgtacggaat gataaacatt gcctgcataa  14340

attcttttat tatatacagc cataatgtca gtagcaaggg agaaaaggtc caaagtcgca  14400

aaaaatttat gagaaacctt tacatgagcc tgacgtcatc gtttatgcgt aagcgtttag  14460

aagctcctac tttgaagaga tatttgcgcg ataatatctc taatattttg ccaaatgaag  14520

tgcctggtac atcagatgac agtactgaag agccagtaat gaaaaaacgt acttactgta  14580

cttactgccc ctctaaaata aggcgaaagg caaatgcatc gtgcaaaaaa tgcaaaaaag  14640

ttatttgtcg agagcataat attgatatgt gccaaagttg tttctgactg actaataagt  14700

ataatttgtt tctattatgt ataagttaag ctaattactt attttataat acaacatgac  14760

tgtttttaaa gtacaaaata agtttatttt tgtaaaagag agaatgttta aaagttttgt  14820

tactttatag aagaaatttt gagtttttgt tttttttaa taaataaata aacataaata  14880

aattgtttgt tgaatttatt attagtatgt aagtgtaaat ataataaaac ttaatatcta  14940

ttcaaattaa taaataaacc tcgatataca gaccgataaa acacatgcgt caattttacg  15000

catgattatc tttaacgtac gtcacaatat gattatcttt ctagggttaa aatgaatgta  15060

agcactttat taacgaaatc tttgggaata tttcgctcat cagcatttta tttgagcagg  15120

agtccgagat gccc                                                     15134
```

<210> SEQ ID NO 57
<211> LENGTH: 1403
<212> TYPE: DNA
<213> ORGANISM: Artificial Sequence
<220> FEATURE:
<223> OTHER INFORMATION: Synthetic construct, partial sequence of a male transcript generated in Drosophila melanogaster from LA3077 transformants that differs to the sequence generated in Medfly LA3077 lines.

<400> SEQUENCE: 57

```
ggccagatct gttgttatta aacgtagatt tggtaatttt aaaagcatat tttttctttt     60

gaaattcata agttatcaat tatcgatgga aatgtattct atggagaacg ttttacccga    120

tgaatgggtg caaaaattat tttaccttca aatctacaat caacacacgc taacttttgt    180

gacttgatca actctcacct ggaaaagcaa ccaactacaa tcaacattct atgggataat    240

cgacaagtga gtaaaattat agccggacct cttagtacag tgtatttaaa aggggaataa    300

tattctatca ataggaataa aaataaggtc agcagccatg acttttccat cattttgaat    360

ataccttatt tgtttcggga ttaattgggg gtcggaaatc ctcttgaatt cagaaacggg    420

aaccggagga aggtgccggt ctttcagaaa gctgtgaaaa ataccaacat ttctgctgcc    480

aagagctcaa taagaagttt caaaaattgt cttggatgtt gcagctgtgg ctgctaagta    540

ataagacatc tattagtatc tagatttgtt agaccattta acatagtgtt ttaaacgatg    600

gggttaatag atgagggtta agaagctagt tatattactg ttgctgtaac gccttcaatt    660

gtcggttaca gagcaaacat tattgaatgt taatgtaaag agtttatttg ttttctagta    720

aacatatagc gattggttag taatcactaa tagaaatttt tcataagtat caaaaaagta    780

aacctctttt tcagtctatg taataagtaa accaaggaaa gggaaaatat ctacaatcaa    840

caagccattg ttgcagcaac aaagcaactg aaactacaat caacattcaa taaacttggg    900

taatttggaa tttaattctc tgggacacct gtggattaca acaatcaact cgaaacttat    960

tatacaatgt aaataaaaat tgatatgcat acatgaagat caagtgaaat tccatttaga   1020

atcaattttt ttcgaatatt aagtttcttg ctttaattta tctgaaagta aatagacatt   1080
```

ccaaattcaa gttaacaaat taataatgaa ttgactagtg atttttaaga gaaaaagata 1140
agatttaaaa aaggaaagcc tttcttgata aatttttgaa ccactttatg ccgtttcaat 1200
cataaaaact tttaagaaca catgactggt aaaattaatt taaaacaaat ttaaattttc 1260
aacgtaacat tcaacaaaaa tggtgaaaac tatcacggaa attgttaata ttaatatgtc 1320
ccaaaaatag cctttgtatg tatatgatac taatccatac atctatggta tctataggtg 1380
aaggctcaaa gcctctggct agc 1403

<210> SEQ ID NO 58
<211> LENGTH: 972
<212> TYPE: DNA
<213> ORGANISM: Bactrocera zonata

<400> SEQUENCE: 58
cggtaattct aattacttac taaatatagt gatatttaaa aatgctatga gatcttgagg 60
cgaacttaaa tgagacaagg tgttagcttg ctcaaatgac gcaccaatca acttaccaag 120
ataatttgga gcaatatgga atattttctt gtcaaagaac tacaatcaac atgcaactgg 180
tataataaag tgagtataaa gtagaaaggt gcggtataat atttttctct aaagtattaa 240
ggtaagtttt taaaaataat ttaataattt ttcagagtgt gcagtattag tgtctaaaag 300
tattgcaatc tttgtgtttt aaaaatttgt gcagaatatc aaaaaatagg acgacctatt 360
gttagtaata ttatgtatat ttacttattt tcaaataaat aaaattattt tctagccttt 420
agaaacagcc ttatactaca atcaacaaac cataaatact ccctgcaaca attacaaagc 480
aacacaaaca acaatcaaca ttccatgaac tcggacaatt tggaaattga tatcttctgg 540
cacatgcgga ttacaacaat caactcaaac ctattagatg atgtaaataa atataaacct 600
tcatattcaa taacttaatt cgtgatagaa atttagagtt aattactgtt taatcgaaat 660
ttgaacgtct cgtttgaatt cactttaacg tttgaaagat gatctttaaa tagtgactgg 720
agacttaaat tttaatcttt ttaattaaat aatctaacaa agttctttct tattctaatc 780
ttaatatata atcttgtttt aaaatttgaa ttaaacttat ttcgttgagt aacaattaaa 840
tgatttgaat cgtaaaaaat atcattataa ttattcaaca aaaagctgaa ggctgcgatg 900
aaaaattgtt gatatataaa tcaaatttat ttttataaat cactaatagt gacattaacc 960
gtattcacag gt 972

<210> SEQ ID NO 59
<211> LENGTH: 1312
<212> TYPE: DNA
<213> ORGANISM: Ceratitis rosa

<400> SEQUENCE: 59
tggtaatttt aaaagcatat ttttttttga aattcataag ctatcaatta tcgatggaag 60
tttattcgat ggagaacgtt ttgcctgatg aatgtgtaca aaattatttt accttcaaat 120
ctacaatcaa cacacgctaa cttttgcgac ttgatcaact ctcacctgga aaagcaaaca 180
actacaatca acataacatt ctatgggata atggacaagt gagtaaaatt atagccggaa 240
cacttacaat aggaataaaa ataaggtcag cagtcatgac attccccacta ttttgaatac 300 accttattaa taagacatgt tttgtttcgg ggttaattgg gggccggaaa tcctgctgaa 360
ctccgacaac ggagaccggg gaaggtgccg gtggttcaga aagctgtgaa aaacacctac 420
ttcctgctgc caagtgttag taaaaagttt caaaacttat attaattatt attttaaacg 480

-continued

```
catttatttc ctttaaatat gaccaaaatc gacagctgtg gctgcttaat caaaaagaag    540

ttttgctaag taattagaca tctattaata tctagatttg ttacaagcaa tggagttaat    600

agataagggt taagaagcta ggtatatctg gatgcaaaga gtttatttgt tttctattaa    660

acttatagcg attggttagt aatcactaat agaaatttta caatagtatc aaaaaagtca    720

aacatctttt tcagtctatg tagtaagtaa accaaggaaa aggaaaatat ctccaatcaa    780

caagccattg ttgcaataac aaaacaactg aaactacaat caacattcaa taaacttggg    840

aattcggaat ttaatacttc gggacacctg cggattacaa caatcaactc gaaacttatt    900

atacaatgta aataaaaatt gatacacaca tacatgatga tgaagtaaaa tttcatttaa    960

aaaagaattg attcgaatat ttagtttctt gctttaattt gtcttaaagt aaatagacat   1020

tgcaaattta aattaataaa ttaataatga attgacagtt aagatttaaa aaaagtaaag   1080

ttttacttga taaatttttg aaacgcttta cttgcagttt tattcataaa tacttttaat   1140

aacacatgac tggtaaaatt agttaaaaaa tatttaagtt ttcaaagtaa acattcaaca   1200

aaaatggtaa aaactatcac ggaaattgtt gatattttta acattaatat gccaaaaaaa   1260

aaagcattta tatgtatatg atactaattc atacatccat ggtatcttta gg           1312
```

<210> SEQ ID NO 60
<211> LENGTH: 21
<212> TYPE: DNA
<213> ORGANISM: Artificial Sequence
<220> FEATURE:
<223> OTHER INFORMATION: Synthetic construct, spl-agdsx-e3 primer

<400> SEQUENCE: 60

```
cgagcccaat ggctgttgga g                                                21
```

<210> SEQ ID NO 61
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 61

```
gtcaaggttc agggcccgat cg                                               22
```

<210> SEQ ID NO 62
<211> LENGTH: 21
<212> TYPE: DNA
<213> ORGANISM: Artificial Sequence
<220> FEATURE:
<223> OTHER INFORMATION: Synthetic construct, primer spl-agdsx-e3

<400> SEQUENCE: 62

```
cgagcccaat ggctgttgga g                                                21
```

<210> SEQ ID NO 63
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 63

```
gtcaaggttc agggcccgat cg                                               22
```

<210> SEQ ID NO 64
<211> LENGTH: 20

<212> TYPE: DNA
<213> ORGANISM: Artificial Sequence
<220> FEATURE:
<223> OTHER INFORMATION: Synthetic construct, aedesxF1 primer

<400> SEQUENCE: 64
tcaatggctc ctggagaagc 20

<210> SEQ ID NO 65
<211> LENGTH: 25
<212> TYPE: DNA
<213> ORGANISM: Artificial Sequence
<220> FEATURE:
<223> OTHER INFORMATION: Synthetic construct, aedesxR5 primer

<400> SEQUENCE: 65
accattcttg cagaagtctt gggac 25

<210> SEQ ID NO 66
<211> LENGTH: 19
<212> TYPE: DNA
<213> ORGANISM: Artificial Sequence
<220> FEATURE:
<223> OTHER INFORMATION: Synthetic construct, aedesxR2 primer

<400> SEQUENCE: 66
aacattctcc gcgcacagg 19

<210> SEQ ID NO 67
<211> LENGTH: 23
<212> TYPE: DNA
<213> ORGANISM: Artificial SeqUence
<220> FEATURE:
<223> OTHER INFORMATION: Synthetic construct, Agexon1 primer

<400> SEQUENCE: 67
gacgctcgct ctggtacagt tcg 23

<210> SEQ ID NO 68
<211> LENGTH: 20
<212> TYPE: DNA
<213> ORGANISM: Artificial Sequence
<220> FEATURE:
<223> OTHER INFORMATION: Synthetic construct, Tra (tTAV) seq+ primer

<400> SEQUENCE: 68
cctgccagga ctcgccttcc 20

<210> SEQ ID NO 69
<211> LENGTH: 23
<212> TYPE: DNA
<213> ORGANISM: Artificial Sequence
<220> FEATURE:
<223> OTHER INFORMATION: Synthetic construct, Agexon1 primer

<400> SEQUENCE: 69
gacgctcgct ctggtacagt tcg 23

<210> SEQ ID NO 70
<211> LENGTH: 26
<212> TYPE: DNA
<213> ORGANISM: Artificial Sequence
<220> FEATURE:
<223> OTHER INFORMATION: Synthetic construct, Exon 3 primer

<400> SEQUENCE: 70
gttgtcgctt tgactggcaa tgtcgc 26

<210> SEQ ID NO 71
<211> LENGTH: 632
<212> TYPE: DNA
<213> ORGANISM: Pectinophora gossypiella

<400> SEQUENCE: 71
gaactgccac aaactgctgg aaaagttcca ctactcctgg gaaatgatgc ccctggtgct 60
ggtcattcta aactacgccg gctccgacct cgacgaggct tctagaaaaa ttgatgaagg 120
gaagatgatc atcaacgagt acgcgaggga gcacaatctg aacatcttcg atggccacga 180
gctgaggaac tcgactcgcc agaaaatgct gagcgaaatt aataatataa gtggtgtact 240
atcgtcgtcc atgaagttat tttgcgaatg atactttgtt ttgtatgtgc tgtgtgttgt 300
gtggactttt gctgtgcgtt gctgtttgcg atggaaggac tattgtgtcg tcgccacgct 360
ggactattcg cacattgggt ggtccaccag tggcggatgt acgagcggtc gctgtgctcg 420
ctcctggagc tgcaagcgcg caaagggacg tactcggtgt gctgctcacc ccgctacgtc 480
atcgcgcccg agtacgcgtc acacctgttg cctctgccgc ttaccacgca gagatcatcc 540
ccgccgcccg cgcacttgta gcgatgcgaa cctgcgccgc gggaagcggc gcaagaaccc 600
gccgatgccc cggcgtcgtc gtcgggtgcc ac 632

<210> SEQ ID NO 72
<211> LENGTH: 222
<212> TYPE: DNA
<213> ORGANISM: Drosophila melanogaster

<400> SEQUENCE: 72
atgcagatct ttgtgaagac tttgaccgga aagaccatca ccctcgaggt agagccatcg 60
gacaccattg agaatgtaaa ggccaagatt caggataagg agggaatccc cccagatcag 120
cagcgtctga tcttcgctgg caagcaactg gaagacggac gcaccctgtc cgattacaac 180
atccagaagg agtccaccct tcacttggtc cttcgtctcc gt 222

<210> SEQ ID NO 73
<211> LENGTH: 74
<212> TYPE: PRT
<213> ORGANISM: Drosophila melanogaster

<400> SEQUENCE: 73

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 74
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 74
caagcaaagt gaacacgtcg ctaagcgaaa gcta 34

<210> SEQ ID NO 75
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 75
gcgggtggca gctggtgtac tg 22

<210> SEQ ID NO 76
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 76
caagcaaagt gaacacgtcg ctaagcgaaa gcta 34

<210> SEQ ID NO 77
<211> LENGTH: 24
<212> TYPE: DNA
<213> ORGANISM: Artificial Sequence
<220> FEATURE:
<223> OTHER INFORMATION: Synthetic construct, primer

<400> SEQUENCE: 77
gcggaacgac ttggcgttat tgcg 24

<210> SEQ ID NO 78
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 78
ggaagggtcc ttacgctata gagcgcag 28

<210> SEQ ID NO 79
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 79
ccaggcgaag ttgttattaa gcgtagattt g 31

<210> SEQ ID NO 80
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 80
cgtcgctttg aaacagaggc tttgagcctt ctc 33

<210> SEQ ID NO 81
<211> LENGTH: 48

<212> TYPE: DNA
<213> ORGANISM: Artificial Sequence
<220> FEATURE:
<223> OTHER INFORMATION: Synthetic construct, primer

<400> SEQUENCE: 81
gctagcaacc accatggcgg taattctaat tacttactaa atatagtg 48

<210> SEQ ID NO 82
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 82
ccgggatgta gaaggccacc tgtgaatacg gttaatgtca c 41

<210> SEQ ID NO 83
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 83
cagtcagtca cgagtttgtt accactgcga c 31

<210> SEQ ID NO 84
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 84
gcgggtggca gctggtgtac tg 22

<210> SEQ ID NO 85
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 85
cggagcacat ctgatagaac g 21

<210> SEQ ID NO 86
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 86
cgcggctgta ggcgctgccg ctc 23

<210> SEQ ID NO 87
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 87
ccaggcgaag ttgttattaa gcgtagattt g 31

<210> SEQ ID NO 88
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 88
cgtcgctttg aaacagaggc tttgagcctt ctc 33

<210> SEQ ID NO 89
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 89
gctagcaacc accatggcgg taattttaaa agcatatttt tttttgaaat tc 52

<210> SEQ ID NO 90
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 90
ccgggatgta gaaggccacc taaagatacc atggatgtat g 41

<210> SEQ ID NO 91
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 91
cagtcagtca cgagtttgtt accactgcga c 31

<210> SEQ ID NO 92
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 92
gcgggtggca gctggtgtac tg 22

<210> SEQ ID NO 93
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 93
gttgcaagtt gacactggcg g 21

<210> SEQ ID NO 94
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 94
aggtgtggga ggttttttaa agc 23

<210> SEQ ID NO 95
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 95
cctgtaatac gactcactat agggcgtttt tttttttttt tttttttttt tt 52

<210> SEQ ID NO 96
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 96
gcaaacggca atcagacggg cccaggctca gga 33

<210> SEQ ID NO 97
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 97
cctgtaatac gactcactat agggcgtt 28

<210> SEQ ID NO 98
<211> LENGTH: 37
<212> TYPE: DNA
<213> ORGANISM: Artificial Sequence
<220> FEATURE:
<223> OTHER INFORMATION: Synthetic construct, primer

<400> SEQUENCE: 98
gggatcgagc tagatcggcc tgagccgcca gtggtga 37

<210> SEQ ID NO 99
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 99
cctgtaatac gactcactat agggcgtt 28

<210> SEQ ID NO 100
<211> LENGTH: 32
<212> TYPE: DNA
<213> ORGANISM: Artificial Sequence
<220> FEATURE:
<223> OTHER INFORMATION: Synthetic construct, primer

<400> SEQUENCE: 100
cgctccatgg gatcggcgag ctgcgactcc gt 32

<210> SEQ ID NO 101
<211> LENGTH: 27
<212> TYPE: DNA
<213> ORGANISM: Artificial Sequence
<220> FEATURE:
<223> OTHER INFORMATION: Synthetic construct, primer

<400> SEQUENCE: 101
gcaacaacca gcggtgtccc ttgaaac 27

<210> SEQ ID NO 102
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 102
cctgtaatac gactcactat agggcgtt 28

<210> SEQ ID NO 103
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 103
gctagtggag aactgccaca aactgctg 28

<210> SEQ ID NO 104
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 104
caagcaaagt gaacacgtcg ctaagcgaaa gcta 34

<210> SEQ ID NO 105
<211> LENGTH: 25
<212> TYPE: DNA
<213> ORGANISM: Artificial Sequence
<220> FEATURE:
<223> OTHER INFORMATION: Synthetic construct, primer

<400> SEQUENCE: 105
gccctcgatg gtagacccgt aattg 25

<210> SEQ ID NO 106
<211> LENGTH: 14874
<212> TYPE: DNA
<213> ORGANISM: Artificial Sequence
<220> FEATURE:
<223> OTHER INFORMATION: Synthetic construct, LA1172, including plasmid backbone

<400> SEQUENCE: 106
gggctggccg caaccattgt gggaaccgtg cgatcaaaca aacgcgagat accggaagta 60
ctgaaaaaca gtcgctccag gccagtggga acatcgatgt tttgttttga cggacccctt 120
actctcgtct catataaacc gaagccagct aagatggtat acttattatc atcttgtgat 180
gaggatgctt ctatcaacga aagtaccggt aaaccgcaaa tggttatgta ttataatcaa 240

-continued

```
actaaaggcg gagtggacac gctagaccaa atgtgttctg tgatgacctg cagtaggaag    300
acgaataggt ggcctatggc attattgtac ggaatgataa acattgcctg cataaattct    360
tttattatat acagccataa tgtcagtagc aagggagaaa aggtccaaag tcgcaaaaaa    420
tttatgagaa acctttacat gagcctgacg tcatcgttta tgcgtaagcg tttagaagct    480
cctactttga agagatattt gcgcgataat atctctaata ttttgccaaa tgaagtgcct    540
ggtacatcag atgacagtac tgaagagcca gtaatgaaaa aacgtactta ctgtacttac    600
tgcccctcta aaataaggcg aaaggcaaat gcatcgtgca aaaaatgcaa aaaagttatt    660
tgtcgagagc ataatattga tatgtgccaa agttgtttct gactgactaa taagtataat    720
ttgtttctat tatgtataag ttaagctaat tacttatttt ataatacaac atgactgttt    780
ttaaagtaca aaataagttt atttttgtaa aagagagaat gtttaaaagt tttgttactt    840
tatagaagaa attttgagtt tttgtttttt tttaataaat aaataaacat aaataaattg    900
tttgttgaat ttattattag tatgtaagtg taaatataat aaaacttaat atctattcaa    960
attaataaat aaacctcgat atacagaccg ataaaacaca tgcgtcaatt ttacgcatga   1020
ttatctttaa cgtacgtcac aatatgatta tctttctagg gttaaataat agtttctaat   1080
tttttttatta ttcagcctgc tgtcgtgaat accgtatatc tcaacgctgt ctgtgagatt   1140
gtcgtattct agccttttta gtttttcgct catcgacttg atattgtccg acacattttc   1200
gtcgatttgc gttttgatca aagacttgag cagagacacg ttaatcaact gttcaaattg   1260
atccatatta acgatatcaa cccgatgcgt atatggtgcg taaaatatat tttttaaccc   1320
tcttatactt tgcactctgc gttaatacgc gttcgtgtac agacgtaatc atgttttctt   1380
ttttggataa aactcctact gagtttgacc tcatattaga ccctcacaag ttgcaaaacg   1440
tggcattttt taccaatgaa gaatttaaag ttattttaaa aaatttcatc acagatttaa   1500
agaagaacca aaaattaaat tatttcaaca gtttaatcga ccagttaatc aacgtgtaca   1560
cagacgcgtc ggcaaaaaac acgcagcccg acgtgttggc taaaattatt aaatcaactt   1620
gtgttatagt cacggatttg ccgtccaacg tgttcctcaa aaagttgaag accaacaagt   1680
ttacggacac tattaattat ttgattttgc cccacttcat tttgtgggat cacaattttg   1740
ttatatttta aacaaagctt ggcactggcc gtcgttttac aacgtcgtga ctgggaaaac   1800
cctggcgtta cccaacttaa tcgccttgca gcacatcccc ctttcgccag ctggcgtaat   1860
agcgaagagg cccgcaccga tcgcccttcc caacagttgc gcagcctgaa tggcgaatgg   1920
cgcctgatgc ggtattttct ccttacgcat ctgtgcggta tttcacaccg catatatggt   1980
gcactctcag tacaatctgc tctgatgccg catagttaag ccagccccga cacccgccaa   2040
cacccgctga cgcgccctga cgggcttgtc tgctcccggc atccgcttac agacaagctg   2100
tgaccgtctc cgggagctgc atgtgtcaga ggttttcacc gtcatcaccg aaacgcgcga   2160
gacgaaaggg cctcgtgata cgcctatttt tataggttaa tgtcatgata ataatggttt   2220
cttagacgtc aggtggcact tttcggggaa atgtgcgcgg aacccctatt tgtttatttt   2280
tctaaataca ttcaaatatg tatccgctca tgagacaata accctgataa atgcttcaat   2340
aatattgaaa aaggaagagt atgagtattc aacatttccg tgtcgccctt attccctttt   2400
ttgcggcatt ttgccttcct gtttttgctc acccagaaac gctggtgaaa gtaaaagatg   2460
ctgaagatca gttgggtgca cgagtgggtt acatcgaact ggatctcaac agcggtaaga   2520
tccttgagag ttttcgcccc gaagaacgtt ttccaatgat gagcactttt aaagttctgc   2580
tatgtggcgc ggtattatcc cgtattgacg ccgggcaaga gcaactcggt cgccgcatac   2640
```

actattctca gaatgacttg gttgagtact caccagtcac agaaaagcat cttacggatg 2700
gcatgacagt aagagaatta tgcagtgctg ccataaccat gagtgataac actgcggcca 2760
acttacttct gacaacgatc ggaggaccga aggagctaac cgcttttttg cacaacatgg 2820
gggatcatgt aactcgcctt gatcgttggg aaccggagct gaatgaagcc ataccaaacg 2880
acgagcgtga caccacgatg cctgtagcaa tggcaacaac gttgcgcaaa ctattaactg 2940
gcgaactact tactctagct tcccggcaac aattaataga ctggatggag gcggataaag 3000
ttgcaggacc acttctgcgc tcggcccttc cggctggctg gtttattgct gataaatctg 3060
gagccggtga gcgtgggtct cgcggtatca ttgcagcact ggggccagat ggtaagccct 3120
cccgtatcgt agttatctac acgacgggga gtcaggcaac tatggatgaa cgaaatagac 3180
agatcgctga gataggtgcc tcactgatta agcattggta actgtcagac caagtttact 3240
catatatact ttagattgat ttaaaacttc atttttaatt taaaaggatc taggtgaaga 3300
tcctttttga taatctcatg accaaaatcc cttaacgtga gttttcgttc cactgagcgt 3360
cagaccccgt agaaaagatc aaaggatctt cttgagatcc tttttttctg cgcgtaatct 3420
gctgcttgca aacaaaaaaa ccaccgctac cagcggtggt ttgtttgccg gatcaagagc 3480
taccaactct ttttccgaag gtaactggct tcagcagagc gcagatacca aatactgtcc 3540
ttctagtgta gccgtagtta ggccaccact tcaagaactc tgtagcaccg cctacatacc 3600
tcgctctgct aatcctgtta ccagtggctg ctgccagtgg cgataagtcg tgtcttaccg 3660
ggttggactc aagacgatag ttaccggata aggcgcagcg gtcgggctga acggggggtt 3720
cgtgcacaca gcccagcttg gagcgaacga cctacaccga actgagatac ctacagcgtg 3780
agcattgaga aagcgccacg cttcccgaag ggagaaaggc ggacaggtat ccggtaagcg 3840
gcagggtcgg aacaggagag cgcacgaggg agcttccagg gggaaacgcc tggtatcttt 3900
atagtcctgt cgggtttcgc cacctctgac ttgagcgtcg atttttgtga tgctcgtcag 3960
gggggcggag cctatggaaa aacgccagca acgcggcctt tttacggttc ctggcctttt 4020
gctggccttt tgctcacatg ttctttcctg cgttatcccc tgattctgtg gataaccgta 4080
ttaccgcctt tgagtgagct gataccgctc gccgcagccg aacgaccgag cgcagcgagt 4140
cagtgagcga ggaagcggaa gagcgcccaa tacgcaaacc gcctctcccc gcgcgttggc 4200
cgattcatta atgcagctgg cacgacaggt ttcccgactg gaaagcgggc agtgagcgca 4260
acgcaattaa tgtgagttag ctcactcatt aggcacccca ggctttacac tttatgcttc 4320
cggctcgtat gttgtgtgga attgtgagcg gataacaatt tcacacagga aacagctatg 4380
accatgatta cgaatttcga cctgcaggca tgcaagcttg catgcctgca ggtcgacgct 4440
cgcgcgactt ggtttgccat tctttagcgc gcgtcgcgtc acacagcttg gccacaatgt 4500
ggtttttgtc aaacgaagat tctatgacgt gtttaaagtt taggtcgagt aaagcgcaaa 4560
tctttttaa ccctagaaag atagtctgcg taaaattgac gcatgcattc ttgaaatatt 4620
gctctctctt tctaaatagc gcgaatccgt cgctgtgcat ttaggacatc tcagtcgccg 4680
cttggagctc ccgtgaggcg tgcttgtcaa tgcggtaagt gtcactgatt ttgaactata 4740
acgaccgcgt gagtcaaaat gacgcatgat tatcttttac gtgactttta agatttaact 4800
catacgataa ttatattgtt atttcatgtt ctacttacgt gataacttat tatatatata 4860
ttttcttgtt atagatatcg tgactaatat ataataaaat gggtagttct ttagacgatg 4920
agcatatcct ctctgctctt ctgcaaagcg atgacgagct tgttggtgag gattctgaca 4980
gtgaaatatc agatcacgta agtgaagatg acgtccagag cgatacagaa gaagcgttta 5040
tagatgaggt acatgaagtg cagccaacgt caagcggtag tgaaatatta gacgaacaaa 5100
atgttattga acaaccaggt tcttcattgg cttctaacag aatcttgacc ttgccacaga 5160
ggactattag aggtaagaat aaacattgtt ggtcaacttc aaagtccacg aggcgtagcc 5220
gagtctctgc actgaacatt gtcagatcgg ccaggccggc cagatttaaa tgagcggccg 5280
catggtacca tactcggtgg cctccccacc accaactttt ttgcactgca aaaaaacacg 5340
cttttgcacg cgggcccata catagtacaa actctacgtt tcgtagacta ttttacataa 5400
atagtctaca ccgttgtata cgctccaaat acactaccac acattgaacc tttttgcagt 5460
gcaaaaaagt acgtgtcggc agtcacgtag gccggcctta tcgggtcgcg tcctgtcacg 5520
tacgaatcac attatcggac cggacgagtg ttgtcttatc gtgacaggac gccagcttcc 5580
tgtgttgcta accgcagccg gacgcaactc cttatcggaa caggacgcgc ctccatatca 5640
gccgcgcgtt atctcatgcg cgtgaccgga cacgaggcgc ccgtcccgct tatcgcgcct 5700
ataaatacag cccgcaacga tctggtaaac acagttgaac agcatctgtt acagcgacac 5760
aacatgagcc ggtccaacaa cgccaacgcg cccacgccat ccaaccgccg ccgcaacctg 5820
tctctggtgg atcccacccc acccaagaag aagcgcaaac cggtcgccac catggcctcc 5880
tccgagaacg tcatcaccga gttcatgcgc ttcaaggtgc gcatggaggg caccgtgaac 5940
ggccacgagt tcgagatcga gggcgagggc gagggccgcc cctacgaggg ccacaacacc 6000
gtgaagctga aggtgaccaa gggcggcccc ctgcccttcg cctgggacat cctgtccccc 6060
cagttccagt acggctccaa ggtgtacgtg aagcaccccg ccgacatccc cgactacaag 6120
aagctgtcct tccccgaggg cttcaagtgg gagcgcgtga tgaacttcga ggacggcggc 6180
gtggcgaccg tgacccagga ctcctccctg caggacggct gcttcatcta caaggtgaag 6240
ttcatcggcg tgaacttccc ctccgacggc cccgtgatgc agaagaagac catgggctgg 6300
gaggcctcca ccgagcgcct gtacccccgc gacggcgtgc tgaagggcga gacccacaag 6360
gccctgaagc tgaaggacgg cggccactac ctggtggagt tcaagtccat ctacatggcc 6420
aagaagcccg tgcagctgcc cggctactac tacgtggacg ccaagctgga catcacctcc 6480
cacaacgagg actacaccat cgtggagcag tacgagcgca ccgagggccg ccaccacctg 6540
ttcctgagat ctcgacccaa gaaaaagcgg aaggtggagg acccgtaaga tccaccggat 6600
ctagataact gatcataatc agccatacca catttgtaga ggttttactt gctttaaaaa 6660
acctcccaca cctccccctg aacctgaaac ataaaatgaa tgcaattgtt gttgttaact 6720
tgtttattgc agcttataat ggttacaaat aaagcaatag catcacaaat ttcacaaata 6780
aagcattttt ttcactgcat tctagttgtg gtttgtccaa actcatcaat gtatcttaac 6840
gcgagttaat taatccattg ctgggcgagc tgcgccaatc gatgccaacg ccaccctgca 6900
tggcgagcgg caggccggcg gctaccatgg gcgtcaccat gccctgaccg cccccggagg 6960
gcagtgaaaa atgtgtgggg ggtggtgggg gctgcgcagg aactgattgt gattatggtt 7020
gtgcccatgg ccatgttgtc caagtccatg gacgtgggca tgcttgttgt agcccaaatc 7080
ggcgtttccg tttccaccag gaaacatctc tgcttgtagt tcgaatatgc tctttaaatc 7140
ccagctgtat tcctcagtta tcgaggtttt cttcacgagt gaaacgaatt ttcgtcgcct 7200
tctacgccat tttcttgctc agcccgtttt gtcattcgca gcgaagcggt aacagcgggt 7260
cgctcatatg acggtatttt ttaatacact tcagctatac tgttatttca aaaacatatt 7320
tcttttgtta ctttttatgc agttcatttg ccaccaaaaa gtagtctttt ggattgattt 7380

```
atttcaaaaa atggtgtaat tcaagaaatt cagagggcca agtaatatac ttaatgaccg   7440
ttatttaaaa cacactcaag gagatttatt taaacggcta caatggtttt ccaaataact   7500
tatttactgt tgacttctat aaaacatagg tgtatatatt attatttcct tattgagttt   7560
gagataattt taatttccac aatatttttt cttgtgatta acagagaaag tcaaactaca   7620
taacatttat cgggtaaaag tctctatgaa ggtagcggtt aacagtgaag tcgcaaaagt   7680
ggtggccgta cgccaatcga gcgtagtacc cctaacctgc aatattttta gttggttttt   7740
tccgcaatag ccccagtttt ctcaaagagt gcaacaagtg attctgttta tgttttcaac   7800
aacttctctc tgcggaactt aacgtgagcg gacgtatgcg gacgcgccat ggtttaaact   7860
cgctagcact gggaagttga cgttgatata gagccgaatt gaacttcacc gctgcttggt   7920
aattactcta caagttcatt taggagaacc ggattcgaaa gatgattttc cagcgtttag   7980
ctttcagatg gccgcataca ttttgcacca ccaaaccgaa actcactagc gtatccaatc   8040
gttcgttttt tggtgccggt gtgttacgaa ctttagctat caagctaaag caatttgctc   8100
tggtcttccg tgctaaaaag aaaaaaaaac tgtttttttt ttggttttga tatttgcgct   8160
atttttactt gggccttaat tgaacaaact tttgaaagtt tccacagcga aatcgttttc   8220
gacgatgcca tttttggtaa catttgcatt ttcttgctca aattgcttgc aaaacccgtg   8280
aaagacatta atattcgata gtgtcatcca aaatcacgaa aatgattgtt gcaaaacgtt   8340
gaacaattta cacatgtaaa aaacaaccat cgattaatgt ttattcaaac tttttacaag   8400
aagggttatt ctgatcaatg tcaccccgct gatgaatgtt accccggatt acacttctcg   8460
aaaagtggtt caaaatgcta cttgagaatt tttatctgtc aaaggaagca aattcgagtc   8520
gaattaaatg gtatagtcct gaattaggtt tccatttact tacaggtatt ccactaaata   8580
gctggaagat ttattttaca caataatgat aattcgtacc ccaaagagtg tagccctact   8640
tttttctctc tttttttttt gtaaattttc atcgctgcgt gccagcttac cgacatgtcg   8700
cgacagcata aagagcctgt caagagatga agaaaaatga caaggagtca gtggtcaggt   8760
ctctgtatca atatttgacg tcctgacttt ccaatatacc tttccttaaa gagtagagat   8820
catgcgatac gtgaataaat atcgtttgga cttcgaaata gaacataatt taaggtagct   8880
gatcagtagt tgaacatctt cagacttctg ggacaagaag tgtttttttg tttgtagaaa   8940
aggtttttgt taaattatat ttgtaagata attcaatgaa tatatctctg attcagtaat   9000
caatccgtac cacgcaccgt ttaagaaaca ccctgtaggt ttgcatcacg tctcagacaa   9060
aagtgtatcg atgtgcgaac actgcatacc ggcgctttgc aaataatgcc aaatttagat   9120
atgcattaca ttgtcacttc gcaaaacaca cactcccaaa tgcgtcggaa acctcacccg   9180
aacgcacgat cgtaacgcga tcgatcgccg attgattgat cggaattaac tatctcaatc   9240
gatccttcta tggactgatg catgggccgg cacttccgag tataaaaccc cggtaaaccc   9300
aaggaatcac tcacaatcgg attttgacgc tcgctctggt acagttcgat acggtctagt   9360
gaaaccgagg ataacgacga aggtttttcc ccattgatcc aggtcggtgt ttatgattgg   9420
tggaaaaaga ctcgagaaaa gttccatcga agccgttgga aatgtgccgt cttcctgtga   9480
cgtcttgtgg atccagttcc ttgttcacgt ctggtgatcg tgtaaaatgt gctgtcttgt   9540
ggcgtcatat gtgttccaga tccagtgatt acgatccgat gtgatgttga tcccttgtga   9600
acgtcttatc ctgttccgtg tgcaccatgc ataatgtcgt attacgtaag ttctgaagtg   9660
aaacagaaga gtgaattgaa agttttttta ttcaacatca acctaaatat ggactttact   9720
```

-continued ttccaagaaa attatgcctg atcaactgtg gatagttaca aaaaaaaaag gtttattaat 9780
taaattttat gattacataa tgtgttgaaa agaacaactg aaattttaga agaagatctt 9840
ttcgtgcatc aggctttgcc aattaattga tgataaatta tcatagcaaa ttaacgtaga 9900
gactaaaagg tatatcgtca aatagggctt cttttgacac tattttggca ttcttgctct 9960
ttgagaactt gcaaccctaa aatgggatct tcatcagcct agtggttaga ttcagcagct 10020
acaaagcaaa accatgctga agggttcgat tcccggtcgt ttcaggatct tttcgtaatt 10080
gaaatatcct tgactaccct aagtatcatt gtgcttgcca tttacgaata tacatattac 10140
gatatacgaa tgagaaaatg acaactttgg aaaataaagc tctcaatgtt tcaataagaa 10200
ataaatacta catcagtatt gaaggctaat aacaattaca gattagaacc tttaaacatc 10260
atttctgcaa caggctggat aaagtacagt tggaggatta aattatgcga ttttgcaatt 10320
ttttccgatt aaattcatat ttattcctgg tttggttttt acaaaaaaata tttttacatg 10380
acgtttgacc ccgattccct caactttgat tgttatattt ttttttggac aggttgagtt 10440
tgtgggtttt ttcctagtgt tgctttgctt tatgggctct ggttatttaa aattaaaatt 10500
tgacaatctt actacacact ccgaaaaaat catgcgattt tacgtctttt ggatgcacat 10560
aaaagaagcg agccaaatga ggtgaatttg tgtcacattt taaatacgat ggtgtctgat 10620
tcgggaaatg tcaatgatag tgtcattcaa tcataatgtg aattacgtcc gcagtaattt 10680
tcattatttt taagagtgta ctactattta cactacaaaa attttgatac cccagggggg 10740
aacgaggtcc cggatgtcca gctggccaga ttgttggcaa cgagccctgt acctattgat 10800
cgagtcacca aagcactcct caagtgtttt aatctcgacc agacggtgga cctcggttgt 10860
tctcattctc ggagggcgat ttcgcaatca ttagtaccaa ccacatgtcg aagtcgggag 10920
atgttataaa attataacca attattcaaa aaatgacatc attcaatttg aacaaacgtt 10980
cgatagaaat tatatatgat ttcacatgat attaaactac gaagaaaatt ttacataagg 11040
aagtggtata aaacgtaata tgcttaataa aaactttaac ccttttggga ggataatatt 11100
cagaagttct gattcagaac catctctcat gttatgttcg tttttgttg cttgtccttt 11160
atatgccaca tgaacaataa caccaatatc tatcccattt ccaggaccta acggaccttg 11220
aagcggcgcc aaaacgtgtg acgatgatgc tggtaccctg gcggtaagtt gatcaaagga 11280
aacgcaaagt tttcaagaaa aaacaaaact aatttgattt ataacacctt tagaaaccac 11340
catgggcagc cgcctggata agtccaaagt catcaactcc gcgttggagc tgttgaacga 11400
agttggcatt gagggactga cgacccgcaa gttggcgcag aagctgggcg tggagcagcc 11460
caccctctac tggcacgtga agaataagcg ggcgctgctg gatgccctgg ccatcgagat 11520
gctcgaccgc caccacacgc atttttgccc gttggaaggc gagtcctggc aggacttcct 11580
ccgcaataac gccaagtcgt tccgctgcgc tctgctgtcc caccgagacg gtgccaaagt 11640
ccatctcggc acgcgcccga ccgaaaagca atacgagaca ctggagaacc agctcgcgtt 11700
cctgtgccag caaggcttca gcctggaaaa tgctctctac gctctgagcg ccgtcggtca 11760
ctttaccctg ggctgcgtgc tggaggacca agagcatcaa gtcgcaaaag aggagcgcga 11820
gaccccaaca accgattcga tgccccccact gctgcgtcag gcaatcgagc tgttcgatca 11880
tcaaggagcc gagccggcat tcctgttcgg cttggagctg attatctgcg gattggaaaa 11940
gcaactgaaa tgcgagtcgg gctcgggccc cgcgtacagc cgcgcgcgta cgaaaaacaa 12000
ttacgggtct accatcgagg gcctgctcga tctcccggac gacgacgccc ccgaagaggc 12060
ggggctggcg gctccgcgcc tgtcctttct ccccgcggga cacacgcgca gactgtcgac 12120

```
ggcccccccg accgatgtca gcctggggga cgagctccac ttagacggcg aggacgtggc  12180
gatggcgcat gccgacgcgc tagacgattt cgatctggac atgttggggg acggggattc  12240
cccgggtccg ggatttaccc cccacgactc cgccccctac ggcgctctgg atatggccga  12300
cttcgagttt gagcagatgt ttaccgatgc ccttggaatt gacgagtacg gtgggtagtt  12360
ctagaattgt ccaccgcaag tgcttctaag ccgatcccga ttgtactgat taccataagc  12420
gacattgcca gtgaaagcga caacagcagc atcaaagtac atttgtcata ctgattcggc  12480
tactaccacc atccggaatc agcttgcatc gaacatcaaa tcacgttatt caatgtatct  12540
gtcatccagc tcagacaagt cggagctttt ccagtcgcga aaatctgcga ctccagcgga  12600
aagcaccgaa ccacagagag gactcgtatg aaagccaggg aagaaaccat cattcacctt  12660
gcagcaaata ggaaaaaaaa cggacatctt caacaaacaa aagcccatgc gctaacttgg  12720
tttaggagtt tagtgtgaca ccatgacccc gctgatgatc tttacttagc acaccataac  12780
cacctttatg cgttcgttca tccaaaatct acaggatatc actgcagccg cgagaagaac  12840
tcgtgaacca tcctgttttc ttttttatta tattcttact tttaacttca aattattttc  12900
agtaataaaa cgtctcaaaa taataagttc ataatgagtt taattttacg gaataagaac  12960
aaccatttaa gttattaaat ccttagattt aatggaatta gattgattat atggaaccca  13020
gacttggtaa aaaataaact ccacgttaaa tttctttctg agacttaaaa ttctttcggg  13080
aaagctggga gcaattctcg caccggtgct agggccgcat agtcgacatt tcgagtttac  13140
cactccctat cagtgataga gaaaagtgaa agtcgagttt accactccct atcagtgata  13200
gagaaaagtg aaagtcgagt ttaccactcc ctatcagtga tagagaaaag tgaaagtcga  13260
gtttaccact ccctatcagt gatagagaaa agtgaaagtc gagtttacca ctccctatca  13320
gtgatagaga aaagtgaaag tcgagtttac cactccctat cagtgataga gaaaagtgaa  13380
agtcgagttt accactccct atcagtgata gagaaaagtg aaagtcgagc tcggtacccg  13440
ggtcgaggta ggcgtgtacg gtgggaggcc tatataagca gagctcgttt agtgaaccgt  13500
cagatcgcct ggagacgcca tccacgctgt tttgacctcc atagaagaca ccgggaccga  13560
tccagcctcc gcggccccga attcgagctc ggtacccggg gatccccgct cgaccaccat  13620
gggcgctctc ctgggcctgc ccgaaagcca aacggagctt gataatctta cagaatacaa  13680
cacggcccac aatcggcgca tctcaatgct gggcatcgat gatgatacca atatgcgaaa  13740
gcaaaacgcc ttgaaacagg gacggcgcac tcgaaatgtc acatttaacg atgaggagat  13800
tgtcatcaat cctgaggatg tggatcctaa tgtgggacgc ttcaggaact tggtacaaac  13860
cactgtggtg cccgccaaga gggctcgctg cgacgtcaac cattagtgat aacgcgtcta  13920
gctagagctg agaacttcag ggtgagtttg gggacccttg attgttcttt ctttttcgct  13980
attgtaaaat tcatgttata tggagggggc aaagttttca gggtgttgtt tagaatggga  14040
agatgtccct tgtatcacca tggaccctca tgataatttt gtttctttca ctttctactc  14100
tgttgacaac cattgtctcc tcttattttc ttttcatttt ctgtaacttt ttcgttaaac  14160
tttagcttgc atttgtaacg aatttttaaa ttcacttttg tttatttgtc agattgtaag  14220
tactttctct aatcactttt ttttcaaggc aatcagggta tattatattg tacttcagca  14280
cagttttaga gaacaattgt tataattaaa tgataaggta gaatatttct gcatataaat  14340
tctggctggc gtggaaatat tcttattggt agaaacaact acaccctggt catcatcctg  14400
cctttctctt tatggttaca atgatataca ctgtttgaga tgaggataaa atactctgag  14460
```

-continued

```
tccaaaccgg gcccctctgc taaccatgtt catgccttct tctctttcct acagctcctg    14520

ggcaacgtgc tggttgttgt gctgtctcat cattttggca aagaattcac tcctcaggtg    14580

caggctgcct atcagaaggt ggtggctggt gtggccaatg ccctggctca caaataccac    14640

tgagatcttt ttccctctgc caaaaattat ggggacatca tgaagcccct tgagcatctg    14700

acttctggct aataaaggaa atttattttc attgcaatag tgtgttggaa ttttttgtgt    14760

ctctcactcg gaaggacata tgggagggca aatcatttaa aacatcagaa tgagtatttg    14820

gtttagagtt tggcaacata tgcccatagc ggccctagcg gcgcgccata gccc          14874
```

EXPRESSION SYSTEMS

CROSS REFERENCE TO RELATED APPLICATIONS

This application is a Continuation-in-Part of U.S. application Ser. No. 10/566,448, filed Jan. 27, 2006, which is the National Stage of International Application No. PCT/GB2004/003263, filed Jul. 28, 2004, which claims the priority from GB 0317656.7, filed Jul. 28, 2003. All applications are hereby incorporated by reference in their entirety.

INTRODUCTION

The present invention relates to a gene expression system, in combination with splice control sequences, said control sequences providing a mechanism for alternative splicing.

Alternative splicing is also known as pre-mRNA splicing and involves the removal of one or more introns and ligation of the flanking exons. This reaction is catalyzed by the spliceosome, a macromolecular machine composed of five RNAs and hundreds of proteins (Jurica, M. S. & Moore, M. J. (2003) *Mol. Cell* 12, 5-14). Alternative splicing generates multiple mRNAs from a single gene, thus increasing proteome diversity (Graveley, B. R. (2001) *Trends Genet* 17, 100-107).

Alternative splicing also plays a key role in the regulation of gene expression in many developmental processes ranging from sex determination to apoptosis (Black, D. L. (2003) *Annu. Rev. Biochem.* 72, 291-336), and defects in alternative splicing have been linked to many human disorders (Caceres, J. F. & Kornblihtt, A. R. (2002) *Trends Genet.* 18, 186-193). In general, alternative splicing is regulated by proteins that associate with the pre-mRNA and function to either enhance or repress the ability of the spliceosome to recognize the splice site(s) flanking the regulated exon (Smith, C. W. & Valcarcel, J. (2000) *Trends Biochem. Sci.* 25, 381-388).

Whether a particular alternative exon will be included or excluded from an mRNA in each cell is thought to be determined by the relative concentration of a number of positive and negative splicing regulators and the interactions of these factors with the pre-mRNA and components of the spliceosome (Smith, C. W. & Valcarcel, J. (2000) *Trends Biochem. Sci.* 25, 381-388).

Although at least 74% of human genes encode alternatively spliced mRNAs (Johnson, J. M., Castle, J., Garrett-Engele, P., Kan, Z., Loerch, P. M., Armour C. D., Santos, R., Schadt, E. E., Stoughton, R. & Shoemaker, D. D. (2003) *Science* 302, 2141-2144), relatively few splicing regulators have been identified.

SUMMARY OF THE INVENTION

The present invention provides, in a first aspect, a gene expression system comprising at least one coding sequence to be expressed in an organism, at least one promoter operably linked thereto, and at least one splice control sequence which, in cooperation with a spliceosome, mediates alternative splicing of RNA transcripts of the coding sequence, the mediation being selected from at least one of the group consisting of: sex-specific, stage-specific, germline-specific and tissue-specific mediation.

The gene expression system comprises a gene, capable of expressing a protein of interest, under the control of a promoter therefor, in combination with splice control sequences, preferably intronic sequences that control alternative splicing. Optionally, an enhancer or a transcriptional transactivator protein binding sequence is also present in the gene expression system.

The splice control sequences provide alternative splices of the at least one protein, for instance in a sex-, stage-tissue or germline-specific manner. This differential expression of the at least one protein allows the user to combine two levels of control of expression an, therefore, to express proteins in a previously unobtainable manner.

It is preferred, therefore, that alternative splicing of the RNA transcribed from the gene of interest leads to differential expression of the at least one protein in at least one of the above-mentioned specific manners.

Spliceosomes are large complexes of small nuclear RNA and protein particles (snRNPs) which assemble with pre-mRNA to achieve RNA splicing, by removing introns from eukaryotic nuclear RNAs, thereby producing mRNA which is then translated to protein in ribosomes.

The splice control sequences are preferably substantially intronic. Although it is envisaged that they may comprise a portion of exonic or coding sequence, this is not preferred according to one embodiment of the invention.

The gene expression system is capable of expressing at least one protein of interest. Said at least one protein may have a therapeutic effect or may, preferably, be a marker, for instance DsRed, Green Fluorescent Protein (GFP) or one or more of their mutants or variants, or other markers that are well known in the art.

Most preferably, the at least one protein has a lethal, deleterious or sterilizing effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

A lethal effect resulting in sterilization is particularly preferred, as this allows the organism to compete in the natural environment ("in the wild") with wild-type organisms, but the sterile insect cannot then produce offspring. In this way, the present invention achieve a similar result to techniques such as the Sterile Insect Technique (SIT) in insects, without the problems associated with SIT, such as the cost, danger to the user, and reduced competitiveness of the irradiated organism.

Preferably, the gene expression system comprises at least one positive feedback mechanism as described herein, namely at least one gene to be expressed and at least one promoter therefor, wherein a product of a gene to be expressed serves as a positive transcriptional control factor for the at least one promoter, and whereby the product, or the expression of the product, is controllable.

Preferably, the at least one protein is an apoptosis-inducing factor, such as the AIF protein described for instance in Cande et al (*Journal of Cell Science* 115, 47274734 (2002)) or homologues thereof. AIF homologues are found in mammals and even in invertebrates, including insects, nematodes, fungi, and plants, meaning that the AIF gene has been conserved throughout the eukaryotic kingdom.

Also preferred is Hid, the protein product of the head involution defective gene of *Drosophila melanogaster*, or Reaper (Rpr), the product of the reaper gene of *Drosophila*, or mutants thereof. Use of Hid was described by Heinrichs and Scott (*Proc. Natl Acad. Sci USA* 97, 8229-8232 (2000). Use of a mutant derivative, $Hid^{Ala5}$ was described by Horn and Wimmer (*Nature Biotechnology* 21, 64-70 (2003)). Use of a mutant derivative of Rpr, $Rpr^{KR}$, is described herein (see also White et al 1996, Wing et al., 2001, and Olson et al., 2003).

Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al., 2002, Vernooy et al., 2000) even though their own sequence is not well conserved.

Also preferred is Nipp1Dm, the *Drosophila* homologue of mammalian Nipp1 (Parker et al *Biochemical Journal* 368, 789-797 (2002); Bennett et al., *Genetics* 164, 235-245 (2003)). Nipp1Dm is another example of a protein with lethal effect if expressed at a suitable level, as would be understood by the skilled person. Indeed, many other examples of proteins with a lethal effect will be known to the person skilled in the art.

It is also preferred that the protein of interest is itself a transcriptional transactivator, such as the tTAV system described herein.

It is preferred that the promoter can be activated by environmental conditions, for instance the presence or absence of a particular factor such as tetracycline in the tet system described herein, such that the expression of the gene of interest can be easily manipulated by the skilled person. Alternatively, a preferred example of a suitable promoter is the hsp70 heat shock promoter, allowing the user to control expression by variation of the environmental temperature to which the hosts are exposed in a lab or in the field, for instance. Another preferred example of temperature control is described in Fryxell and Miller (*Journal of Economic Entomology* 88, 1221-1232 (1995)).

Also preferred as a promoter is the sryα embryo-specific promoter (Horn & Wimmer (2003) from *Drosophila melanogaster*, or its homologues, or promoters from other embryo-specific or embryo-active genes, such as that of the *Drosophila* gene slow as molasses, or its homologues from other species.

It is also preferred that the genetic system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcMNPV.

The splice control mechanism allows an additional level of control of protein expression, in addition to the promoter and/or enhancer of the gene. For instance, tissue or sex-specific expression in embryos only would be extremely difficult by conventional methods. Promoters with this specificity are unknown, even in *Drosophila*. However, using combinatorial control according to the present invention, an embryo-specific promoter, for example sryα, can be combined with a suitable alternative splicing system.

It is preferred that any combination of promoter and alternative splicing mechanism is envisaged. The promoter is preferably specific to a particular protein having a short temporal or confined spatial effect.

Alternatively, it is preferred that the promoter may be specific for a broader class of proteins or a specific protein that has a long-term and/or wide system effect, such as a hormone, positive or negative growth factor, morphogen or other secreted or cell-surface signaling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e. the morphogen can still act and have an effect) beyond that life-cycle stage. Preferred examples would be the morphogen/signaling molecules Hedgehog, Wingless/WNTs, TGFβ/BMPs, EGF and their homologues, which are well-known evolutionarily-conserved signalling molecules.

It is also envisaged that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germ-line- and sex-specific control.

It is also envisaged that more than one promoter, and optionally an enhancer therefor, can be used in the present system, either as alternative means for initiating transcription of the same protein or by virtue of the fact that the genetic system comprises more than one gene expression system (i.e. more than one gene and its accompanying promoter).

In a further aspect, the present invention provides a method of transformation, comprising expressing alternative splices of a protein in an organism by contacting the organism with the gene expression system and preferably inducing expression of the expression system. Methods of introduction or transformation of the gene system and induction of expression are well known in the art with respect to the relevant organism.

Also provided are organisms (i.e. transformants) transformed by the present system.

Where reference to a particular nucleotide or protein or SEQ ID NO is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences or SEQ ID NO.

DESCRIPTION OF THE FIGURES AND SEQUENCE LISTINGS

The present invention will now be described with reference to the following non-limiting Figures and Sequence Listings, wherein.

Figure 19:
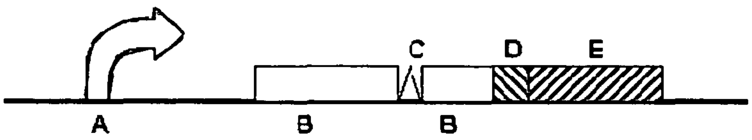

FIG. 19: One use of the P element in generating germline-specific expression of a gene of interest (Gene E).

Insertion of the P element IVS3 and flanking exonic sequences upstream of an ubiquitin-Gene E fusion with allow germline-specific expression of Gene E under a germline active promoter. A—Germline active promoter; B—P-element open reading frame; C—P intron 'IVS3'; D—Ubiquitin; E—Coding region for protein of Interest e.g. tTAV.

Figure 20:
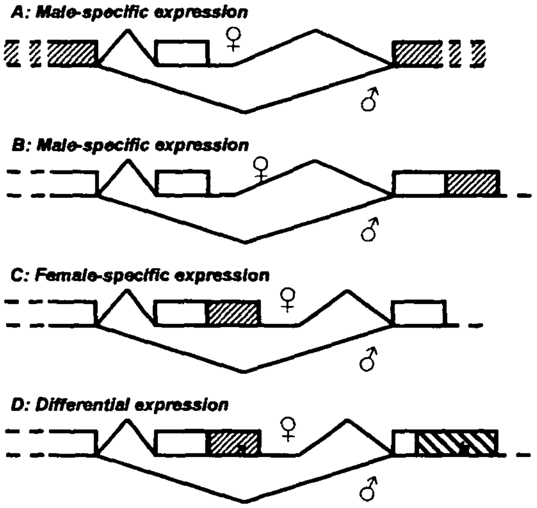

FIG. 20: Sex-specific expression using dsx.

A: Intron used as Cctra intron above, but giving male-specific expression. A fragment of dsx (here the *Anopheles* version) is inserted into a heterologous coding region (shaded boxes). The intron is completely removed in males, but in females the coding region is prematurely terminated.

B: An alternative approach to male-specific expression, in which a heterologous coding region is fused to a fragment of dsx.

C: Female-specific expression: the heterologous coding region is inserted into the female-specific exon, either as an in-frame fusion to a fragment of Dsx, or with its own start and stop codons.

D: Differential expression: designs B and C can be combined to give expression of gene a in females and b in males.

Figure 21:
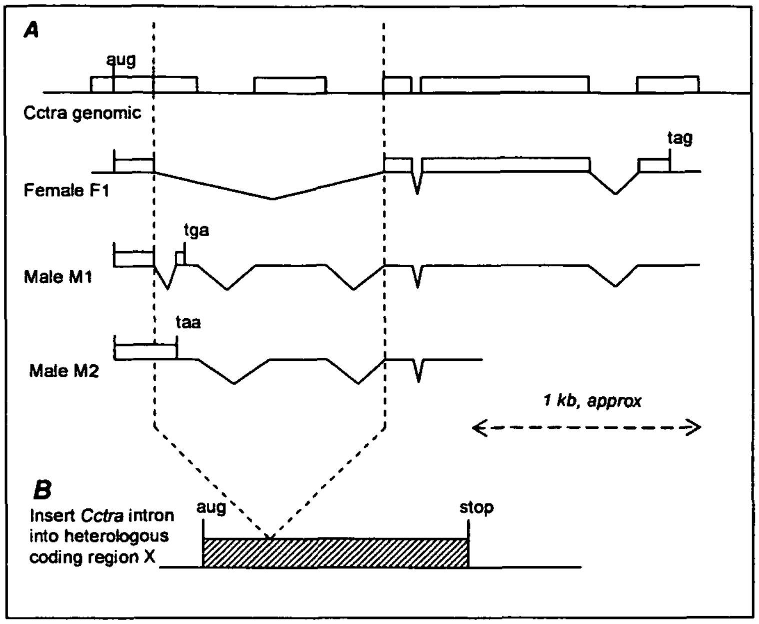

FIG. 21: Sex-specific alternative splicing of Cctra A: Cctra is spliced in females to produce three transcripts: F1, which encodes functional Tra protein, and M1 and M2, which do not, because they include additional exons with stop codons (redrawn from Pane et al. 2002). Males produce only transcripts M1 and M2 and therefore do not produce functional Tra protein at all.

B: If this intron were to function similarly in a heterologous coding region, this would similarly allow females, but not males, to produce functional protein X.

Figure 22:
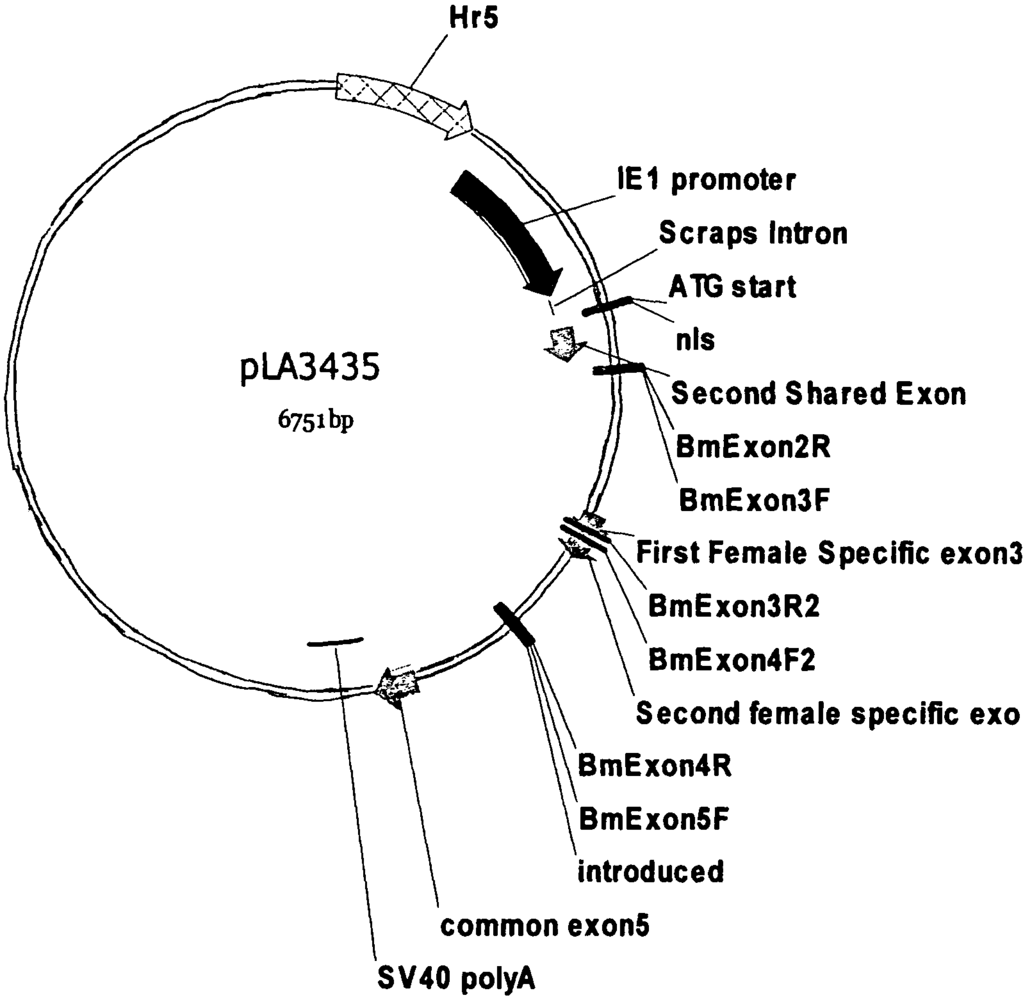

FIG. 22: Diagrammatic representation of pLA3435 construct/plasmid (SEQ ID NO. 46).

Figure 23:
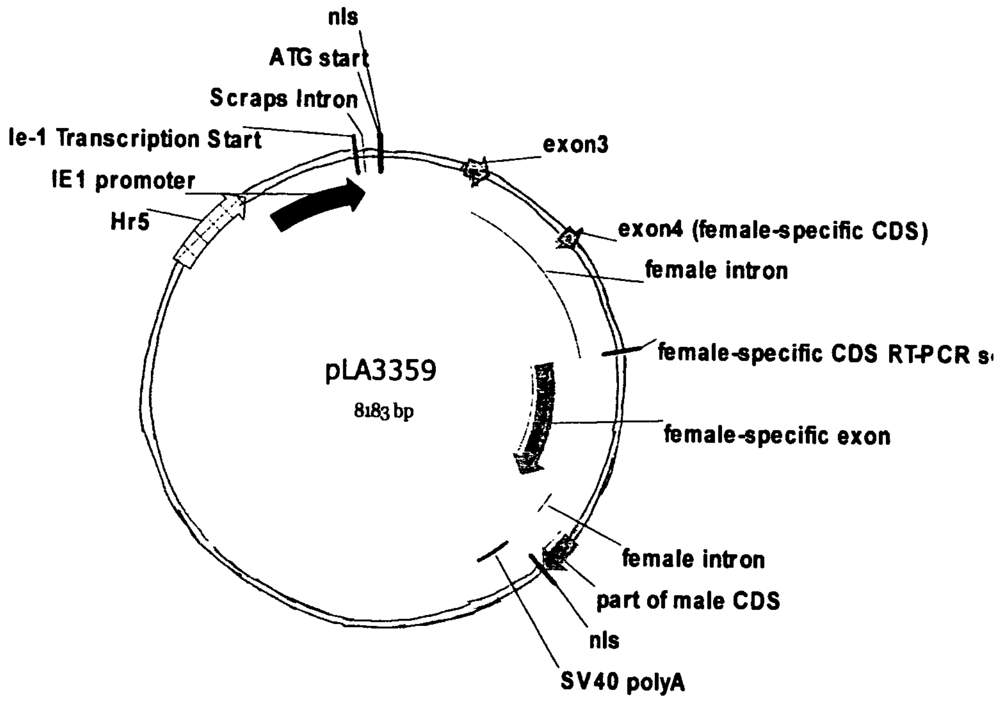

FIG. 23: Plasmid map of pLA3359 *Anopheles gambiae* dsx gene placed under the control of a Hr5-IE1 promoter for assessing splicing via transient expression.

Figure 24:
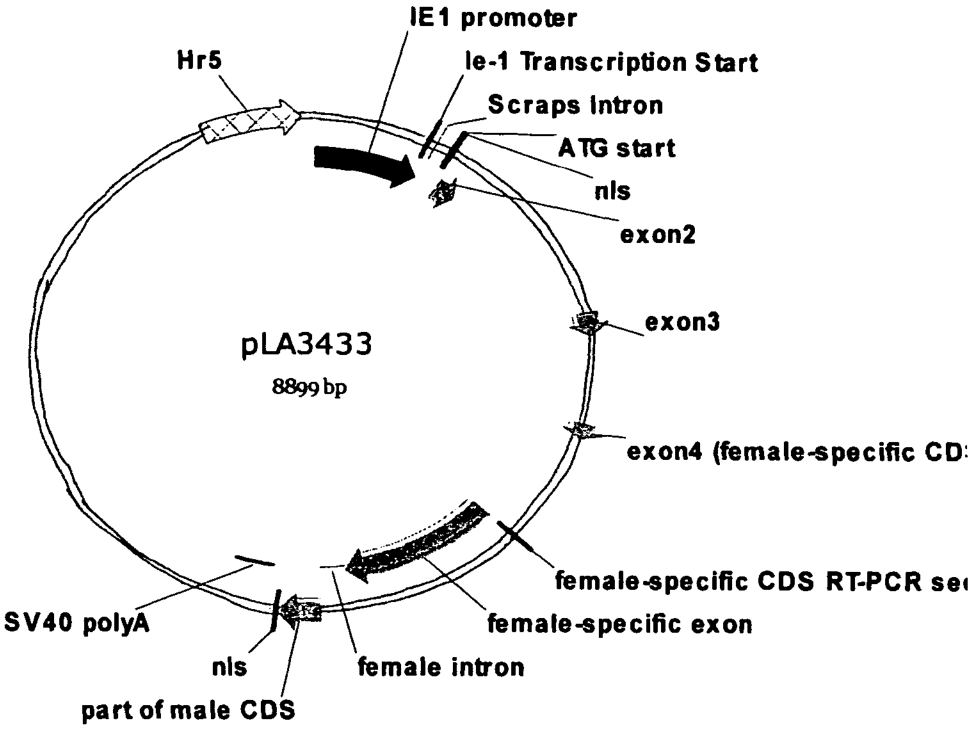

FIG. 24: pLA3433-*Anopheles gambiae* dsx gene placed under the control of a Hr5-IE1 promoter, with the addition of exon 2, for assessing splicing via transient expression.

Figure 25:
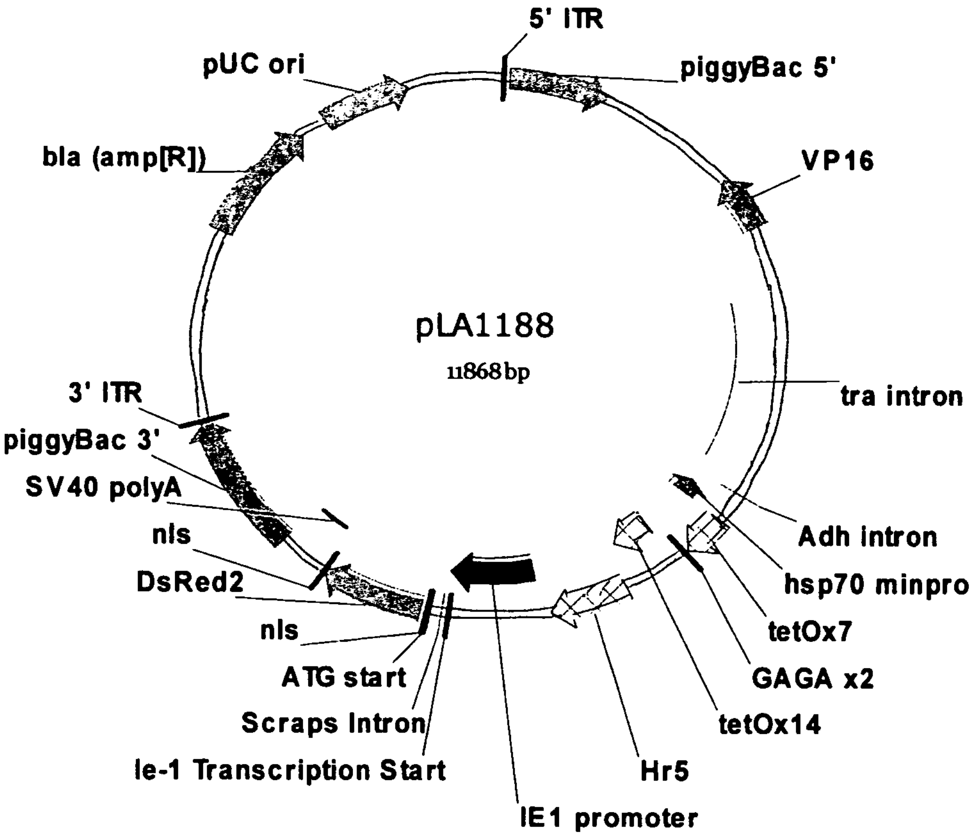

FIG. 25: Schematic representation of pLA1188 construct.

Figure 26:
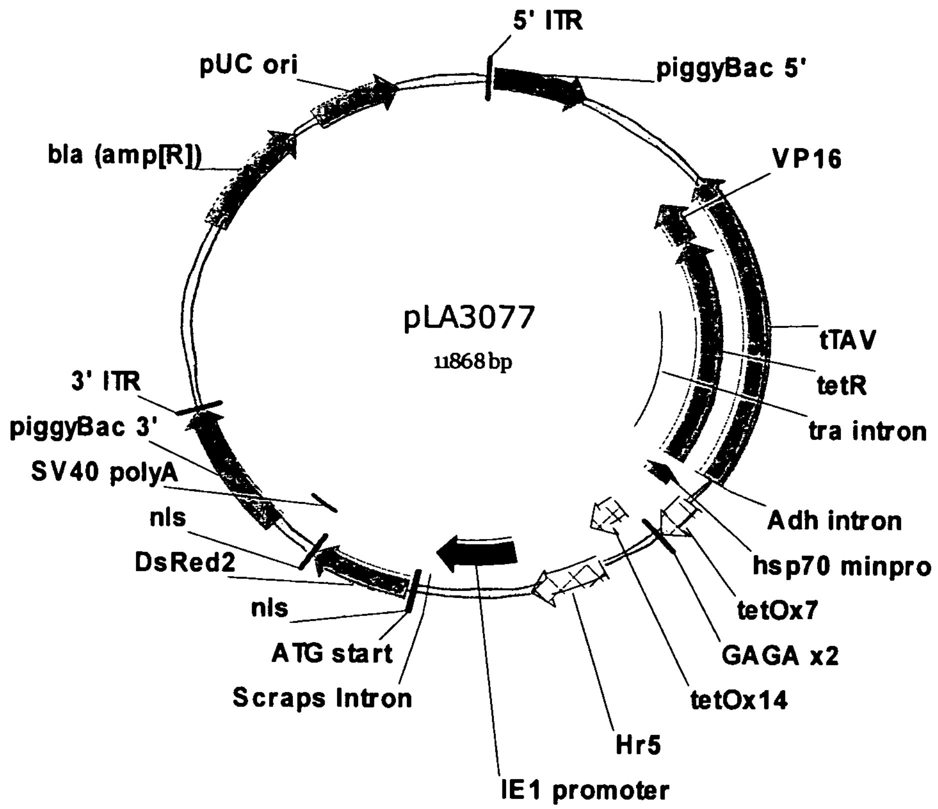

FIG. 26: Schematic diagram of pLA3077 construct.

Figure 27:
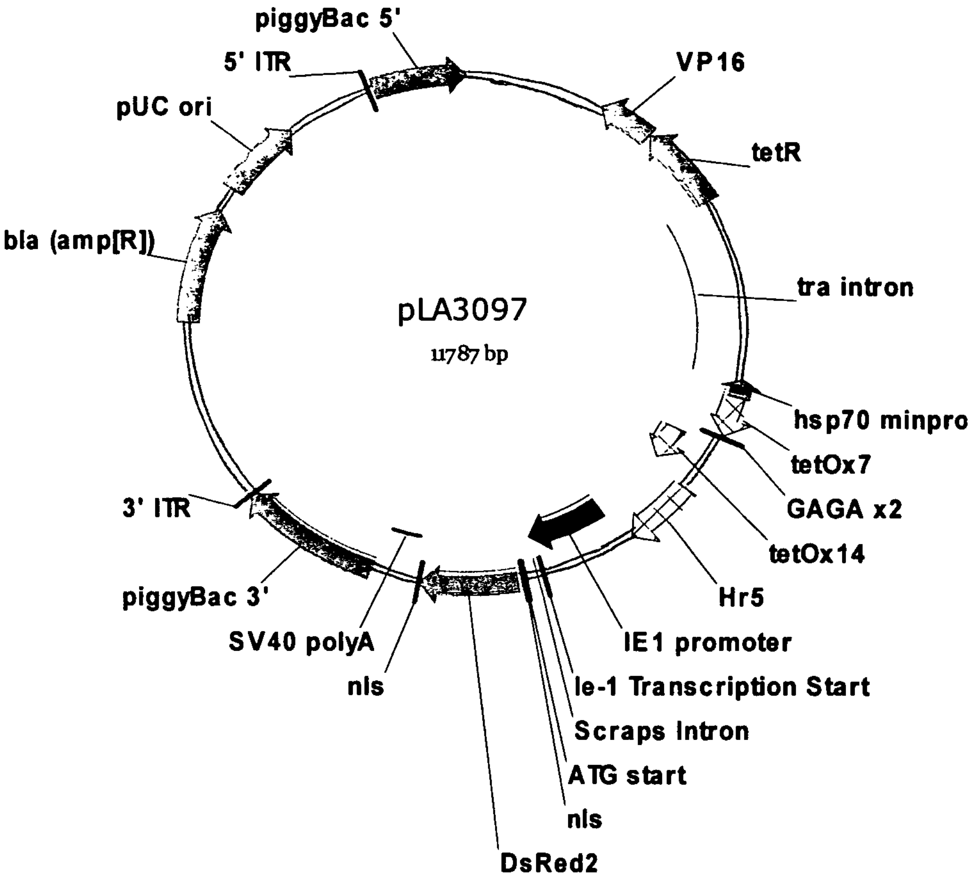

FIG. 27: Schematic diagram of pLA3097 construct.

Figure 28:
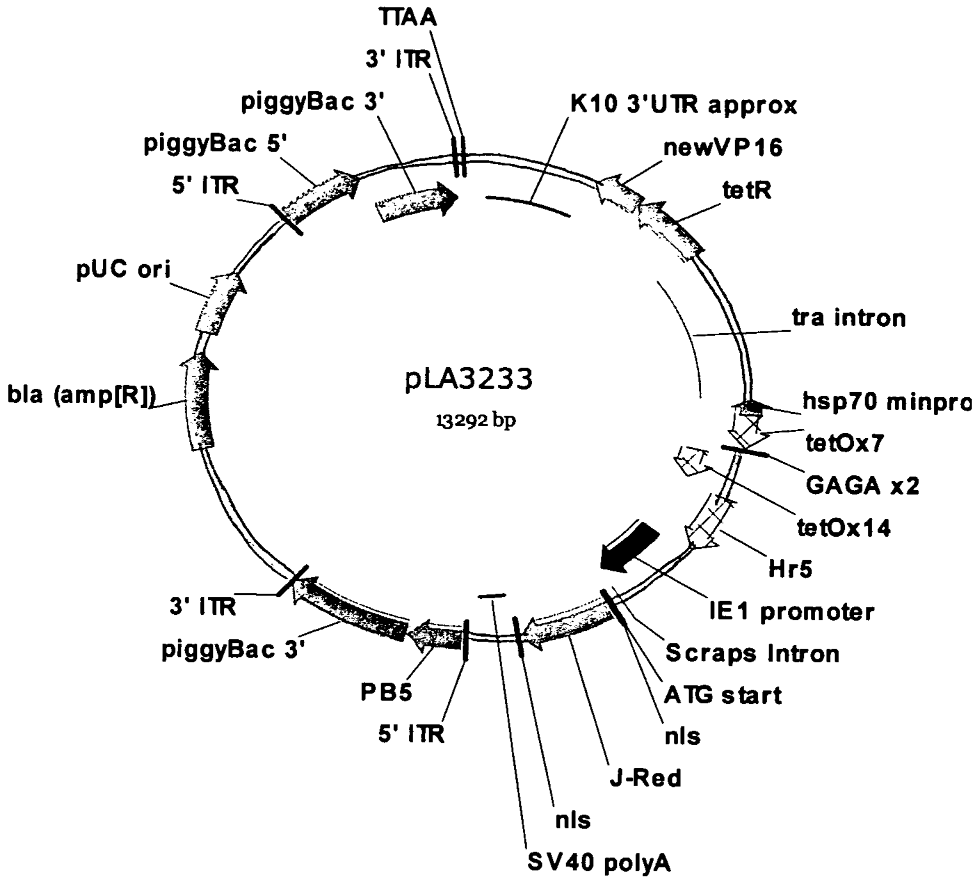

FIG. 28: Schematic diagram of pLA3233 construct.

Figure 29:
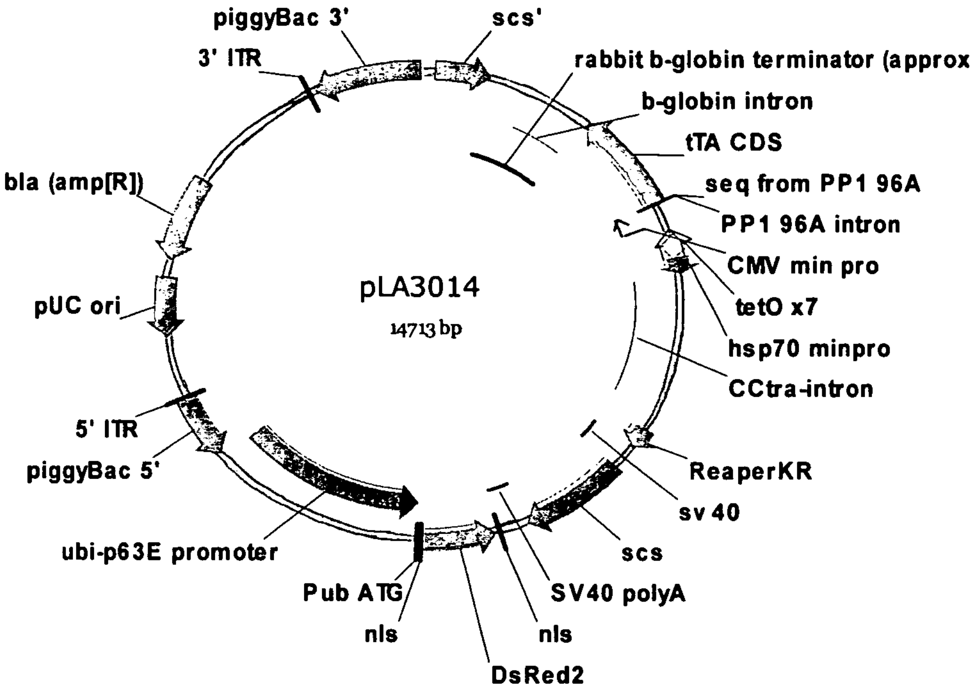

FIG. 29: Schematic diagram of pLA3014 construct.

Figure 30:
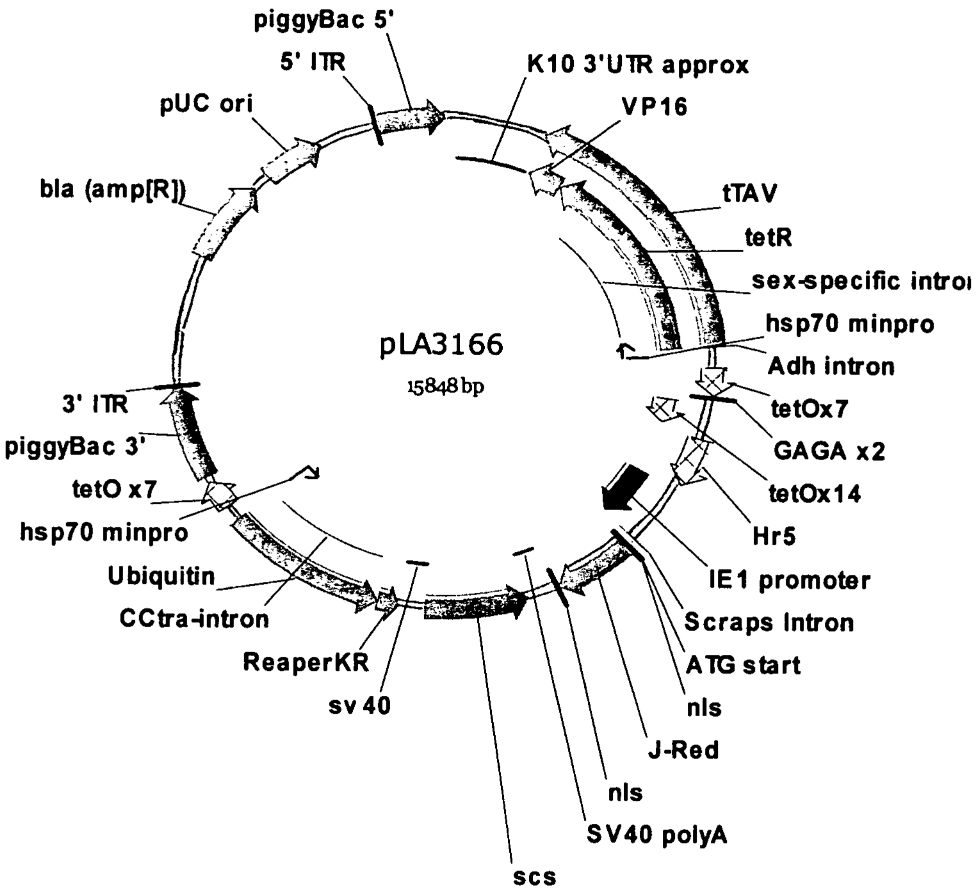

FIG. 30: Schematic diagram of pLA3166 construct.

Figure 31:
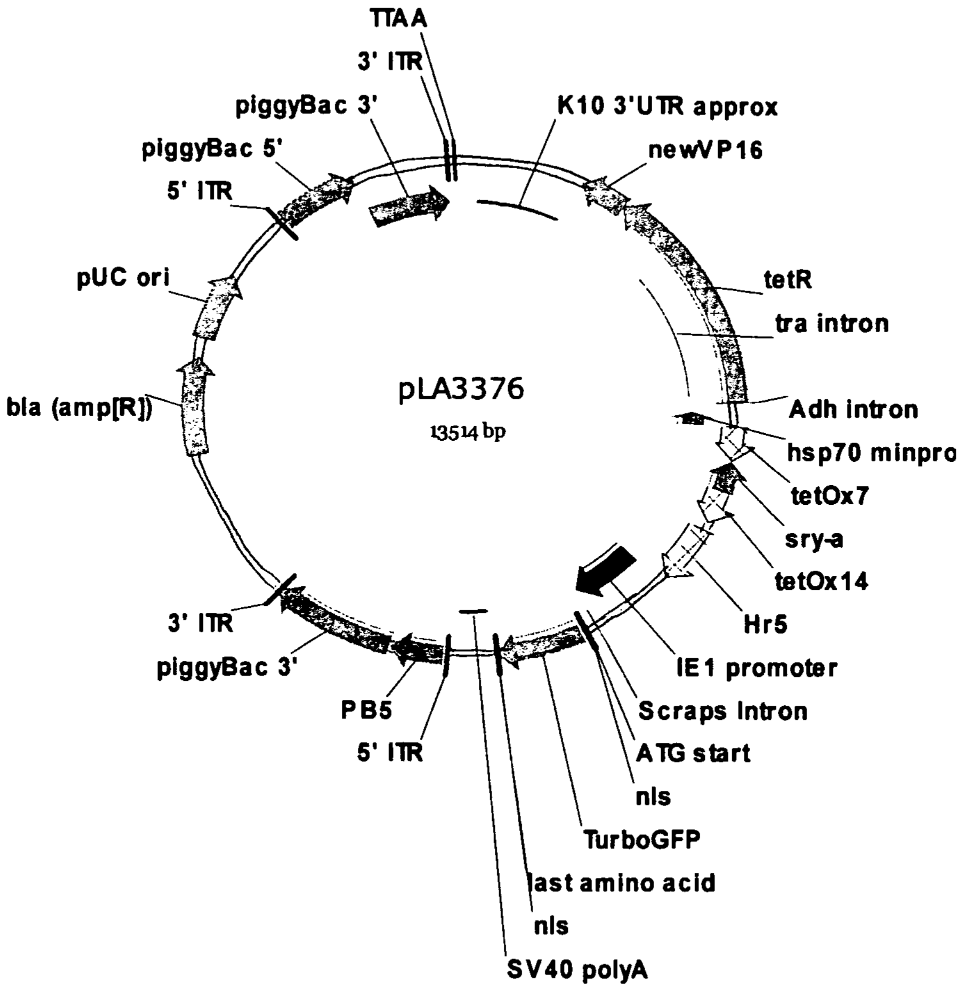

FIG. 31: Schematic diagram of pLA3376 construct.

Figure 32:
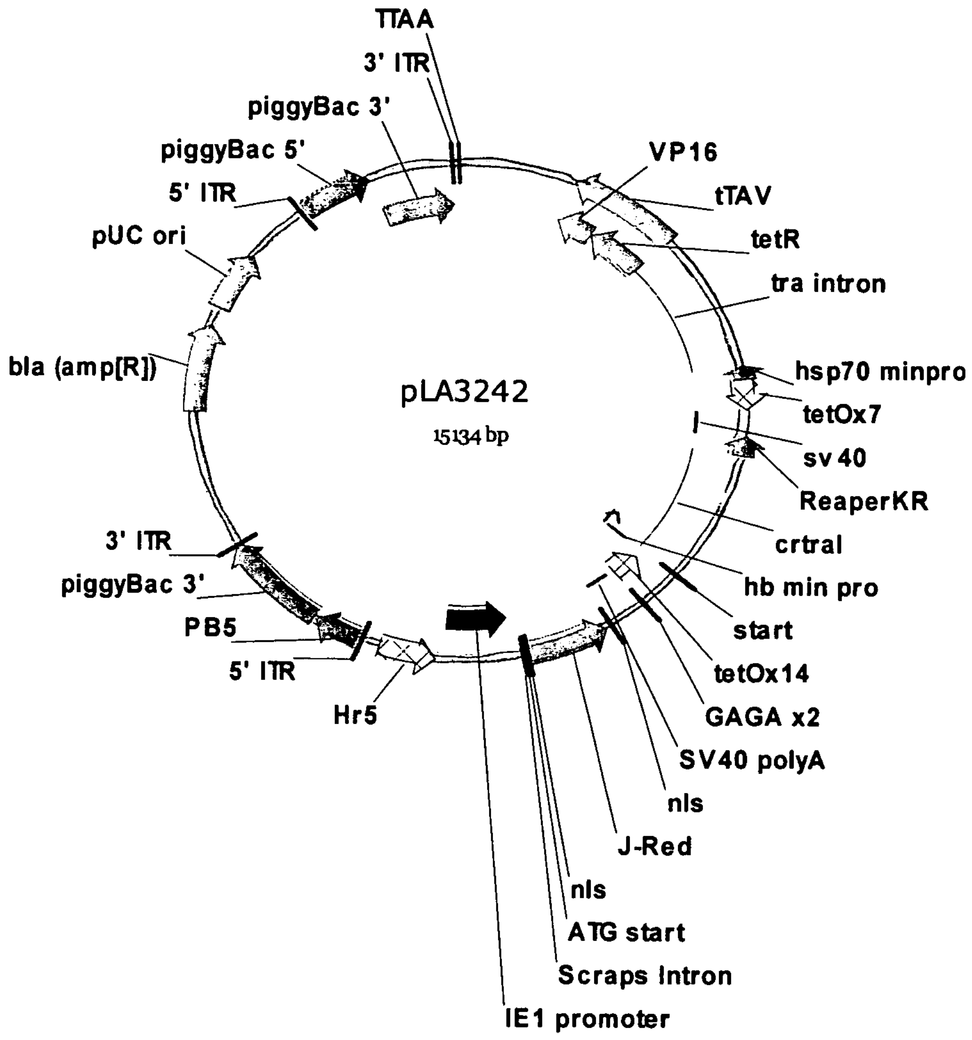

FIG. 32: Schematic diagram of pLA3242 construct.

FIG. 33: Flanking sequence of Cctra

Splicing of the Cctra intron in LA3077 and LA3097 is exactly as you would see in the native Cctra intron. Splicing in LA1188 results in the removal of 4 additional nucleotides. In all cases the introns are flanked by 5' exonic TG and 3' GT.

Figure 34:
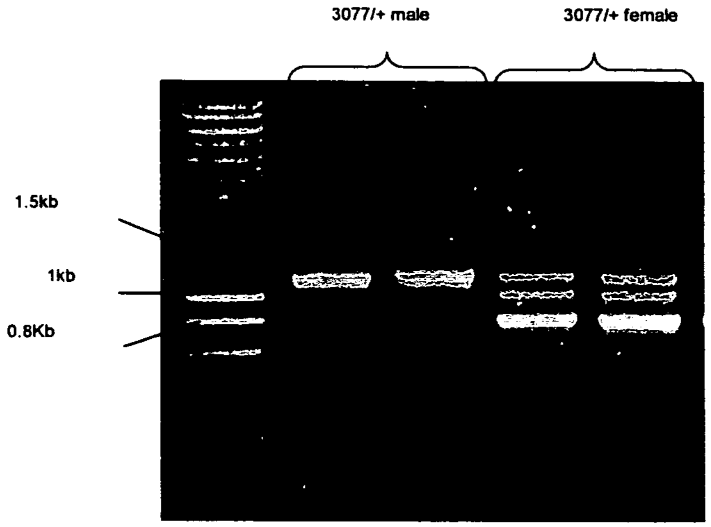

FIG. 34: Gel showing correct sex-specific splicing of intron(s) derived from CcTra (776 bp band in females) in *Ceratitis capitata* transformed with LA3077. Lane 1: Marker (SmartLadder™ from Eurogentec, bands of approx 0.8, 1.0 and 1.5 kb are indicated); Lanes 2 and 3: *Ceratitis capitata* LA3077/+ males; Lanes 4 and 5: *Ceratitis capitata* LA3077/+ females.

FIG. 35: Phenotypic data for transformed female specific constructs in *Ceratitis capitata*. Column 1: Construct designation LA#, e.g. LA3077, LA3097, LA3233, etc, is indicated by number, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 36:
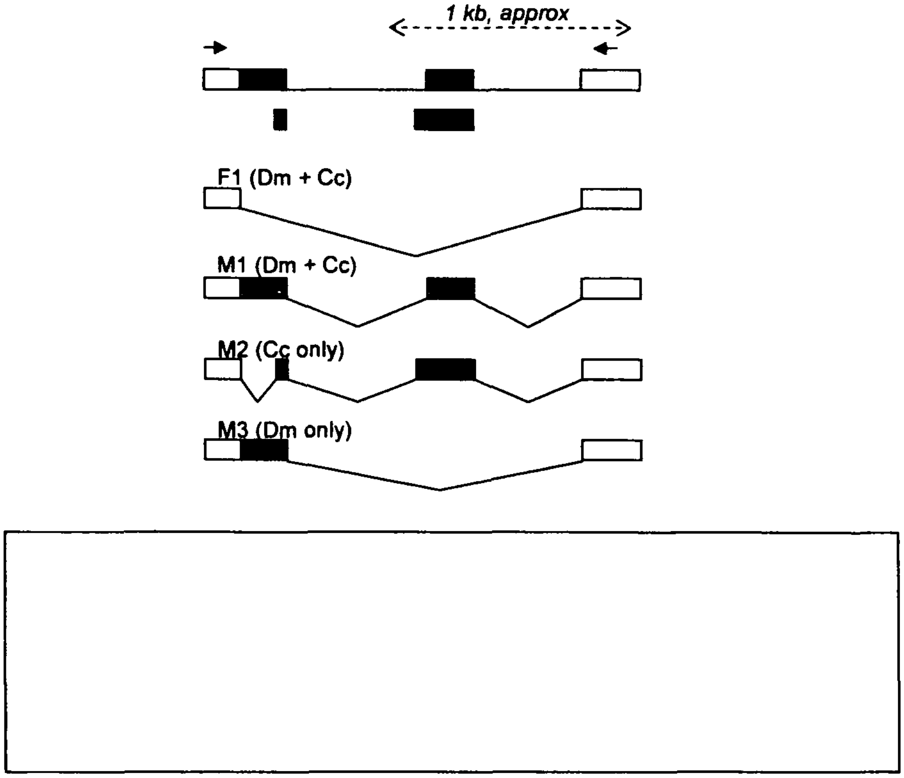

FIG. 36: Transcripts of Cctra intron constructs in *Drosophila* and *Ceratitis capitata.*

The top line represents the construct DNA containing tra intron flanked by desired gene (the open box). The red box represents the male specific exons. Introns are represented by solid lines. Arrow above the first line represents the positions of the oligonucleotides used in the RT-PCR experiments. The bar indicates the scale of the figure.

Figure 37:
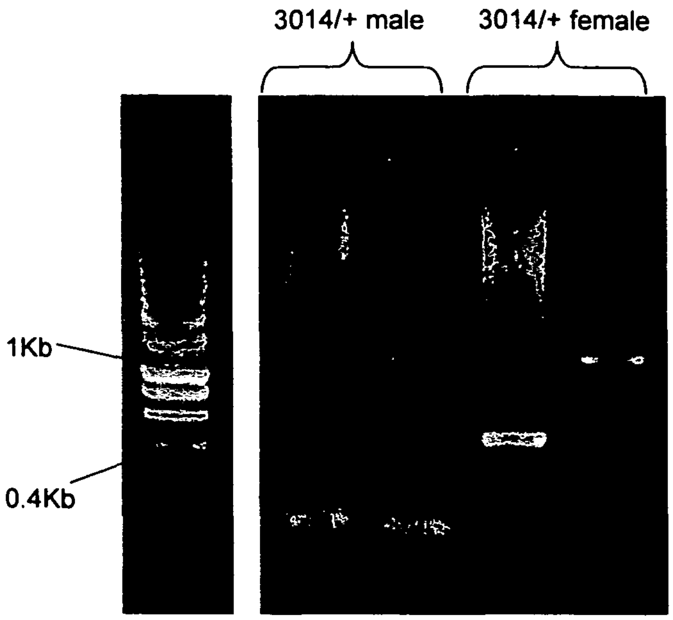

FIG. 37: Gel showing correct female specific splicing of CcTRA-derived sequence (508 bp band) in female *Ceratitis capitata* transformed with LA3014. Lane 1: Marker (SmartLadder™ from Eurogentec, bands of approx 0.4 and 1.0 kb are indicated); Lane 2 *Ceratitis capitata* LA3014/+ male; Lane 4: *Ceratitis capitata* LA3014/+ female; Lanes 3 and 5: no reverse transcriptase negative controls (background bands, probably from genomic DNA, can be seen in lanes 2 and 4).

FIG. 38: Phenotypic data for transgenic *Anastrepha ludens* transformed with LA3097 or LA3233. Column 1: Construct LA# (LA3097 or LA3233) indicated, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 39:
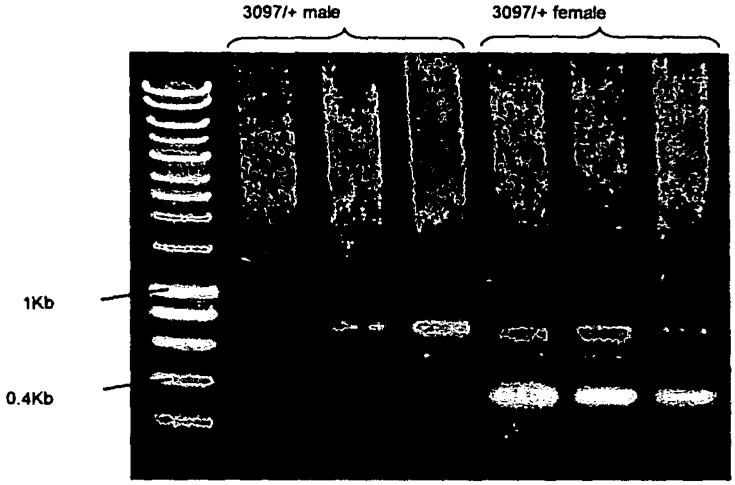

FIG. 39: Gel showing correct sex-specific splicing of CcTRA splicing (348 bp band in females) in *Anastrepha ludens* transformed with LA3097. Lane 1: Marker (SmartLadder™ from Eurogentec, bands of approx 0.4 and 1.0 kb are indicated); Lanes 2, 3 and 4: *A. ludens* LA3097/+ males; Lanes 5, 6 and 7: *A. ludens* LA3097/+ females.

Figure 40:
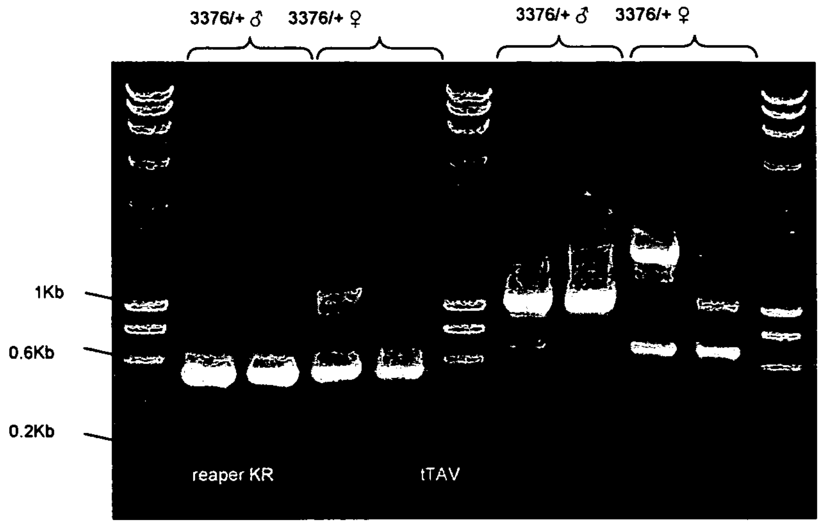

FIG. 40: Gel showing correct sex-specific splicing of BZTRA in reaperKR (200 bp band in females) and tTAV3 (670 bp band in females) regions of LA3376, in *Ceratitis capitata* transformed with LA3376. Lane 1: Marker (SmartLadder™ from Eurogentec, bands of approx 0.2, 0.6 and 1.0 kb are indicated); Lanes 2 and 3: *C. capitata* LA3376/+ males tested for splicing in reaperKR; Lanes 4 and 5: *C. capitata* LA3376/+ females tested for splicing in reaperKR; Lane 6: SmartLadder™; Lanes 7 and 8: *C. capitata* LA3376/+ males tested for splicing in tTAV; Lanes 9 and 10: *C. capitata* LA3376/+ females tested for splicing in tTAV; Lane 11: SmartLadder™.

Figure 41:
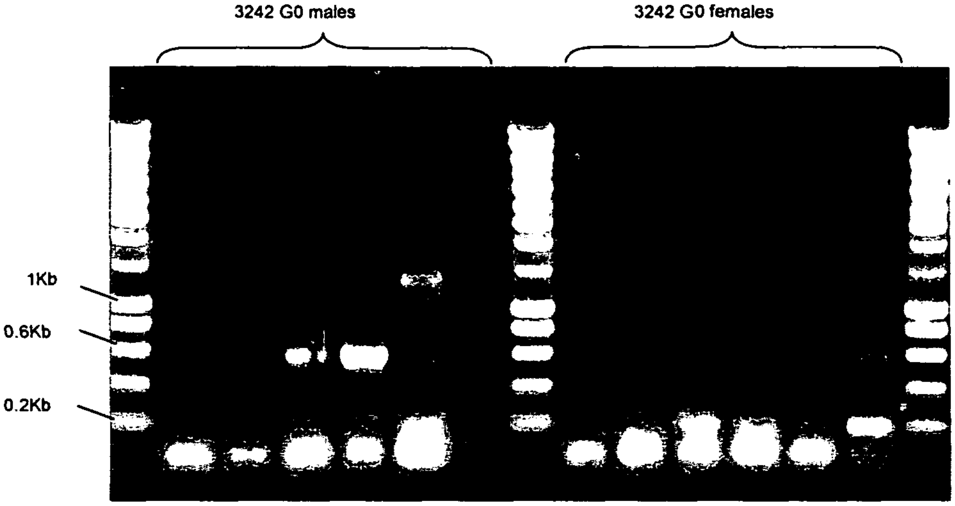

FIG. 41: Gel showing correct sex-specific CrTRA splicing in CrTRA-reaperKR (200 bp band in females) in *Ceratitis capitata* injected with LA3242. Lane 1: Marker (SmartLadder™ from Eurogentec, bands of approx 0.2, 0.6 and 1.0 kb are indicated); Lanes 2-7: *C. capitata* wild type males injected with LA3242; Lane 8: SmartLadder™; Lanes 9-14: *C. capitata* wild type females injected with LA3242; Lane 15: SmartLadder™.

Figure 42:
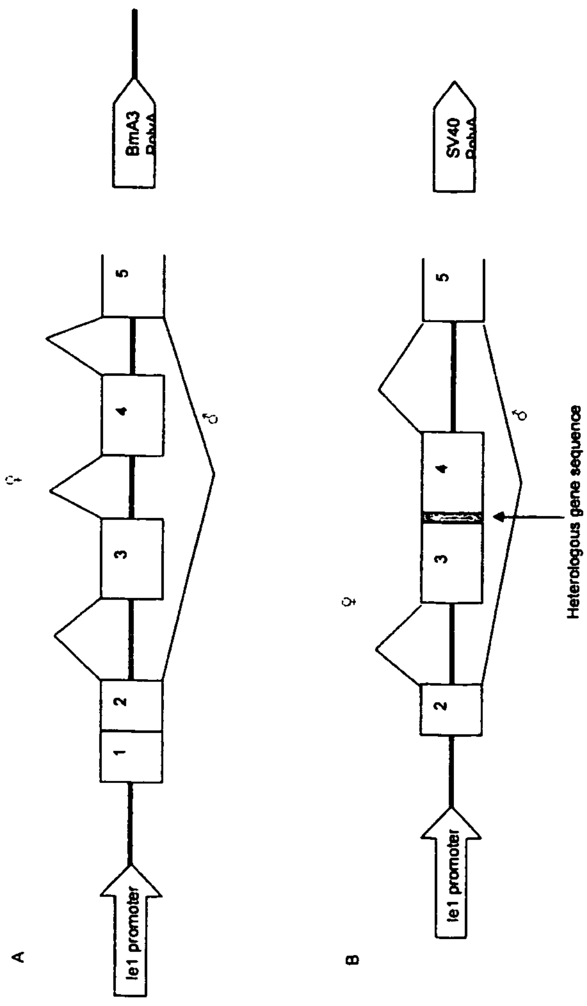

FIG. 42: Schematic representation of Bmdsx minigene constructs.

Figure 15:
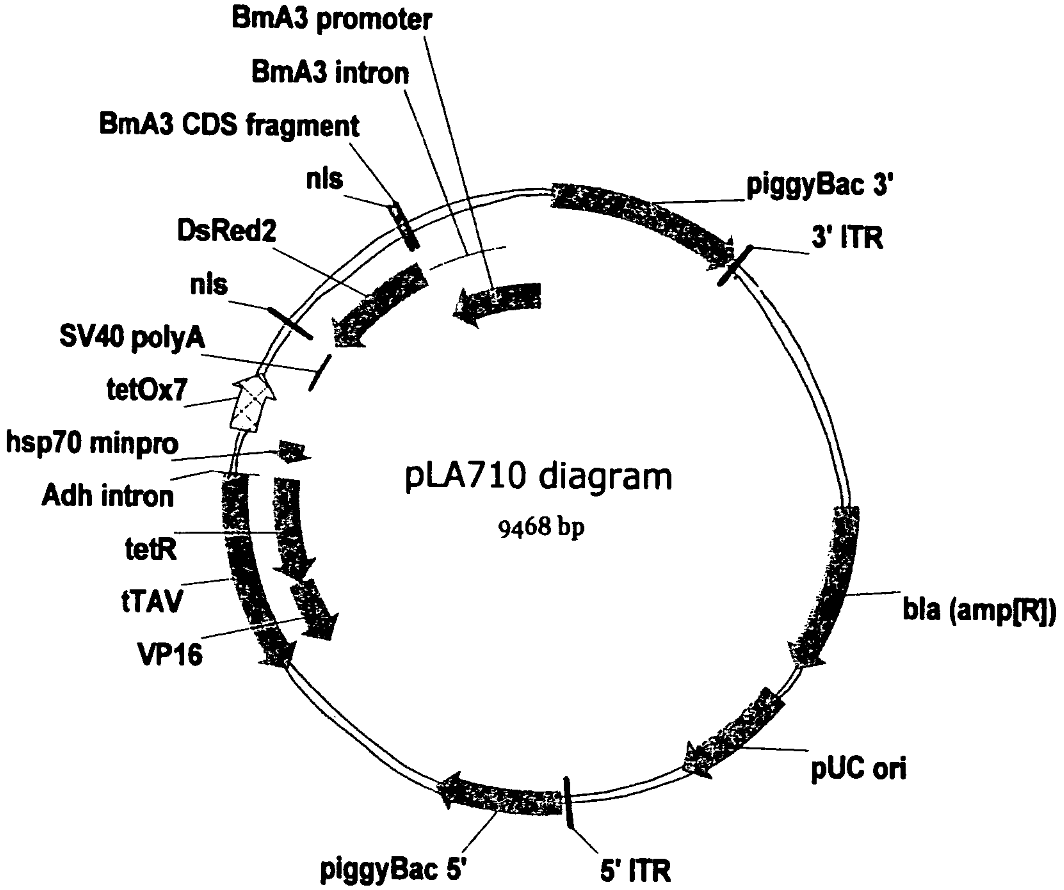
FIG. 15 is a schematic diagram of pLA710.

Two minigene constructs derived from the *Bombyx mori* dsx gene are illustrated diagrammatically, together with the predicted alternative splicing of these constructs (female pattern shown above the construct, male pattern below). (A) is the *Bombyx mori* dsx mini-gene construct used in Funaguma et al., 2005) (B) is pLA3435. A and B differ from each other in several ways: (i) Exon 1 is excluded from pLA3435, (ii) the intron between female specific exons 3 and 4 has been removed and a short heterlogous sequence has been inserted in pLA3435 (iii) Funaguma et al., use the ie 1 promoter from the baculovirus BmNPV and a BmA3 3'UTR compared with pLA3435 which uses the hr5-Ie1 enhancer/promoter from the baculovirus AcNPV and a 3'SV40 3'UTR. (iv) pLA3435 uses slightly longer intron sequences when compared with (A) (see FIG. 15 for sequence). Two minigene constructs derived from the *Bombyx mori* dsx gene are illustrated diagrammatically, together with the predicted alternative splicing of these constructs (female pattern shown above the construct, male pattern below).

Figure 43:
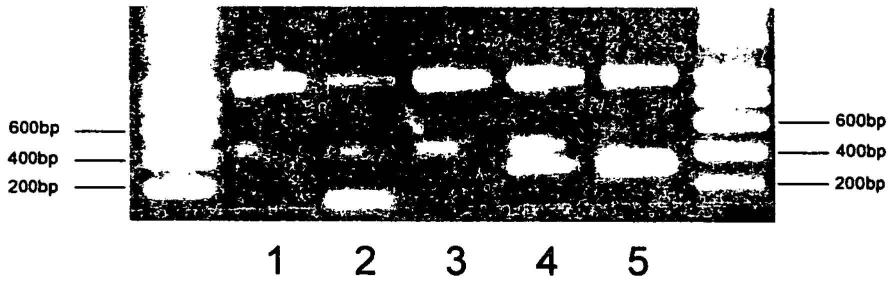

FIG. 43: Sex-specific splicing of BMdsx mini-gene construct in PBW.

Analysis of transient expression from pLA3435 using RT-PCR show the presence of a 442 bp fragment (Lanes 1, 2, 3 and 4) in males and a 612 bp fragment in females (Lane 5), showing that the BMdsx mini-gene with a heterologous fragment inserted between exon 3 and 4 is able to splice correctly in the divergent moth, PBW. Markers are SmartLadder™ from Eurogentec; bands of approx 0.2, 0.4 and 0.6 kb are indicated FIG. 44: Sex-specific splicing of *Anopheles gambiae* dsx.

*Anopheles* (A) shows the splicing that was reported by Scali et al 2005. However, when RT-PCR was performed using our primers (spl-agdsx-e3 (SEQ ID NO. 60) and spl-agdsx-m (SEQ ID NO. 61)) a different splicing pattern for females was revealed, represented by *Anopheles* (B).

Figure 45:
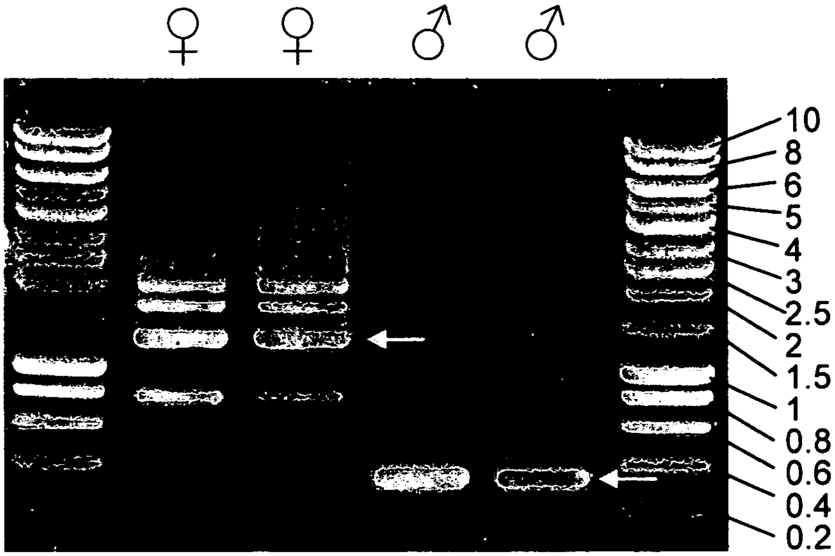

FIG. 45: Identification of male and female *Anopheles gambiae* using dsx primers.

RNA was extracted from male and female *Anopheles gambiae* and the dsx transcripts were amplified by RT-PCR using the primers spl-agdsx-e3 (SEQ ID NO. 62) and spl-agdsx-m (SEQ ID NO. 63); the resulting banding pattern is shown in the gel above. The expected bands for the male and female transcripts are indicated by the white arrows, the bands have been cloned and sequenced and are identical to the predicted sequence of our version of the dsx transcript (see SEQ ID NO. 47 (LA3359) and SEQ ID NO. 48 (LA3433)). The molecular weight markers are shown in kb (SmartLadder™ from Eurogentec; sizes are approximate).

Figure 46:
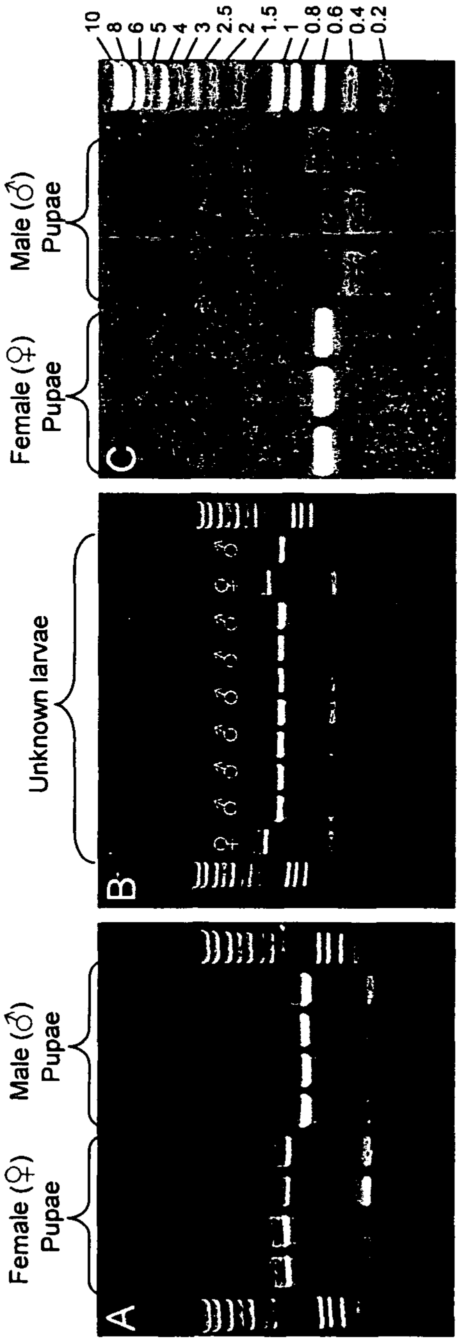

FIG. 46; Identification of male and female *Stegomyia aegypti* using dsx primers.

The primers for the *Stegomyia aegypti* RT-PCR for A and B were aedesxF1 (SEQ ID NO. 64) and aedesxR5 (SEQ ID NO. 65) were tested initially on pupae, a life stage of *Stegomyia aegypti* that can be sexed conveniently and accurately; the resulting RT-PCR amplification is shown on gel image (A). The male and female pupae show a distinctive sex specific band. Then the primers were tested on RNA extractions from larvae, which can not be readily sexed by their morphology and the resulting RT-PCR amplification shown on gel image (B). The larvae show a clear banding pattern which distinguishes males from females unambiguously. Gel image (C) shows an approximately 600 bp band from RT-PCR using the primers aedessxF1 and aedesxR2 (SEQ ID NO. 66) from individual male and female pupa. Sequencing of this band showed a female specific splice variant which does not appear to possess the male shared exon to which aedesxR5 is predicted to anneal (exon 7, see FIG. 56). The molecular weight markers are shown in kb (SmartLadder™ from Eurogentec; sizes are approximate).

Figure 47:
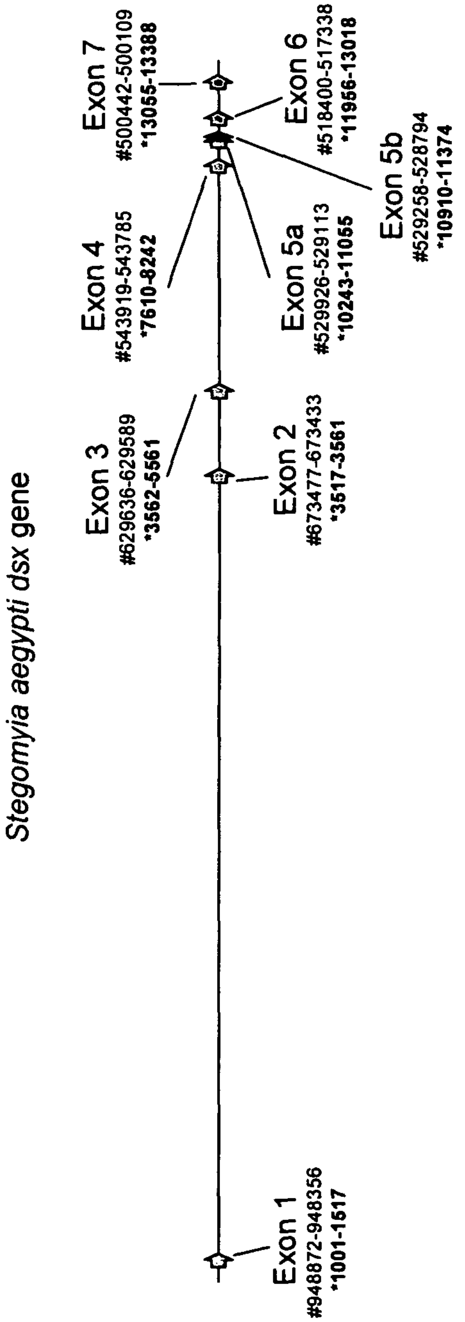

FIG. 47: Diagrammatic representation of part of the *Stegomyia aegypti* dsx gene (not to scale).

A fragment of the *Stegomyia aegypti* dsx gene is represented above. Exons 5a and 5b are female specific and exon 6 is a male specific exon. Two female-specific splice variants have been found (F1 and F2) which comprise exons 1-4, 5b, 6 and 7 (F1) or 1-4, 5a (F2); transcripts in males (M1) comprise exons 1-4, 6 and 7 but not exon 5a or 5b and a transcript (C1) of 1-4 and 7 but not exons 5a, 5b or 6 is shown in males and females. The numbers for each of the exons after # relates to contig 1.370 ( (on the world-wide web, address broad.mit-.edu/annotion/disease_vecter/aedes_aegypti/),which reads in the opposite orientation, and after * relate to the nucleotide sequence shown in SEQ ID NO. 43.

Figure 48:
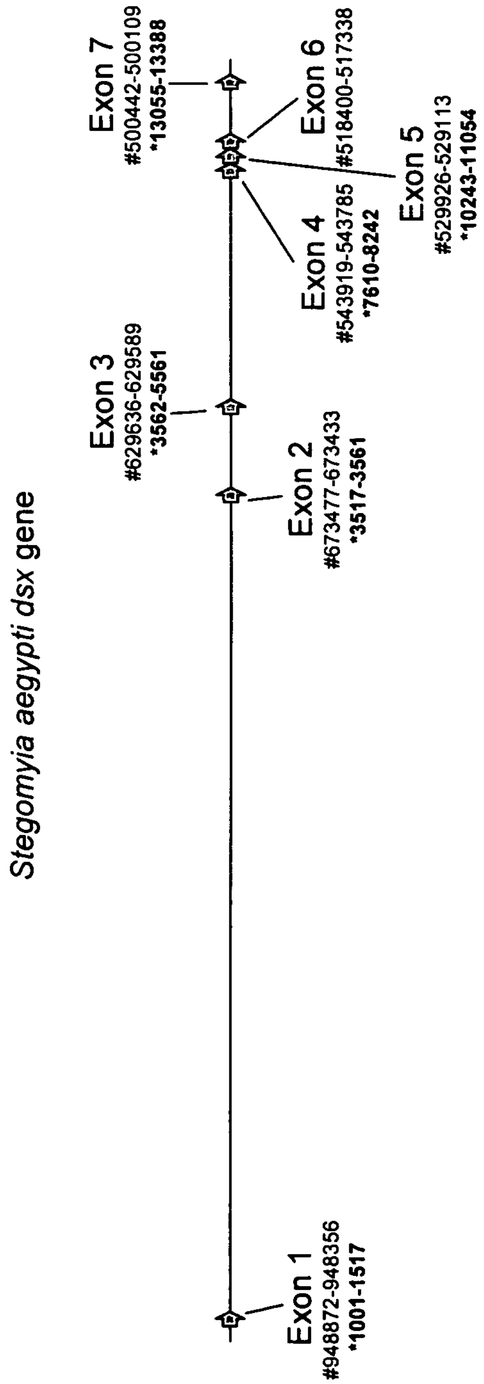

FIG. 48: Diagrammatic representation of the *Stegomyia aegypti* dsx gene.

Figure 12:
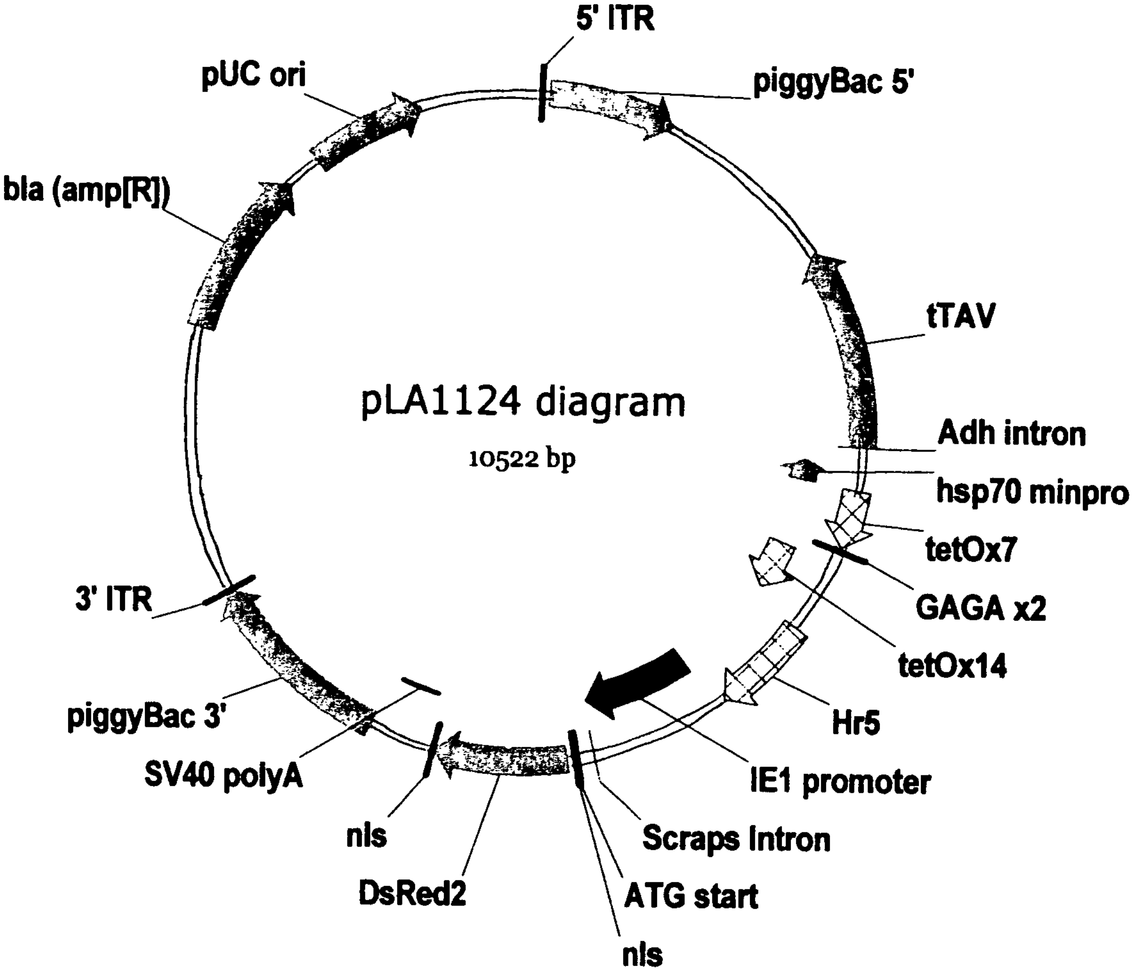
FIG. 12 is a schematic diagram of pLA1124.

The entire *Stegomyia aegypti* dsx gene is represented above Exon 5 is the female specific exon and exon 6 is a putative male specific exon. In principle, transcripts in females comprise exons 1, 2, 3, 4, 5 and 7, and males comprise exons 1, 2, 3, 4, 6 and 7. The numbers for each of the exons after # relates to contig 1.370 ) (on the world-wide web, address broad.mit-.edu/annotion/disease_vecter/aedes_aegypti/), reading in the opposite orientation, and after * relate to FIG. 12.

Figure 49:
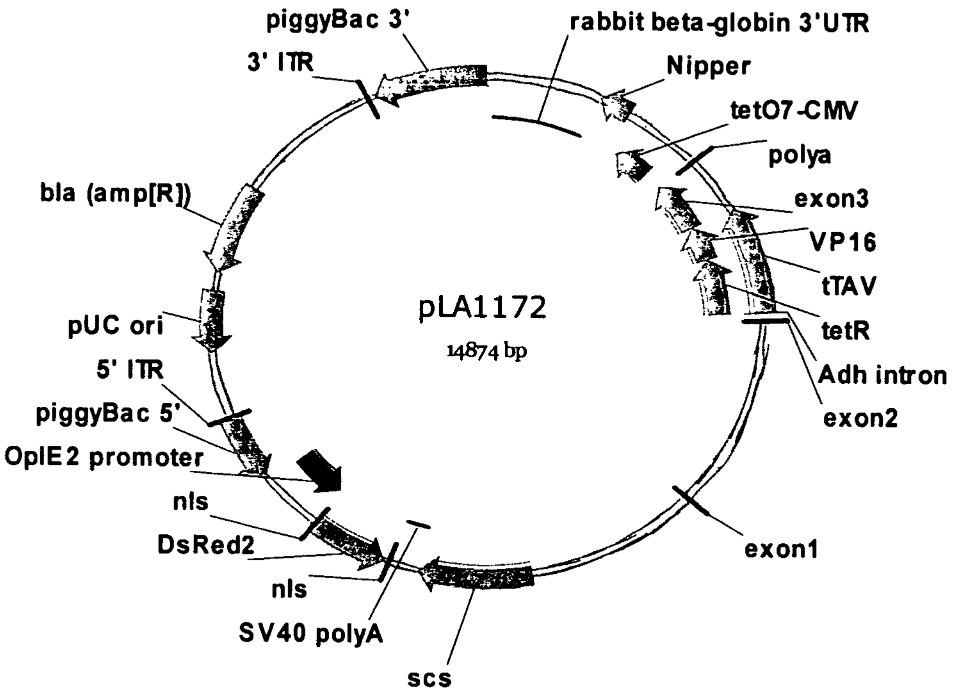

FIG. 49: Plasmid map of pLA 1172.

A coding region for tTAV has been placed under the control of a fragment from the *Stegomyia aegypti* actin-4 gene (Munoz et al 2005) which includes the 5' UTR, first intron, and upstream sequences (putative promoter). The construct also contains a tet$O_7$ Nipper sequence. The construct has piggyBac ends and a DsRed2 marker for stable integration into a genome.

Figure 50:
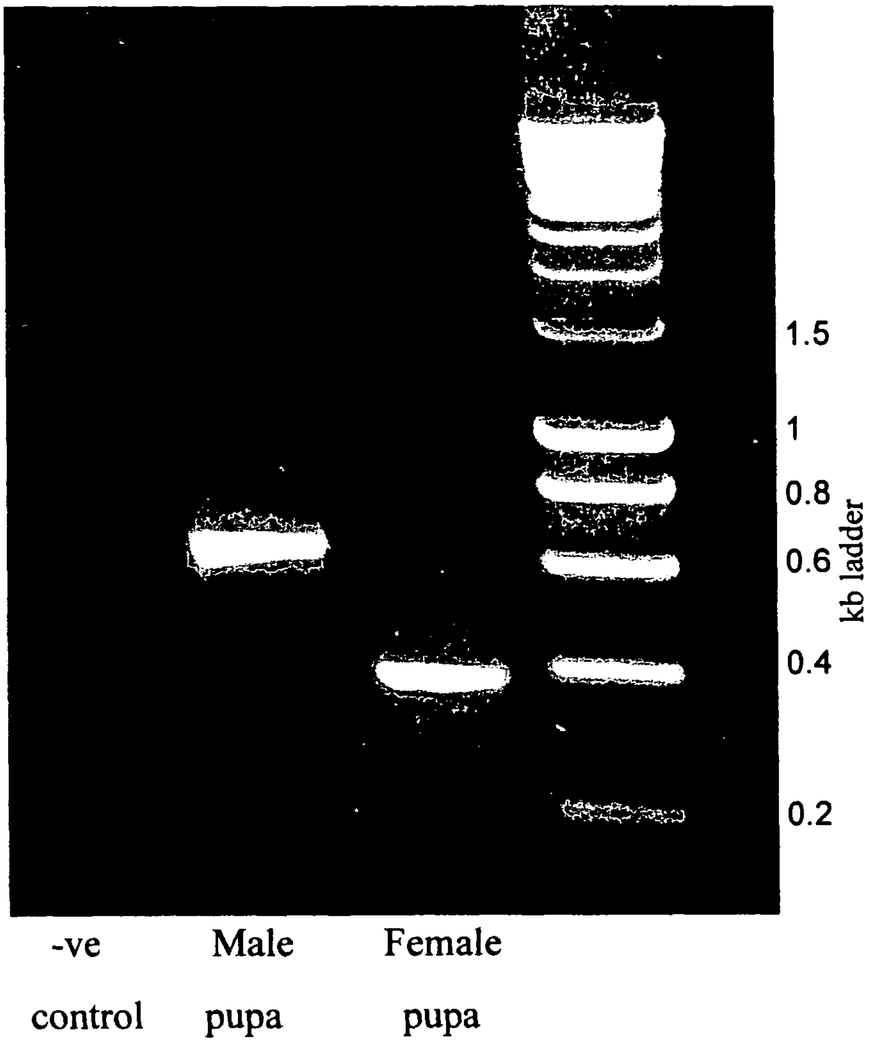

FIG. 50: Sex-specific splicing of tTAV in LA1172 (SEQ ID NO. 106) transformants.

Gel image of RT-PCR of RNA extracted from LA1172 line 2 male and female pupa. The primers used were Agexon1 (SEQ ID NO. 67) and Tra (tTAV) seq+ (SEQ ID NO. 68). Sequencing of the RT-PCR bands showed the expected splicing occurring in males and females. The data shown in the above diagram is for LA1172 line 2, line 8 showed exactly the same results (data not shown). Markers are SmartLadder™ from Eurogentec; approximate sizes are indicated, in kb).

Figure 51:
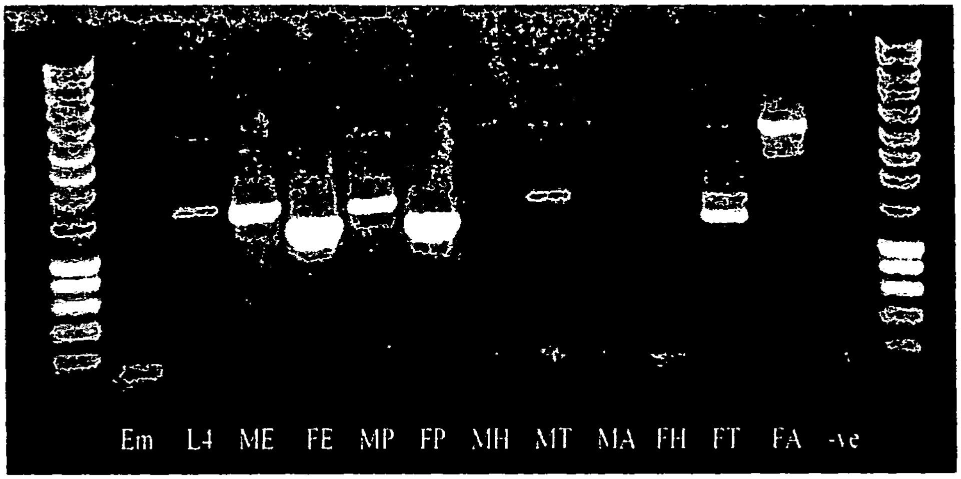

FIG. 51: RT-PCR of wild type samples, showing sex-specific splice variants of the *Stegomyia aegypti* Actin-4 gene.

Gel image of RT-PCR of RNA extracted from different developmental stages, and dissections of adults, of LA1172 line 8. The primers used were Agexon1 (SEQ ID NO. 69) and Exon 3 (SEQ ID NO. 70). The gel image shows that strong expression from the Actin-4 gene only occurs at the pupal stage, and that adult expression is generally limited to the female thorax where the flight muscles are found. Table 17, below show the contents of each lane.

TABLE 17

| | |
|---|---|
| E = pool of ~100 embryos | MH = head from male adult |
| L4 = $4^{th}$ instar larva | MT = thorax from male adult |
| ME = early male pupa (<4hours old) | MA = abdomen from male adult |
| FE = early female pupa (<4hours old) | FH = head from female adult |
| MP = male pupa | FT = thorax from female adult |
| FP = female pupae | FA = abdomen from female adult |
| | −ve = water control |

Sequence Listings

SEQ ID NOS. 1-13 and 23-33 are described in Examples 1-12. JY2004-tTA (SEQ ID NO. 14)—sequence of the tet$O_7$-tTA region only pP[Casper-Act5C-tTA] (SEQ ID NO. 15)
pLA513 (SEQ ID NO. 16)
pLA517 (SEQ ID NO. 17)
pLA656 (SEQ ID NO. 18)
pLA670 (SEQ ID NO. 23)
pLA710 (SEQ ID NO. 19)
pLA928 (SEQ ID NO. 20)
pLA1038 (SEQ ID NO. 24)
pLA1124 (SEQ ID NO. 21)

pLA1188 (SEQ ID NO. 22)

SEQ ID NO. 34: Open reading frame of tTAV

SEQ ID NO. 35: Protein sequence of tTAV

SEQ ID NO. 36: Open reading frame of tTAV2

SEQ ID NO. 37: Protein sequence of tTAV2

SEQ ID NO. 38: Open reading frame of tTAV3

SEQ ID NO. 39: Protein sequence of tTAV3

SEQ ID NO. 40: Pink Bollworm dsx female specific sequence fragment 1

SEQ ID NO. 41: Pink Bollworm (PBW, *Pectinophora gossypiella*) dsx female specific sequence fragment 2

SEQ ID NO. 42: Pink Bollworm (PBW, *Pectinophora gossypiella*) dsx male specific sequence SEQ ID NO. 43: Partial gene sequence of *Aedes aegypti* dsx. All exonic sequence is included, but only partial intronic sequence—see FIGS. 47 and 48 for annotation.

SEQ ID NO. 44: Codling moth (*Cydia pomonella*) dsx female gene sequence: includes a stretch of unknown nucleotides, preferably than then 100, preferably less than 50, more preferably less than 20, more preferably less than 10, and most preferably less than 5.

SEQ ID NO. 45: Codling moth (*Cydia pomonella*) dsx-male sequence.

SEQ ID NO. 46: Sequence of pLA3435-*Bombyx mori-dsx* construct/plasmid.

SEQ ID NO. 47: Sequence of pLA3359-*Anopheles gambiae* dsx construct.

SEQ ID NO. 48: Sequence of pLA3433-Agdsx (*Anopheles gambiae*) construct with exon 2 included.

SEQ ID NO. 49: Sequence of pLA1188-cctra intron construct

SEQ ID NO. 50: Sequence of pLA3077-a Cctra intron-tTAV construct.

SEQ ID NO. 51: Sequence of pLA3097-a Cctra intron-tTAV construct.

SEQ ID NO. 52: Sequence of pLA3233-Cctra-intron-tTAV2 construct.

SEQ ID NO 53: Sequence of pLA3014-Cctra-intron-Ubiquitin-reaperKR construct.

SEQ ID NO. 54: Sequence of pLA3166-Cctra intron-Ubiquitin-reaperKR construct.

SEQ ID NO. 55: Sequence of pLA3376-Bztra intron-reaperKR and Bztra-intron-tTAV3.

SEQ ID NO. 56: Sequence of pLA3242-Crtra intron-reaperKR construct.

SEQ ID NO. 57: Partial sequence of a male transcript generated in *Drosophila melanogaster* from LA3077 transformants that differs to the sequence generated in Medfly LA3077 lines. This sequence corresponds to the M3 transcript depicted in FIG. 36.

SEQ ID NO. 58: Partial sequence of *Bactrocera zonatra* tra homologue. Sequence of intron predicted to be spliced out in a female-specific transcript of *B. zonata* tra (+3 to +970 bp in sequence). Exonic flanking nucleotides are at positions 1-2 and 971-972, i.e. at the 5' and 3' ends of the intronic sequence. In fact, it is worth noting that the intronic sequence is flanked on its 5' end by a Guanine nucleotide, which is thought critical for a clean exit of the intron.

SEQ ID NO 59: Partial sequence of *Ceratitis rosa* tra homologue. Sequence of intron predicted to be spliced out in a female-specific transcript of C. *rosa* tra (+3 to 1311 bp in sequence). Exonic flanking nucleotides are present at positions 1-2 and 1312-3. Again, it is noteworthy that the intronic sequence is flanked on its 5' end by a Guanine nucleotide, which is thought critical for a clean exit of the intron.

SEQ ID NOS. 60-70: Primers as referred to in FIGS. 44-46 and 50-51.

SEQ ID NO. 71: Pink Bollworm (PBW, *Pectinophora gossypiella*) dsx female specific fragment 3.

SEQ ID NO. 72: Open reading frame of *Drosophila melanogaster* ubiquitin.

SEQ ID NO. 73: Protein sequence of *Drosophila melanogaster* Ubiquitin.

SEQ ID NOS. 74-105 are primers as discussed below in the Examples.

SEQ ID NO. 106 is pLA1172.

DETAILED DESCRIPTION OF THE INVENTION

The key tissue for development of filarial worms in their *Culex* mosquito hosts is the adult female in direct flight muscle (IFM). Although it is highly desirable to express an anti-filarial effector molecule in this tissue only, no promoter with this specificity is known. The *Drosophila* IFM Actin gene Act88F is known to be expressed correctly in the IFM's of these mosquitoes (Allen et al, 2004). Therefore, as provided in the present invention, combining the Act88F Actin gene promoter with a suitable alternative splicing mechanism that is sex-specific to the female, allows expression of an effector molecule in this tissue, in females only. Accordingly, such a system is preferred.

Many examples of suitable effector molecules are known to the person skilled in the art, for example pro-apoptotic proteins, e.g. Hid and Reaper and their suitable mutant derivatives, as described above.

The above is an example of a sex-specific alternative splicing mechanism that is capable of exerting a level of male-specific or female-specific control on the expression of a gene of interest, in this case the anti-filarial effecter molecule. Further examples of sex-specific alternative splicing mechanisms are given below, but the invention also extends to tissue-specific, stage-specific, and germ-line-specific alternative splicing mechanisms. Expression with this specificity would be very useful, but extremely difficult to obtain by any other method.

Thus it is also preferred that the at least one protein differentially expressed due to alternative splicing is effective against a pathogen, i.e. is capable of reducing or preventing the transmission of a pathogen, or human, plant or livestock disease, by a non-human transmission vector. Examples are proteins having an effector function capable of preventing transmission of the malarial parasite in mosquitoes or the parasite responsible for sleeping sickness borne by the Tsetse Fly.

Preferably, the protein blocks parasite invasion or entry into the host. Beard et al. (Beard, C. B., Cordon-Rosales, C and Durvasula, R. V. (2002). Bacterial symbionts of the triatominae and their potential use in control of Chagas disease transmission. Ann. Rev. Ent. 47:123-141.) took the bacteria which live in the gut of the Kissing Bug (which transmits Chagas disease), modified it to secrete a peptide and/or protein and re-inserted the bacteria back into the Bug. This was shown to reduce transmission of the parasitic protozoan *Trypanosoma cruzi* and, therefore, the disease.

Therefore, it is envisaged that a similar approach be taken with the malaria parasite. It is known to take bacteria (*E. coli*) which live in the gut of mosquitoes (*Anopheles stephenis*) and engineer them so they express a 'killer' gene such as ricin, and an antibody which is targeted against an essential cell surface molecule of the parasite. When these genetically modified bacteria are reintroduced back into the gut of the mosquito, this resulted in a 95% reduction in the number of oocysts formed (Yoshida, S., Ioka, D., Matsuoka, H., Endo, H. and Ishii, A. (2001). Bacteria expressing single-chain immonotoxin inhibit parasite development in mosquitoes. Mol. Biochem. Parisitol. 113:89-96).

It is also preferred that two or more alternative splicing mechanisms may be combined, to give a further level of combinatorial control. So, for example, a sex-specific alternative splicing mechanism is combined with another splicing system, for example the stage-specific splicing of *Drosophila melanogaster* Mhc exon 18, as described above, to provide a transcript expressed only in embryonic and larval male (or, alternatively, female) muscles.

A wide range of alternative splicing systems will be known to the person skilled in the art. For example, the European Bioinformatics Institute of the European Molecular Biology Organization (EMBL-EBI) hosts a database of alternatively spliced genes and sequences, and computational tools for identifying such a (on the world-wide web, obi.ac.uk/asd) and Clark and Thanaraj, 2002; Thanaraj et al., 2004). Other examples may readily be found in the literature, for example in (Black, 2003; Burset et al., 2001; Cartegni et al., 2002; Maniatis and Tasic, 2002; Pan et al., 2004; Park et al., 2004; Smith and Valcarcel, 2000; Venables, 2002, Venables, 2004) and references contained therein. Non-limiting, The present invention may use any suitable alternative splicing system, selectable by the skilled person on the basis of the combination of expression required from his common general knowledge including those described in the art discussed herein, which is hereby incorporated by reference.

The system, therefore, preferably comprises splice control sequences derived from, of rinstance AaActin-4, Dsx, Bztra or Cctra. These and other particularly preferred examples are discussed below.

By "derived" it will be understood that it is meant that the splice control sequence is a sequence from that gene. The splice control sequence itself is a sequence, usually an intron or a substantial part is intronic sequence, which is capable of regulating or mediating the alternative splicing of the pre-mRNA transcript of the coding sequence from that that particular gene.

Tissue-Specific Splicing

Tissue-specific alternative splicing mechanisms are a wide spread phenomena, occurring in both the animal and plant kingdoms. Examples in plants can be found, for instance in The Plant Alternative Splicing Database, http://pasdb.genomicx.org.cn, incorporated by reference.

Preferred examples of tissue-specific alternative splicing mechanisms are given below.

In rice, the KNOX family class 2 homeobox transcripts undergo tissue-specific alternative splicing. The products of these alternative splicing events are suggested to have different degrees of abilities for activation and repression of transcription of target genes in the different organs in which they are expressed (Ito et al., 2002).

In humans, tissue-specific alternative splicing occurs in the Leukocyte common antigen mRNA. The differential splicing of LCA has a functional importance to T cells, since human T4+ cells are divided into two functionally distinct sub-populations based on expression of LCA isoforms. The sequences controlling this differential splicing can be found within exon 4, which is found in B cell mRNA but not thymocyte mRNA sequences (Streuli and Saito, 1989).

The yellow fever mosquito (*Aedes aegypti*) uses alternative splicing to generate two distinct isoforms of the lipophorin receptor (LpR). This receptor is the main transport vehicle, delivering lipids through the hemolymph to various organs. One isoform (AaLpRov) is expressed exclusively in ovarian germline cells, nurse cells and oocytes throughout the previtellogenic and vitellogenic stages, where it is utilized in yolk protein uptake. In contrast the fat-body specific AaLpRfb transcript is restricted to the post-vittellogenic period where it is important in the storage of lipid, carbohydrate and protein (Seo et al., 2003).

Stage-Specific Splicing

Stage-specific alternative splicing is also known in a range of organisms, and preferred examples are given below.

Stage-specific alternative splicing of the spinach and tobacco chloroplast ascorbate peroxidase (chlAPX) pre-mRNAs, generating distinct isoenzymes are important for changing the ratio and amount of chlAPX isoenzymes during germination and subsequent greening (Yoshimura et al., 2002).

*Drosophila melangaster* exhibits a diversity of functionally distinct muscle types in various tissues at different stages of development. Alternative splicing of muscle-specific contractile proteins such as myosin, actin, tropomyosin, and troponin are key in generating this functional diversity in muscle types. Myosin heavy chain (Mhc) mRNA is predicted to produce up to 480 MHC isoforms (George et al., 1989). It is expressed in not only a tissue-specific manner but also a stage specific manner. Alternative splicing of the penultimate exon 18 results in its inclusion in adult indirect flight muscles and other adult muscles mRNAs, exclusion of this exon occurs in all embryonic and larval muscle Mhc mRNA (Kazzaz and Rozek, 1989, Hastings and Emerson, 1991).

Sex-Specific Splicing

Sex-specific splicing is discussed elsewhere, and it will also be appreciated that sex-specific splicing also occurs in plants and examples are well-known. A preferred example is from *Marchantia polymorpha*, a liverwort. This is a sexually heteromorphic plant and displays sex-specific alternative splicing of a calcium-dependent protein kinase, a molecule involved in intracellular signaling events. In addition, tra-2 transcripts are found exclusively in the male sexual organ (Nishiyama et al., 1999 and Nishiyama et al., 2000).

Germline-Specific Splicing.

Preferred examples of germline-specific alternative splicing systems are given below.

Alternative splicing of the Wilms Tumour 1 (WT1) gene results in the incorporation of three amino acids (K, T, and S) which are thought to convert WT1 from a transcription factor to a splicing factor. This splicing factor isoform is essential for male sex determination in mice (Hammes, A et al., 2001) and regulates the expression of the SRY gene.

C3G is a ubiquitously expressed guanine nucleotide-releasing protein that binds to adaptor protein SH3 domains and is involved in the processes of cell growth, differentiation and apoptosis. The germ cell and somatic forms of this molecule are tightly regulated as there is no overlap in their expression pattern (Shivakrupa, et al 1999). The somatically expressed PKCδ is cleaved by caspase 3 resulting in its deregulation. The testes-specific variant contains an extra 78 bp which results in the addition of 26 amino acids that block caspase 3 cleavage.

The *Drosophila* P element taught in Siebel et al, 1992, is particularly preferred. Under the use of this alternative splicing mechanism, a gene of interest, such as an effector molecule or a marker, for instance, can be expressed in the germ line of the host under the control of an appropriate promoter. An example of this is given below and with reference to FIG. 19.

The P transposable element in *Drosophila* is 2907 bp in length and encodes an 87 kDa transposase protein, the 'full-length' canonical form. Variants are also known, especially deletion derivatives. Synthesis of a functional transposase protein is restricted to the germ line. This can only occur when all introns including the third intron (IVS3) are spliced out of pre-mRNA. Splicing of IVS3 is restricted to germ-line cells and in somatic cells is prevented by the binding of a protein complex to 30 bp of regulatory sequence at the 3' end of the second to last exon (exon 2). The presence of this intron, which contains a stop codon, left unspliced, produces a 66 kDa inactive protein which acts as a repressor towards functional transposase protein.

It is preferred to use this P element to generate germline-specific expression of a gene of interest (Gene E) by placing a portion of the P element ORF containing both exonic (at least 30 bp) and intron 3 (IVS3) upstream of a ubiquitin-Gene E fusion (See FIG. 19).

An ubiquitin fusion to the gene of interest is preferred because correct splicing of IVS3 requires exonic sequence. This sequence (P-element exon/IVS3-Ubiquitin-Gene of interest) can then be placed downstream of any promoter having germline activity, or to prevent non-specific expression, a germline-specific promoter.

This germline-specific intron can preferably be used in combination with any germline-active promoter with a desired expression pattern, for example a constitutive, sex-specific or inducible promoter (such as heatshock or GeneSwitch) as described elsewhere. This could alter the expression pattern of these promoters to become germline-specific, thereby providing a level of germ-line control of protein expression in combination with another level of control, such as environmental conditions, the presence of a hormone or inducer of protein transcription and expression.

A simple method for determining whether there is sufficient flanking sequence, or the minimal flanking sequence, required for correct germline-specific splicing is provided as follows:

(1) make a construct of the form promoter-5'flanking sequence-intron-3'flanking sequence.

(2) transfect into suitable cells, e.g. by electroporation, chemical transformation, microinjection or other suitable means known to the person skilled in the art.

(3) after incubation for a suitable period of time, which will depend in part on the species and cell type, extract RNA, RT-PCR the RNA corresponding to the construct and analyse, e.g. by gel electrophoresis and/or sequencing, to determine the splicing pattern.

If this is suitable for the purpose, there is sufficient flanking sequence. If not, more flanking sequence must be included and this can be repeated. If it is desired to determine the minimum suitable flanking sequence, then make a series of deletion derivatives of the construct until this is determined.

It is particularly preferred, however, that the alternative splicing mechanism is sex-specific. This allows expression of a protein of interest in a sex-dependent manner. For instance, if the promoter and/or enhancer of the gene expression system are switched on in muscles, the inclusion of a sex-specific alternative splicing mechanism means that expression of the protein can be either in male muscles only, or, alternatively, in female muscles only.

A particularly preferred example is the sex-specific control of the tetracycline transcriptional transactivator protein, tTA, or suitable variants and mutants thereof, such as tTAV, as described herein in Example 12, and tTAV2 and tTAV3.

For instance, under the control of an alternative splicing mechanism, a functional transcriptional transactivator protein can be produced only in females, with the result that expression of the system is found only in females, such that the females are adversely affected, and may indeed die as a consequence. However, in males, a different splicing combination is achieved, such that the transcriptional transactivator protein is not expressed or is not functional, with the result that the lethal effecter gene is not expressed so that the males survive. In this way, males and females may be easily separated.

Suitable organisms under which the present system can be used include mammals such as mice, rats and farm animals. Also preferred are fish, such as salmon and trout. Plants are also preferred, but it is particularly preferred that the host organism is an insect, preferably a dipteran or tephritid. Preferably, the organism is not a human, preferably non-mammalian, preferably not a bird, preferably an invertebrate, preferably an arthropod.

In particular, it is preferred that the insect is from the Order Diptera, especially higher Diptera and particularly that it is a tephritid fruit fly, preferably Medfly (*Ceratitis capitata*), preferably Mexfly (*Anastrepha ludens*), preferably Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha oblique*). It is also particularly preferred that the host organism is a mosquito, preferably from the genera *Stegomyia, Aedes, Anopheles* or *Culex*. Particularly preferred are *Stegomyia aegyptae*, also known as *Aedes aegypti, Stegomyia albopicta* (also known as *Aedes albopictus*), *Anopheles stephensi, Anopheles albimanus* and *Anopheles gambiae.*

Within Diptera, another preferred group is Calliphoridae, particularly the New world screwworm (*Cochliomyia hominivorax*), Old world screwworm (*Chrysomya bezziana*) and Australian sheep blowfly (*Lucilia cuprina*). Lepidoptera and Coleoptera are also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae. Among Coleoptera, Japanese beetle (*Popilla japonica*), White-fringed beetle (*Graphognatus* spp.), Boll weevil (*Anthonomous grandis*), corn root worm (*Diabrotica* spp) and Colorado potato beetle (*Leptinotarsa decemlineata*) are particularly preferred.

It is, as mentioned above, particularly preferred that the alternative splicing mechanism is sex-specific. Preferably, this may include the AaActin-4 mechanism, which is a gene from *Stegomyia aegypti* which shows tissue, stage and sex-specific splicing (see Act4-tTAV-LA1172, for instance in Example 20). It is also preferred that the splicing mechanism comprises at least a fragment of the *Drosophila* doublesex gene. However, it is particularly preferred that the alternative splicing mechanism is derived from the Medfly transformer gene Cctra, or from another ortholog or homolog of the *Drosophila* transformer gene, especially one derived from a tephritid fruit fly. This will be discussed in greater detail below and, although these are preferred examples, they are not limiting on the scope of the invention.

Although there a number of recent discussions in the art of combining gene expression systems with alternative splicing mechanisms to result in recombinant gene regulation, none of these groups have actually been successful in providing a construct capable of achieving this end.

In particular, Rafael et al (February 2004) disclose that “a similar approach could be achievable in any insect, including tephritids, provided that species-specific regulatory elements and lethality genes or genetic constructs are isolated. The yolk protein regulatory elements, which have been isolated from *B. tryoni*, may form the basis for female-specific expression of a transgene in this species. Alternately, the regulatory elements which control dsx sex-specific splicing may be manipulated such that the effects of a lethal gene are only observed in females of a line which carries an engineered dsx construct."

Similarly, Crisanti's and Scali's (2005) paper on the Doublesex gene derived from *Anopheles gambiae* hints that "[t]he identification of female- and male-specific transcripts of Agdsx represents an important step towards the understanding of the sex differentiation process in *A. gambiae* and will facilitate the development of genetic tools to induce male sterility or manipulate sex ratios in mosquitoes, for instance by constitutively expressing the female-specific form of dsx in the male gonads or by inducing the sex-specific splicing of a dominant lethal".

Therefore, although there is some discussion in the recent art of the need for effective systems combining alternative splicing with heterologous gene expression, these have been only desiratum and have not led to working examples. Indeed, Scott et al (Scott et al., 2004) try to use a composite system, comprising more than one splicing cassette, including part of *Drosophila* doublesex, but concluded that the constructs spliced in the expected "female-specific" pattern in both males and females. Accordingly, they were not able to achieve sex-specific splicing, as a single splice variant was found in both males and females.

It is preferred that the present system uses a single splicing cassette for reasons of efficiency and to avoid the risk that the function of the alternatively spliced intron is modified or compromised by heterologous sequence placed close to it.

Surprisingly, the present inventor has discovered that it is possible to provide an alternative splicing mechanism that can be used, optionally together with additional splice control sequences, in combination with a gene expression system for at least one gene or protein of interest, whereby the alternative splicing mechanism is capable of providing a level of additional control, for instance in a sex-specific or tissue-specific manner, as discussed elsewhere. Stage-specific and germline-specific alternative splicing mechanisms are also preferred. However, sex-specific alternative splicing mechanisms are most preferable.

Whilst it is preferred that the alternative splicing mechanism comprises at least fragments of any of the following genetic elements, selected from the group comprising 5' and/or 3' flanking sequences, exonic sequences, 5' untranslated region (UTR), the 3' untranslated region (3' UTR) and, of course, the intron, it is preferred that the alternative splicing mechanism comprises only short exonic sequences from the flanking regions surrounding the intron in its native context, preferably shorter than 50 nucleotides at each end, and particularly preferred that the alternative splicing mechanism consists entirely of the intron alone or fragments thereof, i.e. without any additional sequences from the flanking regions, the UTR's or exons which would be adjacent to the intron in its native context.

By "native context" it is meant that that the intron, for instance in its wild-type form in nature, is found in association with exon(s) and a promoter, and thus had specific sequences adjacent to it. However, it is preferred to use the intron substantially without these adjacent sequences, i.e. it may be used including only a fragment of these adjacent sequences, but is it preferred that none of the residues of these adjacent sequences are included.

However, when used according to the present invention, the intron will be surrounded by exonic sequences, which will preferably be new or heterologous sequences.

Although the Cctra intron will splice without requiring any specific exonic sequences derived from the Cctra gene, it is not obvious that this is the case for all introns. Exonic splice enhancers (ESEs) and silencers (ESSs) are prevalent in most, if not all, exons and can be important in alternative splicing (Cartegni, et al., 2002). Where exonic sequences are required for efficient operation of the alternative splicing mechanism, it is preferred that the system also include an ubiquitin protein cleavage system (Varshavsky, 2000). The ubiquitin fusion technique greatly increases the ranges and ease of application of alternative splicing as a method for controlling gene expression.

Many proteins will still function with additional amino acids fused to their amino (N) or carboxy (C) termini. This is widely used, for example to fuse an epitope tag, or a fluorescent protein, to a protein of interest, without disrupting its normal function. It is, therefore, preferred to use alternative splicing cassettes which encode one or more amino acids in all alternative splicing variants, by fusing part or all of the alternatively spliced protein to the protein of interest, typically with the alternatively spliced protein at the N-terminus.

FIG. 20 illustrates this, using dsx as example of alternative splicing. Application of this principle to other forms of alternative splicing will be clear to the person skilled in the art.

Of these, version A gives male-specific expression by inserting additional exonic material in the female, disrupting or modifying the function of the protein in females (e.g.) by addition of another protein domain, or premature termination. Version B gives male-specific expression by fusing the protein of interest to the male-specific coding sequence, as can versions C and D, though alternative configurations are also possible. In each case, this would represent the fusion of heterologous sequence to the N-terminus of the protein of interest.

Though the function of many proteins is known not to be affected by such N-terminal fusions, this is not true for all proteins. For example, many secreted or transmembrane proteins have a signal sequence that must form the N-terminus of the coding region. As another example, the proapoptotic protein Reaper is known to have a functional domain, probably involved in binding to dIAP1/Thread, which must be at the N-terminus of the protein. Fusions to the N-terminus, in some cases even of a single amino acid can, therefore, tend to inactivate Reaper (Olson et al., 2003).

However, in order to overcome the limitation of N-terminal fusions, it is particularly preferred to use amino acid or polynucleotide residues coding for at least the cleavage site portion of ubiquitin, more preferably the full protein sequence.

The nucleotide and protein sequences for ubiquitin are SEQ ID NOS 72 and 73, respectively.

It is preferred that the expression system, therefore, comprises nucleotides encoding at least the cleavage site of ubiquitin, and preferably the nucletode sequence according to SEQ ID NO. 72. This is preferably arranged such that the unbiquitin orp portion thereof is substantially N-terminal to the protein of interest, but more preferably immediately N-terminal (i.e. immediately adjacent) the protein of interest.

This arrangement will reduce the size of, or eliminate, the N-terminal fusion to the post-cleavage (mature) protein. However, in the specific case of a signal peptide, it is known that in some cases, in order to function normally, this signal must be present at the N-terminus of the primary translation product. In such a case it is preferred that the protein be expressed without a fusion N-terminal of the signal sequence.

Ubiquitin proteases will then cleave the protein of interest from the ubiquitin moiety, allowing the correct folding of the N-terminus of the downstream protein. So, if the entire fusion protein is:

Start codon-segment of alternatively spliced gene-ubiquitin-protein of interest the protein of interest will cleaved from the ubiquitin moiety and retain normal folding and function.

Where suitable ubiquitin proteases are not constitutively expressed or expressed at a suitable level, it is preferred that the present invention comprises polynucleotides coding therefor, preferably under the control of a suitable promoter, such that expression of the ubiquitin protease is preferably linked to expression of the fusion protein.

Using this particularly preferred method, alternative splicing can be used, even if the alternative splicing requires exonic signals some distance from the intron itself, and if the specific alternative splicing strategy requires the intron to be in a translated region (and therefore requires the synthetic construct to have a significant amount of coding region derived from the source of the alternative splicing) and if the protein of interest will not tolerate fusions.

If required, several proteins could be controlled by the same regulatory system, by inserting a ubiquitin moiety between each. In such a case, it is preferred that a stabilized mutant derivative of ubiquitin, for example ubiquitin$^{K48R}$ (Rasoulpour et al., 2003; Finley, et al., 1994), be used as the ubiquitin moiety.

Indeed, where reference is made to the term "ubiquitin" is made, it will ube inderstodd that it includes ubi$^{K48R}$ and all suitable substrates of ubiquitin. Under some circumstances, a similar effect could be obtained by using a stop codon and an internal ribosome entry sequence (IRES) to separate the coding regions.

It is also preferred to vary the level of control by using alternative splicing, e.g. the as dsx system above, to provide different C-termini for a protein. Specific signals, for instance a prenylation motif (such as—CAAX from Ras) differentially incorporated into these alternate C-termini affect protein function and/or location.

In order to differentially affect protein stability, it is preferred to incorporate signals regulating stability into the genetic system, such as PEST sequences, as are found in many rapidly degraded proteins. These sequences have been suggested to serve as signals for proteolytic degradation. From a survey of the amino acid sequences of 10 short-lived eukaryotic proteins, Rogers et al. [Science. 1986; 234:364-368] found the proteins to contain one or more regions rich in proline (P), glutamic acid (E), serine (S), and threonine (T). These regions are often flanked by positively charged amino acids.

Similarly, it is also preferred to incorporate [polynucleotides encoding RNA stability or instability signals into the genetic system according to the present invention, or signals affecting protein or RNA location, translation, for instance.

The issue of saturation is another generic objection raised in the art to the artificial use of alternative splicing to regulate gene expression. However, this is overcome by a preferred embodiment of the present invention. It is suggested in the att that the factors regulating alternative splicing are thought to be in relatively short supply, so that the alternative splicing pathway or system can be saturated if too much pre-mRNA (primary transcript) is provided (Stoss et al., 1999, Stoss 2001, Yali and Pin Ouyang., 2006).

We have, surprisingly, shown that this is not the case, in Cctra in positive feedback constructs, in that the system is not prevented from functioning as desired. For tra, the default splicing is in the male pattern; female-type splicing to give transcript F1 (FIG. 21) occurs only in the presence of a splicing complex which includes Tra and Tra-2 proteins.

Tra is expressed only in females and so this complex is present only in females. There is no reason to think that these are particularly abundant proteins. For the female-specific positive feedback system to work, i.e. to kill females, very large amounts of tTA need to be produced.

tTA is only produced from transcripts spliced in the female (F1) form, so correspondingly large amounts of this transcript have to be produced. That this is readily accomplished implies that the Tra/Tra2-dependent sex-specific splicing system is not easily saturated.

We have optimized and resynthesized the original tTA sequence for use in *Anopheles gambiae, Bombyx mori* and *Drosophila melanogaster* and generated the variants tTAV (SEQ ID NO. 34—DNA, SEQ ID NO. 35—protein), tTAV2 (SEQ ID NO. 36—DNA, SEQ ID NO. 37—protein) and tTAV3 (SEQ ID NO. 38—DNA and SEQ ID NO. 39—protein).

Thus, in a preferred aspect of the invention, the expression system comprises nucleotides encoding tTA or its functional variants and mutants, in particular those selected from the group consisting of: tTAV (SEQ ID NOS. 34 and 35), tTAV2 (SEQ ID NOS. 36 and 37), and tTAV3 (SEQ ID NOS. 38 and 39), being highly effective tTA variants.

It is, therefore, particularly preferred that the present invention comprises a repressible transactivator protein in combination with the alternative splicing mechanism.

Preferably this is the tet system described herein, and in particular, comprises the tTAV variants described above.

Thus, it is also particularly preferred that the genetic system is used in combination with a further control system. A preferred further control system is the positive feedback system described herein.

AaActin-4

An example of a sex-specific alternative splicing mechanism is AaActin-4. This is a gene from *Stegomyia aegypti* (formerly *Aedes aegypti*), which also shows sex-specific splicing. We have shown that a fragment of this gene, including the intron, a large amount of 5' flanking sequence and a little 3' flanking sequence, splices correctly when reintroduced into this mosquito.

There is a single publication on this gene, which does not mention sex-specific splicing (Muñoz et al., 2004). We've made transgenic mosquitoes (*Stegomyia aegypti*) carrying a fragment of this gene, which is spliced correctly, but a fragment that contained the female intron only was not correctly spliced in Medfly (spliced in the male pattern in both males and females).

It is preferred that Actin-4 is used in combination with the tTAV variant system discussed above.

Dsx and Tra

It is more preferable, however, that the alternative splicing mechanism is dependent on the transformer (tra) gene from insects such as *Drosophila* or Medfly, or its homologues. This protein acts in a complex that also comprises the product of the transformer-2 (tra-2) gene, or its homologues; this complex is involved in the genetic control of sexual differentiation (Pane et al., 2002; Saccone et al., 2002). In particular, these genes and their gene products act on the doublesex genes from *Drosophila*, and its homologues in other species; homologues of dsx are present throughout the insect world, for instance. Tra/tra-2 also act on the Medfly transformer gene which acts as an additional level of control in Medfly and similar insects including *Ceratitis rosa, Drosophila melanogaster, Bactrocera zonata*, and *Anastrepha ludens*.

When the doublesex alternative splicing mechanism is used, it is preferred that the genetic system is used in Diptera, preferably including those described above.

Particularly in the case of Dipterans, it is preferred that tra and/or tra-2 are expressed in either the male or the female host or organism.

Alternatively, it is also preferred that tra/tra-2 themselves form part of the genetic system and the respective proteins may be encoded by nucleic acids provided in a construct or constructs which form part of the genetic system according to the present invention, under the control of suitable promoters.

In this way, the skilled person will be able to separately control the expression of tra and/or tra-2 and, therefore, allow the user an additional level of spatial or temporal control, i.e. to allow the user to initiate alternative splicing at predetermined point. This could be achieved by linking the tra/tra-2 genes to a promoter, such as the hsp70 heat shock promoter, which can be initiated by high temperatures, thereby leading to expression of the tra and tra-2 proteins, which in turn allow alternative splicing to proceed, at a user-defined time and in an easily controllable manner.

For instance, this allows both and control of, for instance, the Cctra intron in species that have divergent tra (or no tra at all), by expressing tra in a particular stage- or tissue-specific manner. It also allows regulated expression in males, who would not normally express tra. However, to ensure sex-specific expression, by this mechanism, in a species that doesn't have equivalent tra, one may need to arrange differential sex-specific expression of tra, as will be apparent to the skilled person.

When using an alternative splicing mechanism comprising the doublesex mechanism, it is preferred that exonic signals from the doublesex gene are present. In this instance, it is particularly preferred that the following sequences are used:

1) the tra/tra2 binding sites (T/A)C(T/A)(T/A)C(A/G)AT-CAACA (Hedley et al., 1991, Hoshijima et al., 1991, Ryner et al., 1991);
2) Medfly dsx mRNA (Genbank ID number AF435087: on the world-wide web, ncbi.nlm.nih.gov/entrez/viewer.fcgi?db=nucleotide&val=24637185)
3) Pink boll worm dsx female specific 1 exonic sequence (SEQ ID NO. 40);
4) PBW dsx-female specific 2 sequence (SEQ ID NO. 41);
5) PBW male specific sequence (SEQ ID NO. 42);
6) *Anopheles gambiae* dsx gene sequence (Genbank ID number GiI9611767);
7) *Aedes aegypti* dsx gene sequence (Supercontig 1.370 (on the world-wide web address broad.mit.edu/annotation/disease_vector/aedes_aegypti/) and SEQ ID NO. 43);
8) Codling moth dsx gene sequence from females (SEQ ID NO. 44) and males (SEQ ID NO. 45).

Dsx

Where the genetic system of the present invention consists or comprises construct, it is preferred that the construct is selected from the group consisting of: LA3435 (SEQ ID NO. 46 and FIG. 22—vector map), LA3359 (SEQ ID NO. 47 and FIG. 23—vector map) and LA3433 (SEQ ID NO. 48 and FIG. 24—vector map). Dsx is also discussed in more detail elsewhere.

Tra

A particularly preferred example of an alternative splicing mechanism that is sex-specific is the transformer intron from Medfly, referred to as Cctra. This is an example of an "intron-only" alternative splicing mechanism, as it does not necessarily require the presence of exonic, 5' or 3' flanking or untranslated region sequences.

Figure 16:
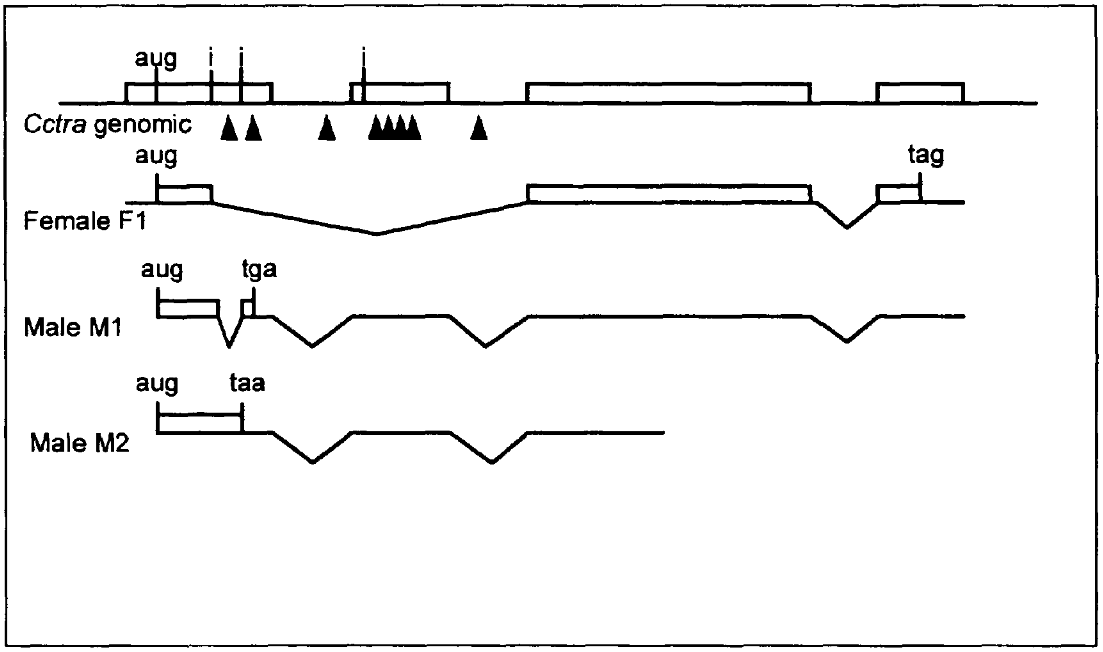
FIG. 16 illustrates the sex-specific splicing of Cctra in medfly.

The splicing mechanism of Cctra was first described in Pane et al (2002) as referred to in Example 12 and accompanying FIG. 16. The disclosure of Pane et al 2002 is hereby incorporated by reference.

This alternative splicing mechanism or cassette produces 3 splice variants in females, one of which is female-specific (called F1). The other two are called M1 and M2 and are also found in males. Thus, F1 is found only in females, whilst M1 and M2 are found in both males and females. Since each of the non-sex-specific transcripts (i.e. M1 and M2) contain additional exonic material with stop codons, only the female splice variant (F1) produces functional protein. Thus, where each genetic system comprises or consists of a construct, it is preferred that said construct is LA1188 and, most preferably, LA3077 or LA3097.

Although LA1188 (SEQ ID NO. 49 and FIG. 25—vector map) is functional, it is not preferred, as it can induce a frame shift.

Thus, it is particularly preferred that the construct comprises LA3077 (SEQ ID NO. 50 and FIG. 26—schematic), LA3097 (SEQ ID NO. 51 and FIG. 27—schematic), LA3233 (SEQ ID NO. 52—sequence and FIG. 28—schematic), LA3014 (Figure SEQ ID NO. 53 and FIG. 29—schematic), LA3166 (SEQ ID NO. 54 and FIG. 30—schematic), LA3376 (SEQ ID NO. 55 and FIG. 31—schematic) and LA3242 (SEQ ID NO. 56 and FIG. 32—schematic).

Other constructs, for instance plasmids, preferably comprise a 5' TG immediately adjacent the intronic sequence, and preferably also comprise a flanking GT sequence immediately 3' to the end of the intronic sequence. In particular, it is preferred that the intron is flanked on both 5' and 3' ends by Guanine nucleotides, in order to ensure a "clean exit" when the intron is spliced out, such that additional nucleotides are not also spliced out which may lead to a frame shift. However, if additional nucleotides are to be excised, in the splicing process, then it is preferred that these are excised in blocks or multiples of 3, so that there is no significant frame shift.

It is most particularly preferred, however, that the intronic sequences flanked on its 5'end by a Guanine nucleotide as this is of greatest importance when seeking to ensure a clean exit. It will be apparent to the person skilled in the art that a flanking G nucleotide can be readily provided without the incorporation of specific flanking exonic sequences from the gene from which the intron is derived, by identifying suitable sequences (e.g. TGGT, 5'G, etc) within the sequence of interest (that into which the intron is to be inserted). The redundancy of the genetic code means that this can readily accomplished.

Since protein coding regions generally begin with the nucleotide sequence 5'-ATG-3', in a particularly preferred embodiment, the TG of this A TG sequence comprise the nucleotides immediately preceding the intron, for example 5=UTR-ATG-intron-GT-3'.

Within this, preferred examples place the coding sequence for either ubiquitin or tTA, or their functional mutants and or variants such as tTAV, tTAV2 or tTAV3, 3' to the intron. These are arranged so that these elements are substantially adjacent to the 3' end of the intron, more preferably the such that the coding region starts within 20 nucleotides or less of the 3' intron boundary), and most preferably, immediately adjacent the 3' end of the intron. Preferred examples of constructs according to the present invention are listed in Table 16, below.

TABLE 16

| Construct NO. (FIGS #.) | Species tra intron is from | position from ATG | tra intron is fused to- |
|---|---|---|---|
| LA3014 (29) | Medfly | +22 bp | Ubiquitin |
| LA3166 (30) | Medfly | +136 bp | Ubiquitin |
| LA3097 (27) | Medfly | +0 bp | tTAV |
| LA3077 (26) | Medfly | +61 bp | tTAV |
| LA3233 (28) | Medfly | +0 bp | tTAV2 |
| LA3376 (31) | Medfly | +0 bp | tTAV2 |
| LA3376 (31) | *B. zonata* | +3 bp | Reaper KR |
| LA3376 (31) | *B. zonata* | +0 bp | tTAV3 |
| LA3242 (32) | *C. rosa* | +3 bp | reaperKR |

Table 16 shows constructs which contain a tra intron. The introns were derived from from *C. capitata, B. zonata* or *C. rosa* (column 1). Said intron was inserted within the coding region such that the distance between the putative initiator ATG and the last nucleotide of the exon immediately preceding the tra intron was as should in column 2. Intron is inserted into or adjacent to coding region for either ubiquitin, tTAV or reaper$^{KR}$, as shown in column 3. These were generated and shown to successfully splice, by RT-PCR or phenotypically in Medfly and, in some cases, also either in *Drosophila melanogaster* (LA3077) or *Anastrepha ludensi* (LA3097, LA3233). In addition, the distance between the ATG and the end of the exon immediately preceeding the tra intron (assuming splicing in F1-like form) can range from 0 bp to +228 bp without adverse consequences to splicing (see Table 16, column 3).

As mentioned above when an intron is placed 5' to a protein coding region (ORF-X), it is preferred to position or use ubiquitin 3' to the intron, 5' to ORF-X, thus and providing female-specific regulation of ORF-X, whilst introducing physical separation between that sequence and the tra intron, thereby reducing the chance that sequences within ORF-X will interfere with the splicing of the tra intron.

Composite constructs and sequences are also envisaged, for example of the form:

X-ubi-Y with the alternatively spliced intron inserted between coding region X and the region encoding ubiquitin (ubi), or within the ubiquitin coding region, or between the region encoding ubiquitin and coding region Y. Thus X will be expressed irrespective of the splicing of the intron, while Y will only be expressed when the intron is spliced in a suitable form. Further configurations and arrangements of this general type will be apparent to the person skilled in the art.

Of course, it may be that the skilled person wishes to introduce a frame shift during the splicing process so that the pre-mRNA is spliced into mRNA that is not capable of being transcribed into a functional protein.

The frame-shift may be useful for a number of reasons. Firstly, as discussed above, it may be to introduce a stop codon or may otherwise result in a protein having reduced or no activity.

Alternatively, the frame-shift may be employed, in a manner similar to retro-viruses, for instance, to encode at least two different proteins from the same nucleotide sequence, by using overlapping coding sequences. One can, therefore, introduce a frame shift so that a sequence is read in one frame if the (preceding) intron is spliced in one form and a different frame if spliced in another. This allows one to get two different encoded proteins without tampering with sequence internal to the intron.

It has also been found that it is possible to employ a positive feedback mechanism both to enhance the effect of an insect promoter, as well as to control its expression.

Thus, in a further aspect, the present invention provides a gene expression system, comprising at least one gene to be expressed and at least one promoter therefor, wherein a product of a gene to be expressed serves as a positive transcriptional control factor for the at least one promoter, and whereby the product, or the expression of the product, is controllable. Preferably, the system is for expression in insects.

As used herein, the term "gene" refers to any DNA sequence that may transcribed or translated into a product, at least one such having activity or function in vivo. Such a gene will normally have at least a transcription promoter and a terminator operably associated therewith.

The product capable of positive transcriptional control may act in any suitable manner. In particular, the product may bind to an enhancer located in proximity to the promoter or promoters, thereby serving to enhance polymerase binding at the promoter, for example. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, for example, or the product may bind the inhibitor directly, thereby preventing inhibition of transcription or translation.

More preferably, the mechanism is a positive feedback mechanism, wherein the product, which may either be RNA or the translation product thereof, acts at a transcription enhancer site, normally by binding the site, thereby enhancing promoter activity. Enhancement of the promoter activity then serves to increase transcription of the gene for the product which, in turn, further serves to either lift inhibition or enhance promotion, thereby leading to a positive feedback loop.

Control of the product may be by any suitable means, and may be effective at any level. In particular, it is preferred that the control be effective either to block transcription of the control factor gene or to block translation of the RNA product thereof, or to prevent or inhibit action of the translation product of the gene.

For example, the gene product of tTA (tetracycline-repressible transcription activator) acts at the tetO operator sequence (Baron and Bujard, 2000; Gossen et al., 1994; Gossen and Bujard, 1992). Upstream of a promoter, in either orientation, tetO is capable of enhancing levels of transcription from a promoter in close proximity thereto, when bound by the product of the tTA gene. If the tTA gene is part of the cassette comprising the tetO operator together with the promoter, then positive feedback occurs when the tTA gene product is expressed.

Control of this system is readily achieved by exposure to tetracycline, which binds to the gene product and prevents transactivation at tetO.

The tTA system also has the advantage of providing stage-specific toxicity in a number of species. In particular, "squelching" is observed in the development phases of many insects, the precise phase of susceptible insects being species-dependent. Some insects may reach pupation before the larva dies, while others die early on. Susceptibility ranges from 100% fatality to a small reduction in survival rates. In general, though, adult insects appear to be immune to the squelching effect of tTA, so that it is possible to raise insects comprising a tTA positive feedback system in the presence of tetracycline, and then to release the adult insects into the wild. These insects are at little or no competitive disadvantage to the wild type, and will breed with the wild type insects, but larvae carrying the tTA positive feedback cassette will die before reaching maturity.

It is relatively straightforward to modify the tTA sequence to enhance compatibility with the desired insect species, and this has been demonstrated, in the accompanying Examples, with tTAV, which has an additional two amino acids to provide a protease site, but which is encoded by a sequence substantially changed from that of tTA in order to more closely follow *Drosophila* usage.

Accordingly, in a preferred aspect, the present invention provides a system as described, wherein at least one gene is tTA, or is a gene encoding a similar product to tTA effective to up-regulate the tetO promoter.

Thus, the present invention is useful in combination with a dominant lethal gene, allowing selective expression of the dominant lethal gene, or stage specific expression, as desired, of the lethal gene or the lethal phenotype. It will be appreciated that the dominant lethal gene does not need to be an integral part of the positive feedback mechanism, but may be part of a bicistronic cassette, for example. Use of the present invention in association with RIDL (Release of Insects carrying a Dominant Lethal) is particularly preferred.

Control of the feedback mechanism, in the case of tTA or an analogue thereof, is simply effected by the presence or absence of tetracycline, or by modulating tetracycline concentration, when the tTA gene product is used. In the case of another preferred positive feedback system, GAL4, this may be controlled by temperature, for example, thereby suppressing the effective gene, preferably a dominant lethal gene, until release of the insect.

Other mechanisms may also be employed, such as ribozymes or antisense or partially self-complementary RNA molecules, such as hairpin RNA, to inhibit or prevent expression of an activating peptide, or blocking agents that prevent binding of the activator to the enhancer site.

Such blocking agents may be expressed by the insect itself under selective conditions, or may be administered as part of the culture medium, for example.

Where the blocking, or controlling agents are produced by the insect, then it is preferred that their expression be selective, such as being sex specific. Administration of the blocking agent in the culture medium, for example, will enable suppression of the positive feedback cassette under all circumstances until release of the insect, after which stage- or sex-specific selection will occur, preferably in a succeeding generation, particularly preferably the following generation.

More preferably, the cassette comprising the positive feedback mechanism is associated with stage- or sex-specificity. For example, sex specific splicing is observed with the transformer and doublesex mechanisms seen in most insects, and can be employed to limit expression of the feedback system to a particular sex, either by employing sex specific splicing to delete all or part of the effector gene, or to incorporate a frameshift or stop codon, or to modulate RNA stability or mRNA translational efficiency, for example, or otherwise to affect expression so as to differentiate between the sexes. Targeting the females of pest species is particularly preferred.

Although it is possible to provide the effector gene in a separate location and even on a separate chromosome, it is generally preferable to link the effector gene with the feedback gene. This may be achieved either by placing the two genes in tandem, including the possibility of providing the two as a fusion product, or for example by providing each gene with its own promoter in opposite orientations but in juxtaposition to the enhancer site.

An effector gene is the gene whose expression it is desired to enhance. Where a positive feedback product is also effective as a stage-specific lethal, such as tTA in many species, then the effector and the feedback gene may be one and the same, and this is a preferred embodiment.

The effector gene will often be a lethal gene, and it is envisaged that the system of the present invention will most frequently be employed in the control of insect pest populations, particularly in combination with the RIDL technique or related method, as described hereinunder.

It is preferred to include a marker with the systems of the invention, such as DsRed, green fluorescent protein, and variants thereon, as transformation success rates in insects are extremely low, so that it is useful to be able to select in some way.

The promoter may be a large or complex promoter, but these often suffer the disadvantage of being poorly or patchily utilised when introduced into non-host insects. Accordingly, it is preferred to employ minimal promoters, such as the Hsp70 promoter which, while having a naturally somewhat low level of activity, can be substantially enhanced by a positive feedback scenario, such as by the use of tTA and tetO.

A promoter is a DNA sequence, generally directly upstream to the coding sequence, required for basal and/or regulated transcription of a gene. In particular, a promoter has sufficient information to allow initiation of transcription, generally having a transcription initiation start site and a binding site for the polymerase complex. A minimal promoter will generally have sufficient additional sequence to permit these two to be effective. Other sequence information, such as that which determines tissue specificity, for example, is usually lacking, and preferred minimal promoters are, normally as a direct result of this deficiency, substantially inactive in the absence of an active enhancer. Thus, a cistron, or system, the two terms preferably being generally interchangeable herein, of the invention will generally be inactive when the or each promoter is a minimal promoter, until a suitable enhancer or other regulatory element is de-repressed or activated, typically the gene product.

Thus, it will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from hsp70, a P minimal promoter (exemplified hereinunder as WTP-tTA), a CMV minimal promoter (exemplified hereinunder as JY2004-tTA), an Act5C-based minimal promoter, a BmA3 promoter fragment, and an Adh core promoter (Bieschke, E., Wheeler, J., and Tower, J. (1998). Doxycycline-induced transgene expression during *Drosophila* development and aging. Mol Gen Genet 258, 571-579). Act5C responds to tTA in transgenic *Aedes*, for example, and the invention.

Not all minimal promoters will necessarily work in all species of insect, but it is readily apparent to those skilled in the art as to how to ensure that the promoter is active. For example, a plasmid, or other vector, comprising a cistron of the invention with the minimal promoter to be tested further comprises a marker, such a gene encoding a fluorescent protein, under the control of a promoter known to work in that species, the method further comprising assaying putative transgenic individuals for expression of the marker, and wherein individuals expressing the marker are then assayed for expression of the gene under the control of the minimal promoter, such as by assaying transcribed RNA. Presence of the RNA above background levels under induced or de-repressed conditions is indicative that the minimal promoter is active in the species under investigation; absence or presence at low levels only of such RNA in non-induced or repressed conditions is indicative that the minimal promoter has low intrinsic basal activity.

We have used the following marker promoters, by way of example, only, but many more are useful and apparent to those skilled in the art:

mini-white (white promoter): WTP2-tTA, JY2004-tTA

Act5C promoter: LA513 and LA517 ubi-p63E promoter: LA656 and LA1038

BmA3 promoter: LA710 hr enhancer and ie1 promoter: LA928, LA1124 and LA1188 and all of these are useful as, or in the preparation of, minimal promoters.

It will be appreciated that a cistron or system of the invention may comprise two or more cistrons. A system may further comprise non-linked elements, such as where a second gene to be expressed is remote from the positive feedback cistron.

Figure 1:
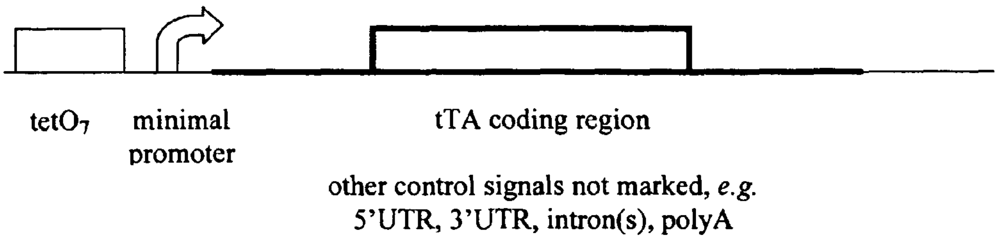
FIG. 1 shows a tetracycline-repressible transcription activator scenario.

Thus, in a preferred aspect, the present invention provides positive feedback constructs of the general form shown in accompanying FIG. 1. In this scenario, the tetracycline-repressible transcription activator (tTA) protein, when expressed, binds to the tetO operator sequence and drives expression from a nearby minimal promoter. In the configuration shown, this then drives expression of tTA, which then binds to tetO, and so on, creating a positive feedback system. This system is inhibited by tetracycline, which binds to tTA and prevents it binding tetO.

Expression is controllable, and this may be achieved by operably linking the promoter to a controllable transcription factor. As illustrated above, this may be tTA (tetracycline-repressible or tetracycline-inducible), or any other factor controllable system, such as GAL4 (which is somewhat cold-sensitive, and can be further controlled by use of GAL80 or mutants thereof), or the streptogrammin regulated expression system, for example. It will be appreciated that other binding sites for the appropriate transcription factor will depend on the transcription factor concerned, such as $UAS_{GAL4}$ (upstream activation sequence) for GAL4, for example.

Preferred systems of the present invention have high levels of induced expression, preferably available at several induced levels, with a low basal level of expression of the regulated gene but also of any other component, and preferably across a range of species. Basal levels are preferably low or substantially non-existent where expression is strongly deleterious, but acceptable levels will depend on the effect of the product. Maximum levels will not generally be an issue, as the positive feedback condition will often provide fatal levels of expression and, even where the expression product is not fatal, or associated with fatal consequences, it is likely to be expressed in far higher concentrations than most gene products.

Where a basal level of expression is desired, then a promoter sequence that does not need the presence of the enhancer may be employed, although there will then, generally, be feedback. Unless there is a cut-off level of feedback, below which the feedback product will not work, then it will be appreciated that it is preferred to keep to a minimum feedback gene expression Different constructs of the invention (described in the accompanying Examples) have varying activity, according to the components of the constructs. For example, in *Drosophila:*

WTP-tTA gives a low level of induced (non-repressed) expression

JY2004-tTA gives strong expression when not repressed, approximately equivalent to Act5C-tTA LA513 is lethal when not repressed.

The first two appear to give constitutive expression, as judged by use of a reporter gene (tRE-EGFP), this is difficult to assess for the lethal LA513, although at 10 μg/ml tet, just sufficient for good survival, LA513 in *Drosophila* drives expression of a $tetO_7$-EGFP reporter gene in both the male and female germline in adults, as well as in somatic cells. This distinguishes it from Act5C, commonly used as a "ubiquitous, constitutive" promoter, which does not, in fact, express well in these cells.

The properties of these constructs are shown in Table 1, below.

TABLE 1

| | Max expression | Minimal promoter | Intron | Optimised coding region? | 3'UTR and polyA |
|---|---|---|---|---|---|
| WTP-tTA | Low | P | PP1α96A | No | fs(1)K10 |
| JY2004-tTA | High | CMV | Rabbit β-globin | No | Rabbit β-globin |
| LA513 | V. high (lethal) | Hsp70 | Adh | Yes | fs(1)K10 |

Accordingly, it will be appreciated that the induced or non-repressed expression level can be modified in a useful and predictable way by adjusting the sequence of the positive feedback system. Toxicity and/or activity of the tTA protein can be modified independently of the transcriptional and translational control signals by several approaches, e.g. use of a nuclear localisation signal, modification of the activation domain, etc. (see Fussenegger, 2001 for more examples).

The lethality of LA513 is useful, for the reasons given above, and more particularly because:

a) It provides a compact, highly effective repressible lethal gene system;

b) As it uses only simple control elements from *Drosophila* (hsp70 minimal promoter, a small intron and a terminator from fs(1)K10), it, or its expression cassette, functions across a wide phylogenetic range;

c) It has very little, if any, deleterious effect on adults, even in the absence of tetracycline. This is a highly desirable and surprising property for field use, for example in a RIDL-based control programme, as the released adults must be competitive and long-lived for full efficacy of the programme. It will be appreciated that the effect of the system of the invention could be further modified by the incorporation of an adult-effective lethal, for example in the "positive feedback—bi-directional expression" configuration described herein; and d) By its nature, "cross-talk" between various elements is minimised. This is because: (i) the core of the construct is only a single composite element, rather than the normal two in bipartite expression systems; (ii) the principal enhancer of the autoregulatory component, the tTA binding sites, is substantially active only in the absence of tetracycline and (iii) modest expression of tTA under the influence of a nearby enhancer, whether in another part of the construct or in nearby chromatin, is unlikely to be significantly deleterious.

JY2004-tTA is also useful, in the present invention.

Without being bound by theory, the mechanism by which LA513 kills embryos and early larvae, but not adults, appears to be an inherent property of its toxicity. tTA toxicity is believed to derive from "transcriptional squelching", in which high level expression of the transcriptional activator domain (in the case of tTA this is VP16 or a fragment thereof)

binds elements of the transcriptional machinery and titrates them, leading to a general effect on transcription, although it may also act to saturate the ubiquitin degradation pathway. Transcriptional squelching is the effect which is thought to lead to deleterious effects in mammalian cell lines expressing tTA at high levels; in the optimised expression context of LA513 positive feedback drives tTA expression to lethal levels. However, developing stages may be more sensitive to disruption of transcription than adults: they have to express genes in a highly coordinated fashion to allow proper development, while adults may be more tolerant of disruption.

The development of LA513 heterozygotes on media with an intermediate level of tet (3 or 10 μg/ml), just sufficient for survival, showed a significant delay, relative to their wild type siblings. Parallel experiments using higher concentrations of tetracycline, e.g. 100 μg/ml, did not show any developmental delay, thereby suggesting that sub-lethal expression of tTA can adversely affect the normal development of the insects.

It is preferred that a positive feedback system show a higher on:off ratio and switch from on to off over a narrower concentration range than a conventional system, thereby allowing the use of a wider range of effector molecules. Lower-toxicity (lower specific activity) effector molecules can be used, as they can be expressed at a high level under active conditions without leading to problems of toxicity at basal levels. Conversely, more toxic (higher specific activity) ones can be used as the necessary low basal level does not preclude high levels of expression when de-repressed or induced. Since basal level of expression is only partly determined by the level of tTA, this advantage is particularly clear in the case of lower-toxicity molecules. tTA is a preferred example of a low specific activity effector molecule that can be used as a lethal in the positive feedback context of LA513, for example. The advantage of switching from on to off over a narrow concentration range is that a modest concentration of repressor can be used without risk of residual (not fully repressed) expression leading to adverse effects and potentially selecting for resistance. Conversely, for an inducible system, modest concentrations of the activator can give full expression.

Activated or de-repressed drivers are useful for expressing effector molecules. Examples of effector molecules include functional RNA's, such as hairpin RNA's, ribozymes etc., and one or more encoded proteins. It will be appreciated that, for different applications, different levels of expression are appropriate. Since the sequence-specific transcription factors used to drive the positive feedback system can also be used to express other genes in a bipartite expression system, this may be achieved by making two separate constructs, one with the driver (normally a promoter-transcription factor construct, here the positive feedback construct), the other with the gene or molecule of interest under the control of a composite promoter (binding site+minimal promoter) responsive to the transcription factor (Bello et al., 1998; Brand et al., 1994). This is also appropriate for these positive feedback drivers. Alternatively, the two elements may be combined on the same construct. This embodiment has significant advantages for most field applications, as it very substantially reduces the risk that the two functional elements can be separated by recombination. Further, the complete expression system can be introduced with only a single transformation event, as well as meaning that insects homozygous for the system are homozygous at only one locus rather than two, which makes them easier to construct by breeding, and tends to reduce the fitness cost due to insertional mutagenesis.

Figure 2:
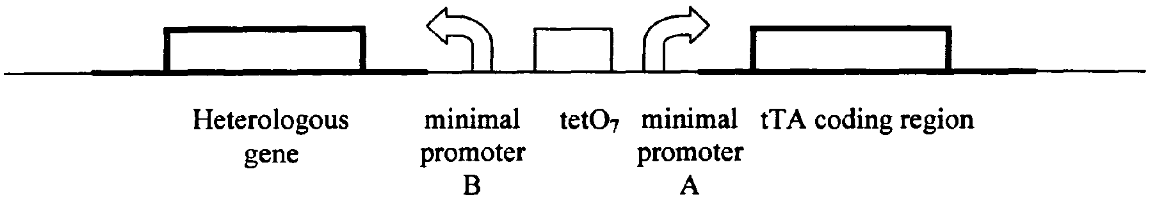
FIG. 2 shows a system of the invention using a bi-directional enhancer.

It is also possible to condense such an expression system into a more compact form, such as is illustrated in accompanying FIG. 2.

This exploits the bi-directional nature of enhancers, in this case the tetO binding site in the presence of tTA. This arrangement further allows, or facilitates, the use of insulator elements to reduce the effect of enhancers or suppressors in the adjacent chromatin: in this arrangement the entire expression cassette can be flanked by insulators. This arrangement also removes the need to duplicate the transcription factor binding sites within the construct. Such duplication is preferably avoided, as it can lead to instability through homologous recombination. For similar reasons, it is generally preferred that non-identical insulators, such as scs and scs' are used, rather than using the same one twice.

Figure 3:
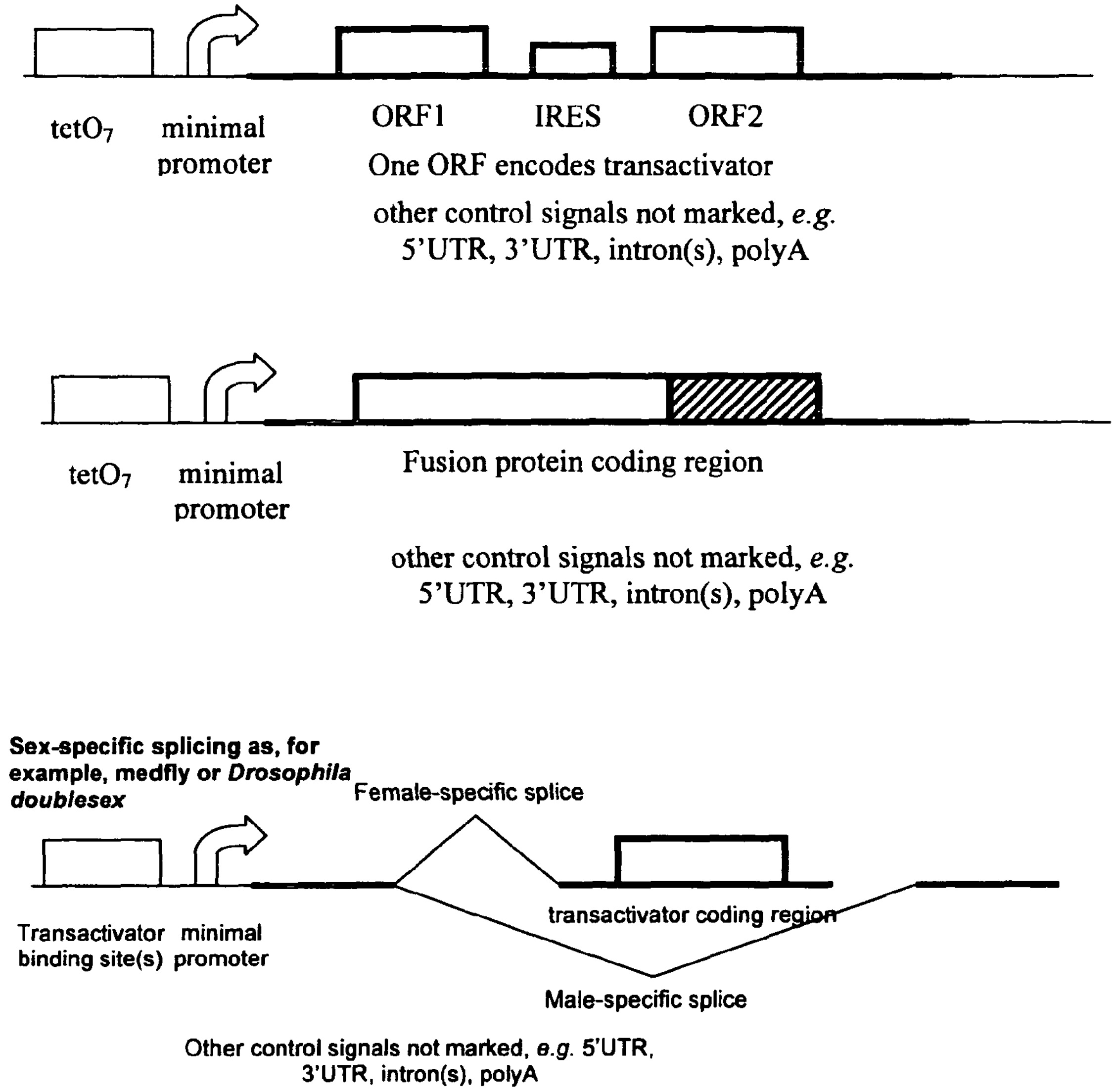
FIG. 3 shows a sex-specific system.

It is further possible to condense the system to provide a single transcript, either bicistronic or expressing a single polypeptide, which may potentially be further processed into more than one protein, for example by use of the ubiquitin fusion technique (Varshavsky, 2000). Each of these approaches (bi-directional expression, bicistronic expression, fusion protein with transactivator) tends to reduce the size of the construct, which in turn will tend to increase the transformation frequency and reduce the mutagenic target. Such condensation can be achieved in several ways, as shown, diagrammatically, in accompanying FIG. 3. Appropriate extensions to and variations of the arrangements shown diagrammatically will be apparent to those skilled in the art.

As an example of the utility of such a system, a general transformation marker might be constructed by using a transactivator system known to function over a wide phylogenetic range, for example those based on tetR, GAL4, lexA or AcNPV ie-1. Such a transactivator, functionally linked to a coding region for a fluorescent protein by any of the above methods (bi-directional expression, bicistronic expression, fusion protein with transactivator), would provide a genetic marker expressed in a wide range of tissues and developmental stages across a broad phylogenetic range. Such a marker would be useful not only for detecting transgenics in transformation and other lab experiments, but also for distinguishing, for example, transgenic flies from wild type flies in the field, or those caught in the field.

Another example is expression of a transposase. Integrated into the chromosomes, this would be a "jump-starter" construct, for example piggyBac transposase integrated into an insect chromosome using mariner/mos1. Such constructs are useful to remobilise piggyBac elements. A widely-applicable jump-starter should be expressed at a significant level across a wide phylogenetic range. The expression system of this invention provides this. Furthermore, such a construct (piggyBac transposase under the control of a positive feedback system of one of the above structures) would also be useful in insect transformation via transient expression (co-expression of a "helper" plasmid, the most widely-used method for insect transformation), and again would be useful and functional across a wide phylogenetic range.

It is advantageous to regulate the action of an expression system at stage-, sex- or other levels, in addition to being able to regulate the expression level by changing environmental conditions. Suitable examples are as follows:

1. Expression of a Repressor Protein.

Repressor proteins are known or can be constructed for the main expression systems, e.g. GAL80 or its mutant derivatives for the GAL4 system, tetR fused to inhibitory proteins for the tet system, etc. Another alternative is gene silencing of the transcription factor using a hairpin RNA directed against part of the expression cassette. Basal expression from the positive feedback system is rather low, therefore it can readily be suppressed by expression of such an inhibitor.

Expression of a suitable inhibitor under suitable control will tend to inhibit expression from the positive feedback expression cassette where the inhibitor is expressed. Female-specific expression, for example, can therefore be achieved by expressing an inhibitor in males.

2. Integrating Specificity into the Positive Feedback System.

Specificity can be integrated into the positive feedback system by using components that are themselves specific. For example, the hsp70 minimal promoter+SV40 intron and polyA signal combination of PUAST is known not to be expressed in the female germline of *Drosophila*, while the P minimal promoter+P intron+fs(1)K10 polyA signal of pUASp is so expressed (Rorth, 1998). Positive feedback expression systems can, therefore, be constructed which specifically do or do not express in this tissue, depending on the use of appropriate regulatory elements.

Figure 4:
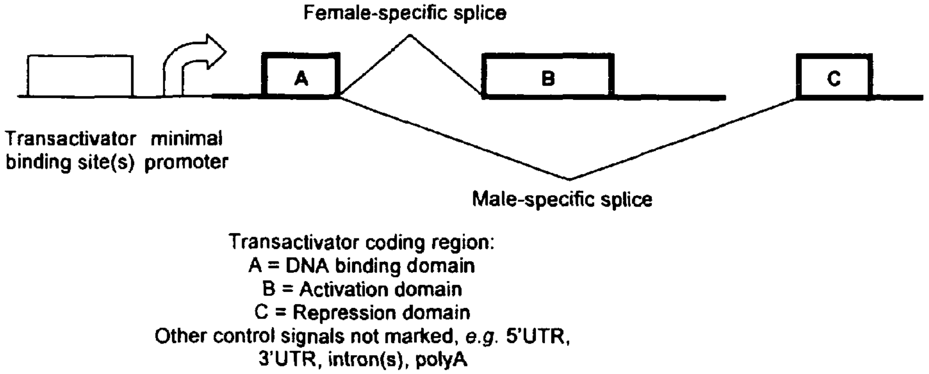
FIG. 4 shows another sex-specific system.

In another embodiment, sex-specificity can be integrated into the system by use of sex-specific splicing. The sex-specific splicing of doublesex and its homologues is a conserved regulatory mechanism and, therefore, available for use in this way across a wide phylogenetic range. Sex-specific splicing of transformer and its homologues is another alternative. The use of sex-specific splicing to integrate specificity into a positive feedback expression system can be achieved in several ways, as shown, diagrammatically, in accompanying FIG. 4. Appropriate extensions to and variations of the arrangements shown diagrammatically will be apparent to those skilled in the art.

In another configuration, a specific splice site can be inserted into the transactivator coding region so that two (or more) alternative proteins are produced in different conditions, e.g. in different cell types or in different sexes. This can be arranged so that a transcriptional activator is produced in one cell type but a transcriptional repressor is produced in another cell type. This arrangement has the advantage that it is relatively robust to inefficient (imperfect) splicing—production of a relatively low proportion of transcriptional activator in the inappropriate cell type, e.g. in male cells, will be less likely to produce the positive feedback amplification as these cells are also producing a larger amount of repressor. Discrimination in output (ratio of levels of transcriptional activator in the two cell types, or ratio of expression of a reporter or other RNA or protein functionally linked to the expression of the transcriptional activator) between the two cell types is thereby enhanced.

It will be readily apparent to those skilled in the art that any of these specific transactivator arrangements can readily be combined with any of the arrangements disclosed herein for expression of an additional protein or RNA, e.g. bi-directional expression, bi- or multi-cistronic expression, expression of a fusion protein, or combined with one or more separate expression cassettes dependent on, or partly dependent on, expression of the transactivator, either combined on the same construct or elsewhere in the genome or cell.

3. Using a Specific Effector Molecule

Specificity in phenotypic consequence can also be introduced by use of a specific effector molecule. Where a molecule, e.g. RNA or protein, expressed under the control of any of the expression systems described herein, has a specific effect only in particular cells, tissues, or sex, etc, then phenotypic specificity can be obtained with broader or less specific expression of the transactivator. For example, in the context of a RIDL-type mass-release insect population control programme, using the system to express a molecule only toxic, or preferentially toxic, to pre-adult stages, results in adults which are fully, or reasonably competitive, relative to wild type. This is desirable as the effectiveness of the programme depends on the competitiveness and longevity of the adult forms, when released into the wild. Since their internal repressor (e.g. tetracycline) concentration is likely to decline in the wild, it would be advantageous to ensure that induction (de-repression) of the expression system, as and when it occurs in adults, has a minimal negative effect on them.

As another example, sex separation, or sex-specific effects, can be achieved by expression in both males and females of a molecule with differential effects in males and females. For example, expression of the Transformer protein in male *Drosophila* will tend to transform them into females, but have no effect on females. Similarly, expression of Male specific lethal-2 (Msl-2) protein in *Drosophila* will tend to kill females, but not males (Gebauer et al., 1998; Kelley et al., 1995; Matsuo et al., 1997; Thomas et al., 2000). Conversely, expression of a partially self-complementary RNA molecule with substantial homology in its self-complementary or double-strand-forming region to ("hairpin RNA against") transformer will tend to transform genetic females into phenotypic males, while not affecting genetic males, and expression of hairpin RNA against msl-2 will tend to be lethal to males but not to females. Expression of hairpin RNA against the male- or female-specific exons of doublesex will tend to affect those sexes only, and simultaneous expression of RNA encoding the other form of doublesex (i.e. DsxM in females or DsxF in males) will tend to modify or enhance this effect. This simultaneous expression of a protein and a hairpin RNA molecule can readily be accomplished by combining the bicistronic or fusion protein approach described above with expression of a hairpin RNA using the bi-directional expression system also described above. Sex-, stage- or other specificity can be further added to such a system by incorporation of appropriate specific splicing or other transcriptional, translational or other post-translational control signals to either part of the system as will be apparent to the person skilled in the art.

Multi-functional hairpin RNA molecules may be constructed and are envisaged. For example, RNAi against transformer in the Mediterranean fruit fly *Ceratitis capitata* Wiedmann (medfly) will tend to transform genetic females into fertile males. For an area-wide population control program based on mass-release of such insects, it is preferable to sterilise the released flies. This can be accomplished by using a composite RNA molecule that simultaneously disrupts expression of both transformer and a gene required for spermatogenesis or embryonic or larval viability. Many such genes are known in *Drosophila* with homologues in mosquitoes or other animals. With medfly, a suitable homologue can readily be isolated, using techniques known to those skilled in the art. We prefer the use of a gene which allows the production of seminal fluid, and preferably also of sperm, to reduce the tendency of the female to re-mate after insemination by the affected male. We particularly prefer to direct this second part of the hairpin RNAi molecule against a paternal effect lethal, so that no viable progeny can be produced, or against a zygotically expressed gene required for embryonic or larval viability or development, so that progeny inheriting the construct will be affected. Other configurations are envisioned and will be readily apparent to those skilled in the art: for example expression of a female-specific lethal protein by bicistronic expression and a hairpin RNA leading to paternal-effect lethality by bi-directional expression. In common with the composite hairpin RNA against a suitable sex-determination gene and a paternal effect lethal, this allows the generation of a single-sex (male-only) population of insects, all of whose progeny die through the action of the paternal-effect lethal, irrespective of whether their progeny or mates feed on tetracycline. Thus, the present invention provides a controlled promoter, as defined, wherein the promoter is operably linked with DNA encoding an RNAi causing lethality or sterility. In this case, lethality may correspond to low fitness, such as flightless, rather than outright lethality, provided that the likelihood of breeding on is substantially reduced.

4. Using Site-Specific Recombinase(s)

Specificity can also be introduced into the positive feedback system by inserting a "stuffer" fragment which inactivates it. If this "stuffer" fragment is flanked by target sites for a suitable site-specific recombinase, then it will tend to be excised in the presence of active recombinase. Any system for selective expression of active recombinase, for example, expression of the recombinase under the control of a female-specific promoter, will therefore tend to lead to selective expression of the positive feedback system, in this case in females only. If the recombinase is expressed in somatic cells only, for example by using the method described above, then the version transmitted to the next generation includes the stuffer fragment, which can again be daughters but not sons. Conversely, if the recombinase is expressed in the genome only, provision of active recombinase will lead to offspring in which the expression system is active, from parents in which it is inactive. This can be used, for example, to generate gametes containing an active dominant lethal or sterile gene system (e.g. female-specific or non-sex-specific) for use in an insect population control strategy.

In a preferred embodiment, the stuffer fragment encodes the recombinase. This embodiment is particularly compact. In another preferred embodiment, the stuffer fragment encodes a transcriptional repressor which tends to inactivate the positive feedback expression system—this embodiment tends to reduce the basal expression of the system in the presence of the stuffer fragment.

Conversely, the system can be specifically inactivated in certain cells, or clones of cells, by introducing target sites for a suitable site-specific recombinase at suitable positions, and then expressing or introducing the appropriate active recombinase in appropriate cells, such that one or more key functional elements of the expression system are removed or disrupted by recombination between the target sites for the recombinase.

Suitable recombinase systems include cre/lox and Flp/FRT.

The present invention will now be described with reference to the following, non-limiting Examples.

All references cited herein are hereby incorporated by reference.

EXAMPLES

A series of constructs was made with tTA in a positive feedback configuration, i.e. with tTA expression regulated by tTA binding to tetO. Transgenic insects carrying these constructs were obtained and their properties analysed.

tTAV

In some cases, the intention was to obtain very high levels of expression of tTA in the absence of tetracycline. In various exemplified constructs described hereinbelow, tTA expression was so high as to be lethal. As part of the process of obtaining strong expression of tTA, part of the tTA open reading frame was redesigned to express a similar protein, but with codon usage closer to the norm for *Drosophila melanogaster*, and lacking some potential cryptic splice sites present in the original nucleotide sequence. This variant tTA sequence was named tTAV (SEQ ID NO. 31, protein sequence SEQ ID NO. 32).

Example 1

WTP-tTA and JY2004-tTA in *Drosophila melanogaster*

The tTA coding region (SEQ ID NO. 29, tTA protein sequence SEQ ID NO. 30) from pUHD15-1 (SEQ ID NO. 33, Gossen et al., 1994; Gossen and Bujard, 1992) was placed under tetO control, in a positive feedback configuration, by inserting it into pWTP2 (Bello et al., 1998) or pJY2004, a version of pJY2000 that lacks insulators (Stebbins and Yin, 2001). These constructs were named pWTP-tTA and pJY2004-tTA, respectively. A diagram of $tetO_7$-tTA region of pJY2004 is provided as accompanying FIG. 5, and is SEQ ID NO. 14.

Figure 5:
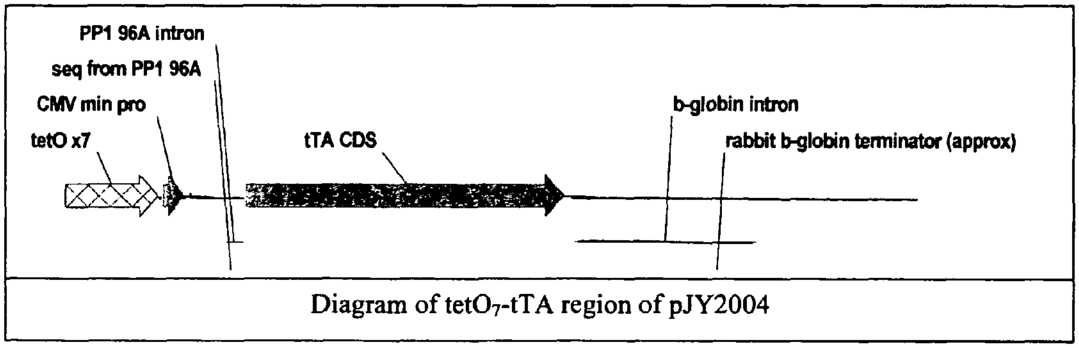
FIG. 5 is a diagram of the $tetO_7$-tTA region of pJY2004.

In pWTP-tTA, the $tetO_7$ binding sites are followed by a minimal promoter from the P element, a leader sequence from *Drosophila* hsp70, a short intron from the *Drosophila* PP1αL96A gene, the tTA coding region and a transcription terminator from *Drosophila* hsp70. In pJY2004-tTA, the minimal promoter and leader sequences are from CMV, followed by the tTA coding region and a transcription terminator from rabbit β-globin, as shown in FIG. 5.

Transgenic *Drosophila melanogaster* carrying either of these constructs were fully viable, even without dietary tetracycline. Insects doubly heterozygous for WTP-EGFP and either of these constructs were examined for green fluorescence characteristic of EGFP expression. Insects with WTP-tTA and WTP-EGFP showed very weak fluorescence only slightly above background autofluorescence. In contrast, insects with JY2004-tTA and WTP-EGFP showed strong fluorescence, similar to that seen in insects carrying EGFP under the control of the Actin5C promoter, which is widely used as a strong, constitutive promoter in *Drosophila* (e.g. Reichhart and Ferrandon, 1998). Expression of EGFP was repressed to undetectable levels when the insects were raised on diet supplemented with tetracycline to 100 μg/ml. Control insects heterozygous for either WTP-EGFP, JY2004-tTA or WTP-tTA showed no fluorescence above background whether or not they were raised on a diet containing tetracycline.

We placed tTA under the control of the Actin5C promoter, in plasmid pP [Casper-Act5C-tTA]. Transgenic flies carrying this construct and WTP-EGFP, raised on a diet lacking tetracycline, showed green fluorescence at a comparable intensity to that observed in equivalent flies with JY2004-tTA and WTP-EGFP.

These results show that positive feedback constructs can be used to give strong (JY2004-tTA) or weak (WTP-tTA), tetracycline-repressible expression from a suitable construct (here WTP-EGFP).

EGFP is widely used as a neutral reporter. We further tested JY2004-tTA flies by crossing them to flies with constructs capable of expressing proteins known or predicted to be deleterious. We inserted the central domain of Nipp1Dm (Bennett et al., 2003; Parker et al., 2002) ("nipper"), into pJY2004, to make pJY2004-nipper, and transformed *Drosophila* with this construct. We also used flies carrying tetO-hid (Heinrich and Scott, 2000). In each case, crossing to JY2004-tTA flies gave tetracycline-repressible lethality. Data from two example crosses are presented in Table 2, below.

TABLE 2

Use of positive feedback constructs to drive expression of lethal genes in *Drosophila*.

| JY2004-tTA | CyO | [tetracycline] (μg/ml) |
|---|---|---|
| Male JY2004-tTA/CyO × Female tetO-hid/tetO-hid | | |
| 0 | 15 | 0 |
| 9 | 10 | 100 |
| Male JY2004-tTA/CyO × Female JY2004-nipper/JY2004-nipper | | |
| 0 | 20 | 0 |
| 16 | 13 | 100 |

Example 2

LA513 in *Drosophila melanogaster*

Figure 6:
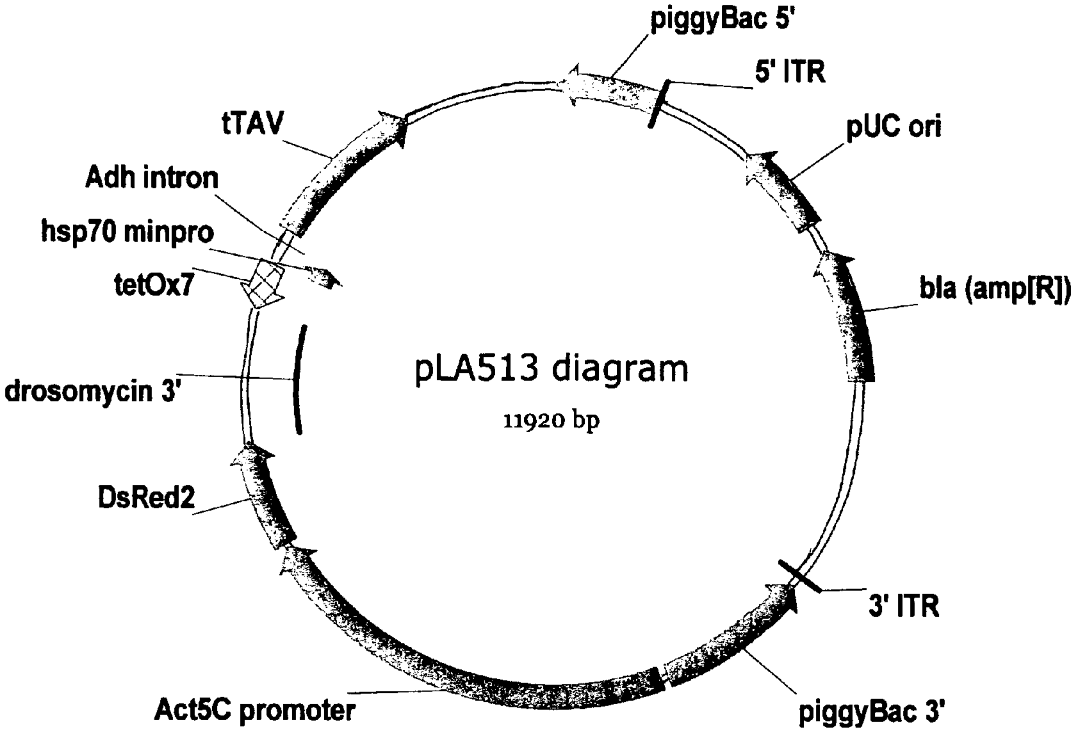
FIG. 6 is a schematic diagram of pLA513.
Figure 7:
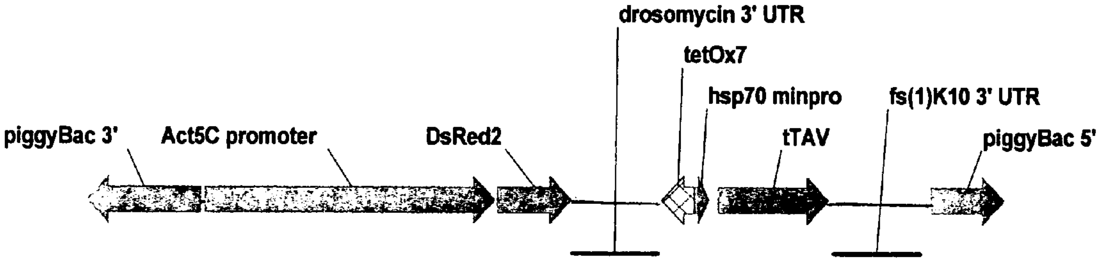
FIG. 7 is a schematic diagram of the LA513 transposon.

We made construct pLA513 (SEQ ID NO. 16, schematic diagram shown in FIG. 6), containing a non-autonomous piggyBac transposon. We generated transgenic *Drosophila melanogaster* carrying this construct by co-injection with a helper plasmid into a white-eyed strain (Handler, 2002; Handler and James, 2000). Potential transgenics were screened for fluorescence characteristic of DsRed2. 5 transgenic lines were recovered, and were designated O513, M8, M13, F23 and F24. A schematic diagram of the LA513 transposon is shown in accompanying FIG. 7.

*Drosophila melanogaster* stocks were maintained at 25° C. on yeast/sugar/maize/tetracycline medium (tetracycline (Sigma) at 100 μg/ml final concentration), unless stated otherwise. All experiments were performed at 25° C.

Survival of LA5131+Transgenics with and without Tetracycline

Heterozygous transgenics were crossed in at least triplicate to wild type on media with or without Tc (tetracycline). In the absence of any lethality, it would be expected that approximately half the progeny of such a cross would be transgenic. Progeny were scored as young adults for DsRed marker fluorescence [Matz et al., 1999] using an Olympus SZX12 microscope with fluorescence capability, and the ratio of fluorescent (transgenic) to total flies was calculated. The results are shown in Table 3, below. In these experiments, all 5 transgenic lines showed 100% lethality, in the absence of tetracycline, and good survival (i.e. fluorescent:non-fluorescent ratio ~1:1), in the presence of 100 μg/ml tetracycline. Inspection of the vials showed few or no large fluorescent larvae in the absence of Tc, although many very small fluorescent larvae were present, at a time when non-fluorescent (wild type for LA513) larvae were visible at all sizes. This suggests that, in the absence of tetracycline, LA513 causes lethality at an early (embryonic and/or early larval) developmental stage.

TABLE 3

LA513 insertions are tetracycline-repressible dominant lethals

| | 0 μg/ml tetracycline | | 100 μg/ml tetracycline | | |
|---|---|---|---|---|---|
| LA513 line | # Flies | # Fluorescent | # Flies | # Fluorescent | Ratio |
| O513 | 490 | 0 | 1963 | 937 | 0.48 |
| M8 | 74 | 0 | 66 | 25 | 0.38 |
| M13 | 657 | 0 | 1838 | 892 | 0.49 |

TABLE 3-continued

LA513 insertions are tetracycline-repressible dominant lethals

| | 0 μg/ml tetracycline | | 100 μg/ml tetracycline | | |
|---|---|---|---|---|---|
| LA513 line | # Flies | # Fluorescent | # Flies | # Fluorescent | Ratio |
| F23 | 473 | 0 | 1914 | 845 | 0.44 |
| F24 | 61 | 0 | 114 | 60 | 0.53 |
| Total | 1755 | 0 | 5895 | 2759 | 0.47 |

Dominant lethality could have several causes. Without being restricted by theory, it seems likely that, in the absence of tetracycline, tTAV accumulates to a relatively high concentration and that this is lethal, possibly due to transcriptional squelching, or interference with protein degradation. An alternative is that, in the absence of tetracycline, tTAV binds to tetO and acts as a long-range enhancer, perturbing the expression of genes near to the LA513 insertion. This appears unlikely, as all 5 transgenic lines gave similar results. Each of these lines was derived from a different G0 injection survivor, and these lines are, therefore, likely to carry LA513 integrated at different genomic sites. We verified this by inverse PCR. Table 4, below, shows the integration sites for 3 of the lines; in each case the LA513 insertion was at a TTAA sequence, as expected from the known insertion site preference of the piggyBac transposon. As expected, the 3 insertions were indeed at 3 different sites in the *Drosophila* genome.

TABLE 4

Insertion sites of LA513 in Drosophila genome

| Line | Sequence Amplified or at Site of Integration | Predicted chromosome arm | Predicted Drosophila cytology | Nearest predicted gene |
|---|---|---|---|---|
| O513 | Cacagcgcatgatgagcaca**TTAA**caaaatgtagtaaaatagga (SEQ ID NO. 1) | 2L | 25F4-25F5 | CG9171 |
| M8 | Gtttcgataaatattgctat**TTAA**aatgcttattttcaatgcta (SEQ ID NO. 2) | 2L | 36F6-36F6 | CG15160 |
| F24 | Tttgttttctaacgttaaag**TTAA**agagagtccagccacatttt (SEQ ID NO. 3) | 2L | 21C4-21C5 | CG13691 |

Flanking sequence is shown with the TTAA insertion site capitalised. Predicted chromosome locations, and the nearest predicted gene, are also shown; these are based on the published *Drosophila* genome sequence.

Example 3

Reducing the Toxicity of tTAV

The toxic effect of high level expression of tTAV is thought to be due to transcriptional squelching and/or interference with ubiquitin-dependent proteolysis, via the VP16-derived section (Gossen and Bujard, 1992; Salghetti et al., 2001). We, therefore, modified tTAV by removing the VP16 section and replacing it with a synthetic sequence which encodes 3 copies of a peptide (PADALDDFDLDML) derived from VP16

Figure 8:
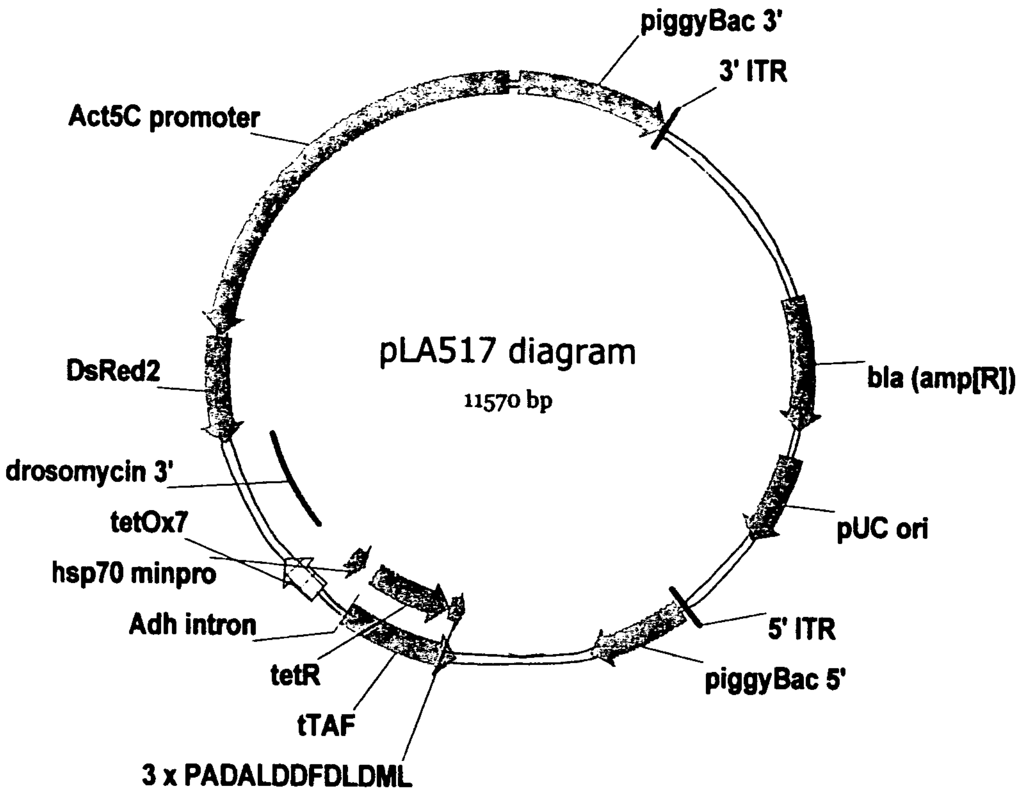
FIG. 8 is a schematic diagram of pLA517.

(Baron and Bujard, 2000; Baron et al., 1997). This derivative was named tTAF; the resulting plasmid was named pLA517, and is SEQ ID NO. 17, and is shown, diagrammatically, in accompanying FIG. 8.

*Drosophila melanogaster* were transformed with this construct, and one transgenic line was obtained. LA513 heterozygous males were crossed to wild type (for LA513) females and the progeny scored for fluorescence (as adults). If all progeny are equally likely to survive, the expected proportion of the total progeny that are fluorescent is 50%. In the absence of tetracycline, this proportion was 32%, only a modest reduction compared with 48% when parents and progeny were raised on diet supplemented with tetracycline to 100 μg/ml. The results are shown in Table 5, below. We tested whether supplying tetracycline in the diet of the parents but not of the progeny could reduce this lethality. In this case, we observed an intermediate proportion of 0.37, indicating that maternally contributed tetracycline has a modest beneficial effect.

TABLE 5

Effect of tetracycline on the survival of LA517/+ *Drosophila* and their +/+ siblings
LA517

| Parent [Tc] μg/ml | Progeny [Tc] μg/ml | Non-Fluorescent | Fluorescent |
|---|---|---|---|
| 0 | 0 | 165 | 78 |
| 100 | 100 | 524 | 482 |
| 100 | 0 | 502 | 297 |

Since LA517, alone, had little impact on viability, unlike the closely related construct LA513, we tested whether it was capable of driving expression of a heterologous gene under tetO control. For this we used tetO-hid (Heinrich and Scott, 2000). Flies homozygous for tetO-hid were crossed with flies heterozygous for LA517. In the absence of tetracycline, only 3.4% of the adult progeny carried LA517. In the presence of 100 μg/ml tetracycline, this proportion was 42%. LA517 is, therefore, capable of driving effective expression of a heterologous gene.

TABLE 6

Effect of tetracycline on the survival of LA517/+, +/tetO-hid *Drosophila*and their +/+, +/tetO-hid siblings
TetO-Hid × LA517/+

| [Tc] | Non-Fluorescent | Fluorescent |
|---|---|---|
| 0 | 636 | 23 |
| 100 | 174 | 127 |

Example 4

Use of Analogues of Tetracycline

Line F23 was used to determine whether chemical analogues of tetracycline could be used in place of tetracycline to suppress the lethality of LA513. For this purpose we tested 3 analogues at a range of concentrations from 0 to 100 μg/ml (suppliers: tetracycline and doxycycline, Sigma; 4-epi-oxytetracycline, Acros Organics; chlortetracycline Fuzhou Antibiotic Group Corp.). We calculated the concentrations required for half-maximal survival. These are shown in Table 7, below.

TABLE 7

Efficacy of Tc analogues

| Line | Tc/Analogue | Concentration for half-maximal survival, μg/ml |
|---|---|---|
| F23 | Tetracycline | 5.0 |
| F23 | Doxycycline | 3.9 |
| F23 | 7-chlortetracycline | 1.7 |
| F23 | 4-epi-oxytetracycline | 42.0 |

Example 5

Longevity of LA513/+ Adults in the Absence of Tetracycline

LA513 clearly confers dominant lethality, active at an embryonic and/or early larval stage. Larvae were raised on a diet supplemented with 100 μg/ml tetracycline. After eclosion, adults were transferred to a diet lacking tetracycline. The lifespan of these adults was measured, and also of comparable $w^{1118}$ non-transgenic adults. As shown in Table 8, below, the transgenic lines showed good adult survival relative to the non-transgenic control. This suggests that stage-specificity can be obtained in this way—here LA513 is a larval/embryonic lethal, but not an adult lethal.

TABLE 8

Mean adult lifespan of LA513/+ transgenic *Drosophila.*

| Line | Mean post-eclosion survival time, days | Standard deviation | Number of Flies |
|---|---|---|---|
| O513 | 40.3 | 12.3 | 66 |
| M8 | 26.1 | 2.5 | 9 |
| M13 | 29.5 | 9.9 | 47 |
| F23 | 29.6 | 11.3 | 83 |
| F24 | 19.9 | 10.0 | 9 |
| $W^{1118}$ | 22.2 | 8.6 | 88 |

It is possible to explain these longevity data by postulating that larvae accumulate tetracycline by feeding, and retain this tetracycline into adulthood, so that they survive even in the absence of dietary tetracycline as adults. To examine this, flies heterozygous for LA513/+ (M13 line) were raised as larvae on various concentrations of tetracycline. After eclosion, adults were transferred to diet lacking tetracycline and the lifespan of these adults was measured, as above. As shown in Table 9, below, the concentration of dietary tetracycline as larvae had no obvious effect on subsequent adult longevity in the absence of tetracycline, implying that adult survival is not primarily due to retention of tetracycline from larval feeding. At a concentration of 1 μg/ml, no transgenics survived to adulthood, and at 3 μg/ml only about half of the expected number survived to adulthood, so that this concentration is close to the minimum for larval survival.

TABLE 9

Effect of larval tetracycline on adult longevity

| Larval tetracycline μg/ml | Mean post-eclosion survival time, days | Standard deviation | Number of Flies |
|---|---|---|---|
| 1 | — | — | — |
| 3 | 33.5 | 13.2 | 9 |
| 10 | 28.4 | 9.6 | 17 |
| 30 | 26.3 | 11.3 | 23 |
| 100 | 29.5 | 9.9 | 47 |

Another possible explanation for the survival of LA513/+ adults is that tTAV is inactive in adults, so that the positive feedback cycle does not work, and tTAV does not accumulate. We examined this by measuring the amount of tTAV mRNA by quantitative PCR following a reverse transcriptase reaction (quantitative rt-PCR, or qPCR). We used Tagman chemistry and reagents (ABI), and an ABI Prism 7000 qPCR instrument. Each sample was assayed in triplicate; data are the mean of these three assays. The 18S primers anneal to *Drosophila melanogaster, Ceratitis capitata* and *Aedes aegypti* 18S RNA, so these primers were used for all three species.

Primers Used:

| | SEQ ID NO. |
|---|---|
| 18S RNA | |
| Forward Primer: ACGCGAGAGGTGAAATTCTTG | 4 |
| Reverse Primer: GAAAACATCTTTGGCAAATGCTT | 5 |
| TaqMan MGB Probe: 6-Fam-CCGTCGTAAGACTAAC-MGB | 6 |
| tTAV | |
| Forward Primer: CATGCCGACGCGCTAGA | 7 |
| Reverse Primer: GTAAACATCTGCTCAAACTCGAAGTC | 8 |
| TaqMan MGB Probe: VIC-TCGATCTGGACATGTTGG-MGB | 9 |

We found that O513 raised on 100 µg/ml tetracycline had a tTA:18S ratio of 0.00016 (larvae) and 0.00013 (adult). Adults raised as larvae on 100 µg/ml tetracycline, but then transferred to non-tetracycline diet as adults had ratios of 0.0061, 0.0047, 0.0087 and 0.011 after 1, 2, 4 and 8 days without tetracycline, respectively. This 28- to 64-fold increase in expression relative to the tetracycline-fed control indicates that the tTAV-based positive feedback expression system is functional in adults.

Example 6

LA513 in *Aedes aegypti*

*Aedes aegypti* (the yellow fever mosquito, also the major vector of urban dengue fever) were transformed with LA513. Two independent insertion lines, LA513A and LA513B, were obtained.

Males heterozygous for LA513A (reared as larvae on 30 µg/ml tetracycline) were allowed to mate with wild type females. Eggs were collected and the resulting larvae raised in normal media, or in media supplemented with tetracycline (Tc) to 30 µg/ml. The number of transgenic and non-transgenic adults resulting from these eggs was determined. Data are the sum of at least 5 experiments. Larvae were reared at a density of ≤250 individuals per liter; all the eggs in "no tetracycline" experiments were washed twice before submergence to avoid transferring tetracycline. For the "with tetracycline" experiments, the parental blood and sugar-water was supplemented with tetracycline to 30 µg/ml; for the "no tetracycline" experiments it was not. $X^2$ test for differentiation in ratio of the transgene and wild types for survival to adult: "with tetracycline", either orientation: $P>0.05$; "without tetracycline, either orientation $P<0.001$ (null hypothesis: genotype with respect to LA513 has no effect on survival).

LA513A is, therefore, a repressible dominant lethal, with a penetrance in these experiments of 95-97%. LA513B is also a repressible dominant lethal, with a penetrance in these experiments of 100%. The results are shown in Table 10, below.

TABLE 10

Effect of tetracycline on the survival of LA513/+ *Aedes aegypti* and their +/+ siblings.

| Parents | | Progeny | | | | | | | | |
|---|---|---|---|---|---|---|---|---|---|---|
| Male | Female | Egg | Tc as larvae | Genotype | 1st instar larvae | 2nd | 3rd | 4th | Pupae | Adults |
| LA513A/+ | +/+ | 1000 | Yes | LA513A/+ | 489 | 468 | 446 | 442 | 437 | 434 |
| | | | | Wild type | 444 | 431 | 403 | 400 | 396 | 392 |
| +/+ | LA513A/+ | 1000 | Yes | LA513A/+ | 442 | 420 | 404 | 399 | 393 | 383 |
| | | | | Wild type | 466 | 444 | 428 | 417 | 412 | 404 |
| LA513A/+ | +/+ | 540 | No | LA513A/+ | 274 | 265 | 235 | 208 | 155 | 7 |
| | | | | Wild type | 233 | 225 | 214 | 212 | 209 | 206 |
| +/+ | LA513A/+ | 497 | No | LA513A/+ | 216 | 205 | 181 | 168 | 131 | 9 |
| | | | | Wild type | 241 | 225 | 216 | 214 | 211 | 207 |
| LA513B/+ | +/+ | 377 | Yes | LA513B/+ | 161 | 153 | 147 | 141 | 139 | 131 |
| | | | | Wild type | 178 | 171 | 165 | 160 | 157 | 153 |
| +/+ | LA513B/+ | 442 | Yes | LA513B/+ | 189 | 181 | 170 | 166 | 161 | 153 |
| | | | | Wild type | 203 | 198 | 185 | 182 | 180 | 176 |
| LA513B/+ | +/+ | 188 | No | LA513B/+ | 69 | 19 | 0 | 0 | 0 | 0 |
| | | | | Wild type | 85 | 84 | 83 | 83 | 82 | 81 |
| +/+ | LA513B/+ | 240 | No | LA513B/+ | 91 | 60 | 0 | 0 | 0 | 0 |
| | | | | Wild type | 107 | 104 | 99 | 98 | 95 | 93 |

We examined the survival of LA513A/+ males that had been raised on tetracycline (30 µg/ml), as larvae, but not given tetracycline as adults. We found that all males tested survived for three weeks, irrespective of genotype (LA513A/LA513A, LA513A/+ or +/+) or the presence or absence of tetracycline in their diet (n≥40 for each genotype).

We investigated the induction kinetics of tTAV in adult LA513B/+ mosquitoes after withdrawal of tetracycline, using qPCR. As shown in Table 11, below, tTAV increased in males and females following withdrawal of tetracycline. Induction of tTA expression is fairly rapid after removal of Tc, as with *Drosophila*. In each case, shifting between diets containing different levels of tetracycline provides a level of control over the expression level of genes controlled by tTA (here exemplified by tTA itself), using such a positive feedback system.

TABLE 11

Induction of tTA expression in LA513B/+ males following withdrawal of tetracycline

| Sex | Time (days) without tetracycline | tTA:18S expression ratio | tTA:18S expression relative to male with tetracycline |
|---|---|---|---|
| Male | 0 | 0.00036 | 1 |
| Female | 0 | 0.00060 | 1.7 |
| Male | 3 | 0.0043 | 12 |
| Female | 3 | 0.014 | 38 |
| Male | 4 | 0.054 | 150 |
| Female | 4 | 0.019 | 530 |
| Male | 8 | 0.012 | 34 |
| Female | 8 | 0.52 | 1500 |
| Male | 16 | 0.10 | 280 |
| Female | 16 | 0.032 | 88 |

Example 7

Tetracycline-Repressible Enhancement of a Nearby Promoter by tTAV in a Positive Feedback Configuration We observed that the fluorescent marker in LA513A and LA513B transgenic mosquitoes showed a different pattern of fluorescence in the absence of tetracycline, compared with the pattern in the presence of tetracycline. Fluorescence in the presence of tetracycline was typical of Actin5C-driven expression in mosquitoes (Catteruccia et al., 2000; Pinkerton et al., 2000), and limited largely to the swollen part of the thorax. In contrast, in the absence of tetracycline, expression was much stronger and evident substantially throughout the body of transgenic individuals. In each case, assessment of fluorescence intensity and expression pattern was made by visual observation using fluorescence microscopy.

Elevated expression of tTAV in this positive feedback situation appears, therefore, to be stimulating expression from the nearby Actin5C promoter. This is illustrated, diagrammatically, in FIG. 9. We also found that intermediate concentrations of tetracycline, just sufficient substantially to suppress the lethality of LA513, did not suppress this broader expression pattern of fluorescence. At these intermediate concentrations of tetracycline, tTAV accumulates to an intermediate level—sub-lethal, but higher than in 30 μg/ml tetracycline, and which still influences the expression of DsRed2. This again exemplifies the additional control available by modulating tetracycline concentration.

Figure 9:
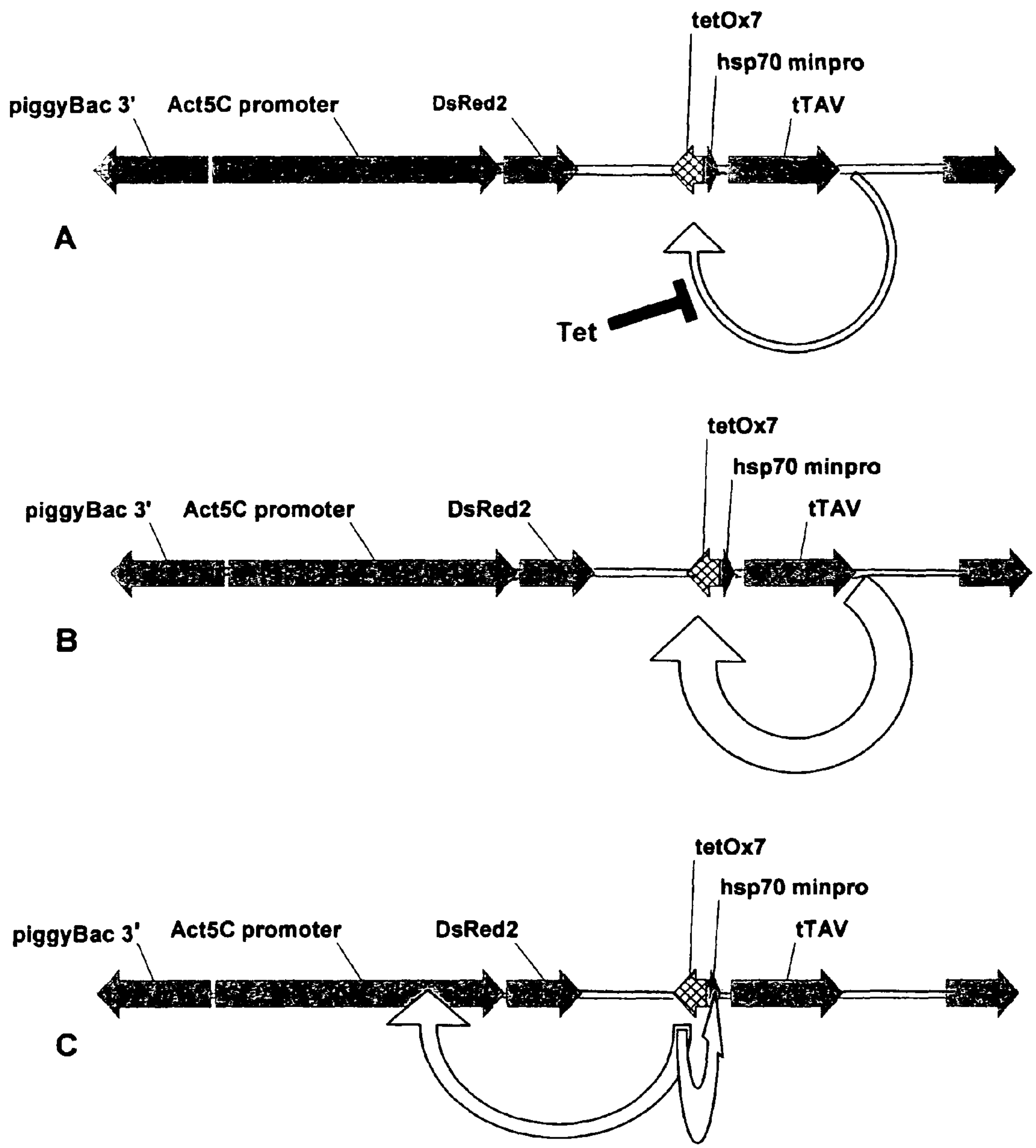
FIG. 9 illustrates the bi-directional action of $tetO_7$ in 513A and 513B mosquitoes.

FIG. 9 illustrates the bi-directional action of $tetO_7$ in 513A and 513B mosquitoes. In 513, DsRed2 is under the transcriptional control of the *Drosophila* Actin5C promoter.

(A) In the presence of tetracycline, relatively little tTAV is produced, this binds tetracycline and has little or no effect on DsRed2 expression. DsRed2 is seen in a pattern typical of Actin5C expression in mosquitoes.

(B) In the absence of tetracycline, tTAV stimulates its own expression in a positive feedback loop.

(C) tTAV binding to the tetO sites enhances expression of both the hsp70 minimal promoter, and hence tTAV, but also the Actin5C promoter, and hence DsRed2.

Example 8

LA656, LA928 and LA1124 in *Ceratitis capitata*

Figure 10:
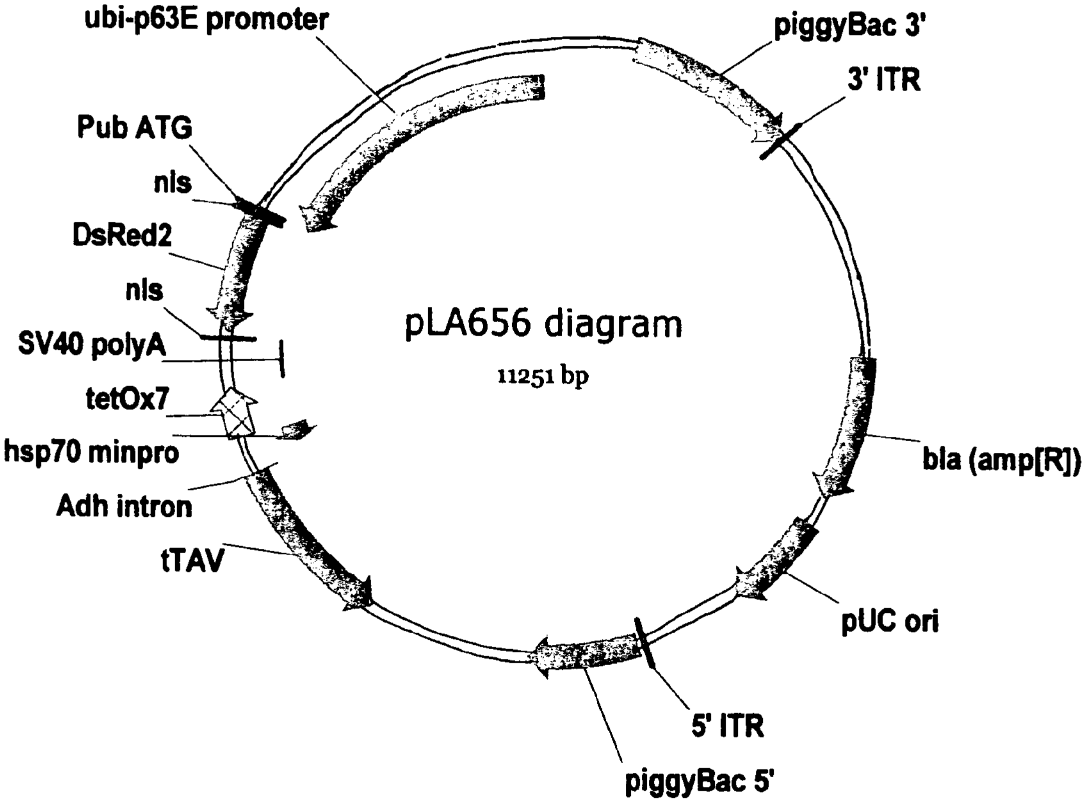
FIG. 10 is a schematic diagram of pLA656.
Figure 11:
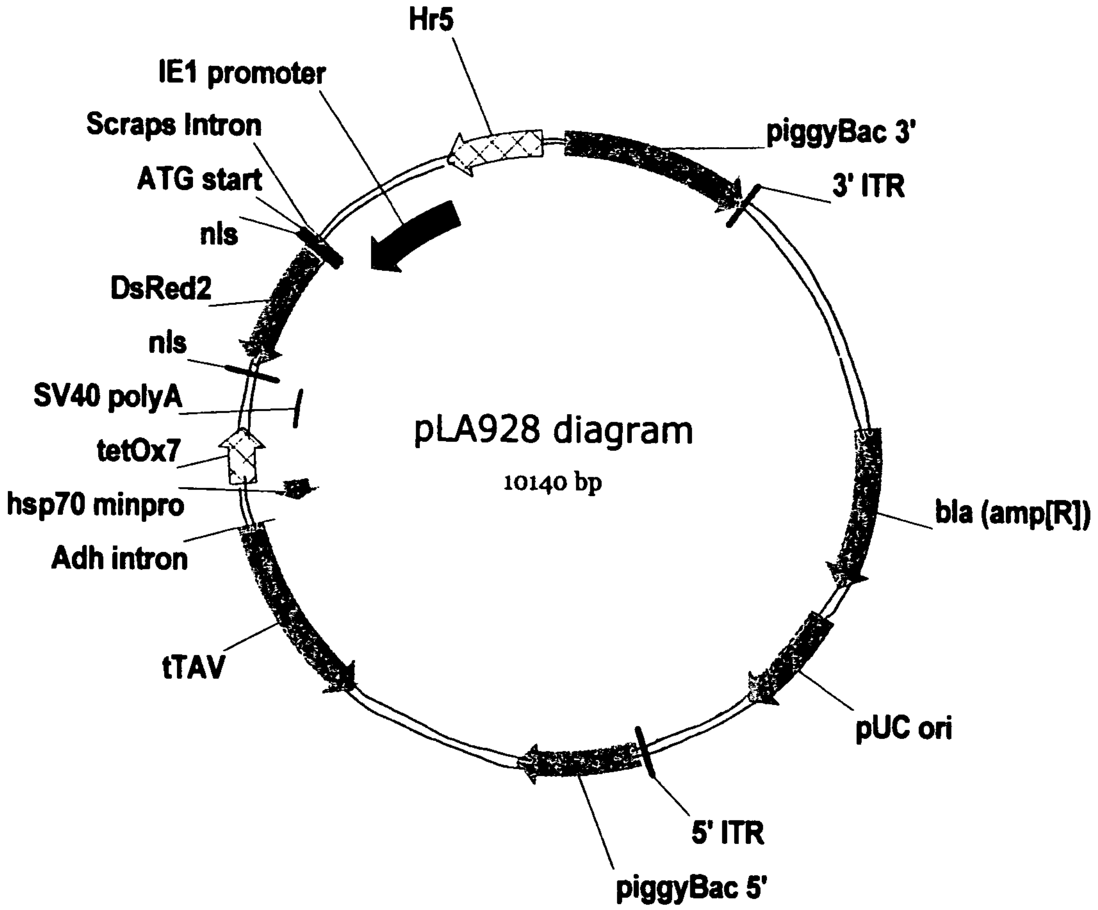
FIG. 11 is a schematic diagram of pLA928.

No transgenic lines of the Mediterranean fruit fly (medfly, *Ceratitis capitata* Wiedmann) were obtained, using pLA513, probably indicating that the Actin5C-based marker of pLA513 is inappropriate for use in medfly. This emphasises the desirability of expression constructs with a wide species range. We, therefore, modified the construct to include a polyubiquitin (ubi-p63E)-based marker instead of the Actin5C-based one of pLA513. One such construct is pLA656. We also made two additional constructs, pLA928 and pLA1124 (SEQ ID NO's 18, 20 and 21, respectively, and shown, diagrammatically, in FIGS. 10, 11 and 12), using a marker based on the hr5 enhancer and ie1 promoter from a baculovirus (*Autographica californica* nuclear polyhedrosis virus, ACMNPV). These differ in the orientation of the marker with respect to the tetO-tTAV cassette. The hr enhancer is closer to the tetO-tTAV cassette in pLA1124 than in pLA928. Furthermore, pLA1124 has 21, rather than 7, copies of tetO and additionally has a putative GAGA-factor binding region related to that of pUASp (Rorth, 1998).

One transgenic line was obtained from pLA656, three for pLA928, and three for pLA1124. These lines are assumed to have independent insertions, as they were derived from different G0 injection survivors.

Males heterozygous for each line were crossed to wild type females. The progeny were raised on standard yeast/sugar/wheatgerm or yeast/sugar/maize *Drosophila* diet, supplemented with tetracycline as appropriate. The parents were raised on the same diet, supplemented with tetracycline to 100 μg/ml in the case of the transgenic males. The wild type females to which these males were mated were raised without tetracycline, to eliminate any potential maternal contribution of tetracycline. The number of transgenic and non-transgenic pupae and adults obtained from each cross was determined by scoring for DsRed2 by fluorescence microscopy.

The results of these crosses are shown in Table 12, below. In each case, in the absence of tetracycline, survival of the heterozygous transgenics was less than 2% relative to their wild type siblings. The survival of these wild type siblings is a good control, as they are genetically similar, and raised in the same environment. In each case, this highly penetrant dominant lethality was substantially repressed by the addition of tetracycline to 100 μg/ml. In the case of LA656 and LA928, the survival rates on intermediate concentrations of tetracycline indicated that 0.1 μg/ml was insufficient for significant viability, and that viability increased in the range 1 μg/ml to 100 μg/ml. Thus, varying the concentration of dietary tetracycline provides a convenient level of control over the expression level of genes controlled by tTAV (here exemplified by tTAV itself, using such a positive feedback system. Three additional methods, shifting between diets containing different levels of tetracycline, modifying the construct, and using position effect, are discussed elsewhere herein.

TABLE 12

Effect of tetracycline on the survival of transgenic medfly heterozygous for various constructs, and their +/+ siblings

| | Progeny [Tc] (μg/ml) | F/NF pupae | Pupal survival ratio (%) | F male | F female | NF male | NF female | Adult survival ratio (%) |
|---|---|---|---|---|---|---|---|---|
| LA656 | 0 | 84/1161 | 7 | 6 | 2 | 530 | 551 | 0.7 |
| | 0.1 | 16/423 | 4 | 0 | 0 | 205 | 177 | 0 |
| | 1 | 124/384 | 32 | 34 | 12 | 155 | 174 | 14 |
| | 3 | 258/370 | 70 | 84 | 53 | 165 | 133 | 46 |
| | 10 | 249/252 | 99 | 91 | 98 | 107 | 127 | 81 |
| | 100 | 330/307 | 107 | 151 | 150 | 134 | 148 | 107 |
| LA928m1 | 0 | 28/1499 | 1.87 | 5 | 1 | 661 | 639 | 0.46 |
| | 0.1 | 0/765 | 0 | 0 | 0 | 347 | 246 | 0 |
| | 1 | 190/256 | 74 | 62 | 59 | 119 | 101 | 55 |
| | 3 | 290/302 | 96 | 133 | 98 | 143 | 107 | 92 |
| | 10 | nd | nd | nd | nd | nd | nd | nd |
| | 100 | 222/286 | 77 | 117 | 84 | 146 | 126 | 74 |
| LA928m3 | 0 | 68/1026 | 6.6 | 13 | 4 | 489 | 449 | 1.8 |
| | 0.1 | 0/265 | 0 | 0 | 0 | 117 | 91 | 0 |
| | 1 | 358/446 | 80 | 154 | 100 | 228 | 164 | 65 |
| | 3 | 105/105 | 100 | 39 | 35 | 42 | 38 | 93 |
| | 10 | nd | nd | nd | nd | nd | nd | nd |
| | 100 | 245/245 | 100 | 109 | 121 | 117 | 108 | 100 |
| LA928f1 | 0 | 17/1331 | 1.3 | 2 | 0 | 639 | 599 | 0.16 |
| | 0.1 | 2/254 | 0.8 | 0 | 0 | 100 | 84 | 0 |
| | 1 | 461/567 | 81 | 218 | 146 | 244 | 181 | 85 |
| | 3 | 520/527 | 99 | 214 | 182 | 249 | 202 | 88 |
| | 10 | 350/399 | 91 | 139 | 112 | 131 | 159 | 87 |
| | 100 | 126/117 | 108 | 63 | 57 | 57 | 49 | 113 |
| LA1124f1 | 0 | 104/213 | 51 | 0 | 3 | 95 | 62 | 1.9 |
| | 100 | 478/536 | 89 | 218 | 208 | 205 | 203 | 104 |
| LA1124m1 | 0 | 337/437 | 77 | 2 | 1 | 176 | 207 | 0.78 |
| | 100 | 84/90 | 93 | 35 | 31 | 30 | 26 | 118 |
| LA1124m2 | 0 | 104/145 | 72 | 0 | 1 | 46 | 34 | 1.3 |
| | 100 | 77/77 | 100 | 24 | 14 | 19 | 13 | 119 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals were to survive to adulthood, then this would give an "adult survival ratio" of 100%.

We further investigated the expression of tTA in these transgenic lines by quantitative (real-time) rt-PCR (qPCR). The results are given in Table 13, below.

TABLE 13

Expression levels of tTA in wild type and transgenic medfly

| Sample | tTA/18S ratio | NT/T ratio |
|---|---|---|
| Larvae | | |
| WT tet | 3.13E−06 | |
| WT NT | 2.81E−06 | |
| 656 tet | 5.80E−06 | 1.00 |
| 656 NT | 2.06E−04 | 36 |
| 670A tet | 2.71E−06 | 1.00 |
| 670A NT | 1.10E−04 | 41 |
| 670e tet | 9.70E−06 | 1.00 |
| 670e NT | 8.40E−05 | 8.7 |
| Adults | | |
| WT female | 2.83E−06 | |
| WT male | 2.16E−07 | |
| Heterozygous | | |
| 656 tet M 0 d | 5.52E−06 | 1.00 |
| 656 tet M 8 d | 1.12E−05 | 2.0 |
| 656 NT M 0 d | 4.49E−05 | 8.1 |
| 656 NT M 2 d | 2.77E−04 | 50 |
| 656 NT M 4 d | 2.22E−04 | 40 |
| 656 NT M 8 d | 9.71E−05 | 18 |
| 656 NT M 16 d | 1.49E−04 | 27 |
| 670 M tet | 4.21E−06 | 1.00 |
| 670 F tet | 2.86E−06 | 0.68 |
| 670 M NT S | 6.93E−05 | 16.45 |
| 670 F NT S | 1.92E−04 | 45.57 |
| 928Am1 F tet | 7.17E−06 | 1.00 |
| 928Am1 M tet | 8.56E−06 | 1.19 |
| 928Am1 M NT 2 d | 1.71E−04 | 23.81 |
| 928Am1 M NT 4 d | 5.36E−04 | 74.72 |
| 928Am1 M NT 8 d | 1.91E−04 | 26.66 |
| 928Am1 M NT 16 d | 1.01E−05 | 1.41 |
| 928Am1 M tet 8 d | 1.11E−06 | 0.16 |
| 928Am1 M NT S | 2.22E−04 | 31.02 |
| 928Am1 M NT S | 1.51E−04 | 21.11 |
| 928Am3 F tet | 9.09E−07 | 1.00 |
| 928Am3 M tet | 9.09E−07 | 1.00 |
| 928Am3 F NT S | 3.62E−05 | 39.85 |
| 928Am3 F NT S | 8.74E−04 | 962.07 |
| 928Am3 F NT S | 2.99E−04 | 329.32 |
| 928Am3 M NT S | 5.53E−05 | 60.83 |
| 928Am3 M NT S | 9.18E−04 | 1009.90 |
| 1124f1 F tet | 2.86E−05 | 1.00 |
| 1124f1 F NT 7 d | 4.11E−04 | 14.35 |
| 1124m1 M tet | 1.62E−05 | 1.00 |
| 1124m1 F NT S | 9.30E−04 | 57.55 |

TABLE 13-continued

Expression levels of tTA in wild type and transgenic medfly

| Sample | tTA/18S ratio | NT/T ratio |
|---|---|---|
| 1124m2 F tet | 8.98E−05 | 1.00 |
| 1124m2 F NT 7 d | 7.90E−04 | 8.79 |
| homozygous | | |
| 656 tet 8 d | 1.49E−05 | 1.00 |
| 656 NT 0 d | 9.23E−05 | 6.2 |
| 656 NT 2 d | 3.90E−03 | 262 |
| 656 NT 4 d | 1.92E−03 | 129 |
| 656 NT 8 d | 4.70E−03 | 316 |
| 656 NT 16 d | 8.58E−04 | 58 |

M: male;
F: female;
tet: raised on diet supplemented with tetracycline to 100 μg/ml;
NT S: raised on standard diet (0 μg/ml tetracycline);
d: days post-eclosion;
NT (n)d: raised on tet diet, then held as adults on non-tet (NT) diet for n days, as indicated;
tet (n)d: raised on tet diet, then held as adults on tet diet for n days, as indicated.

Example 9

LA670 in *Ceratitis capitata*

Figure 13:
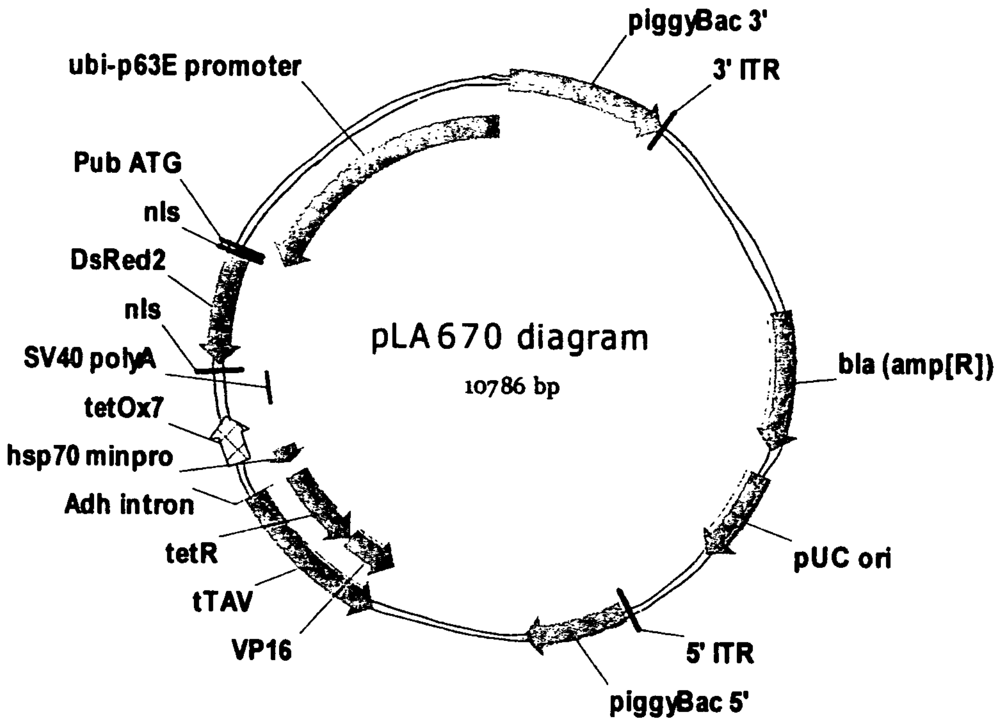
FIG. 13 is a schematic diagram of pLA670.

We obtained a single transgenic line of medfly by transformation with pLA670, a construct which closely resembles pLA656. This plasmid is illustrated in accompanying FIG. 13, and is SEQ ID NO. 23.

However, this transgenic line gave a significant number of adult transgenic progeny, even when raised as larvae on diet lacking tetracycline (Table 14). However, this LA670 insertion line does produce a readily detectable amount of tTAV mRNA in the absence of tetracycline, and this is substantially reduced by dietary tetracycline (assessed by qPCR, results shown in Table 13, above). LA670, therefore, represents a useful regulatable source of tTAV with which to drive the expression of tTAV-responsive genes. The difference in phenotype between LA656 and LA670, which are extremely similar in structure, is probably due to position effect, which is the variation in expression of transgenes depending on where they have inserted in the genome. Such variation is also shown by the variation in phenotype and tTAV expression levels between different transgenic lines with the same construct, as shown in Table 13, above. A simple method for obtaining transgenic lines carrying positive feedback constructs with different expression levels and phenotypic consequences is therefore provided, comprising generating a panel of insertion lines and screening for suitable basal and de-repressed expression levels and patterns.

TABLE 14

Effect of tetracycline on the survival of transgenic medfly heterozygous for LA670, and their +/+ siblings

| LA670 | Progeny [Tc] (μg/ml) | F/NF pupae | Pupal survival ratio (%) | F male | F female | NF male | NF female | Adult survival ratio (%) |
|---|---|---|---|---|---|---|---|---|
| | 0 | 182/220 | 83 | 72 | 35 | 102 | 103 | 52 |
| | 100 | 10/8 | 125 | 5 | 3 | 5 | 3 | 100 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals survived to adulthood, this would give an "adult survival ratio" of 100%.

Figure 14:
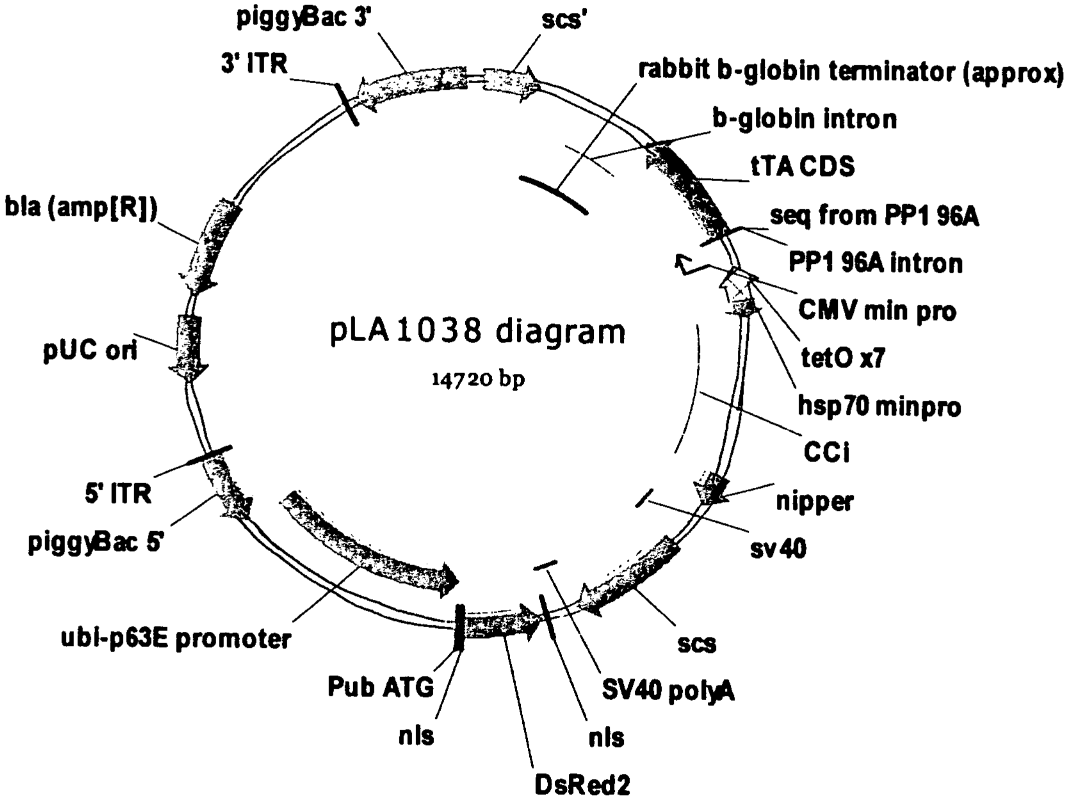
FIG. 14 is a schematic diagram of pLA1038.

We tested the ability of LA670 to drive expression of sequences placed under the transcriptional control of tetO. We analysed the expression of two potential mRNAs from pLA1038 (FIG. 14, SEQ ID NO. 24), which contains two potential tTA-responsive transcription units, divergently transcribed. These are CMV-tTA and hsp70-Cctra-nipper. PCR analysis, with controls, was performed on the expression of these transcription units in the presence and absence of pLA670. Both transcription units are expressed in the presence of pLA670. CMV-tTA is expressed at a lower, but detectable, level in LA1038/+ transgenics in the absence of LA670. hsp70-Cctra-nipper is not detectably expressed in the absence of pLA670, showing that expression is indeed driven by, and dependent on, tTAV supplied by pLA670.

Example 10

LA710 in *Pectinophora gossypiella*

*Pectinophora gossypiella* (pink bollworm, a lepidopteran) was transformed with LA710 (FIG. 15, SEQ ID NO. 19) by standard methods (Peloquin et al., 2000). Four transgenic lines were recovered. Males of these lines were crossed with females wild type for LA710. Newly hatched larvae were placed in individual 1.7 ml vials with diet, either with or without 7-chlortetracycline (40 μg/ml), and scored for fluorescence. No significant difference was observed in the numbers of transgenics surviving to adulthood relative to numbers of their wild type siblings, either with or without chlortetracycline. We conclude that LA710 does not typically lead to the accumulation of lethal levels of tTAV, even in the absence of dietary chlortetracycline.

We examined the expression of tTAV mRNA in LA710 transgenics by PCR following a reverse transcriptase reaction (rt-PCR). We found that tTAV mRNA was not detectable in chlortetracycline-fed larvae, but was detectable in larvae which had not received chlortetracycline (data not shown). This positive feedback construct LA710, therefore, provides, in these moths, a source of tTAV that can be regulated by supplying dietary chlortetracycline, and for which de-repressed expression, though readily detectable, is non-lethal. We also observed significant variation in the intensity of the band corresponding to tTAV mRNA in samples from different lines.

Example 11

LA1124 in *Pectinophora gossypiella*

*Pectinophora gossypiella* (pink bollworm, a lepidopteran) was transformed with LA1124 (FIG. 12, SEQ ID NO. 21) by standard methods (Peloquin et al., 2000). A single transgenic line was recovered. Males of this line were crossed with females wild type for LA1124. Newly hatched larvae were placed in individual 1.7 ml vials with diet, either with or without 7-chlortetracycline (40 μg/ml), and scored for fluorescence. These larvae were screened again when they had had time to develop to a late larval stage. All larvae survived, except for the fluorescent (LA1124/+) larvae on diet lacking chlortetracycline, as shown in Table 15, below.

TABLE 15

Pink bollworm: survival from early to late larval stage of LA1124/+ or their wild type siblings, on diet with or without chlortetracycline

| 100 μg/ml chlortetracycline | | 0 μg/ml chlortetracycline | |
|---|---|---|---|
| LA1124/+ | Wild-type | LA1124/+ | Wild-type |
| 3 (0 dead) | 11 (0 dead) | 8 (8 dead) | 7 (0 dead) |

We examined the expression of tTAV mRNA in LA1124 pink bollworm by PCR following a reverse transcriptase reaction (rt-PCR). We found that tTAV mRNA was readily detectable in chlortetracycline-fed larvae, but considerably elevated in larvae which had not received chlortetracycline (data not shown). The significant basal expression of tTAV mRNA in this construct is probably due to the inclusion in LA1124 of the hr enhancer, which was included for this reason. Comparison of the structure and function of LA1124 with that of LA710 clearly illustrates that basal and maximum levels of the gene product can readily be selected by appropriate modification of the expression construct, this principle being demonstrated, here, by regulating levels of expression of a tTAV-dependent RNA (in this case the tTAV mRNA).

Example 12

Sex-Specific Expression Using Positive Feedback

It is preferred to control, by design, the expression of tTAV from a positive feedback construct, so that it can be differentially expressed in different tissues, or different developmental stages, or different sexes, for example. One application for this is in genetic sexing, in which a sexual dimorphism is induced between the two sexes and this is used as a basis for separating the two sexes. In the context of the Sterile Insect Technique, e.g. for medfly, this preferably means killing the females, most preferably at an early stage in their development. No early-acting female-specific promoters are known for medfly, which limits the potential of the two-component repressible dominant lethal system exemplified for *Drosophila* using promoters or enhancers from yolk protein genes (Heinrich and Scott, 2000; Thomas et al., 2000). It would clearly be advantageous to be able to combine the beneficial characteristics of a conditional positive feedback system with a mechanism conferring female specificity.

We, therefore, modified a non-sex-specific positive feedback construct by inserting a sex-specific intronic region from Cctra, the medfly homologue of the *Drosophila melanogaster* gene transformer (Pane et al., 2002). The sex-specific splicing of Cctra is illustrated diagrammatically in FIG. 16, which is adapted from (Pane et al., 2002) supra. FIG. 16 shows the genomic organisation of the medfly tra gene. The top line represents the genomic Cctra locus. Exons are shown as blocks; aug marks the shared start codon. The alternate splice junctions are marked i. Putative tra/tra-2 binding sites are marked with arrowheads. Transcript F1, the only one to encode functional Cctra protein, is specific to females. Transcripts M1 and M2 are found in both males and females.

Three main transcripts are produced: M1, M2 and F1. Transcript F1 is found only in females, and is the only one to encode full-length, functional Cctra protein. Transcripts M1 and M2 are found in both males and females, and include additional exonic sequence, which inserts one or more stop codons relative to transcript F1, leading to truncation of the open reading frame.

Figure 17:
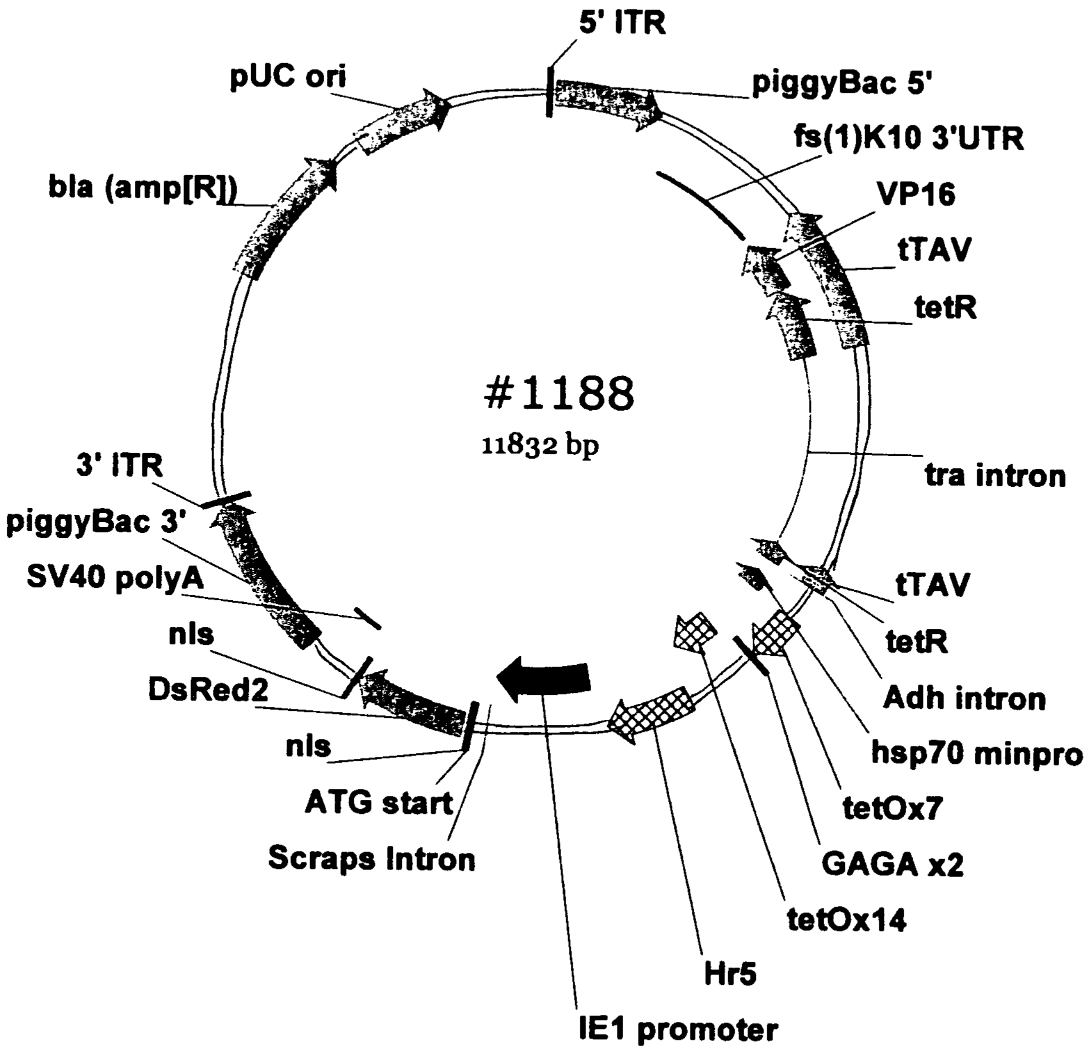
FIG. 17 is a schematic diagram of pLA1188.

We inserted the Cctra intron into the open reading frame of tTAV, so that excision by splicing of the complete intron, in the manner of transcript F1, would reconstitute an intact tTAV coding region, but splicing in the manner of either M1 or M2 would result in a truncated protein incapable of acting as a transcriptional enhancer. The resulting plasmid, pLA1188 (FIG. 17, SEQ ID NO. 22), was injected into medfly embryos. Surviving larvae were recovered, and extracts from these larvae were analysed by rt-PCR to determine the splicing pattern of the tTAV transcript.

Figure 18:
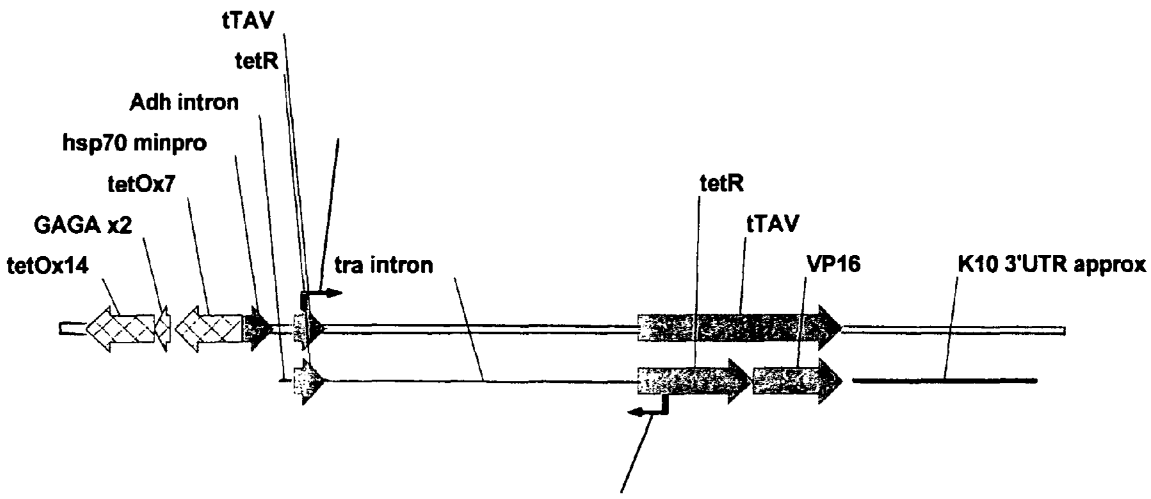
FIG. 18 illustrates sex-specific splicing in medfly.

Female larvae yielded PCR products corresponding to the expected sizes that would result from splicing in the pattern of the endogenous Cctra gene, in other words corresponding to splicing in the M1, M2 and F1 patterns. These data indicate that the Cctra intron can splice correctly in a heterologous context and, therefore, provides a suitable method for introducing sex-specificity into a positive feedback construct. Furthermore, since tra function is conserved across a wide phylogenetic range (Saccone et al., 2002), and other sex-specific introns are known, e.g. in the *Drosophila melanogaster* gene double-sex (dsx), which is also well conserved, this provides a general method for manipulating the expression of genes. It will be apparent to the person skilled in the art that such manipulations can alternatively, or additionally, be applied to other genes responsive to a transcriptional activator, so that sex-specific expression of a target gene can be achieved by combining non-sex-specific expression of a transcriptional activator with sex-specific expression, e.g. through splicing, of a functional RNA under the transcriptional control of the transcriptional activator. Furthermore, it will also be apparent that this provides a simple mechanism for differential expression of two, or more, different target genes, or gene products, such that one, or one group, is expressed in both sexes and the other, or other group, in only one sex. This is illustrated for medfly in FIG. 18.

The primers used were:

```
Tra(tTAV)Seq+:
5'-CCTGCCAGGACTCGCCTTCC          (SEQ ID NO. 12)

Tra(tTAV)Seq-:
5'-GTCATCAACTCCGCGTTGGAGC        (SEQ ID NO. 13)
```

RT-PCR products of ~600 and ~200 bp were produced when cDNA derived from female medflies 1 and 2 was used as a template, representing "male" (M1 and M2) and female-specific (F1) spliced forms of mRNA respectively (data not shown). The ~200 bp product could have been produced due to contamination with tTAV DNA—the female spliced form completely removes the Cctra intron an so leads to a PCR product that is identical to that which would be obtained from any of several tTAV-containing plasmids or samples handled in the same laboratory. The ~600 bp band, in contrast, retains ~400 bp of Cctra sequence and is diagnostic of correct splicing of the construct.

In another experiment (data not shown), expression of transcripts from LA1038 in response to tTAV from LA670 was analysed by gel chromatography (data not shown), using:

A: rt-PCR for expression of CMV-tTA from LA1038 in extracts from LA1038/+, LA670/+ double heterozygotes;

B: rt-PCR for expression of hsp70-Cctra-nipper in extracts from LA1038/+, LA670/+ double heterozygotes; and C: rt-PCR for expression of CMV-tTA from LA1038 in extracts from LA1038/+ heterozygotes without LA670.

All flies were raised in the absence of dietary tetracycline. In A and C, two bands were present between 200 bp and 400 bp and represent cDNA from spliced mRNA (lower molecular weight band) and genomic DNA or cDNA from unspliced message (higher molecular weight band) respectively. In B, a band at approximately 200 bp represents cDNA from mRNA spliced in the pattern of the Cctra female-specific F1 transcript, an upper band of approximately 1500 bp representing genomic DNA or cDNA from unspliced message, and bands of intermediate size representing cDNA spliced in the pattern of the Cctra non-sex-specific M1 and M2 transcripts, or non-specific bands.

Primer sequences used were:

```
hsp70-Cctra-nipper: NIP:
5'-CATCGATGCCCAGCATTGAGATG
and

HSP:
5'-CAAGCAAAGTGAACACGTCGCTAAGCGAAAGCTA;

CMV-tTA: CMV:
5'-GCCATCCACGCTGTTTTGACCTCCATAG
and

TTA:
5'-GCCAATACAATGTAGGCTGCTCTACAC
```

These data (not shown) demonstrate that the hsp-Cctra-nipper section of LA1038 is shown to be correctly spliced in the female form in 6/6 females, and in the male form in 6/6 males.

Transformer

Example 13

*Ceratitis capitata* tra Intron

We have prepared an insertion of a Cctra intron cassette into a synthetic open reading frame (ORF). Two versions of this splice correctly in Medfly, in other words the splicing of the Cctra intron cassette faithfully recapitulates what it would normally do in the context of the endogenous Cctra gene. This is to produce 3 (major or only) splice variants in females, one of which is female-specific (called F1), while the other two are found in both males and females (called M1 and M2). Since each of the non-sex-specific transcripts contain additional exonic material with stop codons, we have also arranged this so that only the female splice variant produces functional protein.

Each of these constructs (LA3077 and LA3097) has the Cctra intron flanked by TG and GT (to give 5' . . . TG¦intron¦GT . . . 3'. An older construct, which does not work perfectly, is LA1188. LA1188 is quite well characterized—splicing is exactly as above except that an additional 4 nucleotides are removed. The intron is in the context 5' . . . TGGCAC¦intron¦GT . . . 3'; splicing removes an additional 4 bases, i.e. 5' . . . TG¦GCACintron¦GT . . . 3' (FIG. 33).

In all cases the intron is invariant, and is simply the complete Cctra intron sequence. As is normal for introns, it begins GT and ends AG. Almost all introns start with GT, so the use of the rare alternative GC in LA1188 is surprising [GC-AG introns are a known alternative—in one large-scale survey, 0.5% of all introns were reported to use GC-AG (Burset et al., 2001), though this may be an underestimate, particularly for alternatively spliced introns, of which perhaps 5% might use GC-AG (Thanaraj and Clark, 2001)].

RT-PCR analysis was performed on LA3077, (a positive feedback construct with the CcTRA intron in the tTAV open reading frame). Transformed adult flies of both sexes were reared on diet substantially free of tetracycline ("off tetracycline") for 7 days. Flies were then collected for RNA extraction and RT PCR using primers (HSP—SEQ ID NO. 104 and VP16 SEQ ID NO. 105) were used to analyse the splicing pattern of the CcTRA intron (FIG. 34). In two female samples we found the correct splice pattern of the Cctra (776 bp, corresponding to precise removal of the Cctra intron) and saw no such band in males.

We found that LA3077 and LA3097 correspondingly gave repressible female-specific lethality. LA3077 was tested phenotypically through crossing flies heterozygous for LA3077 to wild type, on and off tetracycline. Female lethality ranged from 50 to 70%. LA3097 (a modified version of LA3077 whereby the Cctra intron immediately follows the start codon in the tTAV ORF), demonstrated a much higher level of female specific lethality, peaking at 100% (FIG. 35). The Cctra intron was also inserted in tTAV2 at the same position as LA3097, in construct LA3233, and this gave a similar phenotypic result as LA3097 (FIG. 35).

We have also prepared transformants of LA3077 in *Drosophila*. Phenotypically, the construct works perfectly, which is to say it is a highly effective female-specific lethal. However, sequencing of the splice variants of one of these insertions has shown that the splicing of this construct in *Drosophila* is not quite the same as it is in Medfly (SEQ ID NO. 57). The critical transcript, the female-specific one, is the same in both, but at least one of the non-sex-specific transcripts is different. It still incorporates extra exonic sequence, with stop codons, but the splice junctions are not quite the same (FIG. 36). This observation is extremely important in that it shows that this method (regulation of gene expression by use of alternatively spliced introns) can be used across quite a wide phylogenetic range.

A simple test to determine whether an as yet uncharacterized exonic splice regulator (such as enhancers and suppressors) may be modifying the function of the alternatively spliced intron, could include making the construct and introducing it into a target tissue, then examining its splice pattern. In many cases this will not require germline transformation, so the test can be quite rapid, for instance by transient expression in suitable tissue culture cells or in vivo. For instance, in vivo testing in insects could be achieved by delivering the DNA by microinjection. However, as the skilled person will appreciate, microinjection coupled with electroporation, or electroporation, chemical transformation, ballistic methods, for instance, have all been used in a number of various contexts and such methods of plasmid introduction and protein expression therefrom are will known in the art.

We have also recently made, and have obtained transgenics with, the Cctra intron in a different gene (LA3014) (all the above examples are in tTAV). LA3014 contains a ubiquitin-reaper$^{KR}$ fusion downstream of a Cctra intron. Phenotypic data (FIG. 35) shows that LA3014 transgenic Medfly gave repressible female-specific lethality. RT-PCR analysis on RNA extracted from adult males and females raised off tetracycline, using primers (HSP, SEQ ID NO 74) and ReaperKR (SEQ ID NO. 75), demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly (FIG. 35).

We have also recently made, and have obtained transgenics with, 'intron-only' Cctra-based constructs with the intron in a different gene (all the above examples are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above.

In order to demonstrate the phylogenetic range of the Cctra intron we generated transgenic LA3097 and LA3233 *Anastrepha ludens*. LA3097 and LA3233 were selected for injection into *Anastrepha ludens* as they demonstrated the best female specific lethality in *Ceratitis capitata* (see Example 13). Phenotypic data was generated for 4 independent LA3097 lines and 1 LA3233 line (see FIG. 38). Female specific lethality was generally somewhat lower in *Anastrepha ludens* when compared to *C. capitata* but reached 100% in one line.

*Anastrepha ludens* transformed with LA3097 and raised on tetracycline until eclosion were isolated and maintained off tetracycline for 7 days. RNA was then extracted and RT-PCR analysis was performed using primers HSP (SEQ ID NO. 76) and TETRR1 (SEQ ID NO. 77). The correct female specific (F1-like) splice pattern was observed RNA isolated from in females (348 bp) but not from males demonstrating the function of the Cctra intron in a different species (FIG. 39)

The brightest male band and the female specific band were purified and precipitated for sequencing. The female specific transcript was found to be correctly spliced in Mexfly females as expected for LA3097:

```
LA3097:
AGCCACCATG|GT . . . intron . . . AG|GTCAGCCGCC
```

Example 14

*Bactocera zonata* tra Intron

We isolated the tra intron from *Bactocera zonata* (*B. zonata*) (SEQ ID NO. 58) using primers ROSA1 (SEQ ID NO. 78), ROSA2 (SEQ ID NO. 79), and ROSA3 (SEQ ID NO. 80).

These primer sequences were designed based on conserved coding sequence of *Ceratitis capitata* and *Bactrocera oleae* tra homologs. Using ROSA2 and ROSA3 or ROSA1 and ROSA3 as primers, the tra intron and its flanking coding region were amplified from *Bactrocera zonata* genomic DNA. Then we used these PCR products as a template and amplified the tra intron fragment to make the construct-LA3376 (FIG. 31 and SEQ ID NO. 55). The primers (BZNHE—SEQ ID NO. 81 and BZR—SEQ ID NO. 82) were used for making the constructs; these primers contain additional sequences for cloning purposes. The Bztra intron in LA3376 is cloned into the ORF of tTAV3 and also of reaper$^{KR}$. Medfly transformants were generated and RNA extracted from male and female flies.

RT-PCR was then performed on both the reaper$^{KR}$ (HB—SEQ ID NO. 83) and Reaper KR—SEQ ID NO. 84) and tTAV3 (SRY—SEQ ID NO. 85) and AV3F—SEQ ID NO. 86) splice. The expected fragments of 200 bp for reaper$^{KR}$ and 670 bp for tTAV3, corresponding to splicing in a pattern equivalent to the F1 transcript of Cctra (Pane et al., 2002), were generated in females (FIG. 40).

Example 15

Isolation and Splicing of the *Ceratitis rosa* (*C. rosa*, Natal Fruit Fly) Tra Intron Primers ROSA2 (SEQ ID NO. 87) and ROSA3 (SEQ ID NO. 88) were designed based on conserved coding sequence of *Ceratitis capitata* and *Bactrocera oleae*. Using ROSA2 and ROSA3 as primers, the tra intron and its flanking coding region were amplified from *Ceratitis rosa* genomic DNA (SEQ ID NO. 59). We then used the PCR products as a template and amplified the tra intron fragment to make constructs. The primers (CRNHE—SEQ ID NO 89 and CRR SEQ ID NO 90) were used during the construction of LA3242 (SEQ ID NO. 56 and FIG. 32. LA3242 contains the *C. rosa* intron at the 5' end of the reaper$^{KR}$ ORF. *Ceratitis capitata* embryos were injected with DNA of LA3242, injected embryos were raised to adulthood on a diet substantially free of tetracycline. RNA was extracted from adult males and females; this was used as a template for RT PCR using primers HB (SEQ ID NO. 91) and ReaperKR (SEQ ID NO. 92). The expected female-specific splice band (200 bp), corresponding to splicing in the equivalent pattern to that of transcript F1 of Cctra, was observed in females and not males (FIG. 41).

Double-Sex

Example 16

*Bombyx mori* dsx in PBW

The sequence of a *Bombyx mori* (silk moth) homolog of *Drosophila* Dsx (Bmdsx) has been previously described and a male- and a female-specific splice product have been identified (Suzuki et al, 2001). Both males and females use the same 3' polyA, and there are two female specific exons. One paper has suggested that the sex-specific splicing is not dependent on tra/tra2, in other words even though the pattern looks the same, the underlying mechanism may be different (Suzuki et al., 2001), though their data, principally the lack of recognisable tra-tra2 binding sites, however, is not compelling. In addition, a *B. mori* dsx mini-gene construct (containing exonic sequence and truncated intronic sequence) has been transformed into *B. mori* and the germline transformants show sex-specific splicing (Funaguma et al., 2005).

We have generated a Bmdsx minigene based on the sequence used in the Funaguma et al paper, with some significant changes, and injected this into the moth Pink Bollworm to ascertain if one can obtain sex-specific splicing in a divergent species. The mini-gene construct we generated does not included exon 1, which is present in both males and females. In addition, we removed the intron between exon 3 and 4 (the two female specific exons), included a heterologous sequence (containing multiple cloning sites, MCS), used the Hr5-IE1 enhancer/promoter sequence from the baculovirus AcNPV and used a 3' transcriptional termination sequence derived from SV40 (see FIG. 42 for a schematic). The individual exon/flanking intron fragments used were amplified and recombined together by PCR and ligated into a construct carrying a Hr5/IE1 enhancer promoter fragment and SV40 3'UTR (FIG. 22 and SEQ ID NO. 22).

LA3435 was injected into pink bollworm (*Pectinophora gossypiella*) embryos. First instar larvae were collected after 5-7 days and analysed individually by RT-PCR (using primers IE1 transcr—SEQ ID NO. 93 and SV40-RT-P2—SEQ ID NO. 94) to determine if BMdsx can undergo male and female specific splicing (FIG. 43). Our analysis detected the male specific band (predicted to be 442 bp) in 4 samples (Lanes 1, 2, 3 and 4) and the female specific band (predicted to be 612 bp) in 1 sample (Lane 5).

The correct splicing of *B. mori* dsx in PBW demonstrates that we can achieve (have achieved) sex-specific expression of a heterologous sequence (here, the MCS) in a Lepidopteran by utilizing an alternative splicing system. Furthermore, since this splicing system was derived from a heterologous species, this suggests that such constructs might work over a wide phylogenetic range. However, the identification of alternative splicing systems in the species of interest is also envisioned, and methods for identifying such alternative splicing systems are provided herein or will be known to the person skilled in the art. By providing a MCS in our Example (see FIG. 42), the expression of a sequence of interest, for example a coding region for a protein of interest could readily be achieved by inserting said sequence. If said sequence encoded a suitable protein, a sex-specific phenotype, for example conditional sex-specific lethality, could thereby be introduced, for example into pink bollworm.

Example 17

Isolation of Codling Moth dsx

The dsx gene from Codling moth (*Cydia pomonella*) was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using the TT7T25 primer (SEQ ID NO. 95).

PCR was performed using the primers ds1c (SEQ ID NO. 96) and TT7 (SEQ ID NO. 97). Two rounds of nested PCR were then performed on the product of the first PCR using the primers codling 2a (SEQ ID NO. 98) and TT7 (SEQ ID NO. 99) and the product of the second round of PCR using Codling 2b (SEQ ID NO. 100) and TT7. The isolated male and female specific sequences share sequence similarity to previously isolated dsx homologues (Male—SEQ ID NO. 43 and Female—SEQ ID NO. 42).

Example 18

Isolation of PBW dsx

The dsx gene from pink bollworm was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using TT7T25 (sequence defined herein). PCR was performed using the primers Pbwdsx2 (SEQ ID NO. 101) and TT7 (SEQ ID NO. 102). Nested PCR was then performed on the product of the first PCR using the primers Pbwdsx3 (SEQ ID NO. 103) and TT7. Three female specific sequences were isolated: PBWdsx-F1 (SEQ ID NO. 40), PBWdsx-F2 (FIG. 10), and PBWdsx-F3 (SEQ ID NO. 71) and one male specific sequence (SEQ ID NO. 42). The isolated male and female specific sequences share sequence similarity to previously isolated dsx homologues.

Example 19 dsx in *Anopheles gambiae*

Figure 44:
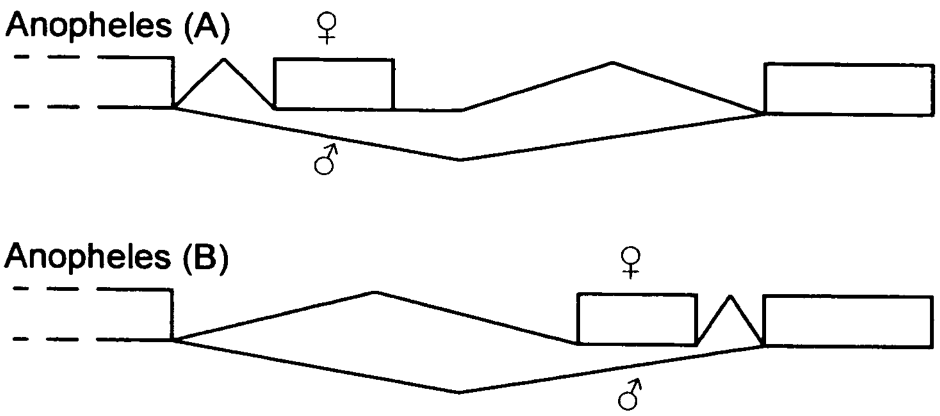

The sequence of the dsx gene of *Anopheles gambiae* has previously been described (Scali et al 2005). However, when we have tried to repeat the work described in the paper we find that there are some differences in the splicing that occurs. When we tried to repeat the amplification of the female specific transcript using primers designed from the mRNA sequence (Accession; AY903308 for female coding sequence and AY903307 for male coding sequence), the amplification failed. However, when Scali and colleagues showed that there was a shared exon, which had previously not been described, we designed primers to amplify the entire dsx transcript and gene. Using these primers and primers designed from genomic DNA sequence (Accession; GI:19611767) we find that the splicing of the female transcript is different from that described by Scali et al 2005 (FIG. 44). The transcript showed that the female exon was in a different position. There are several explanations for these differences, but the most likely are either some sort of strain difference in the *Anopheles* that we used to get the data from, or the published sequence is not from *Anopheles gambiae*, or there is more than one female isoform as shown for *Stegomyia aegypti* in Example 20.

We have also successfully used primers, designed around our version of the *Anopheles gambiae* dsx splicing, that are able to distinguish between males and females of *Anopheles gambiae* (FIG. 45). This provides good evidence that the system will be functional as a sex-specific splicing mechanism when fused to a protein of interest, such as tTAV or a killer.

The *Anopheles gambiae* dsx gene that we have isolated from genomic DNA, which has several changes in nucleotide sequence compared to the reported genomic sequence, was cloned into LA3359 (SEQ ID NO. 47) and LA3433 (SEQ ID NO. 48), schematics can be found in FIG. 23 and FIG. 24, respectively.

Example 20 dsx in *Stegomyia aegypti*

The splicing of the gene appears to be similar to *Anopheles gambiae* dsx (Scali et al 2005). The *Stegomyia aegypti* dsx gene is illustrated diagrammatically in FIG. 47 or 48. A male-specific transcript (M1) is produced which does not include exons 5a or 5b. Two female specific splice variants (F1 and F2) have the following structure; F1 comprises exons 1-4, 5a, 6 and 7 but not 5b, F2 comprises exons 1-4 and 5b (FIG. 46). In addition, a further transcript (C1) is present in both males and females; this comprises exons 1-4 and 7, but not exons 5a, 5b or 6.

The splicing of the gene appears to be similar to *Anopheles gambiae* dsx (Scali et al 2005). The *Stegomyia aegypti* dsx gene is illustrated diagrammatically in FIG. 47 or 48.

Actin 4

Example 21

*Stegomyia aegypti* Actin-4 Gene

One way to get sex-, tissue- and stage-specific expression of a gene of interest is to link it with the *Stegomyia aegypti* Actin-4 (AeAct-4) gene. This gene is only expressed in the developing flight muscles of female *Stegomyia aegypti* (Munoz et al 2004). They used in-situ hybridisation to an RNA to detect the expression profile of AeAct-4. We have taken a fragment of the *Stegomyia aegypti* Actin-4 gene, comprising a putative promoter region, an alternatively spliced intron, and a section of 5' untranslated region (UTR) and placed it in front of sequence coding for tTAV (FIG. 49) to test the function of the sex specific splicing when fused to tTAV.

We integrated LA1172 into the *Stegomyia aegypti* genome using piggyBac. Two independent lines were generated (lines 2 and 8). Both of these lines show the correct splicing of the Actin-4-tTAV gene (FIGS. 50 and 51). The Actin-4 promoter and alternatively spliced intron can therefore be used successfully to provide sex-, tissue- and stage-specific splicing of a gene of interest in *Stegomyia aegypti*.

References Part 1

Alphey, L. (2002). Re-engineering the Sterile Insect Technique. Insect Biochem Mol Biol 32, 1243-1247.

Alphey, L., and Andreasen, M. H. (2002). Dominant lethality and insect population control. Mol Biochem Parasitol 121, 173-178.

Alphey, L., Beard, B., Billingsley, P., Coetzee, M., Crisanti, A., Curtis, C. F., Eggleston, P., Godfray, C., Hemingway, J., Jacobs-Lorena, M., et al. (2002). Malaria control with genetically modified vectors. Science 298, 119-121.

Baron, U., and Bujard, H. (2000). Tet repressor-based system for regulated gene expression in eukaryotic cells: principles and advances. Meth Enzymol 327.

Baron, U., Gossen, M., and Bujard, H. (1997). Tetracycline-controlled transcription in eukaryotes: novel transactivators with graded transactivation potential. Nucl Acids Res 25, 2723-2729.

Bello, B., Resendez-Perez, D., and Gehring, W. (1998). Spatial and temporal targeting of gene expression in *Drosophila* by means of a tetracycline-dependent transactivator system. Development 125, 2193-2202.

Benedict, M., and Robinson, A. (2003). The first releases of transgenic mosquitoes: an argument for the sterile insect technique. Trends Parasitol 19, 349-355.

Bennett, D., Szoor, B., Gross, S., Vereshchagina, N., and Alphey, L. (2003). Ectopic expression of inhibitors of Protein Phosphatase type 1 (PP1) can be used to analyse roles of PP1 in *Drosophila* development. Genetics 164, 235-245.

Berger, S. L., Cress, W. D., Cress, A., Triezenberg, S. J., and Guarente, L. (1990). Selective inhibition of activated but not basal transcription by the acidic activation domain of VP16: evidence for transcriptional adaptors. Cell 61, 1199-1208.

Berghammer, A. J., Klingler, M., and Wimmer, E. A. (1999). A universal marker for transgenic insects. Nature 402, 370-371.

Brand, A., Manoukian, A., and Perrimon, N. (1994). Ectopic expression in *Drosophila*. Meth Cell Biol 44, 635-654.

Catteruccia, F., Nolan, T., Loukeris, T., Blass, C., Savakis, C., Kafatos, F., and Crisanti, A. (2000). Stable germline transformation of the malaria mosquito *Anopheles stephensi*. Nature 405, 959-962.

Coates, C., Jasinskiene, N., Miyashiro, L., and James, A. (1998). Mariner transposition and transformation of the yellow fever mosquito, *Aedes aegypti*. Proc Natl Acad Sci USA 95, 3748-3751.

Damke, H., Gossen, M., Freundlieb, S., Bujard, H., and Schmid, S. (1995). Tightly regulated and inducible expression of dominant interfering dynamin mutant in stably transformed HeLa cells. Meth Enz 257, 209-220.

Fussenegger, M. (2001). The impact of mammalian gene regulation concepts on functional genomic research, metabolic engineering, and advanced gene therapies. Biotechnol Prog 17, 1-51.

Fussenegger, M., Mazur, X., and Bailey, J. (1998a). pTRIDENT, a novel vector family for tricistronic expression in mammalian cells. Biotech Bioeng 57, 1-10.

Fussenegger, M., Moser, S., and Bailey, J. (1998b). pQuattro vectors allow one-step transfection and auto-selection of quattrocistronic artificial mammalian operons. Cytotechnology 28, 229-235.

Gebauer, F., Merendino, L., Hentze, M. W., and Valcarcel, J. (1998). The *Drosophila* splicing regulator sex-lethal directly inhibits translation of male-specific-lethal 2 mRNA. RNA 4, 142-150.

Gill, G., and Ptashne, M. (1988). Negative effect of the transcriptional activator GAL4. Nature 334, 721-724.

Gossen, M., Bonin, A., Freundlieb, S., and Bujard, H. (1994). Inducible gene expression systems for higher eukaryotic cells. Curr Opin Biotechnol 5, 516-520.

Gossen, M., and Bujard, H. (1992). Tight control of gene expression in mammalian cells by tetracycline-responsive promoters. Proc Natl Acad Sci USA 89, 5547-5551.

Handler, A. (2002). Use of the piggyBac transposon for germ-line transformation of insects. Insect Biochem Mol Biol 32, 1211-1220.

Handler, A., and James, A. (2000). Insect transgenesis: methods and applications (Boca Raton, CRC Press).

Heinrich, J., and Scott, M. (2000). A repressible female-specific lethal genetic system for making transgenic insect strains suitable for a sterile-release program. Proc Nat'l Acad Sci (USA) 97, 8229-8232.

Horn, C., Schmid, B., Pogoda, F., and Wimmer, E. (2002). Fluorescent transformation markers for insect transgenesis. Insect Biochem Mol Biol 32, 1221-1235.

Jasinskiene, N., Coates, C., Benedict, M., Cornel, A., Rafferty, C., James, A., and Collins, F. (1998). Stable transformation of the yellow fever mosquito, *Aedes aegypti*, with the Hermes element from the housefly. Proc Natl Acad Sci USA 95, 3743-3747.

Kelley, R. L., Solovyeva, I., Lyman, L. M., Richman, R., Solovyev, V., and Kuroda, M. I. (1995). Expression of msl-2 causes assembly of dosage compensation regulators on the X chromosomes and female lethality in *Drosophila*. Cell 81, 867-877.

Lobo, N., Hua-Van, A., Li, X., Nolen, B., and Fraser, M. (2002). Germ line transformation of the yellow fever mosquito, *Aedes aegypti*, mediated by transpositional insertion of a piggyBac vector. Insect Molecular Biology 11, 133-139.

Lozovsky, E., Nurminsky, D., Wimmer, E., and Hartl, D. (2002). Unexpected stability of mariner transgenes in *Drosophila*. Genetics 160, 527-535.

Matsuo, T., Takahashi, K., Kondo, S., Kaibuchi, K., and Yamamoto, D. (1997). Regulation of cone cell formation by Canoe and Ras in the developing *Drosophila* eye. Development 124, 2671-2680.

McCombs, S., and Saul, S. (1995). Translocation-based genetic sexing system for the oriental fruit-fly (Diptera, Tephritidae) based on pupal color dimorphism. Ann Ent Soc Am 88, 695-698.

Moreira, L., Wang, J., Collins, F., and Jacobs-Lorena, M. (2004). Fitness of anopheline mosquitoes expressing transgenes that inhibit *Plasmodium* development. Genetics 166, 1337-1341.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Parker, L., Gross, S., Beullens, M., Bollen, M., Bennett, D., and Alphey, L. (2002). Functional interaction between NIPP1 and PP1 in *Drosophila*: lethality of over-expression of NIPP1 in flies and rescue by the over-expression of PP1. Biochem J 368, 789-797.

Peloquin, J. J., Thibault, S. T., Staten, R., and Miller, T. A. (2000). Germ-line transformation of pink bollworm (Lepidoptera: *gelechiidae*) mediated by the piggyBac transposable element. Insect Mol Biol 9, 323-333.

Perera, O., Harrell, R., and Handler, A. (2002). Germ-line transformation of the South American malaria vector, *Anopheles albimanus*, with a piggyBac-EGFP tranposon vector is routine and highly efficient. Insect Molecular Biology 11, 291-297.

Pinkerton, A., Michel, K., O'Brochta, D., and Atkinson, P. (2000). Green fluorescent protein as a genetic marker in transgenic *Aedes aegypti*. Insect Molecular Biology 9, 1-10.

Reichhart, J., and Ferrandon, D. (1998). Green balancers. *Drosophila* Information Service 81, 201-202.

Rorth, P. (1998). Gal4 in the *Drosophila* female germline. Mech Dev 78, 113-118.

Saccone, G., Pane, A., and Polito, C. (2002). Sex determination in flies, fruitfles and butterflies. Genetica 116, 15-23.

Salghetti, S., Caudy, A., Chenoweth, J., and Tansey, W. (2001). Regulation of transcriptional activation domain function by ubiquitin. Science 293, 1651-1653.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Shockett, P., Difilippantonio, M., Hellman, N., and Schatz, D. (1995). A modified tetracycline-regulated system provides autoregulatory, inducible gene expression in cultured cells and transgenic mice. Proc Nat'l Acad Sci (USA) 92, 6522-6526.

Stebbins, M., and Yin, J. (2001). Adaptable doxycycline-regulated gene expression systems for *Drosophila*. Gene 270, 103-111.

Thomas, D., Donnelly, C., Wood, R., and Alphey, L. (2000). Insect population control using a dominant, repressible, lethal genetic system. Science 287, 2474-2476.

Varshavsky, A. (2000). Ubiquitin fusion technique and its descendants. Meth Enz 327.

References, Part 2

Allen M L, Christensen B M. Related 2004 Flight muscle-specific expression of act88F: GFP in transgenic *Culex quinquefasciatus* Say (Diptera: Culicidae). Parasitol Int. 53(4):307-14.

Bennett D, Szoor B, Gross S, Vereshchagina N, Alphey L. 2003 Ectopic expression of inhibitors of protein phosphatase type 1 (PP1) can be used to analyze roles of PP1 in *Drosophila* development. Genetics. 164(1):235-45.

Black, D. (2003). Mechanisms of alternative pre-messenger RNA splicing. Annu Rev Biochem 72, 291-336.

Burset, M., Seledtsov, I., and Solovyev, V. (2001). SpliceDB: database of canonical and non-canonical splice sites in mammalian genomes. Nucleic Acids Research 29, 255-259.

Caceres J F, Kornblihtt A R. 2002 Alternative splicing: multiple control mechanisms and involvement in human disease. Trends Genet. 18(4):186-93.

Cande C, Cecconi F, Dessen P, Kroemer G. 2002 Apoptosis-inducing factor (AIF): key to the conserved caspase-independent pathways of cell death? J Cell Sci. 115(24):4727-34.

Cartegni, L., Chew, S., and Krainer, A. (2002). Listening to silence and understanding nonsense: exonic mutations that affect splicing. Nature Reviews Genetics 3, 285-298.

Clark, F., and Thanaraj, T. (2002). Categorization and characterization of transcript-confirmed constitutively and alternatively spliced introns and exons from human. Human Molecular Genetics 11, 451-464.

Funaguma, S., Suzuki, M., Tamura, T., and Shimada, T. (2005). The Bmdsx transgene including trimmed introns is sex-specifically spliced in tissues of the silkworm, *Bombyx mori*. J Insect Sci 5, 17.

George, E. L., Ober, M. B. and Emerson Jr, C. P. (1989). Functional domains of the *Drosophila melanogaster* muscle myosin heavy-chain gene are encoded by alternatively spliced exons. Mol. Cell Biol. 9:2957-2974.

Graveley B R. 2001 Alternative splicing: increasing diversity in the proteomic world. Trends Genet. 17(2):100-7.

Hammes, A., Guo, J. K., Lutsch, G., Leheste, J. R., Landrock, D., Zeigler, U., Gubler, M. C. and Schedl, A. (2001). Two splice variants of the Wilms' Tumour 1 gene have distinct functions during sex determination and nephron formation. Cell 106:319-329.

Hastings, G. A. and Emerson Jr, C. P (1991). Myosin functional domains encoded by alternative exons are expressed in specific thoracic muscles of *Drosophila*. J. Cell Biol. 114: 263-276.

Hedley, M. L. and Maniatis (1991). Sex-specific splicing and polyadenylation of dsx pre-mRNA requires a sequence that binds specifically to a tra-2 protein in vivo. Cell 65:579-586.

Heinrich J. C. and Scott M. J. 2000 A repressible female-specific lethal genetic system for making transgenic insect strains suitable for a sterile-release program PNAS 97 (15): 8229-8232

Horn C, Wimmer E A. 2003 A transgene-based, embryo-specific lethality system for insect pest management. Nat Biotechnol. 21(1):64-70.

Hoshijima, K. K, Inoue, L., Higuchi, I., Sakamoto, H. and Shimura, Y. (1991). Control of doublesex alternative splicing by transformer and transformer-2 in *Drosophila*. Science 252:833-836.

Huang, Q., Deveraux, Q. L., Maeda, S., Salvesen, G. S., Stennicke, H. R., Hammock, B. D. and Reed, J. C. (2002). Evolutionary conservation of apoptosis mechanisms: Lepidopteran and baculoviral inhibitor of apoptosis proteins are inhibitor of mammalian caspase-9. Agricultural Sciences 97(4): 1427-1432.

Ito, Y., Hirochicka, H. and Kurata, N. (2002). Organ-specific alternative transcripts of KNOX family class 2 homeobox genes of rice. Gene 288:41-47.

Johnson J M, Castle J, Garrett-Engele P, Kan Z, Loerch P M, Armour C D, Santos R, Schadt E E, Stoughton R, Shoemaker D D. 2003 Genome-wide survey of human alternative pre-mRNA splicing with exon junction microarrays. Science. 302(5653):2141-4.

Jurica M S, Moore M J. 2003 Pre-mRNA splicing: awash in a sea of proteins. *Mol Cell.* 12(1):5-14.

Kazzaz J A, Rozek C E. 1989 Tissue-specific expression of the alternately processed *Drosophila* myosin heavy-chain messenger RNAs. Dev Biol. 133(2):550-61.

Maniatis, T., and Tasic, B. (2002). Alternative pre-mRNA splicing and proteome expansion in metazoans. Nature 418, 236-243.

Muñoz, D., Jimenez, A., Marinotti, O., and James, A. (2004). The AeAct-4 gene is expressed in the developing flight muscles of females *Aedes aegypti*. Insect Molecular Biology 13, 563-568.

Nishiyama, R., Mizuno, H., Okada, S., Yamaguchi, T., Takenaka, M., Fukuzawa, H. and Ohyama, K. (1999). Two mRNA species encoding calcium-dependent protein kinases are differentially expressed in sexual organs of *Marchantia polymorpha* through alternative splicing. Plant Cell Physiol. 40(2):205-212.

Nishiyama, R., Yamato, K. T., Miura, K., Sakida, M., Okada, S., Kono, K., Takahama, M., Sone, T., Takenaka, M., Fukuzawa, H. and Ohyama, K. (2000). Comparison of expressed sequence tags from male and female sexual organs of *Marchantia polymorpha*. DNA Res. 7:165-174.

Olson, M. R., Holley, C. L., Ji Yoo, S., Huh, J. R, Hay, B. A. and Kornbluth, S. (2003). Reaper is regulated by IAP-mediated Ubiquitination. J. Biol. Chem., 278(6):4028-4034.

Olson, M. R., Holley, C. L., Gan, E. C., Colon-Ramos, D. A., Kaplan, B. and Kornbluth, S. (2003). A GH3-like domain in reaper is required for mitochondrial localization and induction of IAP degradation. J. Biol. Chem. 278(45): 44758-44768.

Pan, Q., Shai, O., Misquitta, C., Zhang, W., Saltzman, A., Mohammad, N., Babak, T., Siu, H., Hughes, T., Morris, Q., et al. (2004). Revealing global regulatory features of mammalian alternative splicing using a quantitative microarray platform. Mol Cell 16, 929-941.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Park, J., Parisky, K., Celotto, A., Reenan, R., and Graveley, B. (2004). Identification of alternative splicing regulators by RNA interference in *Drosophila*. Proc Nat'l Acad Sci (USA) 101, 15974-15979.

Parker L, Gross S, Beullens M, Bollen M, Bennett D, Alphey L. 2002 Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1. Biochem J. 368(3):789-97.

Raphael, K. A., Whyard, S., Shearman, D., An, X. and Frommer, M. (2004). *Bactrocera tyroni* and closely related pest-tephritids-molecular analysis and prospects for transgenic control strategies. Insect Biochem. Mol. Biol. 34:167-176.

Ryner, L. and Baker, B. S. (1991). Regulation of doublesex pre-mRNA processing occurs by 3'-splice site activation. Genes Dev. 5:2071-2085.

Saccone, G., Pane, A., and Polito, C. (2002). Sex determination in flies, fruitfles and butterflies. Genetica 116, 15-23.

Scali, C., Catteruccia, F., Li, Q., and Crisanti, A. (2005). Identification of sex-specific transcripts of the *Anopheles gambiae* doublesex gene. J Exp Biol 208, 3701-3709.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Seo, S-J., Cheon, H-M., Sun, J., Sappington, T. W. and Raikhel, A. S. (2003). Tissue- and stage-specific expression of two lipophorin receptor variants with seven and eight ligand-binding repeats in the adult mosquito. J. Biol. Chem. 278(43):41954-41962.

Siebel C W, Fresco L D, Rio D C. 1992 The mechanism of somatic inhibition of *Drosophila* P-element pre-mRNA splicing: multiprotein complexes at an exon pseudo-5' splice site control U1 snRNP binding. Genes Dev. 6(8): 1386-401.

Shivikrupa, Singh., R and Swarup, G. (1999). Identification of a novel splice variant of C3G which shows tissue-specific expression. DNA Cell Biol. 18: 701-708.

Smith, C., and Valcarcel, J. (2000). Alternative pre-mRNA splicing: the logic of combinatorial control. Trends Biochem Sci 25, 381-388.

Stoss, O., Stoilov, P., Hartmann, A. M., Nayler, O., and Stamm, S. (1999). The in vivo minigene approach to analyze tissue-specific splicing. Brain Research Protocols 4, 383-394.

Stoss, O., Olbrich, M, Hartmann, A. M., Konig, H., Memmott, J., Andreadis, A and Stamm, S. (2001). The STAR/GSG family protein rSLM-2 regulates the selection of alternative splice sites. J. Biol. Chem. 276(12):8665-8673.

Streuli, M. and Saito, H. (1989). Regulation of tissue-specific alternative splicing: exon-specific cis-elements govern the splicing of leukocyte common antigen pre-mRNA. EMBO J. 8(3): 787-796.

Suzuki, M., Ohbayashi, F., Mita, K., and Shimada, T. (2001). The mechanism of sex-specific splicing at the doublesex gene is different between *Drosophila melanogaster* and *Bombyx mori*. Insect Biochem Mol Biol 31, 1201-1211.

Thanaraj, T., and Clark, F. (2001). Human GC-AG alternative intron isoforms with weak donor sites show enhanced consensus at acceptor exon positions. Nucleic Acids Research 29, 2581-2593.

Thanaraj, T., Stamm, S., Clark, F., Reithoven, J., Le Texier, V., and Muilu, J. (2004). ASD: the Alternative Splicing Database. Nucleic Acids Research 32, D64-D69.

Varshavsky, A. (2000). Ubiquitin fusion technique and its descendants. Meth Enz 327.

Venables, J. (2002). Alternative splicing in the testes. Curr Opin Genet Dev 12, 615-619.

Venables J P. 2004 Aberrant and alternative splicing in cancer. Cancer Res. 64(21):7647-54.

Vernooy, S. Y., Copeland, J., Ghaboosi, N., Griffin, E. E., Yoo, S. J. and Hay, B. A. (2000). J. Cell Biol. 150(2):F69-F75.

White, K., Tahoaglu, E. and Steller, H. (1996). Cell killing by the *Drosophila* gene reaper. Science 271 (5250): 805-807.

Wing, J. P., Zhou, L., Schwartz, L. M. and Nambu, J. R. (2001) Distinct cell killing properties of the *Drosophila* reaper, head involution defective, and grim genes. Cell Death Diffn 5(11): 930-939

Yali Chiu A., and Pin Ouyang, A. B., (2006). Loss of Pnn expression attenuates expression levels of SR family splicing factors and modulates alternative pre-mRNA splicing in vivo. Bioch. Biophys. Res. Comm. 341:663-671.

Yoshimura, K., Yabuta, Y., Ishikawa, T. and Shigeoka, S. (2002). Idenitification of a cis element for tissue-specific alternative splicing of chloroplast Ascorbate Peroxidase pre-mRNA in higher plants. J. Biol. Chem 277 (43):40623-40632.

The invention claimed is:

1. A gene expression system comprising a coding sequence to be expressed in an insect, a promoter operably linked thereto, and an intronic splice control sequence, which is flanked on its 5' end by a guanine (G) nucleotide,
wherein said intronic splice control sequence, in cooperation with a spliceosome, is capable of sex-specifically mediating alternative splicing of RNA transcripts of the coding sequence, the coding sequence encodes a protein having a lethal, deleterious or sterilizing effect and is not a sequence associated with or linked to the intronic splice control sequence in a native context,
wherein the intronic splice control sequence is obtained from AaActin-4, Dsx, Bztra or Cctra, and
wherein the insect is selected from the group consisting of mosquito, bollworm and medfly.

2. The gene expression system of claim 1, further comprising a coding sequence encoding a marker.

3. The gene expression system of claim 1, wherein a product of the coding sequence serves as a positive transcriptional control factor for the promoter, whereby the product, or the expression of the product, is controllable.

4. The gene expression system of claim 1, wherein the protein is an apoptosis-inducing factor.

5. The gene expression system of claim 4, wherein the protein is selected from the group consisting of: AIF, Hid, and Reaper (Rpr).

6. The gene expression system of claim 1, wherein the protein has a lethal effect.

7. The gene expression system of claim 1, wherein the intronic splice control sequence is obtained from Dsx and the expression system comprises a sequence selected from the group consisting of: SEQ ID NO. 40, SEQ ID NO. 41, SEQ ID NO. 42, SEQ ID NO. 43, SEQ ID NO. 44, SEQ ID NO. 45, and SEQ ID NO. 71.

8. The gene expression system of claim 1, wherein the intronic splice control sequence is obtained from Dsx, the expression system comprising a construct selected from the group consisting of: pLA3435(SEQ ID NO. 46), pLA3359 (SEQ ID NO. 47), pLA3433 (SEQ ID NO. 48).

9. The gene expression system of claim 1, wherein the intronic splice control sequence is obtained from Cctra, the expression system comprising a construct selected from the group consisting of:: pLA1188 (SEQ ID NO. 49), pLA3077 (SEQ ID NO. 50), pLA3097(SEQ ID NO. 51), pLA3233 (SEQ ID NO. 52), pLA3014 (SEQ ID NO 53), pLA3166 (SEQ ID NO. 54), and pLA3242 (SEQ ID NO. 56).

10. The gene expression system of claim 1, wherein the intronic splice control sequence is obtained from Bztra, the expression system comprising a construct set forth in pLA3376 (SEQ ID NO. 55).

11. The gene expression system of claim 1, wherein the protein is a ubiquitin protein which has the sequence according to SEQ ID NO. 73.

12. The gene expression system of claim 1, comprising two or more splice control sequences.

* * * * *